(12) United States Patent
Cortez et al.

(10) Patent No.: US 10,973,826 B2
(45) Date of Patent: Apr. 13, 2021

(54) ANTIBODY CONJUGATES COMPRISING TOLL-LIKE RECEPTOR AGONIST

(71) Applicants: Alex Cortez, San Diego, CA (US); Bernhard Hubert Geierstanger, Solana Beach, CA (US); Timothy Z. Hoffman, San Diego, CA (US); Shailaja Kasibhatla, San Diego, CA (US); Tetsuo Uno, San Diego, CA (US); Xing Wang, San Diego, CA (US); Tom Yao-Hsiang Wu, San Diego, CA (US)

(72) Inventors: Alex Cortez, San Diego, CA (US); Bernhard Hubert Geierstanger, Solana Beach, CA (US); Timothy Z. Hoffman, San Diego, CA (US); Shailaja Kasibhatla, San Diego, CA (US); Tetsuo Uno, San Diego, CA (US); Xing Wang, San Diego, CA (US); Tom Yao-Hsiang Wu, San Diego, CA (US)

(73) Assignee: Novartis AG, Basel (CH)

( * ) Notice: Subject to any disclaimer, the term of this patent is extended or adjusted under 35 U.S.C. 154(b) by 535 days.

(21) Appl. No.: 15/333,285

(22) Filed: Oct. 25, 2016

(65) Prior Publication Data

US 2017/0121421 A1   May 4, 2017

Related U.S. Application Data

(60) Provisional application No. 62/247,896, filed on Oct. 29, 2015.

(51) Int. Cl.
| | | |
|---|---|---|
| *A61K 31/52* | (2006.01) | |
| *A61K 47/68* | (2017.01) | |
| *C07D 487/04* | (2006.01) | |
| *C07H 15/26* | (2006.01) | |
| *C07K 16/28* | (2006.01) | |
| *C07K 16/32* | (2006.01) | |

(52) U.S. Cl.
CPC .......... *A61K 31/52* (2013.01); *A61K 47/6849* (2017.08); *C07D 487/04* (2013.01); *C07H 15/26* (2013.01); *C07K 16/2863* (2013.01); *C07K 16/32* (2013.01); *C07K 2317/24* (2013.01); *C07K 2317/51* (2013.01); *C07K 2317/515* (2013.01); *C07K 2317/52* (2013.01); *C07K 2317/94* (2013.01)

(58) Field of Classification Search
CPC .. A61K 47/6849; A61K 31/519; A61K 31/52; A61K 47/6851
See application file for complete search history.

(56) References Cited

U.S. PATENT DOCUMENTS

| | | |
|---|---|---|
| 5,120,525 A | 6/1992 | Goldenberg |
| 5,609,846 A | 3/1997 | Goldenberg |
| 5,686,578 A | 11/1997 | Goldenberg |
| 5,698,178 A | 12/1997 | Goldenberg |
| 5,843,397 A | 12/1998 | Goldenberg |
| 6,113,918 A | 9/2000 | Johnson et al. |
| 6,238,667 B1 | 5/2001 | Kohler |
| 6,248,564 B1 | 6/2001 | Walter et al. |
| 6,303,347 B1 | 10/2001 | Johnson et al. |
| 6,355,257 B1 | 3/2002 | Johnson et al. |
| 6,468,530 B1 | 10/2002 | Goldenberg |
| 6,573,245 B1 | 6/2003 | Marciane |
| 6,630,588 B2 | 10/2003 | Rice et al. |
| 6,764,840 B2 | 7/2004 | Johnson et al. |
| 6,916,925 B1 | 7/2005 | Rice et al. |
| 7,060,283 B1 | 6/2006 | Smith et al. |
| 7,063,967 B2 | 6/2006 | Johnson et al. |
| 7,067,128 B2 | 6/2006 | Goldenberg |
| 7,189,816 B1 | 3/2007 | Brodin et al. |
| 7,326,535 B2 | 2/2008 | Smith et al. |
| 7,375,180 B2 | 5/2008 | Gorden et al. |
| 7,387,772 B1 | 6/2008 | Hansen et al. |
| 7,427,629 B2 | 9/2008 | Kedl et al. |
| 7,442,778 B2 | 10/2008 | Gegg et al. |
| 7,521,541 B2 | 4/2009 | Eigenbrot et al. |
| 7,541,020 B2 | 6/2009 | Johnson et al. |
| 7,560,111 B2 | 7/2009 | Kao et al. |
| 7,569,674 B2 | 8/2009 | Kohlher et al. |
| 7,687,628 B2 | 3/2010 | Gutman et al. |
| 7,731,967 B2 | 6/2010 | O'Hagan et al. |
| 7,786,089 B2 | 8/2010 | Kandimalla et al. |
| 7,799,800 B2 | 9/2010 | Wightman |
| 7,923,560 B2 | 4/2011 | Wightman et al. |

(Continued)

FOREIGN PATENT DOCUMENTS

| | | |
|---|---|---|
| CA | 2958097 | 5/2019 |
| CN | 104650228 A | 5/2015 |

(Continued)

OTHER PUBLICATIONS

Chari et al, Angewandte Chemie International Edition, 2014, vol. 53, pp. 3796-3827 (Year: 2014).*
Chatterjee et al, Cancer Research, 2014, vol. 74, pp. 5008-5018 (Year: 2014).*
Kawai and Akira, Nature Immunology, 2010, vol. 11, pp. 373-384 (Year: 2010).*
Bhatelia et al, Cellular Signalling, 2014, vol. 26, pp. 2350-2357 (Year: 2014).*
Wille-Reece, Ulrike, et al., "Immunization with HIV-1 Gag Protein Conjugated to a TLR7/8 Agonist Results in the Generation of HIV-a Gag-Specific Th1 and CD8+ T Cell Responses", J Immunol, 174:7676-7683, (2005).

(Continued)

*Primary Examiner* — Karen A. Canella
(74) *Attorney, Agent, or Firm* — Kun Wang; Novartis Institutes for BioMedical Research, Inc.

(57) ABSTRACT

Provided herein are antibody conjugates comprising toll-like receptor agonists and the use of such conjugates for the treatment of cancer. In some embodiments, the conjugates comprise anti-HER2 antibodies.

28 Claims, 8 Drawing Sheets

Specification includes a Sequence Listing.

(56) References Cited

U.S. PATENT DOCUMENTS

| | | |
|---|---|---|
| 7,988,972 B2 | 8/2011 | Smith et al. |
| 8,008,453 B2 | 8/2011 | Gegg et al. |
| 8,080,662 B2 | 12/2011 | Gutman et al. |
| 8,153,141 B2 | 4/2012 | Lipford et al. |
| 8,529,906 B2 | 9/2013 | O'Hagan et al. |
| 8,658,607 B2 | 2/2014 | Lipford et al. |
| 8,951,528 B2 | 2/2015 | Stoermer et al. |
| 8,961,477 B2 | 2/2015 | Wolter et al. |
| 9,358,307 B2 | 6/2016 | Pitcovski et al. |
| 2002/0048588 A1 | 4/2002 | Johnson et al. |
| 2002/0120141 A1 | 8/2002 | Rice et al. |
| 2002/0187141 A1 | 12/2002 | Goldenberg |
| 2003/0092643 A1 | 5/2003 | Johnson et al. |
| 2003/0103984 A1 | 6/2003 | Kohler |
| 2003/0134826 A1 | 7/2003 | Glusenkamp et al. |
| 2003/0170175 A1 | 9/2003 | Goldenberg |
| 2003/0185835 A1 | 10/2003 | Braun |
| 2003/0190308 A1 | 10/2003 | Braun et al. |
| 2003/0199460 A1 | 10/2003 | Johnson et al. |
| 2003/0232010 A2 | 12/2003 | Goldenberg |
| 2003/0232074 A1 | 12/2003 | Lipford et al. |
| 2004/0013665 A1 | 1/2004 | Smith et al. |
| 2004/0071692 A1 | 4/2004 | Goldenberg |
| 2004/0091491 A1 | 5/2004 | Kedl et al. |
| 2004/0162309 A1 | 8/2004 | Gorden et al. |
| 2004/0185039 A1 | 9/2004 | Kohler et al. |
| 2004/0202720 A1 | 10/2004 | Wightman et al. |
| 2004/0248215 A1 | 12/2004 | Keler et al. |
| 2004/0258698 A1 | 12/2004 | Wightman et al. |
| 2004/0265351 A1 | 12/2004 | Miller et al. |
| 2005/0033033 A1 | 2/2005 | Kohler et al. |
| 2005/0048072 A1 | 3/2005 | Kedl et al. |
| 2005/0085500 A1 | 4/2005 | Gutman et al. |
| 2005/0107322 A1 | 5/2005 | O'Hagan et al. |
| 2005/0175630 A1 | 8/2005 | Raz et al. |
| 2005/0180983 A1 | 8/2005 | Keler et al. |
| 2005/0239733 A1 | 10/2005 | Jurk et al. |
| 2005/0256070 A1 | 11/2005 | Braun et al. |
| 2005/0266024 A1 | 12/2005 | Braun et al. |
| 2005/0271663 A1 | 12/2005 | Ignatovich et al. |
| 2005/0287154 A1 | 12/2005 | Kohler et al. |
| 2006/0002941 A1 | 1/2006 | Mahairas |
| 2006/0019923 A1 | 1/2006 | Davis et al. |
| 2006/0045885 A1 | 3/2006 | Kedl et al. |
| 2006/0088542 A1 | 4/2006 | Braun |
| 2006/0135459 A1 | 6/2006 | Epstein et al. |
| 2006/0142202 A1 | 6/2006 | Alkan et al. |
| 2006/0172966 A1 | 8/2006 | Lipford et al. |
| 2006/0189644 A1 | 8/2006 | Wightman |
| 2007/0112179 A1 | 5/2007 | Brodin et al. |
| 2007/0129320 A9 | 6/2007 | Davis et al. |
| 2007/0148088 A1 | 6/2007 | Goldenberg |
| 2007/0166384 A1 | 7/2007 | Zarraga |
| 2007/0219153 A1 | 9/2007 | Kandimalla et al. |
| 2008/0031887 A1 | 2/2008 | Lustgarten |
| 2008/0113929 A1 | 5/2008 | Lipford et al. |
| 2008/0175849 A1 | 7/2008 | Smith et al. |
| 2008/0193460 A1 | 8/2008 | Hansen et al. |
| 2009/0017021 A1 | 1/2009 | Davis et al. |
| 2009/0028874 A1 | 1/2009 | Van Der Burg et al. |
| 2009/0035323 A1 | 2/2009 | Stoermer et al. |
| 2009/0074711 A1 | 3/2009 | Glennie |
| 2009/0075339 A1 | 3/2009 | Kohler et al. |
| 2009/0117100 A1 | 5/2009 | Mao et al. |
| 2009/0208418 A1 | 8/2009 | Kohler et al. |
| 2009/0258420 A1 | 10/2009 | van Vlijmen et al. |
| 2009/0274710 A1 | 11/2009 | Kohler et al. |
| 2009/0317379 A1 | 12/2009 | Kohler et al. |
| 2009/0324622 A1 | 12/2009 | Keler et al. |
| 2010/0017898 A1 | 1/2010 | Kohler et al. |
| 2010/0184984 A1 | 7/2010 | Gutman et al. |
| 2010/0196362 A1 | 8/2010 | Stavenhagen et al. |
| 2010/0215646 A1 | 8/2010 | Kandimalla et al. |
| 2010/0239607 A1 | 9/2010 | O'Hagan et al. |
| 2011/0123629 A1 | 5/2011 | Pitcovski et al. |
| 2011/0206658 A1 | 8/2011 | Crowley et al. |
| 2011/0301334 A1 | 12/2011 | Bhakta et al. |
| 2012/0039916 A1 | 2/2012 | Zurawski et al. |
| 2012/0052068 A1 | 3/2012 | Kohler et al. |
| 2012/0052515 A1 | 3/2012 | Kohler et al. |
| 2012/0064593 A1 | 3/2012 | Kohler et al. |
| 2012/0076804 A1 | 3/2012 | Epstein et al. |
| 2012/0135012 A1 | 5/2012 | Kohler et al. |
| 2012/0231023 A1 | 9/2012 | Zurawski et al. |
| 2012/0328605 A1 | 12/2012 | Larocque et al. |
| 2014/0135487 A1 | 5/2014 | Lipford et al. |
| 2014/0294849 A1 | 10/2014 | Larocque et al. |
| 2015/0044279 A1 | 2/2015 | Miller et al. |
| 2015/0141625 A1 | 5/2015 | Stoermer et al. |
| 2015/0174268 A1 | 6/2015 | Li et al. |
| 2015/0191546 A1 | 7/2015 | Molldrem et al. |
| 2015/0239892 A1 | 8/2015 | McGowan et al. |
| 2015/0284416 A1 | 10/2015 | Zhao |
| 2015/0322155 A1 | 11/2015 | Zhao |
| 2016/0008485 A1 | 1/2016 | Marquette et al. |
| 2016/0206754 A1 | 7/2016 | Chang |
| 2016/0208020 A1 | 7/2016 | Chang |
| 2016/0208021 A1 | 7/2016 | Chang |
| 2018/0370976 A1 | 12/2018 | Ding et al. |
| 2019/0040071 A1 | 2/2019 | Ding et al. |

FOREIGN PATENT DOCUMENTS

| | | |
|---|---|---|
| EP | 0530537 A1 | 3/1993 |
| EP | 1791565 B1 | 4/2016 |
| KR | 20030091103 | 12/2003 |
| RU | 2361880 C2 | 7/2009 |
| WO | 8909061 A2 | 10/1989 |
| WO | 9406470 A2 | 3/1994 |
| WO | 1995033752 A1 | 12/1995 |
| WO | 9604313 A2 | 2/1996 |
| WO | 9739774 A2 | 10/1997 |
| WO | 9850399 A2 | 11/1998 |
| WO | 9911775 A2 | 3/1999 |
| WO | 9914244 A2 | 3/1999 |
| WO | 9955715 A | 11/1999 |
| WO | 0030680 A2 | 6/2000 |
| WO | 200000447788 A1 | 8/2000 |
| WO | 20000068213 A1 | 11/2000 |
| WO | 0109187 A2 | 2/2001 |
| WO | 0130854 A2 | 5/2001 |
| WO | 0134617 A2 | 5/2001 |
| WO | 0134709 A1 | 5/2001 |
| WO | 0187347 A2 | 11/2001 |
| WO | 0192339 A2 | 12/2001 |
| WO | 02097041 A2 | 12/2002 |
| WO | 03045431 A2 | 6/2003 |
| WO | 03080112 A2 | 10/2003 |
| WO | 03080114 A2 | 10/2003 |
| WO | 03086280 A2 | 10/2003 |
| WO | 2004032829 A2 | 4/2004 |
| WO | 2004038002 A2 | 5/2004 |
| WO | 2004071459 A | 8/2004 |
| WO | 04078146 A2 | 9/2004 |
| WO | 2004074432 A2 | 9/2004 |
| WO | 2004091500 A2 | 10/2004 |
| WO | 2004098509 A2 | 11/2004 |
| WO | 2004108072 A2 | 12/2004 |
| WO | 200501855 A2 | 1/2005 |
| WO | 2005001022 A1 | 1/2005 |
| WO | 2005018574 A2 | 3/2005 |
| WO | 2005020912 A2 | 3/2005 |
| WO | 2005033049 A2 | 4/2005 |
| WO | 2005060993 A1 | 7/2005 |
| WO | 05070959 A2 | 8/2005 |
| WO | 2005080393 A1 | 9/2005 |
| WO | 2005107760 A1 | 11/2005 |
| WO | 2005110013 A2 | 11/2005 |
| WO | 2006026394 A2 | 3/2006 |
| WO | 2006034488 A2 | 3/2006 |
| WO | 06052900 A2 | 5/2006 |
| WO | 06073493 A2 | 7/2006 |
| WO | 2006080946 A2 | 8/2006 |
| WO | 2006101783 A2 | 9/2006 |

(56) References Cited

FOREIGN PATENT DOCUMENTS

| WO | 06116423 A2 | 11/2006 | |
|---|---|---|---|
| WO | 06119291 A2 | 11/2006 | |
| WO | 2006134423 A2 | 12/2006 | |
| WO | 07075626 A2 | 7/2007 | |
| WO | 2007100634 A2 | 9/2007 | |
| WO | 2008052187 A2 | 5/2008 | |
| WO | 09002939 A2 | 12/2008 | |
| WO | 2009093250 A2 | 7/2009 | |
| WO | 2009098236 A1 | 8/2009 | |
| WO | 10048149 A2 | 7/2010 | |
| WO | 10080537 A1 | 7/2010 | |
| WO | 2011003811 A1 | 1/2011 | |
| WO | 2011005481 A1 | 1/2011 | |
| WO | 2011061246 A2 | 5/2011 | |
| WO | 2011061492 A2 | 5/2011 | |
| WO | 2011084496 A1 | 7/2011 | |
| WO | 11140338 A1 | 11/2011 | |
| WO | 2011/152485 A1 | 12/2011 | |
| WO | 11162515 A2 | 12/2011 | |
| WO | 2012021834 A2 | 2/2012 | |
| WO | 2012122396 A2 | 9/2012 | |
| WO | 13037960 A1 | 3/2013 | |
| WO | 2013093809 A1 | 6/2013 | |
| WO | 2014011489 A2 | 1/2014 | |
| WO | 14056953 A1 | 4/2014 | |
| WO | 2014124258 A2 | 8/2014 | |
| WO | 2014124316 A2 | 8/2014 | |
| WO | 2014151030 A1 | 9/2014 | |
| WO | 2014165277 A2 | 10/2014 | |
| WO | 14012479 A2 | 11/2014 | |
| WO | 2014/207082 A1 | 12/2014 | |
| WO | 2015103987 A1 | 7/2015 | |
| WO | 2015103989 A1 | 7/2015 | |
| WO | WO-2015103987 A1 * | 7/2015 | ............ A61K 45/06 |
| WO | WO-2015112749 A2 * | 7/2015 | ......... A61K 31/7105 |
| WO | 15138615 A2 | 9/2015 | |
| WO | 15155753 A2 | 10/2015 | |
| WO | 15157504 A1 | 10/2015 | |
| WO | 15168269 A1 | 11/2015 | |
| WO | 15168279 A1 | 11/2015 | |
| WO | 15189791 A2 | 12/2015 | |
| WO | 2005118588 A1 | 12/2015 | |
| WO | 16004875 A2 | 1/2016 | |
| WO | 16004876 A2 | 1/2016 | |
| WO | 16011347 A2 | 1/2016 | |
| WO | 16011422 A2 | 1/2016 | |
| WO | 16019472 A2 | 2/2016 | |
| WO | 16020791 A2 | 2/2016 | |
| WO | 16034085 A2 | 3/2016 | |
| WO | 16059622 A2 | 4/2016 | |
| WO | 16061574 A2 | 4/2016 | |
| WO | 16071856 A2 | 5/2016 | |
| WO | 2016/091698 A1 | 6/2016 | |
| WO | 20160112870 A1 | 7/2016 | |
| WO | 20160184426 A1 | 11/2016 | |
| WO | 2017/033121 A1 | 3/2017 | |
| WO | 2017/075124 A1 | 5/2017 | |
| WO | 2017/076346 A1 | 5/2017 | |
| WO | 2017/133684 A1 | 8/2017 | |

OTHER PUBLICATIONS

Wille-Reece, Ulrike, et al., "HIV Gag protein conjugated to a Toll-like receptor 718 agonist improves the magnitude and duality of Th1 and CD8+ T cell responses in nonhuman primates", Proc. Natl Acad. Sci USA, 102(42):15190-15194, (2005).

Dela Cruz, J., et al., "Anti-HER2/neu IgG3-(IL-2) and anti-HER2/neu IgG3-(GM-CSF) promote HER2/neu processing and presentation by dendritic cells: Implications in immunotherapy and vaccination strategies", Molecular Immunology, 43:667-676, (2006).

Cirone, et al., "A Novel Approach to Tumor Suppression with Microencapsulated Recombinant Cells", Human Gene Therapy, 13:1157-1166 (2002).

* cited by examiner

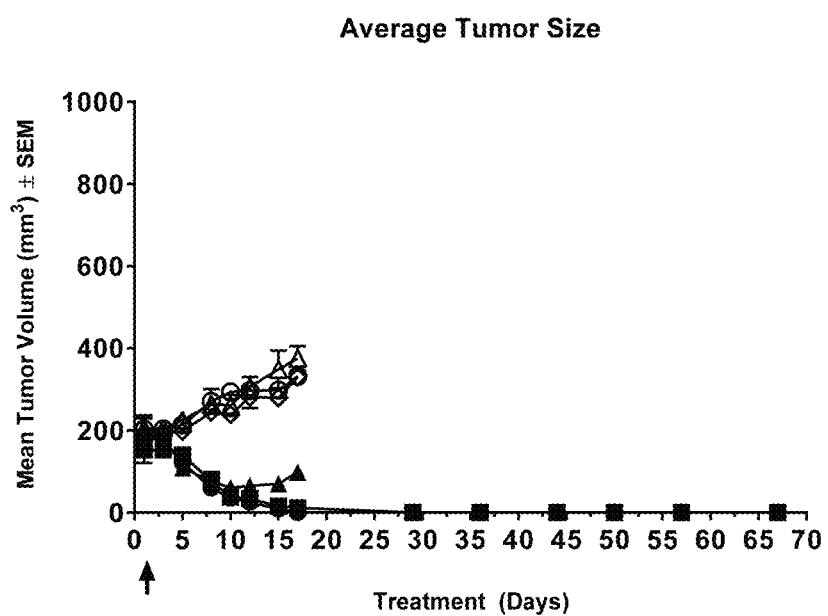

```
                       SEQUENCE LISTING

<160> NUMBER OF SEQ ID NOS: 34

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Thr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Tyr Pro Thr Asn Gly Tyr Thr Arg Tyr Ala Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Gly Gly Asp Gly Phe Tyr Ala Met Asp Tyr
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Asn Ile Lys Asp Thr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Tyr Pro Thr Asn Gly Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Asn Ile Lys Asp Thr Tyr Ile His
1               5                   10

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 8
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gaggttcagc tggtggagtc tggcggtggc ctggtgcagc caggggggctc actccgtttg      60 tcctgtgcag cttctggctt caacattaaa gacacctata tacactgggt gcgtcaggcc     120
ccgggtaagg gcctggaatg ggttgcaagg atttatccta cgaatggtta tactagatat     180
gccgatagcg tcaagggccg tttcactata agcgcagaca catccaaaaa cacagcctac     240
ctgcagatga acagcctgcg tgctgaggac actgccgtct attattgttc tagatgggga     300
ggggacggct tctatgctat ggactactgg ggtcaaggaa ccctggtcac cgtctcctcg     360

<210> SEQ ID NO 9
```

```
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Asn | Ile | Lys | Asp | Thr |
| | | | 20 | | | | | 25 | | | | | 30 | | |
| Tyr | Ile | His | Trp | Val | Arg | Gln | Ala | Pro | Gly | Lys | Gly | Leu | Glu | Trp | Val |
| | | | 35 | | | | | 40 | | | | | 45 | | |
| Ala | Arg | Ile | Tyr | Pro | Thr | Asn | Gly | Tyr | Thr | Arg | Tyr | Ala | Asp | Ser | Val |
| | 50 | | | | | 55 | | | | | 60 | | | | |
| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ser | Arg | Trp | Gly | Gly | Asp | Gly | Phe | Tyr | Ala | Met | Asp | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Cys | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | | 195 | | | | | 200 | | | | | 205 | | |
| Pro | Ser | Asn | Thr | Lys | Val | Asp | Lys | Arg | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | | 275 | | | | | 280 | | | | | 285 | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | | 355 | | | | | 360 | | | | | 365 | | |
| Thr | Cys | Leu | Val | Lys | Gly | Phe | Tyr | Pro | Cys | Asp | Ile | Ala | Val | Glu | Trp |

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 10
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gaggttcagc tggtggagtc tggcggtggc ctggtgcagc caggggggctc actccgtttg      60 tcctgtgcag cttctggctt caacattaaa gacacctata tacactgggt gcgtcaggcc     120
ccgggtaagg gcctggaatg ggttgcaagg atttatccta cgaatggtta tactagatat     180
gccgatagcg tcaagggccg tttcactata agcgcagaca catccaaaaa cacagcctac     240
ctgcagatga acagcctgcg tgctgaggac actgccgtct attattgttc tagatgggga     300
ggggacggct tctatgctat ggactactgg ggtcaaggaa ccctggtcac cgtctcctcg     360
gctagcacca agggcccaag tgtgtttccc ctggccccca gcagcaagtc tacttccggc     420
ggaactgctg ccctgggttg cctggtgaag gactacttcc cctgtcccgt gacagtgtcc     480
tggaactctg ggctctgac ttccggcgtg cacaccttcc ccgccgtgct gcagagcagc     540
ggcctgtaca gcctgagcag cgtggtgaca gtgccctcca gctctctggg aacccagacc     600
tatatctgca acgtgaacca caagcccagc aacaccaagg tggacaagag agtggagccc     660
aagagctgcg acaagaccca cacctgcccc cctgcccag ctccagaact gctgggaggg     720
ccttccgtgt tcctgttccc ccccaagccc aaggacaccc tgatgatcag caggaccccc     780
gaggtgacct gcgtggtggt ggacgtgtcc cacgaggacc cagaggtgaa gttcaactgg     840
tacgtggacg gcgtggaggt gcacaacgcc aagaccaagc ccagagagga gcagtacaac     900
agcacctaca gggtggtgtc cgtgctgacc gtgctgcacc aggactggct gaacggcaaa     960
gaatacaagt gcaaagtctc caacaaggcc ctgccagccc caatcgaaaa gacaatcagc    1020
aaggccaagg gccagccacg ggagccccag gtgtacaccc tgcccccag ccgggaggag    1080 atgaccaaga accaggtgtc cctgacctgt ctggtgaagg gcttctaccc ctgtgatatc    1140
gccgtggagt gggagagcaa cggccagccc gagaacaact acaagaccac ccccccagtg    1200
ctggacagcg acggcagctt cttcctgtac agcaagctga ccgtggacaa gtccaggtgg    1260
cagcagggca acgtgttcag ctgcagcgtg atgcacgagg ccctgcacaa ccactacacc    1320
cagaagtccc tgagcctgag ccccggcaag                                      1350

<210> SEQ ID NO 11
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 11

Arg Ala Ser Gln Asp Val Asn Thr Ala Val Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ala Ser Phe Leu Tyr Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln His Tyr Thr Thr Pro Pro Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gln Asp Val Asn Thr Ala
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ala Ser
1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Tyr Thr Thr Pro Pro
1               5
```

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 18
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gatatccaga tgacccagtc cccgagctcc ctgtccgcct ctgtgggcga tagggtcacc    60
atcacctgcc gtgccagtca ggatgtgaat actgctgtag cctggtatca acagaaacca   120
ggaaaagctc cgaaactact gatttactcg gcatccttcc tctactctgg agtcccttct   180
cgcttctctg gatccagatc tgggacggat ttcactctga ccatcagcag tctgcagccg   240
gaagacttcg caacttatta ctgtcagcaa cattatacta ctcctcccac gttcggacag   300
ggtaccaagg tggagatcaa a                                             321
```

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gatatccaga tgacccagtc cccgagctcc ctgtccgcct ctgtgggcga tagggtcacc      60
atcacctgcc gtgccagtca ggatgtgaat actgctgtag cctggtatca acagaaacca     120
ggaaaagctc cgaaactact gatttactcg gcatccttcc tctactctgg agtcccttct     180
cgcttctctg gatccagatc tgggacggat ttcactctga ccatcagcag tctgcagccg     240
gaagacttcg caacttatta ctgtcagcaa cattatacta ctcctcccac gttcggacag     300
ggtaccaagg tggagatcaa acgtacggtg gccgctccca gcgtgttcat cttccccccc     360
agcgacgagc agctgaagag tggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga aagcataag gtgtacgcct gcgaggtgac ccaccagggc     600
ctgtccagcc ccgtgaccaa gagcttcaac aggggcgagt gc                        642

<210> SEQ ID NO 21
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

Tyr Ile His Trp Val Arg Gln Ala Pro Gly Lys Gly Leu Glu Trp Val
 35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Cys Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Cys Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys

<210> SEQ ID NO 22
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gaggttcagc tggtggagtc tggcggtggc ctggtgcagc caggggggctc actccgtttg      60
tcctgtgcag cttctggctt caacattaaa gacacctata tacactgggt gcgtcaggcc     120
ccgggtaagg gcctggaatg ggttgcaagg atttatccta cgaatggtta tactagatat     180
gccgatagcg tcaagggccg tttcactata agcgcagaca catccaaaaa cacagcctac     240
ctgcagatga acagcctgcg tgctgaggac actgccgtct attattgttc tagatgggga     300
ggggacggct tctatgctat ggactactgg ggtcaaggaa ccctggtcac cgtctcctcg     360
gctagcacca agggcccag cgtgttcccc ctggccccca gcagcaagag caccagcggc     420
ggcacagccg ccctgggctg cctggtgaag gactacttcc cttgtcccgt gaccgtgtcc     480
tggaacagcg gagccctgac ctccggcgtg cacaccttcc ccgccgtgct gcagagcagc     540
ggcctgtaca gcctgtccag cgtggtgaca gtgcccagca gcagcctggg cacccagacc     600
tacatctgca acgtgaacca caagcccagc aacaccaagg tggacaagaa agtggagccc     660
aagagctgcg acaagaccca cacctgcccc ccctgcccag ccccagagct gctgggcgga     720
ccctccgtgt tcctgttccc ccccaagccc aaggacaccc tgatgatcag caggacccc     780
gaggtgacct gcgtggtggt ggacgtgagc cacgaggacc cagaggtgaa gttcaactgg     840
tacgtggacg gcgtggaggt gcacaacgcc aagaccaagc cagagagga gcagtacaac     900
agcacctaca gggtggtgtc cgtgctgacc gtgctgcacc aggactggct gaacggcaag     960
gaatacaagt gcaaggtctc caacaaggcc ctgccagccc ccatcgaaaa gaccatcagc    1020
aaggccaagg gccagccacg ggagccccag gtgtacaccc tgccccctc ccggaggag    1080
atgaccaaga accaggtgtc cctgacctgt ctggtgaagg gcttctaccc ctgcgacatc    1140
gccgtggagt gggagagcaa cggccagccc gagaacaact acaagaccac acctccagtg    1200
ctggacagcg acggcagctt cttcctgtac agcaagctga ccgtggacaa gtccaggtgg    1260
cagcagggca acgtgttcag ctgcagcgtg atgcacgagg ccctgcacaa ccactacacc    1320
cagaagagcc tgagcctgtc ccccggcaag                                     1350
```

<210> SEQ ID NO 23
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
             275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
             355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
             435                 440                 445

Gly Lys
450
```

<210> SEQ ID NO 24
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | | | | | |
|---|---|---|---|---|---|
| gaggttcagc | tggtggagtc | tggcggtggc | ctggtgcagc | caggggctc | actccgtttg | 60 |
| tcctgtgcag | cttctggctt | caacattaaa | gacacctata | tacactgggt | gcgtcaggcc | 120 |
| ccgggtaagg | gcctggaatg | ggttgcaagg | atttatccta | cgaatggtta | tactagatat | 180 |
| gccgatagcg | tcaagggccg | tttcactata | agcgcagaca | catccaaaaa | cacagcctac | 240 |
| ctgcagatga | acagcctgcg | tgctgaggac | actgccgtct | attattgttc | tagatgggga | 300 |
| ggggacggct | tctatgctat | ggactactgg | ggtcaaggaa | ccctggtcac | cgtctcctcg | 360 |
| gctagcacca | agggcccag | cgtgttcccc | ctggccccca | gcagcaagag | caccagcggc | 420 |
| ggcacagccg | ccctgggctg | cctggtgaag | gactacttcc | ccgagccgt | gaccgtgtcc | 480 |
| tggaacagcg | gagccctgac | ctccggcgtg | cacaccttcc | ccgccgtgct | gcagagcagc | 540 |
| ggcctgtaca | gcctgtccag | cgtggtgaca | gtgcccagca | gcagcctggg | cacccagacc | 600 |
| tacatctgca | acgtgaacca | caagcccagc | aacaccaagg | tggacaagaa | agtggagccc | 660 |
| aagagctgcg | acaagaccca | cacctgcccc | ccctgcccag | cccagagct | gctgggcgga | 720 |
| ccctccgtgt | tcctgttccc | ccccaagccc | aaggacaccc | tgatgatcag | caggacccc | 780 |
| gaggtgacct | gcgtggtggt | ggacgtgagc | cacgaggacc | cagaggtgaa | gttcaactgg | 840 |
| tacgtggacg | gcgtggaggt | gcacaacgcc | aagaccaagc | ccagagagga | gcagtacaac | 900 |
| agcacctaca | gggtggtgtc | cgtgctgacc | gtgctgcacc | aggactggct | gaacggcaag | 960 |
| gaatacaagt | gcaaggtctc | caacaaggcc | ctgccagccc | ccatcgaaaa | gaccatcagc | 1020 |
| aaggccaagg | gccagccacg | ggagcccag | gtgtacaccc | tgcccccctc | ccggaggag | 1080 |
| atgaccaaga | accaggtgtc | cctgacctgt | ctggtgaagg | gcttctaccc | cagcgacatc | 1140 |
| gccgtggagt | gggagagcaa | cggccagccc | gagaacaact | acaagaccac | acctccagtg | 1200 |
| ctggacagcg | acggcagctt | cttcctgtac | agcaagctga | ccgtggacaa | gtccaggtgg | 1260 |
| cagcagggca | acgtgttcag | ctgcagcgtg | atgcacgagg | ccctgcacaa | ccactacacc | 1320 |
| cagaagagcc | tgagcctgtc | ccccggcaag | | | | 1350 |

<210> SEQ ID NO 25
<211> LENGTH: 4664
<212> TYPE: DNA
<213> ORGANISM: Homo sapiens

<400> SEQUENCE: 25

| | | | | | |
|---|---|---|---|---|---|
| gcttgctccc | aatcacagga | gaaggaggag | gtggaggagg | agggctgctt | gaggaagtat | 60 |
| aagaatgaag | ttgtgaagct | gagattcccc | tccattggga | ccgagaaaac | caggggagcc | 120 |
| ccccgggcag | ccgcgcgccc | cttccacgg | ggcccttac | tgcgccgcgc | gcccggcccc | 180 |
| caccctcgc | agcaccccgc | gccccgcgcc | ctcccagccg | gtccagccg | agccatggg | 240 |
| gccggagccg | cagtgagcac | catggagctg | gcggccttgt | gccgctgggg | gctcctcctc | 300 |
| gccctcttgc | ccccggagc | cgcgagcacc | caagtgtgca | ccgcacagag | catgaagctg | 360 |
| cggctccctg | ccagtccga | gacccacctg | gacatgctcc | gccacctcta | ccagggctgc | 420 |
| caggtggtgc | agggaaacct | ggaactcacc | tacctgccca | ccaatgccag | cctgtccttc | 480 |

-continued

```
ctgcaggata tccaggaggt gcagggctac gtgctcatcg ctcacaacca agtgaggcag    540
gtcccactgc agaggctgcg gattgtgcga ggcacccagc tctttgagga caactatgcc    600
ctggccgtgc tagacaatgg agaccccgctg aacaatacca cccctgtcac aggggcctcc   660
ccaggaggcc tgcggagct gcagcttcga agcctcacag agatcttgaa aggagggggtc    720 ttgatccagc ggaacccca gctctgctac caggacacga ttttgtggaa ggacatcttc     780
cacaagaaca accagctggc tctcacactg atagacacca accgctctcg ggcctgccac    840
ccctgttctc cgatgtgtaa gggctcccgc tgctggggag agagttctga ggattgtcag    900
agcctgacgc gcactgtctg tgccggtggc tgtgcccgct gcaaggggcc actgcccact    960
gactgctgcc atgagcagtg tgctgccggc tgcacgggcc caagcactc tgactgcctg    1020 gcctgcctcc acttcaacca cagtggcatc tgtgagctgc actgcccagc cctggtcacc    1080
tacaacacag acacgtttga gtccatgccc aatcccgagg gccggtatac attcggcgcc    1140
agctgtgtga ctgcctgtcc ctacaactac ctttctacgg acgtgggatc ctgcacccctc   1200 gtctgcccc tgcacaacca agaggtgaca gcagaggatg aacacagcg gtgtgagaag     1260 tgcagcaagc cctgtgcccg agtgtgctat ggtctgggca tggagcactt gcgagaggtg   1320
agggcagtta ccagtgccaa tatccaggag tttgctggct gcaagaagat ctttgggagc   1380
ctggcatttc tgccggagag ctttgatggg acccagcct caacactgc cccgctccag     1440 ccagagcagc tccaagtgtt tgagactctg aagagatca caggttacct atacatctca    1500
gcatggccgg acagcctgcc tgacctcagc gtcttccaga acctgcaagt aatccgggga    1560
cgaattctgc acaatggcgc ctactcgctg accctgcaag gctgggcat cagctggctg     1620 gggctgcgct cactgaggga actgggcagt ggactggccc tcatccacca taacacccac   1680
ctctgcttcg tgcacacggt gccctgggac cagctctttc ggaacccgca ccaagctctg    1740
ctccacactg ccaaccggcc agaggacgag tgtgtgggcg agggcctggc ctgccaccag   1800
ctgtgcgccc gagggcactg ctggggtcca gggcccaccc agtgtgtcaa ctgcagccag   1860
ttccttcggg gccaggagtg cgtggaggaa tgccgagtac tgcaggggct ccccagggag    1920
tatgtgaatg ccaggcactg tttgccgtgc caccctgagt gtcagcccca gaatggctca    1980
gtgacctgtt ttggaccgga ggctgaccag tgtgtggcct gtgcccacta taaggaccct   2040
cccttctgcg tggcccgctg ccccagcggt gtgaaacctg acctctccta catgcccatc    2100
tggaagtttc cagatgagga gggcgcatgc cagccttgcc ccatcaactg cacccactcc   2160
tgtgtggacc tggatgacaa gggctgcccc gccgagcaga gagccagccc tctgacgtcc    2220
atcatctctg cggtggttgg cattctgctg gtcgtggtct tgggggtggt ctttgggatc    2280
ctcatcaagc gacggcagca gaagatccgg aagtacacga tgcggagact gctgcaggaa    2340
acggagctgg tggagccgct gacacctagc ggagcgatgc caaccaggc gcagatgcgg    2400 atcctgaaag agacggagct gaggaaggtg aaggtgcttg gatctggcgc ttttggcaca    2460
gtctacaagg gcatctggat ccctgatggg gagaatgtga aaattccagt ggccatcaaa    2520
gtgttgaggg aaaacacatc ccccaaagcc aacaaagaaa tcttagacga agcatacgtg    2580
atggctggtg tgggctcccc atatgtctcc cgccttctgg catctgcct gacatccacg    2640 gtgcagctgg tgacacagct tatgcccctat ggctgcctct tagaccatgt ccgggaaaac    2700
cgcggacgcc tgggctccca ggacctgctg aactggtgta tgcagattgc caaggggatg    2760
agctacctgg aggatgtgcg gctcgtacac agggacttgg ccgctcggaa cgtgctggtc    2820
```

| | |
|---|---|
| aagagtccca accatgtcaa aattacagac ttcgggctgg ctcggctgct ggacattgac | 2880 |
| gagacagagt accatgcaga tgggggcaag gtgcccatca agtggatggc gctggagtcc | 2940 |
| attctccgcc ggcggttcac ccaccagagt gatgtgtgga gttatggtgt gactgtgtgg | 3000 |
| gagctgatga cttttggggc caaaccttac gatgggatcc cagcccggga gatccctgac | 3060 |
| ctgctggaaa aggggagcg gctgccccag ccccccatct gcaccattga tgtctacatg | 3120 |
| atcatggtca aatgttggat gattgactct gaatgtcggc caagattccg ggagttggtg | 3180 |
| tctgaattct cccgcatggc cagggacccc cagcgctttg tggtcatcca gaatgaggac | 3240 |
| ttgggcccag ccagtccctt ggacagcacc ttctaccgct cactgctgga ggacgatgac | 3300 |
| atgggggacc tggtggatgc tgaggagtat ctggtacccc agcagggctt cttctgtcca | 3360 |
| gaccctgccc cggcgctgg gggcatggtc caccacaggc accgcagctc atctaccagg | 3420 |
| agtggcggtg gggacctgac actagggctg gagccctctg aagaggaggc ccccaggtct | 3480 |
| ccactggcac cctccgaagg ggctggctcc gatgtatttg atggtgacct gggaatgggg | 3540 |
| gcagccaagg ggctgcaaag cctccccaca catgacccca gccctctaca gcggtacagt | 3600 |
| gaggacccca cagtacccct gccctctgag actgatggct acgttgcccc cctgacctgc | 3660 |
| agcccccagc ctgaatatgt gaaccagcca gatgttcggc cccagcccc ttcgccccga | 3720 |
| gagggccctc tgcctgctgc ccgacctgct ggtgccactc tggaaaggcc caagactctc | 3780 |
| tccccaggga gaatgggggt cgtcaaagac gttttttgcct ttgggggtgc cgtggagaac | 3840 |
| cccgagtact tgacaccca gggaggagct gcccctcagc ccacccctcc tcctgccttc | 3900 |
| agcccagcct tcgacaacct ctattactgg gaccaggacc caccgagcg gggggctcca | 3960 |
| cccagcacct tcaaagggac acctacggca gagaacccag agtacctggg tctggacgtg | 4020 |
| ccagtgtgaa ccgaaggcc aagtccgcag aagccctgat tgtgtcctcag ggagcaggga | 4080 |
| aggcctgact tctgctggca tcaagaggtg ggagggccct ccgaccactt ccaggggaac | 4140 |
| ctgccatgcc aggaacctgt cctaaggaac cttccttcct gcttgagttc ccagatggct | 4200 |
| ggaaggggtc cagcctcgtt ggaagaggaa cagcactggg gagtctttgt ggattctgag | 4260 |
| gccctgccca tgagactct agggtccagt ggatgccaca gcccagcttg ccccttcct | 4320 |
| tccagatcct gggtactgaa agccttaggg aagctggcct gagagggaa gcggccctaa | 4380 |
| gggagtgtct aagaacaaaa gcgacccatt cagagactgt ccctgaaacc tagtactgcc | 4440 |
| ccccatgagg aaggaacagc aatggtgtca gtatccaggc tttgtacaga gtgcttttct | 4500 |
| gtttagtttt tactttttttt gttttgtttt tttaaagatg aaataaagac ccaggggggag | 4560 |
| aatgggtgtt gtatggggag gcaagtgtgg ggggtccttc tccacaccca ctttgtccat | 4620 |
| ttgcaaatat atttttggaaa acagctaaaa aaaaaaaaa aaaa | 4664 |

<210> SEQ ID NO 26
<211> LENGTH: 1255
<212> TYPE: PRT
<213> ORGANISM: Homo sapiens

<400> SEQUENCE: 26

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

```
Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
```

-continued

```
            465                 470                 475                 480
        Pro Trp Asp Gln Leu Phe Arg Asn Pro His Gln Ala Leu Leu His Thr
                        485                 490                 495

Ala Asn Arg Pro Glu Asp Glu Cys Val Gly Glu Gly Leu Ala Cys His
                        500                 505                 510

Gln Leu Cys Ala Arg Gly His Cys Trp Gly Pro Gly Pro Thr Gln Cys
                        515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
        545                 550                 555                 560

Leu Pro Cys His Pro Glu Cys Gln Pro Gln Asn Gly Ser Val Thr Cys
                        565                 570                 575

Phe Gly Pro Glu Ala Asp Gln Cys Val Ala Cys Ala His Tyr Lys Asp
                        580                 585                 590

Pro Pro Phe Cys Val Ala Arg Cys Pro Ser Gly Val Lys Pro Asp Leu
                        595                 600                 605

Ser Tyr Met Pro Ile Trp Lys Phe Pro Asp Glu Glu Gly Ala Cys Gln
                        610                 615                 620

Pro Cys Pro Ile Asn Cys Thr His Ser Cys Val Asp Leu Asp Asp Lys
        625                 630                 635                 640

Gly Cys Pro Ala Glu Gln Arg Ala Ser Pro Leu Thr Ser Ile Ile Ser
                        645                 650                 655

Ala Val Val Gly Ile Leu Leu Val Val Val Leu Gly Val Val Phe Gly
                        660                 665                 670

Ile Leu Ile Lys Arg Arg Gln Gln Lys Ile Arg Lys Tyr Thr Met Arg
                        675                 680                 685

Arg Leu Leu Gln Glu Thr Glu Leu Val Glu Pro Leu Thr Pro Ser Gly
                        690                 695                 700

Ala Met Pro Asn Gln Ala Gln Met Arg Ile Leu Lys Glu Thr Glu Leu
        705                 710                 715                 720

Arg Lys Val Lys Val Leu Gly Ser Gly Ala Phe Gly Thr Val Tyr Lys
                        725                 730                 735

Gly Ile Trp Ile Pro Asp Gly Glu Asn Val Lys Ile Pro Val Ala Ile
                        740                 745                 750

Lys Val Leu Arg Glu Asn Thr Ser Pro Lys Ala Asn Lys Glu Ile Leu
                        755                 760                 765

Asp Glu Ala Tyr Val Met Ala Gly Val Gly Ser Pro Tyr Val Ser Arg
                        770                 775                 780

Leu Leu Gly Ile Cys Leu Thr Ser Thr Val Gln Leu Val Thr Gln Leu
        785                 790                 795                 800

Met Pro Tyr Gly Cys Leu Leu Asp His Val Arg Glu Asn Arg Gly Arg
                        805                 810                 815

Leu Gly Ser Gln Asp Leu Leu Asn Trp Cys Met Gln Ile Ala Lys Gly
                        820                 825                 830

Met Ser Tyr Leu Glu Asp Val Arg Leu Val His Arg Asp Leu Ala Ala
                        835                 840                 845

Arg Asn Val Leu Val Lys Ser Pro Asn His Val Lys Ile Thr Asp Phe
        850                 855                 860

Gly Leu Ala Arg Leu Leu Asp Ile Asp Glu Thr Glu Tyr His Ala Asp
        865                 870                 875                 880

Gly Gly Lys Val Pro Ile Lys Trp Met Ala Leu Glu Ser Ile Leu Arg
                        885                 890                 895
```

```
Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 27
<211> LENGTH: 24
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 27

Met Lys Thr Phe Ile Leu Leu Trp Val Leu Leu Trp Val Ile
1               5                   10                  15

Phe Leu Leu Pro Gly Ala Thr Ala
            20

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Pro Leu Leu Leu Leu Pro Leu Leu Trp Ala Gly Ala Leu Ala
1               5                   10                  15

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Ser Val Leu Thr Gln Val Leu Ala Leu Leu Leu Trp Leu Thr
1               5                   10                  15

Gly Thr Arg Cys
            20

<210> SEQ ID NO 30
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Cys Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Asp Ser Leu Asp Met Leu Glu Trp Ser Leu Met
1               5                   10

<210> SEQ ID NO 32
<211> LENGTH: 462
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Gly Asp Ser Leu Asp Met Leu Glu Trp
385                 390                 395                 400

Ser Leu Met Asn Asn Tyr Lys Thr Thr Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Gly Arg Lys Lys Arg Arg Gln Arg Arg Leu Tyr Arg Ser Pro
1               5                   10                  15

Ala Met Pro Glu Asn Leu
            20

<210> SEQ ID NO 34
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gatatccaga tgacccagtc cccgagctcc ctgtccgcct ctgtgggcga tagggtcacc    60
atcacctgcc gtgccagtca ggatgtgaat actgctgtag cctggtatca acagaaacca   120
ggaaaagctc cgaaactact gatttactcg gcatccttcc tctactctgg agtcccttct   180
cgcttctctg gatccagatc tgggacggat ttcactctga ccatcagcag tctgcagccg   240
gaagacttcg caacttatta ctgtcagcaa cattatacta ctcctcccac gttcggacag   300
ggtaccaagg tggagatcaa acgaacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac agggcgagt gc                       642

ANTIBODY CONJUGATES COMPRISING TOLL-LIKE RECEPTOR AGONIST

CROSS-REFERENCE TO RELATED APPLICATIONS

This application claims the benefit of U.S. Provisional Application No. 62/247,896, filed 29 Oct. 2015, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 5, 2016, is named PAT057064-US-NP_SL.txt and is 54,974 bytes in size.

FIELD OF THE INVENTION

The invention provides antibody conjugates comprising toll-like receptor agonists and the use of such conjugates for the treatment of cancer.

BACKGROUND OF THE INVENTION

Innate immunity is a rapid nonspecific immune response that fights against environmental insults including, but not limited to, pathogens such as bacteria or viruses. Adaptive immunity is a slower but more specific immune response, which confers long-lasting or protective immunity to the host and involves differentiation and activation of naive T lymphocytes into CD4+ T helper cells and/or CD8+ cytotoxic T cells, to promote cellular and humoral immunity. Antigen presentation cells of the innate immune system, such as dendritic cells or macrophages, serve as a critical link between the innate and adaptive immune systems by phagocytosing and processing the foreign antigens and presenting them on the cell surface to the T cells, thereby activating T cell response.

Toll-like receptors (TLRs) are pattern recognition receptors (PRR) that are expressed predominantly on dendritic cells, macrophages, monocytes, natural killer cells, and T lymphocytes. TLRs bind to pathogen-associated molecular patterns (PAMPS) from bacteria, fungi, protozoa and viruses, and act as a first line of defense against invading pathogens. TLR activation leads to increased antigen uptake, maturation, and T-cell stimulatory capacity of the dendritic cells. TLRs comprise an extracellular N-terminal leucine-rich repeat (LRR) domain, followed by a cysteine-rich region, a transmembrane domain, and an intracellular (cytoplasmic) tail that contains a conserved region named the Toll/IL-1 receptor (TIR) domain. The LRR domain is important for ligand binding and associated signaling and is a common feature of PRRs. The TIR domain is important in protein-protein interactions and is associated with innate immunity. TLRs are essential to induce expression of genes involved in inflammatory responses, and play critical roles in the development of antigen-specific acquired immunity.

There remains a need for new immunotherapies for the treatment of diseases, in particular cancer.

SUMMARY OF THE INVENTION

The invention provides antibody conjugates comprising toll-like receptor agonists, pharmaceutically acceptable salts thereof, pharmaceutical compositions thereof and combinations thereof, which are useful for the treatment of diseases, in particular, cancer. The invention further provides methods of treating, preventing, or ameliorating cancer comprising administering to a subject in need thereof an effective amount of an antibody conjugate of the invention. The invention also provides compounds comprising TLR7 agonists and a linker which are useful to conjugate to an anti-HER2 antibody and thereby make the immunostimulatory conjugates of the invention. Various embodiments of the invention are described herein.

In one aspect of the invention are compounds having the structure of Formula (I), and the pharmaceutically acceptable salts thereof, which are TLR7 agonists:

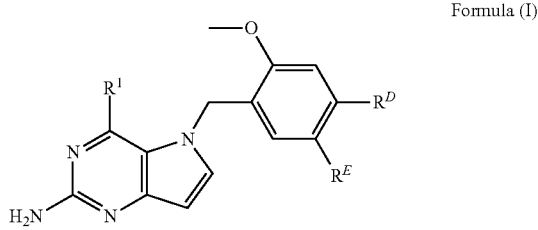

Formula (I)

wherein:

$R^D$ is

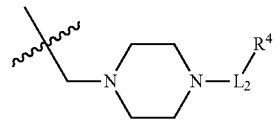

and $R^E$ is H; or $R^E$ is

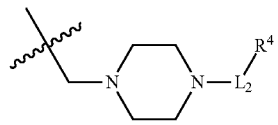

and $R^D$ is H;

$R^1$ is —NHR$^2$ or —NHCHR$^2$R$^3$;

$R^2$ is —C$_3$-C$_6$alkyl or —C$_4$-C$_6$alkyl;

$R^3$ is L$_1$OH;

L$_1$ is —(CH$_2$)$_m$—;

L$_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$—, —((CH$_2$)$_n$O)$_t$(CH$_2$)$_n$NHC(=O)(CH$_2$)$_n$, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$X$_3$C(=O)(CH$_2$)$_n$—, —C(=O)X$_2$C(=O)(CH$_2$)$_n$NHC(=O)(CH$_2$)$_n$—, —C(=O)X$_2$C(=O)(CH$_2$)$_n$NHC(=O)((CH$_2$)$_n$O)$_t$(CH$_2$)$_n$—, —C(=O)(CH$_2$)$_n$C(R$_7$)$_2$—, —C(=O)(CH$_2$)$_n$C(R$_7$)$_2$SS(CH$_2$)$_n$NHC(=O)(CH$_2$)$_n$—, —(CH$_2$)$_n$X$_2$C(=O)(CH$_2$)$_n$NHC(=O)((CH$_2$)$_n$O)$_t$(CH$_2$)$_n$— or —C(=O)(CH$_2$)$_n$C(=O)NH(CH$_2$)$_n$;

$R^4$ is
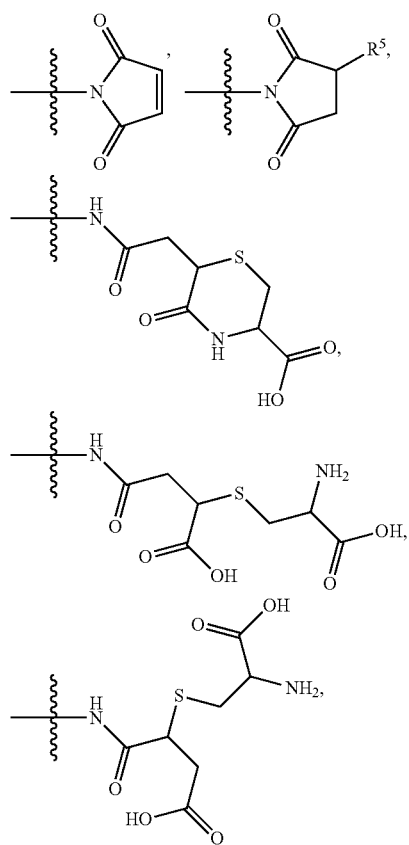
—ONH$_2$, —NH$_2$,
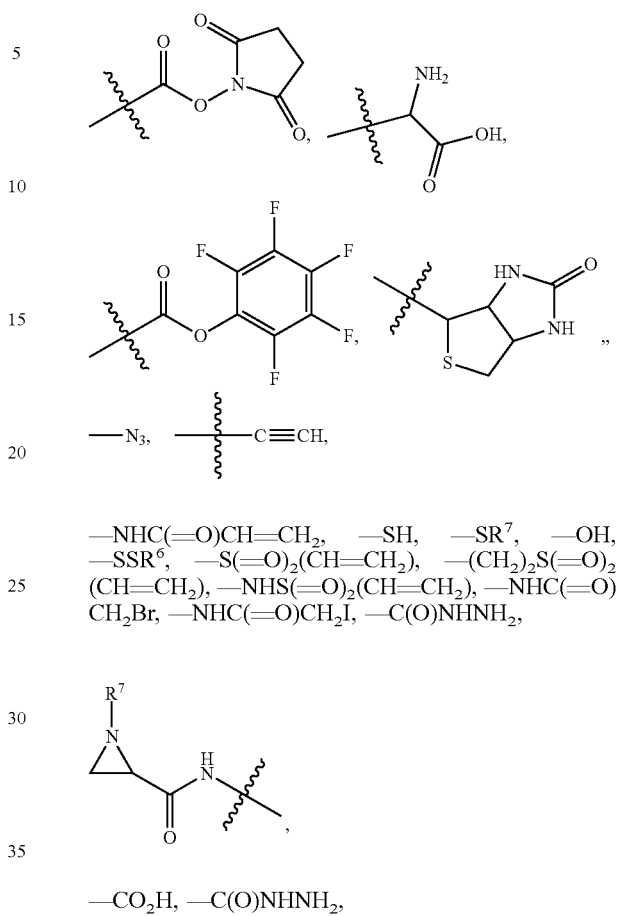
—NHC(=O)CH=CH$_2$, —SH, —SR$^7$, —OH, —SSR$^6$, —S(=O)$_2$(CH=CH$_2$), —(CH$_2$)$_2$S(=O)$_2$(CH=CH$_2$), —NHS(=O)$_2$(CH=CH$_2$), —NHC(=O)CH$_2$Br, —NHC(=O)CH$_2$I, —C(O)NHNH$_2$,
—CO$_2$H, —C(O)NHNH$_2$,
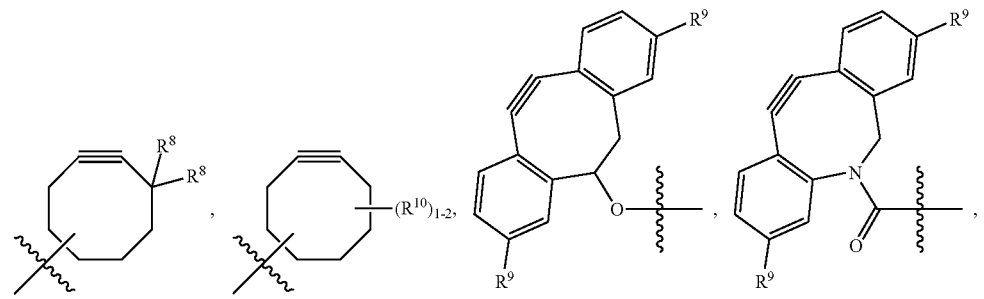
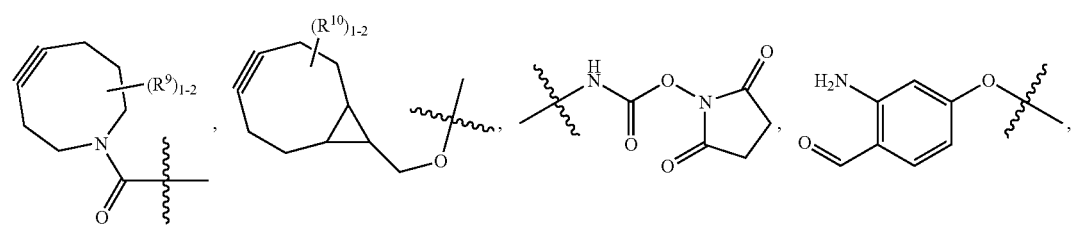

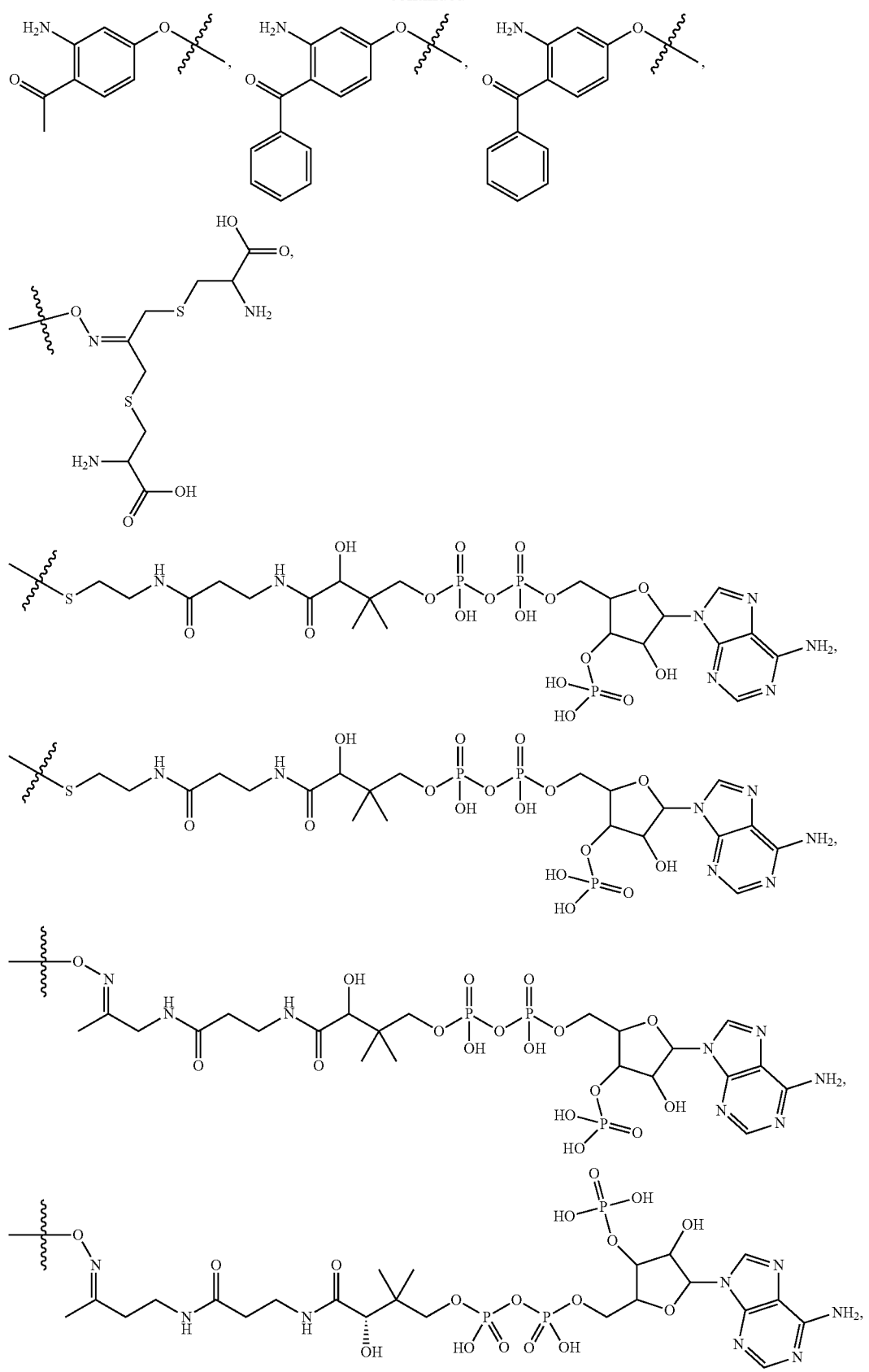

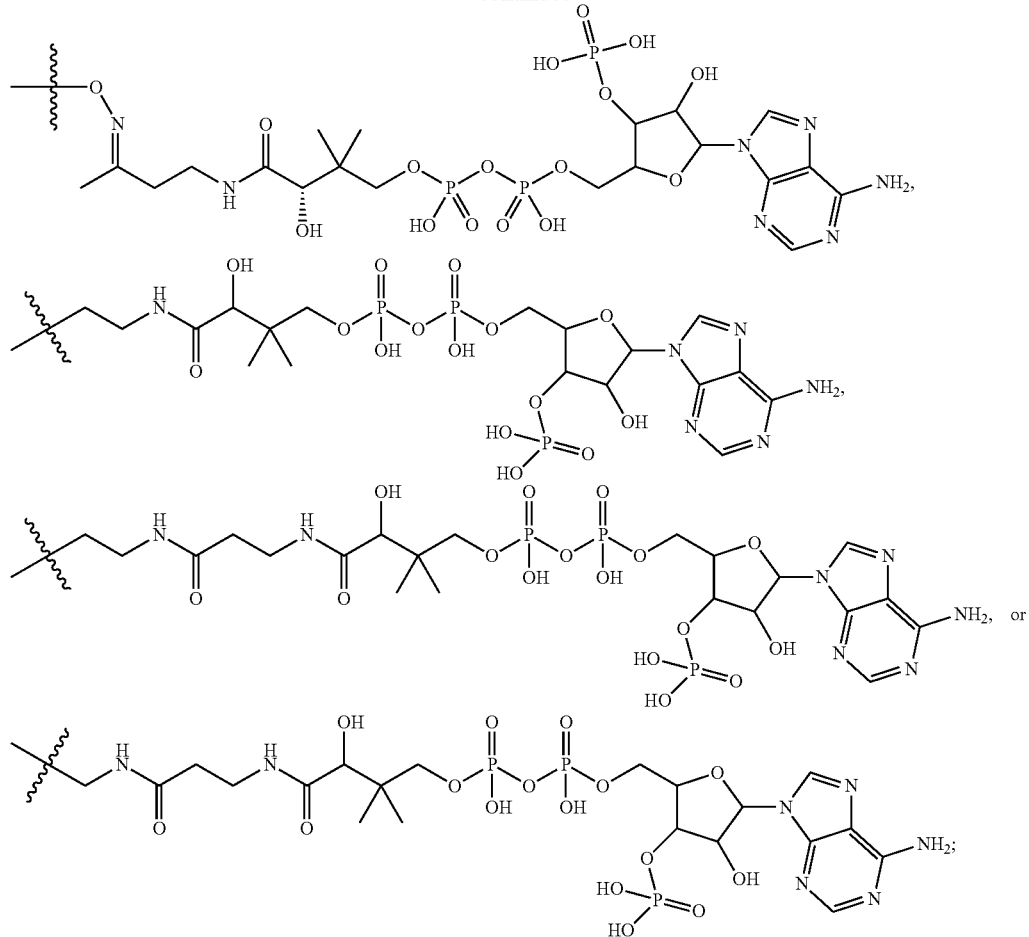
R⁵ is
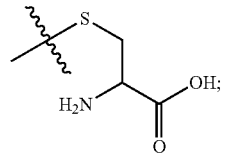 [SMILES: *SCC(N)C(=O)O]
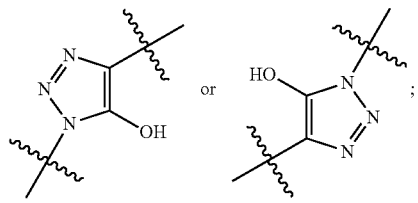
X₁ is
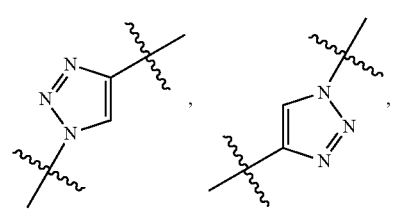
X₂ is
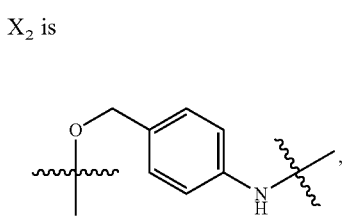

-continued

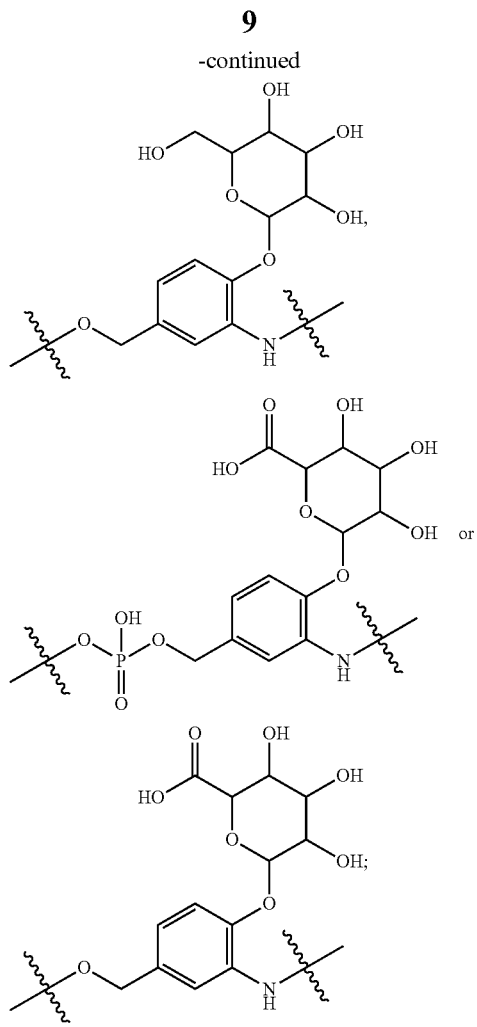

$X_3$ is

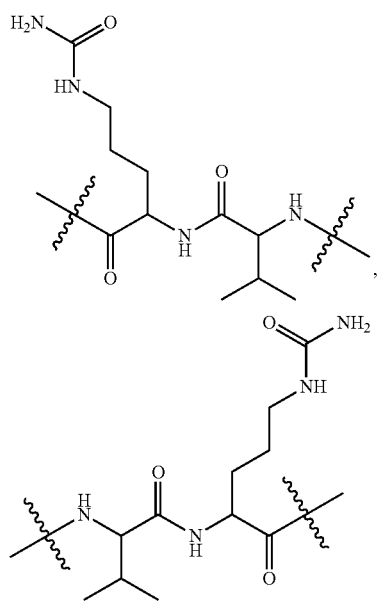

-continued

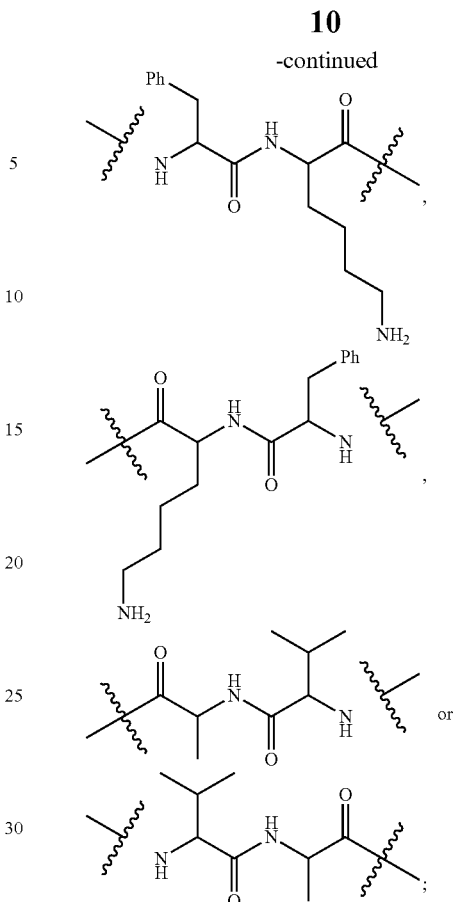

$R^6$ is 2-pyridyl or 4-pyridyl;
each $R^7$ is independently selected from H and $C_1$-$C_6$alkyl;
each $R^8$ is independently selected from H, $C_1$-$C_6$alkyl, F, Cl, and —OH;
each $R^9$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

In one aspect of the invention are compounds having the structure of Formula (I), and the pharmaceutically acceptable salts thereof, which are TLR7 agonists:

Formula (I)

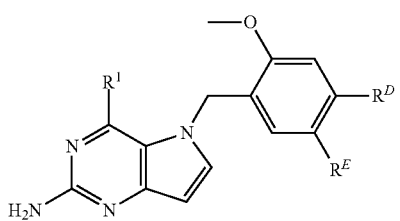

wherein:
R^D is

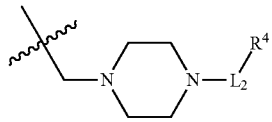

and R^E is H; or R^E is

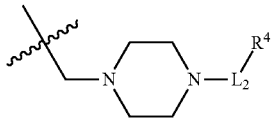

and R^D is H;
R^1 is —NHR^2 or —NHCHR^2R^3;
R^2 is —C_3-C_6alkyl or —C_4-C_6alkyl;
R^3 is L_1OH;
L_1 is —(CH_2)_m—;
L_2 is —(CH_2)_n—, —((CH_2)_nO)_t(CH_2)_n—, —(CH_2)_nX_1(CH_2)_n—, —(CH_2)_nNHC(=O)(CH_2)_n—, —(CH_2)_nNHC(=O)(CH_2)_nC(=O)NH(CH_2)_n—, —((CH_2)_nO)_t(CH_2)_nNHC(=O)(CH_2)_n—, —C(=O)(CH_2)_n—, —C(=O)((CH_2)_nO)_t(CH_2)_n—, —C(=O)((CH_2)_nO)_t(CH_2)_nX_1(CH_2)_n—, —C(=O)((CH_2)_nO)_t(CH_2)_nNHC(=O)(CH_2)_n—, —C(=O)((CH_2)_nO)_t(CH_2)_nC(=O)NH(CH_2)_n—, —C(=O)NH((CH_2)_nO)_t(CH_2)_nX_1(CH_2)_n—, —C(=O)X_2X_3C(=O)((CH_2)_nO)_t(CH_2)_n—, —C(=O)X_2C(=O)(CH_2)_nNHC(=O)(CH_2)_n—, or —C(=O)(CH_2)_nC(=O)NH(CH_2)_n;
R^4 is

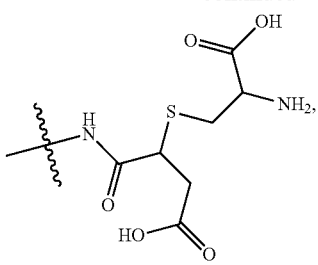

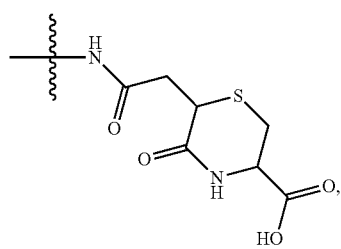

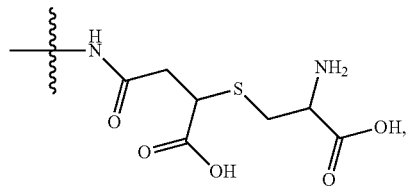

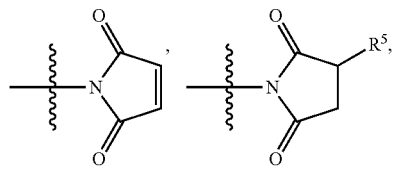

—ONH_2, —NH_2,

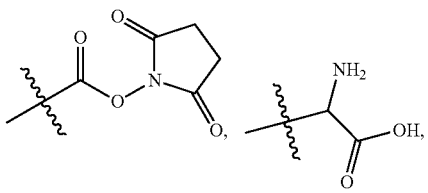

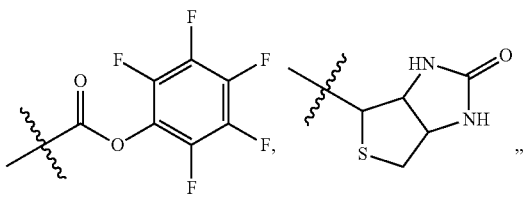

—N_3, 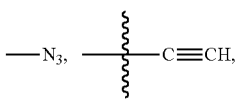

NHC(=O)CH=CH_2, SH, —SSR^6, —S(=O)_2(CH=CH_2), —(CH_2)_2S(=O)_2(CH=CH_2), —NHS(=O)_2(CH=CH_2), —NHC(=O)CH_2Br, —NHC(=O)CH_2I, —C(O)NHNH_2,

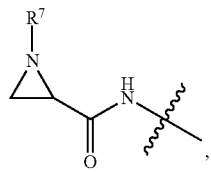

—CO_2H, —C(O)NHNH_2,

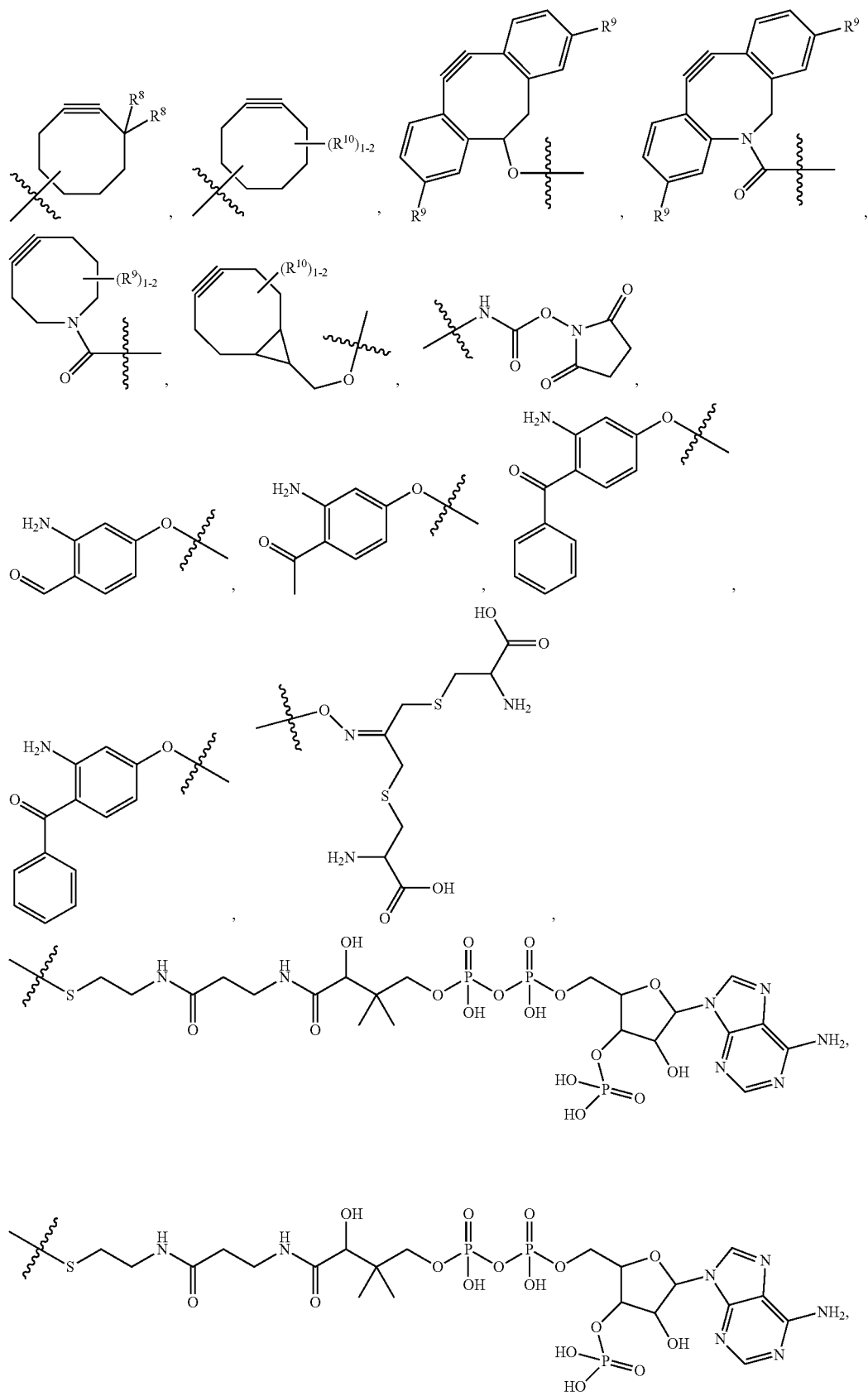

-continued
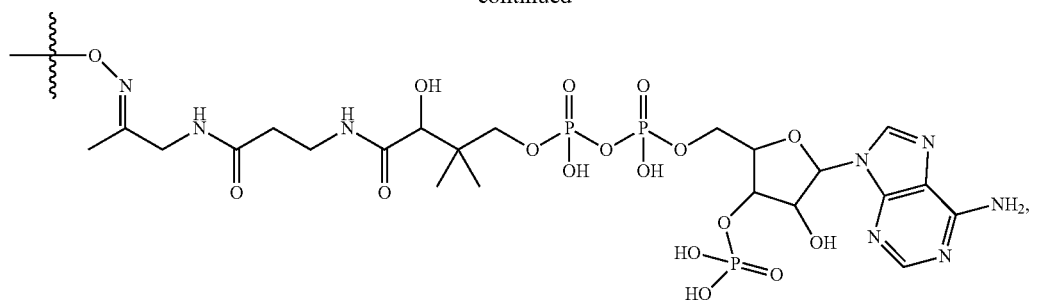
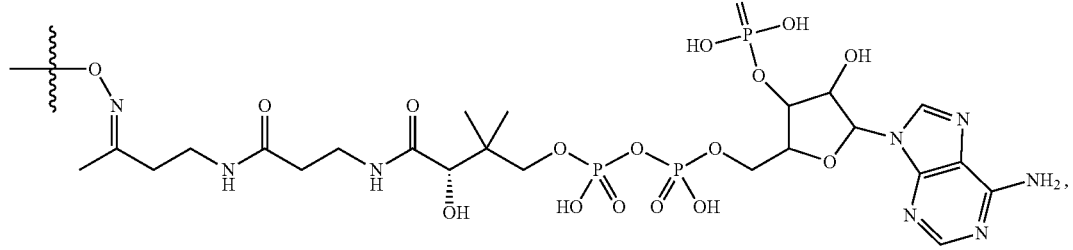
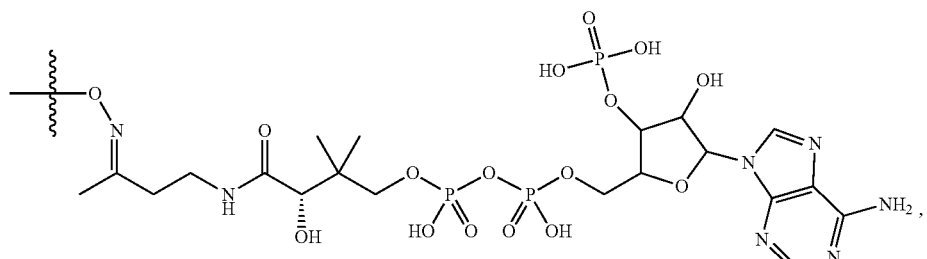
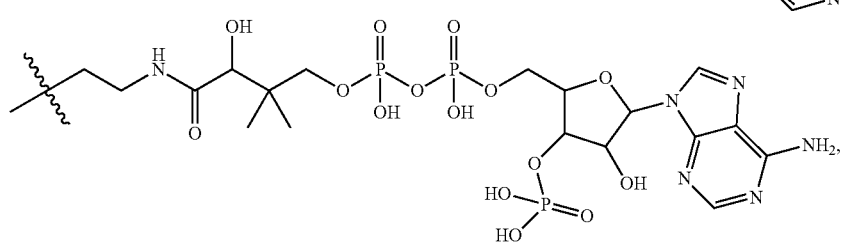
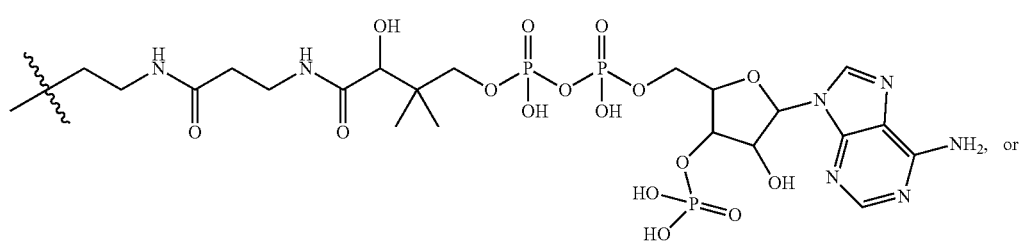
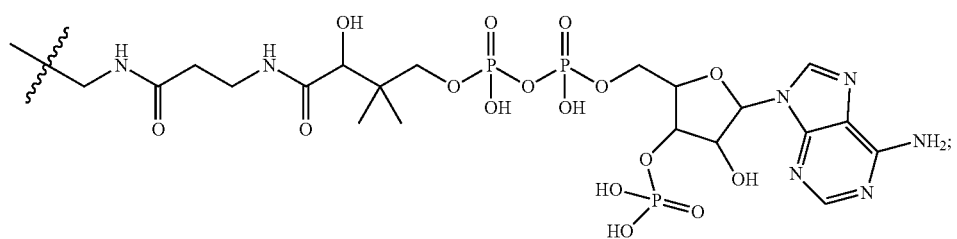

$R^5$ is

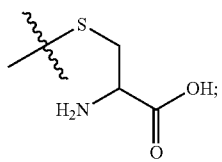 [SMILES: *SCC(N)C(=O)O]

$X_1$ is

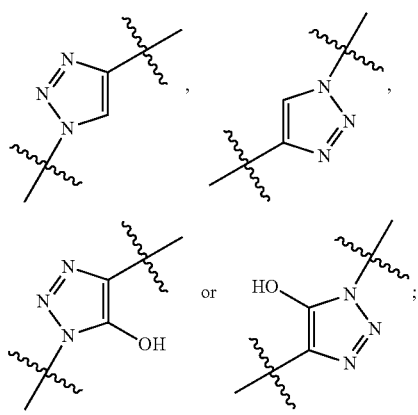

$X_2$ is

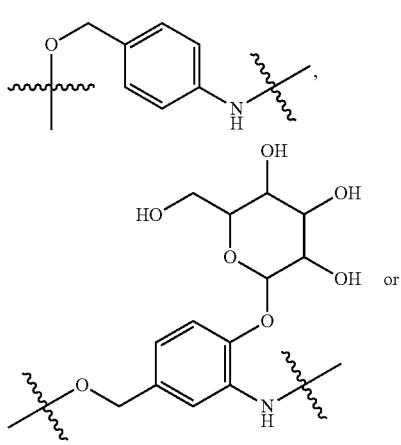

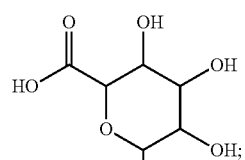

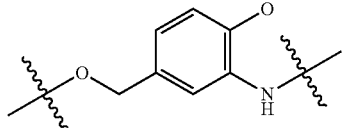

$X_3$ is

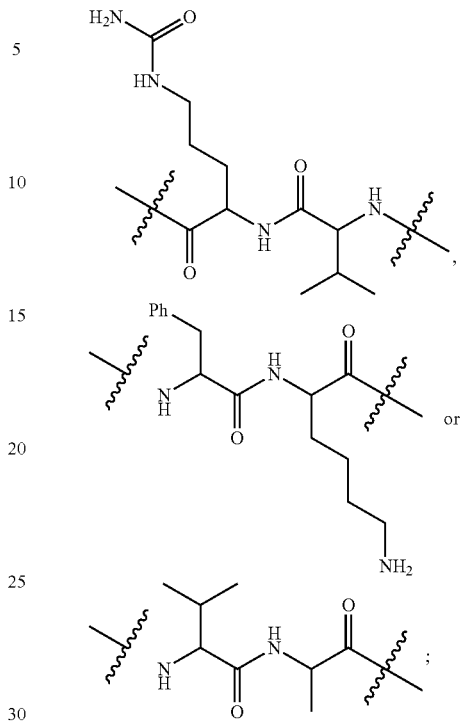

$R^6$ is 2-pyridyl or 4-pyridyl;

each $R^7$ is independently selected from H and $C_1$-$C_6$alkyl;

each $R^8$ is independently selected from H, $C_1$-$C_6$alkyl, F, Cl, and —OH;

each $R^9$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, and 4;

each n is independently selected from 1, 2, 3, and 4; and each t is independently selected from 1, 2, 3, 4, 5, 6, 7, 8, 9, 10, 11, 12, 13, 14, 15, 16, 17 and 18.

In one aspect of the invention are compounds of Formula (I) having the structure of Formula (Ia) or Formula (Ib), and the pharmaceutically acceptable salts thereof:

Formula (Ia)

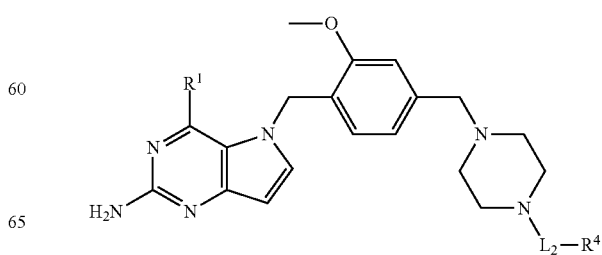

-continued

Formula (Ib)

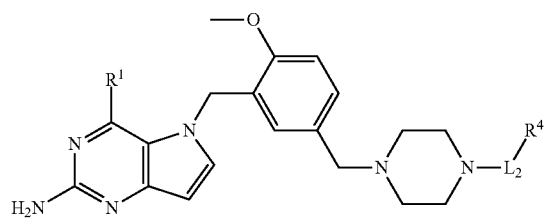

wherein:
R¹ is —NHR² or —NHCHR²R³;
R² is —C₃-C₆alkyl or —C₄-C₆alkyl;
R³ is L₁OH;
L₁ is —(CH₂)$_m$—;
L₂ is —(CH₂)$_n$—, —((CH₂)$_n$O)$_t$(CH₂)$_n$—, —(CH₂)$_n$X₁ (CH₂)$_n$—, —(CH₂)$_n$NHC(=O)(CH₂)$_n$—, —(CH₂)$_n$ NHC(=O)(CH₂)$_n$C(=O)NH(CH₂)$_n$—, —((CH₂)$_n$O)$_t$ (CH₂)$_n$NHC(=O)(CH₂)$_n$—, —C(=O)(CH₂)$_n$—, —C(=O)((CH₂)$_n$O)$_t$(CH₂)$_n$—, —C(=O)((CH₂)$_n$O)$_t$ (CH₂)$_n$X₁(CH₂)$_n$—, —C(=O)((CH₂)$_n$O)$_t$(CH₂)$_n$NHC (=O)(CH₂)$_n$—, —C(=O)((CH₂)$_n$O)$_t$(CH₂)$_n$C(=O) NH(CH₂)$_n$—, —C(=O)NH((CH₂)$_n$O)$_t$(CH₂)$_n$X₁ (CH₂)$_n$—, —C(=O)X₂X₃C(=O)((CH₂)$_n$O)$_t$ (CH₂)$_n$—, —C(=O)X₂X₃C(=O)(CH₂)$_n$—, —C(=O) X₂C(=O)(CH₂)$_n$NHC(=O)(CH₂)$_n$—, —C(=O)X₂C (=O)(CH₂)$_n$NHC(=O)((CH₂)$_n$O)$_t$(CH₂)$_n$—, —C(=O)(CH₂)$_n$C(R₇)₂—, —C(=O)(CH₂)$_n$C(R₇)₂SS (CH₂)$_n$NHC(=O)(CH₂)$_n$—, —(CH₂)$_n$X₂C(=O) (CH₂)$_n$NHC(=O)((CH₂)$_n$O)$_t$(CH₂)$_n$— or —C(=O) (CH₂)$_n$C(=O)NH(CH₂)$_n$;
R⁴ is

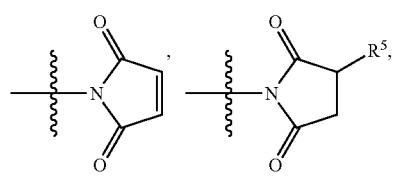

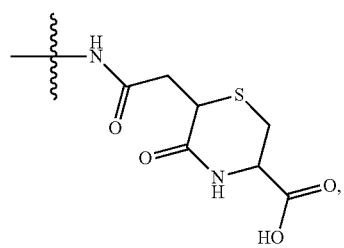

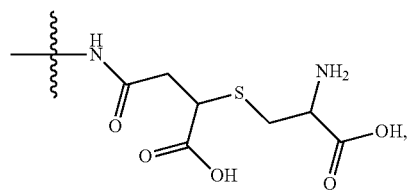

—ONH₂, —NH₂,

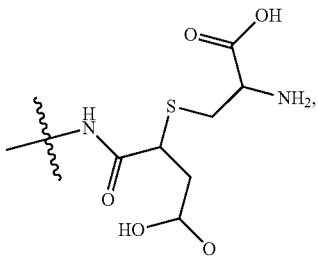

—NHC(=O)CH=CH₂, —N₃,

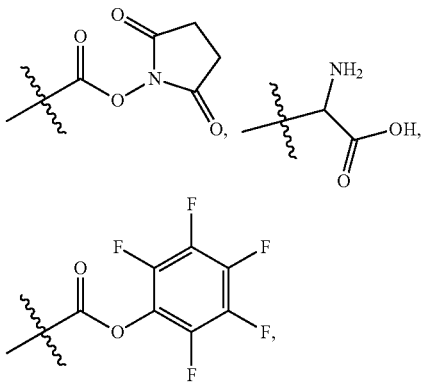

SH, —SR⁷, —OH, —SSR⁶, —S(=O)₂(CH=CH₂), —(CH₂)₂S(=O)₂(CH=CH₂), —NHS(=O)₂ (CH=CH₂), —NHC(=O)CH₂Br, —NHC(=O)CH₂I, —C(O)NHNH₂,

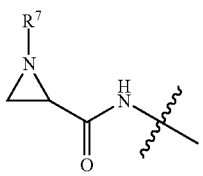

or —CO₂H;
R⁵ is

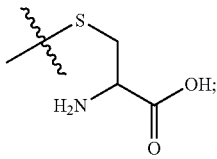 [SMILES: *SCC(N)C(=O)O]

$X_1$ is

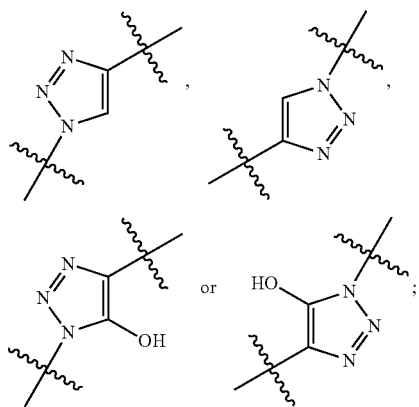

$X_2$ is

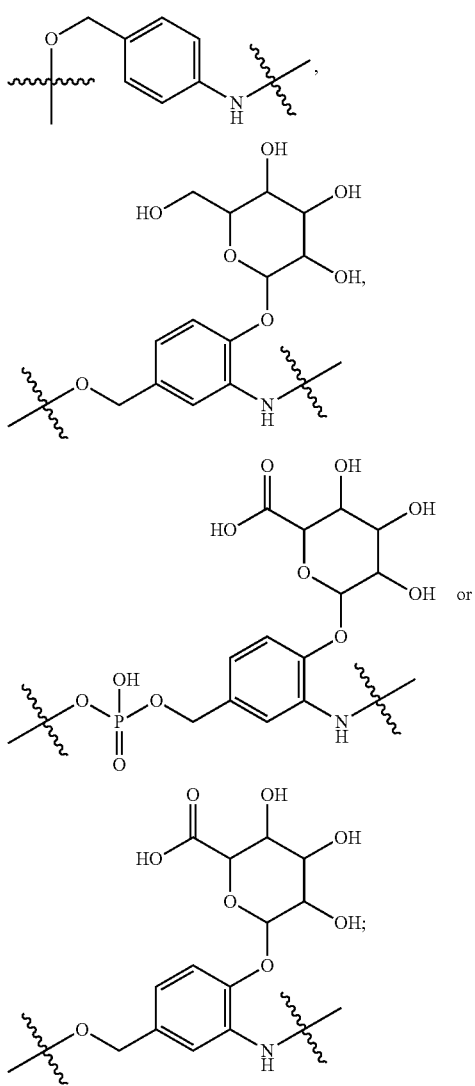

$X_3$ is

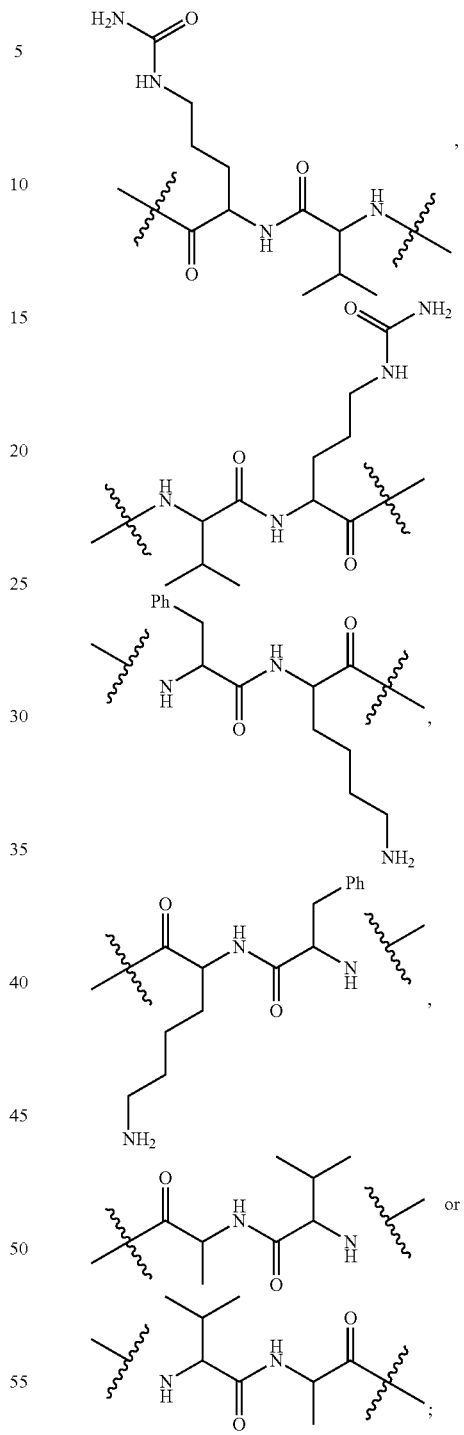

$R^6$ is 2-pyridyl or 4-pyridyl;

each $R^7$ is independently selected from H and $C_1$-$C_6$alkyl;

each m is independently selected from 1, 2, 3, and 4;

each n is independently selected from 1, 2, 3, and 4; and each t is independently selected from 1, 2, 3, 4, 5, 6, 7, 8, 9, 10, 11, 12, 13, 14, 15, 16, 17 and 18.

In one aspect of the invention are compounds of Formula (I) having the structure of Formula (Ia) or Formula (Ib), and the pharmaceutically acceptable salts thereof:

Formula (Ia)

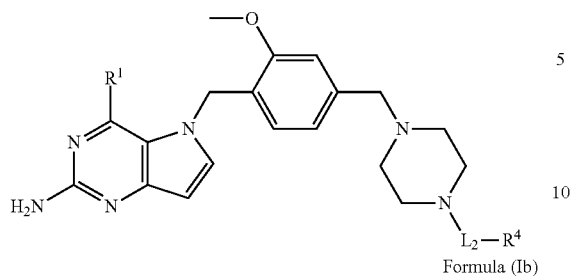

Formula (Ib)

wherein:

R[1] is —NHR[2] or —NHCHR[2]R[3];

R[2] is —C$_3$-C$_6$alkyl or —C$_4$-C$_6$alkyl;

R[3] is L$_1$OH;

L$_1$ is —(CH$_2$)$_m$—;

L$_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$—, —((CH$_2$)$_n$O)$_t$(CH$_2$)$_n$NHC(=O)(CH$_2$)$_n$, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$C(=O)(CH$_2$)$_n$NHC(=O)(CH$_2$)$_n$—, or —C(=O)(CH$_2$)$_n$C(=O)NH(CH$_2$)$_n$;

R[4] is

—ONH$_2$, —NH$_2$,

—NHC(=O)CH=CH$_2$, —N$_3$,

SH, —SSR[6], —S(=O)$_2$(CH=CH$_2$), —(CH$_2$)$_2$S(=O)$_2$(CH=CH$_2$), —NHS(=O)$_2$(CH=CH$_2$), —NHC(=O)CH$_2$Br, —NHC(=O)CH$_2$I, —C(O)NHNH$_2$, or —CO$_2$H;

R[5] is $X_1$ is

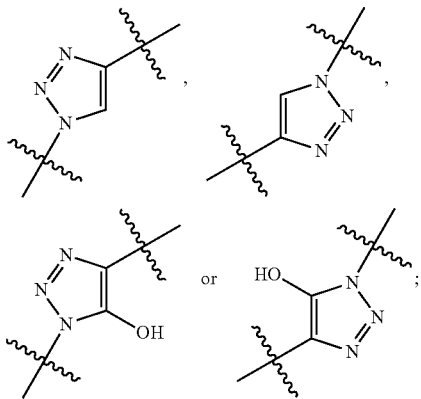

$X_2$ is

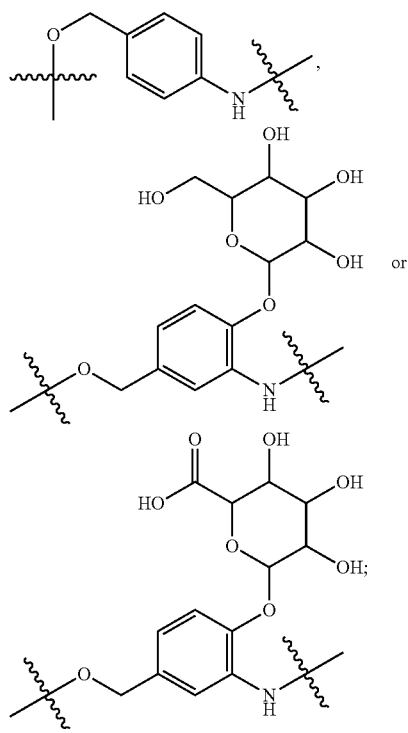

$X_3$ is

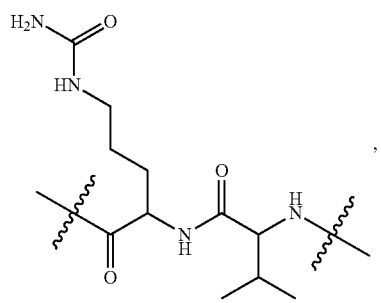

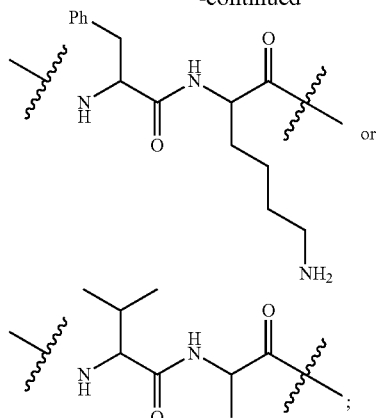

or

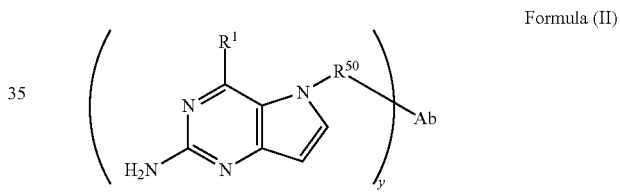

;

$R^6$ is 2-pyridyl or 4-pyridyl;
each $R^7$ is independently selected from H and $C_1$-$C_6$alkyl;
each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

Another aspect of the invention are antibody conjugates having the structure of Formula (II), and the pharmaceutically acceptable salts thereof:

Formula (II)

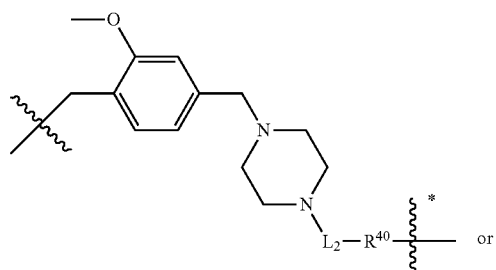

wherein:
$R^{50}$ is

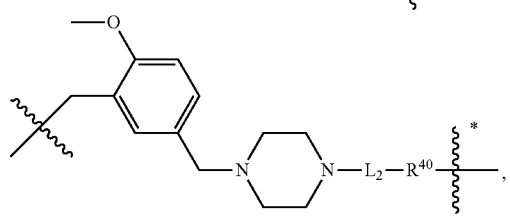

where the * indicates the point of attachment to Ab;
Ab is an antibody or antigen binding fragment thereof that specifically binds to human HER2;

$R^1$ is $-NHR^2$ or $-NHCHR^2R^3$;
$R^2$ is $-C_3-C_6$alkyl or $-C_4-C_6$alkyl;
$R^3$ is $L_1OH$;
$L_1$ is $-(CH_2)_m-$;
$L_2$ is $-(CH_2)_n-$, $-((CH_2)_nO)_t(CH_2)_n-$, $-(CH_2)_nX_1(CH_2)_n-$, $-(CH_2)_nNHC(=O)(CH_2)_n-$, $-(CH_2)_nNHC(=O)(CH_2)_nC(=O)NH(CH_2)_n-$, $-((CH_2)_nO)_t(CH_2)_nNHC(=O)(CH_2)_n-$, $-C(=O)(CH_2)_n-$, $-C(=O)((CH_2)_nO)_t(CH_2)_n-$, $-C(=O)((CH_2)_nO)_t(CH_2)_nX_1(CH_2)_n-$, $-C(=O)((CH_2)_nO)_t(CH_2)_nNHC(=O)(CH_2)_n-$, $-C(=O)((CH_2)_nO)_t(CH_2)_nC(=O)NH(CH_2)_n-$, $-C(=O)NH((CH_2)_nO)_t(CH_2)_nX_1(CH_2)_n-$, $-C(=O)X_2X_3C(=O)((CH_2)_nO)_t(CH_2)_n-$, $-C(=O)X_2X_3C(=O)(CH_2)_n-$, $-C(=O)X_2C(=O)(CH_2)_nNHC(=O)(CH_2)_n-$, $-C(=O)X_2C(=O)(CH_2)_nNHC(=O)((CH_2)_nO)_t(CH_2)_n-$, $-C(=O)(CH_2)_nC(R_7)_2-$, $-C(=O)(CH_2)_nC(R_7)_2SS(CH_2)_nNHC(=O)(CH_2)_n-$, $-(CH_2)_nX_2C(=O)(CH_2)_nNHC(=O)((CH_2)_nO)_t(CH_2)_n-$ or $-C(=O)(CH_2)_nC(=O)NH(CH_2)_n$;
$R^{40}$ is

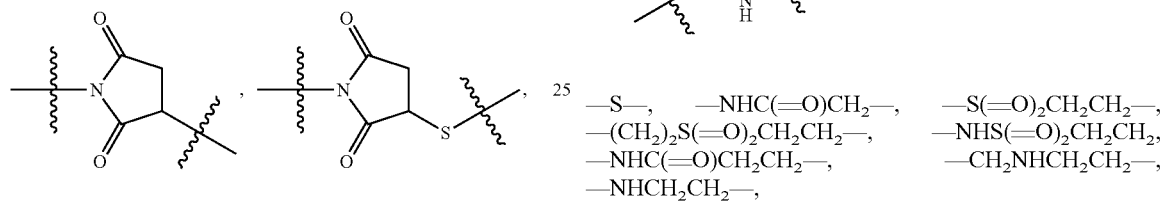

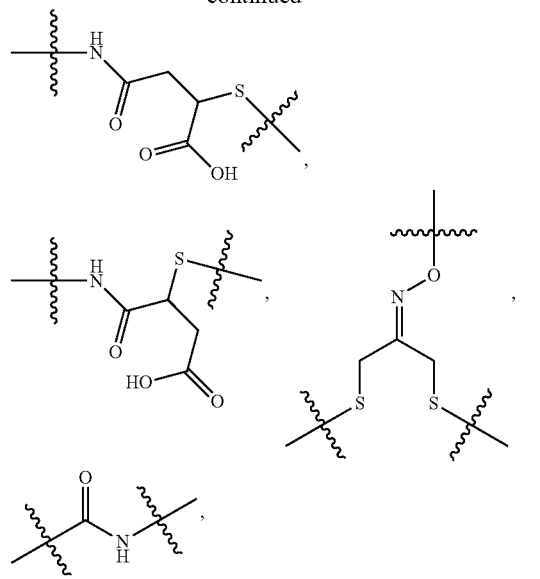

$-S-$, $-NHC(=O)CH_2-$, $-S(=O)_2CH_2CH_2-$,
$-(CH_2)_2S(=O)_2CH_2CH_2-$, $-NHS(=O)_2CH_2CH_2$,
$-NHC(=O)CH_2CH_2-$, $-CH_2NHCH_2CH_2-$,
$-NHCH_2CH_2-$,

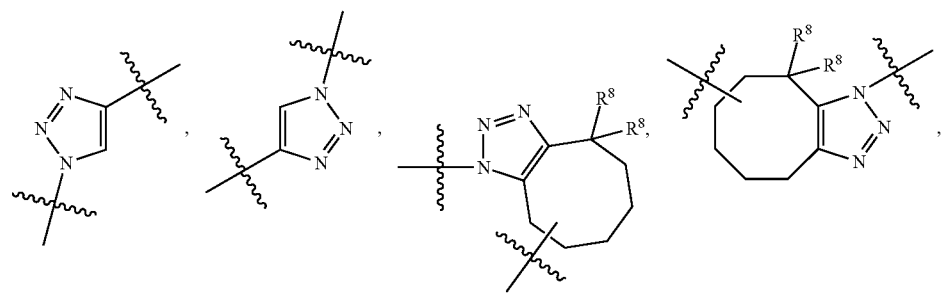

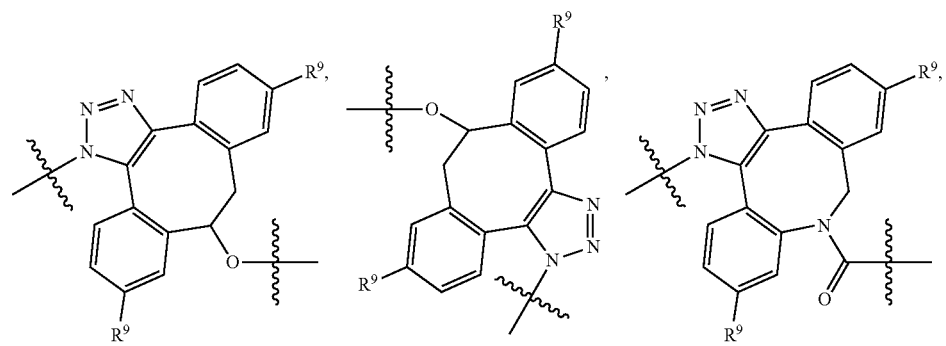

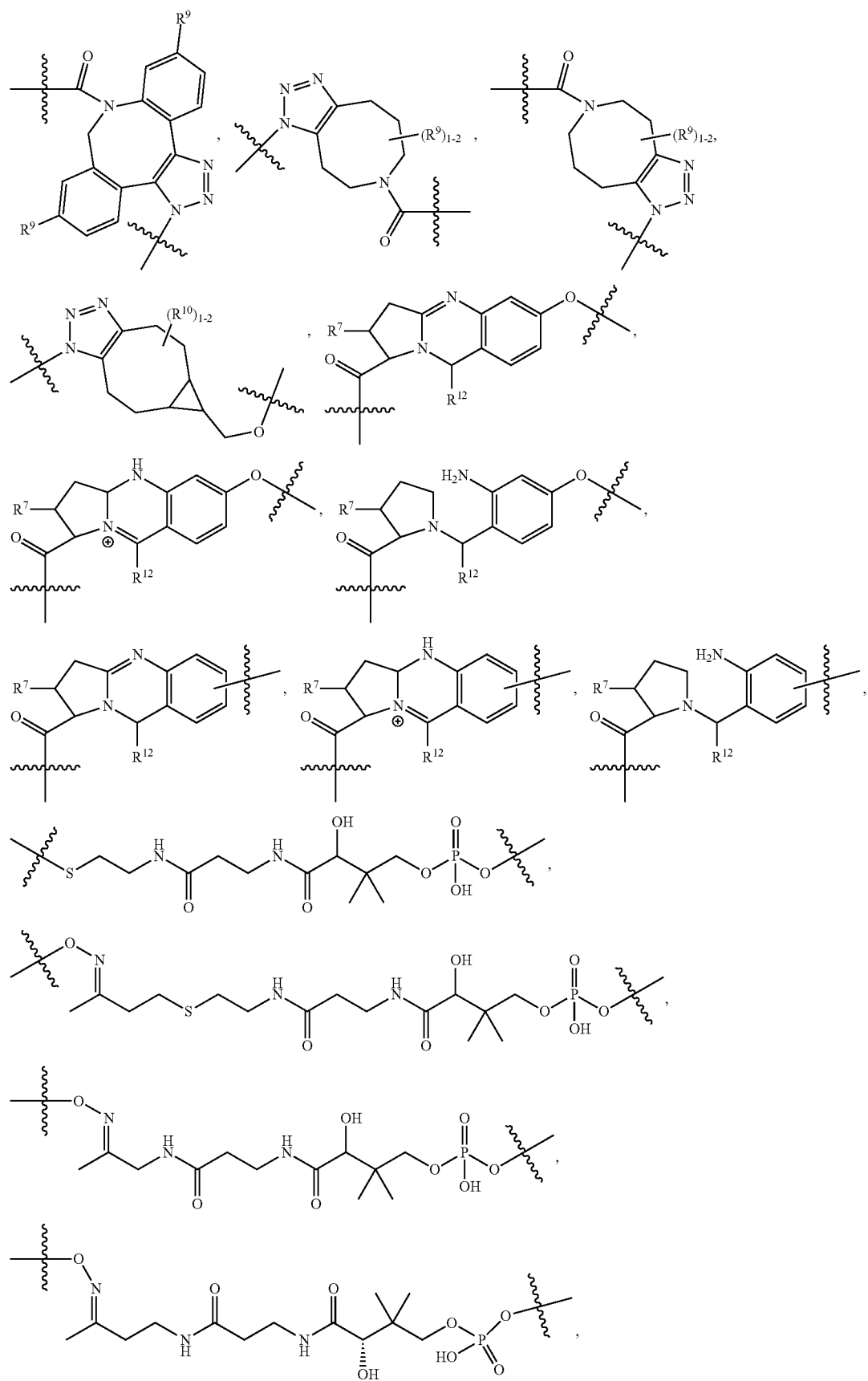

-continued
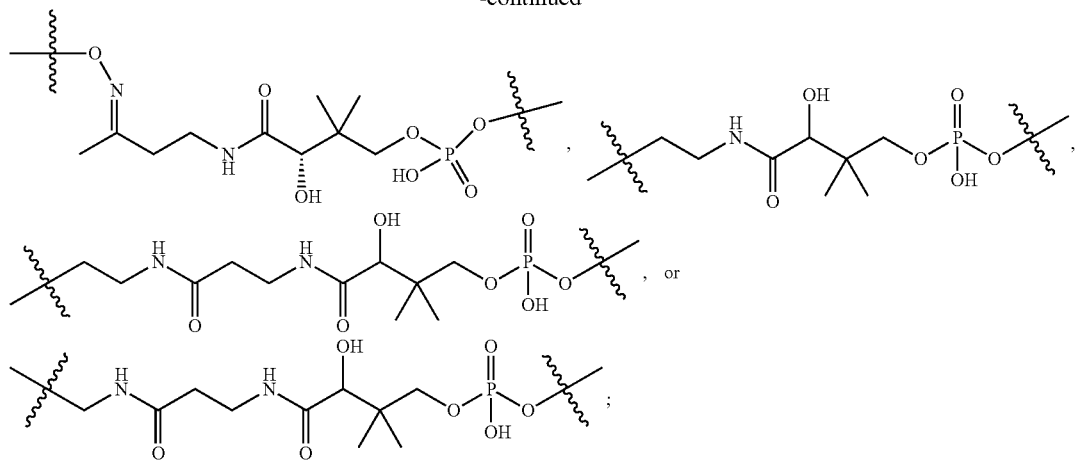
$X_1$ is
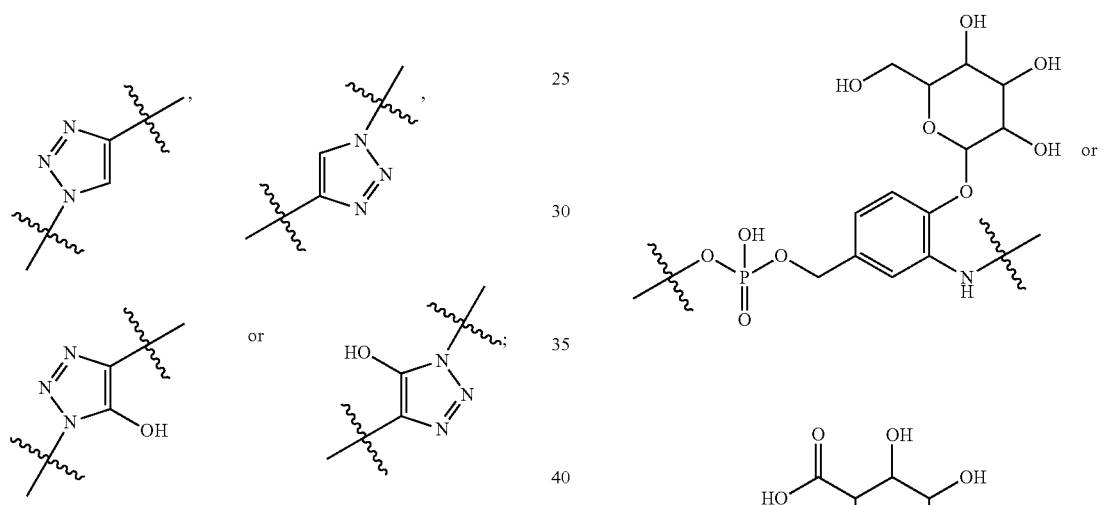
$X_2$ is
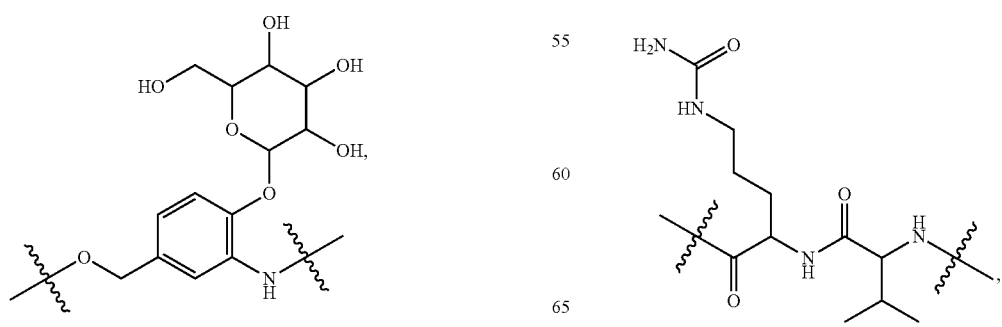
-continued
[structures continued]
$X_3$ is

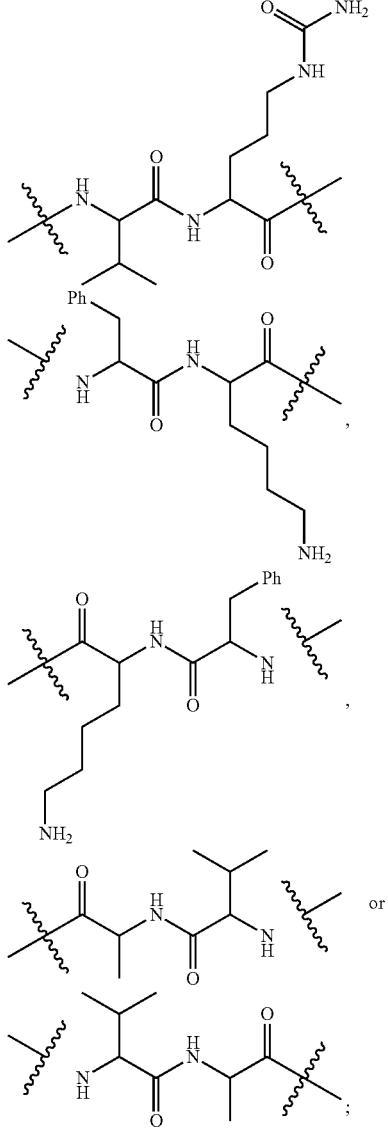

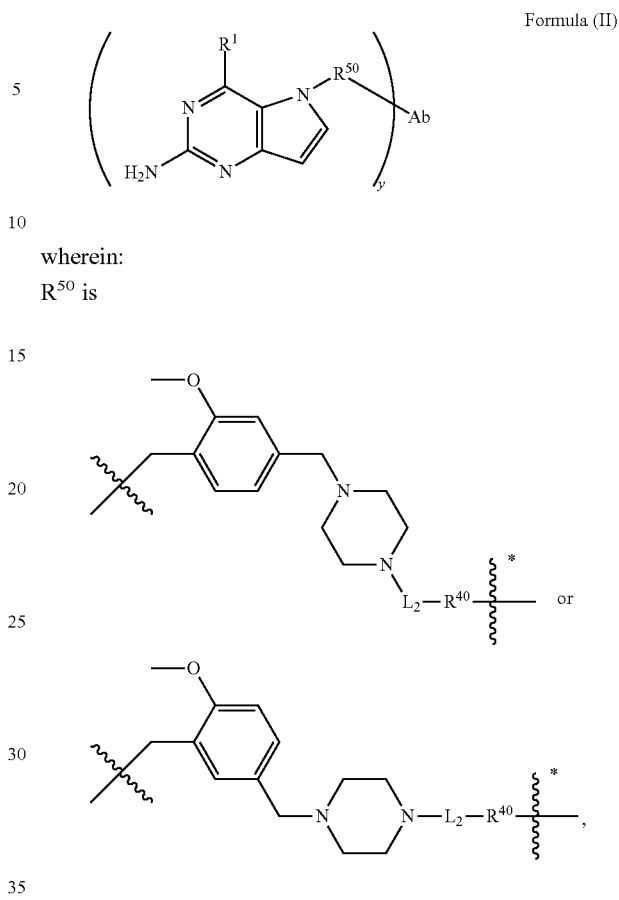

each R[7] is independently selected from H and $C_1$-$C_6$alkyl;

each R[8] is independently selected from H, $C_1$-$C_6$alkyl, F, Cl, and —OH;

each R[9] is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;

each R[10] is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

R[12] is H, methyl or phenyl;

each m is independently selected from 1, 2, 3, and 4;

each n is independently selected from 1, 2, 3, and 4;

each t is independently selected from 1, 2, 3, 4, 5, 6, 7, 8, 9, 10, 11, 12, 13, 14, 15, 16, 17 and 18, and y is an integer from 1 to 16.

Another aspect of the invention are antibody conjugates having the structure of Formula (II), and the pharmaceutically acceptable salts thereof:

where the * indicates the point of attachment to Ab;

Ab is an antibody or antigen binding fragment thereof that specifically binds to human HER2;

R[1] is —NHR[2] or —NHCHR[2]R[3];

R[2] is —$C_3$-$C_6$alkyl or —$C_4$-$C_6$alkyl;

R[3] is $L_1$OH;

$L_1$ is —(CH$_2$)$_m$—;

$L_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$—, —((CH$_2$)$_n$O)$_t$(CH$_2$)$_n$NHC(=O)(CH$_2$)$_n$, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$C(=O)(CH$_2$)$_n$NHC(=O)(CH$_2$)$_n$—, or —C(=O)(CH$_2$)$_n$C(=O)NH(CH$_2$)$_n$;

R[40] is

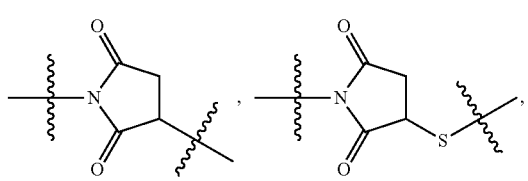

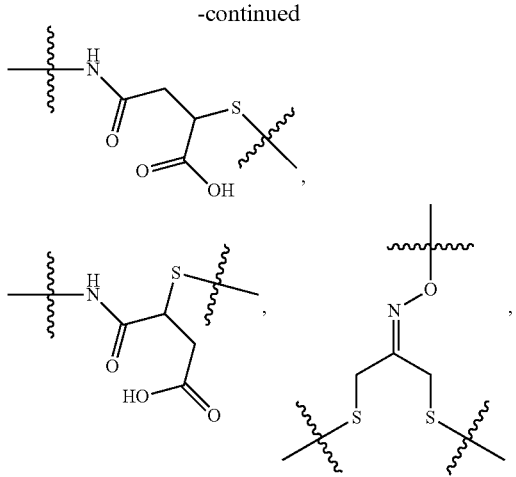
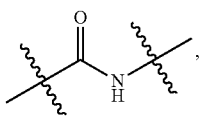
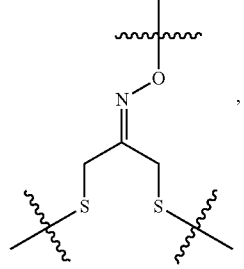
—S—, —NHC(=O)CH$_2$—, —S(=O)$_2$CH$_2$CH$_2$—,
—(CH$_2$)$_2$S(=O)$_2$CH$_2$CH$_2$—, —NHS(=O)$_2$CH$_2$CH$_2$,
—NHC(=O)CH$_2$CH$_2$—, —CH$_2$NHCH$_2$CH$_2$—,
—NHCH$_2$CH$_2$—,
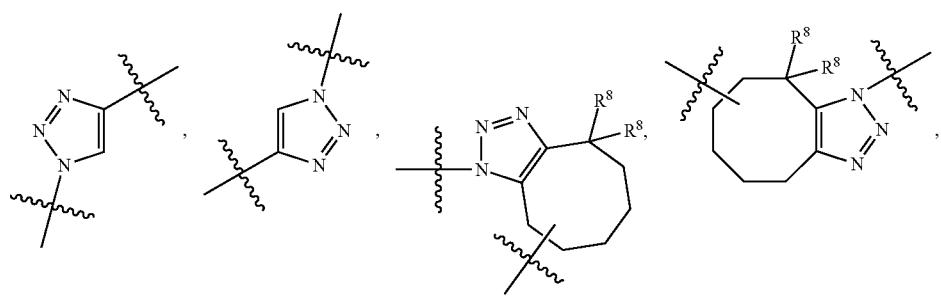
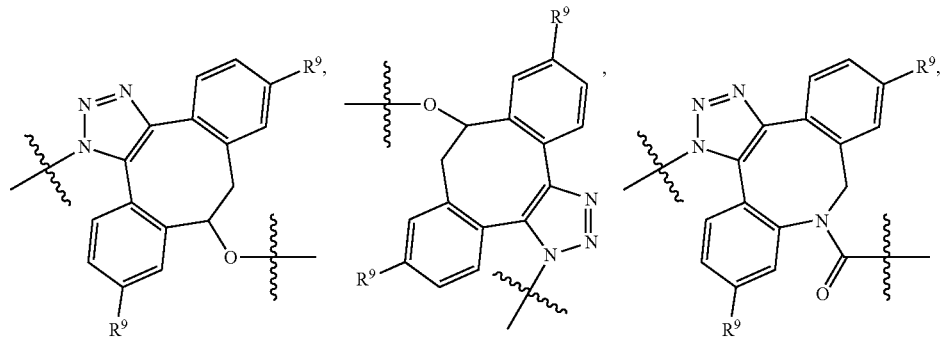
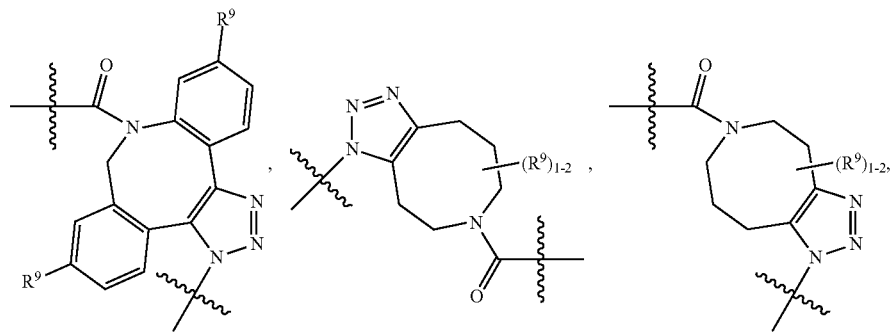
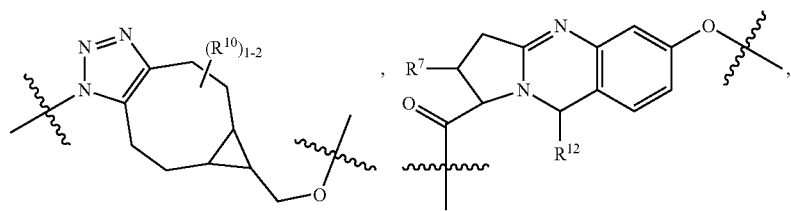

-continued
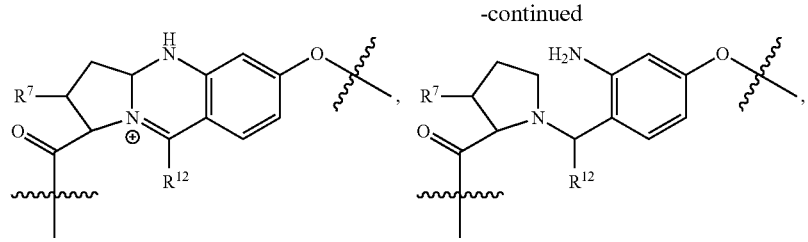
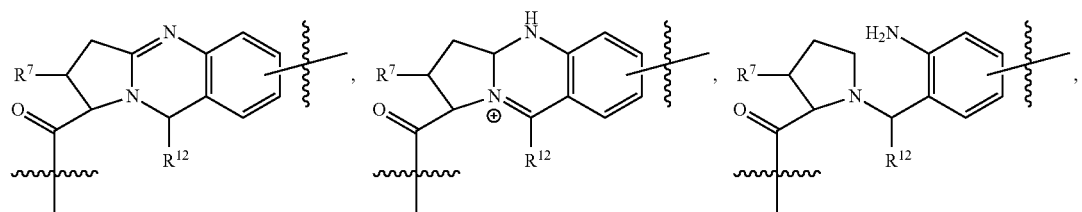
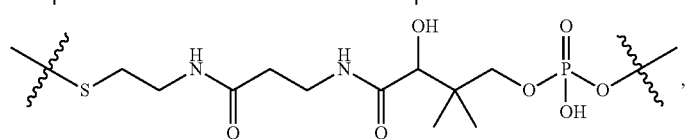
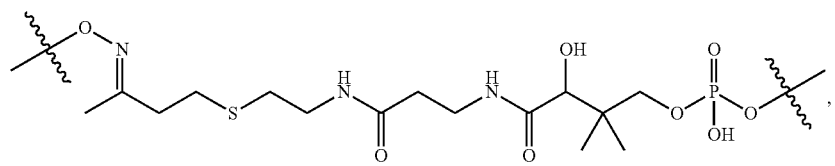
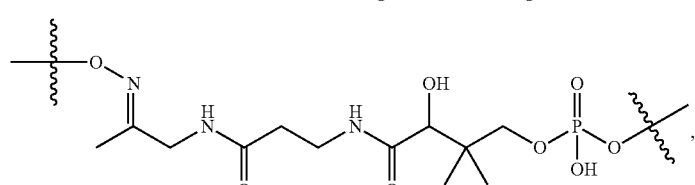
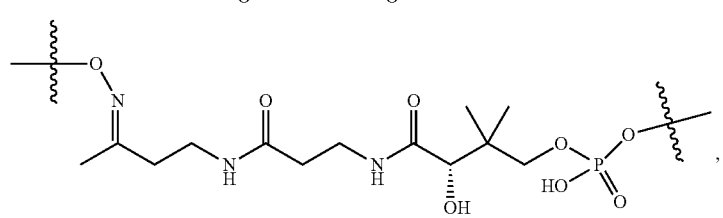
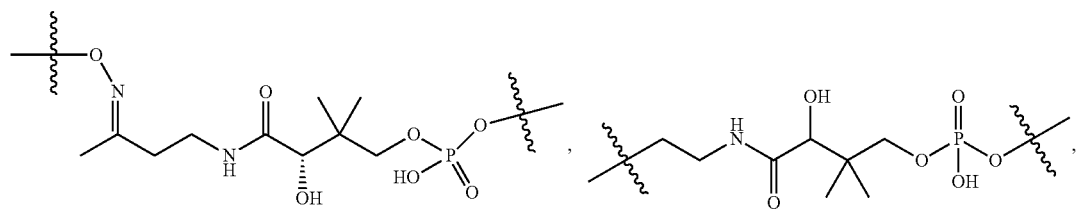
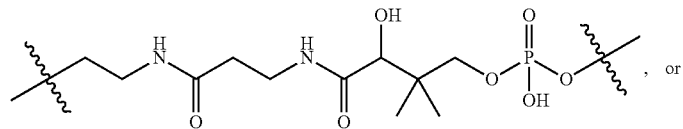, or
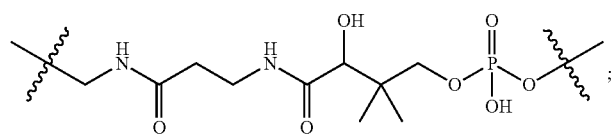;

$X_1$ is

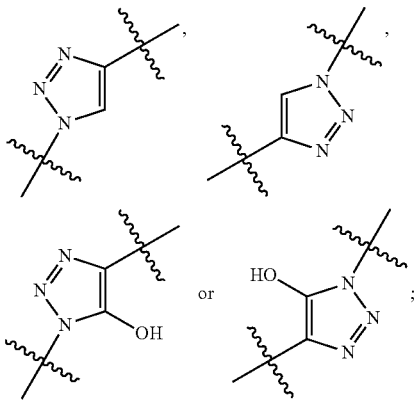

$X_2$ is

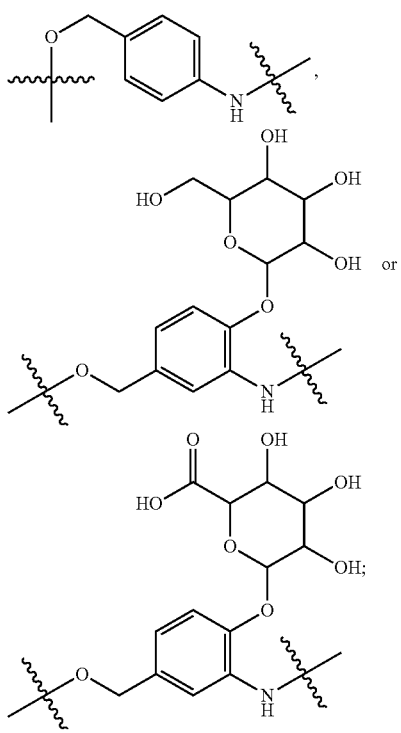

$X_3$ is

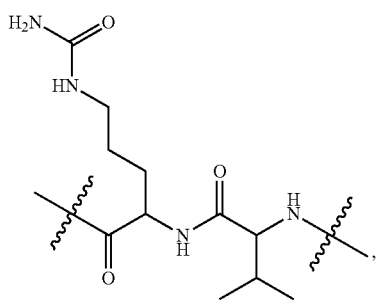

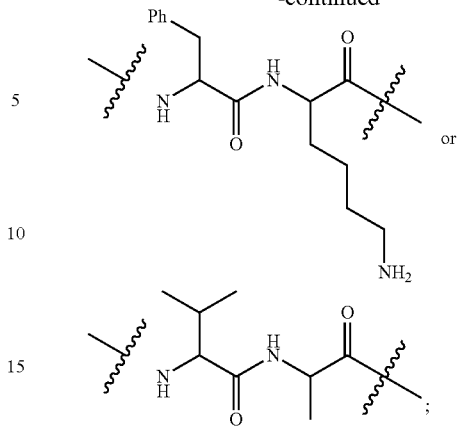

each $R^7$ is independently selected from H and $C_1$-$C_6$alkyl;
each $R^8$ is independently selected from H, $C_1$-$C_6$alkyl, F, Cl, and —OH;
each $R^9$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
$R^{12}$ is H, methyl or phenyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Another aspect of the invention are antibody conjugates of Formula (II) having the structure of Formula (IIa) or Formula (IIb), and the pharmaceutically acceptable salts thereof:

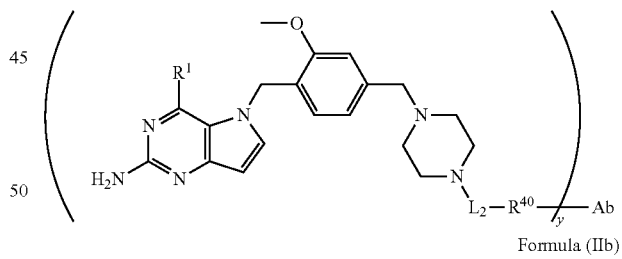
Formula (IIa)

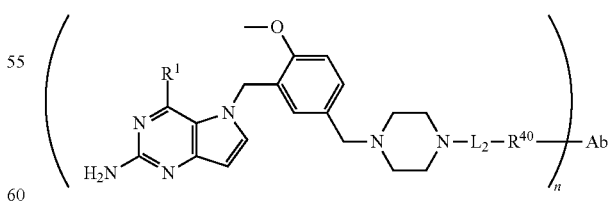
Formula (IIb)

wherein:
Ab is an antibody or antigen binding fragment thereof that specifically binds to human HER2;
$R^1$ is —NHR$^2$ or —NHCHR$^2$R$^3$;
$R^2$ is —C$_3$-C$_6$alkyl or —C$_4$-C$_6$alkyl;
$R^3$ is L$_1$OH;

$L_1$ is $-(CH_2)_m-$;

$L_2$ is $-(CH_2)_n-$, $-((CH_2)_nO)_t(CH_2)_n-$, $-(CH_2)_nX_1(CH_2)_n-$, $-(CH_2)_nNHC(=O)(CH_2)_n-$, $-(CH_2)_nNHC(=O)(CH_2)_nC(=O)NH(CH_2)_n-$, $-((CH_2)_nO)_t(CH_2)_nNHC(=O)(CH_2)_n-$, $-C(=O)(CH_2)_n-$, $-C(=O)((CH_2)_nO)_t(CH_2)_n-$, $-C(=O)((CH_2)_nO)_t(CH_2)_nX_1(CH_2)_n-$, $-C(=O)((CH_2)_nO)_t(CH_2)_nNHC(=O)(CH_2)_n-$, $-C(=O)((CH_2)_nO)_t(CH_2)_nC(=O)NH(CH_2)_n-$, $-C(=O)NH(CH_2)_nO)_t(CH_2)_nX_1(CH_2)_n-$, $-C(=O)X_2X_3C(=O)((CH_2)_nO)_t(CH_2)_n-$, $-C(=O)X_2X_3C(=O)(CH_2)_n-$, $-C(=O)X_2C(=O)(CH_2)_nNHC(=O)(CH_2)_n-$, $-C(=O)X_2C(=O)(CH_2)_nNHC(=O)((CH_2)_nO)_t(CH_2)_n-$, $-C(=O)(CH_2)_nC(R_7)_2-$, $-C(=O)(CH_2)_nC(R_7)_2SS(CH_2)_nNHC(=O)(CH_2)_n-$, $-(CH_2)_nX_2C(=O)(CH_2)_nNHC(=O)((CH_2)_nO)_t(CH_2)_n-$ or $-C(=O)(CH_2)_nC(=O)NH(CH_2)_n$;

$R^{40}$ is

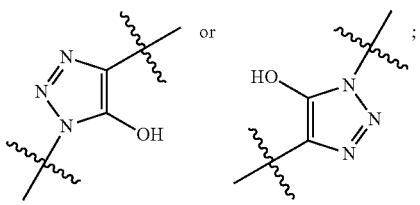

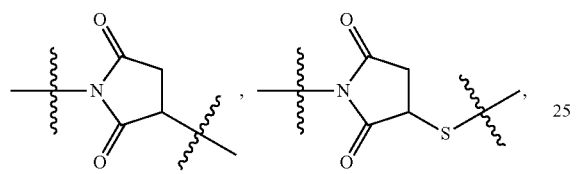,

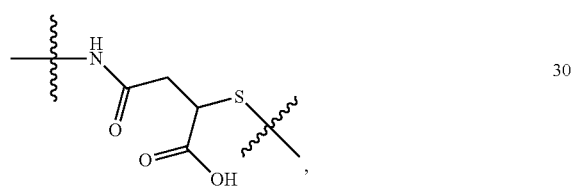,

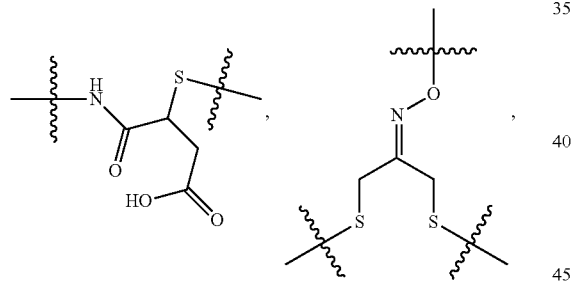,

or $-S-$;

$X_1$ is

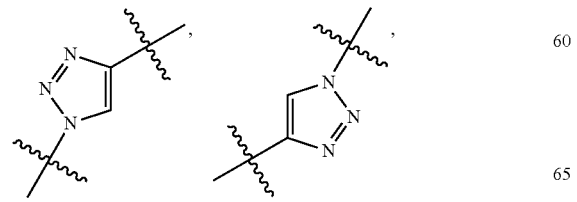,

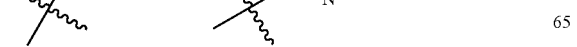

$X_2$ is

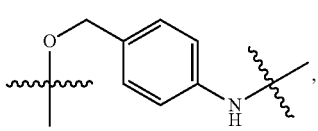,

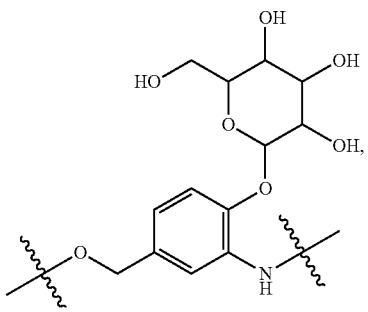

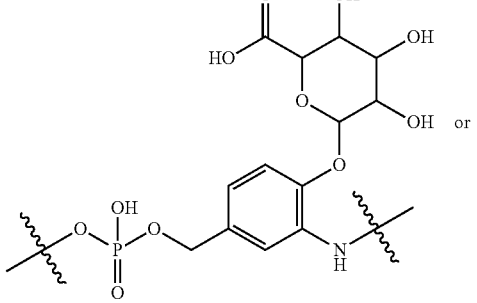

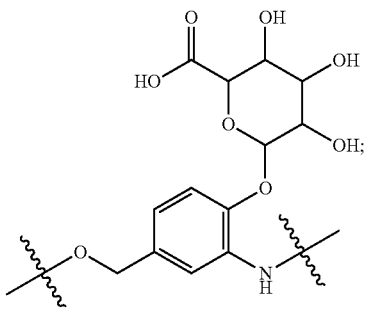

$X_3$ is

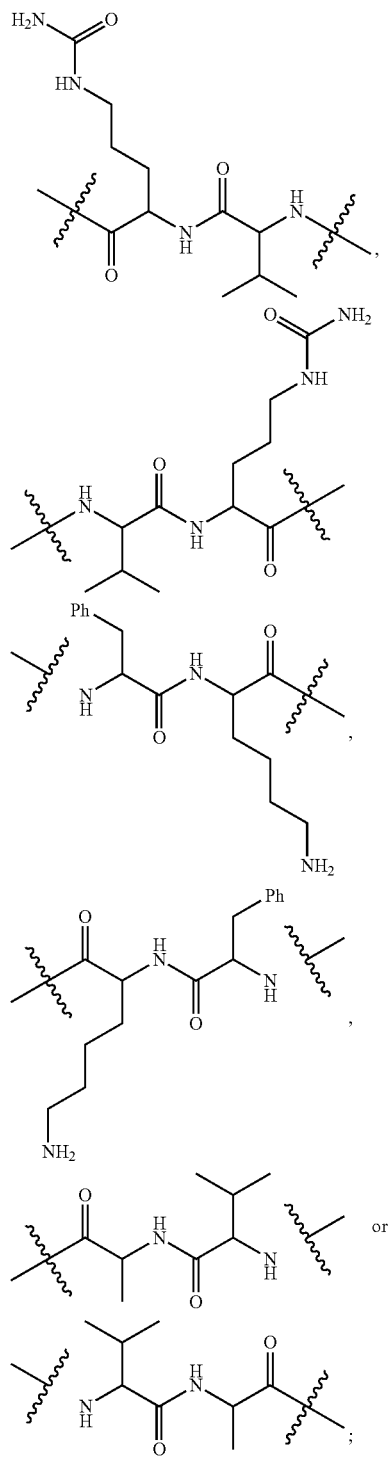

each $R^7$ is independently selected from H and $C_1$-$C_6$alkyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Another aspect of the invention are antibody conjugates of Formula (II) having the structure of Formula (IIa) or Formula (IIb), and the pharmaceutically acceptable salts thereof:

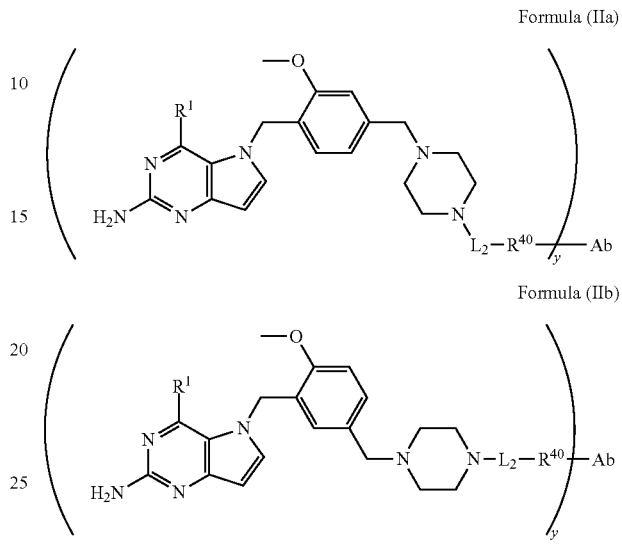

wherein:
Ab is an antibody or antigen binding fragment thereof that specifically binds to human HER2;
$R^1$ is —$NHR^2$ or —$NHCHR^2R^3$;
$R^2$ is —$C_3$-$C_6$alkyl or —$C_4$-$C_6$alkyl;
$R^3$ is $L_1OH$;
$L_1$ is —$(CH_2)_m$—;
$L_2$ is —$(CH_2)_n$—, —$((CH_2)_nO)_t(CH_2)_n$—, —$(CH_2)_nX_1$ $(CH_2)_n$—, —$(CH_2)_nNHC(=O)(CH_2)_n$—, —$(CH_2)_n$ $NHC(=O)(CH_2)_nC(=O)NH(CH_2)_n$—, —$((CH_2)_nO)_t$ $(CH_2)_nNHC(=O)(CH_2)_n$, —$C(=O)(CH_2)_n$—, —$C(=O)((CH_2)_nO)_t(CH_2)_n$—, —$C(=O)((CH_2)_nO)_t$ $(CH_2)_nX_1(CH_2)_n$—, —$C(=O)((CH_2)_nO)_t(CH_2)_nNHC$ $(=O)(CH_2)_n$—, —$C(=O)((CH_2)_nO)_t(CH_2)_nC(=O)$ $NH(CH_2)_n$—, —$C(=O)NH((CH_2)_nO)_t(CH_2)_nX_1$ $(CH_2)_n$—, —$C(=O)X_2X_3C(=O)((CH_2)_nO)_t$ $(CH_2)_n$—, —$C(=O)X_2C(=O)(CH_2)_nNHC(=O)$ $(CH_2)_n$—, or —$C(=O)(CH_2)_nC(=O)NH(CH_2)_n$;
$R^{40}$ is

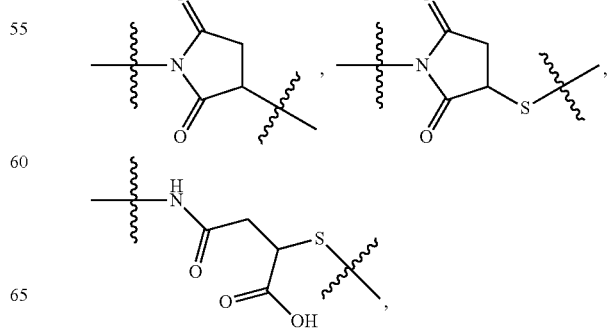

45

-continued

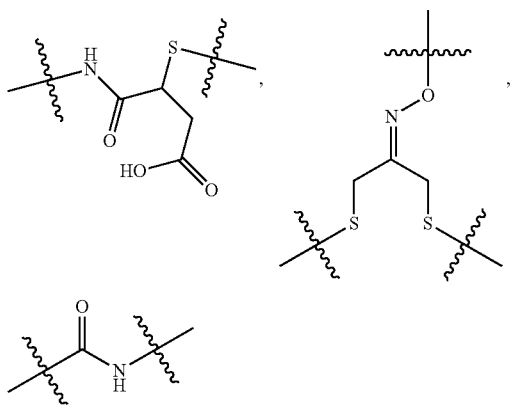

or —S—;

X₁ is

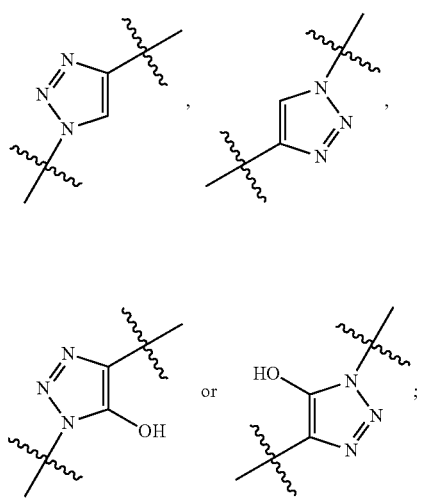

X₂ is

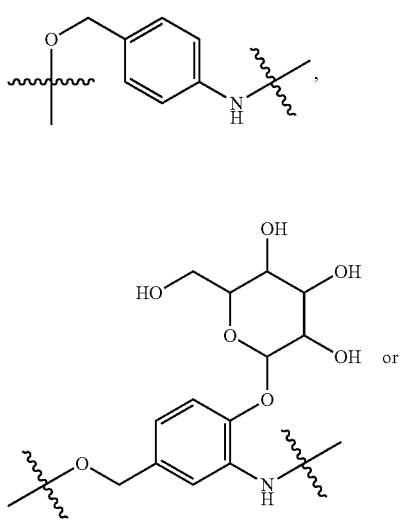

46

-continued

X₃ is each $R^7$ is independently selected from H and $C_1$-$C_6$alkyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Another aspect of the invention is a pharmaceutical composition that includes a therapeutically effective amount of an antibody conjugate of Formula (II), Formula (IIa) or Formula (IIb), or a pharmaceutically acceptable salt thereof, and a pharmaceutically acceptable carrier.

Another aspect of the invention is a method for treating a HER2-positive cancer, wherein the method comprises administering to a subject in need of such treatment an effective amount of antibody conjugate of Formula (II), Formula (IIa) or Formula (IIb), or pharmaceutically acceptable salt thereof. A HER2-positive cancer can be any of gastric cancer, esophageal cancer, gastroesophageal junction adenocarcinoma, colon cancer, rectal cancer, breast cancer, ovarian cancer, cervical cancer, uterine cancer, endometrial cancer, bladder cancer, urinary tract cancer, pancreatic cancer, lung cancer, prostate cancer, osteosarcoma, neuroblastoma, glioblastoma, and head and neck cancer. A HER2-positive cancer can have high HER2 expression (e.g., having 3+ IHC score), or low HER2 expression (e.g., having 2+ IHC score).

Another aspect of the invention is the use of an antibody conjugate of Formula (II), Formula (IIa) or Formula (IIb), or pharmaceutically acceptable salt thereof, in the manufacture of a medicament for treating a HER2-positive cancer.

Another aspect of the invention is an antibody conjugate for use in a method of medical treatment, wherein the method of medical treatment is for treating a HER2-positive cancer, and wherein the antibody conjugate is an antibody conjugate of Formula (II), Formula (IIa) or Formula (IIb), or pharmaceutically acceptable salt thereof. In addition, a further aspect of the invention is an antibody conjugate for use in a method of suppressing a HER2-positive cancer for a sustained period and/or reducing recurrence of a HER2-positive cancer, when compared to an anti-HER2 antibody alone.

The antibody conjugates described herein can be used to treat not only high HER2-expressing tumors (e.g., having 3+ IHC scores), but also lower HER2-expressing tumors (e.g., having 2+ IHC scores).

BRIEF DESCRIPTION OF THE DRAWINGS

FIG. 6 depicts results following treatment of human HCC1954 breast xenograft tumors with a single dose of anti-HER2-mAb1-(C-5). Regression of human HCC1954 xenograft tumors was observed after treatment with 10 mg/kg of anti-HER2-mAb1-(C-5) (filled square) or 3 mg/kg of anti-HER2-mAb1-(C-5) (filled circle), while treatment with 1 mg/kg of anti-HER2-mAb1-(C-5) (filled triangle) resulted in tumor stasis, when compared to untreated animals (open circle). Regression of tumors was not observed in the HCC1954 xenograft mice treated with 10 mg/kg of an isotype control antibody-(C-5) conjugate (open diamond) or unconjugated anti-HER2-mAb1 alone (open triangle) when compared to untreated animals (open circle). Data represent mean tumor volumes (mean+/−SEM) over time (post-dose).

DETAILED DESCRIPTION OF THE INVENTION

Figure 1:
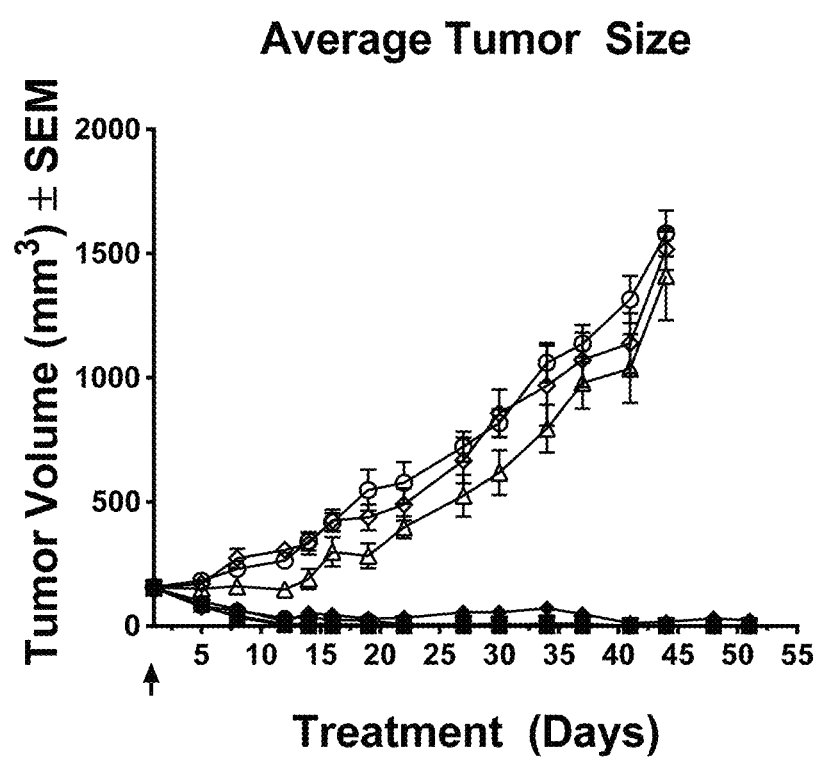
FIG. 1 depicts results following a single treatment of anti-HER2-mAb2-(C-1) conjugate in the N87 xenograft tumor model. Regression of tumor was observed for all doses tested, including 1 mg/kg (filled diamond), 2.5 mg/kg (filled triangle), 5 mg/kg (filled circle), and 10 mg/kg (filled square) when compared to untreated animals (open circle). Regression of N87 gastric tumors was not observed in the N87 xenograft mice treated with 10 mg/kg of unconjugated anti-HER2-mAb2 alone (open triangle), or an isotype control antibody-(C-1) conjugate (open diamond) when compared to untreated animals (open circle). Data represent mean tumor volumes (mean+/−SEM) over time (post-dose).

Various enumerated embodiments of the invention are described herein. It will be recognized that features specified in each embodiment may be combined with other specified features to provide further embodiments of the present invention.

Throughout the text of this application, should there be a discrepancy between the text of the specification (e.g., Table 1) and the sequence listing, the text of the specification shall prevail.

Definitions

The term "$C_4$-$C_6$alkyl", as used herein, refers to a fully saturated branched or straight chain hydrocarbon containing 4 to 6 carbon atoms. Non-limiting examples of ""C$_4$-C$_6$alkyl" groups include n-butyl, isobutyl, sec-butyl, tert-butyl, n-pentyl, isopentyl and hexyl.

As used herein, "HER2" (also known as ERBB2; NEU; NGL; TKR1; CD340; p185; MLN19; HER-2/neu) refers to a transmembrane tyrosine kinase receptor of the epidermal growth factor (EGF) receptor family. HER2 comprises an extracellular binding domain, a transmembrane domain, and an intracellular tyrosine kinase domain. HER2 does not have a ligand binding domain of its own and therefore cannot bind growth factors, however, HER2 binds tightly to other ligand-bound EGF receptor family members such as HER1 or HER3, to form a heterodimer, stabilizing ligand binding and enhancing kinase-mediated activation of downstream signalling pathways. The human HER2/NEU gene is mapped to chromosomal location 17q12, and the genomic sequence of HER2/NEU gene can be found in GenBank at NG_007503.1. In human, there are five HER2 isoforms: A, B, C, D, and E; the term "HER2" is used herein to refer collectively to all HER2 isoforms. As used herein, a human HER2 protein also encompasses proteins that have over its full length at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with HER2 isoforms: A, B, C, D, and E, wherein such proteins still have at least one of the functions of HER2. The mRNA and protein sequences for human HER2 isoform A, the longest isoform, are:

```
Homo sapiens erb-b2 receptor tyrosine kinase 2 (ERBB2),
transcript variant 1, mRNA [NM_004448.3]
                                                     (SEQ ID NO: 25)
   1  gcttgctccc aatcacagga gaaggaggag gtggaggagg agggctgctt gaggaagtat 61  aagaatgaag ttgtgaagct gagattcccc tccattggga ccggagaaac caggggagcc 121  ccccgggcag ccgcgcgccc cttcccacgg ggcccttttac tgcgccgcgc gcccggcccc 181  caccccctcgc agcaccccgc gccccgcgcc ctcccagccg ggtccagccg gagccatggg 241  gccggagccg cagtgagcac catggagctg gcggccttgt gccgctgggg gctcctcctc 301  gccctcttgc cccccggagc cgcgagcacc caagtgtgca ccggcacaga catgaagctg 361  cggctccctg ccagtcccga gacccacctg gacatgctcc gccacctcta ccagggctgc 421  caggtggtgc agggaaacct ggaactcacc tacctgccca ccaatgccag cctgtccttc 481  ctgcaggata tccaggaggt gcagggctac gtgctcatcg ctcacaacca agtgaggcag 541  gtcccactgc agaggctgcg gattgtgcga ggcacccagc tctttgagga caactatgcc 601  ctggccgtgc tagacaatgg agacccgctg aacaatacca cccctgtcac aggggcctcc 661  ccaggaggcc tgcgggagct gcagcttcga agcctcacag agatcttgaa aggaggggtc 721  ttgatccagc ggaaccccca gctctgctac caggacacga ttttgtggaa ggacatcttc 781  cacaagaaca accagctggc tctcacactg atagacacca accgctctcg ggcctgccac 841  ccctgttctc cgatgtgtaa gggctcccgc tgctggggag agagttctga ggattgtcag 901  agcctgacgc gcactgtctg tgccggtggc tgtgcccgct gcaaggggcc actgcccact 961  gactgctgcc atgagcagtg tgctgccggc tgcacgggcc ccaagcactc tgactgcctg 1021  gcctgcctcc acttcaacca cagtggcatc tgtgagctgc actgcccagc cctggtcacc 1081  tacaacacag acacgtttga gtccatgccc aatcccgagg gccggtatac attcggcgcc 1141  agctgtgtga ctgcctgtcc ctacaactac ctttctacgg acgtgggatc ctgcaccctc 1201  gtctgccccc tgcacaacca agaggtgaca gcagaggatg gaacacagcg tgtgtgagaag 1261  tgcagcaagc cctgtgcccg agtgtgctat ggtctgggca tggagcactt gcgagaggtg 1321  agggcagtta ccagtgccaa tatccaggag tttctggct gcaagaagat ctttgggagc 1381  ctggcatttc tgccggagag ctttgatggg gacccagcct ccaacactgc cccgctccag 1441  ccagagcagc tccaagtgtt tgagactctg gaagagatca caggttacct atacatctca 1501  gcatggccgg acagcctgcc tgacctcagc gtcttccaga acctgcaagt aatccgggga 1561  cgaattctgc acaatggcgc ctactcgctg accctgcaag ggctgggcat cagctggctg 1621  gggctgcgct cactgaggga actgggcagt ggactggccc tcatccacca taacacccac 1681  ctctgcttcg tgcacacggt gcctggggac cagctctttc ggaacccgca ccaagctctg 1741  ctccacactg ccaaccggcc agaggacgag tgtgtgggcg agggcctggc ctgccaccag
```

-continued

```
1801  ctgtgcgccc gagggcactg ctggggtcca gggcccaccc agtgtgtcaa ctgcagccag
1861  ttccttcggg gccaggagtg cgtggaggaa tgccgagtac tgcaggggct ccccagggag
1921  tatgtgaatg ccaggcactg tttgccgtgc caccctgagt gtcagcccca gaatggctca
1981  gtgacctgtt ttggaccgga ggctgaccag tgtgtggcct gtgcccacta taaggaccct
2041  cccttctgcg tggcccgctg ccccagcggt gtgaaacctg acctctccta catgcccatc
2101  tggaagtttc cagatgagga gggcgcatgc cagccttgcc ccatcaactg cacccactcc
2161  tgtgtggacc tggatgacaa gggctgcccc gccgagcaga gagccagccc tctgacgtcc
2221  atcatctctg cggtggttgg cattctgctg gtcgtggtct tgggggtggt ctttgggatc
2281  ctcatcaagc gacggcagca aagatccgg aagtacacga tgcggagact gctgcaggaa
2341  acggagctgg tggagccgct gacacctagc ggagcgatgc caaccaggc gcagatgcgg
2401  atcctgaaag agacggagct gaggaaggtg aaggtgcttg gatctggcgc ttttggcaca
2461  gtctacaagg gcatctggat ccctgatggg gagaatgtga aaattccagt ggccatcaaa
2521  gtgttgaggg aaaacacatc ccccaaagcc aacaaagaaa tcttagacga agcatacgtg
2581  atggctggtg tgggctcccc atatgtctcc cgccttctgg gcatctgcct gacatccacg
2641  gtgcagctgg tgacacagct tatgcccat ggctgcctct tagaccatgt ccgggaaaac
2701  cgcggacgcc tgggctccca ggacctgctg aactggtgta tgcagattgc caaggggatg
2761  agctacctgg aggatgtgcg gctcgtacac agggacttgg ccgctcggaa cgtgctggtc
2821  aagagtccca accatgtcaa aattacagac ttcgggctgg ctcggctgct ggacattgac
2881  gagacagagt accatgcaga tgggggcaag gtgcccatca gtggatggc gctggagtcc
2941  attctccgcc ggcggttcac ccaccagagt gatgtgtgga gttatggtgt gactgtgtgg
3001  gagctgatga cttttgggc caaaccttac gatgggatcc cagcccggga gatccctgac
3061  ctgctggaaa aggggagcg gctgccccag ccccccatct gcaccattga tgtctacatg
3121  atcatggtca aatgttggat gattgactct gaatgtcggc caagattccg ggagttggtg
3181  tctgaattct cccgcatggc cagggacccc cagcgctttg tggtcatcca gaatgaggac
3241  ttgggcccag ccagtccctt ggacagcacc ttctaccgct cactgctgga ggacgatgac
3301  atgggggacc tggtggatgc tgaggagtat ctggtacccc agcagggctt cttctgtcca
3361  gaccctgccc cgggcgctgg ggcatggtc caccacaggc accgcagctc atctaccagg
3421  agtggcggtg gggacctgac actagggctg gagccctctg aagaggaggc ccccaggtct
3481  ccactggcac cctccgaagg ggctggctcc gatgtatttg atggtgacct gggaatgggg
3541  gcagccaagg ggctgcaaag cctccccaca catgacccca gccctctaca gcggtacagt
3601  gaggacccca cagtacccct gccctctgag actgatggct acgttgcccc cctgacctgc
3661  agcccccagc ctgaatatgt gaaccagcca gatgttcggc cccagccccc ttcgccccga
3721  gagggccctc tgcctgctgc ccgacctgct ggtgccactc tggaaaggcc caagactctc
3781  tccccaggga gaatggggt cgtcaaagac gttttgcct tgggggtgc cgtggagaac
3841  cccgagtact tgacacccca gggaggagct gcccctcagc ccacccctcc tcctgccttc
3901  agcccagcct tcgacaacct ctattactgg gaccaggacc accagagcg ggggctcca
3961  cccagcacct tcaaaggac acctacggca gagaacccag agtacctggg tctggacgtg
4021  ccagtgtgaa ccagaaggcc aagtccgcag aagccctgat gtgtcctcag ggagcaggga
4081  aggcctgact tctgctggca tcaagaggtg ggagggccct ccgaccactt ccaggggaac
4141  ctgccatgcc aggaacctgt cctaaggaac cttccttcct gcttgagttc ccagatggct
```

```
-continued
4201    ggaaggggtc cagcctcgtt ggaagaggaa cagcactggg gagtctttgt ggattctgag 4261    gccctgccca atgagactct agggtccagt ggatgccaca gcccagcttg gcccttcct 4321    tccagatcct gggtactgaa agccttaggg aagctggcct gagaggggaa gcggccctaa 4381    gggagtgtct aagaacaaaa gcgacccatt cagagactgt ccctgaaacc tagtactgcc 4441    ccccatgagg aaggaacagc aatggtgtca gtatccaggc tttgtacaga gtgcttttct 4501    gtttagtttt tacttttttt gttttgtttt tttaaagatg aaataaagac ccaggggag 4561    aatgggtgtt gtatggggag gcaagtgtgg ggggtccttc tccacaccca ctttgtccat 4621    ttgcaaatat attttggaaa acagctaaaa aaaaaaaaaa aaaa
```

Receptor tyrosine-protein kinase erbB-2 isoform a precursor [*Homo sapiens*] [NP_004439.2]

(SEQ ID NO: 26)

```
MELAALCRWG LLLALLPPGA ASTQVCTGTD MKLRLPASPE THLDMLRHLY

QGCQVVQGNL ELTYLPTNAS LSFLQDIQEV QGYVLIAHNQ VRQVPLQRLR

IVRGTQLFED NYALAVLDNG DPLNNTTPVT GASPGGLREL QLRSLTEILK

GGVLIQRNPQ LCYQDTILWK DIFHKNNQLA LTLIDTNRSR ACHPCSPMCK

GSRCWGESSE DCQSLTRTVC AGGCARCKGP LPTDCCHEQC AAGCTGPKHS

DCLACLHFNH SGICELHCPA LVTYNTDTFE SMPNPEGRYT FGASCVTACP

YNYLSTDVGS CTLVCPLHNQ EVTAEDGTQR CEKCSKPCAR VCYGLGMEHL

REVRAVTSAN IQEFAGCKKI FGSLAFLPES FDGDPASNTA PLQPEQLQVF

ETLEEITGYL YISAWPDSLP DLSVFQNLQV IRGRILHNGA YSLTLQGLGI

SWLGLRSLRE LGSGLALIHH NTHLCFVHTV PWDQLFRNPH QALLHTANRP

EDECVGEGLA CHQLCARGHC WGPGPTQCVN CSQFLRGQEC VEECRVLQGL

PREYVNARHC LPCHPECQPQ NGSVTCFGPE ADQCVACAHY KDPPFCVARC

PSGVKPDLSY MPIWKFPDEE GACQPCPINC THSCVDLDDK GCPAEQRASP

LTSIISAVVG ILLVVVLGVV FGILIKRRQQ KIRKYTMRRL LQETELVEPL

TPSGAMPNQA QMRILKETEL RKVKVLGSGA FGTVYKGIWI PDGENVKIPV

AIKVLRENTS PKANKEILDE AYVMAGVGSP YVSRLLGICL TSTVQLVTQL

MPYGCLLDHV RENRGRLGSQ DLLNWCMQIA KGMSYLEDVR LVHRDLAARN

VLVKSPNHVK ITDFGLARLL DIDETEYHAD GGKVPIKWMA LESILRRRFT

HQSDVWSYGV TVWELMTFGA KPYDGIPARE IPDLLEKGER LPQPPICTID

VYMIMVKCWM IDSECRPRFR ELVSEFSRMA RDPQRFVVIQ NEDLGPASPL

DSTFYRSLLE DDDMGDLVDA EEYLVPQQGF FCPDPAPGAG GMVHHRHRSS

STRSGGGDLT LGLEPSEEEA PRSPLAPSEG AGSDVFDGDL GMGAAKGLQS

LPTHDPSPLQ RYSEDPTVPL PSETDGYVAP LTCSPQPEYV NQPDVRPQPP

SPREGPLPAA RPAGATLERP KTLSPGKNGV VKDVFAFGGA VENPEYLTPQ

GGAAPQPHPP PAFSPAFDNL YYWDQDPPER GAPPSTFKGT PTAENPEYLG

LDVPV
```

The mRNA and protein sequences of the other human HER2 isoforms can be found in GeneBank with the following Accession Nos:

HER2 isoform B: NM_001005862.2 (mRNA) →NP_001005862.1 (protein);

HER2 isoform C: NM_001289936.1 (mRNA) →NP_001276865.1 (protein);

HER2 isoform D: NM_001289937.1 (mRNA) →NP_001276866.1 (protein);

HER2 isoform E: NM_001289938.1 (mRNA) →NP_001276867.1 (protein).

The term "antibody," as used herein, refers to a protein, or polypeptide sequence derived from an immunoglobulin molecule that specifically binds to an antigen. Antibodies can be polyclonal or monoclonal, multiple or single chain, or intact immunoglobulins, and may be derived from natural sources or from recombinant sources. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody can be a monoclonal antibody, human antibody, humanized antibody, camelised antibody, or chimeric antibody. The antibodies can be of any isotype (e.g., IgG, IgE, IgM, IgD, IgA and IgY), class (e.g., IgG1, IgG2, IgG3, IgG4, IgA1 and IgA2) or subclass.

The term "antibody fragment" or "antigen-binding fragment" refers to at least one portion of an antibody, that retains the ability to specifically interact with (e.g., by binding, steric hinderance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nano-bodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type Ill (Fn3) (see U.S. Pat. No. 6,703,199, which describes fibronectin polypeptide minibodies). The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The terms "complementarity determining region" or "CDR," as used herein, refer to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof. In a combined Kabat and Chothia numbering scheme for a given CDR region (for example, HC CDR1, HC CDR2, HC CDR3, LC CDR1, LC CDR2 or LC CDR3), in some embodiments, the CDRs correspond to the amino acid residues that are defined as part of the Kabat CDR, together with the amino acid residues that are defined as part of the Chothia CDR.

The term "epitope" includes any protein determinant capable of specific binding to an immunoglobulin or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." Conformational and linear epitopes are distinguished in that the binding to the former but not the latter is lost in the presence of denaturing solvents.

The phrases "monoclonal antibody" or "monoclonal antibody composition" as used herein refers to polypeptides, including antibodies, bispecific antibodies, etc., that have substantially identical amino acid sequence or are derived from the same genetic source. This term also includes preparations of antibody molecules of single molecular composition. A monoclonal antibody composition displays a single binding specificity and affinity for a particular epitope.

The phrase "human antibody," as used herein, includes antibodies having variable regions in which both the framework and CDR regions are derived from sequences of human origin. Furthermore, if the antibody contains a constant region, the constant region is also derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Al Lazikani et al., (1997) J. Mol. Bio. 273:927 948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mal. Biol. 273:927-948.

The human antibodies of the invention may include amino acid residues not encoded by human sequences (e.g., mutations introduced by random or site-specific mutagenesis in vitro or by somatic mutation in vivo, or a conservative substitution to promote stability or manufacturing). However, the term "human antibody" as used herein, is not intended to include antibodies in which CDR sequences derived from the germline of another mammalian species, such as a mouse, have been grafted onto human framework sequences.

The phrase "recombinant human antibody" as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

The term "binding specificity" as used herein refers to the ability of an individual antibody combining site to react with one antigenic determinant and not with a different antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within an antibody can be replaced with other amino acid residues from the same side chain family and the altered antibody can be tested using the functional assays described herein.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. Percentage of "sequence identity" can be determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

The terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric cancer including gastrointestinal cancer, pancreatic cancer, glioblastoma, neuroblastoma, cervical cancer, ovarian cancer, liver cancer, bladder cancer, urinary tract cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

A "HER2-positive cancer" or "HER2-expressing cancer" is a cancer comprising cells that have HER2 protein present at their cell surface. Many methods are known in the art for detecting or determining the presence of HER2 on a cancer cell. For example, in some embodiments, the presence of HER2 on the cell surface may be determined by immunohistochemistry (IHC), flow cytometry, Western blotting, immunofluorescent assay, radioimmunoassay (RIA), enzyme-linked immunosorbent assay (ELISA), homogeneous time resolved fluorescence (HTRF), or positron emission tomography (PET).

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of the invention and one or more additional therapeutic agent, are administered to a subject simultaneously in the form of a single entity or dosage. The term "non-fixed combination" means that the active ingredients, by way of example, a compound of the invention and one or more additional therapeutic agent, are administered to a subject as separate entities either simultaneously, concurrently or sequentially with no specific time limits, wherein such administration provides therapeutically effective levels of the active ingredients in the body of the subject. The latter also applies to cocktail therapy, e.g. the administration of 3 or more active ingredients.

The terms "composition" or "pharmaceutical composition," as used herein, refers to a mixture of a compound of the invention with at least one and optionally more than one other pharmaceutically acceptable chemical components, such as carriers, stabilizers, diluents, dispersing agents, suspending agents, thickening agents, and/or excipients.

The term "an optical isomer" or "a stereoisomer", as used herein, refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

The term "pharmaceutically acceptable carrier", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "pharmaceutically acceptable salt," as used herein, refers to a salt which does not abrogate the biological activity and properties of the compounds of the invention, and does not cause significant irritation to a subject to which it is administered.

The term "subject", as used herein, encompasses mammals and non-mammals. Examples of mammals include, but are not limited to, humans, chimpanzees, apes, monkeys, cattle, horses, sheep, goats, swine; rabbits, dogs, cats, rats, mice, guinea pigs, and the like. Examples of non-mammals include, but are not limited to, birds, fish and the like. Frequently the subject is a human.

The term "a subject in need of such treatment", refers to a subject which would benefit biologically, medically or in quality of life from such treatment.

The term "therapeutically effective amount," as used herein, refers to an amount of an antibody conjugate of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of an antibody conjugate of the invention that, when administered to a subject, is effective to at least partially alleviate, inhibit, prevent and/or ameliorate a condition, or a disorder or a disease.

The term "TLR7 agonist", as used herein, refers to a compound or antibody conjugate capable of activating Toll-like Receptor 7 (TLR7).

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The compound names provided herein were obtained using ChemDraw Ultra version 12.0 (CambridgeSoft®) or JChem version 5.3.1 (ChemAxon).

Unless specified otherwise, the term "compounds of the present invention", "compounds of the invention" or "compounds provided herein" refers to compounds of Formula (I) and subformulae thereof (i.e. compounds of Formula (Ia) and Formula (Ib)), and pharmaceutically acceptable salts, stereoisomers (including diastereoisomers and enantiomers), tautomers and isotopically labeled compounds (including deuterium substitutions) thereof.

Unless specified otherwise, the term "antibody conjugate of the invention", refers to antibody conjugates of Formula (II) and subformulae thereof (i.e. compounds of Formula (IIa) and Formula (IIb)), and pharmaceutically acceptable salts, stereoisomers (including diastereoisomers and enantiomers), tautomers and isotopically labeled compounds (including deuterium substitutions) thereof.

As used herein, the term "a," "an," "the" and similar terms used in the context of the present invention (especially in the context of the claims) are to be construed to cover both the singular and plural unless otherwise indicated herein or clearly contradicted by the context.

Immunostimulatory Compounds of the Invention

The immunostimulatory compounds of the invention are TLR7 agonists having the structure of Formula (I):

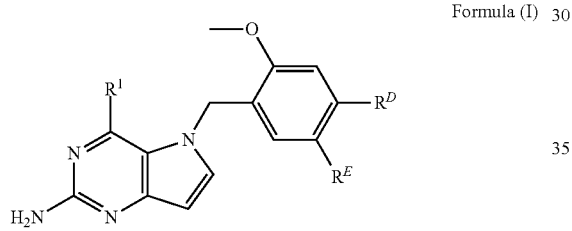

Formula (I)

wherein:
$R^D$ is

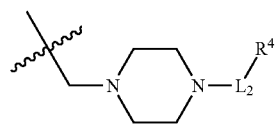

and $R^E$ is H; or $R^E$ is

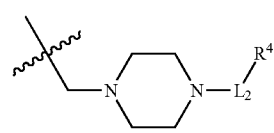

and $R^D$ is H;
$R^1$ is $NHR^2$ or $NHCHR^2R^3$;
$R^2$ is $-C_3-C_6$alkyl or $-C_4-C_6$alkyl;
$R^3$ is $L_1OH$;
$L_1$ is $-(CH_2)_m-$;
$L_2$ is $-(CH_2)_n-$, $-((CH_2)_nO)_t(CH_2)_n-$, $-(CH_2)_nX_1(CH_2)_n-$, $-(CH_2)_nNHC(=O)(CH_2)_n-$, $-(CH_2)_nNHC(=O)(CH_2)_nC(=O)NH(CH_2)_n-$, $-((CH_2)_nO)_t(CH_2)_nNHC(=O)(CH_2)_n$, $-C(=O)(CH_2)_n-$, $-C(=O)((CH_2)_nO)_t(CH_2)_n-$, $-C(=O)((CH_2)_nO)_t(CH_2)_nX_1(CH_2)_n-$, $-C(=O)((CH_2)_nO)_t(CH_2)_nNHC(=O)(CH_2)_n-$, $-C(=O)((CH_2)_nO)_t(CH_2)_nC(=O)NH((CH_2)_nO)_t(CH_2)_nX_1(CH_2)_n-$, $-C(=O)X_2X_3C(=O)((CH_2)_nO)_t(CH_2)_n-$, $-C(=O)X_2X_3C(=O)(CH_2)_n-$, $-C(=O)X_2C(=O)(CH_2)_nNHC(=O)(CH_2)_n-$, $-C(=O)X_2C(=O)(CH_2)_nNHC(=O)((CH_2)_nO)_t(CH_2)_n-$, $-C(=O)(CH_2)_nC(R_7)_2-$, $-C(=O)(CH_2)_nC(R_7)_2SS(CH_2)_nNHC(=O)(CH_2)_n-$, $-(CH_2)_nX_2C(=O)(CH_2)_nNHC(=O)((CH_2)_nO)_t(CH_2)_n-$ or $-C(=O)(CH_2)_nC(=O)NH(CH_2)_n$;

$R^4$ is

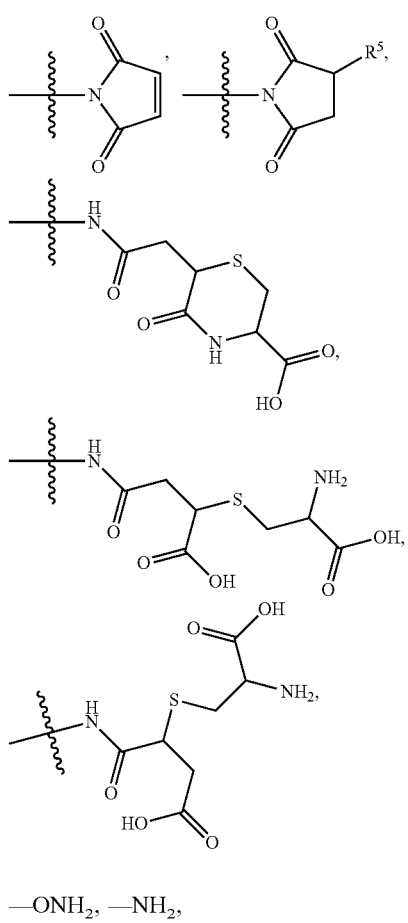

$-ONH_2$, $-NH_2$,

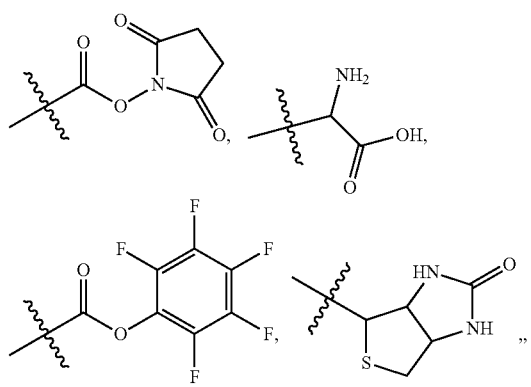

—N₃,
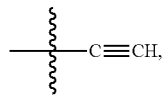
—NHC(=O)CH=CH₂, —SH, —SR⁷, —OH, —SSR⁶, —S(=O)₂(CH=CH₂), —(CH₂)₂S(=O)₂(CH=CH₂), —NHS(=O)₂(CH=CH₂), —NHC(=O)CH₂Br, —NHC(=O)CH₂I, —C(O)NHNH₂,
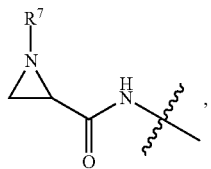
—CO₂H, —C(O)NHNH₂,
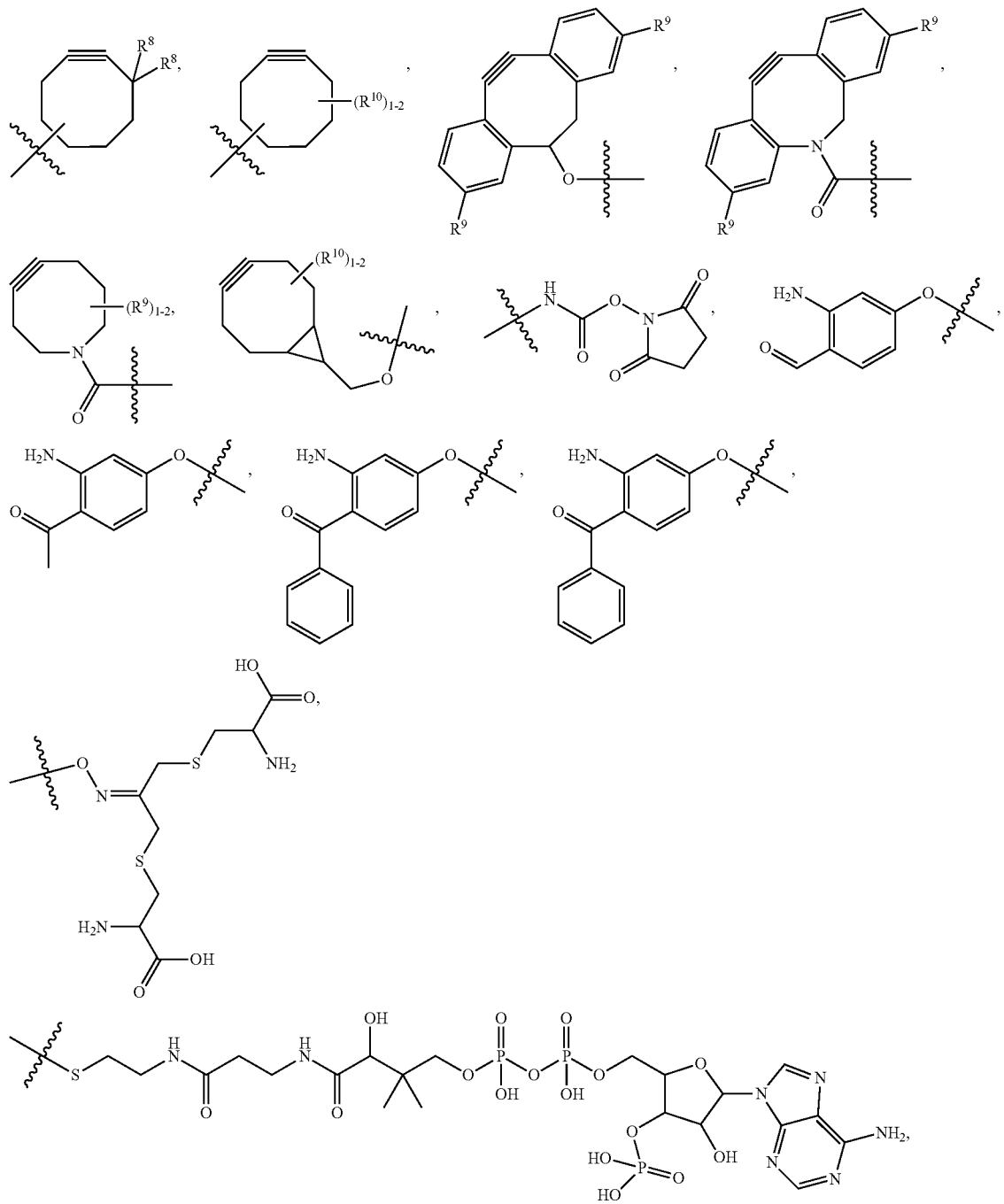

-continued
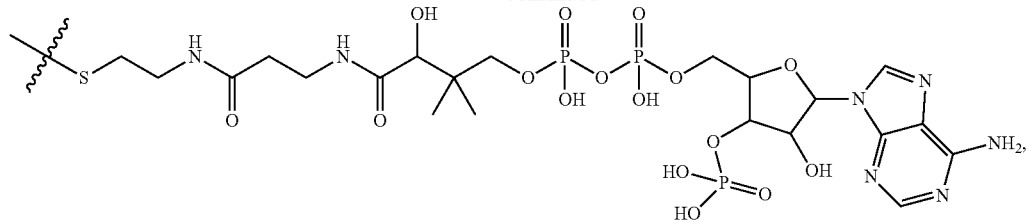
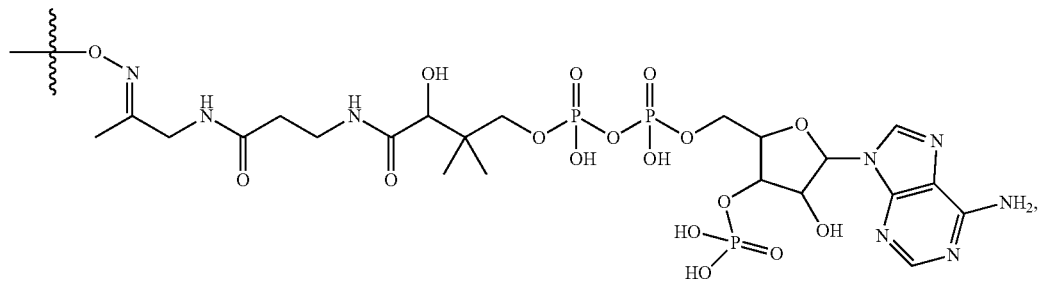
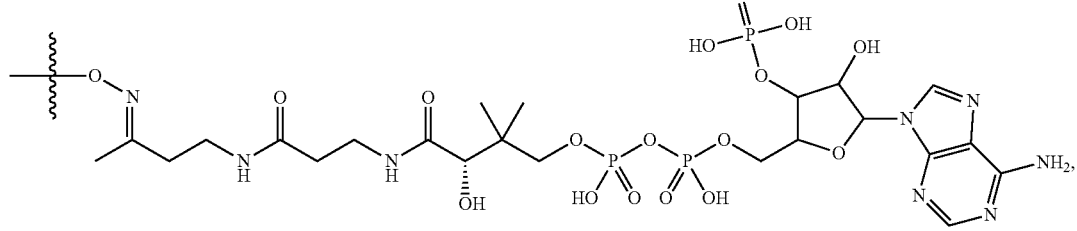
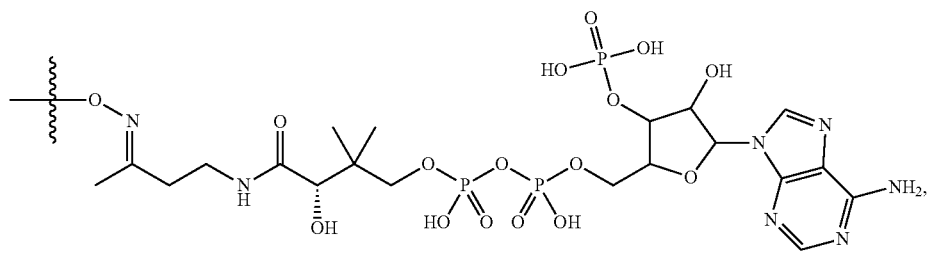
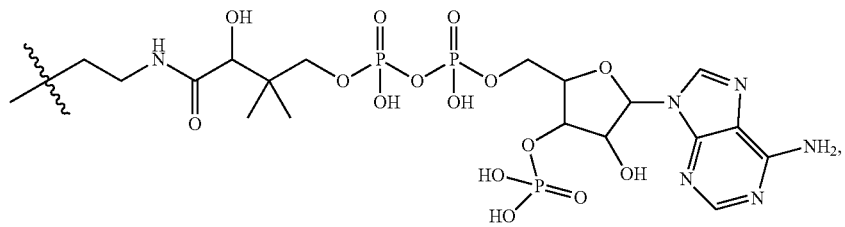
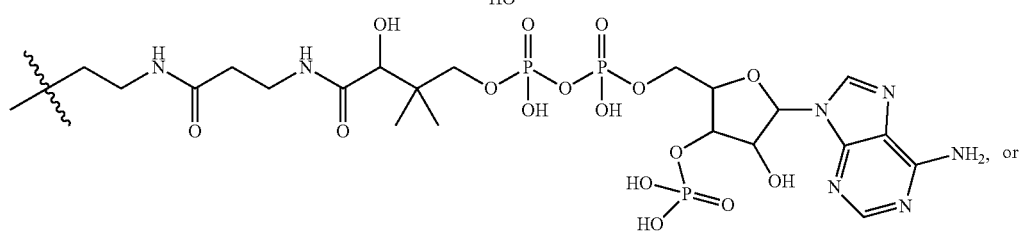
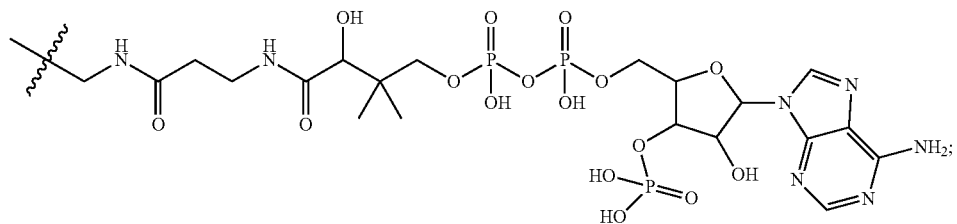

$R^5$ is
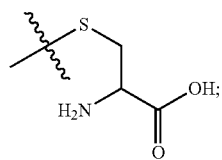 [SMILES: *SCC(N)C(=O)O]
$X_1$ is
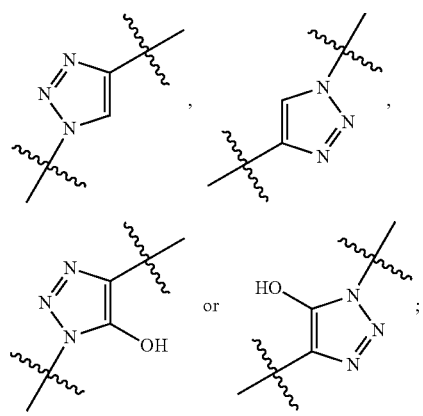
$X_2$ is
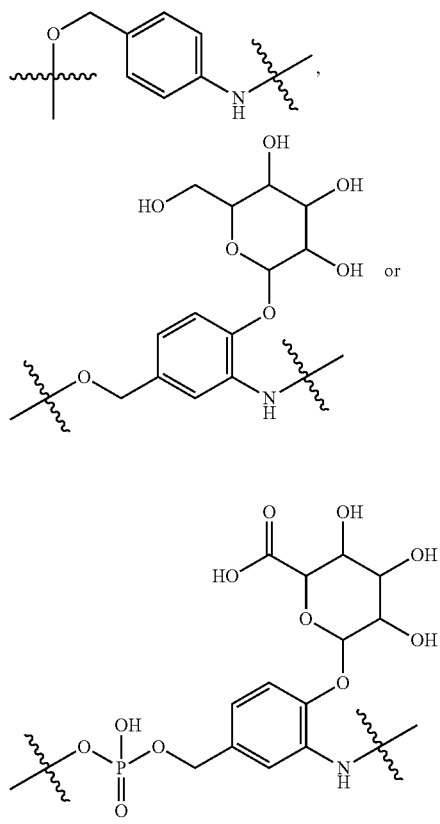
-continued
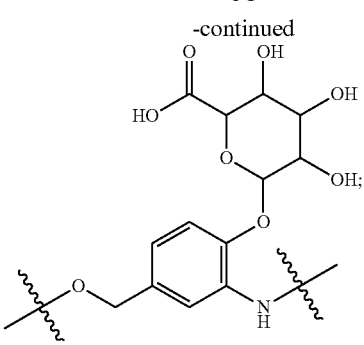
$X_3$ is
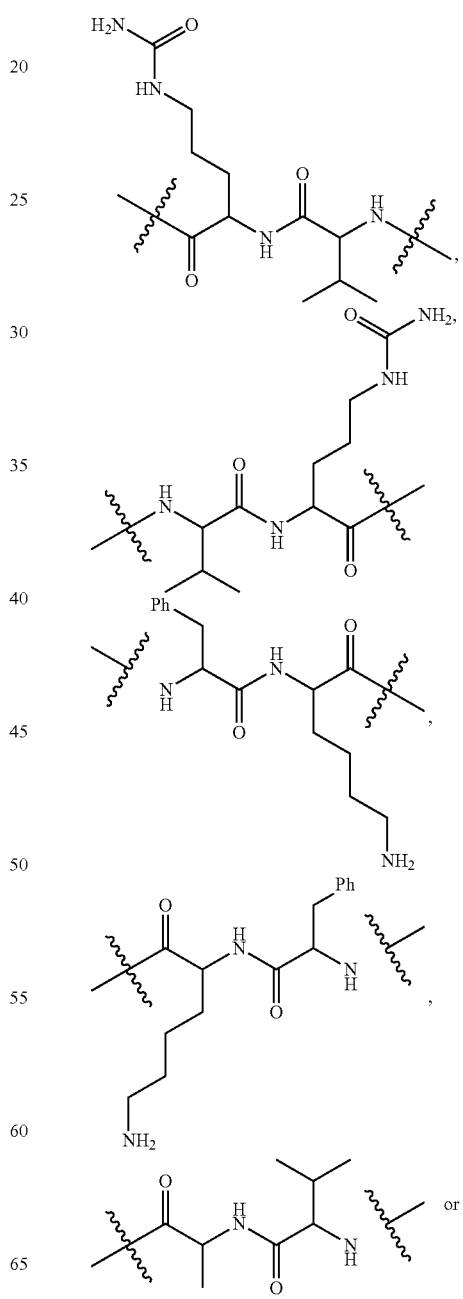

-continued

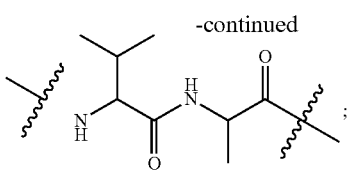

R⁶ is 2-pyridyl or 4-pyridyl;
each R⁷ is independently selected from H and $C_1$-$C_6$alkyl;
each R⁸ is independently selected from H, $C_1$-$C_6$alkyl, F, Cl, and —OH;
each R⁹ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each R¹⁰ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

Certain aspects and examples of the compounds of the invention are provided in the following listing of additional, enumerated embodiments. It will be recognized that features specified in each embodiment may be combined with other specified features to provide further embodiments of the present invention.

Embodiment 1

The compound of Formula (I), and the pharmaceutically acceptable salts thereof, wherein:
$R^D$ is

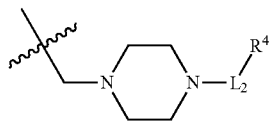

and $R^E$ is H; or $R^E$ is

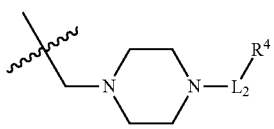

and $R^D$ is H;
$R^1$ is —NHR$^2$ or —NHCHR$^2$R$^3$;
$R^2$ is —$C_3$-$C_6$alkyl or —$C_4$-$C_6$alkyl;
$R^3$ is $L_1$OH;
$L_1$ is —(CH$_2$)$_m$—;
$L_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$—, —((CH$_2$)$_n$O)$_t$(CH$_2$)$_n$NHC(=O)(CH$_2$)$_n$—, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$C(=O)(CH$_2$)$_n$NHC(=O)(CH$_2$)$_n$—, or —C(=O)(CH$_2$)$_n$C(=O)NH(CH$_2$)$_n$;
$R^4$ is

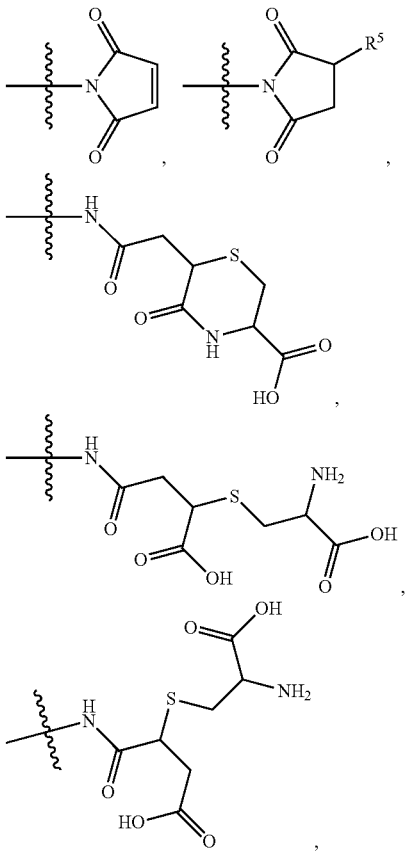

—ONH$_2$, —NH$_2$,

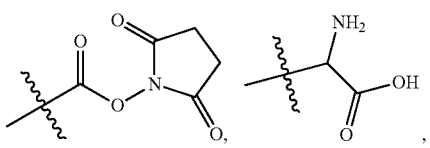

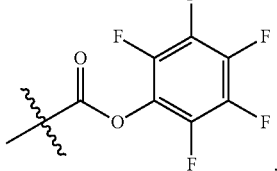

—N$_3$,

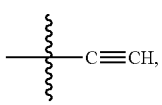

—NHC(=O)CH=CH$_2$, SH, —SSR$^6$, —S(=O)$_2$(CH=CH$_2$), —(CH$_2$)$_2$S(=O)$_2$(CH=CH$_2$), —NHS (=O)₂(CH=CH₂), —NHC(=O)CH₂Br, —NHC(=O)CH₂I, —C(O)NHNH₂,
—CO₂H, —C(O)NHNH₂,
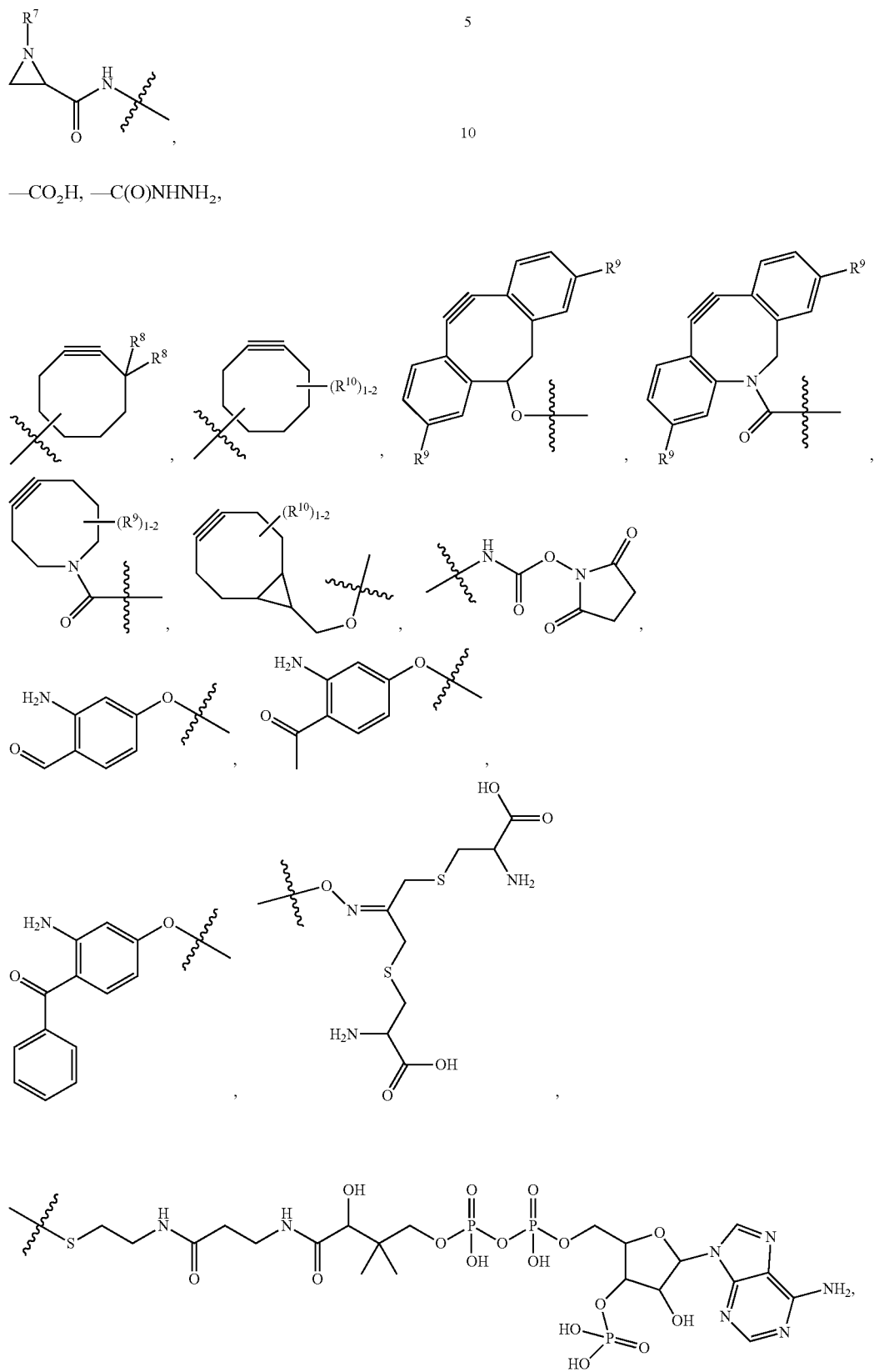

-continued
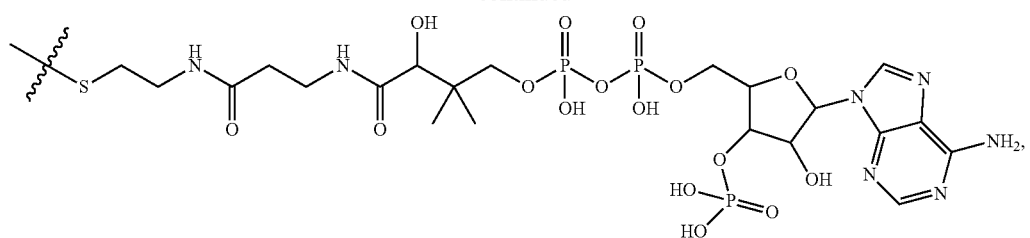
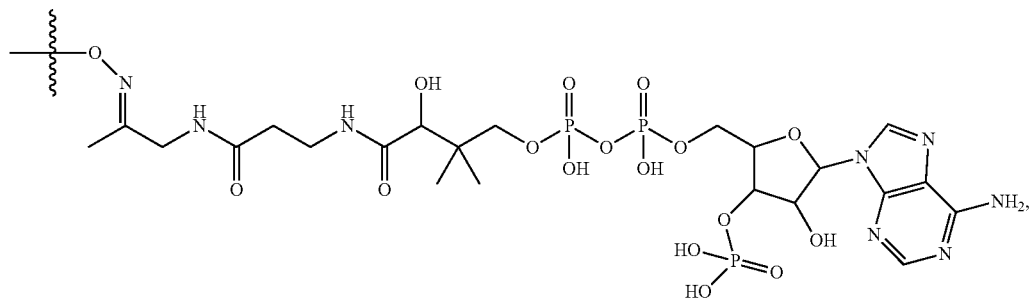
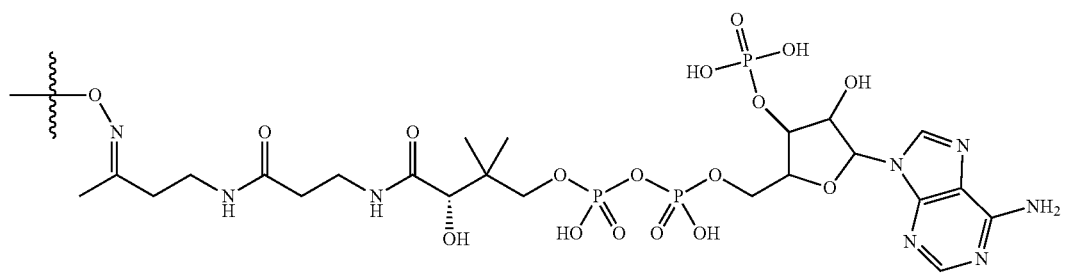
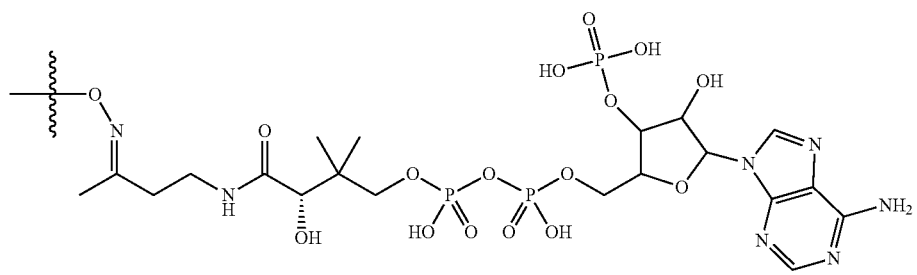
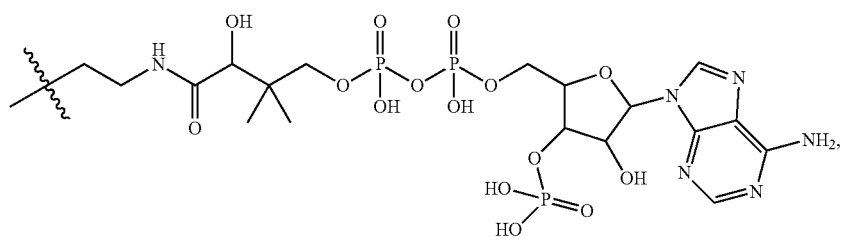
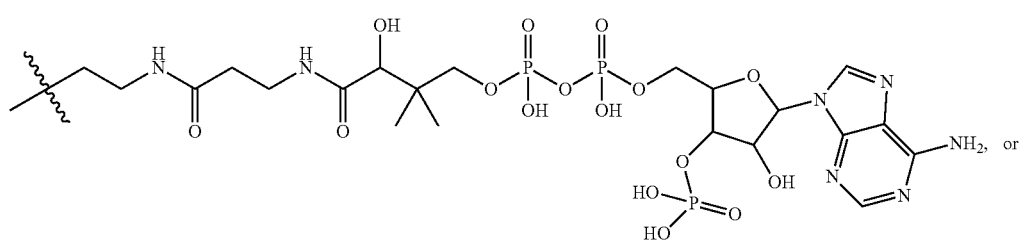

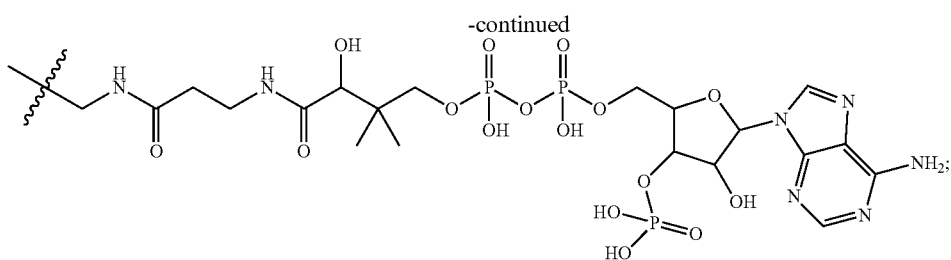
R⁵ is
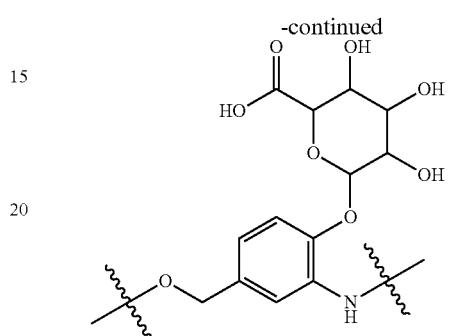
; X₁ is
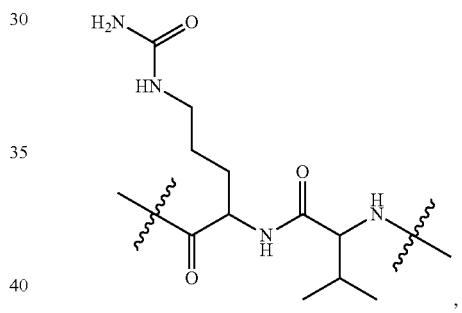
X₂ is
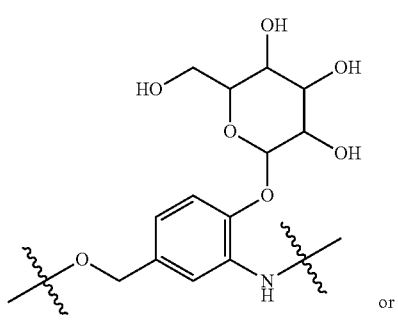 or
X₃ is
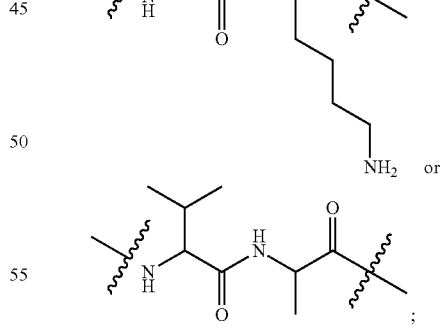
R⁶ is 2-pyridyl or 4-pyridyl;
each R⁷ is independently selected from H and $C_1$-$C_6$alkyl;
each R⁸ is independently selected from H, $C_1$-$C_6$alkyl, F, Cl, and —OH;
each R⁹ is independently selected from H, $C_1$-$C_6$alkyl, F, Cl, —NH₂, —OCH₃, —OCH₂CH₃, —N(CH₃)₂, —CN, —NO₂ and —OH;
each R¹⁰ is independently selected from H, $C_{1-6}$alkyl, fluoro, benzyloxy substituted with —C(=O)OH, benzyl substituted with —C(=O)OH, C$_{1-4}$alkoxy substituted with —C(=O)OH and C$_{1-4}$alkyl substituted with —C(=O)OH;

each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

Embodiment 2

The compound of Formula (I) having the structure of Formula (Ia) or Formula (Ib), and the pharmaceutically acceptable salts thereof:

Formula (Ia)

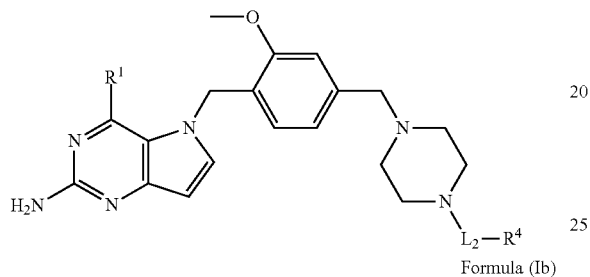

Formula (Ib)

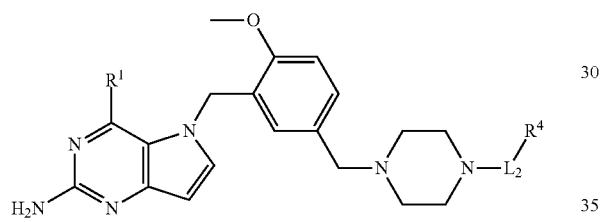

wherein:
R$^1$ is —NHR$^2$ or —NHCHR$^2$R$^3$;
R$^2$ is —C$_3$-C$_6$alkyl or —C$_4$-C$_6$alkyl;
R$^3$ is L$_1$OH;
L$_1$ is —(CH$_2$)$_m$—;
L$_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$—, —((CH$_2$)$_n$O)$_t$(CH$_2$)$_n$NHC(=O)(CH$_2$)$_n$, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$X$_3$C(=O)(CH$_2$)$_n$—, —C(=O)X$_2$C(=O)(CH$_2$)$_n$NHC(=O)(CH$_2$)$_n$—, —C(=O)X$_2$C(=O)(CH$_2$)$_n$NHC(=O)((CH$_2$)$_n$O)$_t$(CH$_2$)$_n$—, —C(=O)(CH$_2$)$_n$C(R$_7$)$_2$—, —C(=O)(CH$_2$)$_n$C(R$_7$)$_2$SS(CH$_2$)$_n$NHC(=O)(CH$_2$)$_n$—, —(CH$_2$)$_n$X$_2$C(=O)(CH$_2$)$_n$NHC(=O)(CH$_2$)$_n$—, —(CH$_2$)$_n$X$_2$C(=O)(CH$_2$)$_n$NHC(=O)((CH$_2$)$_n$O)$_t$(CH$_2$)$_n$— or —C(=O)(CH$_2$)$_n$C(=O)NH(CH$_2$)$_n$;
R$^4$ is

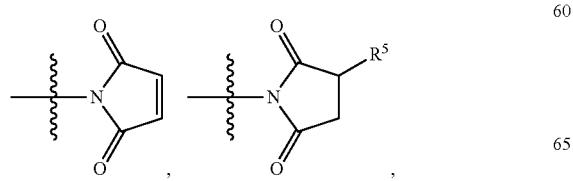

-continued

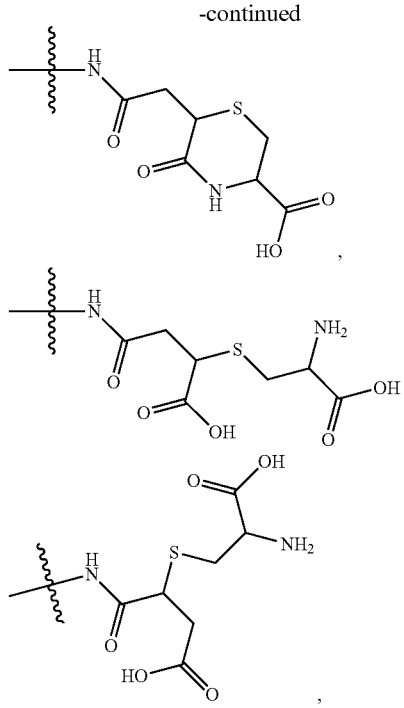

—ONH$_2$, —NH$_2$,

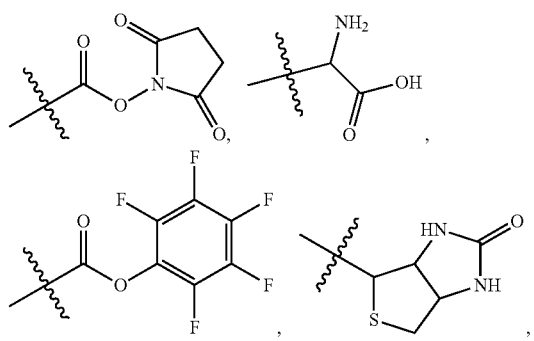

—N$_3$,

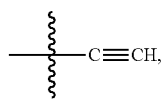

—NHC(=O)CH=CH$_2$, SH, —SR$^7$, —OH, —SSR$^6$, —S(=O)$_2$(CH=CH$_2$), —(CH$_2$)$_2$S(=O)$_2$(CH=CH$_2$), —NHS(=O)$_2$(CH=CH$_2$), —NHC(=O)CH$_2$Br, —NHC(=O)CH$_2$I, —C(O)NHNH$_2$,

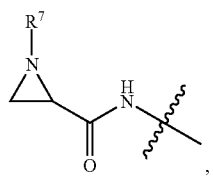

—CO$_2$H, —C(O)NHNH$_2$,

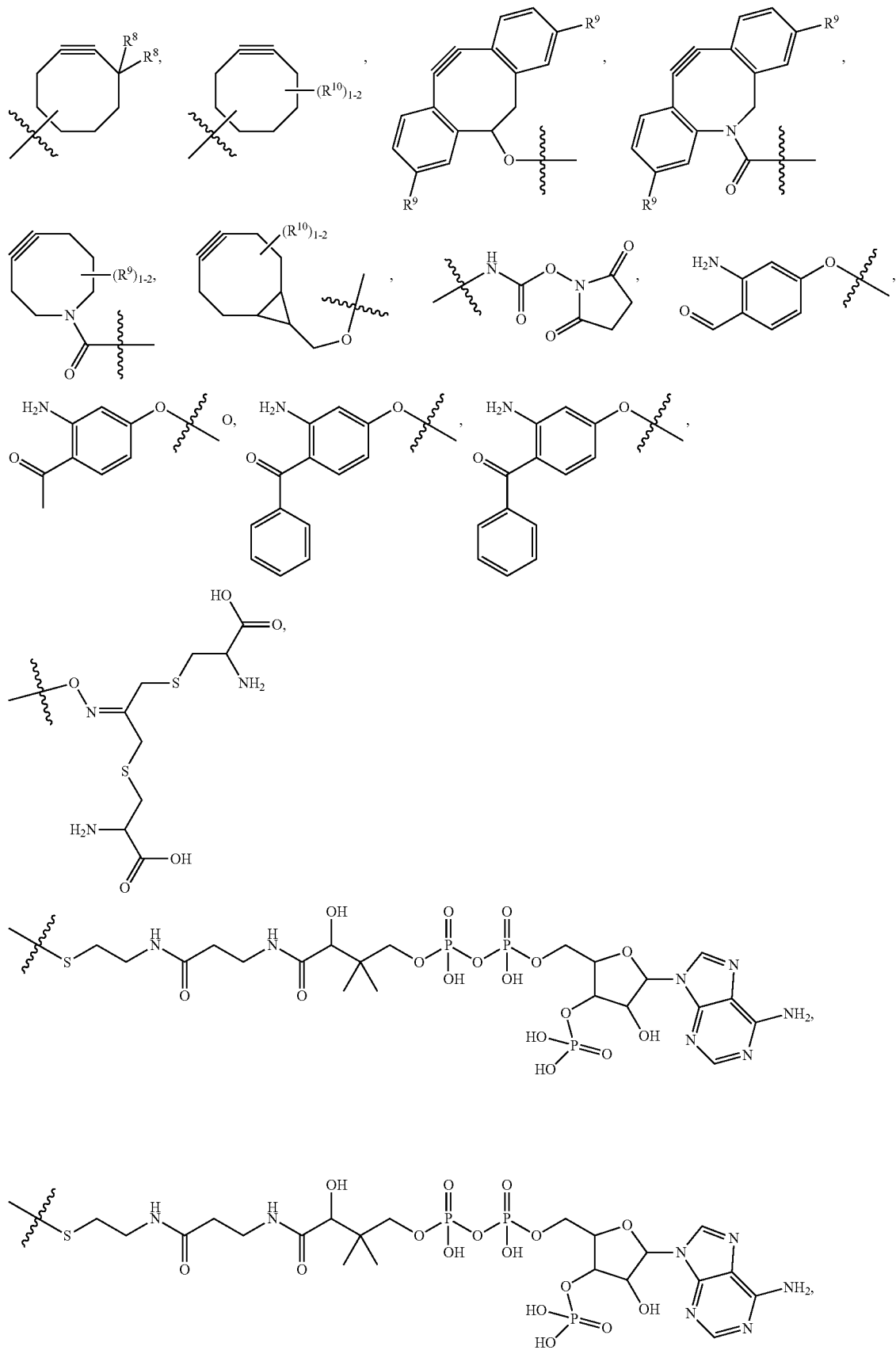

-continued
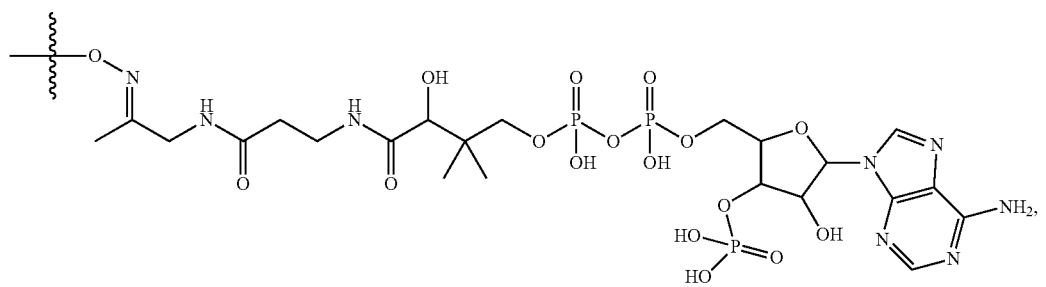
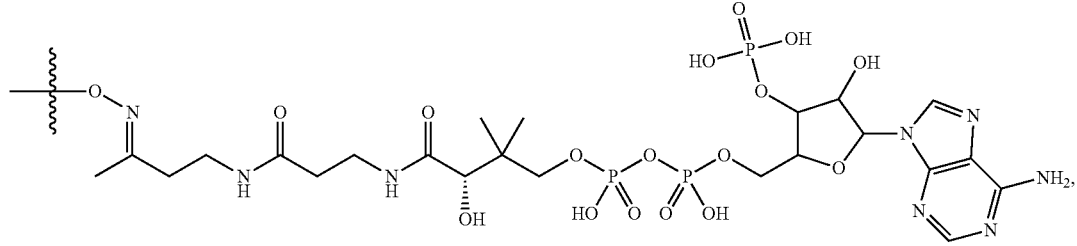
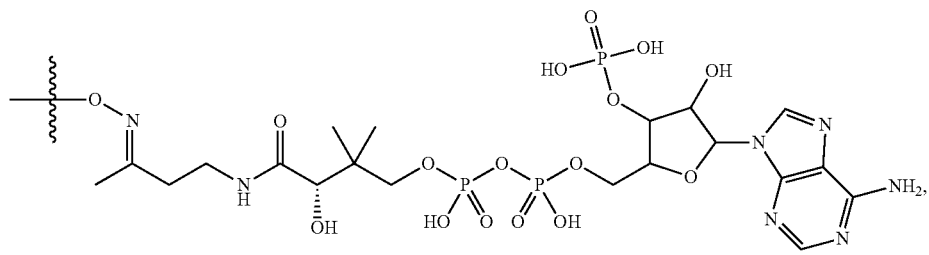
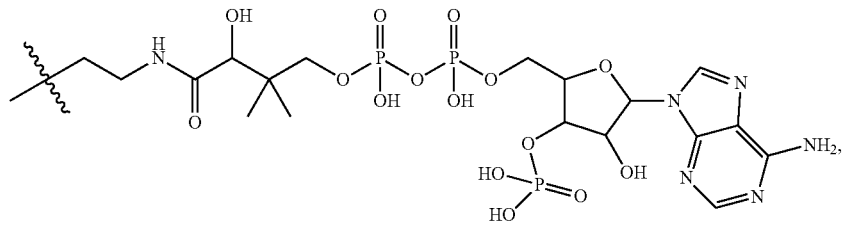
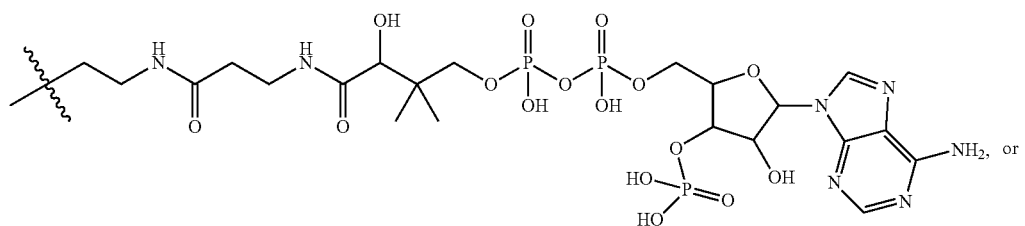
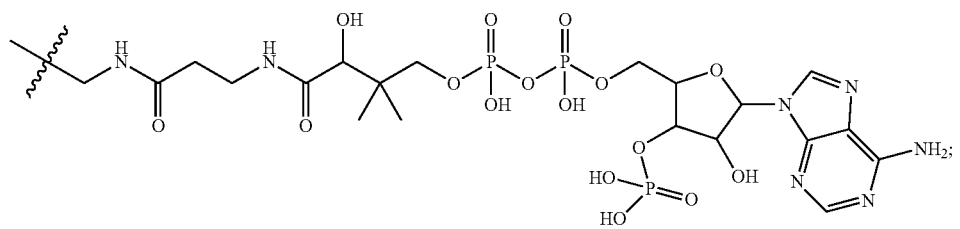

$R^5$ is
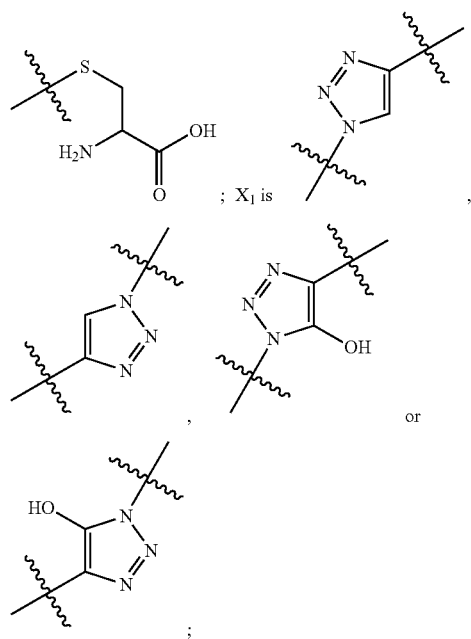
; $X_1$ is
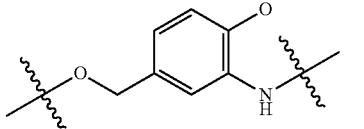,
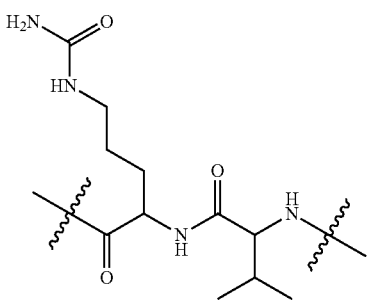
;
$X_2$ is
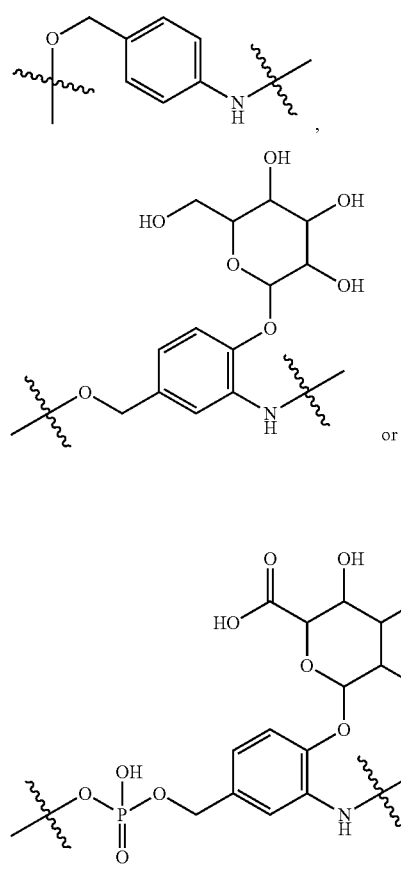
-continued
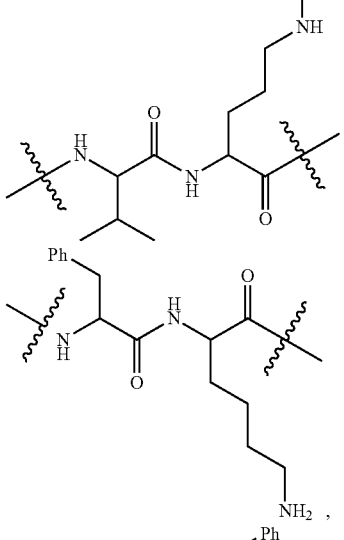
;
$X_3$ is
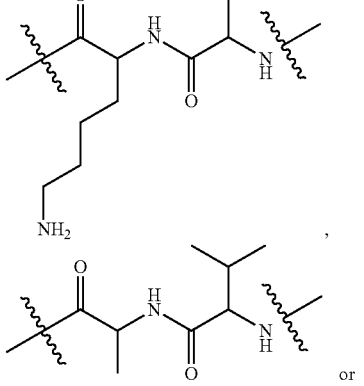

-continued

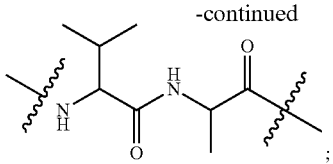

R⁶ is 2-pyridyl or 4-pyridyl;
each R⁷ is independently selected from H and $C_1$-$C_6$alkyl;
each R⁸ is independently selected from H, $C_1$-$C_6$alkyl, F, Cl, and —OH;
each R⁹ is independently selected from H, $C_1$-$C_6$alkyl, F, Cl, —NH₂, —OCH₃, —OCH₂CH₃, —N(CH₃)₂, —CN, —NO₂ and —OH;
each R¹⁰ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

Embodiment 3

The compound of Formula (Ia) or Formula (Ib), and the pharmaceutically acceptable salts thereof, wherein:
R¹ is —NHR² or —NHCHR²R³;
R² is —$C_3$-$C_6$alkyl or —$C_4$-$C_6$alkyl;
R³ is $L_1$OH;
$L_1$ is —(CH₂)$_m$—;
$L_2$ is —(CH₂)$_n$—, —((CH₂)$_n$O)$_t$(CH₂)$_n$—, —(CH₂)$_n$X₁(CH₂)$_n$—, —(CH₂)$_n$NHC(=O)(CH₂)$_n$—, —(CH₂)$_n$NHC(=O)(CH₂)$_n$C(=O)NH(CH₂)$_n$—, —((CH₂)$_n$O)$_t$(CH₂)$_n$NHC(=O)(CH₂)$_n$—, —C(=O)(CH₂)$_n$—, —C(=O)((CH₂)$_n$O)$_t$(CH₂)$_n$—, —C(=O)((CH₂)$_n$O)$_t$(CH₂)$_n$X₁(CH₂)$_n$—, —C(=O)((CH₂)$_n$O)$_t$(CH₂)$_n$NHC(=O)(CH₂)$_n$—, —C(=O)((CH₂)$_n$O)$_t$(CH₂)$_n$C(=O)NH(CH₂)$_n$—, —C(=O)NH((CH₂)$_n$O)$_t$(CH₂)$_n$X₁(CH₂)$_n$—, —C(=O)X₂X₃C(=O)((CH₂)$_n$O)$_t$(CH₂)$_n$—, —C(=O)X₂C(=O)(CH₂)$_n$NHC(=O)(CH₂)$_n$—, or —C(=O)(CH₂)$_n$C(=O)NH(CH₂)$_n$;
R⁴ is

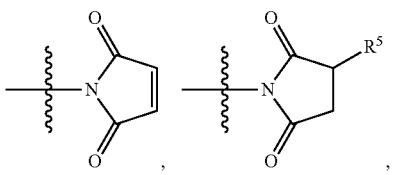

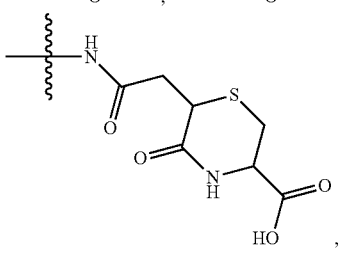

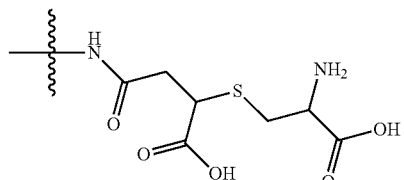

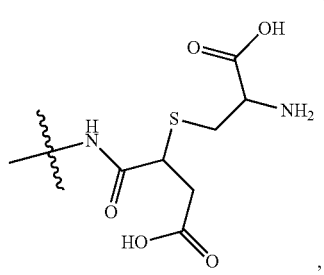

—ONH₂, —NH₂,

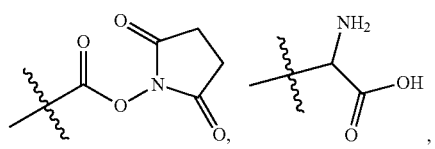

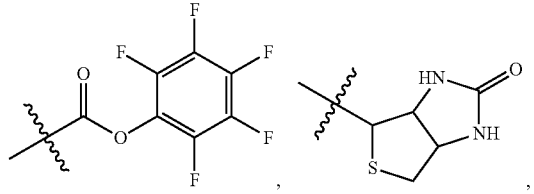

—N₃,

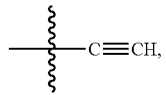

—NHC(=O)CH=CH₂, SH, —SSR⁶, —S(=O)₂(CH=CH₂), —(CH₂)₂S(=O)₂(CH=CH₂), —NHS(=O)₂(CH=CH₂), —NHC(=O)CH₂Br, —NHC(=O)CH₂I, —C(O)NHNH₂,

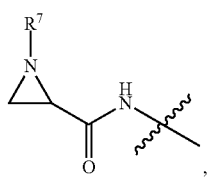

—CO₂H, —C(O)NHNH₂,

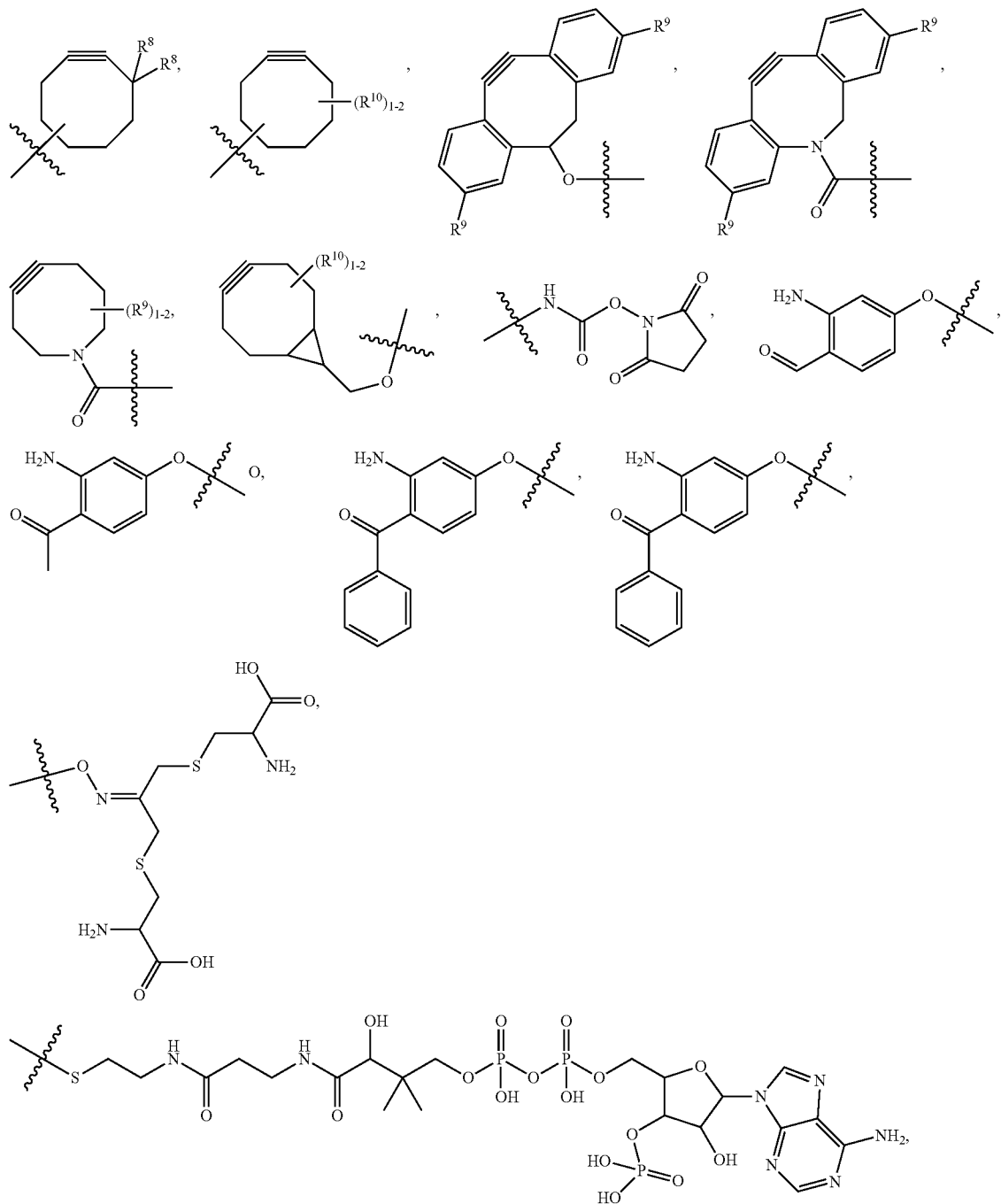

-continued
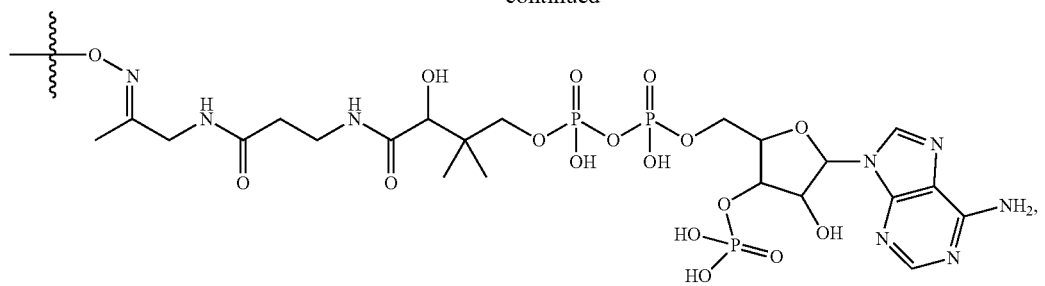
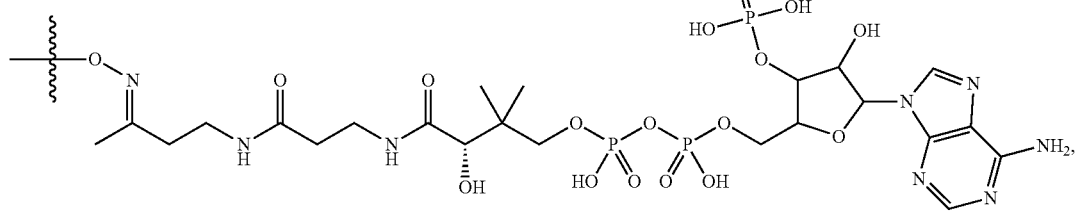
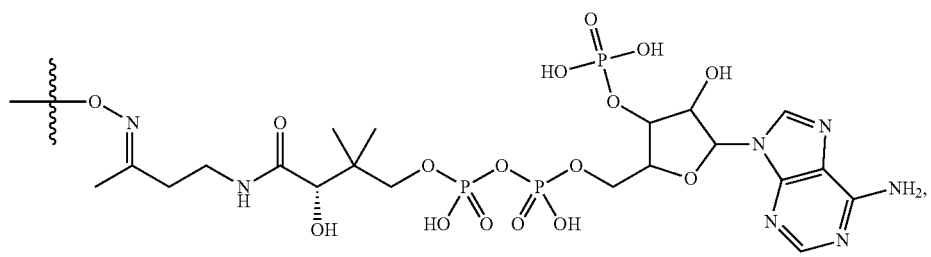
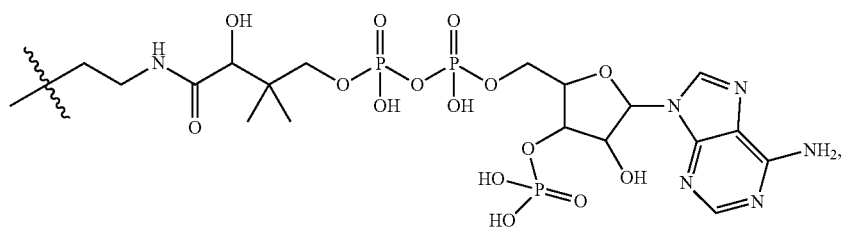
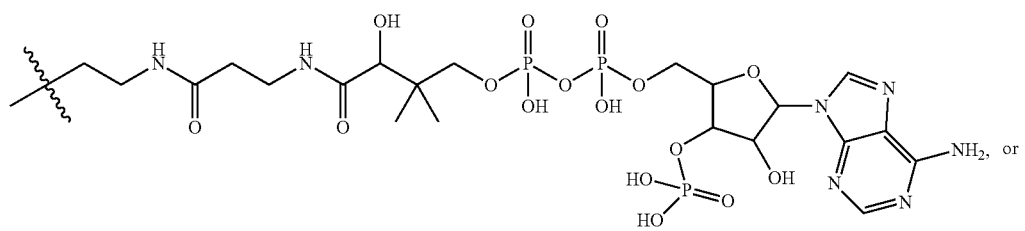
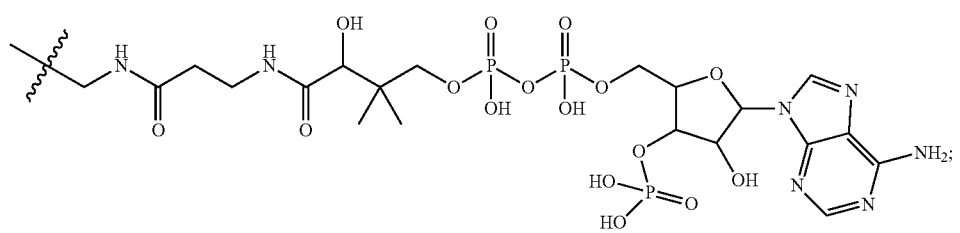

$R^5$ is

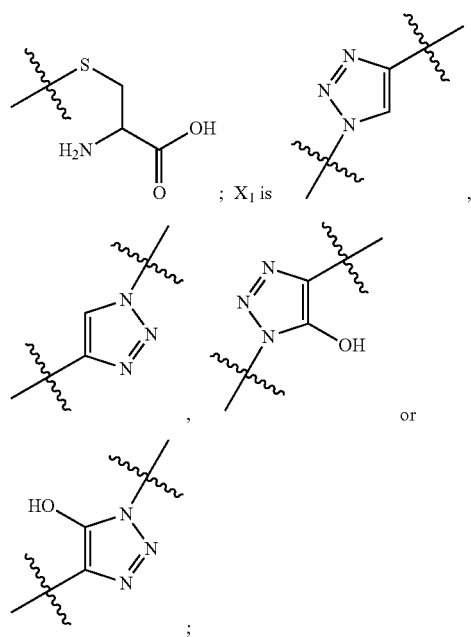

; $X_1$ is $X_2$ is

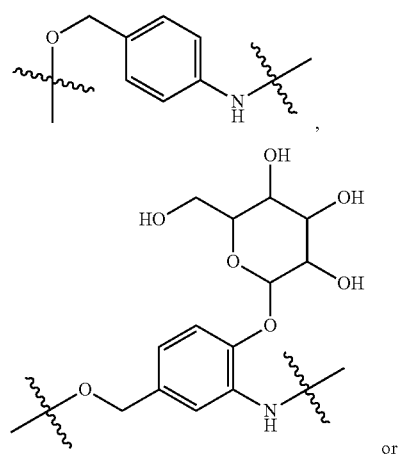

or

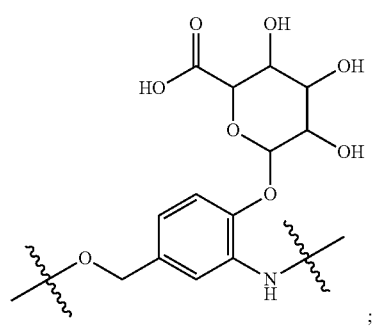

;

$X_3$ is

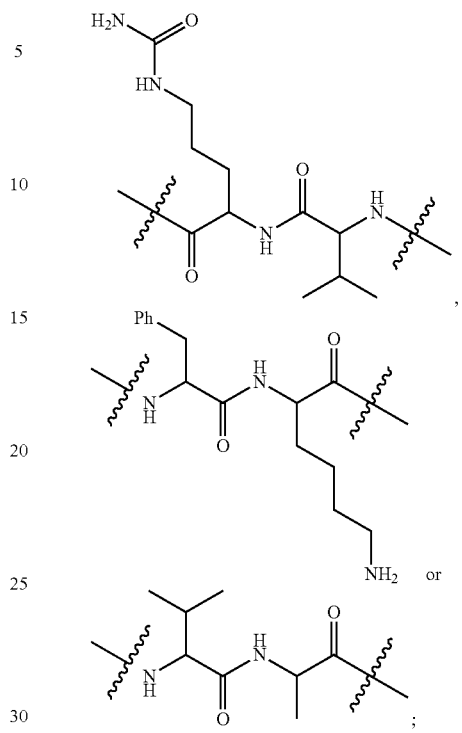

;

$R^6$ is 2-pyridyl or 4-pyridyl;
each $R^7$ is independently selected from H and $C_1$-$C_6$alkyl;
each $R^8$ is independently selected from H, $C_1$-$C_6$alkyl, F, Cl, and —OH;
each $R^9$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

Embodiment 4

The compound of Formula (I) having the structure of Formula (Ia) or Formula (Ib), and the pharmaceutically acceptable salts thereof:

Formula (Ia)

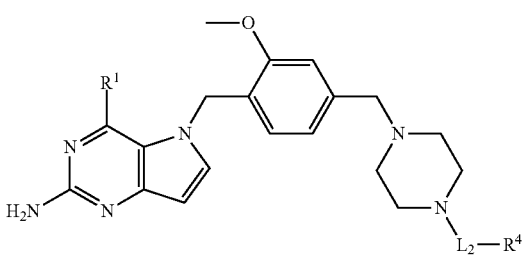

Formula (Ib)

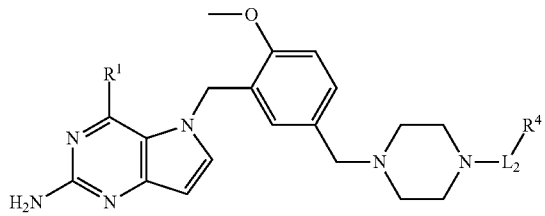

wherein:
R¹ is —NHR² or —NHCHR²R³;
R² is —C₃-C₆alkyl or —C₄-C₆alkyl;
R³ is L₁OH;
L₁ is —(CH₂)$_m$—;
L₂ is —(CH₂)$_n$—, —((CH₂)$_n$O)$_t$(CH₂)$_n$—, —(CH₂)$_n$X₁(CH₂)$_n$—, —(CH₂)$_n$NHC(=O)(CH₂)$_n$—, —(CH₂)$_n$NHC(=O)(CH₂)$_n$C(=O)NH(CH₂)$_n$—, —((CH₂)$_n$O)$_t$(CH₂)$_n$NHC(=O)(CH₂)$_n$, —C(=O)(CH₂)$_n$—, —C(=O)((CH₂)$_n$O)$_t$(CH₂)$_n$—, —C(=O)((CH₂)$_n$O)$_t$(CH₂)$_n$X₁(CH₂)$_n$—, —C(=O)((CH₂)$_n$O)$_t$(CH₂)$_n$NHC(=O)(CH₂)$_n$—, —C(=O)((CH₂)$_n$O)$_t$(CH₂)$_n$C(=O)NH(CH₂)$_n$—, —C(=O)NH((CH₂)$_n$O)$_t$(CH₂)$_n$X₁(CH₂)$_n$—, —C(=O)X₂X₃C(=O)((CH₂)$_n$O)$_t$(CH₂)$_n$—, —C(=O)X₂C(=O)(CH₂)$_n$NHC(=O)(CH₂)$_n$, or —C(=O)(CH₂)$_n$C(=O)NH(CH₂)$_n$;
R⁴ is

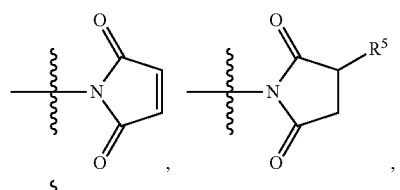

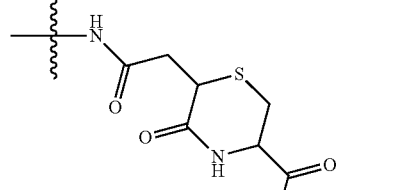

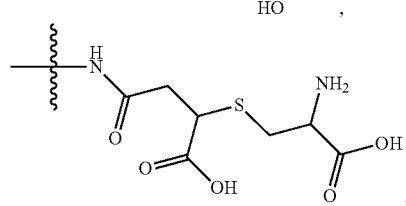

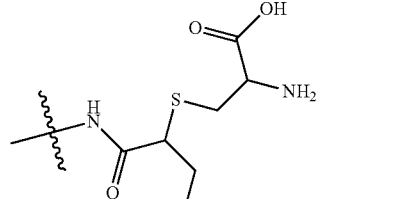

—ONH₂, —NH₂,

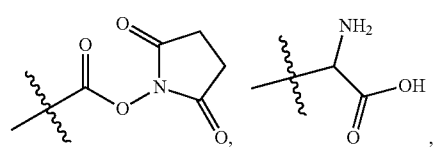

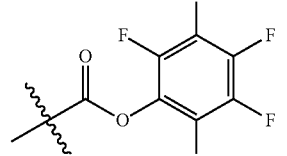

—NHC(=O)CH=CH₂, —N₃,

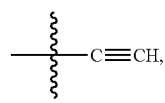

SH, —SSR⁶, —S(=O)₂(CH=CH₂), —(CH₂)₂S(=O)₂(CH=CH₂), —NHS(=O)₂(CH=CH₂), —NHC(=O)CH₂Br, —NHC(=O)CH₂I, —C(O)NHNH₂,

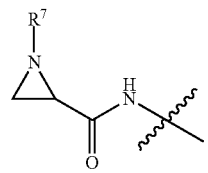

or —CO₂H;
R⁵ is

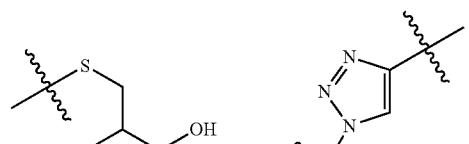

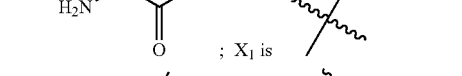

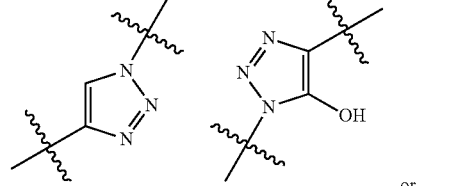

; X₁ is

or

;

$X_2$ is

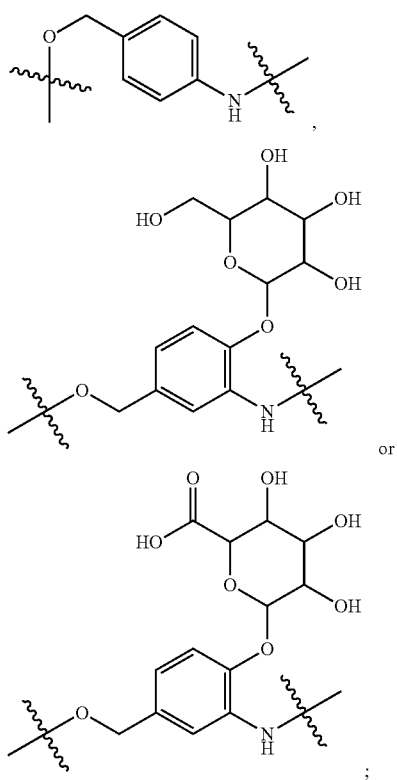

$X_3$ is

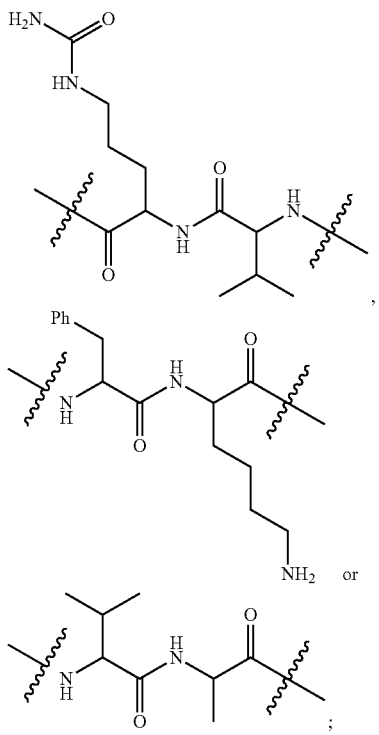

$R^6$ is 2-pyridyl or 4-pyridyl;
each $R^7$ is independently selected from H and $C_1$-$C_6$alkyl;
each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

Embodiment 5

The compound of Formula (I), Formula (Ia) or Formula (Ib), wherein:
$R^1$ is —NHR² or —NHCHR²R³;
$R^2$ is —$C_4$-$C_6$alkyl;
$R^3$ is $L_1$OH;
$L_1$ is —(CH₂)$_m$—;
$L_2$ is —(CH₂)$_n$—, —((CH₂)$_n$O)$_t$(CH₂)$_n$—, —(CH₂)$_n$X₁(CH₂)$_n$—, —(CH₂)$_n$NHC(═O)(CH₂)$_n$—, —(CH₂)$_n$NHC(═O(CH₂)$_n$C(═O)NH(CH₂)$_n$—, —((CH₂)$_n$O)$_t$(CH₂)$_n$NHC(═O)(CH₂)$_n$, —C(═O)(CH₂)$_n$—, —C(═O)((CH₂)$_n$O)$_t$(CH₂)$_n$—, —C(═O)((CH₂)$_n$O)$_t$(CH₂)$_n$X₁(CH₂)$_n$—, —C(═O)((CH₂)$_n$O)$_t$(CH₂)$_n$NHC(═O)(CH₂)$_n$—, —C(═O)((CH₂)$_n$O)$_t$(CH₂)$_n$C(═O)NH(CH₂)$_n$—, —C(═O)NH((CH₂)$_n$O)$_t$(CH₂)$_n$X₁(CH₂)$_n$—, —C(═O)X₂X₃C(═O)((CH₂)$_n$O)$_t$(CH₂)$_n$—, —C(═O)X₂C(═O)(CH₂)$_n$NHC(═O)(CH₂)$_n$—, or —C(═O)(CH₂)$_n$C(═O)NH(CH₂)$_n$—;
$R^4$ is

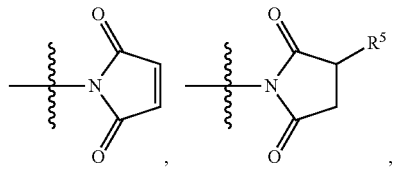

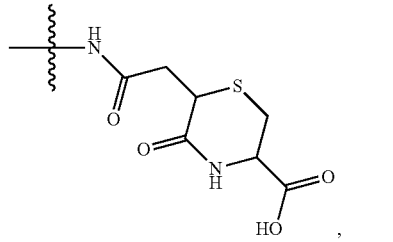

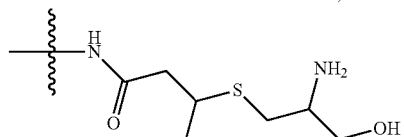

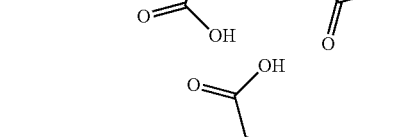

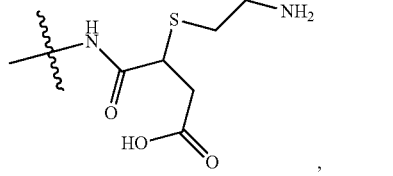

—ONH$_2$, —NH$_2$,

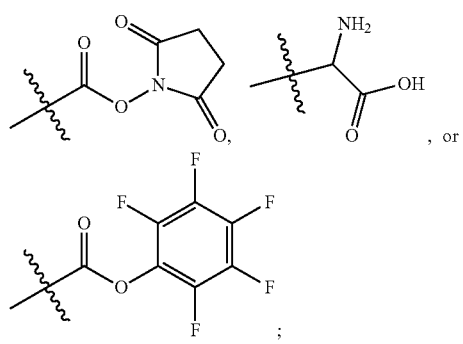

;

R$^5$ is

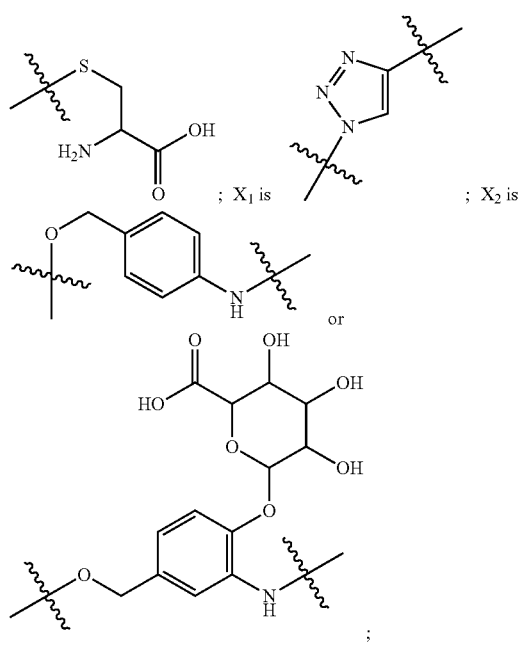

; X$_1$ is <image> ; X$_2$ is <image> or <image>;

X$_3$ is

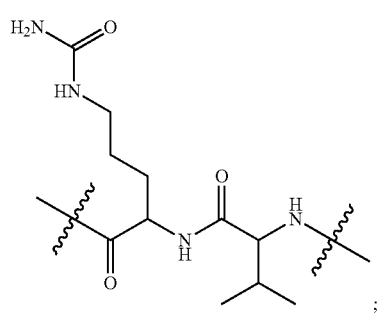 [SMILES: *NC(C(=O)NC(CCCNC(N)=O)C(*)=O)C(C)C]

;

each m is independently selected from 1, 2, 3, and 4;
each n is independently selected from 1, 2, 3, and 4; and
each t is independently selected from 1, 2, 3, 4, 5, 6, 7, 8, 9, 10, 11, 12, 13, 14, 15, 16, 17 and 18.

Embodiment 6

The compound of Formula (I), Formula (Ia) or Formula (Ib), wherein:

R$^1$ is —NHR$^2$; R$^2$ is —C$_4$-C$_6$alkyl;

L$_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$— —((CH$_2$)$_n$O)$_t$(CH$_2$)$_n$NHC(=O)(CH$_2$)$_n$, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)NH(CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$C(=O)(CH$_2$)$_n$NHC(=O)(CH$_2$)$_n$—, or —C(=O)(CH$_2$)$_n$C(=O)NH(CH$_2$)$_n$—;

R$^4$ is

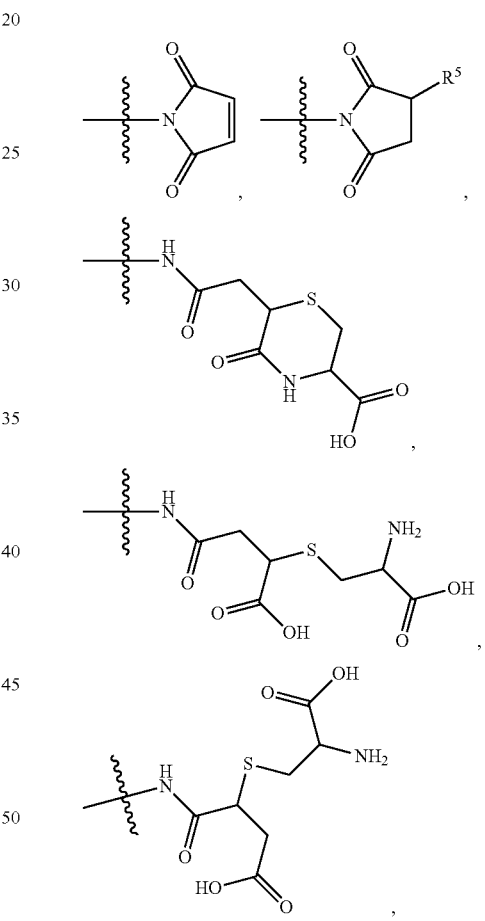

—ONH$_2$, —NH$_2$,

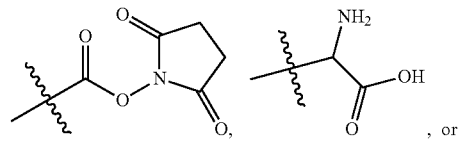

, or

-continued

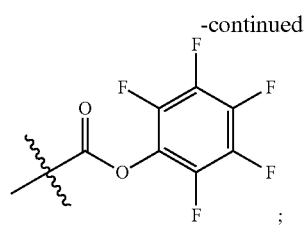

$R^5$ is

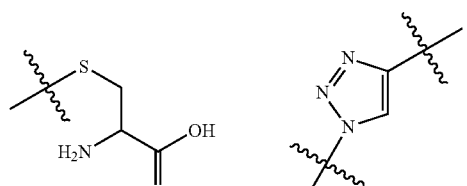

; $X_1$ is  ; $X_2$ is


or


;

$X_3$ is


;

each n is independently selected from 1, 2, 3, and 4, and each t is independently selected from 1, 2, 3, 4, 5, 6, 7, 8, 9, 10, 11, 12, 13, 14, 15, 16, 17 and 18.

Embodiment 7

The compound of Formula (I), Formula (Ia) or Formula (Ib), wherein:
$R^1$ is —NHR²;
$R^2$ is —C₄-C₆alkyl;
$L_2$ is —(CH₂)ₙ—, —((CH₂)ₙO)ₜ(CH₂)ₙ—, —(CH₂)ₙX₁(CH₂)ₙ—, —C(=O)(CH₂)ₙ—, —C(=O)((CH₂)ₙO)ₜ(CH₂)ₙ—, —C(=O)((CH₂)ₙO)ₜ(CH₂)ₙX₁(CH₂)ₙ—, —C(=O)NH((CH₂)ₙO)ₜ(CH₂)ₙX₁(CH₂)ₙ—, —C(=O)X₂X₃C(=O)((CH₂)ₙO)ₜ(CH₂)ₙ— or —C(=O)X₂C(=O)(CH₂)ₙNHC(=O)(CH₂)ₙ—;

$R^4$ is

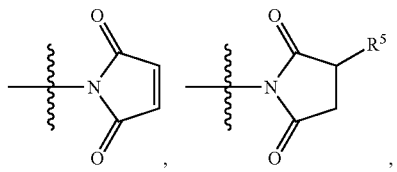

,

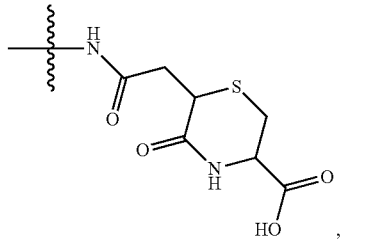

,

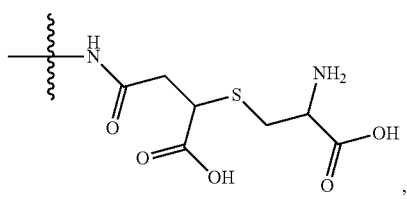

,

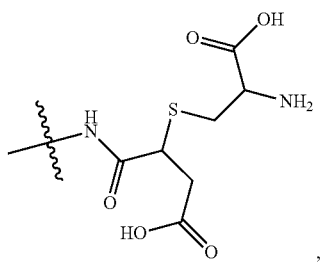

,

—ONH₂, —NH₂,

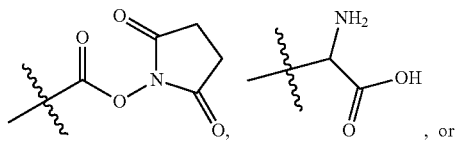

, or

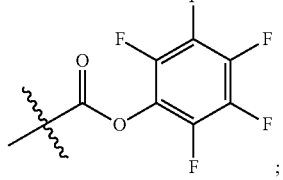

;

$R^5$ is

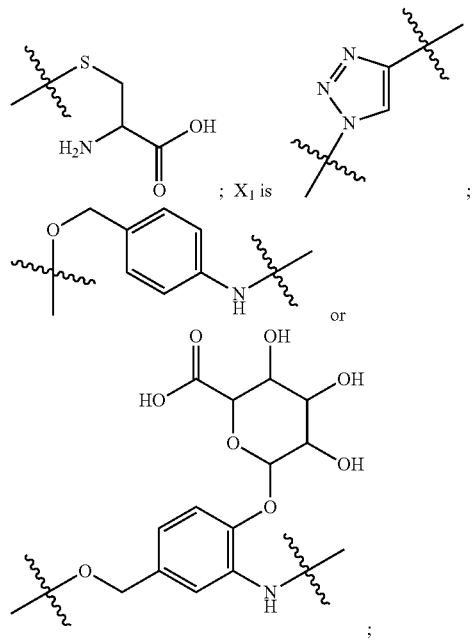
; $X_1$ is 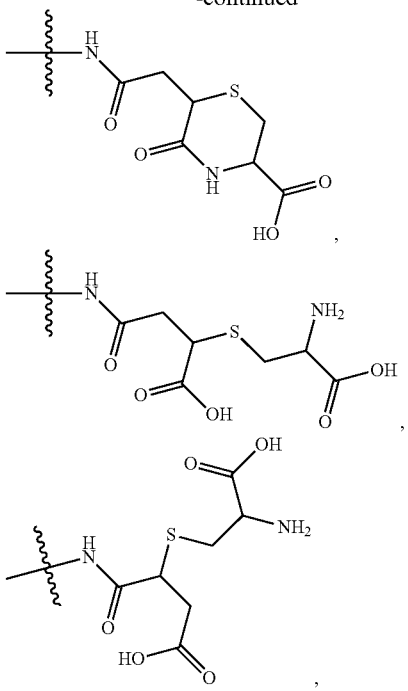 ; $X_2$ is

-continued

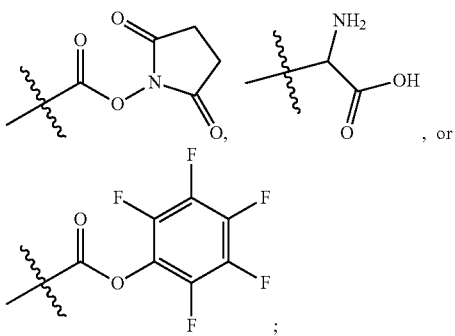

—ONH$_2$, —NH$_2$, $X_3$ is

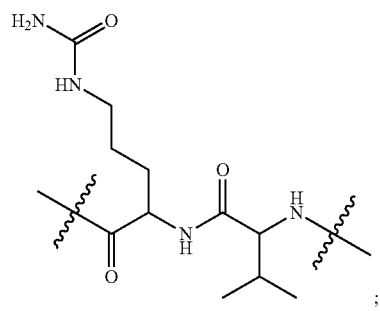 [SMILES: *NC(C(=O)NC(CCCNC(N)=O)C(*)=O)C(C)C]
;

each n is independently selected from 1, 2, 3, and 4, and
each t is independently selected from 1, 2, 3, 4, 5, 6, 7, 8, 9, 10, 11, 12, 13, 14, 15, 16, 17 and 18.

Embodiment 8

The compound of Formula (I), Formula (Ia) or Formula (Ib), wherein:
R$^1$ is NHR$^2$;
R$^2$ is —C$_4$-C$_6$alkyl;
L$_2$ is —(CH$_2$)$_n$— or —C(=O)(CH$_2$)$_n$;
R$^4$ is

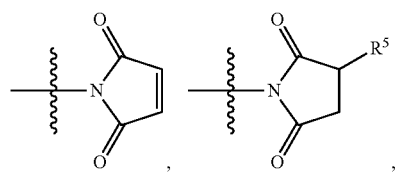
, $R^5$ is

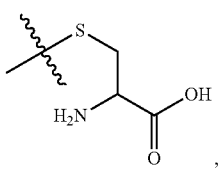 [SMILES: *SCC(N)C(=O)O]
, and
each n is independently selected from 1, 2, 3, and 4.

Embodiment 9

The compound of Formula (I), Formula (Ia) or Formula (Ib), wherein:
R$^1$ is NHR$^2$;
R$^2$ is —C$_4$-C$_6$alkyl;
L$_2$ is —(CH$_2$)$_n$— or —C(=O)(CH$_2$)$_n$;

103

R⁴ is

[structures: maleimide, substituted succinimide with R⁵, thiomorpholinone-carboxylic acid, cysteine-thioether with aspartate, cysteine-thioether with aspartate isomer]

R⁵ is

[structure: cysteine-thioether]

and
each n is independently selected from 1, 2, 3, and 4.

Embodiment 10

The compound of Formula (I), Formula (Ia) or Formula (Ib), wherein:
$R^1$ is $NHR^2$;
$R^2$ is —$C_4$-$C_6$alkyl;
$L_2$ is —$(CH_2)_n$— or —$C(=O)(CH_2)_n$;
$R^4$ is —$ONH_2$ or —$NH_2$;
and
each n is independently selected from 1, 2, 3, and 4.

Embodiment 11

The compound of Formula (I), Formula (Ia) or Formula (Ib), wherein:
$R^1$ is $NHR^2$;
$R^2$ is —$C_4$-$C_6$alkyl;
$L_2$ is —$(CH_2)_n$— or —$C(=O)(CH_2)_n$;

104

R⁴ is

[structures: NHS ester, amino acid, pentafluorophenyl ester]

and
each n is independently selected from 1, 2, 3, and 4.

Embodiment 12

The compound of Formula (I), Formula (Ia) or Formula (Ib), wherein: $R^1$ is —$NHR^2$.

Embodiment 13

The compound of Formula (I), Formula (Ia) or Formula (Ib), wherein: $R^1$ is —$NHCHR^2R^3$.

Embodiment 14

The compound of Formula (I), Formula (Ia) or Formula (Ib), wherein: $R^2$ is —$C_4$alkyl.

Embodiment 15

The compound of Formula (I), Formula (Ia) or Formula (Ib), wherein: $R^2$ is —$C_5$alkyl.

Embodiment 16

The compound of Formula (I), Formula (Ia) or Formula (Ib), wherein: $R^2$ is —$C_6$alkyl.

Embodiment 17

The compound of Formula (I), Formula (Ia) or Formula (Ib), wherein: $R^3$ is $L_1OH$.

Embodiment 18

The compound of Formula (I), Formula (Ia) or Formula (Ib), wherein: $L_1$ is —$(CH_2)$—.

Embodiment 19

The compound of Formula (I), Formula (Ia) or Formula (Ib), wherein: $L_1$ is —$(CH_2CH_2)$—.

Embodiment 20

The compound of Formula (I), Formula (Ia) or Formula (Ib), wherein:
$L_2$ is —$(CH_2)_n$—*, —$((CH_2)_nO)_t(CH_2)_n$—*, —$(CH_2)_nX_1$ $(CH_2)_n$—*, —$(CH_2)_nNHC(=O)(CH_2)_n$—*, —$(CH_2)_n$ NHC(=O)(CH$_2$)$_n$C(=O)NH(CH$_2$)$_n$—*, or —((CH$_2$)$_n$O)$_t$(CH$_2$)$_n$NHC(=O)(CH$_2$)$_n$*, where the * denotes attachment point to R$^4$.

Embodiment 21

The compound of Formula (I), Formula (Ia) or Formula (Ib), wherein:
L$_2$ is —C(=O)(CH$_2$)$_n$*—, —C(=O)((CH$_2$)$_n$O)$_t$(CH$_2$)$_n$—*, —C(=O)((CH$_2$)$_n$O)$_t$(CH$_2$)$_n$X$_1$(CH$_2$)$_n$—*, —C(=O)((CH$_2$)$_n$O)$_t$(CH$_2$)$_n$NHC(=O)(CH$_2$)$_n$—*, —C(=O)((CH$_2$)$_n$O)$_t$(CH$_2$)$_n$C(=O)NH(CH$_2$)$_n$—*, —C(=O)NH(CH$_2$)$_n$O)$_t$(CH$_2$)$_n$X$_1$(CH$_2$)$_n$—*, —C(=O)X$_2$X$_3$C(=O)((CH$_2$)$_n$O)$_t$(CH$_2$)$_n$—*, —C(=O)X$_2$C(=O)(CH$_2$)$_n$NHC(=O)(CH$_2$)$_n$—*, or —C(=O)(CH$_2$)$_n$C(=O)NH(CH$_2$)$_n$—*, where the * denotes attachment point to R$^4$.

Embodiment 22

The compound of Formula (I), Formula (Ia) or Formula (Ib), wherein:
L$_2$ is —(CH$_2$)$_n$—* or —C(=O)(CH$_2$)$_n$—*, where the * denotes attachment point to R$^4$.

Embodiment 23

The compound of Formula (I), Formula (Ia) or Formula (Ib), wherein:
L$_2$ is —(CH$_2$CH$_2$)—* or —C(=O)(CH$_2$CH$_2$)—*, where the * denotes attachment point to R$^4$.

Embodiment 24

The compound of Formula (I), Formula (Ia) or Formula (Ib), wherein:
L$_2$ is —C(=O)X$_2$X$_3$C(=O)(CH$_2$)$_n$—*, —C(=O)X$_2$C(=O)(CH$_2$)$_n$NHC(=O)((CH$_2$)$_n$O)$_t$(CH$_2$)$_n$—*, —C(=O)(CH$_2$)$_n$C(R$_7$)$_2$—*, —C(=O)(CH$_2$)$_n$C(R$_7$)$_2$SS(CH$_2$)$_n$NHC(=O)(CH$_2$)$_n$—*, or —(CH$_2$)$_n$X$_2$C(=O)(CH$_2$)$_n$NHC(=O)((CH$_2$)$_n$O)$_t$(CH$_2$)$_n$—*, where the * denotes attachment point to R$^4$.

Embodiment 25

The compound of Formula (I), Formula (Ia), or Formula (Ib), wherein:
R$^4$ is

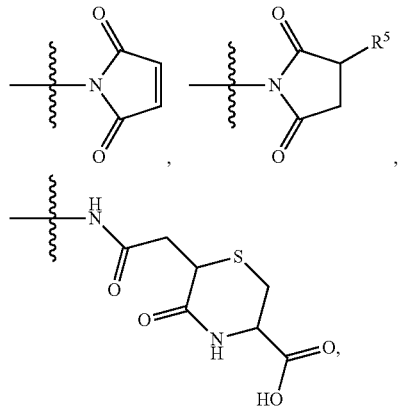

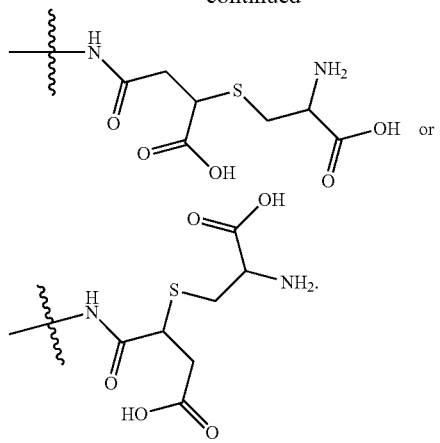

Embodiment 26

The compound of Formula (I), Formula (Ia) or Formula (Ib), wherein:
R$^4$ is —ONH$_2$,

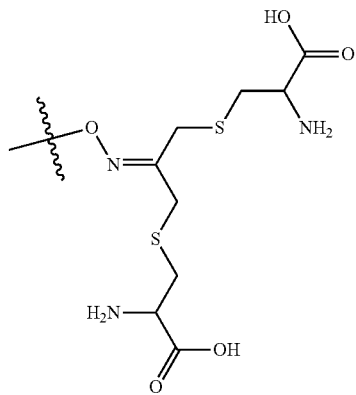 [SMILES: *ON=C(CSCC(N)C(=O)O)CSCC(N)C(=O)O]

or —NH$_2$.

Embodiment 27

The compound of Formula (I), Formula (Ia) or Formula (Ib), wherein:
R$^4$ is

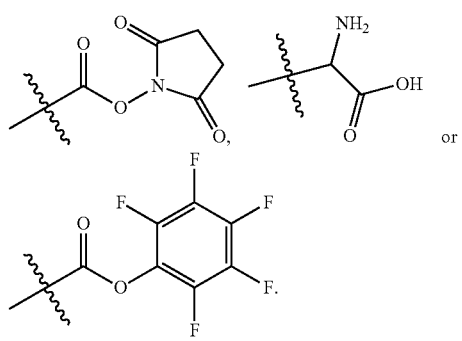

Embodiment 28
The compound of Formula (I), Formula (Ia) or Formula (Ib), wherein:
R$^4$ is —NHC(=O)CH=CH$_2$, —N$_3$,
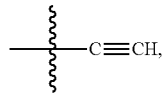
SH, —SSR$^6$, —S(=O)$_2$(CH=CH$_2$), —(CH$_2$)$_2$S(=O)$_2$(CH=CH$_2$), —NHS(=O)$_2$(CH=CH$_2$), —NHC(=O)CH$_2$Br, —NHC(=O)CH$_2$I, —C(O)NHNH$_2$,
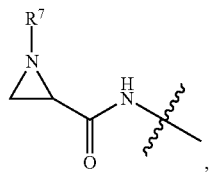
—CO$_2$H, —NHCH(=O) or —NHCH(=S).
Embodiment 29
The compound of Formula (I), Formula (Ia) or Formula (Ib), wherein:
R$^4$ is
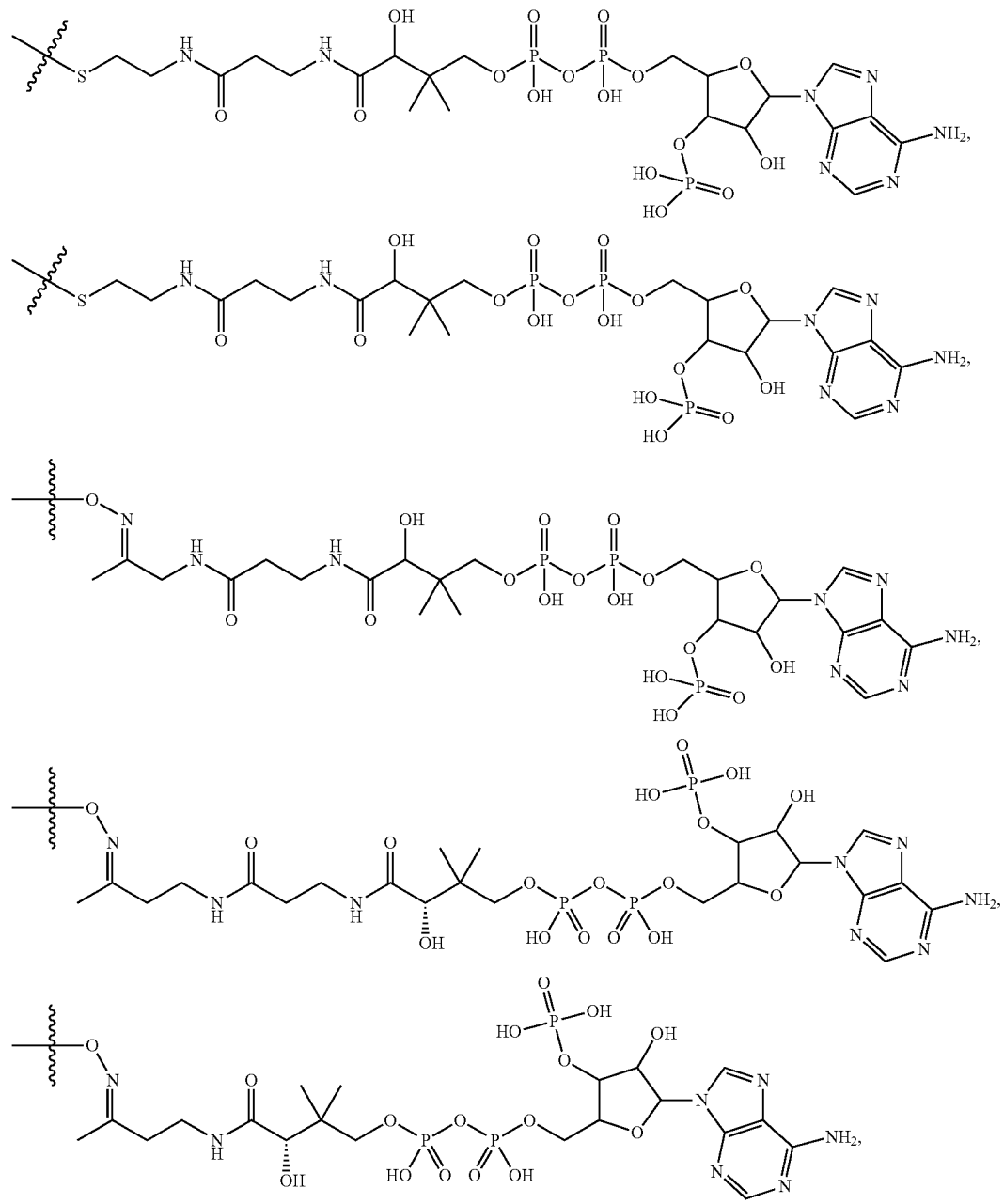

-continued

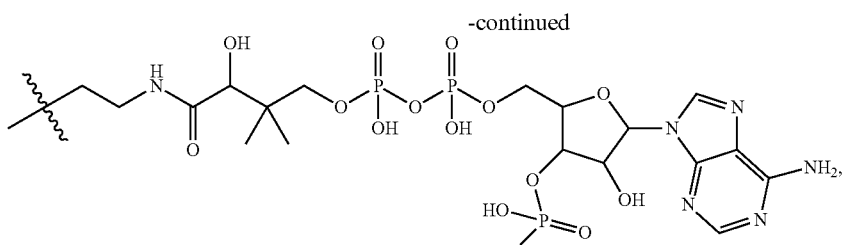

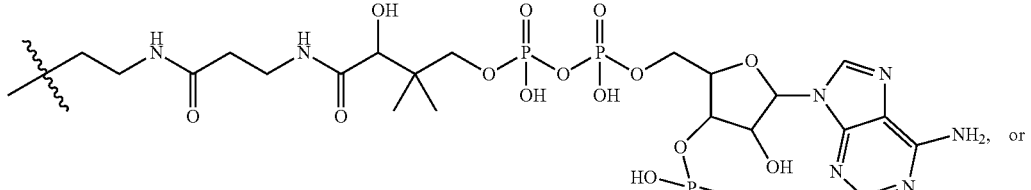

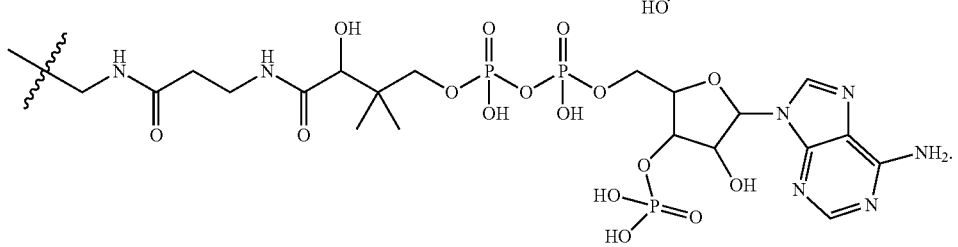

Embodiment 30

The compound of Formula (I), Formula (Ia) or Formula (Ib), wherein:
$R^4$ is —$SR^7$ or —OH.

Embodiment 31

The compound of Formula (I), Formula (Ia) or Formula (Ib), wherein $R^5$ is

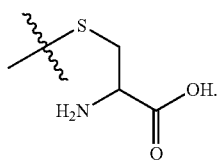 [SMILES: *SCC(N)C(=O)O]

Embodiment 32

The compound of Formula (I), Formula (Ia) or Formula (Ib), wherein: $X_1$ is

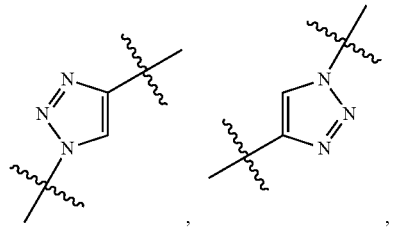

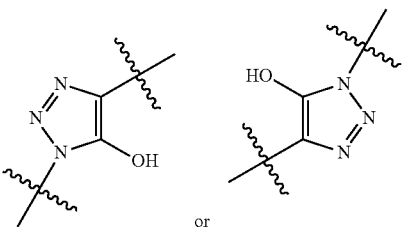

or

Embodiment 33

The compound of Formula (I), Formula (Ia) or Formula (Ib), wherein: $X_1$ is

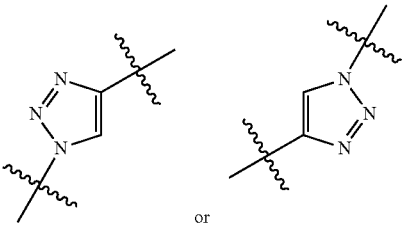

or

Embodiment 34

The compound of Formula (I), Formula (Ia) or Formula (Ib), wherein: $X_1$ is

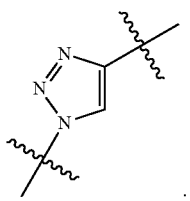 [SMILES: *c1cn(*)nn1]

Embodiment 35

The compound of Formula (I), Formula (Ia) or Formula (Ib), wherein: $X_2$ is

,

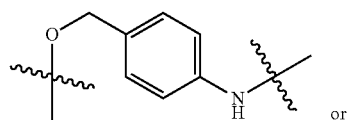 or

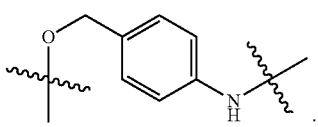 [SMILES: *Nc1ccc(CO*)cc1]

Embodiment 36

The compound of Formula (I), Formula (Ia) or Formula (Ib), wherein: $X_2$ is

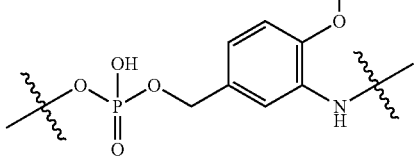

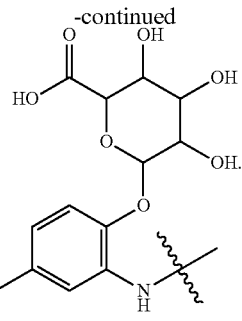

Embodiment 37

The compound of Formula (I), Formula (Ia) or Formula (Ib), wherein: $X_2$ is

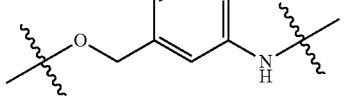.

Embodiment 38

The compound of Formula (I), Formula (Ia) or Formula (Ib), wherein: $X_2$ is

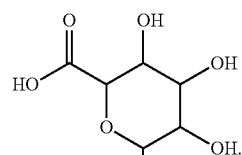

Embodiment 39

The compound of Formula (I), Formula (Ia) or Formula (Ib), wherein: $X_2$ is

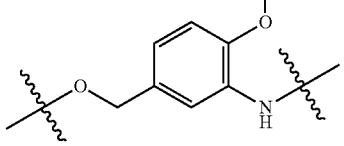

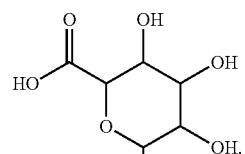

Embodiment 40

The compound of Formula (I), Formula (Ia) or Formula (Ib), wherein: $X_3$ is

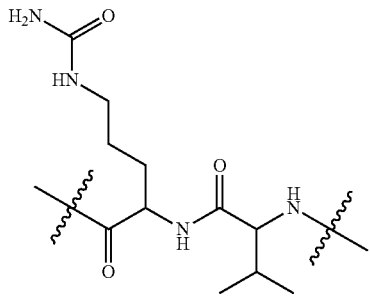

,

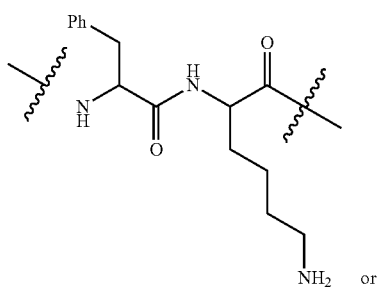

or

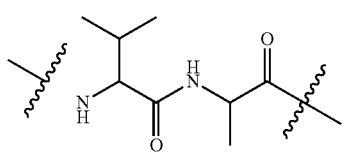

.

Embodiment 41

The compound of Formula (I), Formula (Ia) or Formula (Ib), wherein: $X_3$ is

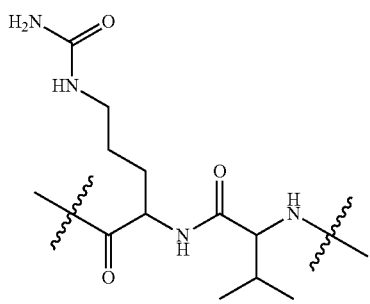

.

Embodiment 42

The compound of Formula (I), Formula (Ia) or Formula (Ib), wherein: $X_3$ is

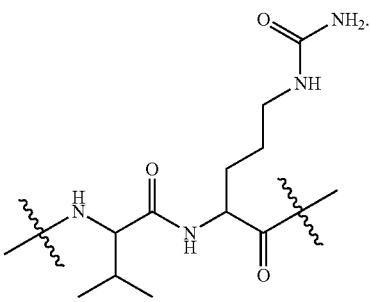 [SMILES: *NC(C(=O)NC(CCCNC(N)=O)C(*)=O)C(C)C]

Embodiment 43

The compound of Formula (I), Formula (Ia) or Formula (Ib), wherein: $X_3$ is

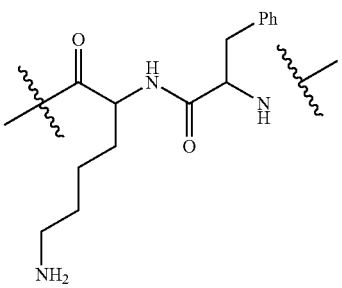

.

Embodiment 44

The compound of Formula (I), Formula (Ia) or Formula (Ib), wherein: $X_3$ is

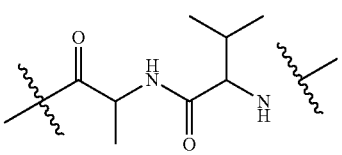

.

Embodiment 45

The compound of Formula (I), Formula (Ia) or Formula (Ib), wherein: $R^6$ is 2-pyridyl or 4-pyridyl.

Embodiment 46

The compound of Formula (I), Formula (Ia) or Formula (Ib), wherein: each $R^7$ is independently selected from H and $C_1$-$C_6$alkyl.

Embodiment 47

The compound of Formula (I), Formula (Ia) or Formula (Ib), wherein: each $R^7$ is H.

Embodiment 48

The compound of Formula (I), Formula (Ia) or Formula (Ib), wherein: each $R^7$ is $C_1$-$C_6$alkyl.

Embodiment 49

The compound of Formula (I), Formula (Ia) or Formula (Ib), wherein: each m is independently selected from 1, 2, 3, and 4.

Embodiment 50

The compound of Formula (I), Formula (Ia) or Formula (Ib), wherein: each m is 1 or 2.

Embodiment 51

The compound of Formula (I), Formula (Ia) or Formula (Ib), wherein: each n is independently selected from 1, 2, 3, and 4.

Embodiment 52

The compound of Formula (I), Formula (Ia) or Formula (Ib), wherein: each n is 2 or 3.

Embodiment 53

The compound of Formula (I), Formula (Ia) or Formula (Ib), wherein: each t is independently selected from 1, 2, 3, 4, 5, 6, 7, 8, 9, 10, 11, 12, 13, 14, 15, 16, 17 and 18.

Embodiment 54

The compound of Formula (I), Formula (Ia) or Formula (Ib), wherein: each t is independently selected from 1, 2, 3, 4, 5 and 6.

Embodiment 55

The compound of Formula (I), Formula (Ia) or Formula (Ib) selected from:
1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-1H-pyrrole-2,5-dione;
(2R)-2-amino-3-((1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-2,5-dioxopyrrolidin-3-yl)thio)propanoic acid;
(6R)-6-(2-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-2-oxoethyl)-5-oxothiomorpholine-3-carboxylic acid;
3-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid;
(S)-3-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid;
(R)-3-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid;
2-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid;
(R)-2-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid;
(S)-2-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid;
1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-pyrrole-2,5-dione;
(2S)-2-amino-3-((1-(2-(4-(4-((2-amino-4-(pentylamino)-5H-pyrrolo[3,2-d]pyrimidin-5-yl)methyl)-3-methoxybenzyl)piperazin-1-yl)ethyl)-2,5-dioxopyrrolidin-3-yl)thio)propanoic acid;
(6R)-6-(2-((2-(4-(4-((2-amino-4-(pentylamino)-5H-pyrrolo[3,2-d]pyrimidin-5-yl)methyl)-3-methoxybenzyl)piperazin-1-yl)ethyl)amino)-2-oxoethyl)-5-oxothiomorpholine-3-carboxylic acid;
3-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid;
(S)-3-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid;
(R)-3-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid;
2-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid;
(R)-2-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid;
(S)-2-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid;
1-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-1H-pyrrole-2,5-dione;
3-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid;
(S)-3-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid;
(R)-3-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid;
2-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid;
(R)-2-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid;
(S)-2-(((R)-2-amino-2-carboxyethyl)thio)-4-((2-(3-(4-(4-((2-amino-4-(pentylamino)-5H-pyrrolo[3,2-d]pyrimidin- 5-yl)methyl)-3-methoxybenzyl)piperazin-1-yl)-3-oxopropoxy)ethyl)amino)-4-oxobutanoic acid;

1-(2-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-pyrrole-2,5-dione;

(2R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,19-dioxo-10,13,16-trioxa-4-thia-7-azanonadecan-1-oic acid;

(2R,5S)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,19-dioxo-10,13,16-trioxa-4-thia-7-azanonadecan-1-oic acid;

(2R,5R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,19-dioxo-10,13,16-trioxa-4-thia-7-azanonadecan-1-oic acid;

(19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,14-dioxo-4,7,10-trioxa-17-thia-13-azaicosan-20-oic acid;

(16R,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,14-dioxo-4,7,10-trioxa-17-thia-13-azaicosan-20-oic acid;

(16S,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,14-dioxo-4,7,10-trioxa-17-thia-13-azaicosan-20-oic acid;

1-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-1H-pyrrole-2,5-dione;

(2R)-2-amino-28-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,28-dioxo-10,13,16,19,22,25-hexaoxa-4-thia-7-azaoctacosan-1-oic acid;

(2R,5S)-2-amino-28-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,28-dioxo-10,13,16,19,22,25-hexaoxa-4-thia-7-azaoctacosan-1-oic acid;

(2R,5R)-2-amino-28-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,28-dioxo-10,13,16,19,22,25-hexaoxa-4-thia-7-azaoctacosan-1-oic acid;

(28R)-28-amino-1-(4-(4-((2-amino-4-(pentylamino)-5H-pyrrolo[3,2-d]pyrimidin-5-yl)methyl)-3-methoxybenzyl)piperazin-1-yl)-25-carboxy-1,23-dioxo-4,7,10,13,16,19-hexaoxa-26-thia-22-azanonacosan-29-oic acid;

(25R,28R)-28-amino-1-(4-(4-((2-amino-4-(pentylamino)-5H-pyrrolo[3,2-d]pyrimidin-5-yl)methyl)-3-methoxybenzyl)piperazin-1-yl)-25-carboxy-1,23-dioxo-4,7,10,13,16,19-hexaoxa-26-thia-22-azanonacosan-29-oic acid;

(25S,28R)-28-amino-1-(4-(4-((2-amino-4-(pentylamino)-5H-pyrrolo[3,2-d]pyrimidin-5-yl)methyl)-3-methoxybenzyl)piperazin-1-yl)-25-carboxy-1,23-dioxo-4,7,10,13,16,19-hexaoxa-26-thia-22-azanonacosan-29-oic acid;

1-((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)-1H-pyrrole-2,5-dione;

(2R)-2-amino-3-((2-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-2-oxoethyl)thio)pentanedioic acid;

N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-3-(2,5-dioxo-2,5-dihydro-1H-pyrrol-1-yl)propanamide;

(19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-(carboxymethyl)-1,11,15-trioxo-4,7-dioxa-17-thia-10,14-diazaicosan-20-oic acid;

(16S,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-(carboxymethyl)-1,11,15-trioxo-4,7-dioxa-17-thia-10,14-diazaicosan-20-oic acid;

(16R,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-(carboxymethyl)-1,11,15-trioxo-4,7-dioxa-17-thia-10,14-diazaicosan-20-oic acid;

(20R)-20-amino-1-(4-(4-((2-amino-4-(pentylamino)-5H-pyrrolo[3,2-d]pyrimidin-5-yl)methyl)-3-methoxybenzyl)piperazin-1-yl)-17-carboxy-1,11,15-trioxo-4,7-dioxa-18-thia-10,14-diazahenicosan-21-oic acid;

(17R,20R)-20-amino-1-(4-(4-((2-amino-4-(pentylamino)-5H-pyrrolo[3,2-d]pyrimidin-5-yl)methyl)-3-methoxybenzyl)piperazin-1-yl)-17-carboxy-1,11,15-trioxo-4,7-dioxa-18-thia-10,14-diazahenicosan-21-oic acid;

(17S,20R)-20-amino-1-(4-(4-((2-amino-4-(pentylamino)-5H-pyrrolo[3,2-d]pyrimidin-5-yl)methyl)-3-methoxybenzyl)piperazin-1-yl)-17-carboxy-1,11,15-trioxo-4,7-dioxa-18-thia-10,14-diazahenicosan-21-oic acid;

5-(4-((4-(3-aminopropyl)piperazin-1-yl)methyl)-2-methoxybenzyl)-N4-pentyl-5H-pyrrolo[3,2-d]pyrimidine-2,4-diamine;

1-(4-(4-((2-amino-4-(pentylamino)-5H-pyrrolo[3,2-d]pyrimidin-5-yl)methyl)-3-methoxybenzyl)piperazin-1-yl)-3-(2-(2-aminoethoxy)ethoxy)propan-1-one;

N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-2-(2,5-dioxo-2,5-dihydro-1H-pyrrol-1-yl)acetamide;

(2R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,9,19-trioxo-13,16-dioxa-4-thia-7,10-diazanonadecan-1-oic acid;

(2R,5S)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,9,19-trioxo-13,16-dioxa-4-thia-7,10-diazanonadecan-1-oic acid;

(2R,5R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,9,19-trioxo-13,16-dioxa-4-thia-7,10-diazanonadecan-1-oic acid;

(19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,11,14-trioxo-4,7-dioxa-17-thia-10,13-diazaicosan-20-oic acid;

(16R,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,11,14-trioxo-4,7-dioxa-17-thia-10,13-diazaicosan-20-oic acid;

(16S,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,11,14-trioxo-4,7-dioxa-17-thia-10,13-diazaicosan-20-oic acid;

4-(4-((2-amino-4-(pentylamino)-5H-pyrrolo[3,2-d]pyrimidin-5-yl)methyl)-3-methoxybenzyl)-N-(2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl)piperazine-1-carboxamide;

3-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid;

(S)-3-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid;

(R)-3-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid;

2-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid;

(R)-2-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid;

(S)-2-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid;

1-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)-1H-pyrrole-2,5-dione;

3-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid;

(S)-3-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid;

(R)-3-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid;

2-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid;

(R)-2-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid;

(S)-2-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid;

1-((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)-1H-pyrrole-2,5-dione;

3-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid;

(S)-3-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid;

(R)-3-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid;

2-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid;

(R)-2-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid;

(S)-2-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid;

N-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-3-(2,5-dioxo-2,5-dihydro-1H-pyrrol-1-yl)propanamide;

4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl 4-(4-((2-amino-4-(pentylamino)-5H-pyrrolo[3,2-d]pyrimidin-5-yl)methyl)-3-methoxybenzyl)piperazine-1-carboxylate;

(2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2,5-dioxo-2,5-dihydro-1H-pyrrol-1-yl)propanamido)propanamido)phenoxy)-3,4,5-trihydroxytetrahydro-2H-pyran-2-carboxylic acid;

(S)-1-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropyl)-1H-pyrrole-2,5-dione;

1-(3-(4-(3-((2-amino-4-(pentylamino)-5H-pyrrolo[3,2-d]pyrimidin-5-yl)methyl)-4-methoxybenzyl)piperazin-1-yl)-3-oxopropyl)-1H-pyrrole-2,5-dione;

3-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid;

(S)-3-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid;

(R)-3-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid;

2-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid;

(R)-2-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid;

(S)-2-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid;

1-(4-(4-((2-amino-4-(pentylamino)-5H-pyrrolo[3,2-d]pyrimidin-5-yl)methyl)-3-methoxybenzyl)piperazin-1-yl)-2-(aminooxy)ethanone;

1-(4-(4-((2-amino-4-(pentylamino)-5H-pyrrolo[3,2-d]pyrimidin-5-yl)methyl)-3-methoxybenzyl)piperazin-1-yl)-3-(2-aminoethoxy)propan-1-one;
N-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-2-(aminooxy)acetamide;
(S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-2-(aminooxy)ethanone;
(S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-(2-(2-aminoethoxy)ethoxy)propan-1-one;
(S)—N-(2-(2-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropoxy)ethoxy)ethyl)-2-(aminooxy)acetamide;
N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-2-(aminooxy)acetamide;
5-(4-((4-(2-(2-(aminooxy)ethoxy)ethyl)piperazin-1-yl)methyl)-2-methoxybenzyl)-N4-pentyl-5H-pyrrolo[3,2-d]pyrimidine-2,4-diamine;
N-(3-(4-(4-((2-amino-4-(pentylamino)-5H-pyrrolo[3,2-d]pyrimidin-5-yl)methyl)-3-methoxybenzyl)piperazin-1-yl)propyl)-2-(aminooxy)acetamide;
5-(4-((4-(2-(2-(2-aminoethoxy)ethoxy)ethyl)piperazin-1-yl)methyl)-2-methoxybenzyl)-N4-pentyl-5H-pyrrolo[3,2-d]pyrimidine-2,4-diamine;
N-(2-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethoxy)ethyl)-2-(aminooxy)acetamide;
2,5-dioxopyrrolidin-1-yl 5-(4-(4-((2-amino-4-(pentylamino)-5H-pyrrolo[3,2-d]pyrimidin-5-yl)methyl)-3-methoxybenzyl)piperazin-1-yl)-5-oxopentanoate;
(S)-2,5-dioxopyrrolidin-1-yl 5-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-5-oxopentanoate;
(S)-2-amino-6-(5-(4-(3-((2-amino-4-(((S)-1-hydroxyhexan-2-yl)amino)-5H-pyrrolo[3,2-d]pyrimidin-5-yl)methyl)-4-methoxybenzyl)piperazin-1-yl)-5-oxopentanamido)hexanoic acid;
(S)-2-amino-6-(5-(4-(4-((2-amino-4-(pentylamino)-5H-pyrrolo[3,2-d]pyrimidin-5-yl)methyl)-3-methoxybenzyl)piperazin-1-yl)-5-oxopentanamido)hexanoic acid;
2,5-dioxopyrrolidin-1-yl 5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanoate;
(S)-2-amino-6-(5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanamido)hexanoic acid;
2,5-dioxopyrrolidin-1-yl 5-(4-(3-((2-amino-4-(pentylamino)-5H-pyrrolo[3,2-d]pyrimidin-5-yl)methyl)-4-methoxybenzyl)piperazin-1-yl)-5-oxopentanoate;
(S)-2-amino-6-(5-(4-(3-((2-amino-4-(pentylamino)-5H-pyrrolo[3,2-d]pyrimidin-5-yl)methyl)-4-methoxybenzyl)piperazin-1-yl)-5-oxopentanamido)hexanoic acid;
perfluorophenyl 5-(4-(4-((2-amino-4-(pentylamino)-5H-pyrrolo[3,2-d]pyrimidin-5-yl)methyl)-3-methoxybenzyl)piperazin-1-yl)-5-oxopentanoate;
perfluorophenyl 3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanoate;
perfluorophenyl 3-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)propanoate;
(S)-2-amino-6-(3-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanamido)hexanoic acid, and
N-(15-(4-(4-((2-amino-4-(pentylamino)-5H-pyrrolo[3,2-d]pyrimidin-5-yl)methyl)-3-methoxybenzyl)piperazin-1-yl)-15-oxo-3,6,9,12-tetraoxapentadecyl)-5-((3aS,4S,6aR)-2-oxohexahydro-1H-thieno[3,4-d]imidazol-4-yl)pentanamide.

Embodiment 56

The compound of Formula (I), Formula (Ia) or Formula (Ib) selected from:
1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-1H-pyrrole-2,5-dione;
1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-pyrrole-2,5-dione;
1-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-1H-pyrrole-2,5-dione, and
1-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)-1H-pyrrole-2,5-dione.

Embodiment 57

The compound of Formula (I), Formula (Ia) or Formula (Ib) selected from:
(2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2-(2,5-dioxo-2,5-dihydro-1H-pyrrol-1-yl)ethoxy)propanamido)propanamido)phenoxy)-3,4,5-trihydroxytetrahydro-2H-pyran-2-carboxylic acid;
4-((R)-6-amino-2-((S)-2-(3-(2,5-dioxo-2,5-dihydro-1H-pyrrol-1-yl)propanamido)-3-phenylpropanamido)hexanamido)benzyl 4-(4-((2-amino-4-(pentylamino)-5H-pyrrolo[3,2-d]pyrimidin-5-yl)methyl)-3-methoxybenzyl)piperazine-1-carboxylate;
4-((S)-2-((S)-2-(3-(2-(2,5-dioxo-2,5-dihydro-1H-pyrrol-1-yl)ethoxy)propanamido)-3-methylbutanamido)propanamido)benzyl 4-(4-((2-amino-4-(pentylamino)-5H-pyrrolo[3,2-d]pyrimidin-5-yl)methyl)-3-methoxybenzyl)piperazine-1-carboxylate;
(2S,3S,4S,5R,6S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2,5-dioxo-2,5-dihydro-1H-pyrrol-1-yl)propanamido)propanamido)phenoxy)-3,4,5-trihydroxytetrahydro-2H-pyran-2-carboxylic acid;
(2S,3S,4S,5R,6S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2-(2,5-dioxo-2,5-dihydro-1H-pyrrol-1-yl)ethoxy)propanamido)propanamido)phenoxy)-3,4,5-trihydroxytetrahydro-2H-pyran-2-carboxylic acid;
N-(2-((5-(4-(4-((2-amino-4-(pentylamino)-5H-pyrrolo[3,2-d]pyrimidin-5-yl)methyl)-3-methoxybenzyl)piperazin-1-yl)-2-methyl-5-oxopentan-2-yl)disulfanyl)ethyl)-3-(2,5-dioxo-2,5-dihydro-1H-pyrrol-1-yl)propanamide;

1-(4-(4-((2-amino-4-(pentylamino)-5H-pyrrolo[3,2-d]pyrimidin-5-yl)methyl)-3-methoxybenzyl)piperazin-1-yl)-4-methyl-4-(methylthio)pentan-1-one;

(2S,3S,4S,5R,6S)-6-(4-((((2-(4-(4-((2-amino-4-(pentylamino)-5H-pyrrolo[3,2-d]pyrimidin-5-yl)methyl)-3-methoxybenzyl)piperazin-1-yl)ethoxy)(hydroxy)phosphoryl)oxy)methyl)-2-(3-(3-(2-(2,5-dioxo-2,5-dihydro-1H-pyrrol-1-yl)ethoxy)propanamido)propanamido)phenoxy)-3,4,5-trihydroxytetrahydro-2H-pyran-2-carboxylic acid;

(2R,2'R)-3,3'-((2-((2-(4-(4-((2-amino-4-(pentylamino)-5H-pyrrolo[3,2-d]pyrimidin-5-yl)methyl)-3-methoxybenzyl)piperazin-1-yl)-2-oxoethoxy)imino)propane-1,3-diyl)bis(sulfanediyl))bis(2-aminopropanoic acid);

(R)-2-amino-6-((((R)-2-amino-2-carboxyethyl)thio)methyl)-17-(4-(4-((2-amino-4-(pentylamino)-5H-pyrrolo[3,2-d]pyrimidin-5-yl)methyl)-3-methoxybenzyl)piperazin-1-yl)-10,17-dioxo-8,14-dioxa-4-thia-7,11-diazaheptadec-6-enoic acid, and 2-(4-(4-((2-amino-4-(pentylamino)-5H-pyrrolo[3,2-d]pyrimidin-5-yl)methyl)-3-methoxybenzyl)piperazin-1-yl)ethan-1-ol.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Processes for Making Compounds of Formula (I) and Subformulae Thereof

General procedures for preparing compounds of Formula (I), and sub-Formulae thereof, are described herein. In the reactions described, reactive functional groups, for example hydroxy, amino, imino, thiol or carboxy groups, where these are desired in the final product, may be protected to avoid their unwanted participation in the reactions. Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

In certain embodiments, compounds of Formula (I) and subformulae thereof, provided herein are prepared as a pharmaceutically acceptable acid addition salt by reacting the free base form of a compound of Formula (I) and subformulae thereof, with a stoichiometric amount of an appropriate pharmaceutically acceptable organic acid or inorganic acid or a suitable anion exchange reagent.

Such reactions are typically carried out in water or in an organic solvent, or in a mixture of the two. Generally, use of non-aqueous media like ether, ethyl acetate, ethanol, isopropanol, or acetonitrile is desirable, where practicable.

Alternatively, the salt forms of compounds of Formula (I) and subformulae thereof, are prepared using salts of the starting materials or intermediates.

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

Pharmaceutically acceptable acid addition salts of compounds of Formula (I) and subformulae thereof, include, but are not limited to, a acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlorotheophyllinate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete and xinafoate salt forms.

The organic acid or inorganic acids used to form certain pharmaceutically acceptable acid addition salts of compounds of Formula (I) and subformulae thereof, include, but are not limited to, acetic acid, adipic acid, ascorbic acid, aspartic acid, benzoic acid, benzenesulfonic acid, carbonic acid, camphor sulfonic acid, capric acid, chlorotheophyllinate, citric acid, ethanedisulfonic acid, fumaric acid, D-glycero-D-gulo-Heptonic acid, galactaric aid, galactaric acid/mucic acid, gluceptic acid, glucoheptonoic acid, gluconic acid, glucuronic acid, glutamatic acid, glutaric acid, glycolic acid, hippuric acid, hydrobromic acid, hydrochloric acid, hydroiodic acid, isethionic acid, lactic acid, lactobionic acid, lauryl sulfuric acid, malic acid, maleic acid, malonic acid, mandelic acid, mesylic acid, methanesulfonic acid, mucic acid, naphthoic acid, 1-hydroxy-2-naphthoic acid, naphthalenesulfonic acid, 2-naphthalenesulfonic acid, nicotinic acid, nitric acid, octadecanoic acid, oleaic acid, oxalic acid, palmitic acid, pamoic acid, phosphoric acid, polygalacturonic acid, propionic acid, sebacic acid, stearic acid, succinic acid, sulfosalicylic acid, sulfuric acid, tartaric acid, p-toluenesulfonic acid, trifluoroacetic acid and triphenylacetic acid.

In one embodiment, the present invention provides 3-(3-fluoro-4-(3-(piperidin-4-yl)propoxy)phenyl)-1-methyl-1H-pyrazolo[3,4-d]pyrimidin-6-amine in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides 3-(4-(((1 r,4r)-4-aminocyclohexyl)methoxy)-3-fluorophenyl)-1-methyl-1H-pyrazolo[3,4-d]pyrimidin-6-amine in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides 3-(4-((4-aminobicyclo[2.2.2]octan-1-yl)methoxy)-3-fluorophenyl)-1-methyl-1H-pyrazolo[3,4-d]pyrimidin-6-amine in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides 3-(4-((4-aminobicyclo[2.2.2]octan-1-yl)methoxy)-3-chlorophenyl)-1-methyl-1H-pyrazolo[3,4-d]pyrimidin-6-amine in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides 4-((2-chloro-4-(6-methoxy-1-methyl-1H-pyrazolo[3,4-d]pyrimidin-3-yl)phenoxy)methyl)bicyclo[2.2.2]octan-1-amine in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

Lists of additional suitable acid addition salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

In certain embodiments, compounds of Formula (I) and subformulae thereof, are prepared or formed, as solvates (e.g., hydrates). In certain embodiments, hydrates of compounds of Formula (I) and subformulae thereof, are prepared by recrystallization from an aqueous/organic solvent mixture, using organic solvents such as dioxin, tetrahydrofuran or methanol. Furthermore, the compounds of the present invention, including their salts, can also be obtained in the form of their hydrates, or include other solvents used for their crystallization.

The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50 enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

In certain embodiments, compounds of Formula (I), or subformulae thereof, are prepared as their individual stereoisomers. In other embodiments, the compounds of Formula (I), or subformulae thereof, are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or subformulae thereof, or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Depending on the choice of the starting materials and procedures, certain embodiments of the compounds of the present invention are present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Intermediates and final products can be worked up and/or purified according to standard methods, e.g. using chromatographic methods, distribution methods, (re-) crystallization, and the like. The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ. All starting materials, building blocks, reagents, acids, bases, dehydrating agents, solvents and catalysts utilized to synthesize the compounds of the present invention are either commercially available or can be produced by organic synthesis methods known to one of ordinary skill in the art.

Compounds of Formula (I) and subformulae thereof (Formula (Ia) and Formula (Ib)) are made by processes described in the general schemes herein and as illustrated in the Examples.

Scheme 1A illustrates a non-limiting synthetic scheme used to make certain compounds of Formula (A1) where the -linker-$R^4$ moiety is attached to intermediate (int-A1) by an amide bond. In Scheme 1A the linker is any linker (L') having a terminal carbonyl moiety (i.e. -L'-C(=O)). Also in Scheme 1A, $R^1$ is as described herein and $R^4$ is a reactive moiety which can react with a thiol, a disulfide, an amine, a ketone, a diketone, an azide or an alkyne. Scheme 1B illustrates a non-limiting synthetic scheme used to make certain compounds of Formula (A1) where the -linker-$R^4$ moiety is attached to intermediate (int-A1) by an amide bond. In Scheme 1B the linker is any linker (L') having a terminal carbonyl moiety (i.e. -L'-C(=O)). Also in Scheme 1B, $R^1$ is as described herein and $R^4$ moiety having an amino group (such as a hydroxyl amine or an amine) and $R^B$ is moiety having a protected amino group, where Prot is a protecting group such as Boc, Fmoc and Cbz.

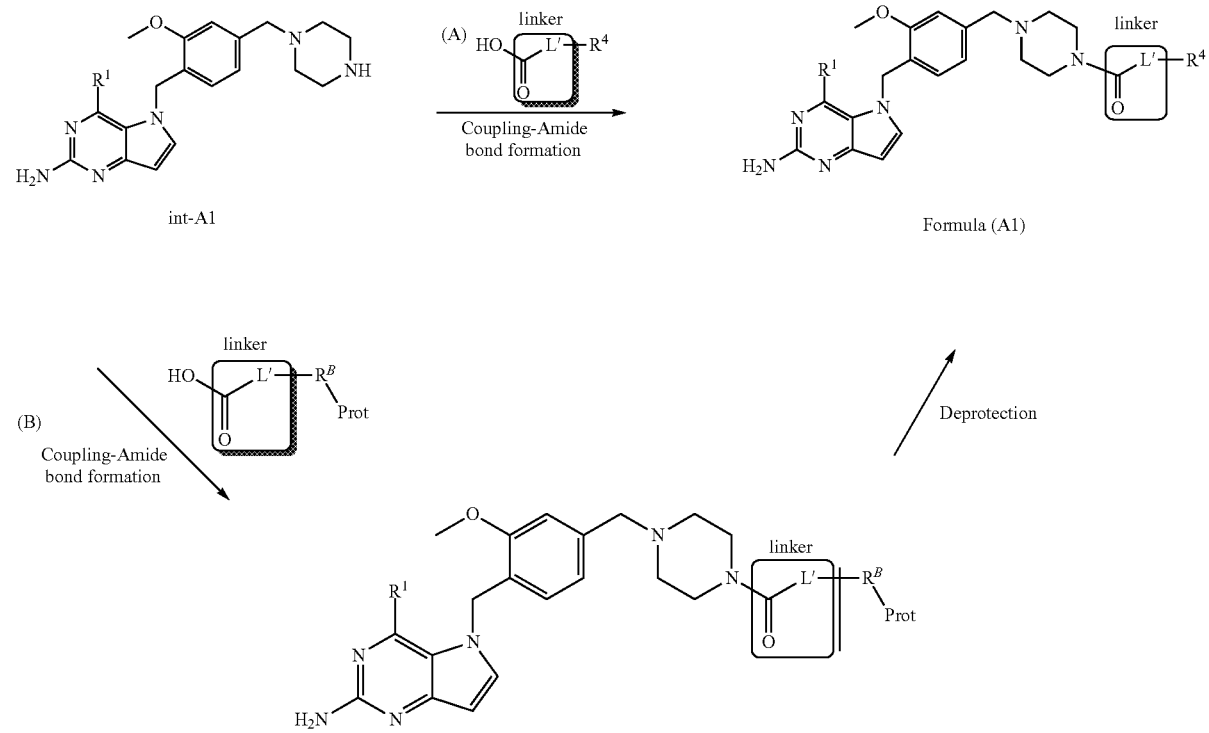

Such amide bond formation can be accomplished using heat, EDCI coupling, HATU coupling, HBTU coupling, TBTU coupling or T3P coupling.

Scheme 2A illustrates a non-limiting synthetic scheme used to make certain compounds of Formula (A2) where the -linker-$R^4$ moiety is attached to intermediate (int-A2) by an amide bond. In Scheme 2A the linker is any linker (L') having a terminal carbonyl moiety (i.e. -L'-C(=O)). Also in Scheme 2A, $R^1$ is as described herein and $R^4$ is a reactive moiety which can react with a thiol, a disulfide, an amine, a ketone, a diketone, an azide or an alkyne. Scheme 2B illustrates a non-limiting synthetic scheme used to make certain compounds of Formula (A2) where the -linker-$R^4$ moiety is attached to intermediate (int-A2) by an amide bond. In Scheme 2B the linker is any linker (L') having a terminal carbonyl moiety (i.e. -L'-C(=O)). Also in Scheme 2B, $R^1$ is as described herein and $R^4$ moiety having an amino group (such as a hydroxyl amine or an amine) and $R^B$ is moiety having a protected amino group, where Prot is a protecting group such as Boc, Fmoc and Cbz.

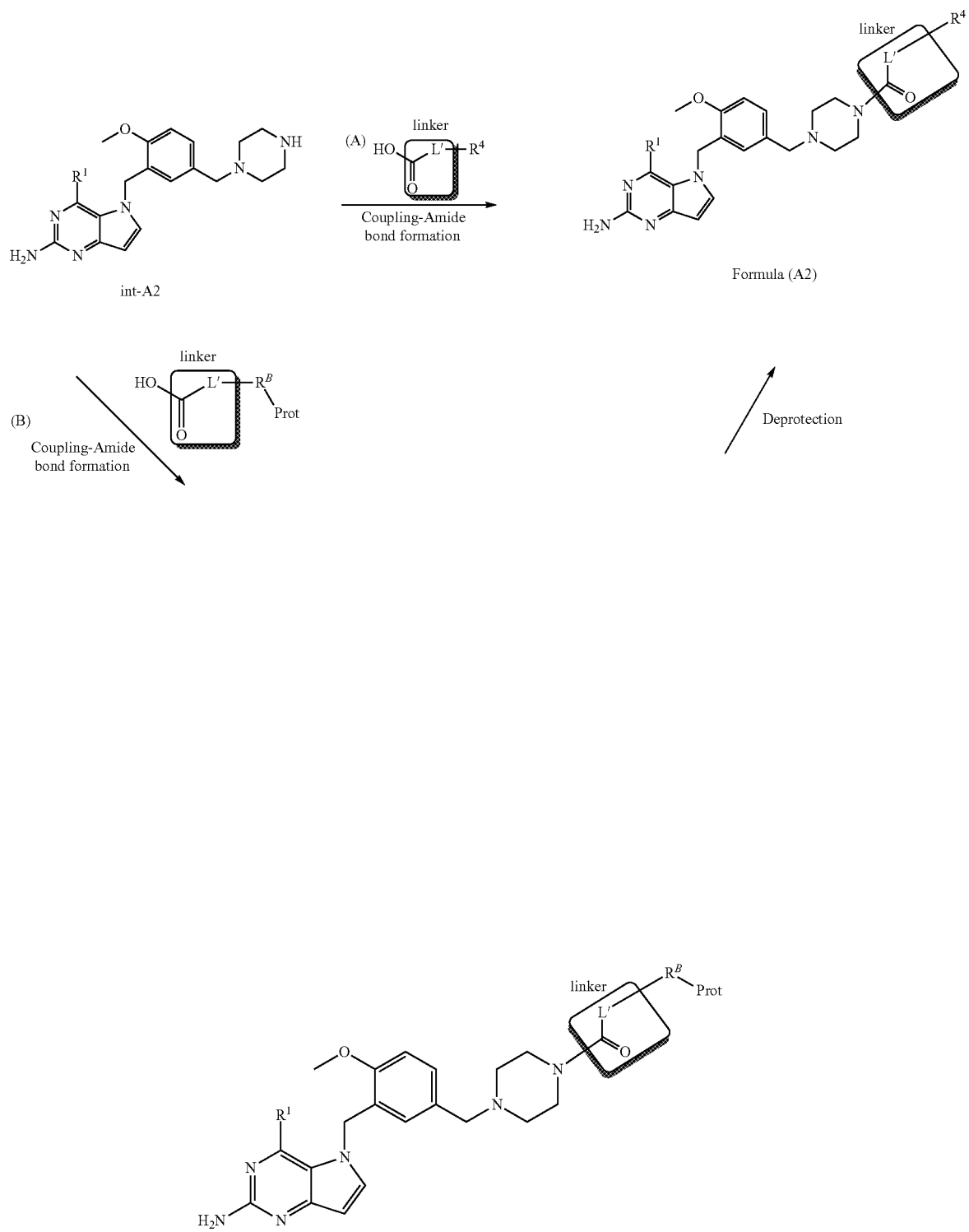

Scheme 2

Such amide bond formation can be accomplished using heat, EDCI coupling, HATU coupling, HBTU coupling, TBTU coupling or T3P coupling.

Scheme 3A illustrates a non-limiting synthetic scheme used to make certain compounds of Formula (Ia) wherein the -$L_2$-$R^4$ moiety is attached to intermediate (int-A1) by an amide bond. Such amide bond formation can be accomplished using heat, EDCI coupling, HATU coupling, HBTU coupling, TBTU coupling or T3P coupling. In Scheme 3A the linker ($L_2$) comprises a linker moiety ($L_A$) having a terminal carbonyl moiety (i.e. -$L_A$-C(=O)). Scheme 3B illustrates a non-limiting synthetic scheme used to make certain compounds of Formula (I) wherein the -$L_2$-$R^4$ moiety is attached to intermediate (int-A1) by an amide bond. Such amide bond formation can be accomplished using heat, EDCI coupling, HATU coupling, HBTU coupling, TBTU coupling or T3P coupling. In Scheme 3B the linker ($L_2$) comprises a linker moiety ($L_A$) having a terminal carbonyl moiety (i.e. -$L_A$-C(=O)), and $R^B$ is moiety having a protected amino group, where Prot is a protecting group such as Boc, Fmoc and Cbz.

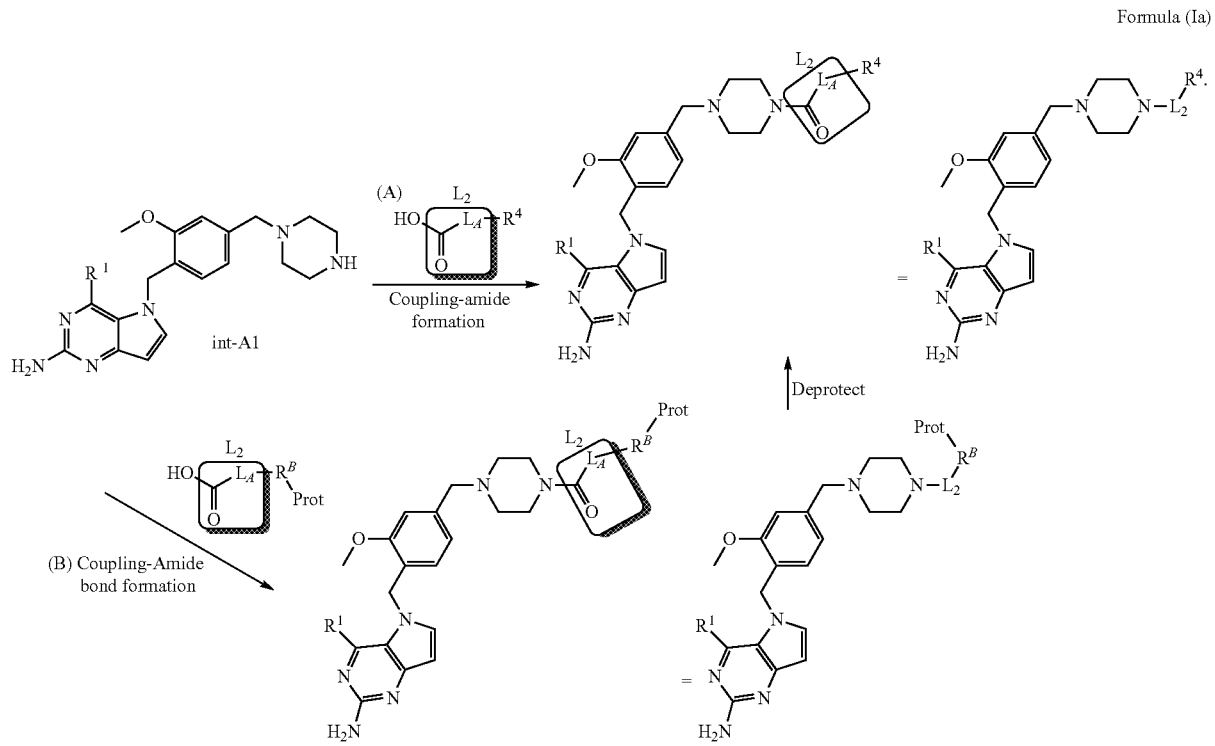

Scheme 3

Scheme 4A illustrates a non-limiting synthetic scheme used to make certain compounds of Formula (Ib) wherein the -$L_2$-$R^4$ moiety is attached to intermediate (int-A2) by an amide bond. Such amide bond formation can be accomplished using heat, EDCI coupling, HATU coupling, HBTU coupling, TBTU coupling or T3P coupling. In Scheme 4A the linker ($L_2$) comprises a linker moiety ($L_A$) having a terminal carbonyl moiety (i.e. -$L_A$-C(=O)). Scheme 4B illustrates a non-limiting synthetic scheme used to make certain compounds of Formula (Ib) wherein the -$L_2$-$R^4$ moiety is attached to intermediate (int-A2) by an amide bond. Such amide bond formation can be accomplished using heat, EDCI coupling, HATU coupling, HBTU coupling, TBTU coupling or T3P coupling. In Scheme 4B the linker ($L_2$) comprises a linker moiety ($L_A$) having a terminal carbonyl moiety (i.e. -$L_A$-C(=O)), and $R^B$ is moiety having a protected amino group, where Prot is a protecting group such as Boc, Fmoc and Cbz.

Scheme 4
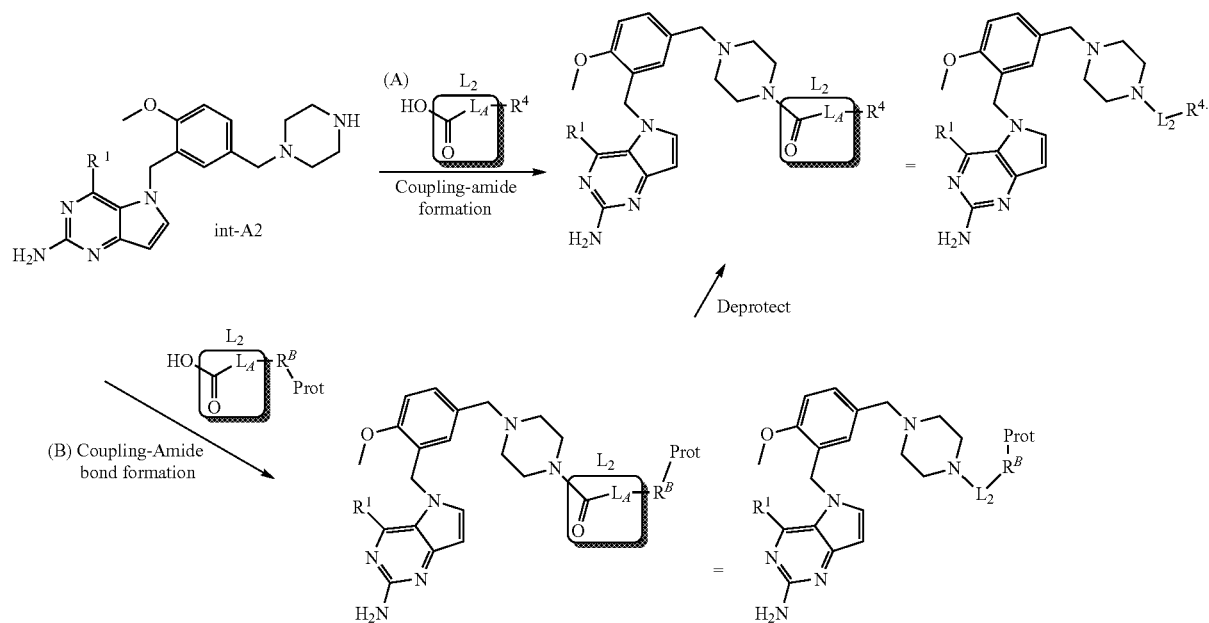
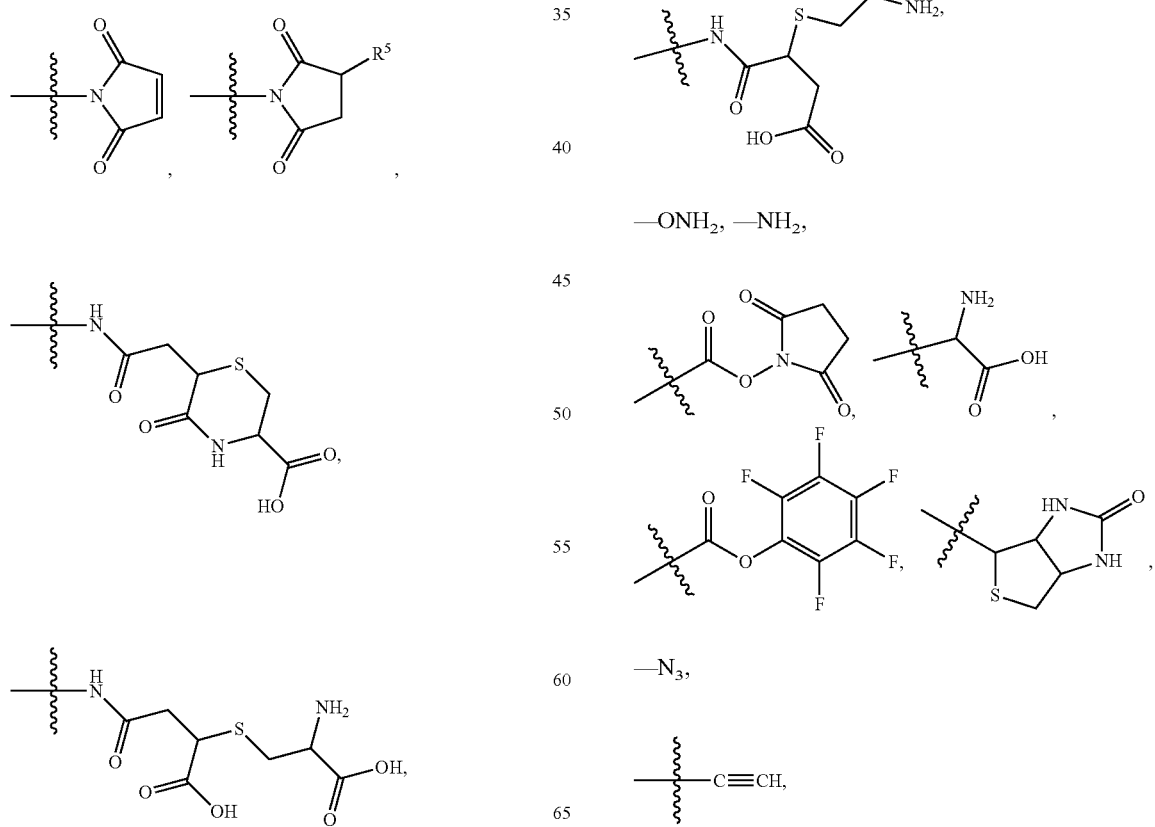
In Schemes 3 and 4,
$R^4$ is

—NHC(=O)CH=CH$_2$, SH, —SSR$^6$, —S(=O)$_2$(CH=CH$_2$), —(CH$_2$)$_2$S(=O)$_2$(CH=CH$_2$), —NHS(=O)$_2$(CH=CH$_2$), —NHC(=O)CH$_2$Br, —NHC(=O)CH$_2$I, —C(O)NHNH$_2$
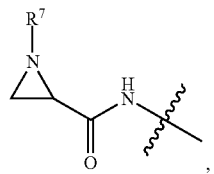
CO$_2$H, —C(O)NHNH$_2$,
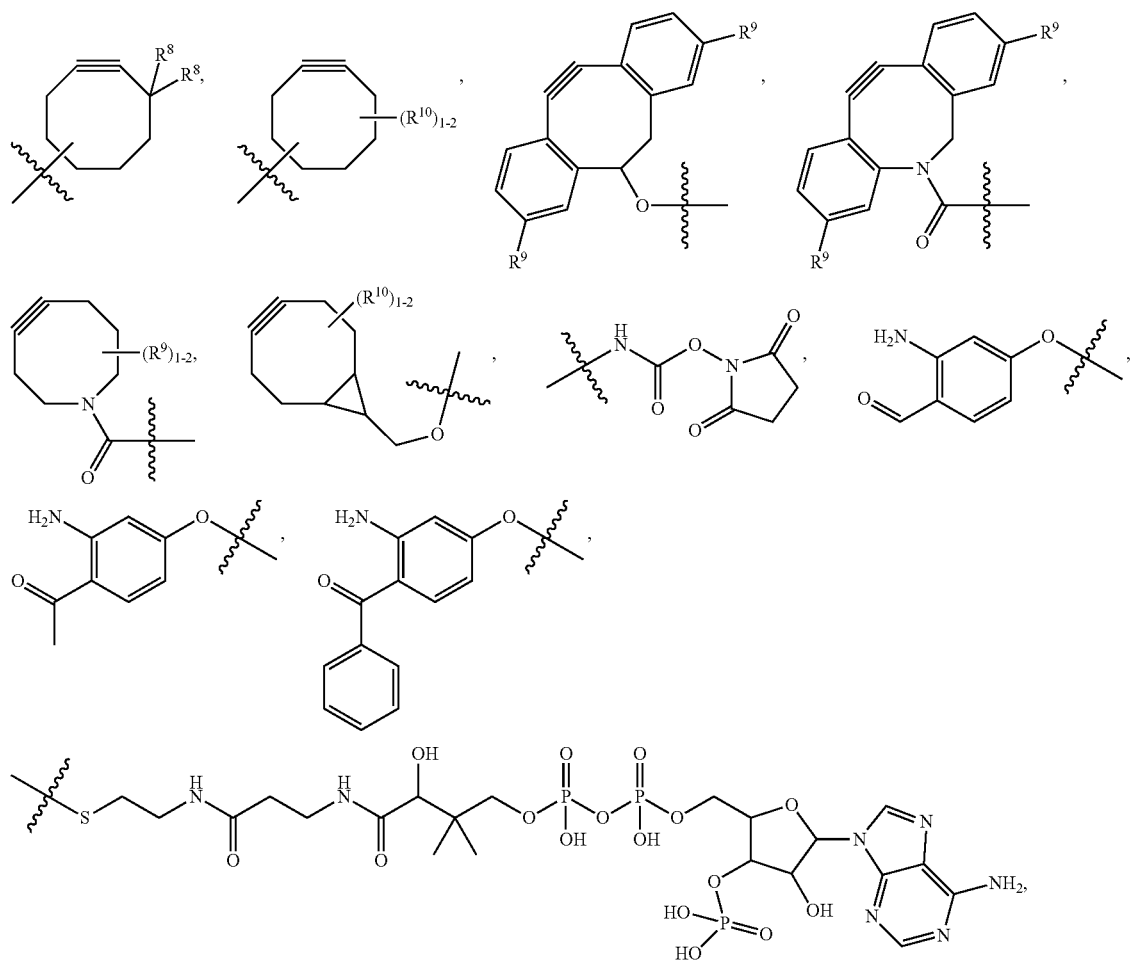
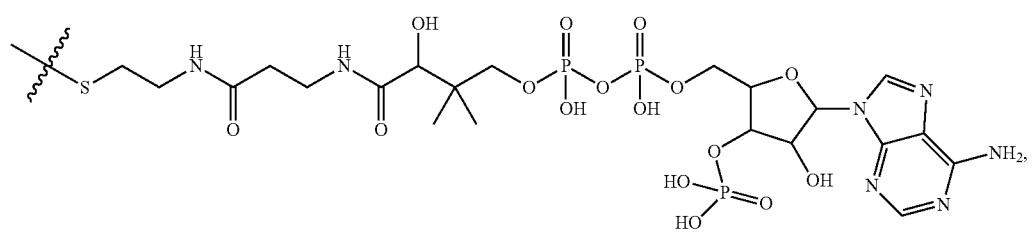

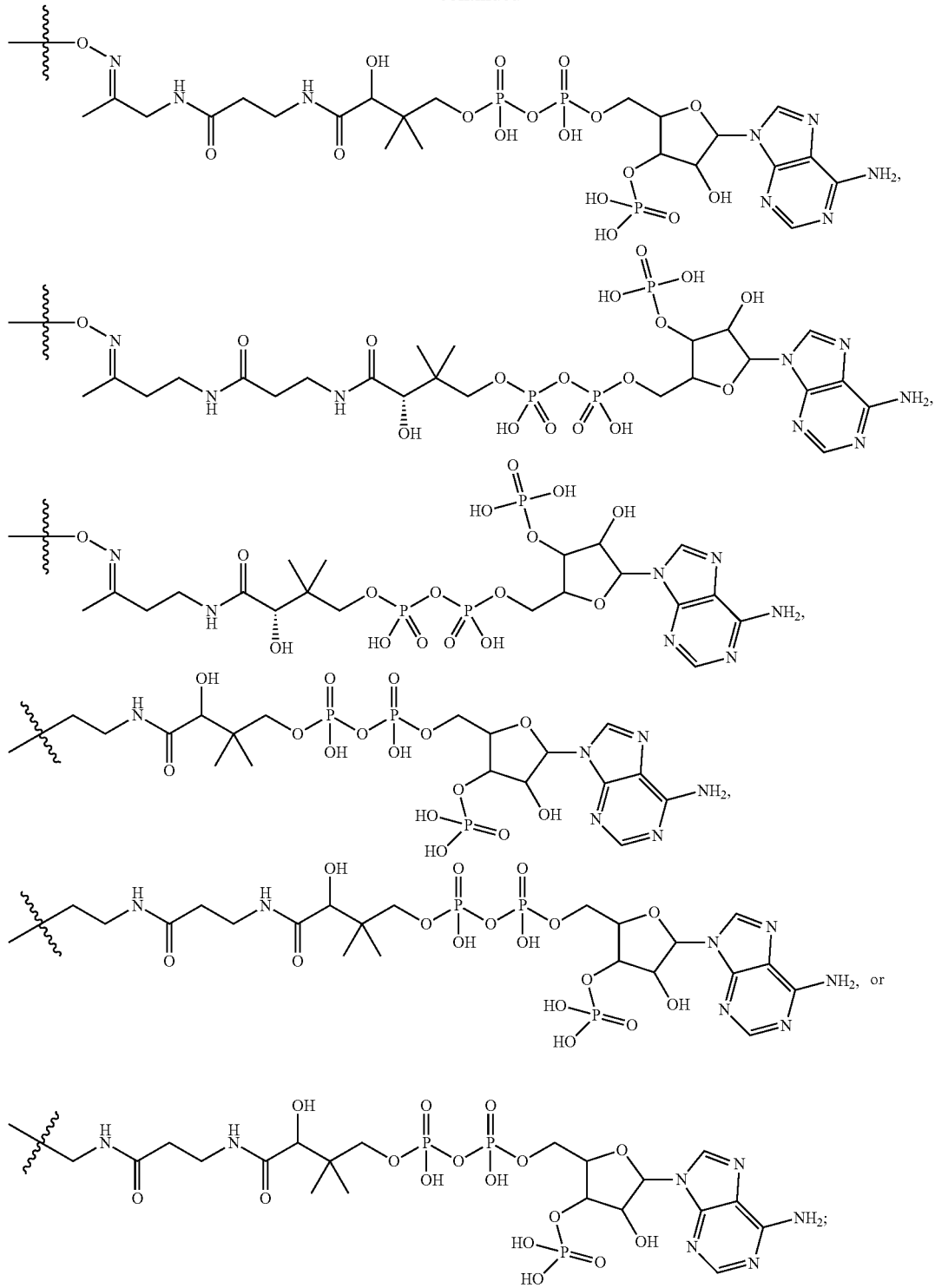

$R^B$ is —ONH—;

$L_A$ is —(CH$_2$)$_n$—, —((CH$_2$)$_n$O)$_t$(CH$_2$)$_n$—, —((CH$_2$)$_n$O)$_t$(CH$_2$)$_n$X$_1$(CH$_2$)$_n$—, —((CH$_2$)$_n$O)$_t$(CH$_2$)$_n$NHC(=O)(CH$_2$)$_n$—, —((CH$_2$)$_n$O)$_t$(CH$_2$)$_n$C(=O)NH(CH$_2$)$_n$—, —NH((CH$_2$)$_n$O)$_t$(CH$_2$)$_n$X$_1$(CH$_2$)$_n$—, —X$_2$X$_3$C(=O)((CH$_2$)$_n$O)$_t$(CH$_2$)$_n$—, —X$_2$C(=O)(CH$_2$)$_n$NHC(=O)(CH$_2$)$_n$—, or —(CH$_2$)$_n$C(=O)NH(CH$_2$)$_n$;

$L_2$ is —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$C(=O)(CH$_2$)$_n$NHC(=O)(CH$_2$)$_n$—, or —C(=O)(CH$_2$)$_n$C(=O)NH(CH$_2$)$_n$;

where $X_1$ is

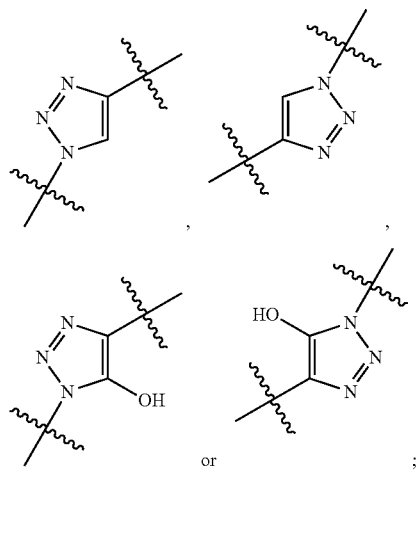

or ;

$X_2$ is

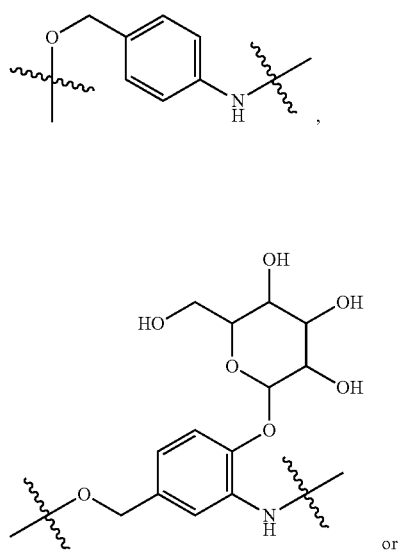

or

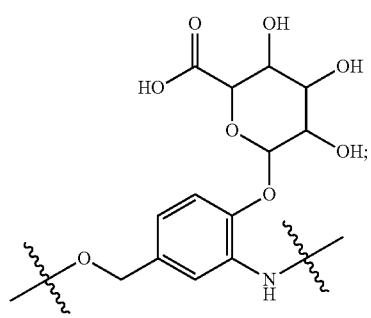

and $X_3$ is

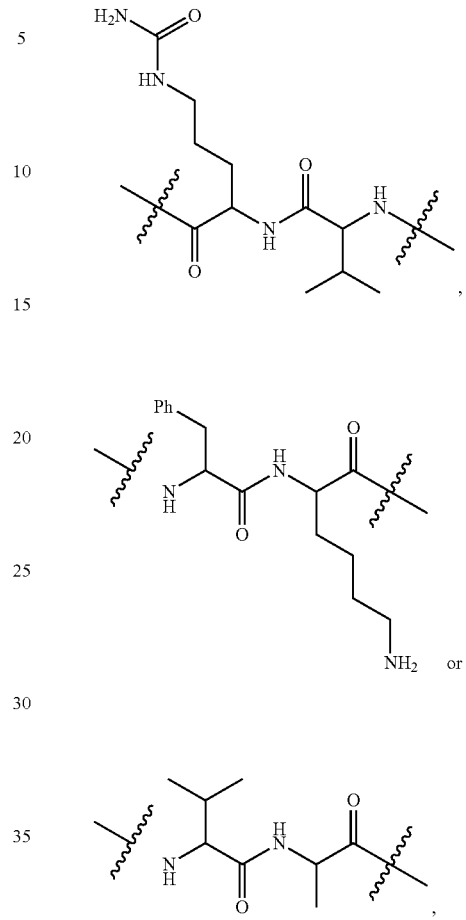

and $R^1$, $R^7$, $R^8$, $R^9$ and $R^{10}$, are as defined herein.

Scheme 5 illustrates a non-limiting synthetic scheme used to make certain compounds of Formula (B1) where the -linker-$R^4$ moiety is attached to intermediate (int-A1) by alkylation of the secondary amine of intermediate (int-A1). In Scheme 5 the linker ($L_A$) is initially functionalized with a terminal aldehyde (i.e. -$L_A$-C(=O)H) and then reacted with the secondary amine of intermediate (int-A1). Also in Scheme 5, $R^1$ is as described herein and $R^4$ is a reactive moiety which can react with a thiol, a disulfide, an amine, a ketone, a diketone, an azide or an alkyne.

Scheme 5

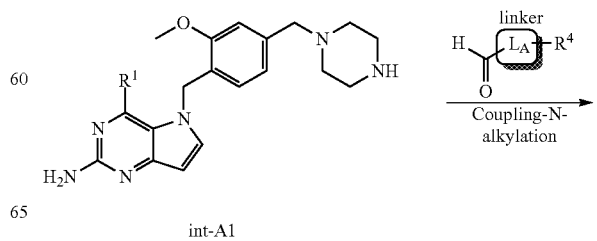

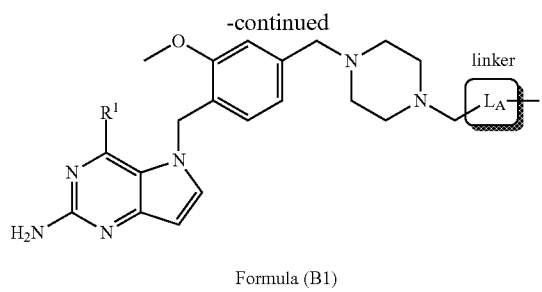

Formula (B1)

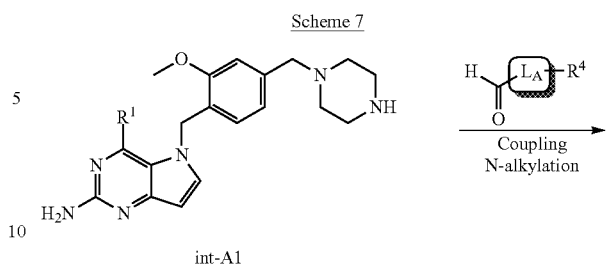

Scheme 7 int-A1

Such N-alkylation can be accomplished using a reducing agent such as $NaCNBH_3$, $NaBH_4$ or $NaBH(OAc)_3$.

Scheme 6 illustrates a non-limiting synthetic scheme used to make certain compounds of Formula (B2) where the -linker-$R^4$ moiety is attached to intermediate (int-A2) by alkylation of the secondary amine of intermediate (int-A2). In Scheme 6 the linker ($L_A$) is initially functionalized with a terminal aldehyde (i.e. -$L_A$-C(=O)H) and then reacted with the secondary amine of intermediate (int-A2). Also in Scheme 6, $R^1$ is as described herein and $R^4$ is a reactive moiety which can react with a thiol, a disulfide, an amine, a ketone, a diketone, an azide or an alkyne.

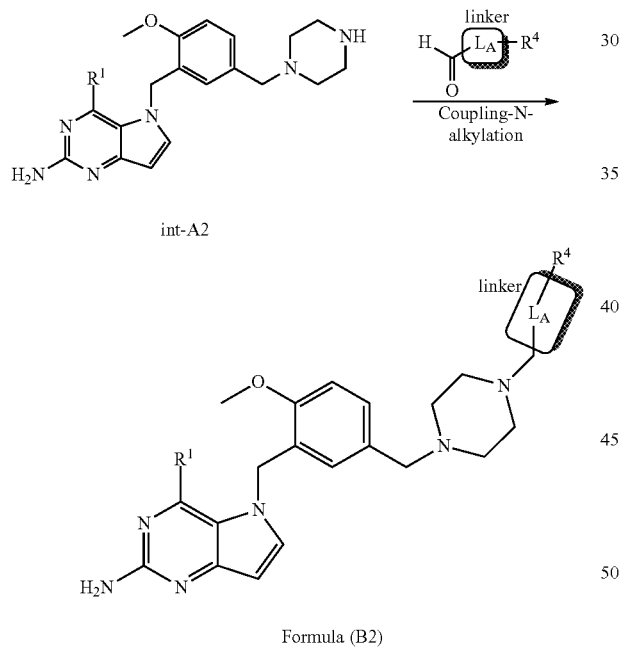

Scheme 6 int-A2

Formula (B2)

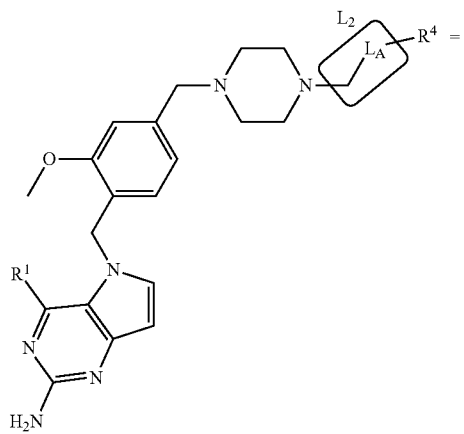

Formula (Ia)

Such N-alkylation can be accomplished using a reducing agent such as $NaCNBH_3$, $NaBH_4$ or $NaBH(OAc)_3$.

Scheme 7 illustrates a non-limiting synthetic scheme used to make certain compounds of Formula (Ia) wherein the -$L_2$-$R^4$ moiety is attached to intermediate (int-A1) by alkylation of the secondary amine of intermediate (int-A1). In Scheme 7 the linker moiety, $L_A$, initially functionalized with a terminal aldehyde (i.e. -L'-C(=O)H) is then reacted with the secondary amine of intermediate (int-A1), thereby forming the linker, $L_2$, which comprises the linker moiety $L_A$ with a terminal —CH2— group. Such N-alkylation can be accomplished using a reducing agent such as $NaCNBH_3$, $NaBH_4$ or $NaBH(OAc)_3$.

Scheme 8 illustrates a non-limiting synthetic scheme used to make certain compounds of Formula (Ib) wherein the -$L_2$-$R^4$ moiety is attached to intermediate (int-A2) by alkylation of the secondary amine of intermediate (int-A2). In Scheme 8 the linker moiety ($L_A$) initially functionalized with a terminal aldehyde (i.e. -L'-C(=O)H) which is then reacted with the secondary amine of intermediate (int-A2), thereby forming the linker, $L_2$, which comprises the linker moiety $L_A$ with a terminal —$CH_2$— group. Such N-alkylation can be accomplished using a reducing agent such as $NaCNBH_3$, $NaBH_4$ or $NaBH(OAc)_3$.

Scheme 8

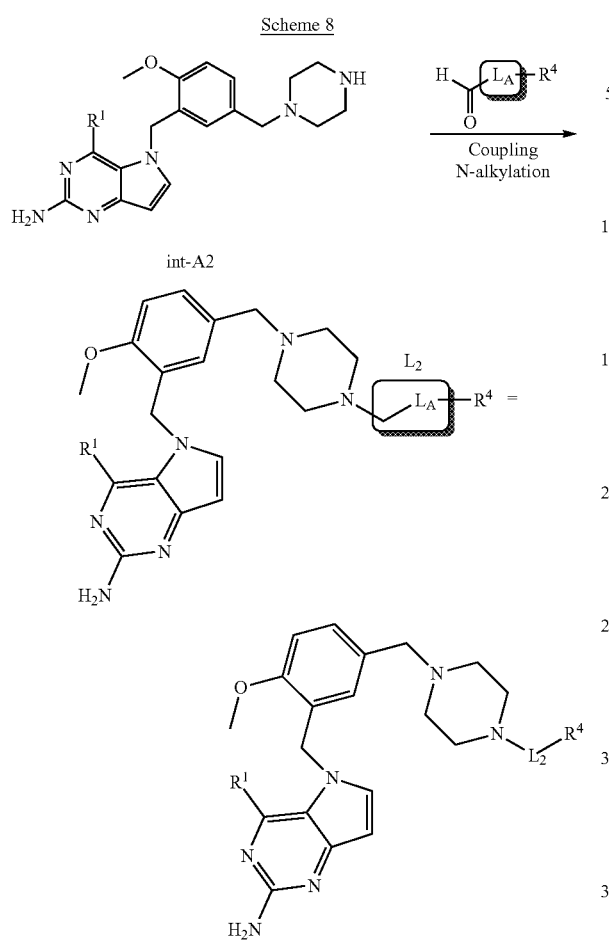

Formula (Ib)

In Schemes 7 and 8, $R^4$ is as defined for Schemes 3 and 4;

$L_A$ is —$(CH_2)_{(n-1)}$—, —$((CH_2)_{(n-1)}O)((CH_2)_nO)_t(CH_2)_n$—, —$(CH_2)_{(n-1)}X_1(CH_2)_n$—, —$(CH_2)_{(n-1)}NHC(=O)(CH_2)_n$—, —$(CH_2)_{(n-1)}NHC(=O(CH_2)_nC(=O)NH(CH_2)_n$— or —$((CH_2)_{(n-1)}O)((CH_2)_nO)_t(CH_2)_nNHC(=O)(CH_2)_n$;

$L_2$ is —$(CH_2)_n$—, —$((CH_2)_nO)_t(CH_2)_n$—, —$(CH_2)_nX_1(CH_2)_n$—, —$(CH_2)_nNHC(=O)(CH_2)_n$—, —$(CH_2)_nNHC(=O(CH_2)_nC(=O)NH(CH_2)_n$— or —$((CH_2)_nO)_t(CH_2)_nNHC(=O)(CH_2)_n$;

where $X_1$ is

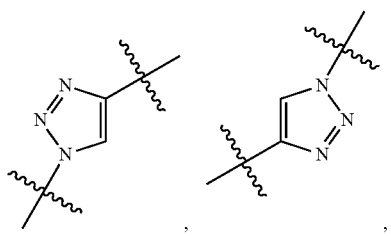

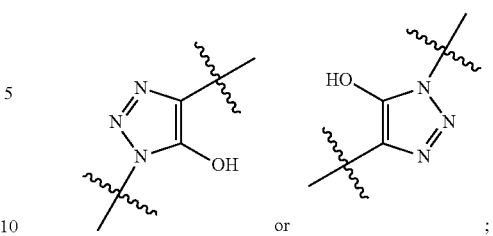

or ;

and $R^1$ and $R^7$ are as defined herein.

Scheme 9 illustrates a non-limiting synthetic scheme used to make certain compounds of Formula (A1) where the -linker-$R^4$ moiety is attached to intermediate (int-A1) by an amide bond. In Scheme 9 the linker is any linker (L') having a terminal carbonyl moiety (i.e. -L'-C(=O)). Also in Scheme 9, $R^1$ is as described herein, $R^4$ is

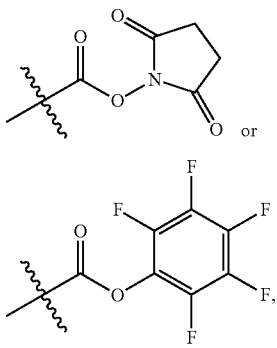

and $R^C$ is

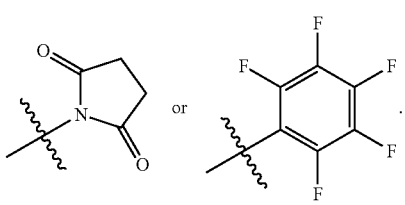 [SMILES: *N1C(=O)CCC1=O ; *c1c(F)c(F)c(F)c(F)c1F]

Scheme 9

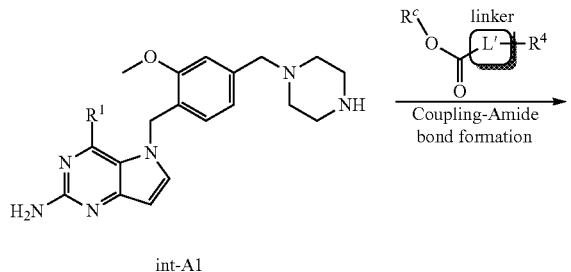

int-A1

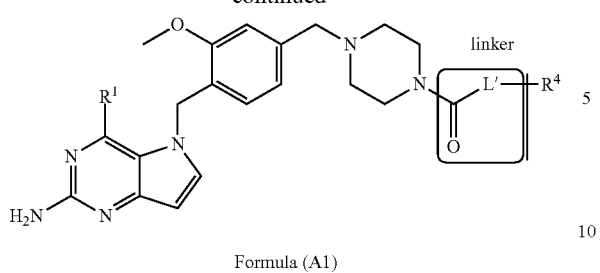

Formula (A1)

Such amide bond formation can be accomplished using heat, EDCI coupling, HATU coupling, HBTU coupling, TBTU coupling or T3P coupling.

Scheme 10 illustrates a non-limiting synthetic scheme used to make certain compounds of Formula (A2) where the -linker-$R^4$ moiety is attached to intermediate (int-A2) by an amide bond. In Scheme 10 the linker is any linker (L') having a terminal carbonyl moiety (i.e. -L'-C(=O)). Also in Scheme 10, $R^1$ is as described herein, $R^4$ is

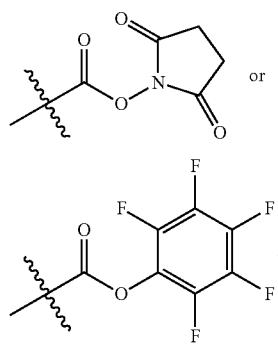

and $R^C$ is

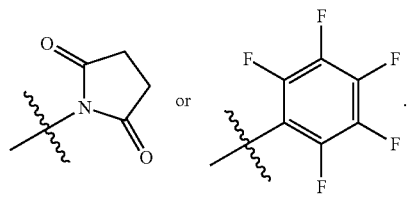 [SMILES: *N1C(=O)CCC1=O ; *c1c(F)c(F)c(F)c(F)c1F]

Scheme 10

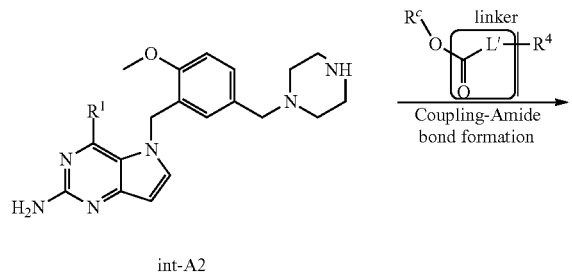

int-A2

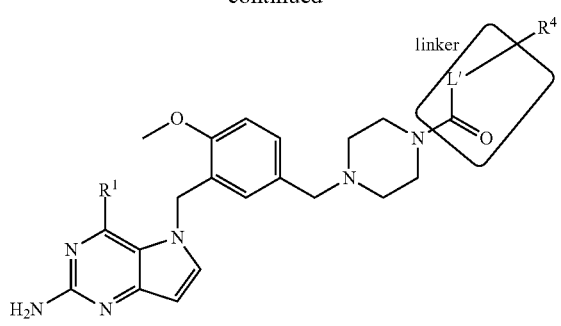

Formula (A2)

Such amide bond formation can be accomplished using heat, EDCI coupling, HATU coupling, HBTU coupling, TBTU coupling or T3P coupling.

Scheme 11 illustrates a non-limiting synthetic scheme used to make certain compounds of Formula (Ia) wherein the -$L_2$-$R^4$ moiety is attached to intermediate (int-A1) by an amide bond. In Scheme 11 the linker ($L_2$) comprises a linker moiety ($L_A$) having a terminal carbonyl moiety (i.e. -$L_A$-C(=O)). Such amide bond formation can be accomplished using heat, EDCI coupling, HATU coupling, HBTU coupling, TBTU coupling or T3P coupling.

Scheme 11

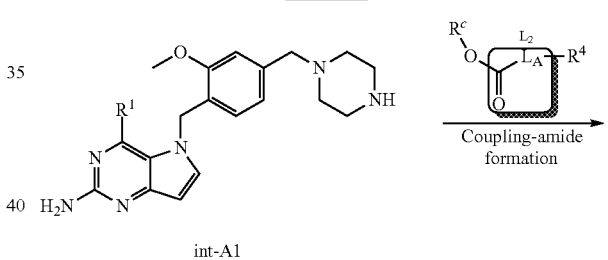

int-A1

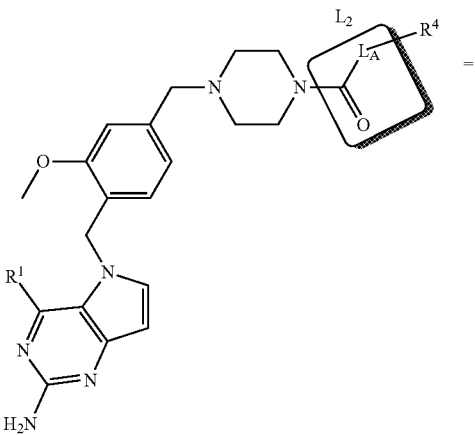

-continued

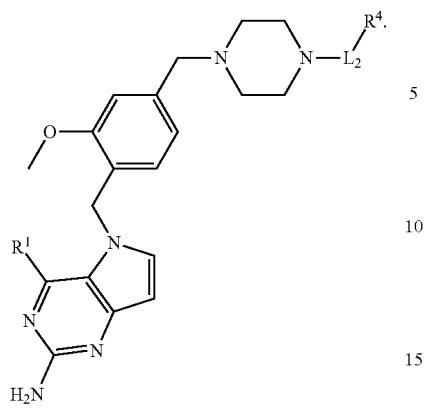

Formula (Ia)

Scheme 12 illustrates a non-limiting synthetic scheme used to make certain compounds of Formula (Ib) wherein the -$L_2$-$R^4$ moiety is attached to intermediate (int-A2) by an amide bond. In Scheme 12 the linker ($L_2$) comprises a linker moiety ($L_A$) having a terminal carbonyl moiety (i.e. -$L_A$-C(=O)). Such amide bond formation can be accomplished using heat, EDCI coupling, HATU coupling, HBTU coupling, TBTU coupling or T3P coupling.

Scheme 12

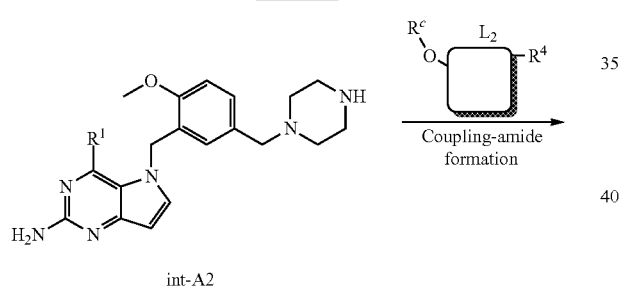

-continued

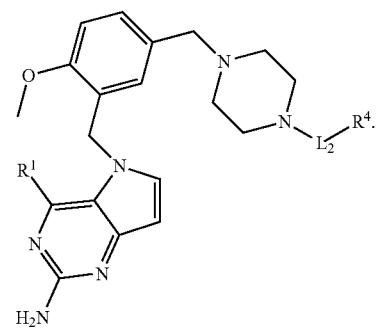

Formula (Ib)

In Schemes 11 and 12,
$R^4$ is

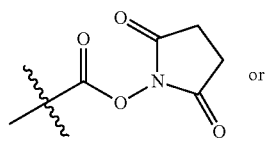

or

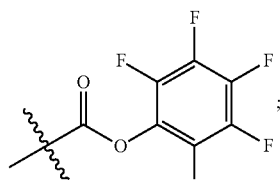

$R^C$ is

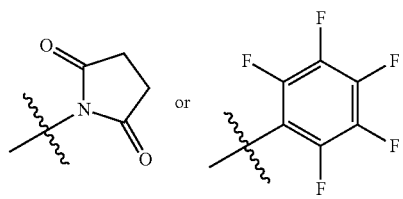 [SMILES: *N1C(=O)CCC1=O ; *c1c(F)c(F)c(F)c(F)c1F]

$L_A$ is —$(CH_2)_n$—, —$((CH_2)_nO)_t(CH_2)_n$—, —$((CH_2)_nO)_t(CH_2)_nX_1(CH_2)_n$—, —$((CH_2)_nO)_t(CH_2)_nNHC(=O)(CH_2)_n$—, —$NH((CH_2)_nO)_t(CH_2)_nX_1(CH_2)_n$—, —$X_2X_3C(=O)((CH_2)_nO)_t(CH_2)_n$—, —$X_2C(=O)(CH_2)_nNHC(=O)(CH_2)_n$—, or —$(CH_2)_nC(=O)NH(CH_2)_n$—;

$L_2$ is —$C(=O)(CH_2)_n$—, —$C(=O)((CH_2)_nO)_t(CH_2)_n$—, —$C(=O)((CH_2)_nO)_t(CH_2)_nX_1(CH_2)_n$—, —$C(=O)((CH_2)_nO)_t(CH_2)_nNHC(=O)(CH_2)_n$—, —$C(=O)NH((CH_2)_nO)_t(CH_2)_nX_1(CH_2)_n$—, —$C(=O)X_2X_3C(=O)((CH_2)_nO)_t(CH_2)_n$—, —$C(=O)X_2C(=O)(CH_2)_nNHC(=O)(CH_2)_n$—, or —$C(=O)NH(CH_2)_nC(=O)NH(CH_2)_n$—; where $X_1$ is

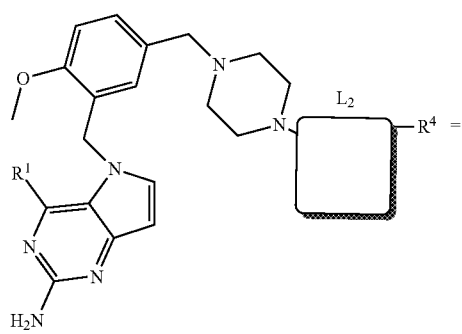

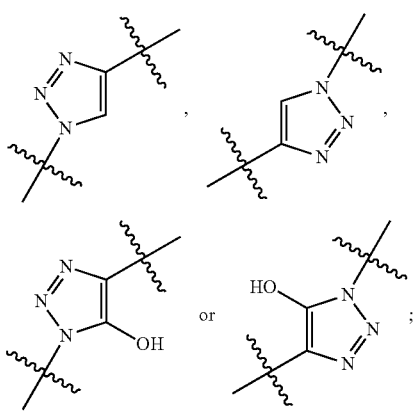
$X_2$ is
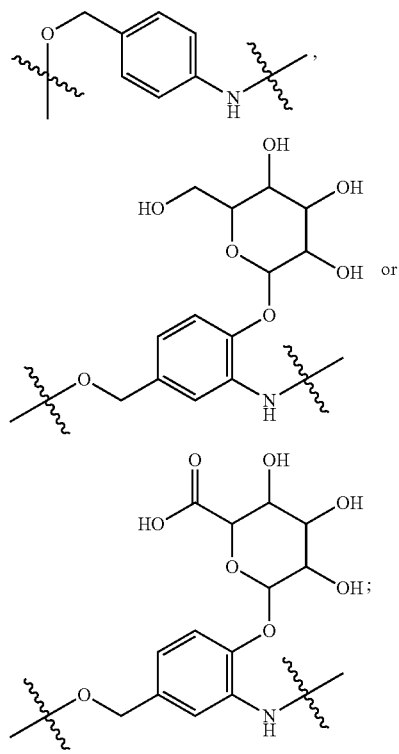
and $X_3$ is
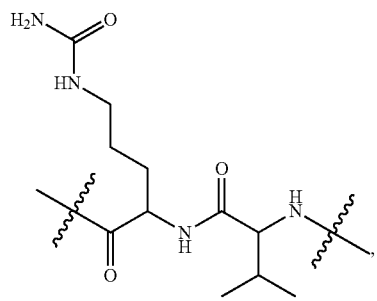
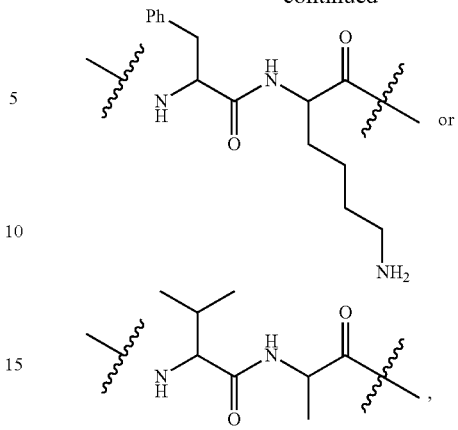
and
R¹ and R⁷ are as defined herein.
INTERMEDIATES
The synthesis of the intermediates used to make the compounds of Formula (I) and subformulae thereof (i.e. compounds of Formula (Ia) and Formula (Ib)) of the invention are given below.
Intermediate 1
Synthesis of 5-(2-methoxy-4-(piperazin-1-ylmethyl)benzyl)-N4-pentyl-5H-pyrrolo[3,2-d]pyrimidine-2,4-diamine (Int-1)
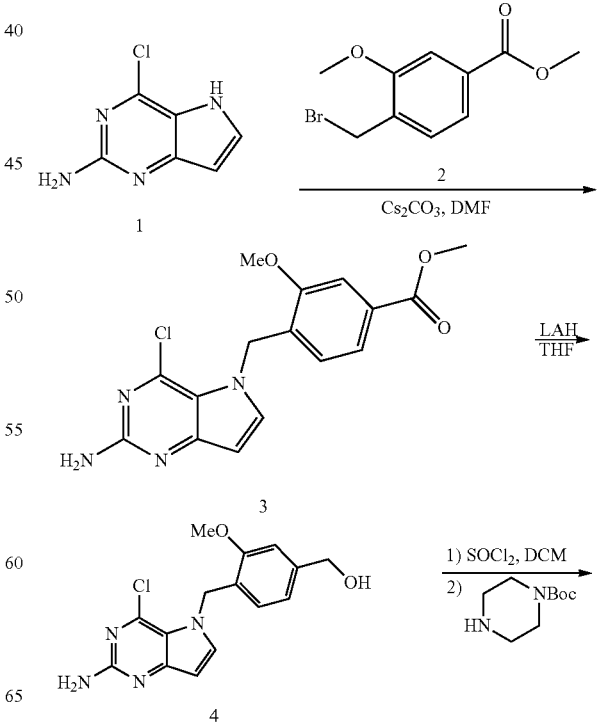

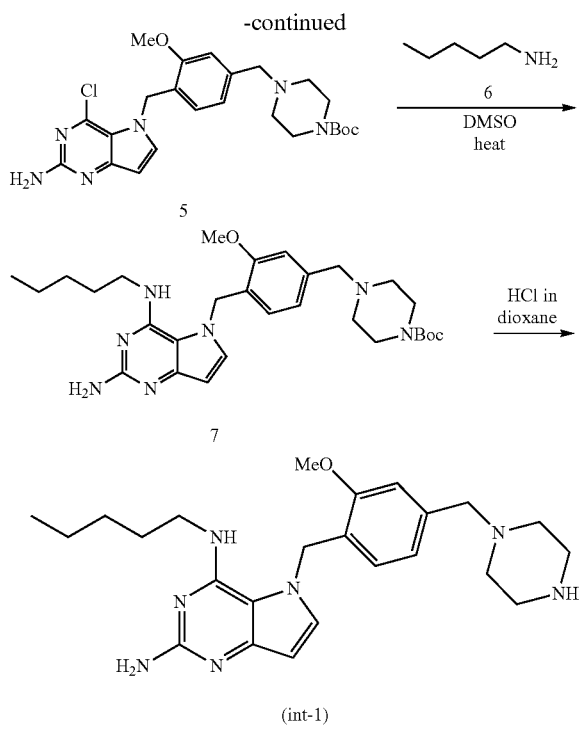

Step 1: Preparation of methyl 4-((2-amino-4-chloro-5H-pyrrolo[3,2-d]pyrimidin-5-yl)methyl)-3-methoxybenzoate (3)

A round bottom flask was charged with 4-chloro-5H-pyrrolo[3,2-d]pyrimidin-2-amine (1, commercially available, 1.0 equiv.), methyl 4-(bromomethyl)-3-methoxybenzoate (2, commercially available, 1.0 equiv.), caesium carbonate (1.0 equiv.) and DMF (1.0 M). The reaction mixture was stirred at room temperature for 18 hours and the solvent was then removed in vacuo. To the resulting mixture was added EtOAc and the solvent was removed in vaccuo. To this mixture was added DCM and the solvent removed in vacuo. The crude reaction mixture was then purified by ISCO chromatography (0-10% MeOH:DCM, gradient) to afford methyl 4-((2-amino-4-chloro-5H-pyrrolo[3,2-d]pyrimidin-5-yl)methyl)-3-methoxybenzoate (3) as a solid.

Step 2: (4-((2-amino-4-chloro-5H-pyrrolo[3,2-d]pyrimidin-5-yl)methyl)-3-methoxyphenyl)methanol (4)

A slurry of lithium aluminum, hydride (LAH) (1.0 equiv., powder) in THF (0.3 M) was prepared in a round bottom flask, cooled to 0° C. and vigorously stirred for 15 minutes. To this mixture was added methyl 4-((2-amino-4-chloro-5H-pyrrolo[3,2-d]pyrimidin-5-yl)methyl)-3-methoxybenzoate (3, 1.0 equiv. from previous step) in portions. The ice bath was removed and the reaction mixture was stirred at room temperature for 4 hours, with additional LAH being added until the reaction was complete). Et₂O was added to the reaction mixture and the mixture then transferred to an Erlenmeyer flask and cooled to 0° C. under vigorously stirring. The reaction was then quenched by the slow addition of a saturated sodium sulfate solution. A white precipitate was obtained and the mixture was filtered through a frit containing Celite and washed with THF and Et₂O. The volatiles were then removed in vacuo and the material used in the next step without further purification.

Step 3: tert-butyl 4-(4-((2-amino-4-chloro-5H-pyrrolo[3,2-d]pyrimidin-5-yl)methyl)-3-methoxybenzyl)piperazine-1-carboxylate (5)

Thionyl chloride (10.0 equiv.) was added to a round bottom flask containing (4-((2-amino-4-chloro-5H-pyrrolo[3,2-d]pyrimidin-5-yl)methyl)-3-methoxyphenyl)methanol (4, 1.0 equiv. from step 2) in DCM (0.1 M) at 0° C. The ice-bath was then removed and the reaction mixture was stirred at room temperature for 4 hours. The reaction mixture was then cooled back to 0° C. and slowly quenched by the addition of NaOH (1.0 M, 40.0 equiv.) and saturated NaHCO₃ (aq.). The material was transferred to a separatory funnel and washed with DCM 3×. The combined organic layers were dried with sodium sulfate, filtered and volatiles removed in vacuo. The resulting crude product was then dissolved in DMF (0.1 M) in a round bottom flask and used without further purification. To this material was added tert-butyl piperazine-1-carboxylate (1.0 equiv.) and Huenig's base (1.2 equiv.) and stirred at room temperature for 18 hours. The reaction mixture was then diluted with EtOAc, transferred to a separatory funnel and washed with saturated NaCl (aq.) 2× and water 2×. The combined organic layers were dried with sodium sulfate, filtered and volatiles removed in vacuo. The crude reaction mixture was purified by ISCO chromatography (0-10% MeOH:DCM, gradient) to afford tert-butyl 4-(4-((2-amino-4-chloro-5H-pyrrolo[3,2-d]pyrimidin-5-yl)methyl)-3-methoxybenzyl)piperazine-1-carboxylate (5) as a solid.

Step 4: tert-butyl 4-(4-((2-amino-4-(pentylamino)-5H-pyrrolo[3,2-d]pyrimidin-5-yl)methyl)-3-methoxybenzyl)piperazine-1-carboxylate (7)

A round bottom flask was charged with tert-butyl 4-(4-((2-amino-4-chloro-5H-pyrrolo[3,2-d]pyrimidin-5-yl)methyl)-3-methoxybenzyl)piperazine-1-carboxylate (5, 1.0 equiv. from step 3), commercially available pentylamine (6, 3.0 equiv.), Huenig's base (5.0 equiv.) and DMSO (0.5 M). The reaction mixture was heated to 120° C. and stirred for 18 hours. The reaction mixture was then cooled to room temperature and water added. This mixture was then frozen and the majority of volatiles removed by lyophilization. The crude reaction mixture was purified by ISCO chromatography (0-10% MeOH (the MeOH contained 0.7 N NH₃):DCM, gradient) to afford tert-butyl 4-(4-((2-amino-4-(pentylamino)-5H-pyrrolo[3,2-d]pyrimidin-5-yl)methyl)-3-methoxybenzyl)piperazine-1-carboxylate (7) as a solid.

Step 5: 5-(2-methoxy-4-(piperazin-1-ylmethyl)benzyl)-N4-pentyl-5H-pyrrolo[3,2-d]pyrimidine-2,4-diamine (Int-1)

HCl in dioxane (4.0 M, 20.0 equiv.) was added to a solution of tert-butyl 4-(4-((2-amino-4-(pentylamino)-5H-pyrrolo[3,2-d]pyrimidin-5-yl)methyl)-3-methoxybenzyl)piperazine-1-carboxylate (6, 1.0 equiv. from step 4) in DCM (0.1 M) in a round bottom flask at 0° C. The ice-bath was then removed and the reaction mixture was stirred at room temperature for 3 hours. NH₃ in MeOH (0.7 N) was then added to the reaction mixture and the volatiles removed in vacuo. The addition of NH₃ in MeOH (0.7 N) and removal of volatiles in vacuo was repeated two more times. The crude reaction mixture was then purified by ISCO chromatography (0-20% MeOH (the MeOH contained 0.7 N NH₃): DCM, gradient) to provide 5-(2-methoxy-4-(piperazin-1-ylmethyl)benzyl)-N4-pentyl-5H-pyrrolo[3,2-d]pyrimidine-2,4-diamine (Int-1) as a solid: ¹H NMR (CD₃OD): δ 7.37 (d, 1H), 7.10 (s, 1H), 6.91 (d, 1H), 6.74 (d, 1H), 6.22 (d, 1H), 5.52 (s, 2H), 3.92 (s, 3H), 3.61 (s, 2H), 3.54 (t, 2H), 3.35 (s, 3H), 3.22 (m, 4H), 2.69 (m, 4H), 1.51 (m, 2H), 1.30 (m, 2H), 1.18 (m, 2H), 0.89 (s, 3H). LRMS [M+H]=438.3.

Intermediate 2

Synthesis of (S)-2-((2-amino-5-(2-methoxy-5-(piperazin-1-ylmethyl)benzyl)-5H-pyrrolo[3,2-d]pyrimidin-4-yl)amino)hexan-1-ol (Int-2)

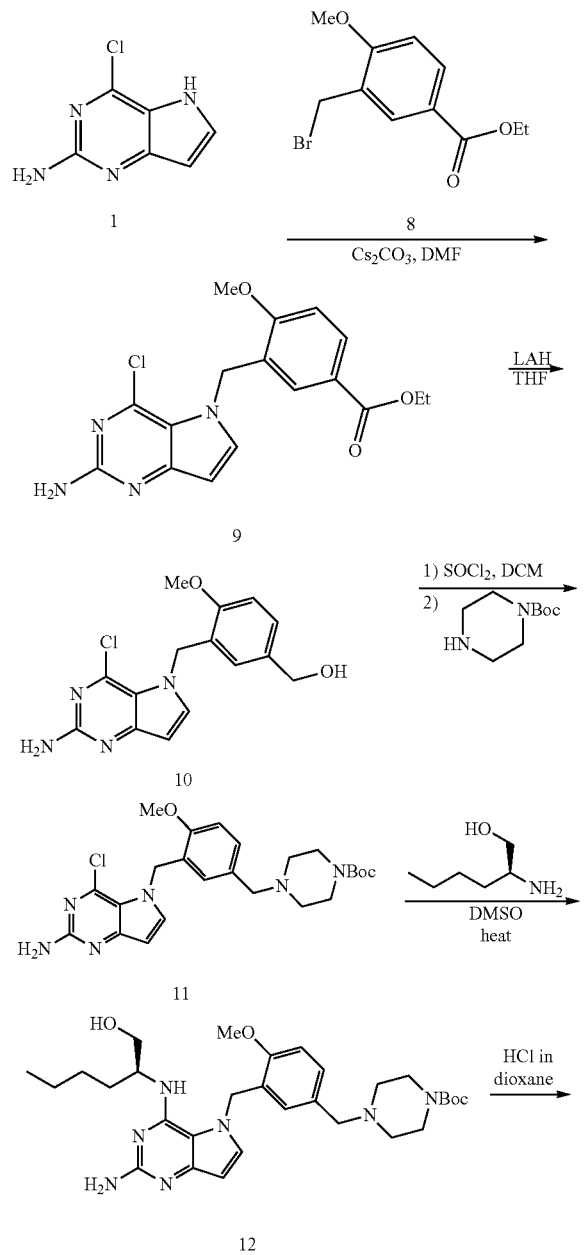

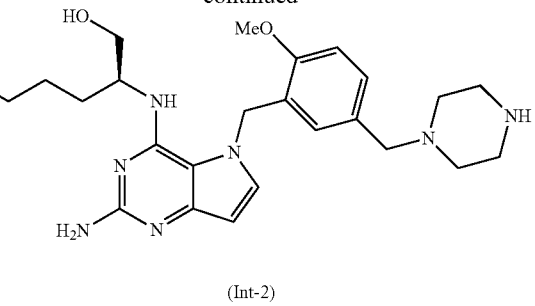

(Int-2)

Step 1: Preparation of ethyl 3-((2-amino-4-chloro-5H-pyrrolo[3,2-d]pyrimidin-5-yl)methyl)-4-methoxybenzoate (9)

A round bottom flask was charged with 4-chloro-5H-pyrrolo[3,2-d]pyrimidin-2-amine (1, commercially available, 1.0 equiv.), ethyl 3-(bromomethyl)-4-methoxybenzoate (8, commercially available, 1.0 equiv.), caesium carbonate (1.0 equiv.) and DMF (1.0 M). The reaction mixture was stirred at room temperature for 18 hours. The solvent was then removed in vaccuo. To the resulting mixture was added EtOAc and the solvent was removed in vacuo. To this mixture was added DCM and the solvent removed in vaccuo. The crude reaction mixture was then purified by ISCO chromatography (0-10% MeOH:DCM, gradient) to afford ethyl 3-((2-amino-4-chloro-5H-pyrrolo[3,2-d]pyrimidin-5-yl)methyl)-4-methoxybenzoate (9) as a solid.

Step 2: (3-((2-amino-4-chloro-5H-pyrrolo[3,2-d]pyrimidin-5-yl)methyl)-4-methoxyphenyl)methanol (10)

A slurry of LAH (1.0 equiv., powder) in THF (0.3 M) was prepared in a round bottom flask, cooled to 0° C. and vigorously stirred for 15 minutes. To this mixture was added ethyl 3-((2-amino-4-chloro-5H-pyrrolo[3,2-d]pyrimidin-5-yl)methyl)-4-methoxybenzoate (9, 1.0 equiv. from step 1) in portions. The ice-bath was then removed and the reaction mixture was stirred at room temperature for 4 hours (if the reaction was not complete by this time additional LAH was added and stirring continued until the reaction was complete). The reaction mixture was then transferred to an Erlenmeyer flask using Et₂O. The mixture was cooled to 0° C. and vigorously stirred. The reaction was then quenched by the slow addition of a saturated sodium sulfate solution. A white precipitate was obtained and the mixture was filtered through a frit containing Celite and washed with THF and Et₂O. The volatiles were then removed in vacuo and the material used in the next step without further purification.

Step 3: tert-butyl 4-(3-((2-amino-4-chloro-5H-pyrrolo[3,2-d]pyrimidin-5-yl)methyl)-4-methoxybenzyl)piperazine-1-carboxylate (11)

Thionyl chloride (10.0 equiv.) was added to a round bottom flask containing (3-((2-amino-4-chloro-5H-pyrrolo[3,2-d]pyrimidin-5-yl)methyl)-4-methoxyphenyl)methanol (10, 1.0 equiv. from step 2) in DCM (0.1 M) at 0° C. The ice-bath was then removed and the reaction mixture stirred at room temperature for 4 hours. The reaction mixture was then cooled to 0° C. and slowly quenched by the addition of NaOH (1.0 M, 40.0 equiv.) and saturated NaHCO$_3$ (aq.). The material was transferred to a separatory funnel and washed with DCM 3×. The combined organic layers were dried with sodium sulfate, filtered and volatiles removed in vacuo. The resulting crude product was then dissolved in DMF (0.1 M) in a round bottom flask and used without further purification. To this material was added tert-butyl piperazine-1-carboxylate (1.0 equiv.) and Huenig's base (1.2 equiv.) and stirred at room temperature for 18 hours. The reaction mixture was then diluted with EtOAc, transferred to a separatory funnel and washed with saturated NaCl (aq.) 2× and water 2×. The combined organic layers were dried with sodium sulfate, filtered and volatiles removed in vacuo. The crude reaction mixture was purified by ISCO chromatography (0-10% MeOH:DCM, gradient) to afford tert-butyl 4-(3-((2-amino-4-chloro-5H-pyrrolo[3,2-d]pyrimidin-5-yl)methyl)-4-methoxybenzyl)piperazine-1-carboxylate (11) as a solid.

Step 4: (S)-tert-butyl 4-(3-((2-amino-4-((1-hydroxy-hexan-2-yl)amino)-5H-pyrrolo[3,2-d]pyrimidin-5-yl)methyl)-4-methoxybenzyl)piperazine-1-carboxylate (12)

A round bottom flask was charged with tert-butyl 4-(3-((2-amino-4-chloro-5H-pyrrolo[3,2-d]pyrimidin-5-yl)methyl)-4-methoxybenzyl)piperazine-1-carboxylate (11, 1.0 equiv. from step 3), commercially available (S)-2-amino-hexan-1-ol (3.0 equiv.), Huenig's base (5.0 equiv.) and DMSO (0.5 M). The reaction mixture was heated to 120° C. and stirred for 18 hours. The reaction mixture was then cooled to room temperature and water added. This mixture was then frozen and the majority of volatiles removed by lyophilization. The crude reaction mixture was purified by ISCO chromatography (0-10% MeOH (the MeOH contained 0.7 N NH$_3$):DCM, gradient) to afford (S)-tert-butyl 4-(3-((2-amino-4-((1-hydroxyhexan-2-yl)amino)-5H-pyrrolo[3,2-d]pyrimidin-5-yl)methyl)-4-methoxybenzyl)piperazine-1-carboxylate (12) as a solid.

Step 5: Example 1—(S)-2-((2-amino-5-(2-methoxy-5-(piperazin-1-ylmethyl)benzyl)-5H-pyrrolo[3,2-d]pyrimidin-4-yl)amino)hexan-1-ol (Int-2)

HCl in dioxane (4.0 M, 20.0 equiv.) was added to a solution of (S)-tert-butyl 4-(3-((2-amino-4-((1-hydroxy-hexan-2-yl)amino)-5H-pyrrolo[3,2-d]pyrimidin-5-yl)methyl)-4-methoxybenzyl)piperazine-1-carboxylate (12, 1.0 equiv. from step 4) in DCM (0.1 M) in a round bottom flask at 0° C. The ice-bath was then removed and the reaction mixture was stirred at room temperature for 3 hours. NH$_3$ in MeOH (0.7 N) was then added to the reaction mixture and the volatiles removed in vacuo. The addition of NH$_3$ in MeOH (0.7 N) and removal of volatiles in vacuo was repeated two more times. The crude reaction mixture was then purified by ISCO chromatography (0-20% MeOH (the MeOH contained 0.7 N NH$_3$):DCM, gradient) to provide (S)-2-((2-amino-5-(2-methoxy-5-(piperazin-1-ylmethyl)benzyl)-5H-pyrrolo[3,2-d]pyrimidin-4-yl)amino)hexan-1-ol (Int-2) as a solid: $^1$H (CD$_3$OD): δ 7.50 (d, 1H), 7.29 (d, 1H), 7.09 (d, 1H), 6.63 (s, 1H), 6.29 (d, 1H), 5.69 (d, 1H), 5.40 (d, 1H), 4.34 (m, 1H), 3.95 (s, 3H), 3.51 (m, 2H), 3.42 (s, 2H), 3.12 (m, 4H), 2.56 (m, 2H), 1.48 (m, 1H), 1.21 (m, 3H), 0.96 (m, 2H), 0.83 (t, 3H). LRMS [M+H]=468.3.

Intermediate 3

Synthesis of 5-(2-methoxy-5-(piperazin-1-ylmethyl)benzyl)-N4-pentyl-5H-pyrrolo[3,2-d]pyrimidine-2,4-diamine (Int-3)

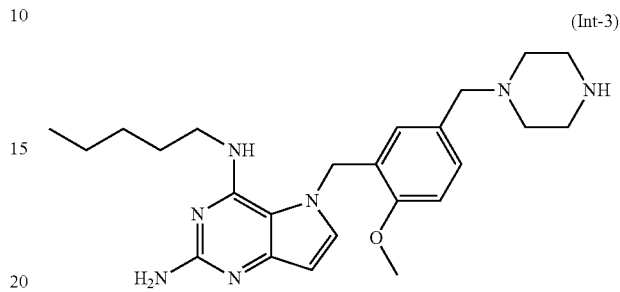

(Int-3)

5-(2-methoxy-5-(piperazin-1-ylmethyl)benzyl)-N4-pentyl-5H-pyrrolo[3,2-d]pyrimidine-2,4-diamine (Int-3) was prepared according to the synthesis of (S)-2-((2-amino-5-(2-methoxy-5-(piperazin-1-ylmethyl)benzyl)-5H-pyrrolo[3,2-d]pyrimidin-4-yl)amino)hexan-1-ol (Int-2), except commercially available N-pentylamine was used in place of (S)-2-aminohexan-1-ol in Step 4. $^1$H NMR (CD$_3$OD): δ 7.42 (d, 1H), 7.32 (d, 1H), 7.09 (d, 1H), 6.70 (s, 1H), 6.25 (d, 1H), 5.54 (d, 2H), 3.92 (s, 3H), 3.52 (t, 2H), 3.46 (s, 2H), 3.14 (m, 4H), 2.60 (m, 4H), 1.48 (m, 2H), 1.30 (m, 2H), 1.13 (m, 2H), 0.88 (t, 3H). LRMS [M+H]=438.3.

Antibody Conjugates of the Invention

The antibody conjugates of the invention comprise a TLR7 agonist and have the structure of Formula (II):

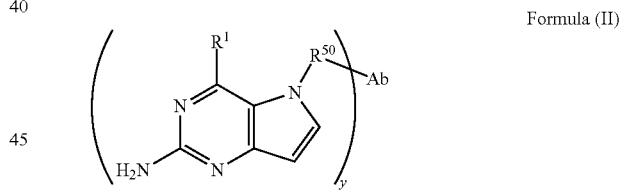

Formula (II)

wherein:

R$^{50}$ is

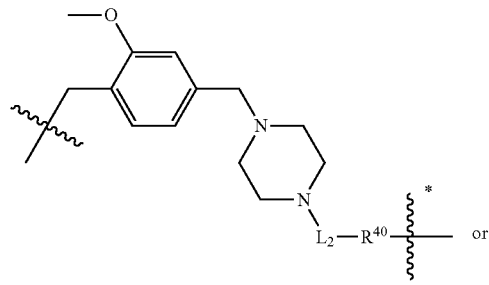

or

-continued

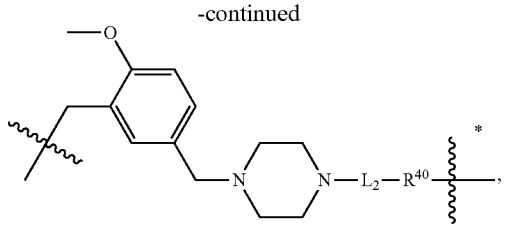

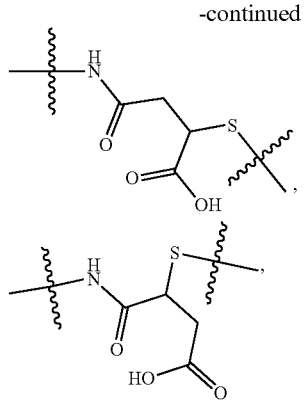

where the * indicates the point of attachment to Ab;
Ab is an antibody or antigen binding fragment thereof that specifically binds to human HER2;
$R^1$ is —$NHR^2$ or —$NHCHR^2R^3$;
$R^2$ is —$C_3$-$C_6$alkyl or —$C_4$-$C_6$alkyl;
$R^3$ is $L_1$OH;
$L_1$ is —$(CH_2)_m$—;
$L_2$ is —$(CH_2)_n$—, —$((CH_2)_nO)_t(CH_2)_n$—, —$(CH_2)_nX_1$ $(CH_2)_n$—, —$(CH_2)_nNHC(=O)(CH_2)_n$—, —$(CH_2)_nNHC$ $(=O)(CH_2)_nC(=O)NH(CH_2)_n$—, —$((CH_2)_nO)_t(CH_2)_n$ $NHC(=O)(CH_2)_n$—, —$C(=O)(CH_2)_n$—, —$C(=O)((CH_2)_n$ $O)_t(CH_2)_n$—, —$C(=O)((CH_2)_nO)_t(CH_2)_nX_1(CH_2)_n$—, —$C(=O)((CH_2)_nO)_t(CH_2)_nNHC(=O)(CH_2)_n$—, —$C(=O)((CH_2)_nO)_t(CH_2)_nC(=O)NH(CH_2)_n$—, —$C(=O)NH((CH_2)_nO)_t(CH_2)_nX_1(CH_2)_n$—, —$C(=O)$ $X_2X_3C(=O)((CH_2)_nO)_t(CH_2)_n$—, —$C(=O)X_2X_3C(=O)$ $(CH_2)_n$—, —$C(=O)X_2C(=O)(CH_2)_nNHC(=O)(CH_2)_n$—, —$C(=O)X_2C(=O)(CH_2)_nNHC(=O)((CH_2)_nO)_t$ $(CH_2)_n$—, —$C(=O)(CH_2)_nC(R_7)_2$—, —$C(=O)(CH_2)_nC$ $(R_7)_2SS(CH_2)_nNHC(=O)(CH_2)_n$—, —$(CH_2)_nX_2C(=O)$ $(CH_2)_nNHC(=O)((CH_2)_nO)_t(CH_2)_n$— or —$C(=O)(CH_2)_n$ $C(=O)NH(CH_2)_n$;
$R^{40}$ is

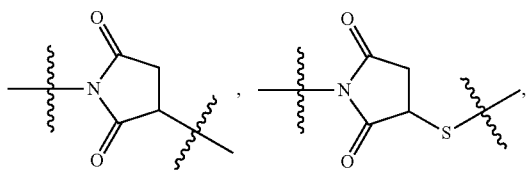

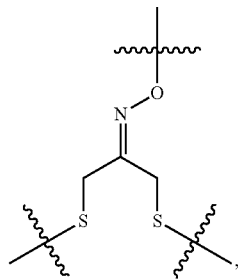

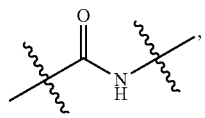

—S—,  —NHC(=O)CH$_2$—,  —S(=O)$_2$CH$_2$CH$_2$—,
—(CH$_2$)$_2$S(=O)$_2$CH$_2$CH$_2$—,  —NHS(=O)$_2$CH$_2$CH$_2$,
—NHC(=O)CH$_2$CH$_2$—,  —CH$_2$NHCH$_2$CH$_2$—,
—NHCH$_2$CH$_2$—,

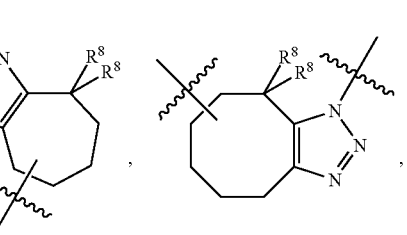

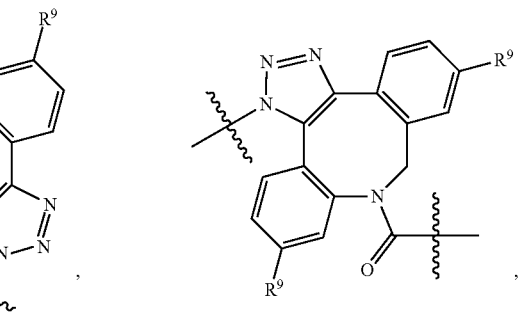

161
162
-continued
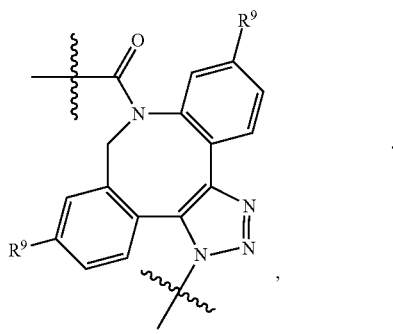, 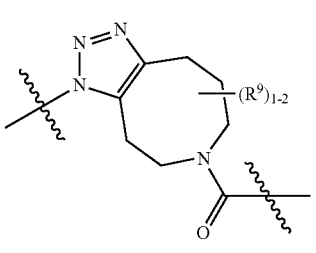, 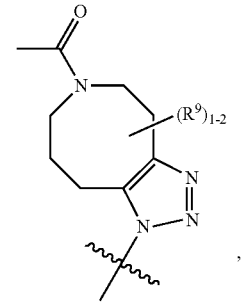,
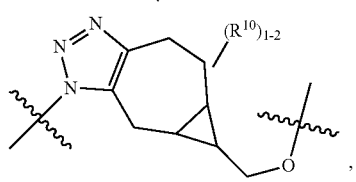, 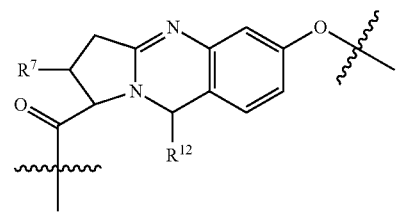,
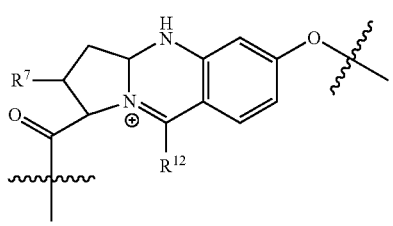, 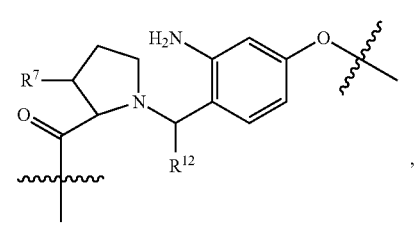,
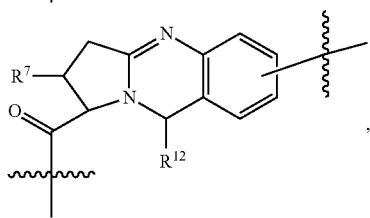, 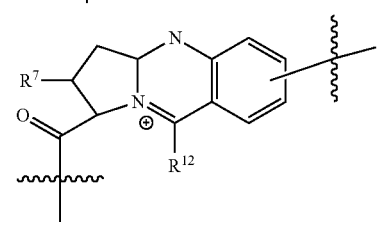,
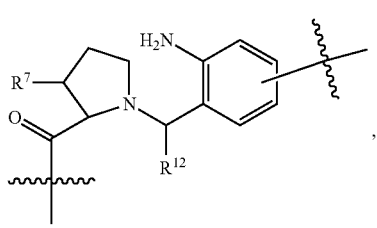, 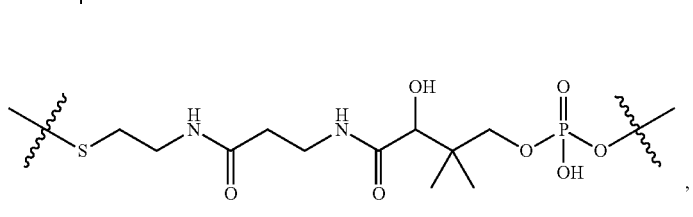,
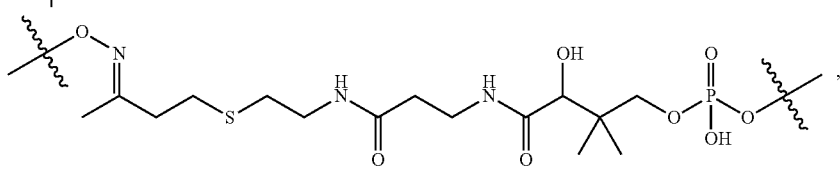,
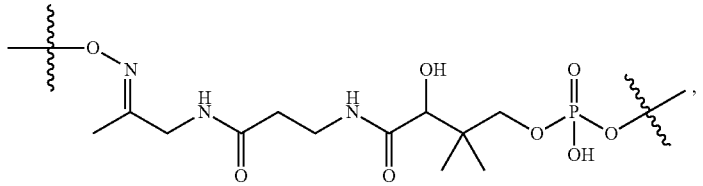,
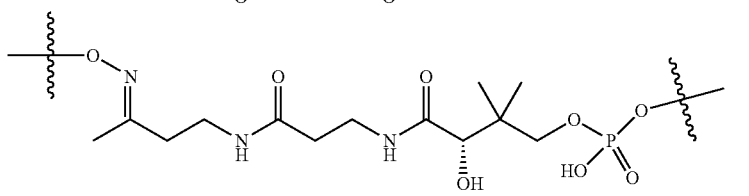

-continued
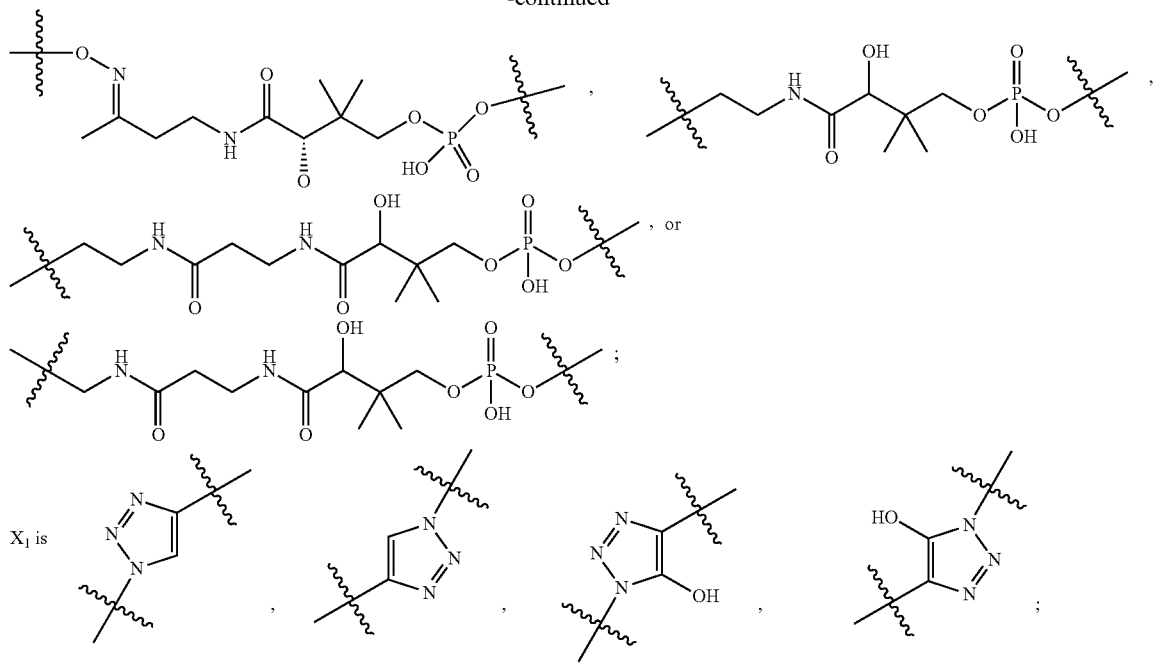
$X_1$ is
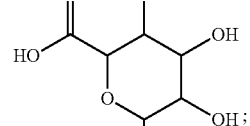, 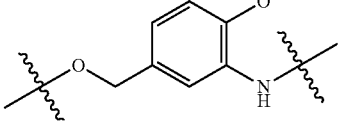;
$X_2$ is
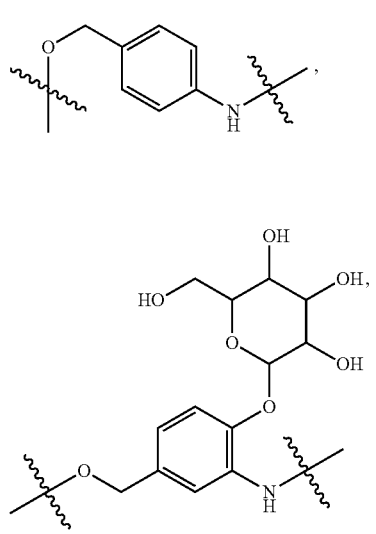
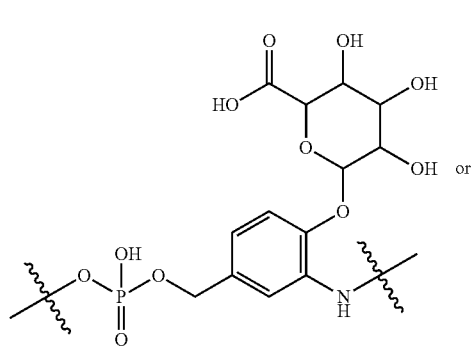
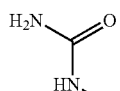
$X_3$ is
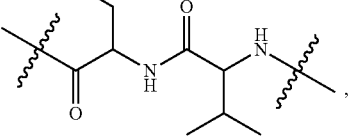,

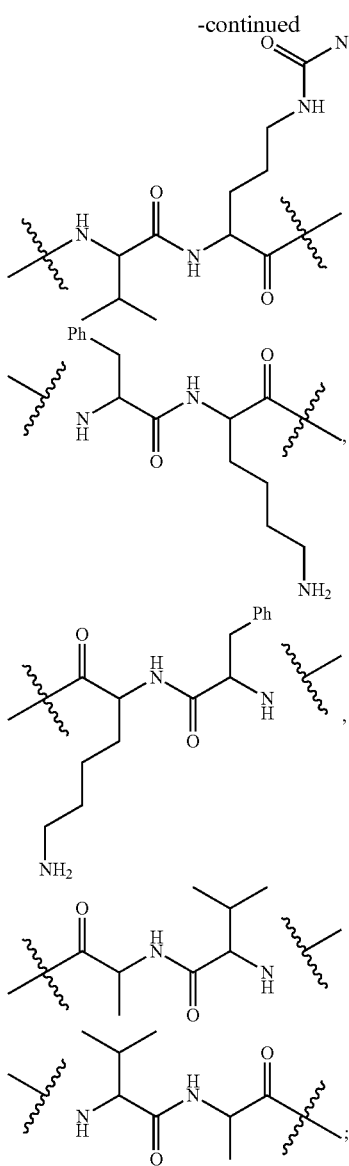

each R[7] is independently selected from H and $C_1$-$C_6$alkyl;
each R[8] is independently selected from H, $C_1$-$C_6$alkyl, F, Cl, and —OH;
each R[9] is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each R[10] is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
R[12] is H, methyl or phenyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Certain aspects and examples of the compounds of the invention are provided in the following listing of additional, enumerated embodiments. It will be recognized that features specified in each embodiment may be combined with other specified features to provide further embodiments of the present invention.

Embodiment 58

The antibody conjugates of Formula (II), wherein:
R[50] is

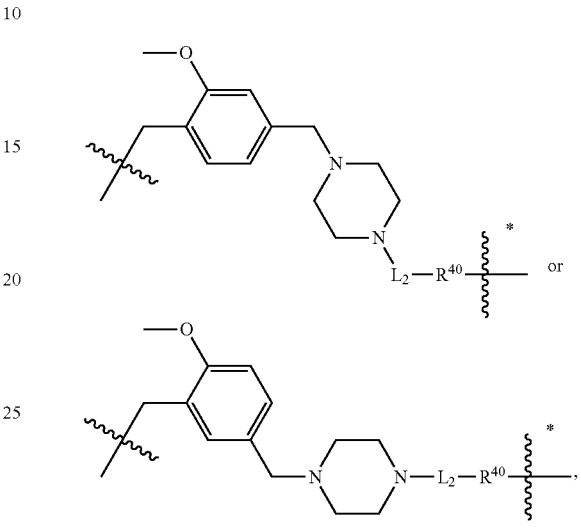

where the * indicates the point of attachment to Ab;
Ab is an antibody or antigen binding fragment thereof that specifically binds to human HER2;
R[1] is —NHR[2] or —NHCHR[2]R[3];
R[2] is —$C_3$-$C_6$alkyl or —$C_4$-$C_6$alkyl;
R[3] is $L_1$OH;
$L_1$ is —$(CH_2)_m$—;
$L_2$ is —$(CH_2)_n$—, —$((CH_2)_nO)_t(CH_2)_n$—, —$(CH_2)_nX_1(CH_2)_n$—, —$(CH_2)_nNHC(=O)(CH_2)_n$—, —$(CH_2)_nNHC(=O)(CH_2)_nC(=O)NH(CH_2)_n$—, —$((CH_2)_nO)_t(CH_2)_nNHC(=O)(CH_2)_n$, —$C(=O)(CH_2)_n$—, —$C(=O)((CH_2)_nO)_t(CH_2)_n$—, —$C(=O)((CH_2)_nO)_t(CH_2)_nX_1(CH_2)_n$—, —$C(=O)((CH_2)_nO)_t(CH_2)_nNHC(=O)(CH_2)_n$—, —$C(=O)((CH_2)_nO)_t(CH_2)_nC(=O)NH(CH_2)_n$—, —$C(=O)NH((CH_2)_nO)_t(CH_2)_nX_1(CH_2)_n$—, —$C(=O)X_2X_3C(=O)((CH_2)_nO)_t(CH_2)_n$—, —$C(=O)X_2C(=O)(CH_2)_nNHC(=O)(CH_2)_n$—, or —$C(=O)(CH_2)_nC(=O)NH(CH_2)_n$;
R[40] is

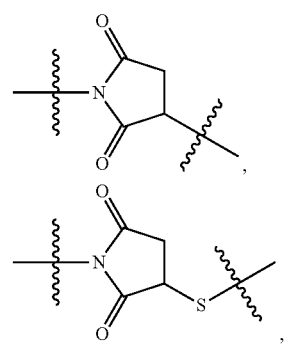

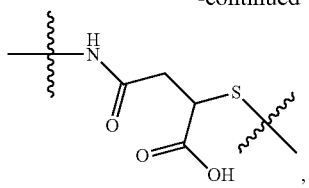
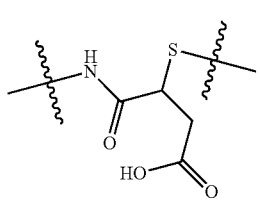
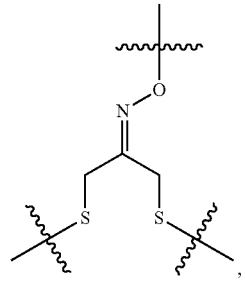
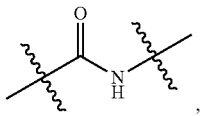
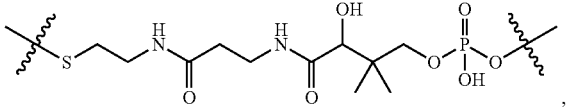
—S—, —NHC(=O)CH$_2$—, —S(=O)$_2$CH$_2$CH$_2$—,
—(CH$_2$)$_2$S(=O)$_2$CH$_2$CH$_2$—, —NHS(=O)$_2$CH$_2$CH$_2$,
—NHC(=O)CH$_2$CH$_2$—, —CH$_2$NHCH$_2$CH$_2$—,
—NHCH$_2$CH$_2$—,
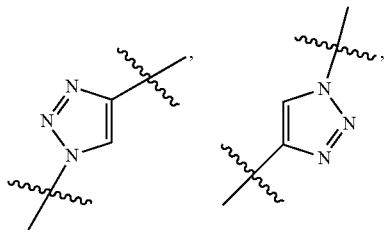
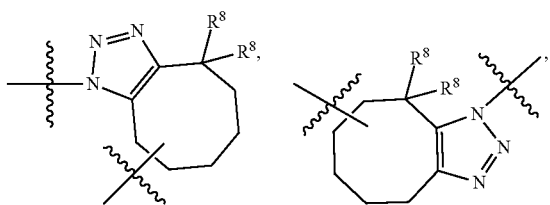
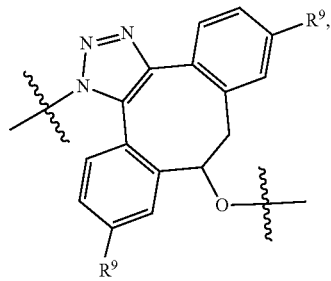
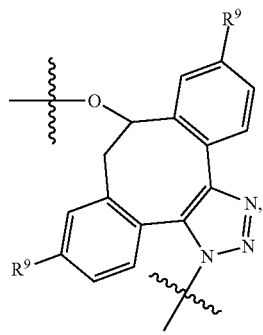

-continued
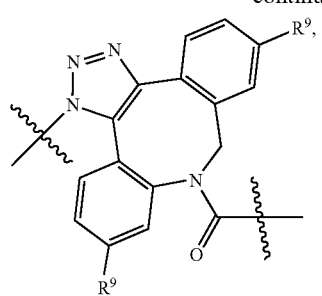
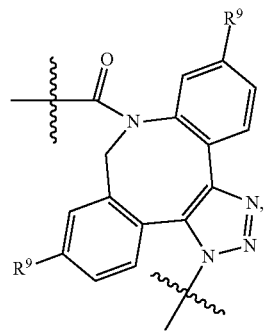
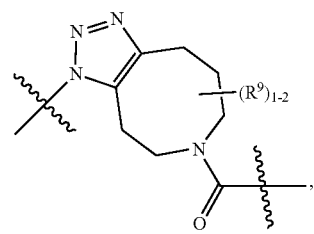
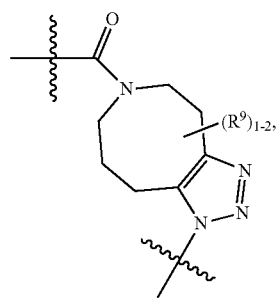
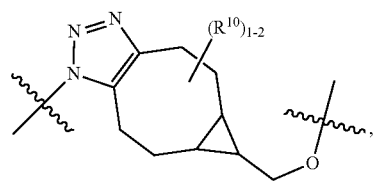
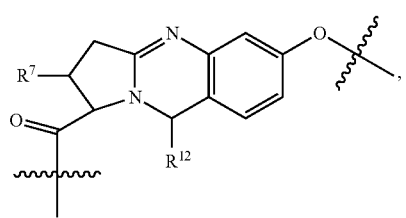

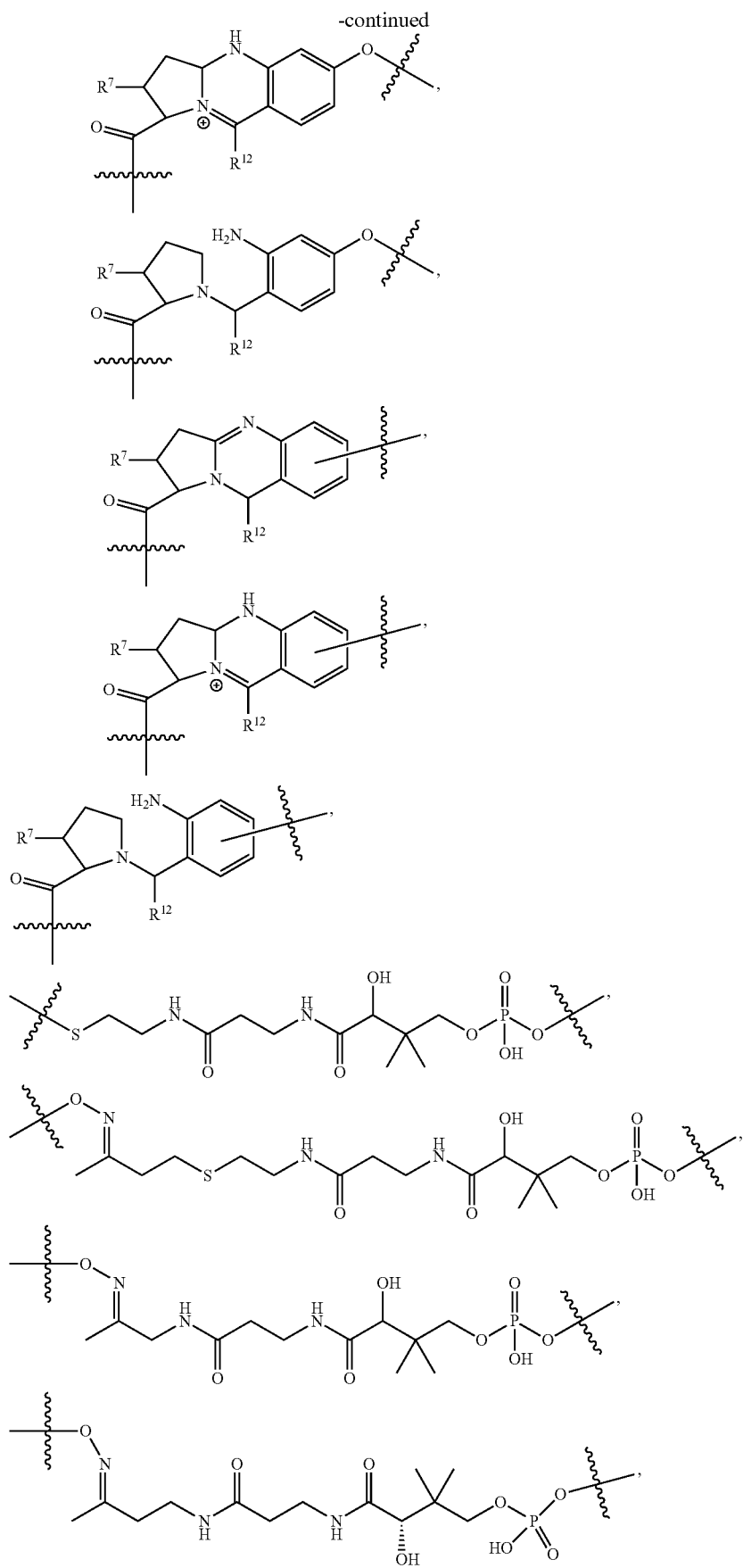

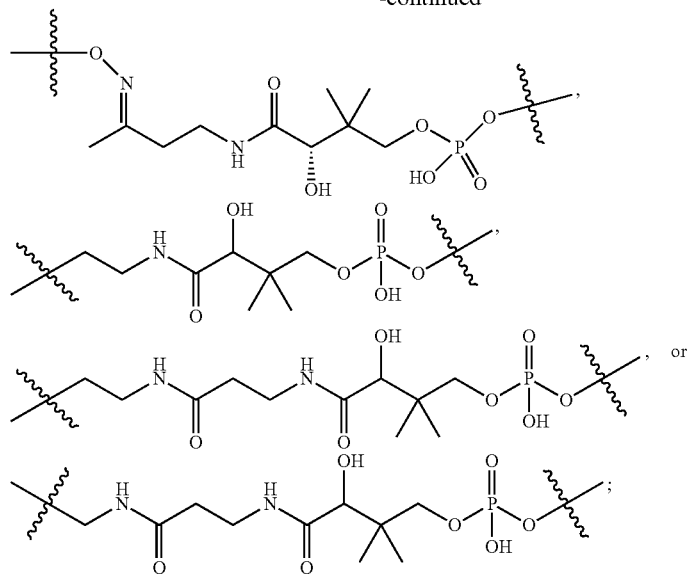
$X_1$ is
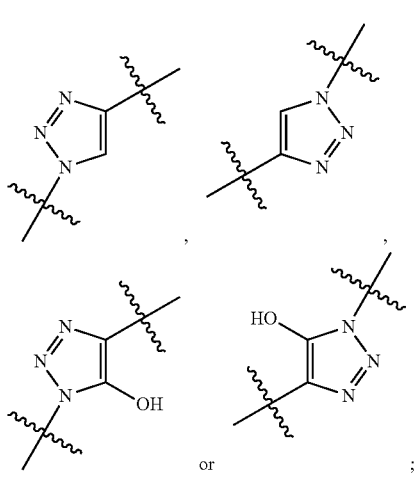
$X_2$ is
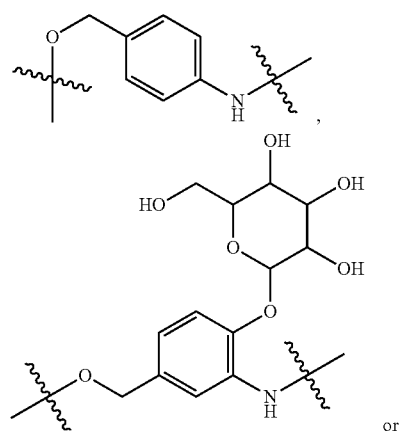
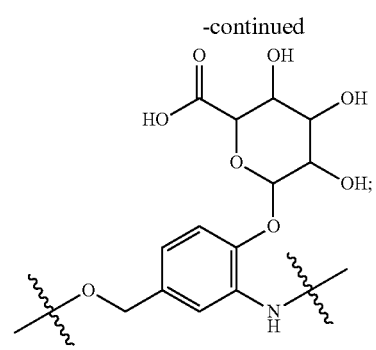
$X_3$ is
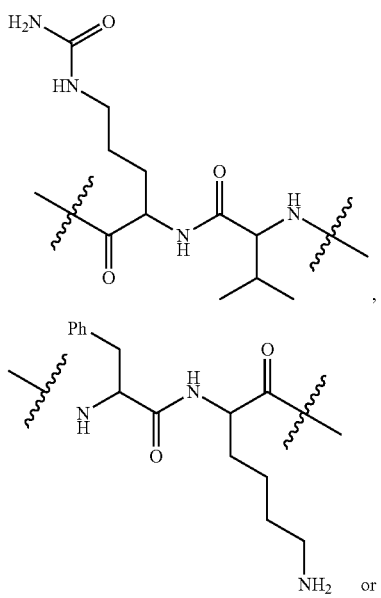

-continued

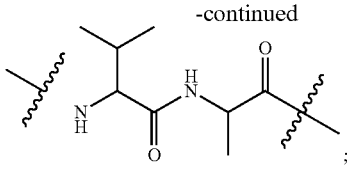

each R[7] is independently selected from H and $C_1$-$C_6$alkyl;
each R[8] is independently selected from H, $C_1$-$C_6$alkyl, F, Cl, and —OH;
each R[9] is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each R[10] is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
R[12] is H, methyl or phenyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 59

The antibody conjugate of Formula (II) having the structure of Formula (IIa) or Formula (IIb), and the pharmaceutically acceptable salts thereof:

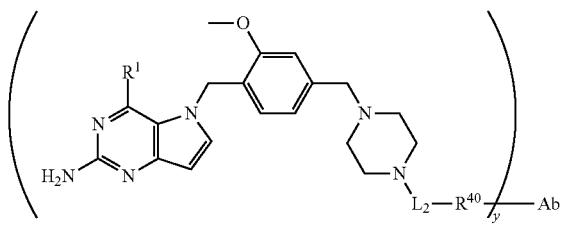
Formula (IIa)

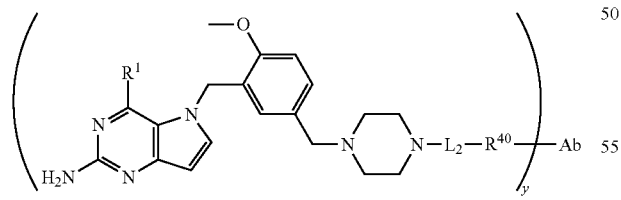
Formula (IIb)

wherein:
Ab is an antibody or antigen binding fragment thereof that specifically binds to human HER2;
R[1] is —NHR[2] or —NHCHR[2]R[3];
R[2] is —$C_3$-$C_6$alkyl or —$C_4$-$C_6$alkyl;
R[3] is $L_1$OH;
$L_1$ is —$(CH_2)_m$—;
$L_2$ is —$(CH_2)_n$—, —$((CH_2)_nO)_t(CH_2)_n$—, —$(CH_2)_nX_1(CH_2)_n$—, —$(CH_2)_nNHC(=O)(CH_2)_n$—, —$(CH_2)_n$NHC(=O)$(CH_2)_n$C(=O)NH$(CH_2)_n$—, —$((CH_2)_nO)_t(CH_2)_n$NHC(=O)$(CH_2)_n$—, —C(=O)$(CH_2)_n$—, —C(=O)$((CH_2)_nO)_t(CH_2)_n$—, —C(=O)$((CH_2)_nO)_t(CH_2)_nX_1(CH_2)_n$—, —C(=O)$((CH_2)_nO)_t(CH_2)_n$NHC(=O)$(CH_2)_n$—, —C(=O)$((CH_2)_nO)_t(CH_2)_n$C(=O)NH$(CH_2)_n$—, —C(=O)NH$((CH_2)_nO)_t(CH_2)_nX_1(CH_2)_n$—, —C(=O)$X_2X_3$C(=O)$((CH_2)_nO)_t(CH_2)_n$—, —C(=O)$X_2X_3$C(=O)$(CH_2)_n$—, —C(=O)$X_2$C(=O)$(CH_2)_n$NHC(=O)$(CH_2)_n$—, —C(=O)$X_2$C(=O)$(CH_2)_n$NHC(=O)$((CH_2)_nO)_t(CH_2)_n$—, —C(=O)$(CH_2)_nC(R_7)_2$—, —C(=O)$(CH_2)_nC(R_7)_2$SS$(CH_2)_n$NHC(=O)$(CH_2)_n$—, —$(CH_2)_nX_2$C(=O)$(CH_2)_n$NHC(=O)$((CH_2)_nO)_t(CH_2)_n$— or —C(=O)$(CH_2)_nC(=O)NH(CH_2)_n$;

R[40] is

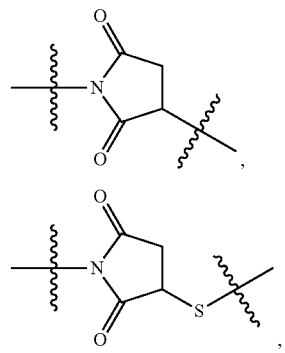

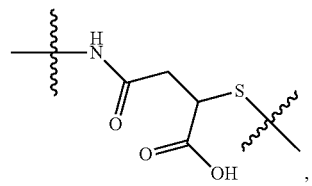

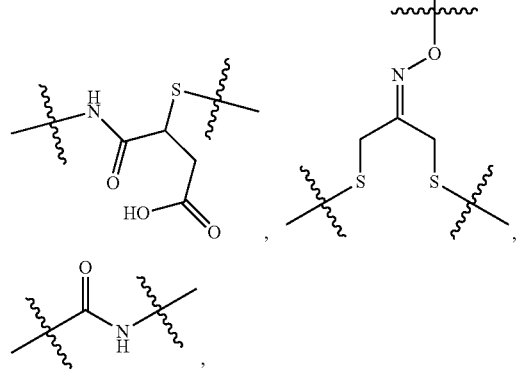

—S—, —NHC(=O)$CH_2$—, —S(=O)$_2CH_2CH_2$—, —$(CH_2)_2$S(=O)$_2CH_2CH_2$—, —NHS(=O)$_2CH_2CH_2$, —NHC(=O)$CH_2CH_2$—, —$CH_2$NH$CH_2CH_2$—, —NH$CH_2CH_2$—,

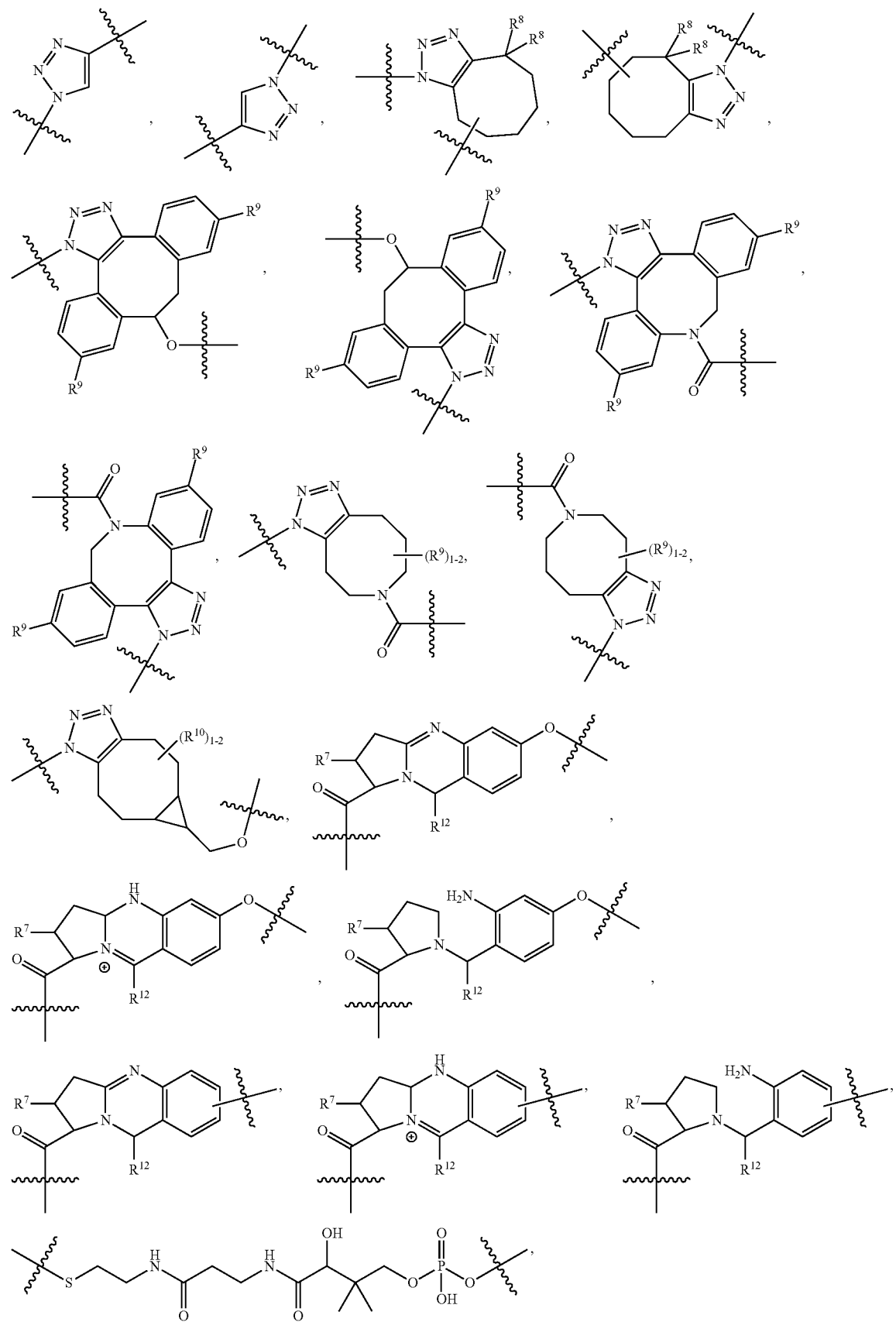

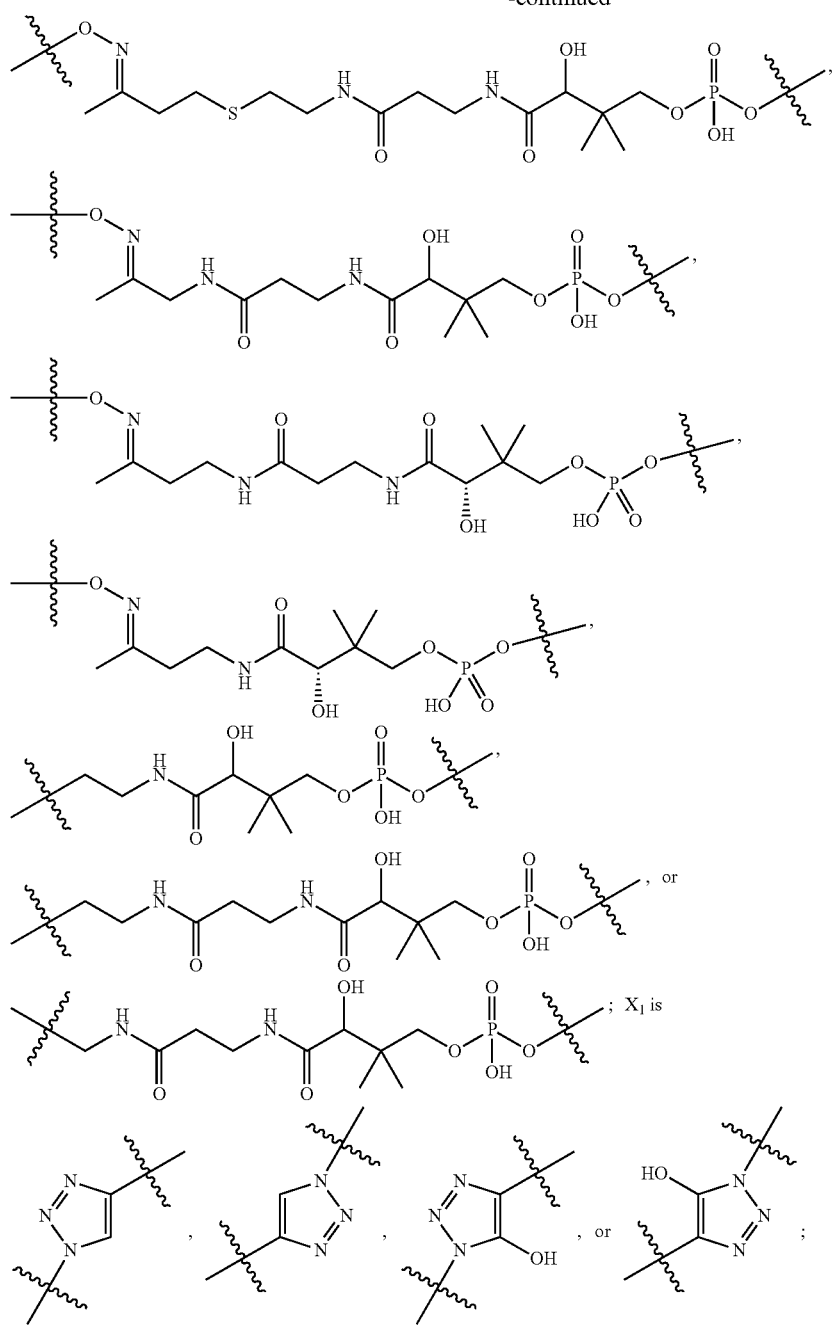
X_2 is
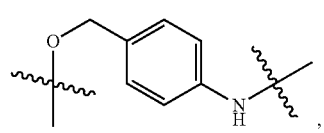
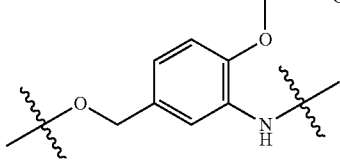

-continued

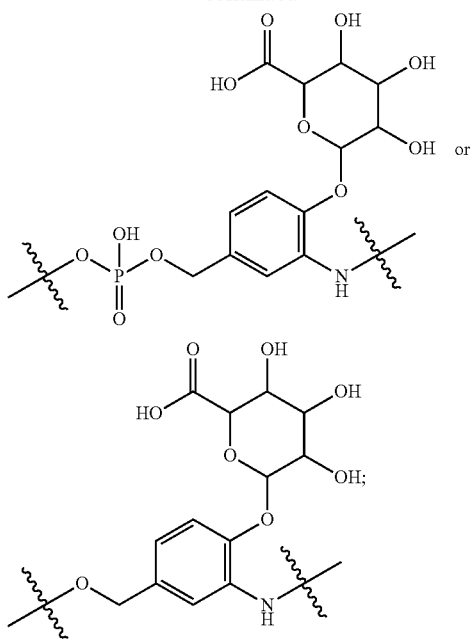

$X_3$ is

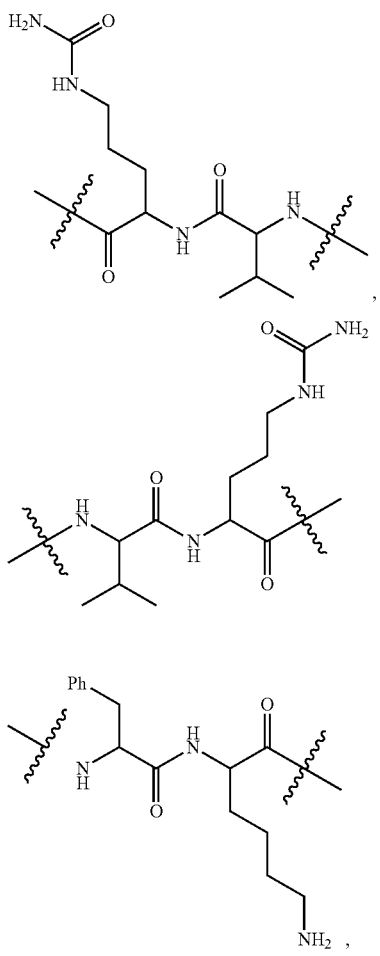

-continued

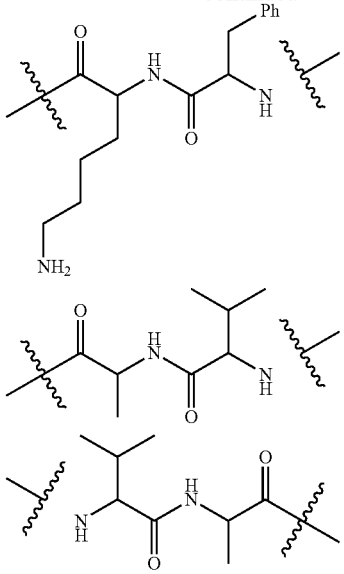

each $R^7$ is independently selected from H and $C_1$-$C_6$alkyl;
each $R^8$ is independently selected from H, $C_1$-$C_6$alkyl, F, Cl, and —OH;
each $R^9$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
$R^{12}$ is H, methyl or phenyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 60

The antibody conjugate of Formula (IIa) or Formula (IIb), and the pharmaceutically acceptable salts thereof, wherein:
Ab is an antibody or antigen binding fragment thereof that specifically binds to human HER2;
$R^1$ is —$NHR^2$ or —$NHCHR^2R^3$;
$R^2$ is —$C_3$-$C_6$alkyl or —$C_4$-$C_6$alkyl;
$R^3$ is $L_1$OH;
$L_1$ is —$(CH_2)_m$—;
$L_2$ is —$(CH_2)_n$—, —$((CH_2)_nO)_t(CH_2)_n$—, —$(CH_2)_nX_1$ $(CH_2)_n$—, —$(CH_2)_nNHC(=O)(CH_2)_n$—, —$(CH_2)_n$ $NHC(=O)(CH_2)_nC(=O)NH(CH_2)_n$—, —$((CH_2)_nO)_t$ $(CH_2)_nNHC(=O)(CH_2)_n$—, —$C(=O)(CH_2)_n$—, —$C(=O)((CH_2)_nO)_t(CH_2)_n$—, —$C(=O)((CH_2)_nO)_t$ $(CH_2)_nX_1(CH_2)_n$—, —$C(=O)((CH_2)_nO)_t(CH_2)_nNHC$ $(=O)(CH_2)_n$—, —$C(=O)((CH_2)_nO)_t(CH_2)_nC(=O)$ $NH(CH_2)_n$—, —$C(=O)NH((CH_2)_nO)_t(CH_2)_nX_1$ $(CH_2)_n$—, —$C(=O)X_2X_3C(=O)((CH_2)_nO)_t$ $(CH_2)_n$—, —$C(=O)X_2C(=O)(CH_2)_nNHC(=O)$ $(CH_2)_n$—, or —$C(=O)(CH_2)_nC(=O)NH(CH_2)_n$;

$R^{40}$ is
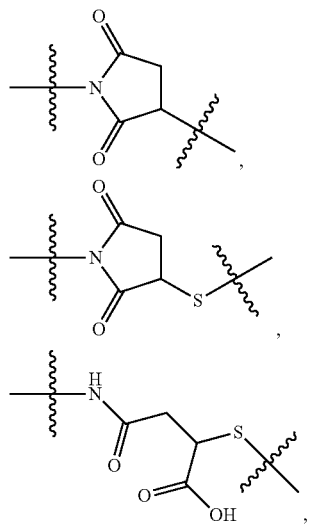
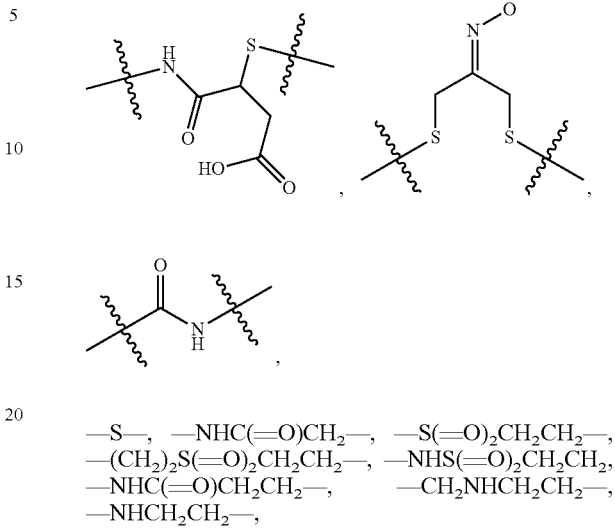
—S—, —NHC(=O)CH$_2$—, —S(=O)$_2$CH$_2$CH$_2$—,
—(CH$_2$)$_2$S(=O)$_2$CH$_2$CH$_2$—, —NHS(=O)$_2$CH$_2$CH$_2$—,
—NHC(=O)CH$_2$CH$_2$—, —CH$_2$NHCH$_2$CH$_2$—,
—NHCH$_2$CH$_2$—,
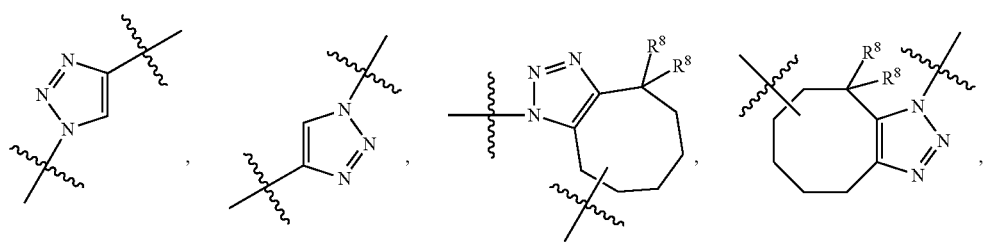
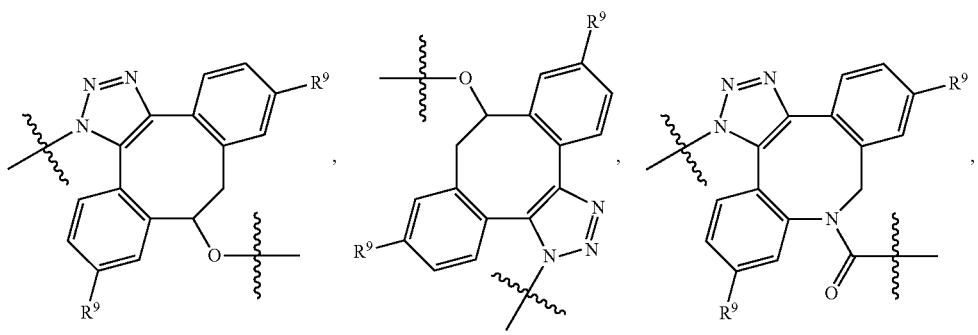
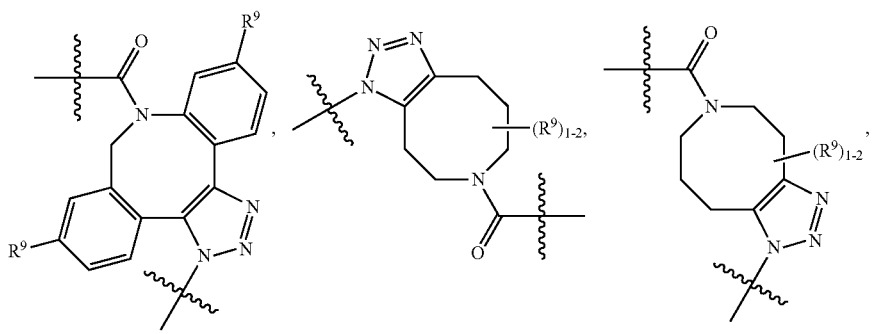

-continued
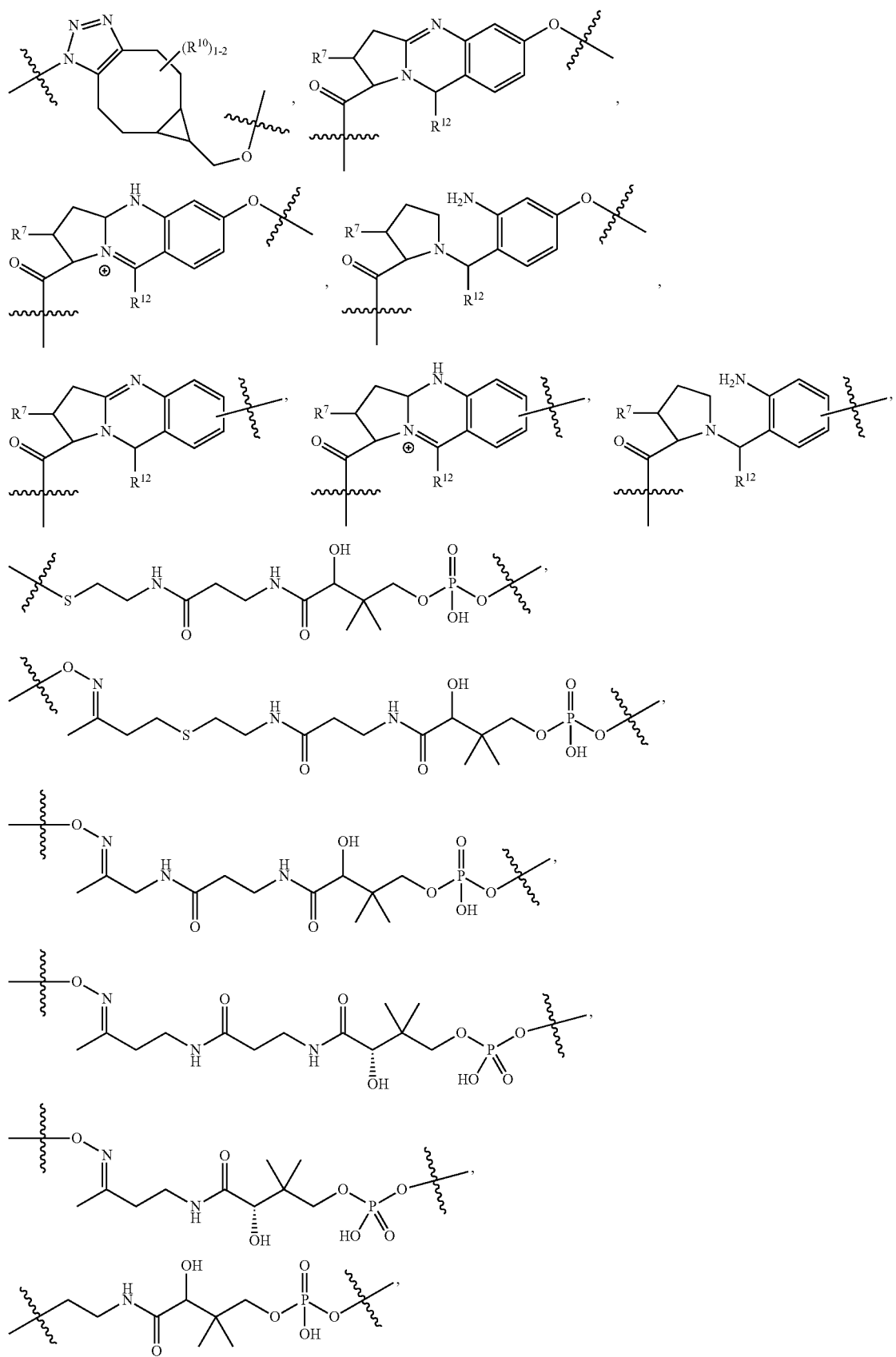

-continued

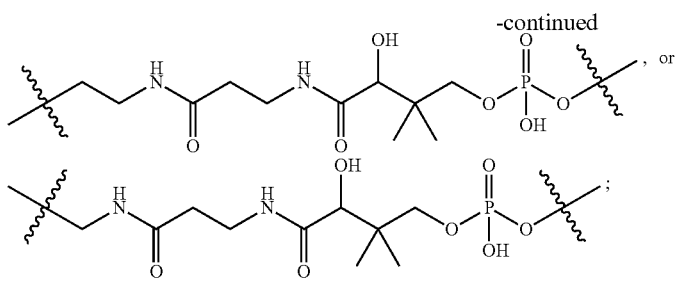

$X_1$ is

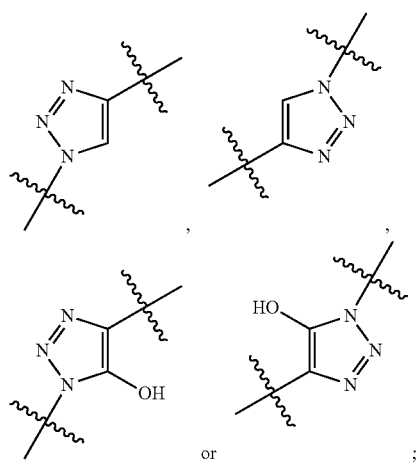

$X_2$ is

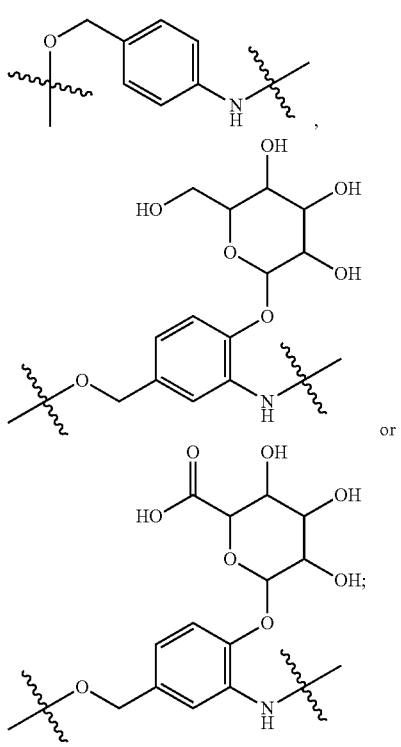

$X_3$ is

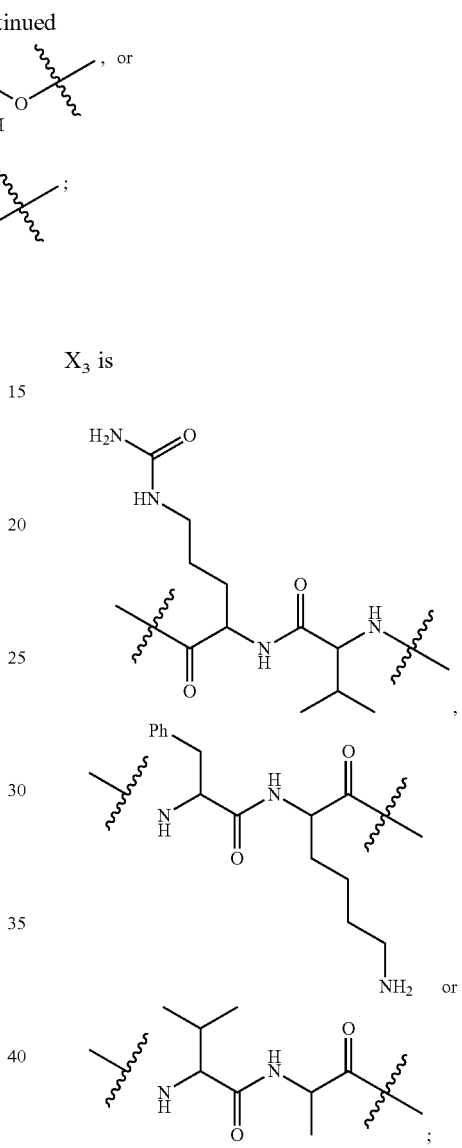

each $R^7$ is independently selected from H and $C_1$-$C_6$alkyl;
each $R^8$ is independently selected from H, $C_1$-$C_6$alkyl, F, Cl, and —OH;
each $R^9$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
$R^{12}$ is H, methyl or phenyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 61

The antibody conjugate of Formula (II) having the structure of Formula (IIa) or Formula (IIb), and the pharmaceutically acceptable salts thereof:

Formula (IIa)

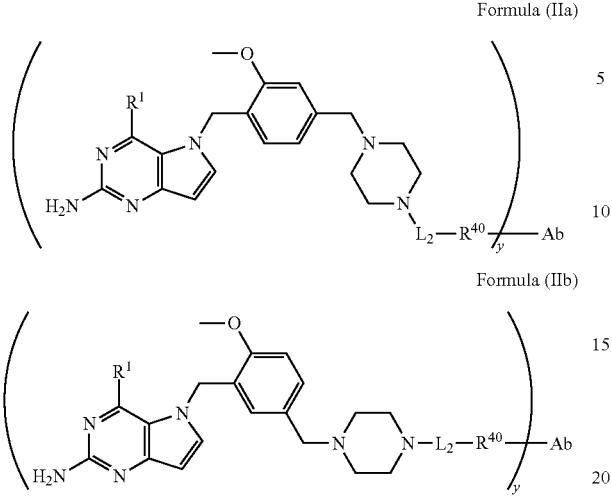

Formula (IIb)

wherein:
Ab is an antibody or antigen binding fragment thereof that specifically binds to human HER2;
$R^1$ is $-NHR^2$ or $-NHCHR^2R^3$;
$R^2$ is $-C_3-C_6$alkyl or $-C_4-C_6$alkyl;
$R^3$ is $L_1OH$;
$L_1$ is $-(CH_2)_m-$;
$L_2$ is $-(CH_2)_n-$, $-((CH_2)_nO)_t(CH_2)_n-$, $-(CH_2)_nX_1(CH_2)_n-$, $-(CH_2)_nNHC(=O)(CH_2)_n-$, $-(CH_2)_nNHC(=O)(CH_2)_nC(=O)NH(CH_2)_n-$, $-((CH_2)_nO)_t(CH_2)_nNHC(=O)(CH_2)_n-$, $-C(=O)(CH_2)_n-$, $-C(=O)((CH_2)_nO)_t(CH_2)_n-$, $-C(=O)((CH_2)_nO)_t(CH_2)_nX_1(CH_2)_n-$, $-C(=O)((CH_2)_nO)_t(CH_2)_nNHC(=O)(CH_2)_n-$, $-C(=O)((CH_2)_nO)_t(CH_2)_nC(=O)NH(CH_2)_n-$, $-C(=O)NH((CH_2)_nO)_t(CH_2)_nX_1(CH_2)_n-$, $-C(=O)X_2X_3C(=O)((CH_2)_nO)_t(CH_2)_n-$, $-C(=O)X_2C(=O)(CH_2)_nNHC(=O)(CH_2)_n-$, or $-C(=O)(CH_2)_nC(=O)NH(CH_2)_n$;
$R^{40}$ is

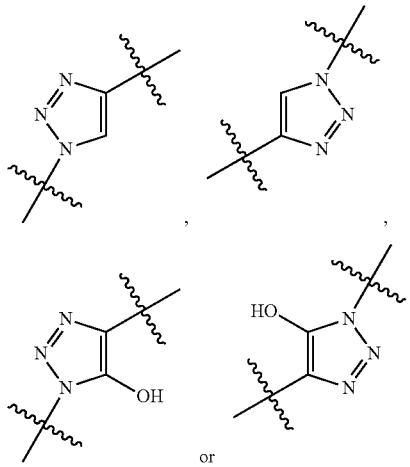

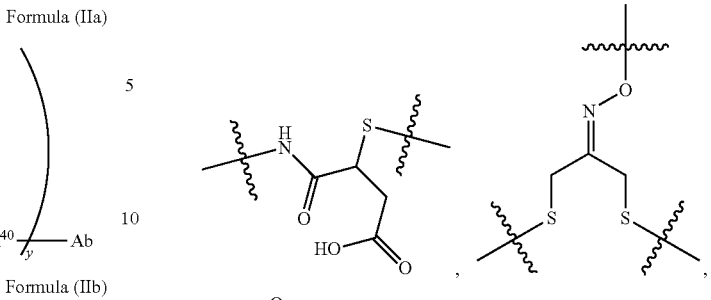

or $-S-$;
$X_1$ is

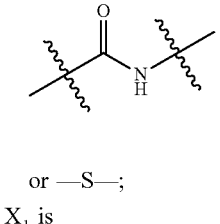

or

;

$X_2$ is

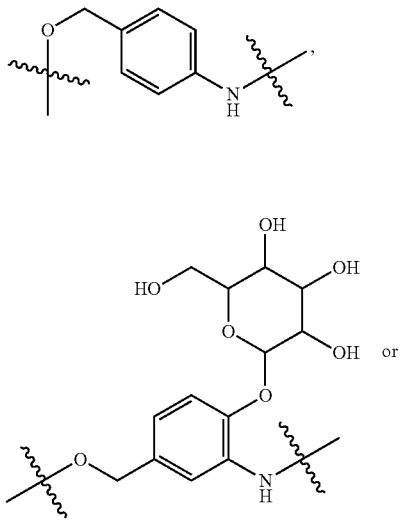

or

-continued

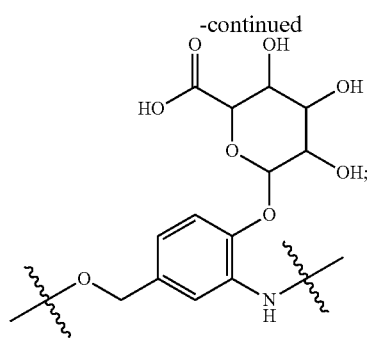

$X_3$ is

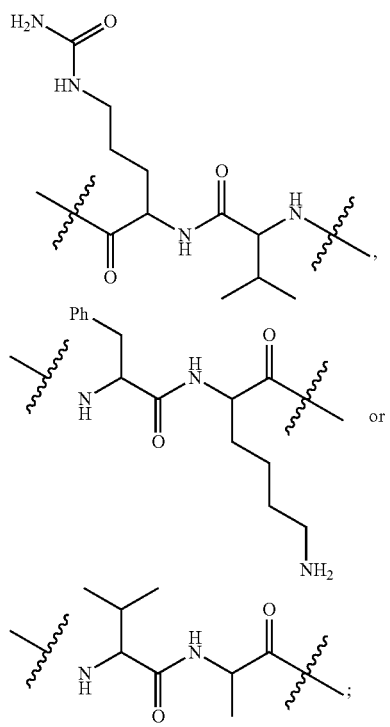

each $R^7$ is independently selected from H and $C_1$-$C_6$alkyl;
each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 62

The antibody conjugate of Formula (II), Formula (IIa) or Formula (IIb), wherein:
Ab is an antibody or antigen binding fragment thereof that specifically binds to human HER2;
$R^1$ is —$NHR^2$ or —$NHCHR^2R^3$;
$R^2$ is —$C_4$-$C_6$alkyl;
$R^3$ is $L_1$OH;
$L_1$ is —$(CH_2)_m$—;
$L_2$ is —$(CH_2)_n$—, —$((CH_2)_nO)_t(CH_2)_n$—, —$(CH_2)_nX_1(CH_2)_n$—, —$(CH_2)_nNHC(=O)(CH_2)_n$—, —$(CH_2)_nNHC(=O)(CH_2)_nC(=O)NH(CH_2)_n$—, —$((CH_2)_nO)_t(CH_2)_nNHC(=O)(CH_2)_n$, —$C(=O)(CH_2)_n$—, —$C(=O)((CH_2)_nO)_t(CH_2)_n$—, —$C(=O)((CH_2)_nO)_t(CH_2)_nX_1(CH_2)_n$—, —$C(=O)((CH_2)_nO)_t(CH_2)_nNHC(=O)(CH_2)_n$—, —$C(=O)((CH_2)_nO)_t(CH_2)_nC(=O)NH(CH_2)_n$—, —$C(=O)NH((CH_2)_nO)_t(CH_2)_nX_1(CH_2)_n$—, —$C(=O)X_2X_3C(=O)((CH_2)_nO)_t(CH_2)_n$—, —$C(=O)X_2C(=O)(CH_2)_nNHC(=O)(CH_2)_n$—, or —$C(=O)(CH_2)_nC(=O)NH(CH_2)_n$;

$R^{40}$ is

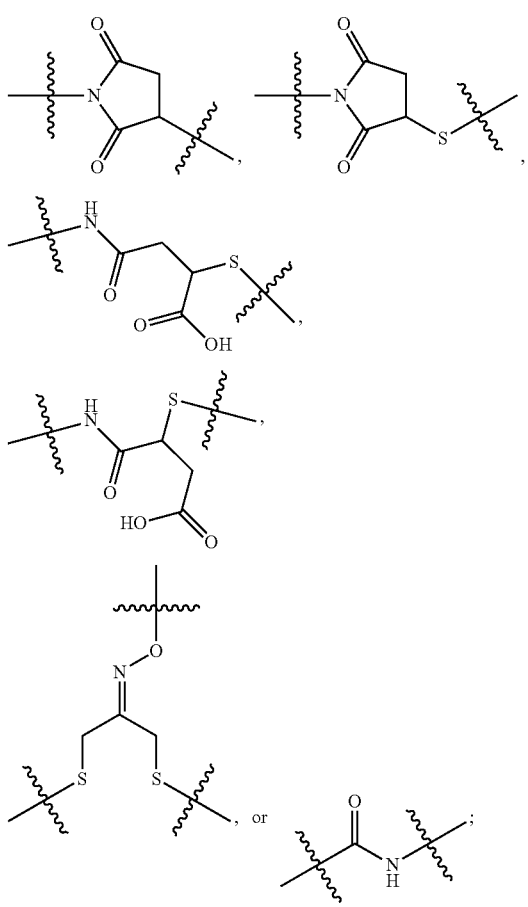

$X_1$ is

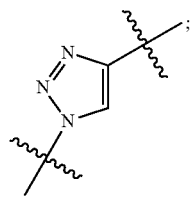 [SMILES: *c1cn(*)nn1]

$X_2$ is

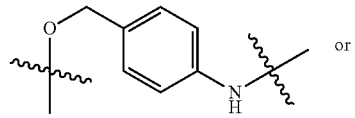

-continued

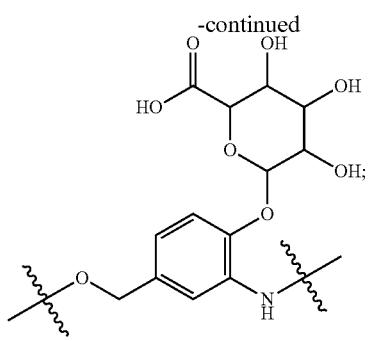

$X_3$ is

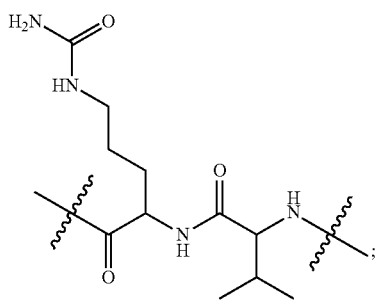 [SMILES: *NC(C(=O)NC(CCCNC(N)=O)C(*)=O)C(C)C]

each m is independently selected from 1, 2, 3, and 4;
each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 63

The antibody conjugate of Formula (II), Formula (IIa) or Formula (IIb), wherein:
Ab is an antibody or antigen binding fragment thereof that specifically binds to human HER2;
$R^1$ is —$NHR^2$;
$R^2$ is —$C_4$-$C_6$alkyl;
$L_2$ is —$(CH_2)_n$—, —$((CH_2)_nO)_t(CH_2)_n$—, —$(CH_2)_nX_1(CH_2)_n$—, —$(CH_2)_nNHC(=O)(CH_2)_n$—, —$(CH2)_nNHC(=O)(CH_2)_nC(=O)NH(CH_2)_n$—, —$((CH_2)_nO)_t(CH_2)_nNHC(=O)(CH_2)_n$—, —$C(=O)(CH_2)_n$—, —$C(=O)((CH_2)_nO)_t(CH_2)_n$—, —$C(=O)((CH_2)_nO)_t(CH_2)_nX_1(CH_2)_n$—, —$C(=O)((CH_2)_nO)_t(CH_2)_nNHC(=O)(CH_2)_n$—, —$C(=O)((CH_2)_nO)_t(CH_2)_nC(=O)NH(CH_2)_n$—, —$C(=O)NH((CH_2)_nO)_t(CH_2)_nX_1(CH_2)_n$—, —$C(=O)X_2X_3C(=O)((CH_2)_nO)_t(CH_2)_n$—, —$C(=O)X_2C(=O)(CH_2)_nNHC(=O)(CH_2)_n$—, or —$C(=O)(CH_2)_nC(=O)NH(CH_2)_n$;
$R^{40}$ is

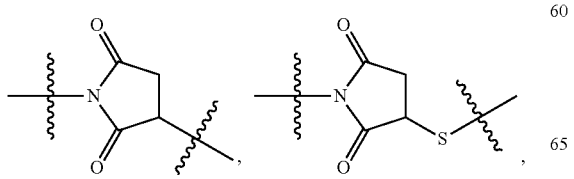

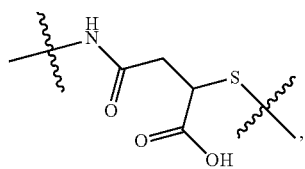

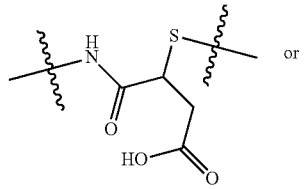

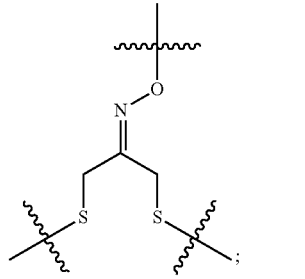

$X_1$ is

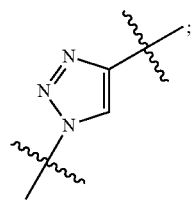 [SMILES: *c1cn(*)nn1]

$X_2$ is

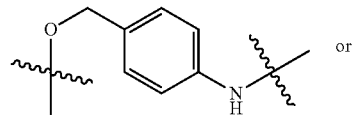

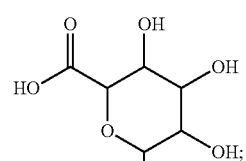

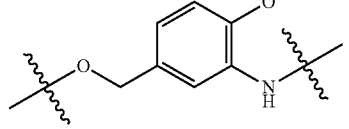

$X_3$ is

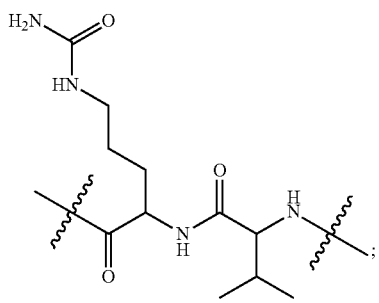 [SMILES: *NC(C(=O)NC(CCCNC(N)=O)C(*)=O)C(C)C]

each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 64

The antibody conjugate of Formula (II), Formula (IIa) or Formula (IIb), wherein:
Ab is an antibody or antigen binding fragment thereof that specifically binds to human HER2;
$R^1$ is —$NHR^2$;
$R^2$ is —$C_4$-$C_6$alkyl;
$L_2$ is —$(CH_2)_n$—, —$((CH_2)_nO)_t(CH_2)_n$—, —$(CH_2)_nX_1(CH_2)_n$—, —$C(=O)(CH_2)_n$—, —$C(=O)((CH_2)_nO)_t(CH_2)_n$—, —$C(=O)((CH_2)_nO)_t(CH_2)_nX_1(CH_2)_n$—, —$C(=O)NH((CH_2)_nO)_t(CH_2)_nX_1(CH_2)_n$—, —$C(=O)X_2X_3C(=O)((CH_2)_nO)_t(CH_2)_n$— or —$C(=O)X_2C(=O)(CH_2)_nNHC(=O)(CH_2)_n$—;
$R^{40}$ is

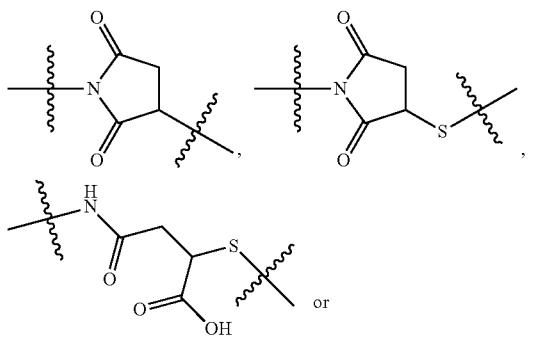

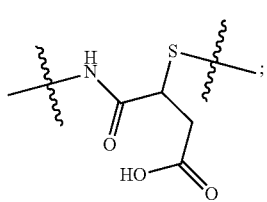

$X_1$ is

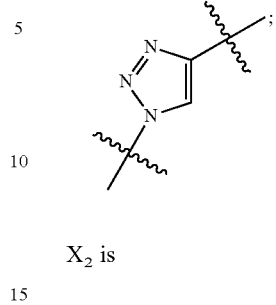

$X_2$ is

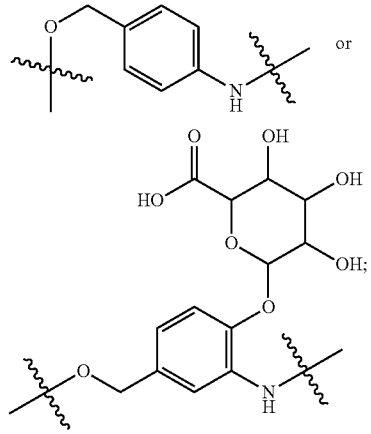

$X_3$ is

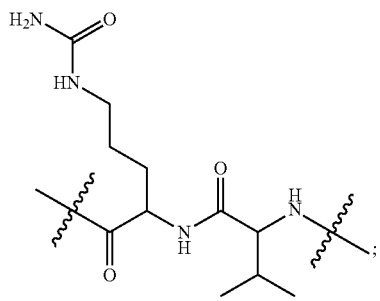

each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 65

The antibody conjugate of Formula (II), Formula (IIa) or Formula (IIb), wherein:
Ab is an antibody or antigen binding fragment thereof that specifically binds to human HER2;
$R^1$ is —$NHR^2$;
$R^2$ is —$C_4$-$C_6$alkyl;
$L_2$ is —$(CH_2)_n$— or —$C(=O)(CH_2)_n$;

R⁴⁰ is

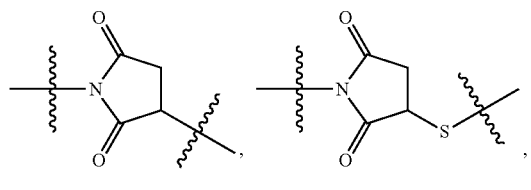

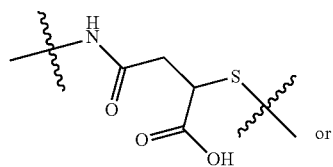

and
each n is independently selected from 1, 2, 3, and 4, and
y is an integer from 1 to 16.

Embodiment 66

The antibody conjugate of Formula (II), Formula (IIa) or Formula (IIb), wherein:
Ab is an antibody or antigen binding fragment thereof that specifically binds to human HER2;
R¹ is —NHR²;
R² is —C₄-C₆alkyl;
L₂ is —(CH₂)ₙ—, —((CH₂)ₙO)ₜ(CH₂)ₙ—, —(CH₂)ₙX₁(CH₂)ₙ—, —C(=O)(CH₂)ₙ—, —C(=O)((CH₂)ₙO)ₜ(CH₂)ₙ—, —C(=O)((CH₂)ₙO)ₜ(CH₂)ₙX₁(CH₂)ₙ—, —C(=O)NH((CH₂)ₙO)ₜ(CH₂)ₙX₁(CH₂)ₙ—, —C(=O)X₂X₃C(=O)((CH₂)ₙO)ₜ(CH₂)ₙ— or —C(=O)X₂C(=O)(CH₂)ₙNHC(=O)(CH₂)ₙ—;
R⁴⁰ is

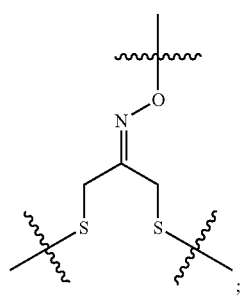 [SMILES: *ON=C(CS*)CS*]

X₁ is

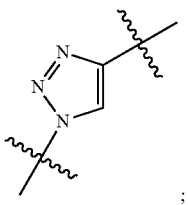 [SMILES: *c1cn(*)nn1]

X₂ is

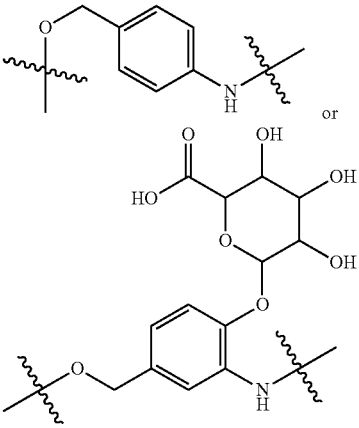

X₃ is

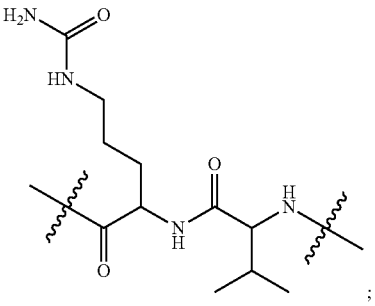

each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

Embodiment 67

The antibody conjugate of Formula (II), Formula (IIa) or Formula (IIb), wherein: R¹ is —NHR².

Embodiment 68

The antibody conjugate of Formula (II), Formula (IIa) or Formula (IIb), wherein: R¹ is —NHCHR²R³.

Embodiment 69

The antibody conjugate of Formula (II), Formula (IIa) or Formula (IIb), wherein: R² is —C₄alkyl.

Embodiment 70

The antibody conjugate of Formula (II), Formula (IIa) or Formula (IIb), wherein: $R^2$ is —$C_5$alkyl.

Embodiment 71

The antibody conjugate of Formula (II), Formula (IIa) or Formula (IIb), wherein: $R^2$ is —$C_6$alkyl.

Embodiment 72

The antibody conjugate of Formula (II), Formula (IIa) or Formula (IIb), wherein: $R^3$ is $L_1$OH;

Embodiment 73

The antibody conjugate of Formula (II), Formula (IIa) or Formula (IIb), wherein: $L_1$ is —(CH$_2$)—;

Embodiment 74

The antibody conjugate of Formula (II), Formula (IIa) or Formula (IIb), wherein: $L_1$ is —(CH$_2$CH$_2$)—;

Embodiment 75

The compound of Formula (I), Formula (Ia) or Formula (Ib), wherein:
$L_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O(CH$_2$)$_n$C(=O)NH(CH$_2$)$_n$—, —((CH$_2$)$_n$O)$_t$(CH$_2$)$_n$NHC(=O)(CH$_2$)$_n$.

Embodiment 76

The compound of Formula (I), Formula (Ia) or Formula (Ib), wherein:
$L_2$ is —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$NHC(=O)(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$C(=O)(CH$_2$)$_n$NHC(=O)(CH$_2$)$_n$—, or —C(=O)(CH$_2$)$_n$C(=O)NH(CH$_2$)$_n$—.

Embodiment 77

The antibody conjugate of Formula (II), Formula (IIa) or Formula (IIb), wherein: $L_2$ is —(CH$_2$)$_n$— or —C(=O)(CH$_2$)$_n$—.

Embodiment 78

The antibody conjugate of Formula (II), Formula (IIa) or Formula (IIb), wherein: $L_2$ is —C(=O)X$_2$X$_3$C(=O)(CH$_2$)$_n$—, —C(=O)X$_2$C(=O)(CH$_2$)$_n$NHC(=O)((CH$_2$)$_n$O)$_t$(CH$_2$)$_n$—, —C(=O)(CH$_2$)$_n$C(R$_7$)$_2$—, —C(=O)(CH$_2$)$_n$C(R$_7$)$_2$SS(CH$_2$)$_n$NHC(=O)(CH$_2$)$_n$— or —(CH2)$_n$X$_2$C(=O)(CH$_2$)$_n$NHC(=O)((CH$_2$)$_n$O)$_t$(CH$_2$)$_n$—.

Embodiment 79

The antibody conjugate of Formula (II), Formula (IIa) or Formula (IIb), wherein:
$R^{40}$ is

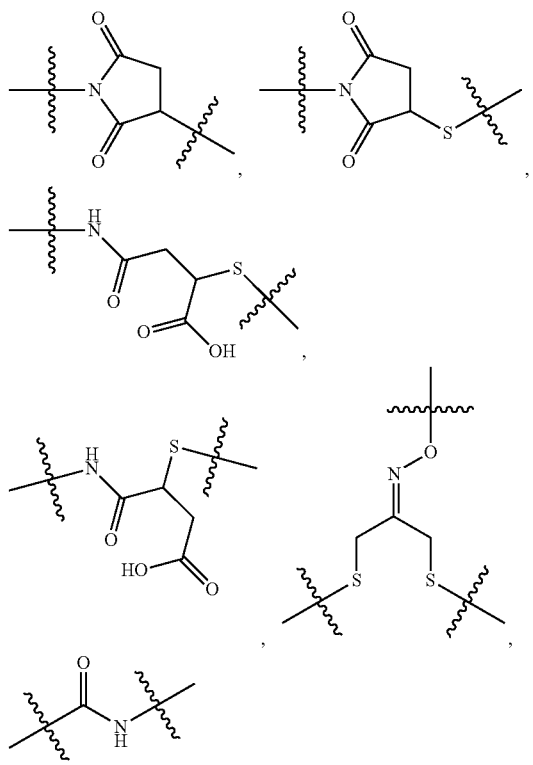

or —S—.

Embodiment 80

The antibody conjugate of Formula (II), Formula (IIa) or Formula (IIb), wherein:
$R^{40}$ is

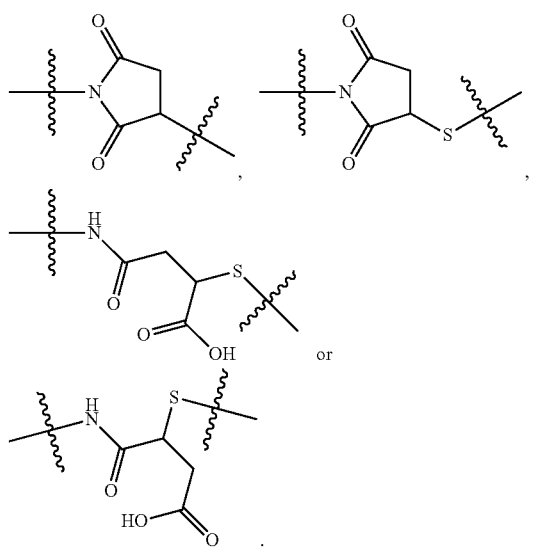

.

Embodiment 81

The antibody conjugate of Formula (II), Formula (IIa) or Formula (IIb), wherein: $R^{40}$ is

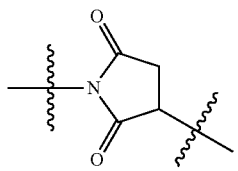

Embodiment 82

The antibody conjugate of Formula (II), Formula (IIa) or Formula (IIb),
wherein: $R^{40}$ is

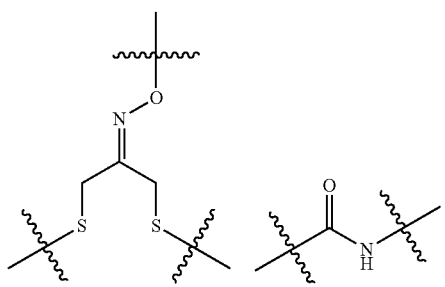

or —S—.

Embodiment 83

The antibody conjugate of Formula (II), Formula (IIa) or Formula (IIb), wherein: $R^{40}$ is

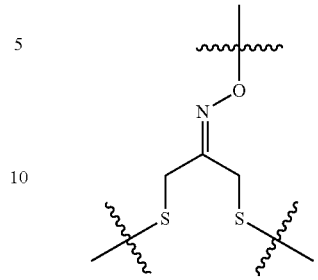

Embodiment 84

The antibody conjugate of Formula (II), Formula (IIa) or Formula (IIb),
wherein: $R^{40}$ is

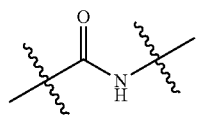

Embodiment 85

The antibody conjugate of Formula (II), Formula (IIa) or Formula (IIb),
wherein:
$R^{40}$ is

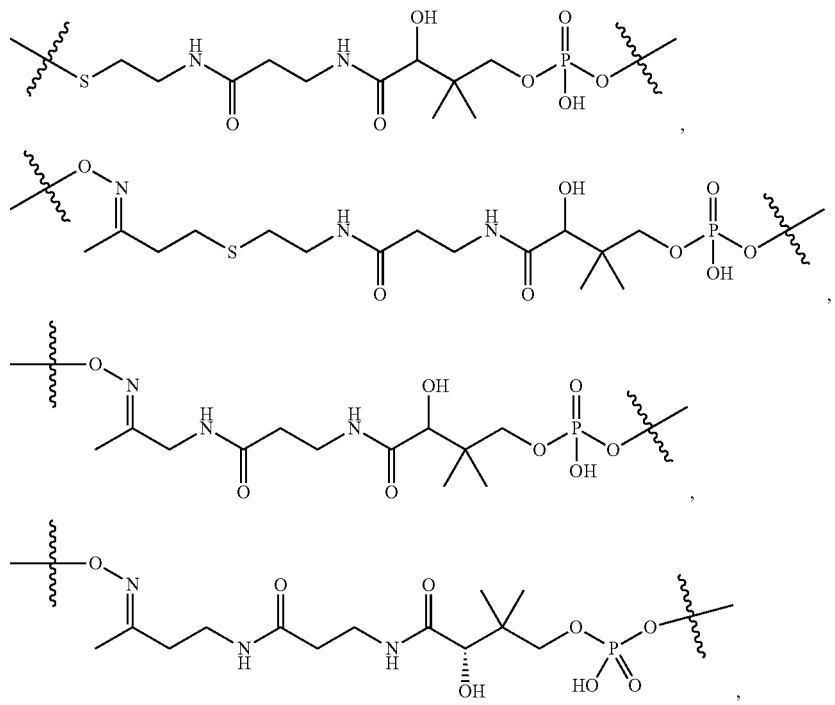

-continued

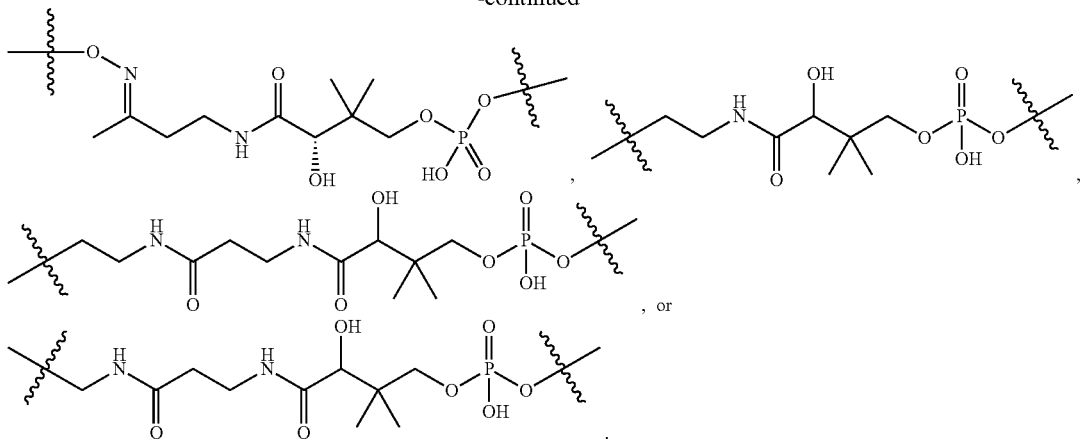

Embodiment 86

The antibody conjugate of Formula (II), Formula (IIa) or Formula (IIb),
wherein: $X_1$ is

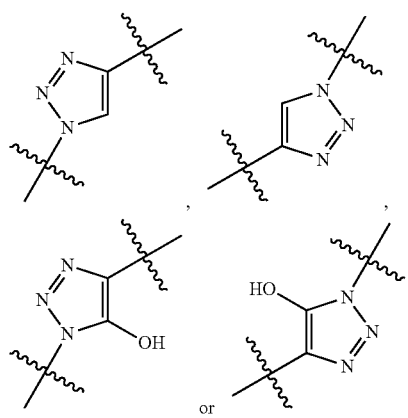

Embodiment 87

The antibody conjugate of Formula (II), Formula (IIa) or Formula (IIb),
wherein: $X_1$ is

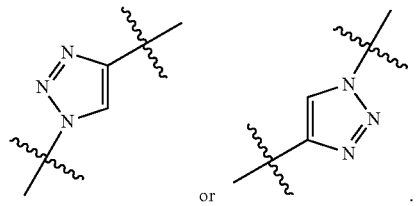 [SMILES: *c1cn(*)nn1 ; *c1cn(*)nn1]

Embodiment 88

The antibody conjugate of Formula (II), Formula (IIa) or Formula (IIb),
wherein: $X_1$ is

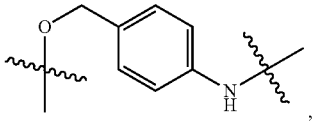

Embodiment 89

The antibody conjugate of Formula (II), Formula (IIa) or Formula (IIb),
wherein: $X_2$ is

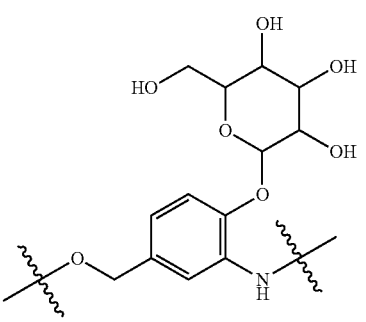

or

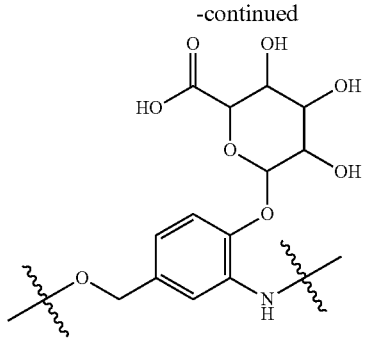

Embodiment 90

The antibody conjugate of Formula (II), Formula (IIa) or Formula (IIb),
wherein: $X_2$ is

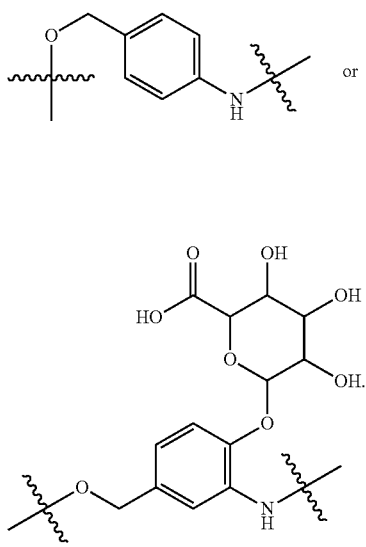

Embodiment 91

The antibody conjugate of Formula (II), Formula (IIa) or Formula (IIb),
wherein: $X_2$ is

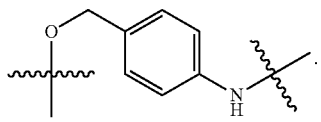 [SMILES: *Nc1ccc(CO*)cc1]

Embodiment 92

The antibody conjugate of Formula (II), Formula (IIa) or Formula (IIb), wherein:
$X_2$ is

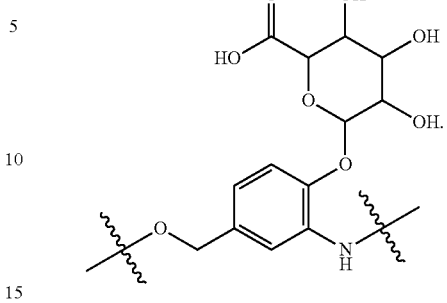

Embodiment 93

The antibody conjugate of Formula (II), Formula (IIa) or Formula (IIb), wherein:
$X_2$ is

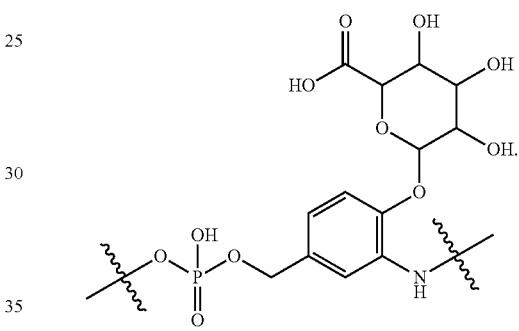

Embodiment 94

The antibody conjugate of Formula (II), Formula (IIa) or Formula (IIb),
wherein: $X_3$ is

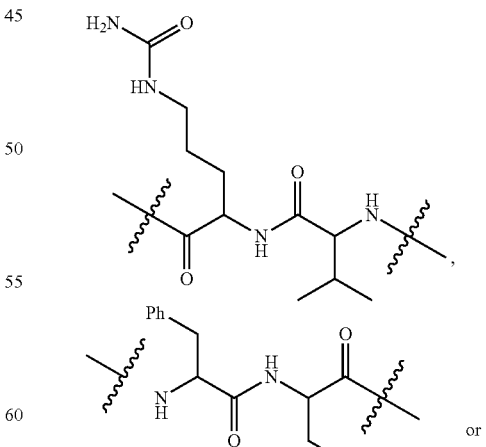

-continued

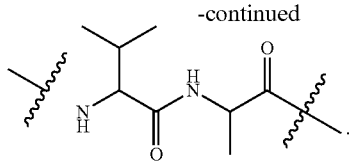

Embodiment 95

The antibody conjugate of Formula (II), Formula (IIa) or Formula (IIb),
wherein: X₃ is

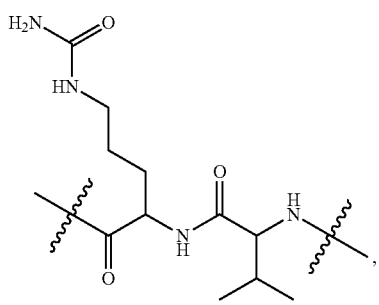 [SMILES: *NC(C(=O)NC(CCCNC(N)=O)C(*)=O)C(C)C]

Embodiment 96

The antibody conjugate of Formula (II), Formula (IIa) or Formula (IIb),
wherein: X₃ is

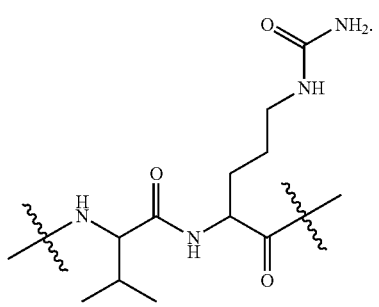 [SMILES: *NC(C(=O)NC(CCCNC(N)=O)C(*)=O)C(C)C]

Embodiment 97

The antibody conjugate of Formula (II), Formula (IIa) or Formula (IIb),
wherein: X₃ is

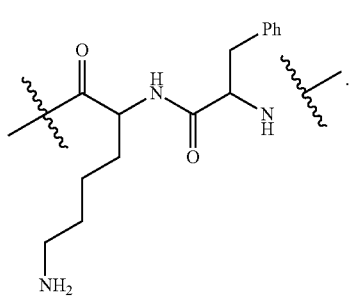

Embodiment 98

The antibody conjugate of Formula (II), Formula (IIa) or Formula (IIb),
wherein: $X_3$ is

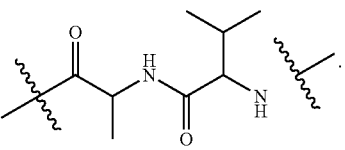

Embodiment 99

The antibody conjugate of Formula (II), Formula (IIa) or Formula (IIb), wherein: each m is independently selected from 1, 2, 3, and 4.

Embodiment 100

The antibody conjugate of Formula (II), Formula (IIa) or Formula (IIb), wherein: each m is 1 or 2.

Embodiment 101

The antibody conjugate of Formula (II), Formula (IIa) or Formula (IIb), wherein: each n is independently selected from 1, 2, 3, and 4.

Embodiment 102

The antibody conjugate of Formula (II), Formula (IIa) or Formula (IIb), wherein: each n is 2 or 3.

Embodiment 103

The antibody conjugate of Formula (II), Formula (IIa) or Formula (IIb), wherein: each t is independently selected from 1, 2, 3, 4, 5, 6, 7, 8, 9, 10, 11, 12, 13, 14, 15, 16, 17 and 18.

Embodiment 104

The antibody conjugate of Formula (II), Formula (IIa) or Formula (IIb), wherein: each t is independently selected from 1, 2, 3, 4, 5 and 6.

Embodiment 105

The antibody conjugate of Formula (II), Formula (IIa) or Formula (IIb), wherein y is an integer from 1 to 16.

Embodiment 106

The antibody conjugate of Formula (II), Formula (IIa) or Formula (IIb), wherein y is an integer from 1 to 8.

Embodiment 107

The antibody conjugate of Formula (II), Formula (IIa) or Formula (IIb), wherein y is an integer from 1 to 4.

Embodiment 108

The antibody conjugate of Formula (II), Formula (IIa) or Formula (IIb) selected from:

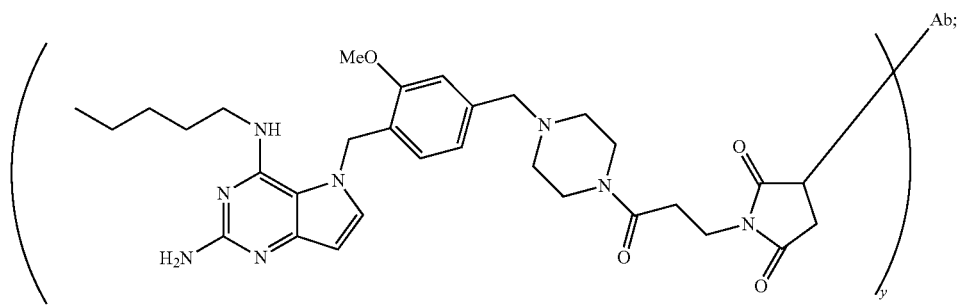
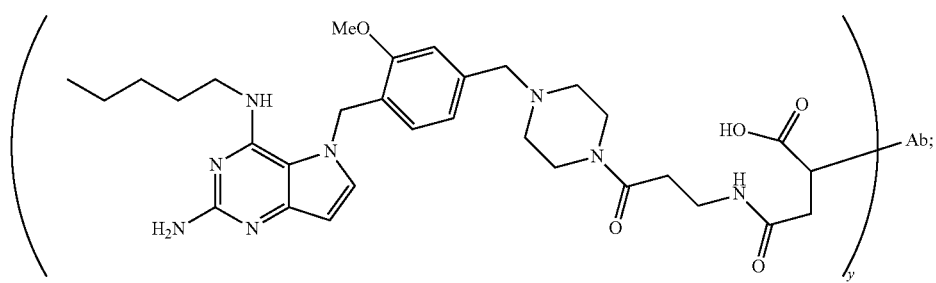
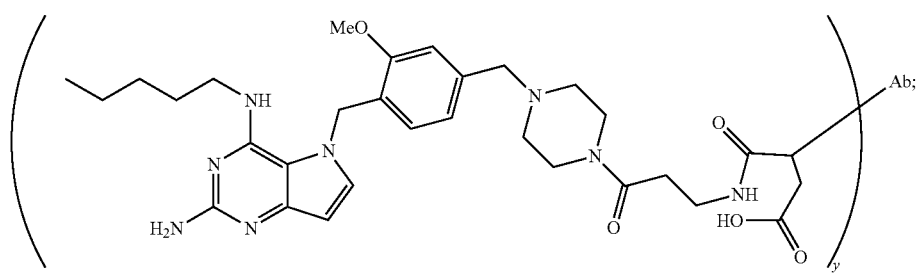
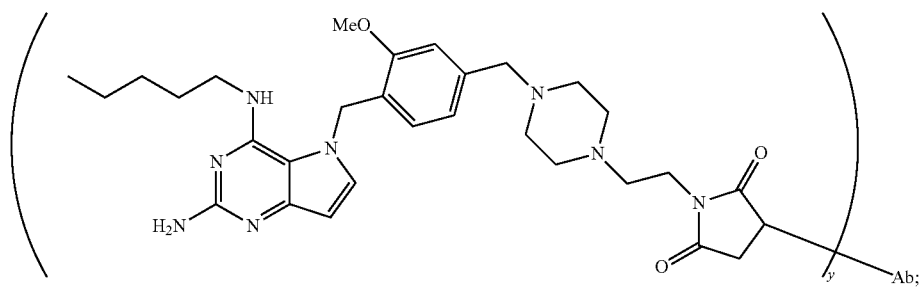
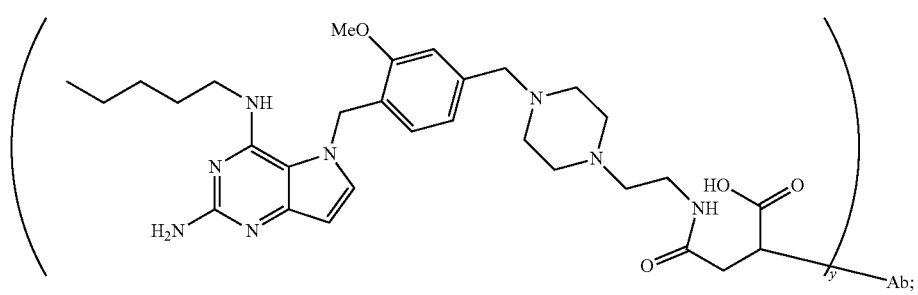

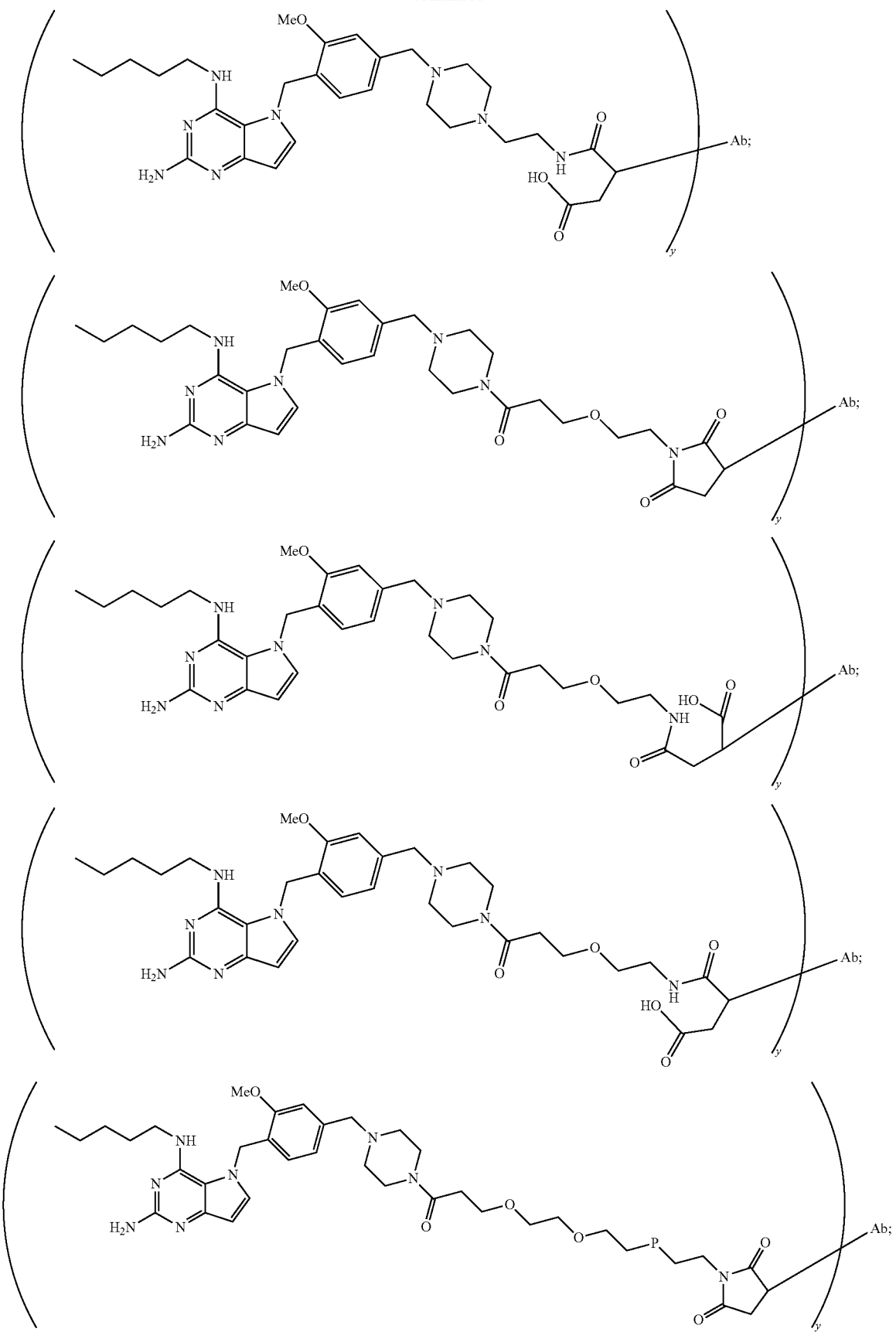

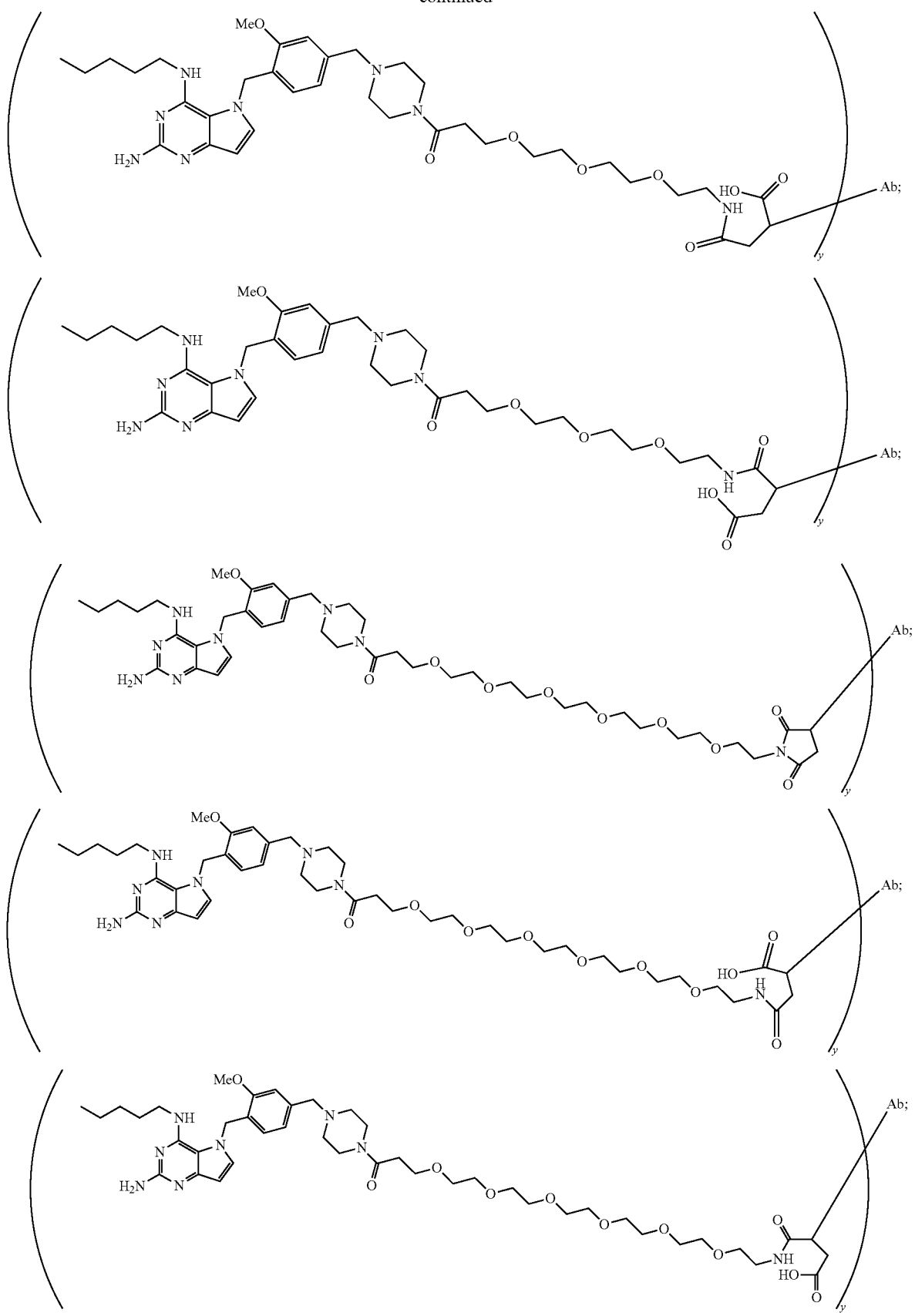
-continued

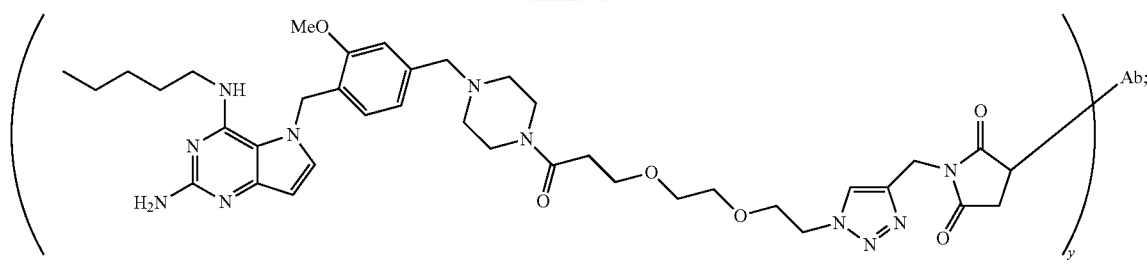
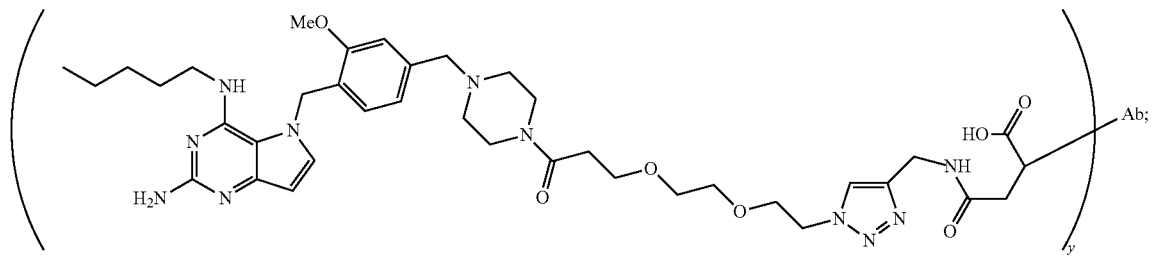
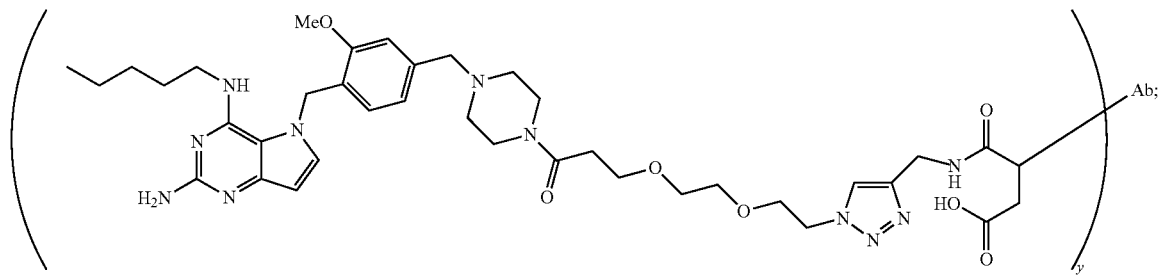
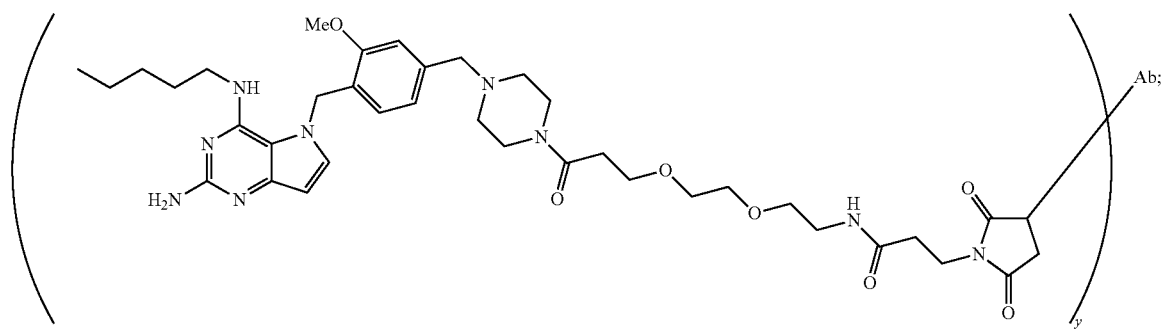
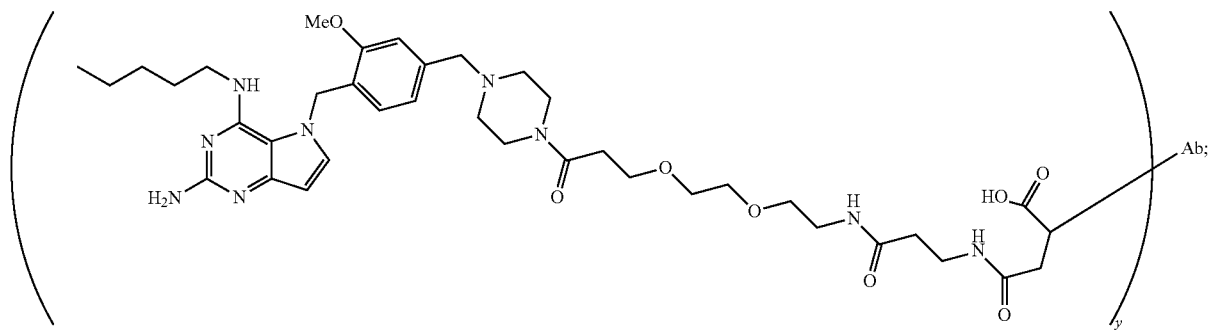

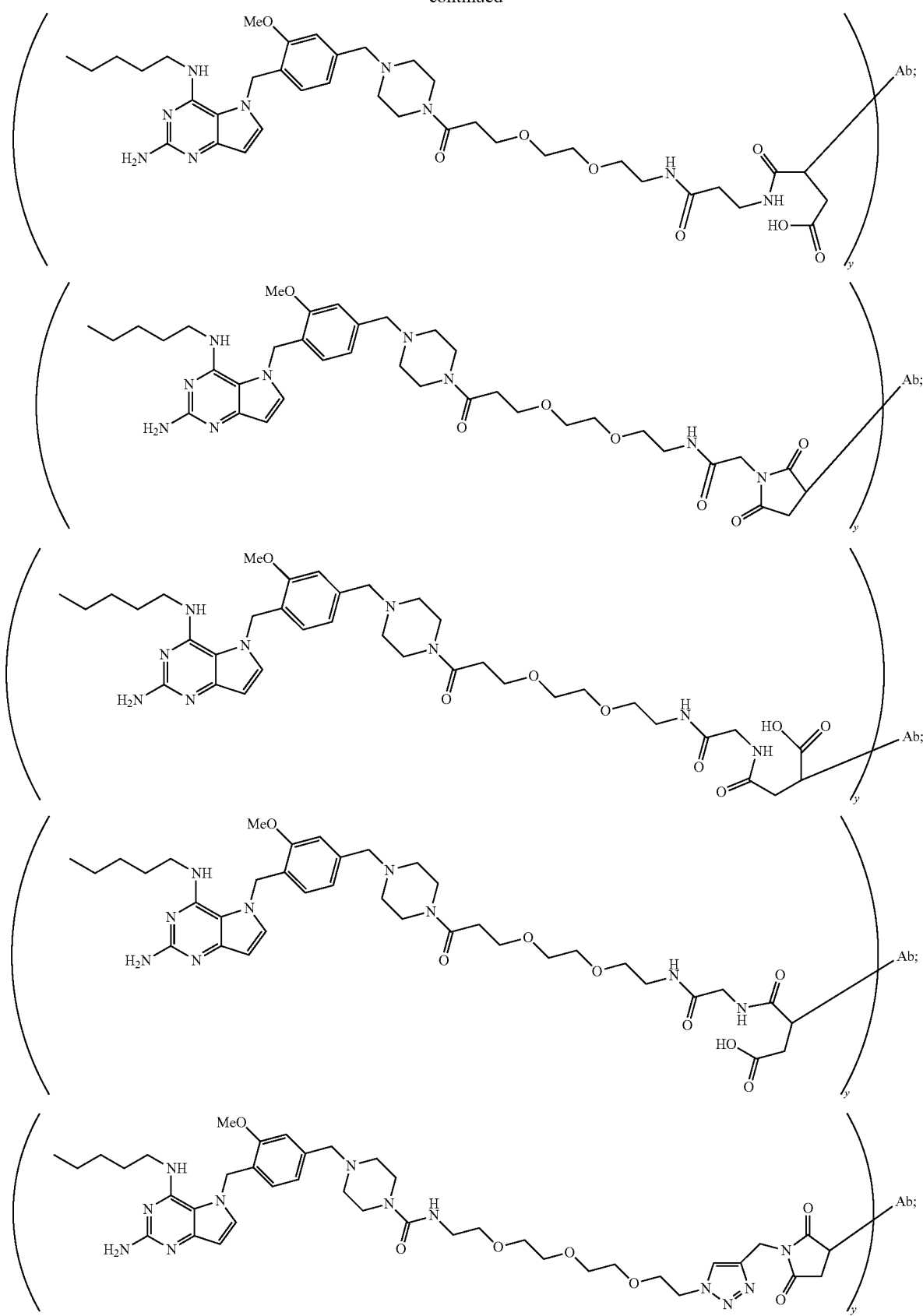

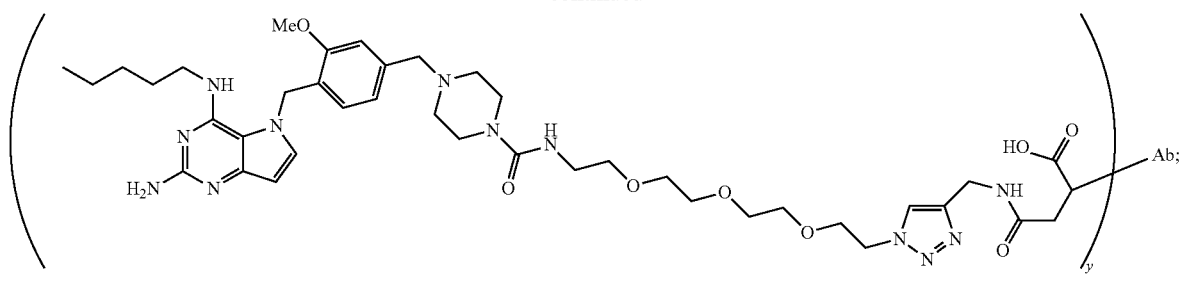
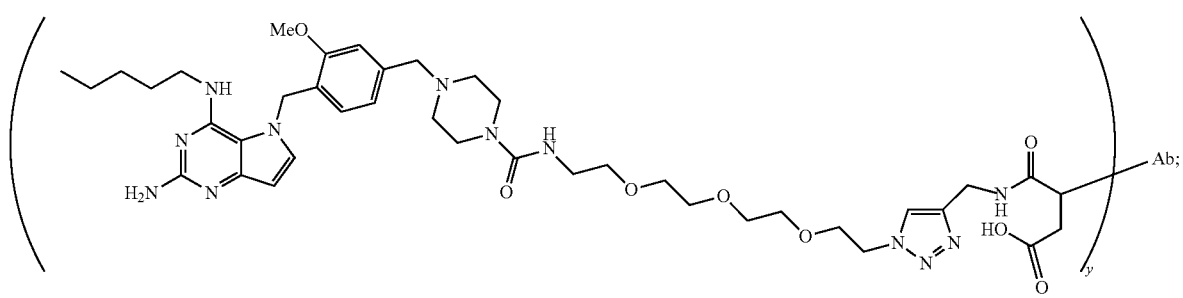
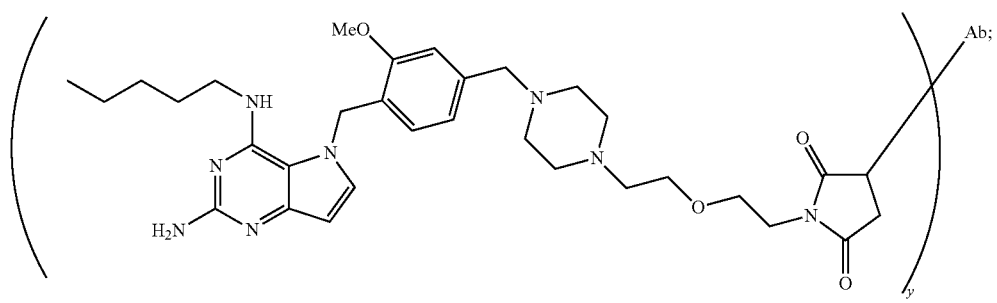
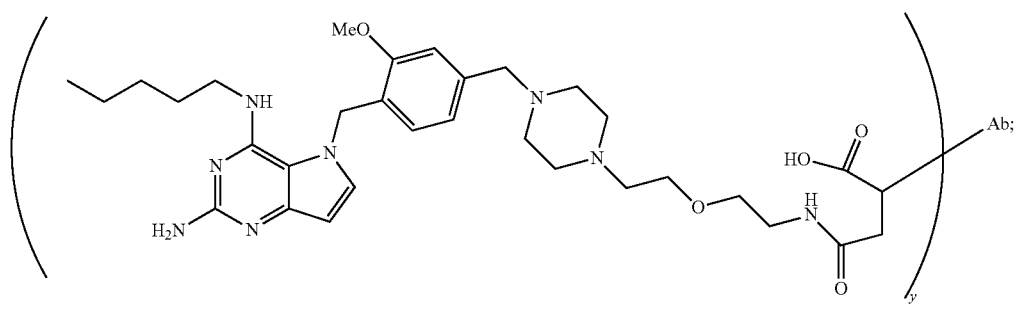
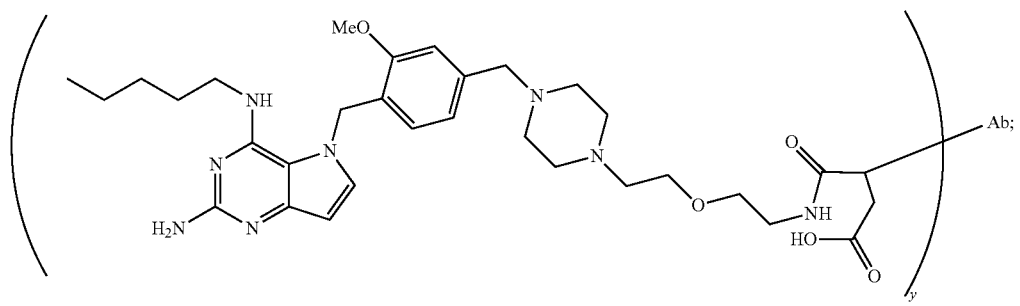

-continued
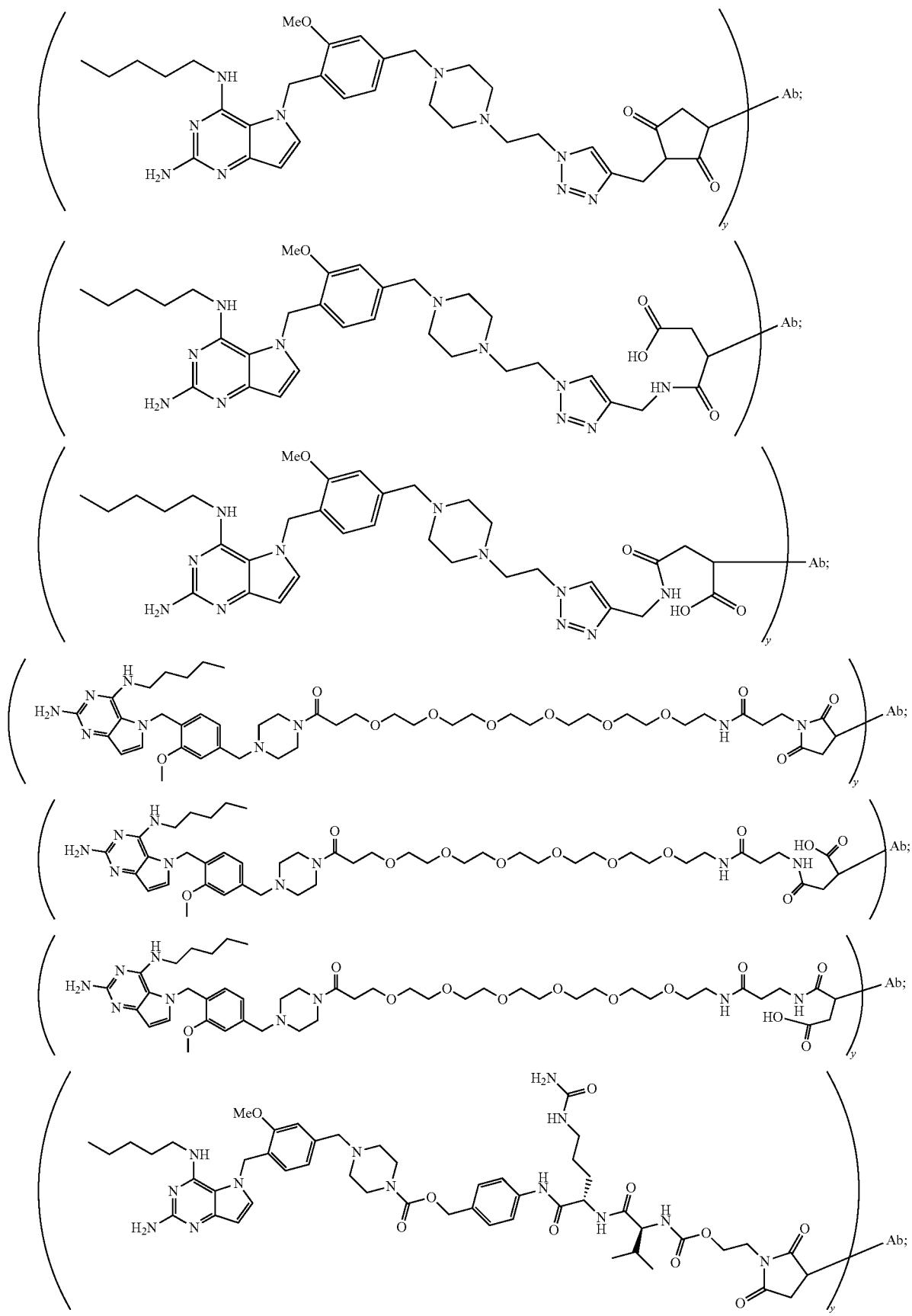

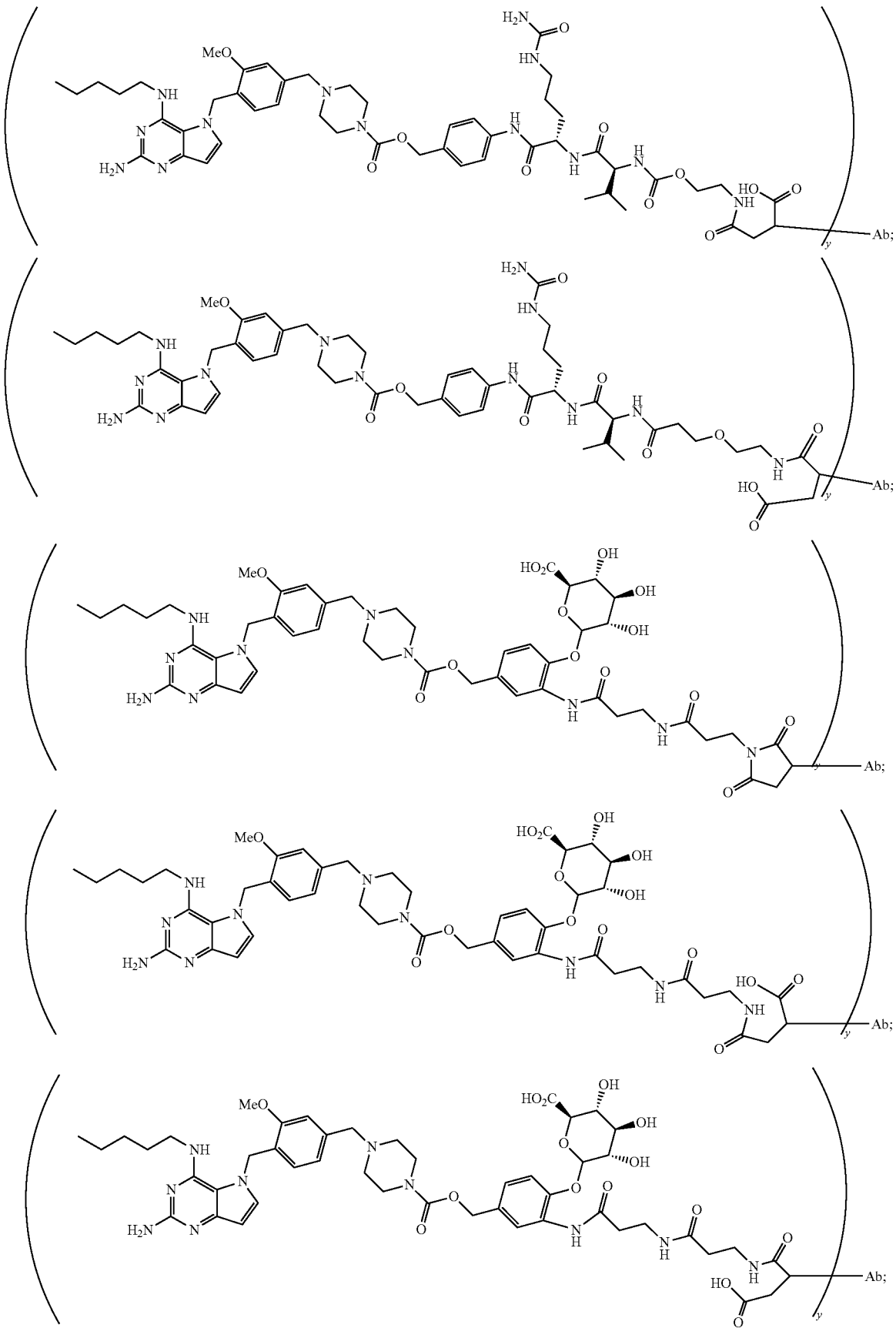

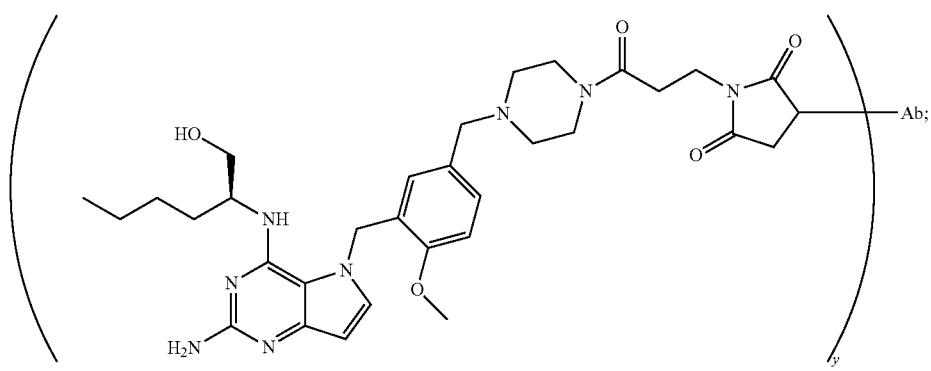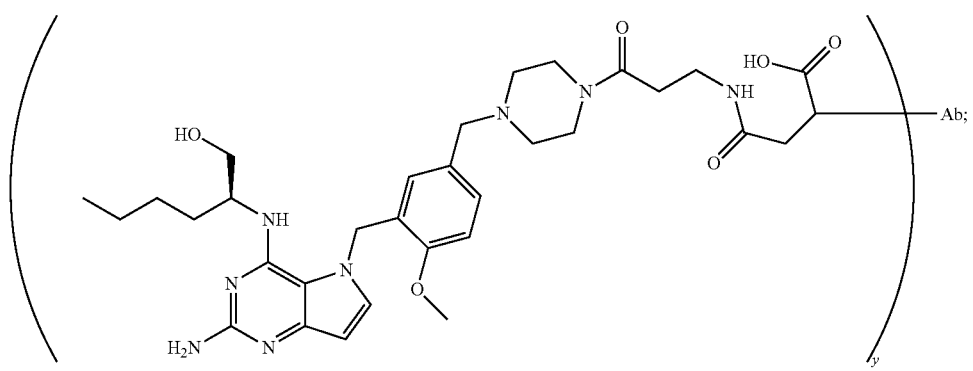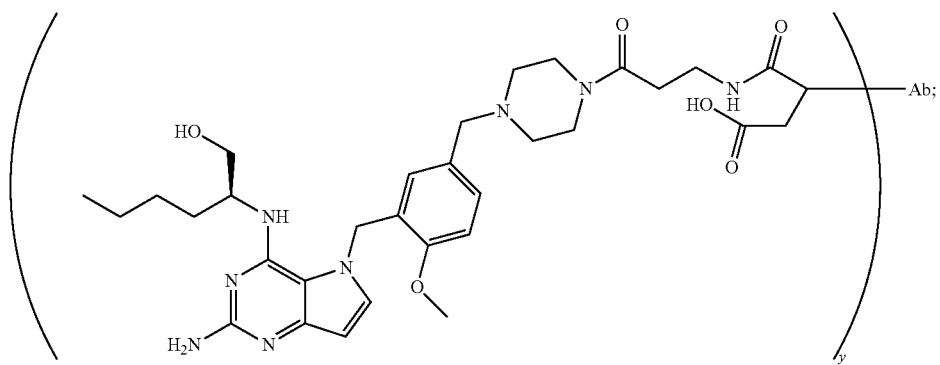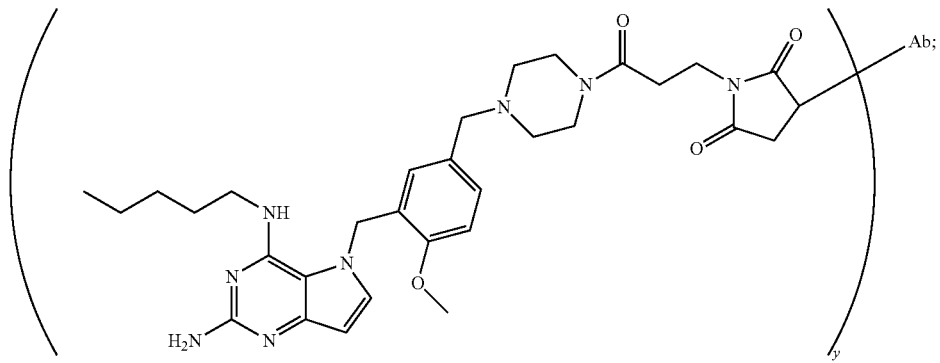

-continued
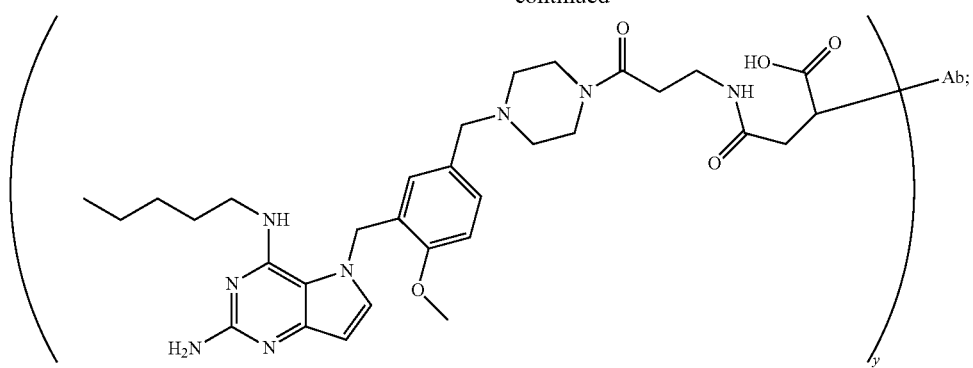
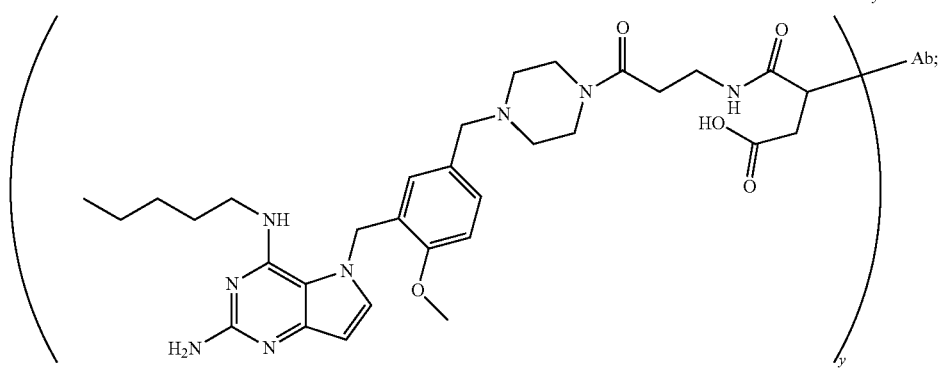
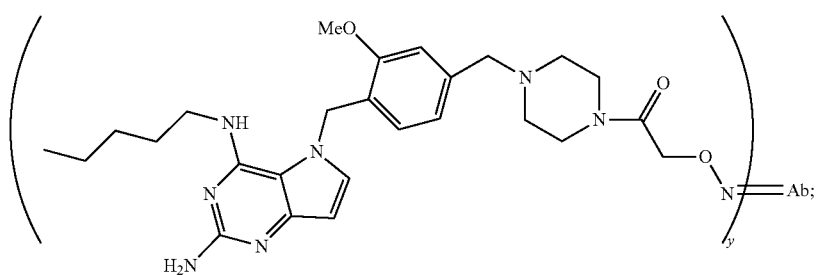
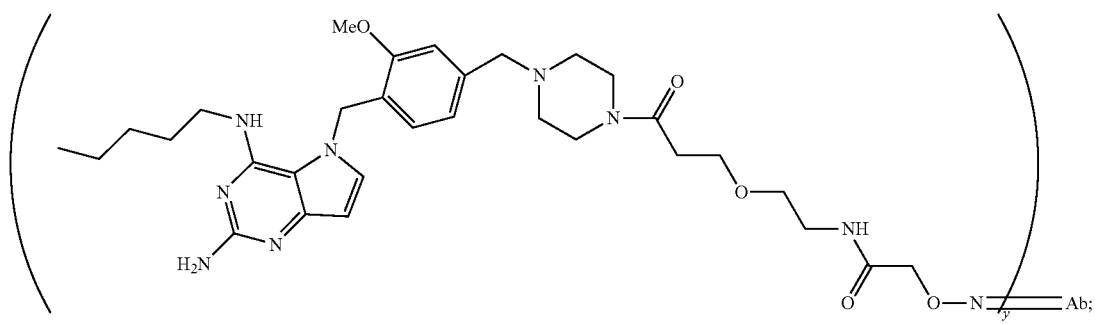
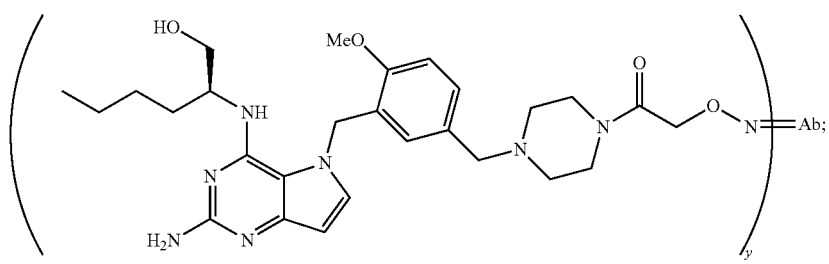

-continued
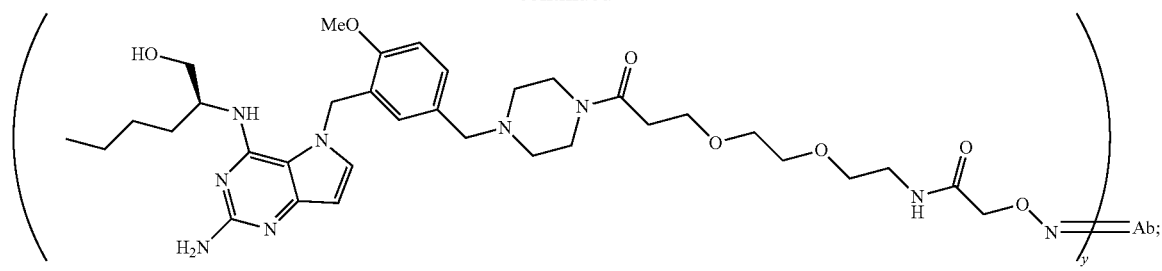
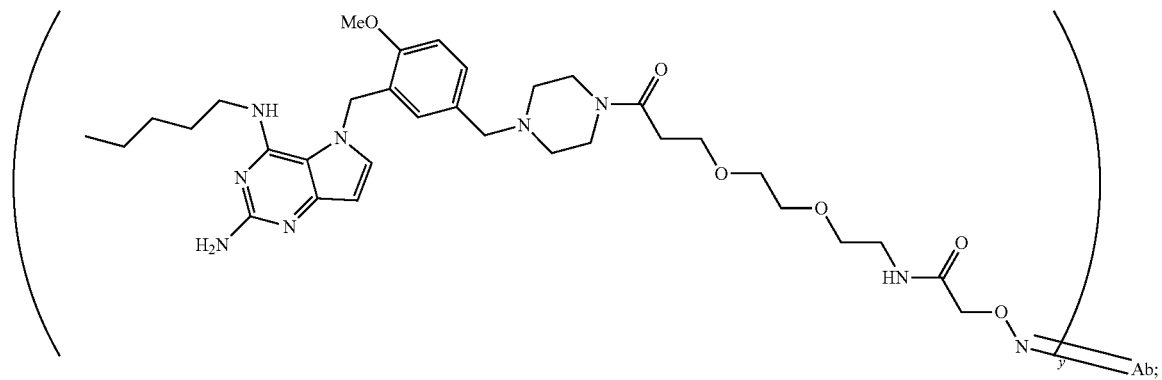
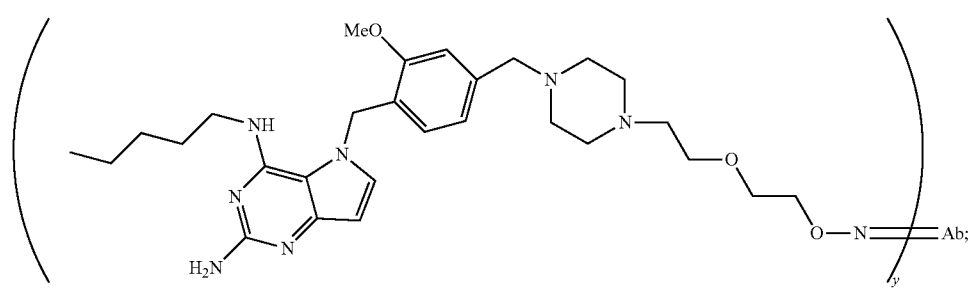
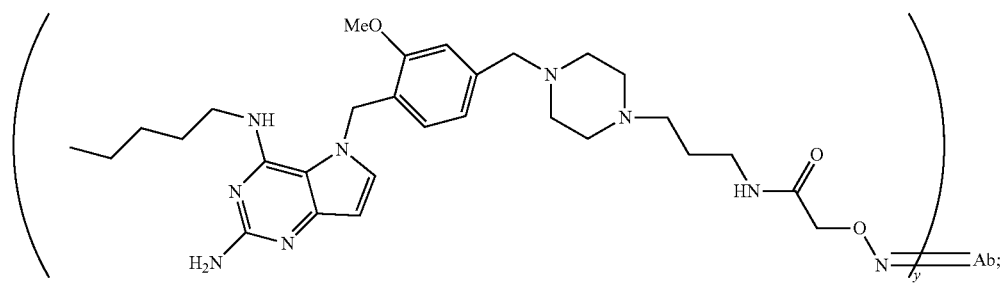
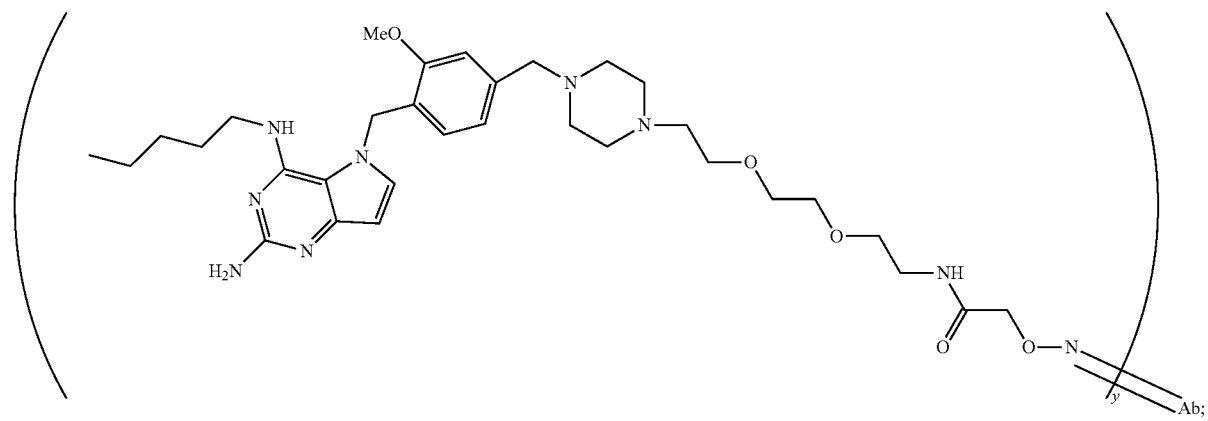

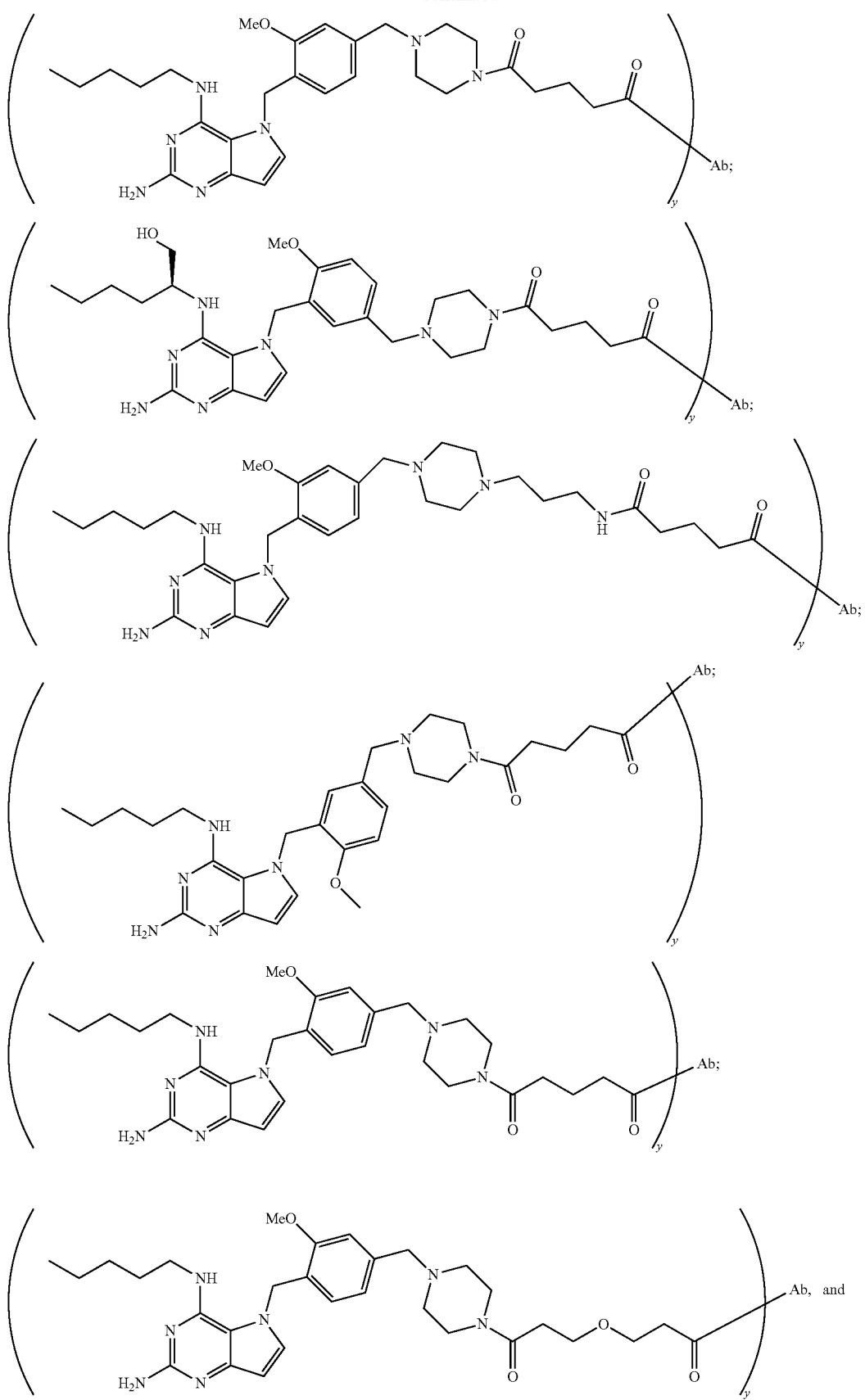

-continued
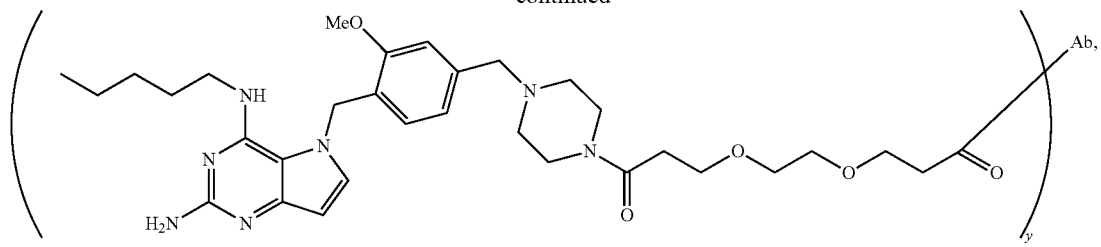
wherein y is an integer from 1 to 4 and Ab is an anti-HER2 antibody or antigen binding fragment thereof.
Embodiment 109
The antibody conjugate of Formula (II), Formula (IIa) or Formula (IIb) selected from:
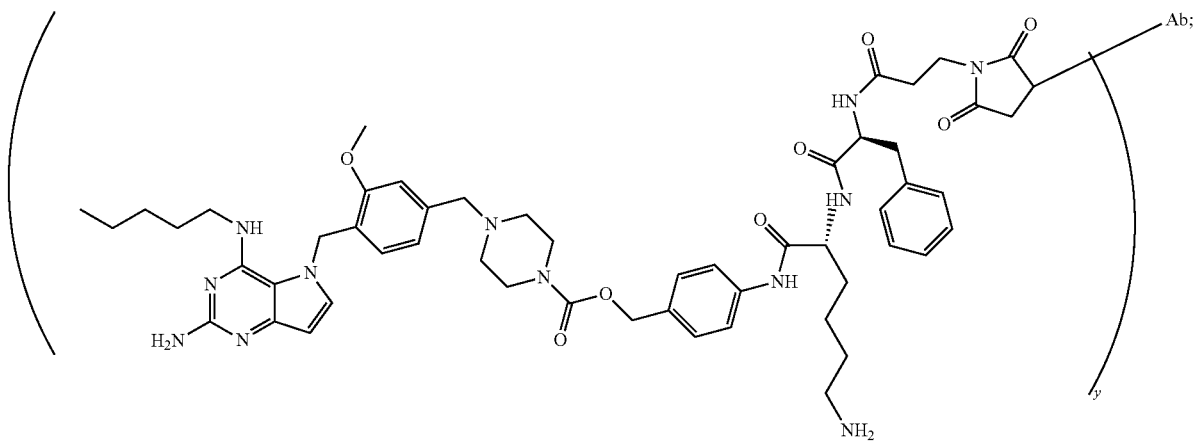
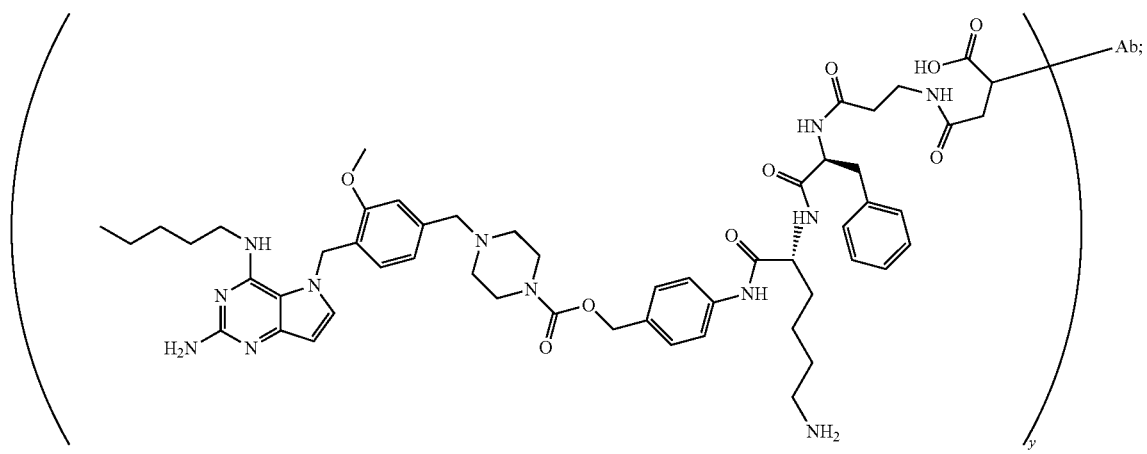

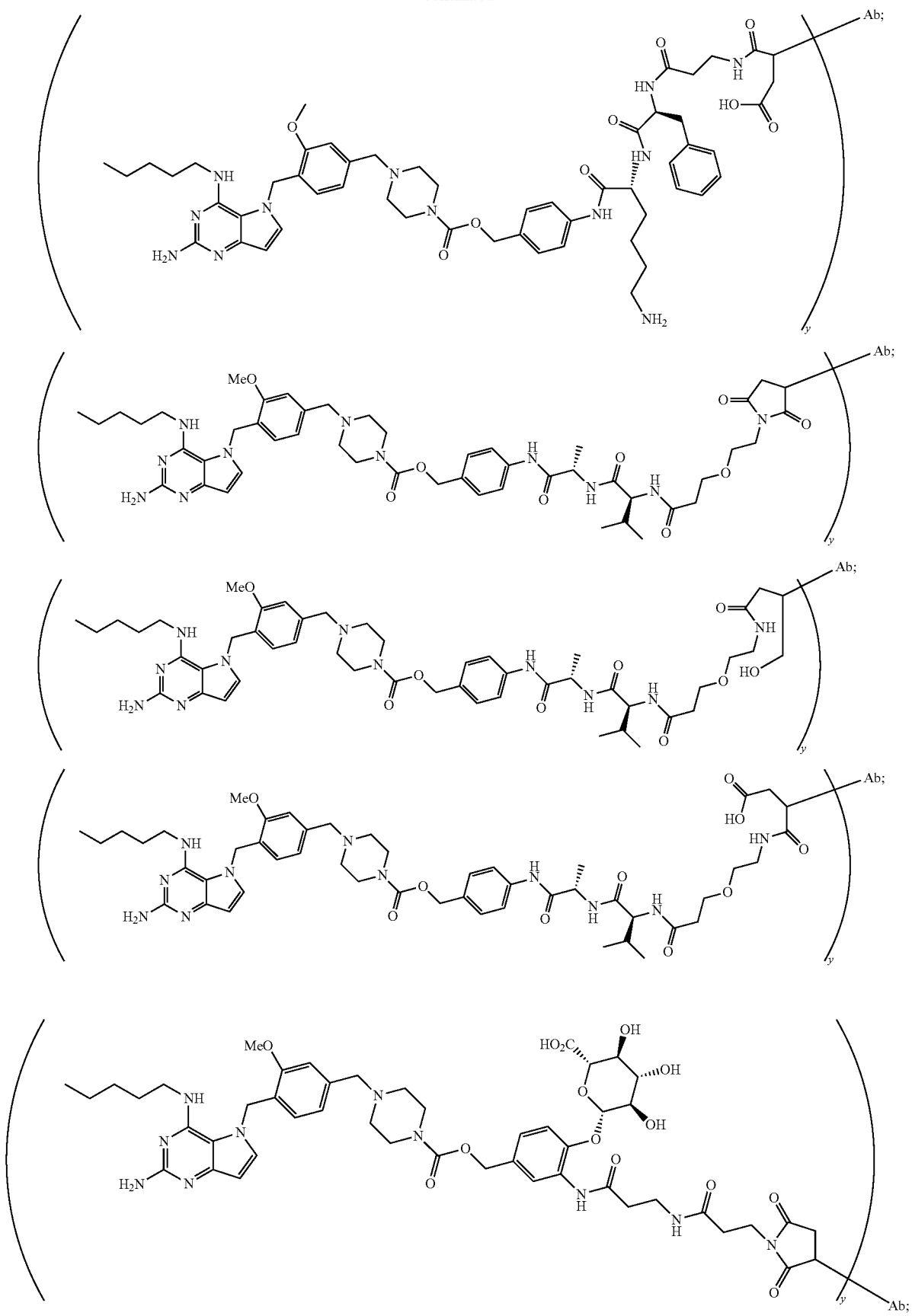

-continued
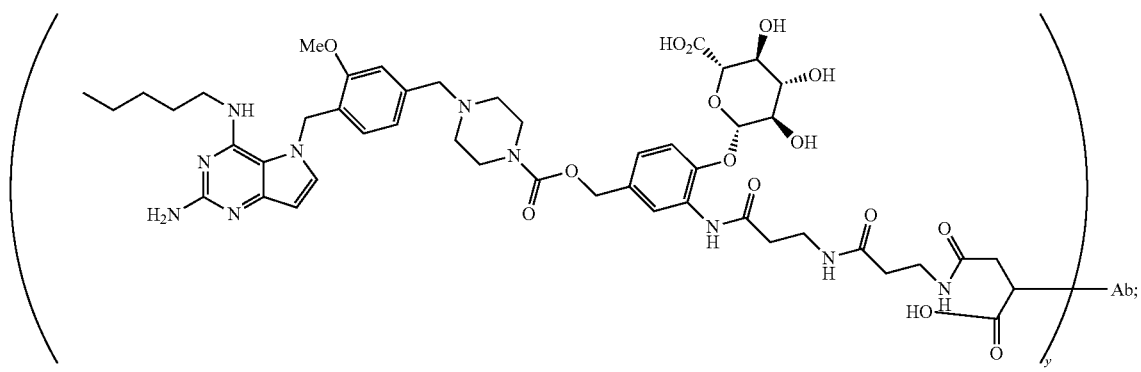
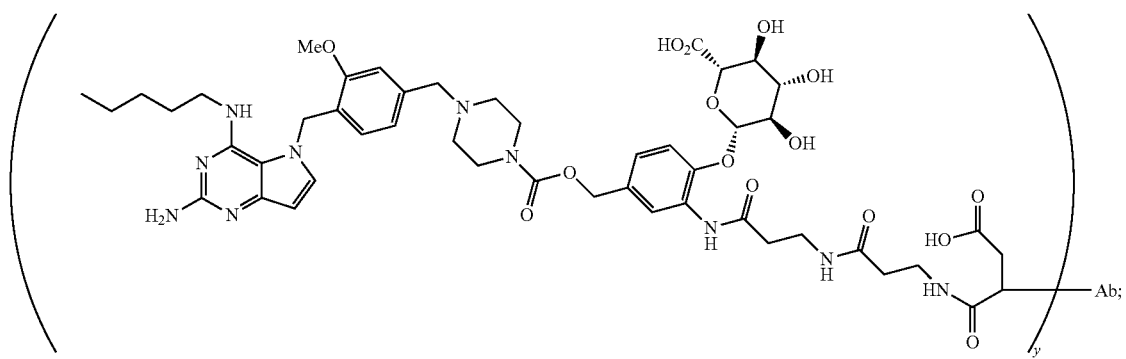
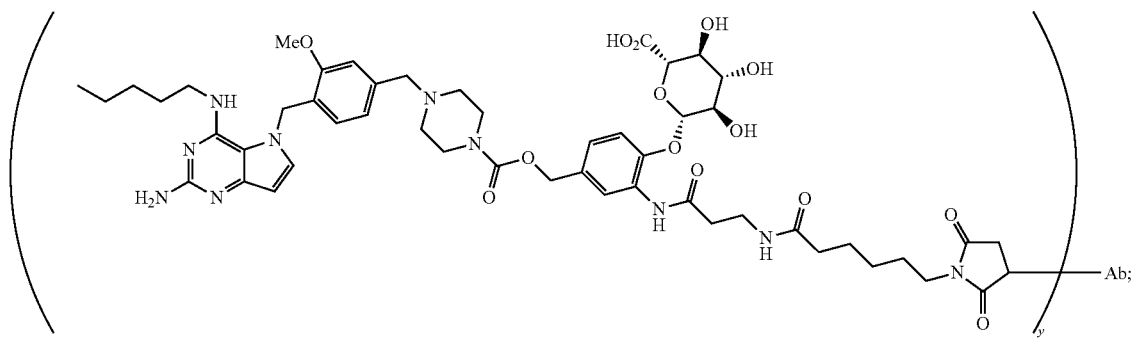
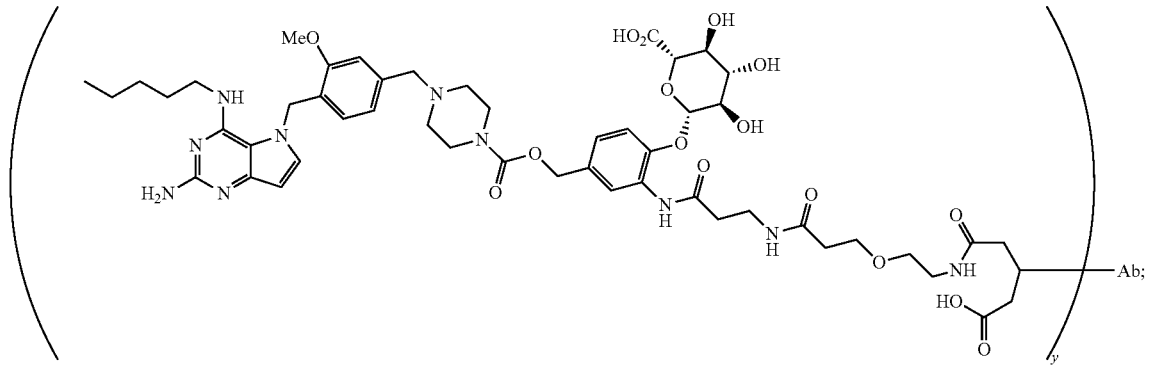

-continued
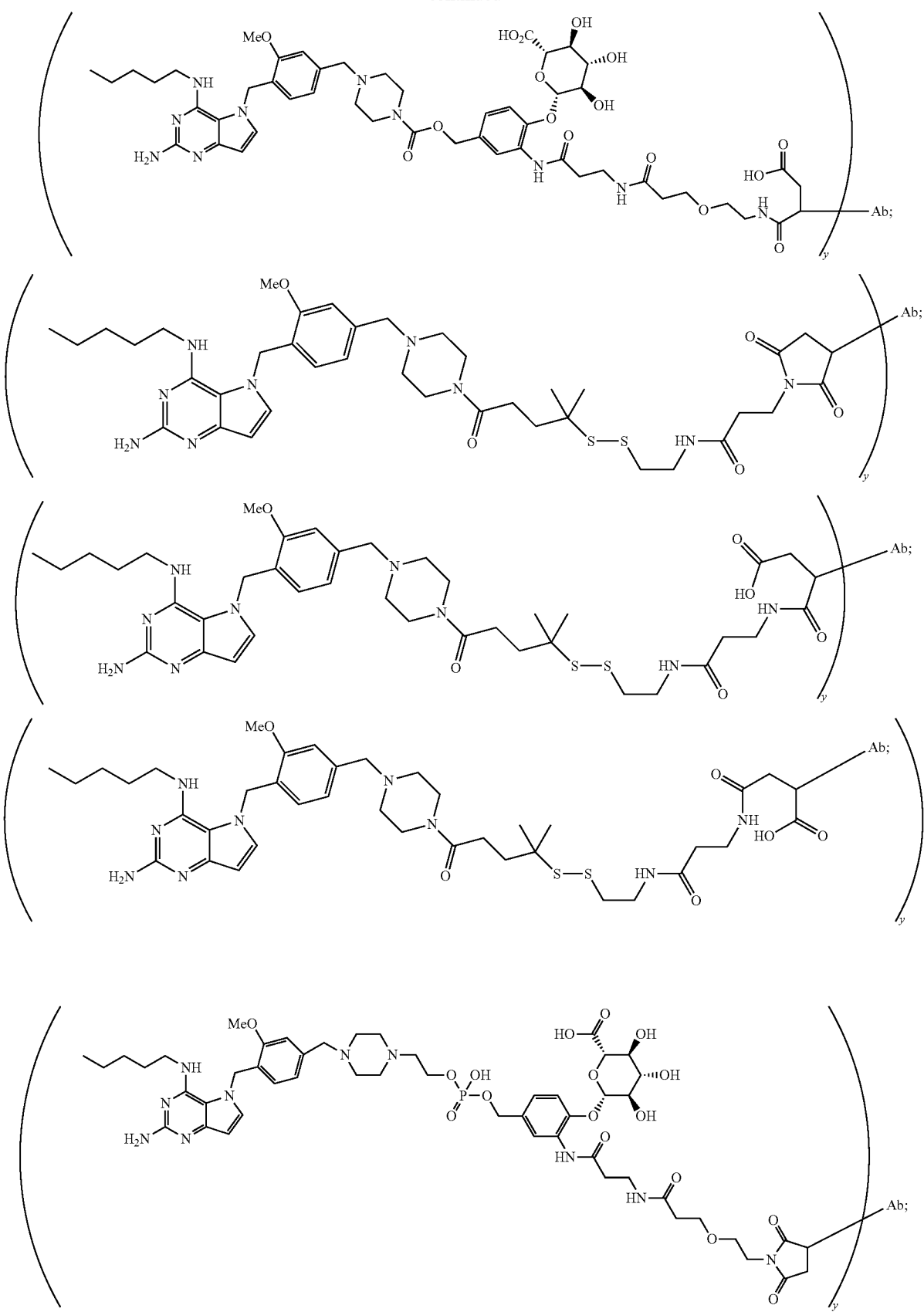

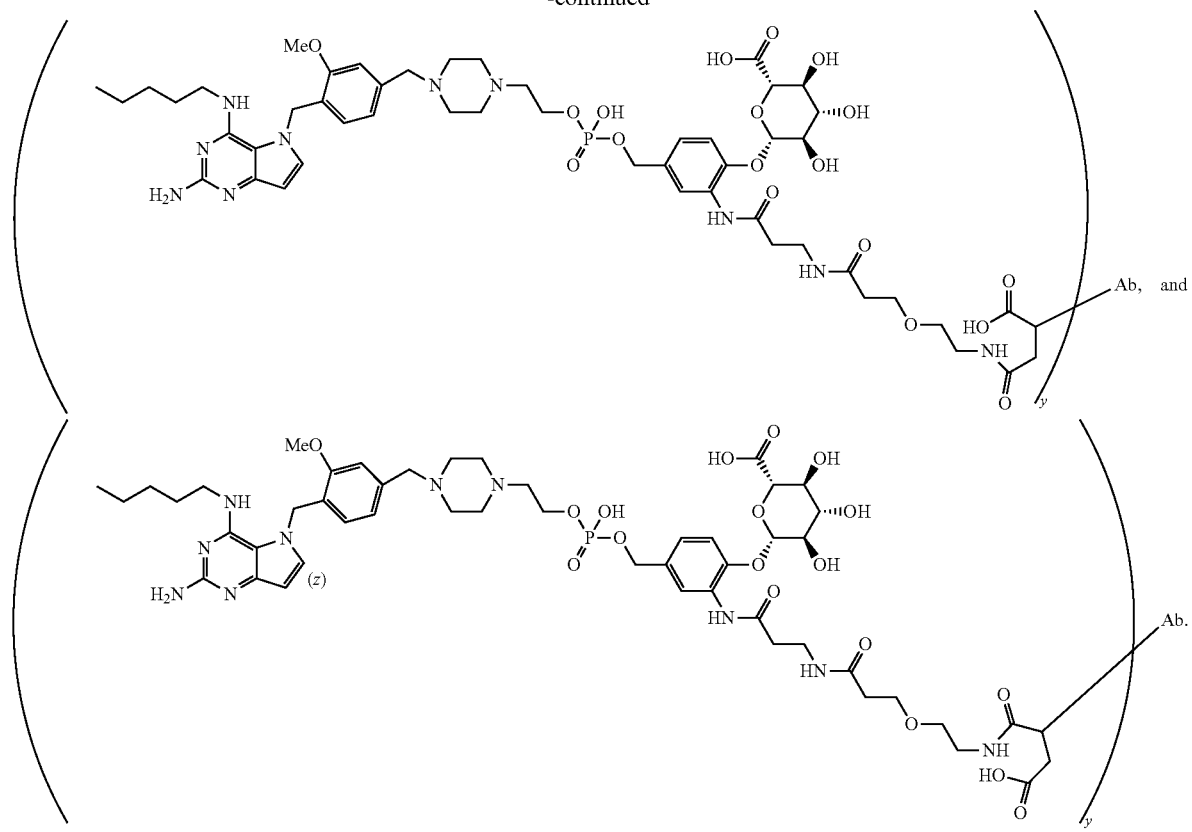

Provided are also protocols for some aspects of analytical methodology for evaluating antibody conjugates of the invention. Such analytical methodology and results can demonstrate that the conjugates have favorable properties, for example properties that would make them easier to manufacture, easier to administer to patients, more efficacious, and/or potentially safer for patients. One example is the determination of molecular size by size exclusion chromatography (SEC) wherein the amount of desired antibody species in a sample is determined relative to the amount of high molecular weight contaminants (e.g., dimer, multimer, or aggregated antibody) or low molecular weight contaminants (e.g., antibody fragments, degradation products, or individual antibody chains) present in the sample. In general, it is desirable to have higher amounts of monomer and lower amounts of, for example, aggregated antibody due to the impact of, for example, aggregates on other properties of the antibody sample such as but not limited to clearance rate, immunogenicity, and toxicity. A further example is the determination of the hydrophobicity by hydrophobic interaction chromatography (HIC) wherein the hydrophobicity of a sample is assessed relative to a set of standard antibodies of known properties. In general, it is desirable to have low hydrophobicity due to the impact of hydrophobicity on other properties of the antibody sample such as but not limited to aggregation, aggregation over time, adherence to surfaces, hepatotoxicity, clearance rates, and pharmacokinetic exposure. See Damle, N. K., Nat Biotechnol. 2008; 26(8):884-885; Singh, S. K., Pharm Res. 2015; 32(11):3541-71. When measured by hydrophobic interaction chromatography, higher hydrophobicity index scores (i.e. elution from HIC column faster) reflect lower hydrophobicity of the conjugates. As shown in Example 70 and Table 3, a majority of the tested antibody conjugates showed a hydrophobicity index of greater than 0.8. In some embodiments, provided are antibody conjugates having a hydrophobicity index of 0.8 or greater, as determined by hydrophobic interaction chromatography.

Anti-HER2 Antibody

Antibody conjugates provided herein include an antibody or antibody fragment thereof (e.g., antigen binding fragment) that specifically binds to human HER2 (anti-HER2 antibody). HER2 overexpression is observed in many types of cancers, such as gastric cancer, esophageal cancer, colon cancer, rectal cancer, breast cancer, ovarian cancer, cervical cancer, uterine cancer, endometrial cancer, bladder cancer, pancreatic cancer, lung cancer, prostate cancer, osteosarcoma, neuroblastoma, or head and neck cancer. Antibody conjugates comprising an anti-HER2 antibody can be specifically targeted to HER2-positive cancers or tumors.

In some embodiments, antibody conjugates provided herein include a monoclonal antibody or antibody fragment thereof that specifically binds to human HER2, e.g., a human or humanized anti-HER2 monoclonal antibody. In some embodiments, the antibody or antibody fragment thereof that specifically binds to human HER2 can be selected from trastuzumab, pertuzumab, margetuximab, or HT-19, or an antibody fragment thereof or a site-specific cysteine mutant thereof.

Trastuzumab (trade name Herceptin or Herclon) is a humanized monoclonal antibody that binds to the juxtamembrane portion of the extracellular domain of the HER2 receptor (Hudis C A, N Engl J Med. 2007; 357(1): 39-51). The amino acid sequences of trastuzumab heavy chain and light chain variable regions were described in U.S. Pat. No. 5,821,337. Trastuzumab interacts with three loop regions formed by residues 557-561, 570-573, and 593-603 of human HER2 (Cho et al., Nature 421: 756-760, 2003). Trastuzumab interferes with HER2 signaling possibly by prevention of HER2-receptor dimerization, facilitation of endocytotic destruction of the HER2 receptor, inhibition of shedding of the extracellular domain (Hudis C A, N Engl J Med. 2007; 357(1):39-51). Another important mechanism of action of an anti-HER2 antibody is the mediation of Antibody Dependent Cellular Cytotoxicity (ADCC). In ADCC, the anti-HER2 antibody binds to tumor cells and then recruits immune cells, such as macrophages, through Fcγ receptor (FcγR) interactions. Trastuzumab has a conserved human IgG Fc region, and is capable of recruiting immune effector cells that are responsible for antibody-dependent cytotoxicity (Hudis C A, N Engl J Med. 2007; 357(1):39-51). Trastuzumab gained U.S. FDA approval in September 1998 for the treatment of metastic breast cancer in patients whose tumors overexpress HER2 and who received one or more chemotherapy regimens for their metastatic disease.

Pertuzumab (also called 2C4, Omnitarg, Perjeta) is a humanized monoclonal antibody that binds to the extracellular domain of the HER2 receptor and inhibits dimerization of HER2 with other HER receptors. The amino acid sequences of pertuzumab heavy chain and light chain were described in U.S. Pat. No. 7,560,111. Pertuzumab mainly interact with residues within region 245-333 of human HER2, particularly residues His 245, Val 286, Ser 288, Leu 295, His 296, or Lys 311 (Franklin et al., Cancer Cell 5: 317-328, 2004). Pertuzumab was shown to be more effective than trastuzumab in disrupting the formation of HER1-HER2 and HER3-HER2 complexes in breast and prostate cancer cell lines (Agus et al., J Clin Oncol. 2005; 23(11): 2534-43. Epub Feb. 7, 2005). Pertuzumab does not require antibody-dependent cellular cytotoxicity for efficacy because an intact Fc region is not required for its activity (Agus et al., J Clin Oncol. 2005; 23(11):2534-43. Epub Feb. 7, 2005). Pertuzumab received U.S. FDA approval for use in combination with trastuzumab and docetaxel for the treatment of patients with HER2-positive metastatic breast cancer who have not received anti-HER2 therapy or chemotherapy for metastic disease in June 2012.

Margetuximab (also called MGAH22) is another anti-HER2 monoclonal antibody (See http://www.macrogenics-.com/products-margetuximab.html). The Fc region of margetuximab was optimized so that it has increased binding to the activating FcγRs but decreased binding to the inhibitory FcγRs on immune effector cells. Margetuximab is currently under clinical trial for treating patients with relapsed or refractory advanced breast cancer whose tumors express HER2 at the 2+ Level by immunohistochemistry and lack evidence of HER2 gene amplification by FISH.

HT-19 is another anti-HER2 monoclonal antibody that binds to an epitope in human HER2 distinct from the epitope of trastuzumab or pertuzumab and was shown to inhibit HER2 signaling comparable to trastuzumab and enhance HER2 degradation in combination with trastuzumab and pertuzumab (Bergstrom D. A. et al., Cancer Res. 2015; 75:LB-231).

Other suitable anti-HER2 monoclonal antibodies include, but are not limited to, the anti-HER2 antibodies described in U.S. Pat. Nos. 9,096,877; 9,017,671; 8,975,382; 8,974,785; 8,968,730; 8,937,159; 8,840,896; 8,802,093; 8,753,829; 8,741,586; 8,722,362; 8,697,071; 8,652,474; 8,652,466; 8,609,095; 8,512,967; 8,349,585; 8,241,630; 8,217,147; 8,192,737; 7,879,325; 7,850,966; 7,560,111; 7,435,797; 7,306,801; 6,399,063; 6,387,371; 6,165,464; 5,772,997; 5,770,195; 5,725,856; 5,720,954; 5,677,171.

In some embodiments, the anti-HER2 antibody or antibody fragment (e.g., an antigen binding fragment) comprises a VH domain having an amino acid sequence of any VH domain described in Table 1. Other suitable anti-HER2 antibodies or antibody fragments (e.g., antigen binding fragments) can include amino acids that have been mutated, yet have at least 80, 85, 90, 95, 96, 97, 98, or 99 percent identity in the VH domain with the VH regions depicted in the sequences described in Table 1. The present disclosure in certain embodiments also provides antibodies or antibody fragments (e.g., antigen binding fragments) that specifically bind to HER2, wherein the antibodies or antibody fragments (e.g., antigen binding fragments) comprise a VH CDR having an amino acid sequence of any one of the VH CDRs listed in Table 1. In particular embodiments, the invention provides antibodies or antibody fragments (e.g., antigen binding fragments) that specifically bind to HER2, comprising (or alternatively, consist of) one, two, three, four, five or more VH CDRs having an amino acid sequence of any of the VH CDRs listed in Table 1.

In some embodiments, the anti-HER2 antibody or antibody fragment (e.g., antigen binding fragments) comprises a VL domain having an amino acid sequence of any VL domain described in Table 1. Other suitable anti-HER2 antibodies or antibody fragments (e.g., antigen binding fragments) can include amino acids that have been mutated, yet have at least 80, 85, 90, 95, 96, 97, 98, or 99 percent identity in the VL domain with the VL regions depicted in the sequences described in Table 1. The present disclosure also provides antibodies or antibody fragments (e.g., antigen binding fragments) that specifically bind to HER2, the antibodies or antibody fragments (e.g., antigen binding fragments) comprise a VL CDR having an amino acid sequence of any one of the VL CDRs listed in Table 1. In particular, the invention provides antibodies or antibody fragments (e.g., antigen binding fragments) that specifically bind to HER2, which comprise (or alternatively, consist of) one, two, three or more VL CDRs having an amino acid sequence of any of the VL CDRs listed in Table 1.

TABLE 1

| Sequences of exemplary anti-HER2 monoclonal antibodies | | |
|---|---|---|
| anti-HER2 mAb1 | | |
| SEQ ID NO: 1 | HCDR1 (Kabat) | DTYIH |
| SEQ ID NO: 2 | HCDR2 (Kabat) | RIYPTNGYTRYADSVKG |
| SEQ ID NO: 3 | HCDR3 (Kabat) | WGGDGFYAMDY |
| SEQ ID NO: 4 | HCDR1 (Chothia) | GFNIKDT |

TABLE 1-continued

Sequences of exemplary anti-HER2 monoclonal antibodies

| SEQ ID NO: 5 | HCDR2 (Chothia) | YPTNGY |
|---|---|---|
| SEQ ID NO: 3 | HCDR3 (Chothia) | WGGDGFYAMDY |
| SEQ ID NO: 6 | HCDR1 (Combined) | GFNIKDTYIH |
| SEQ ID NO: 2 | HCDR2 (Combined) | RIYPTNGYTRYADSVKG |
| SEQ ID NO: 3 | HCDR3 (Combined) | WGGDGFYAMDY |
| SEQ ID NO: 7 | VH | EVQLVESGGGLVQPGGSLRLSCAASGFNIKDTYI HWVRQAPGKGLEWVARIYPTNGYTRYADSVKGR FTISADTSKNTAYLQMNSLRAEDTAVYYCSRWG GDGFYAMDYWGQGTLVTVSS |
| SEQ ID NO: 8 | VH DNA | GAGGTTCAGCTGGTGGAGTCTGGCGGTGGCCT GGTGCAGCCAGGGGGCTCACTCCGTTTGTCCT GTGCAGCTTCTGGCTTCAACATTAAAGACACCT ATATACACTGGGTGCGTCAGGCCCCGGGTAAG GGCCTGGAATGGGTTGCAAGGATTTATCCTAC GAATGGTTATACTAGATATGCCGATAGCGTCAA GGGCCGTTTCACTATAAGCGCAGACACATCCA AAAACACAGCCTACCTGCAGATGAACAGCCTG CGTGCTGAGGACACTGCCGTCTATTATTGTTCT AGATGGGGAGGGGACGGCTTCTATGCTATGGA CTACTGGGGTCAAGGAACCCTGGTCACCGTCT CCTCG |
| SEQ ID NO: 9 | Heavy Chain | EVQLVESGGGLVQPGGSLRLSCAASGFNIKDTYI HWVRQAPGKGLEWVARIYPTNGYTRYADSVKGR FTISADTSKNTAYLQMNSLRAEDTAVYYCSRWG GDGFYAMDYWGQGTLVTVSSASTKGPSVFPLAP SSKSTSGGTAALGCLVKDYFPCPVTVSWNSGAL TSGVHTFPAVLQSSGLYSLSSVVTVPSSSLGTQT YICNVNHKPSNTKVDKRVEPKSCDKTHTCPPCPA PELLGGPSVFLFPPKPKDTLMISRTPEVTCVVVDV SHEDPEVKFNWYVDGVEVHNAKTKPREEQYNST YRVVSVLTVLHQDWLNGKEYKCKVSNKALPAPIE KTISKAKGQPREPQVYTLPPSREEMTKNQVSLTC LVKGFYPCDIAVEWESNGQPENNYKTTPPVLDSD GSFFLYSKLTVDKSRWQQGNVFSCSVMHEALHN HYTQKSLSLSPGK |
| SEQ ID NO: 10 | Heavy Chain DNA | GAGGTTCAGCTGGTGGAGTCTGGCGGTGGCCT GGTGCAGCCAGGGGGCTCACTCCGTTTGTCCT GTGCAGCTTCTGGCTTCAACATTAAAGACACCT ATATACACTGGGTGCGTCAGGCCCCGGGTAAG GGCCTGGAATGGGTTGCAAGGATTTATCCTAC GAATGGTTATACTAGATATGCCGATAGCGTCAA GGGCCGTTTCACTATAAGCGCAGACACATCCA AAAACACAGCCTACCTGCAGATGAACAGCCTG CGTGCTGAGGACACTGCCGTCTATTATTGTTCT AGATGGGGAGGGGACGGCTTCTATGCTATGGA CTACTGGGGTCAAGGAACCCTGGTCACCGTCT CCTCGGCTAGCACCAAGGGCCCAAGTGTGTTT CCCCTGGCCCCCAGCAGCAAGTCTACTTCCGG CGGAACTGCTGCCCTGGGTTGCCTGGTGAAGG ACTACTTCCCCTGTCCCGTGACAGTGTCCTGG AACTCTGGGGCTCTGACTTCCGGCGTGCACAC CTTCCCCGCCGTGCTGCAGAGCAGCGGCCTGT ACAGCCTGAGCAGCGTGGTGACAGTGCCCTCC AGCTCTCTGGGAACCCAGACCTATATCTGCAAC GTGAACCACAAGCCCAGCAACACCAAGGTGGA CAAGAGAGTGGAGCCCAAGAGCTGCGACAAGA CCCACACCTGCCCCCCCTGCCCAGCTCCAGAA CTGCTGGGAGGGCCTTCCGTGTTCCTGTTCCC CCCCAAGCCCAAGGACACCCTGATGATCAGCA GGACCCCCGAGGTGACCTGCGTGGTGGTGGA CGTGTCCCACGAGGACCCAGAGGTGAAGTTCA ACTGGTACGTGGACGGCGTGGAGGTGCACAAC GCCAAGACCAAGCCCAGAGAGGAGCAGTACAA CAGCACCTACAGGGTGGTGTCCGTGCTGACCG TGCTGCACCAGGACTGGCTGAACGGCAAAGAA TACAAGTGCAAAGTCTCCAACAAGGCCCTGCC AGCCCCCAATCGAAAAGACAATCAGCAAGGCCA AGGGCCAGCCACGGGAGCCCCAGGTGTACAC CCTGCCCCCCAGCCGGGAGGAGATGACCAAG AACCAGGTGTCCCTGACCTGTCTGGTGAAGGG |

TABLE 1-continued

Sequences of exemplary anti-HER2 monoclonal antibodies

|  |  |  |
|---|---|---|
|  |  | CTTCTACCCCTGTGATATCGCCGTGGAGTGGG<br>AGAGCAACGGCCAGCCCGAGAACAACTACAAG<br>ACCACCCCCCAGTGCTGGACAGCGACGGCA<br>GCTTCTTCCTGTACAGCAAGCTGACCGTGGAC<br>AAGTCCAGGTGGCAGCAGGGCAACGTGTTCAG<br>CTGCAGCGTGATGCACGAGGCCCTGCACAACC<br>ACTACACCCAGAAGTCCCTGAGCCTGAGCCCC<br>GGCAAG |
| SEQ ID NO: 11 | LCDR1 (Kabat) | RASQDVNTAVA |
| SEQ ID NO: 12 | LCDR2 (Kabat) | SASFLYS |
| SEQ ID NO: 13 | LCDR3 (Kabat) | QQHYTTPPT |
| SEQ ID NO: 14 | LCDR1 (Chothia) | SQDVNTA |
| SEQ ID NO: 15 | LCDR2 (Chothia) | SAS |
| SEQ ID NO: 16 | LCDR3 (Chothia) | HYTTPP |
| SEQ ID NO: 11 | LCDR1 (Combined) | RASQDVNTAVA |
| SEQ ID NO: 12 | LCDR2 (Combined) | SASFLYS |
| SEQ ID NO: 13 | LCDR3 (Combined) | QQHYTTPPT |
| SEQ ID NO: 17 | VL | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIK |
| SEQ ID NO: 18 | VL DNA | GATATCCAGATGACCCAGTCCCCGAGCTCCCT<br>GTCCGCCTCTGTGGGCGATAGGGTCACCATCA<br>CCTGCCGTGCCAGTCAGGATGTGAATACTGCT<br>GTAGCCTGGTATCAACAGAAACCAGGAAAAGC<br>TCCGAAACTACTGATTTACTCGGCATCCTTCCT<br>CTACTCTGGAGTCCCTTCTCGCTTCTCTGGATC<br>CAGATCTGGGACGGATTTCACTCTGACCATCA<br>GCAGTCTGCAGCCGGAAGACTTCGCAACTTAT<br>TACTGTCAGCAACATTATACTACTCCTCCCACG<br>TTCGGACAGGGTACCAAGGTGGAGATCAAA |
| SEQ ID NO: 19 | Light Chain | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIKRTVAAPSVFIFPPSDEQLKSGTASVVCLLN<br>NFYPREAKVQWKVDNALQSGNSQESVTEQDSK<br>DSTYSLSSTLTLSKADYEKHKVYACEVTHQGLSS<br>PVTKSFNRGEC |
| SEQ ID NO: 20 | Light Chain DNA | GATATCCAGATGACCCAGTCCCCGAGCTCCCT<br>GTCCGCCTCTGTGGGCGATAGGGTCACCATCA<br>CCTGCCGTGCCAGTCAGGATGTGAATACTGCT<br>GTAGCCTGGTATCAACAGAAACCAGGAAAAGC<br>TCCGAAACTACTGATTTACTCGGCATCCTTCCT<br>CTACTCTGGAGTCCCTTCTCGCTTCTCTGGATC<br>CAGATCTGGGACGGATTTCACTCTGACCATCA<br>GCAGTCTGCAGCCGGAAGACTTCGCAACTTAT<br>TACTGTCAGCAACATTATACTACTCCTCCCACG<br>TTCGGACAGGGTACCAAGGTGGAGATCAAACG<br>TACGGTGGCCGCTCCCAGCGTGTTCATCTTCC<br>CCCCCAGCGACGAGCAGCTGAAGAGTGGCAC<br>CGCCAGCGTGGTGTGCCTGCTGAACAACTTCT<br>ACCCCCGGGAGGCCAAGGTGCAGTGGAAGGT<br>GGACAACGCCCTGCAGAGCGGCAACAGCCAG<br>GAGAGCGTCACCGAGCAGGACAGCAAGGACT<br>CCACCTACAGCCTGAGCAGCACCCTGACCCTG<br>AGCAAGGCCGACTACGAGAAGCATAAGGTGTA<br>CGCCTGCGAGGTGACCCACCAGGGCCTGTCC<br>AGCCCCGTGACCAAGAGCTTCAACAGGGGCGA<br>GTGC |
|  | anti-HER2 mAb2 |  |
| SEQ ID NO: 1 | HCDR1 (Kabat) | DTYIH |
| SEQ ID NO: 2 | HCDR2 (Kabat) | RIYPTNGYTRYADSVKG |

TABLE 1-continued

Sequences of exemplary anti-HER2 monoclonal antibodies

| SEQ ID NO: 3 | HCDR3 (Kabat) | WGGDGFYAMDY |
| SEQ ID NO: 4 | HCDR1 (Chothia) | GFNIKDT |
| SEQ ID NO: 5 | HCDR2 (Chothia) | YPTNGY |
| SEQ ID NO: 3 | HCDR3 (Chothia) | WGGDGFYAMDY |
| SEQ ID NO: 6 | HCDR1 (Combined) | GFNIKDTYIH |
| SEQ ID NO: 2 | HCDR2 (Combined) | RIYPTNGYTRYADSVKG |
| SEQ ID NO: 3 | HCDR3 (Combined) | WGGDGFYAMDY |
| SEQ ID NO: 7 | VH | EVQLVESGGGLVQPGGSLRLSCAASGFNIKDTYI HWVRQAPGKGLEWVARIYPTNGYTRYADSVKGR FTISADTSKNTAYLQMNSLRAEDTAVYYCSRWG GDGFYAMDYWGQGTLVTVSS |
| SEQ ID NO: 8 | VH DNA | GAGGTTCAGCTGGTGGAGTCTGGCGGTGGCCT GGTGCAGCCAGGGGGCTCACTCCGTTTGTCCT GTGCAGCTTCTGGCTTCAACATTAAAGACACCT ATATACACTGGGTGCGTCAGGCCCCGGGTAAG GGCCTGGAATGGGTTGCAAGGATTTATCCTAC GAATGGTTATACTAGATATGCCGATAGCGTCAA GGGCCGTTTCACTATAAGCGCAGACACATCCA AAAACACAGCCTACCTGCAGATGAACAGCCTG CGTGCTGAGGACACTGCCGTCTATTATTGTTCT AGATGGGGAGGGGACGGCTTCTATGCTATGGA CTACTGGGGTCAAGGAACCCTGGTCACCGTCT CCTCG |
| SEQ ID NO: 21 | Heavy Chain | EVQLVESGGGLVQPGGSLRLSCAASGFNIKDTYI HWVRQAPGKGLEWVARIYPTNGYTRYADSVKGR FTISADTSKNTAYLQMNSLRAEDTAVYYCSRWG GDGFYAMDYWGQGTLVTVSSASTKGPSVFPLAP SSKSTSGGTAALGCLVKDYFPCPVTVSWNSGAL TSGVHTFPAVLQSSGLYSLSSVVTVPSSSLGTQT YICNVNHKPSNTKVDKKVEPKSCDKTHTCPPCPA PELLGGPSVFLFPPKPKDTLMISRTPEVTCVVVDV SHEDPEVKFNWYVDGVEVHNAKTKPREEQYNST YRVVSVLTVLHQDWLNGKEYKCKVSNKALPAPIE KTISKAKGQPREPQVYTLPPSREEMTKNQVSLTC LVKGFYPCDIAVEWESNGQPENNYKTTPPVLDSD GSFFLYSKLTVDKSRWQQGNVFSCSVMHEALHN HYTQKSLSLSPGK |
| SEQ ID NO: 22 | Heavy Chain DNA | GAGGTTCAGCTGGTGGAGTCTGGCGGTGGCCT GGTGCAGCCAGGGGGCTCACTCCGTTTGTCCT GTGCAGCTTCTGGCTTCAACATTAAAGACACCT ATATACACTGGGTGCGTCAGGCCCCGGGTAAG GGCCTGGAATGGGTTGCAAGGATTTATCCTAC GAATGGTTATACTAGATATGCCGATAGCGTCAA GGGCCGTTTCACTATAAGCGCAGACACATCCA AAAACACAGCCTACCTGCAGATGAACAGCCTG CGTGCTGAGGACACTGCCGTCTATTATTGTTCT AGATGGGGAGGGGACGGCTTCTATGCTATGGA CTACTGGGGTCAAGGAACCCTGGTCACCGTCT CCTCGGCTAGCACCAAGGGCCCCAGCGTGTTC CCCCTGGCCCCCAGCAGCAAGAGCACCAGCG GCGGCACAGCCGCCCTGGGCTGCCTGGTGAA GGACTACTTCCCTTGTCCCGTGACCGTGTCCT GGAACAGCGGAGCCCTGACCTCCGGCGTGCA CACCTTCCCCGCCGTGCTGCAGAGCAGCGGC CTGTACAGCCTGTCCAGCGTGGTGACAGTGCC CAGCAGCAGCCTGGGCACCCAGACCTACATCT GCAACGTGAACCACAAGCCCAGCAACACCAAG GTGGACAAGAAAGTGGAGCCCAAGAGCTGCGA CAAGACCCACACCTGCCCCCCCTGCCCAGCCC CAGAGCTGCTGGGCGGACCCTCCGTGTTCCTG TTCCCCCCCAAGCCCAAGGACACCCTGATGAT CAGCAGGACCCCCGAGGTGACCTGCGTGGTG GTGGACGTGAGCCACGAGGACCCAGAGGTGA AGTTCAACTGGTACGTGGACGGCGTGGAGGTG CACAACGCCAAGACCAAGCCCAGAGAGGAGCA GTACAACAGCACCTACAGGGTGGTGTCCGTGC TGACCGTGCTGCACCAGGACTGGCTGAACGGC |

TABLE 1-continued

Sequences of exemplary anti-HER2 monoclonal antibodies

|  |  |  |
|---|---|---|
|  |  | AAGGAATACAAGTGCAAGGTCTCCAACAAGGC<br>CCTGCCAGCCCCCATCGAAAAGACCATCAGCA<br>AGGCCAAGGGCCAGCCACGGGAGCCCCAGGT<br>GTACACCCTGCCCCCCTCCCGGGAGGAGATGA<br>CCAAGAACCAGGTGTCCCTGACCTGTCTGGTG<br>AAGGGCTTCTACCCCTGCGACATCGCCGTGGA<br>GTGGGAGAGCAACGGCCAGCCCGAGAACAAC<br>TACAAGACCACACCTCCAGTGCTGGACAGCGA<br>CGGCAGCTTCTTCCTGTACAGCAAGCTGACCG<br>TGGACAAGTCCAGGTGGCAGCAGGGCAACGT<br>GTTCAGCTGCAGCGTGATGCACGAGGCCCTGC<br>ACAACCACTACACCCAGAAGAGCCTGAGCCTG<br>TCCCCCGGCAAG |
| SEQ ID NO: 11 | LCDR1 (Kabat) | RASQDVNTAVA |
| SEQ ID NO: 12 | LCDR2 (Kabat) | SASFLYS |
| SEQ ID NO: 13 | LCDR3 (Kabat) | QQHYTTPPT |
| SEQ ID NO: 14 | LCDR1 (Chothia) | SQDVNTA |
| SEQ ID NO: 15 | LCDR2 (Chothia) | SAS |
| SEQ ID NO: 16 | LCDR3 (Chothia) | HYTTPP |
| SEQ ID NO: 11 | LCDR1 (Combined) | RASQDVNTAVA |
| SEQ ID NO: 12 | LCDR2 (Combined) | SASFLYS |
| SEQ ID NO: 13 | LCDR3 (Combined) | QQHYTTPPT |
| SEQ ID NO: 17 | VL | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIK |
| SEQ ID NO: 18 | VL DNA | GATATCCAGATGACCCAGTCCCCGAGCTCCCT<br>GTCCGCCTCTGTGGGCGATAGGGTCACCATCA<br>CCTGCCGTGCCAGTCAGGATGTGAATACTGCT<br>GTAGCCTGGTATCAACAGAAACCAGGAAAAGC<br>TCCGAAACTACTGATTTACTCGGCATCCTTCCT<br>CTACTCTGGAGTCCCTTCTCGCTTCTCTGGATC<br>CAGATCTGGGACGGATTTCACTCTGACCATCA<br>GCAGTCTGCAGCCGGAAGACTTCGCAACTTAT<br>TACTGTCAGCAACATTATACTACTCCTCCCACG<br>TTCGGACAGGGTACCAAGGTGGAGATCAAA |
| SEQ ID NO: 19 | Light Chain | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIKRTVAAPSVFIFPPSDEQLKSGTASVVCLLN<br>NFYPREAKVQWKVDNALQSGNSQESVTEQDSK<br>DSTYSLSSTLTLSKADYEKHKVYACEVTHQGLSS<br>PVTKSFNRGEC |
| SEQ ID NO: 34 | Light Chain DNA | GATATCCAGATGACCCAGTCCCCGAGCTCCCT<br>GTCCGCCTCTGTGGGCGATAGGGTCACCATCA<br>CCTGCCGTGCCAGTCAGGATGTGAATACTGCT<br>GTAGCCTGGTATCAACAGAAACCAGGAAAAGC<br>TCCGAAACTACTGATTTACTCGGCATCCTTCCT<br>CTACTCTGGAGTCCCTTCTCGCTTCTCTGGATC<br>CAGATCTGGGACGGATTTCACTCTGACCATCA<br>GCAGTCTGCAGCCGGAAGACTTCGCAACTTAT<br>TACTGTCAGCAACATTATACTACTCCTCCCACG<br>TTCGGACAGGGTACCAAGGTGGAGATCAAACG<br>AACGGTGGCCGCTCCCAGCGTGTTCATCTTCC<br>CCCCCAGCGACGAGCAGCTGAAGAGCGGCAC<br>CGCCAGCGTGGTGTGCCTGCTGAACAACTTCT<br>ACCCCCGGGAGGCCAAGGTGCAGTGGAAGGT<br>GGACAACGCCCTGCAGAGCGGCAACAGCCAG<br>GAGAGCGTCACCGAGCAGGACAGCAAGGACT<br>CCACCTACAGCCTGAGCAGCACCCTGACCCTG<br>AGCAAGGCCGACTACGAGAAGCATAAGGTGTA<br>CGCCTGCGAGGTGACCCACCAGGGCCTGTCC<br>AGCCCCGTGACCAAGAGCTTCAACAGGGGCGA<br>GTGC |

TABLE 1-continued

Sequences of exemplary anti-HER2 monoclonal antibodies anti-HER2 mAb3

| SEQ ID NO: 1 | HCDR1 (Kabat) | DTYIH |
|---|---|---|
| SEQ ID NO: 2 | HCDR2 (Kabat) | RIYPTNGYTRYADSVKG |
| SEQ ID NO: 3 | HCDR3 (Kabat) | WGGDGFYAMDY |
| SEQ ID NO: 4 | HCDR1 (Chothia) | GFNIKDT |
| SEQ ID NO: 5 | HCDR2 (Chothia) | YPTNGY |
| SEQ ID NO: 3 | HCDR3 (Chothia) | WGGDGFYAMDY |
| SEQ ID NO: 6 | HCDR1 (Combined) | GFNIKDTYIH |
| SEQ ID NO: 2 | HCDR2 (Combined) | RIYPTNGYTRYADSVKG |
| SEQ ID NO: 3 | HCDR3 (Combined) | WGGDGFYAMDY |
| SEQ ID NO: 7 | VH | EVQLVESGGGLVQPGGSLRLSCAASGFNIKDTYI<br>HWVRQAPGKGLEWVARIYPTNGYTRYADSVKGR<br>FTISADTSKNTAYLQMNSLRAEDTAVYYCSRWG<br>GDGFYAMDYWGQGTLVTVSS |
| SEQ ID NO: 8 | VH DNA | GAGGTTCAGCTGGTGGAGTCTGGCGGTGGCCT<br>GGTGCAGCCAGGGGGCTCACTCCGTTTGTCCT<br>GTGCAGCTTCTGGCTTCAACATTAAAGACACCT<br>ATATACACTGGGTGCGTCAGGCCCCGGGTAAG<br>GGCCTGGAATGGGTTGCAAGGATTTATCCTAC<br>GAATGGTTATACTAGATATGCCGATAGCGTCAA<br>GGGCCGTTTCACTATAAGCGCAGACACATCCA<br>AAAACACAGCCTACCTGCAGATGAACAGCCTG<br>CGTGCTGAGGACACTGCCGTCTATTATTGTTCT<br>AGATGGGGAGGGGACGGCTTCTATGCTATGGA<br>CTACTGGGGTCAAGGAACCCTGGTCACCGTCT<br>CCTCG |
| SEQ ID NO: 23 | Heavy Chain | EVQLVESGGGLVQPGGSLRLSCAASGFNIKDTYI<br>HWVRQAPGKGLEWVARIYPTNGYTRYADSVKGR<br>FTISADTSKNTAYLQMNSLRAEDTAVYYCSRWG<br>GDGFYAMDYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCPA<br>PELLGGPSVFLFPPKPKDTLMISRTPEVTCVVVDV<br>SHEDPEVKFNWYVDGVEVHNAKTKPREEQYNST<br>YRVVSVLTVLHQDWLNGKEYKCKVSNKALPAPIE<br>KTISKAKGQPREPQVYTLPPSREEMTKNQVSLTC<br>LVKGFYPSDIAVEWESNGQPENNYKTTPPVLDSD<br>GSFFLYSKLTVDKSRWQQGNVFSCSVMHEALHN<br>HYTQKSLSLSPGK |
| SEQ ID NO: 24 | Heavy Chain DNA | GAGGTTCAGCTGGTGGAGTCTGGCGGTGGCCT<br>GGTGCAGCCAGGGGGCTCACTCCGTTTGTCCT<br>GTGCAGCTTCTGGCTTCAACATTAAAGACACCT<br>ATATACACTGGGTGCGTCAGGCCCCGGGTAAG<br>GGCCTGGAATGGGTTGCAAGGATTTATCCTAC<br>GAATGGTTATACTAGATATGCCGATAGCGTCAA<br>GGGCCGTTTCACTATAAGCGCAGACACATCCA<br>AAAACACAGCCTACCTGCAGATGAACAGCCTG<br>CGTGCTGAGGACACTGCCGTCTATTATTGTTCT<br>AGATGGGGAGGGGACGGCTTCTATGCTATGGA<br>CTACTGGGGTCAAGGAACCCTGGTCACCGTCT<br>CCTCGGCTAGCACCAAGGGCCCCAGCGTGTTC<br>CCCCTGGCCCCCAGCAGCAAGAGCACCAGCG<br>GCGGCACAGCCGCCCTGGGCTGCCTGGTGAA<br>GGACTACTTCCCCGAGCCCGTGACCGTGTCCT<br>GGAACAGCGGAGCCCTGACCTCCGGCGTGCA<br>CACCTTCCCCGCCGTGCTGCAGAGCAGCGGC<br>CTGTACAGCCTGTCCAGCGTGGTGACAGTGCC<br>CAGCAGCAGCCTGGGCACCCAGACCTACATCT<br>GCAACGTGAACCACAAGCCCAGCAACACCAAG<br>GTGGACAAGAAAGTGGAGCCCAAGAGCTGCGA<br>CAAGACCCACACCTGCCCCCCTGCCCAGCCC<br>CAGAGCTGCTGGGCGGACCCTCCGTGTTCCTG<br>TTCCCCCCCAAGCCCAAGGACACCCTGATGAT<br>CAGCAGGACCCCCGAGGTGACCTGCGTGGTG |

TABLE 1-continued

Sequences of exemplary anti-HER2 monoclonal antibodies

| | | |
|---|---|---|
| | | GTGGACGTGAGCCACGAGGACCCAGAGGTGA<br>AGTTCAACTGGTACGTGGACGGCGTGGAGGTG<br>CACAACGCCAAGACCAAGCCCAGAGAGGAGCA<br>GTACAACAGCACCTACAGGGTGGTGTCCGTGC<br>TGACCGTGCTGCACCAGGACTGGCTGAACGGC<br>AAGGAATACAAGTGCAAGGTCTCCAACAAGGC<br>CCTGCCAGCCCCCATCGAAAAGACCATCAGCA<br>AGGCCAAGGGCCAGCCACGGGAGCCCCAGGT<br>GTACACCCTGCCCCCCTCCCGGGAGGAGATGA<br>CCAAGAACCAGGTGTCCCTGACCTGTCTGGTG<br>AAGGGCTTCTACCCCAGCGACATCGCCGTGGA<br>GTGGGAGAGCAACGGCCAGCCCGAGAACAAC<br>TACAAGACCACACCTCCAGTGCTGGACAGCGA<br>CGGCAGCTTCTTCCTGTACAGCAAGCTGACCG<br>TGGACAAGTCCAGGTGGCAGCAGGGCAACGT<br>GTTCAGCTGCAGCGTGATGCACGAGGCCCTGC<br>ACAACCACTACACCCAGAAGAGCCTGAGCCTG<br>TCCCCCGGCAAG |
| SEQ ID NO: 11 | LCDR1 (Kabat) | RASQDVNTAVA |
| SEQ ID NO: 12 | LCDR2 (Kabat) | SASFLYS |
| SEQ ID NO: 13 | LCDR3 (Kabat) | QQHYTTPPT |
| SEQ ID NO: 14 | LCDR1 (Chothia) | SQDVNTA |
| SEQ ID NO: 15 | LCDR2 (Chothia) | SAS |
| SEQ ID NO: 16 | LCDR3 (Chothia) | HYTTPP |
| SEQ ID NO: 11 | LCDR1 (Combined) | RASQDVNTAVA |
| SEQ ID NO: 12 | LCDR2 (Combined) | SASFLYS |
| SEQ ID NO: 13 | LCDR3 (Combined) | QQHYTTPPT |
| SEQ ID NO: 17 | VL | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIK |
| SEQ ID NO: 18 | VL DNA | GATATCCAGATGACCCAGTCCCCGAGCTCCCT<br>GTCCGCCTCTGTGGGCGATAGGGTCACCATCA<br>CCTGCCGTGCCAGTCAGGATGTGAATACTGCT<br>GTAGCCTGGTATCAACAGAAACCAGGAAAAGC<br>TCCGAAACTACTGATTTACTCGGCATCCTTCCT<br>CTACTCTGGAGTCCCTTCTCGCTTCTCTGGATC<br>CAGATCTGGGACGGATTTCACTCTGACCATCA<br>GCAGTCTGCAGCCGGAAGACTTCGCAACTTAT<br>TACTGTCAGCAACATTATACTACTCCTCCCACG<br>TTCGGACAGGGTACCAAGGTGGAGATCAAA |
| SEQ ID NO: 19 | Light Chain | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIKRTVAAPSVFIFPPSDEQLKSGTASVVCLLN<br>NFYPREAKVQWKVDNALQSGNSQESVTEQDSK<br>DSTYSLSSTLTLSKADYEKHKVYACEVTHQGLSS<br>PVTKSFNRGEC |
| SEQ ID NO: 34 | Light Chain DNA | GATATCCAGATGACCCAGTCCCCGAGCTCCCT<br>GTCCGCCTCTGTGGGCGATAGGGTCACCATCA<br>CCTGCCGTGCCAGTCAGGATGTGAATACTGCT<br>GTAGCCTGGTATCAACAGAAACCAGGAAAAGC<br>TCCGAAACTACTGATTTACTCGGCATCCTTCCT<br>CTACTCTGGAGTCCCTTCTCGCTTCTCTGGATC<br>CAGATCTGGGACGGATTTCACTCTGACCATCA<br>GCAGTCTGCAGCCGGAAGACTTCGCAACTTAT<br>TACTGTCAGCAACATTATACTACTCCTCCCACG<br>TTCGGACAGGGTACCAAGGTGGAGATCAAACG<br>AACGGTGGCCGCTCCCAGCGTGTTCATCTTCC<br>CCCCCAGCGACGAGCAGCTGAAGAGCGGCAC<br>CGCCAGCGTGGTGTGCCTGCTGAACAACTTCT<br>ACCCCCGGGAGGCCAAGGTGCAGTGGAAGGT<br>GGACAACGCCCTGCAGAGCGGCAACAGCCAG<br>GAGAGCGTCACCGAGCAGGACAGCAAGGACT<br>CCACCTACAGCCTGAGCAGCACCCTGACCCTG |

TABLE 1-continued

Sequences of exemplary anti-HER2 monoclonal antibodies

|  |  |  |
|---|---|---|
|  |  | AGCAAGGCCGACTACGAGAAGCATAAGGTGTA<br>CGCCTGCGAGGTGACCCACCAGGGCCTGTCC<br>AGCCCCGTGACCAAGAGCTTCAACAGGGGCGA<br>GTGC | anti-HER2 mAb4

| SEQ ID NO: 30 | Heavy Chain | EVQLVESGGGLVQPGGSLRLSCAASGFNIKDTYI<br>HWVRQAPGKGLEWVARIYPTNGYTRYADSVKGR<br>FTISADTSKNTAYLQMNSLRAEDTAVYYCSRWG<br>GDGFYAMDYWGQGTLVTVSSASTKGPSVFPLAP<br>SSKSTSGGTAALGCLVKDYFPCPVTVSWNSGAL<br>TSGVHTFPAVLQSSGLYSLSSVVTVPSSSLGTQT<br>YICNVNHKPSNTKVDKKVEPKSCDKTHTCPPCPA<br>PELLGGPSVFLFPPKPKDTLMISRTPEVTCVVVDV<br>SHEDPEVKFNWYVDGVEVHNAKTKPREEQYNST<br>YRVVSVLTVLHQDWLNGKEYKCKVSNKALPAPIE<br>KTISKAKGQPREPQVYTLPPSREEMTKNQVSLTC<br>LVKGFYPSDIAVEWESNGQPENNYKTTPPVLDSD<br>GSFFLYSKLTVDKSRWQQGNVFSCSVMHEALHN<br>HYTQKSLSLSPGK |
|---|---|---|
| SEQ ID NO: 19 | Light Chain | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIKRTVAAPSVFIFPPSDEQLKSGTASVVCLLN<br>NFYPREAKVQWKVDNALQSGNSQESVTEQDSK<br>DSTYSLSSTLTLSKADYEKHKVYACEVTHQGLSS<br>PVTKSFNRGEC | anti-HER2 mAb5

| SEQ ID NO: 32 | Heavy Chain | EVQLVESGGGLVQPGGSLRLSCAASGFNIKDTYI<br>HWVRQAPGKGLEWVARIYPTNGYTRYADSVKGR<br>FTISADTSKNTAYLQMNSLRAEDTAVYYCSRWG<br>GDGFYAMDYWGQGTLVTVSSASTKGPSVFPLAP<br>SSKSTSGGTAALGCLVKDYFPEPVTVSWNSGAL<br>TSGVHTFPAVLQSSGLYSLSSVVTVPSSSLGTQT<br>YICNVNHKPSNTKVDKKVEPKSCDKTHTCPPCPA<br>PELLGGPSVFLFPPKPKDTLMISRTPEVTCVVVDV<br>SHEDPEVKFNWYVDGVEVHNAKTKPREEQYNST<br>YRVVSVLTVLHQDWLNGKEYKCKVSNKALPAPIE<br>KTISKAKGQPREPQVYTLPPSREEMTKNQVSLTC<br>LVKGFYPSDIAVEWESNGQPEGDSLDMLEWSLM<br>NNYKTTPPVLDSDGSFFLYSKLTVDKSRWQQGN<br>VFSCSVMHEALHNHYTQKSLSLSPGK |
|---|---|---|
| SEQ ID NO: 19 | Light Chain | DIQMTQSPSSLSASVGDRVTITCRASQDVNTAVA<br>WYQQKPGKAPKLLIYSASFLYSGVPSRFSGSRSG<br>TDFTLTISSLQPEDFATYYCQQHYTTPPTFGQGT<br>KVEIKRTVAAPSVFIFPPSDEQLKSGTASVVCLLN<br>NFYPREAKVQWKVDNALQSGNSQESVTEQDSK<br>DSTYSLSSTLTLSKADYEKHKVYACEVTHQGLSS<br>PVTKSFNRGEC |

Other anti-HER2 antibodies or antibody fragments (e.g., antigen binding fragments) disclosed herein include amino acids that have been mutated, yet have at least 80, 85, 90, 95, 96, 97, 98, or 99 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

Also provided herein are nucleic acid sequences that encode VH, VL, full length heavy chain, and full length light chain of antibodies and antigen binding fragments thereof that specifically bind to HER2, e.g., the nucleic acid sequences in Table 1. Such nucleic acid sequences can be optimized for expression in mammalian cells.

Other anti-HER2 antibodies disclosed herein include those where the amino acids or nucleic acids encoding the amino acids have been mutated, yet have at least 80, 85, 90 95, 96, 97, 98, or 99 percent identity to the sequences described in Table 1. In some embodiments, antibodies or antigen binding fragments thereof include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each provided antibody binds to HER2, the VH, VL, full length light chain, and full length heavy chain sequences (amino acid sequences and the nucleotide sequences encoding the amino acid sequences) can be "mixed and matched" to create other HER2-binding antibodies disclosed herein. Such "mixed and matched" HER2-binding antibodies can be tested using binding assays known in the art (e.g., ELISAs, assays described in the Exemplification). When chains are mixed and matched, a VH sequence from a particular VH/VL pairing should be replaced with a structurally similar VH sequence. A full length heavy chain sequence from a particular full length heavy chain/full length light chain pairing should be replaced with a structurally similar full length heavy chain sequence. A VL sequence from a particular VH/VL pairing should be replaced with a structurally similar VL sequence. A full length light chain sequence from a particular full length heavy chain/full length light chain pairing should be replaced with a structurally similar full length light chain sequence.

Accordingly, in one embodiment, the invention provides an isolated monoclonal antibody or antigen binding region thereof having: a heavy chain variable region comprising an amino acid sequence of SEQ ID NO: 7; and a light chain variable region comprising an amino acid sequence of SEQ ID NO: 17; wherein the antibody specifically binds to HER2. In another embodiment, the invention provides (i) an isolated monoclonal antibody having: a full length heavy chain comprising an amino acid sequence of any of SEQ ID NOs: 9, 21, 23, 30 or 32; and a full length light chain comprising an amino acid sequence of SEQ ID NO: 19; or (ii) a functional protein comprising an antigen binding portion thereof.

In another embodiment, the present disclosure provides HER2-binding antibodies that comprise the heavy chain CDR1, CDR2 and CDR3 and light chain CDR1, CDR2 and CDR3 as described in Table 1, or combinations thereof. The amino acid sequences of the VH CDR1 s of the antibodies are shown in SEQ ID NOs: 1, 4, and 6. The amino acid sequences of the VH CDR2s of the antibodies and are shown in SEQ ID NOs: 2 and 5. The amino acid sequences of the VH CDR3s of the antibodies are shown in SEQ ID NO: 3. The amino acid sequences of the VL CDR1s of the antibodies are shown in SEQ ID NOs: 11 and 14. The amino acid sequences of the VL CDR2s of the antibodies are shown in SEQ ID NOs 12 and 15. The amino acid sequences of the VL CDR3s of the antibodies are shown in SEQ ID NOs: 13 and 16.

Given that each of the antibodies binds HER2 and that antigen-binding specificity is provided primarily by the CDR1, CDR2 and CDR3 regions, the VH CDR1, CDR2 and CDR3 sequences and VL CDR1, CDR2 and CDR3 sequences can be "mixed and matched" (i.e., CDRs from different antibodies can be mixed and match, although each antibody must contain a VH CDR1, CDR2 and CDR3 and a VL CDR1, CDR2 and CDR3 to create other HER2-binding binding molecules disclosed herein. Such "mixed and matched" HER2-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 1, 4, and 6; a heavy chain CDR2 comprising an amino acid sequence selected from the group consisting of SEQ ID NOs: 2 and 5; a heavy chain CDR3 comprising an amino acid sequence of SEQ ID NO: 3; a light chain CDR1 comprising an amino acid sequence selected from the group consisting of SEQ ID NOs: 11 and 14; a light chain CDR2 comprising an amino acid sequence selected from the group consisting of SEQ ID NOs: 12 and 15; and a light chain CDR3 comprising an amino acid sequence selected from the group consisting of SEQ ID NOs: 13 and 16; wherein the antibody specifically binds HER2.

In certain embodiments, an antibody that specifically binds to HER2 is an antibody or antibody fragment (e.g., antigen binding fragment) that is described in Table 1.

In some embodiments, the antibody that specifically binds to human HER2 comprises a heavy chain complementary determining region 1 (HCDR1) comprising the amino acid sequence of SEQ ID NO: 1; a heavy chain complementary determining region 2 (HCDR2) comprising the amino acid sequence of SEQ ID NO: 2; a heavy chain complementary determining region 3 (HCDR3) comprising the amino acid sequence of SEQ ID NO: 3; a light chain complementary determining region 1 (LCDR1) comprising the amino acid sequence of SEQ ID NO: 11; a light chain complementary determining region 2 (LCDR2) comprising the amino acid sequence of SEQ ID NO: 12; and a light chain complementary determining region 3 (LCDR3) comprising the amino acid sequence of SEQ ID NO: 13.

In some embodiments, the antibody that specifically binds to human HER2 comprises a HCDR1 comprising the amino acid sequence of SEQ ID NO: 4; a HCDR2 comprising the amino acid sequence of SEQ ID NO: 5; a HCDR3 comprising the amino acid sequence of SEQ ID NO: 3; a LCDR1 comprising the amino acid sequence of SEQ ID NO: 14; a LCDR2 comprising the amino acid sequence of SEQ ID NO: 15; and a LCDR3 comprising the amino acid sequence of SEQ ID NO: 16.

In some embodiments, the antibody that specifically binds to human HER2 comprises a heavy chain variable region comprising the amino acid sequence of SEQ ID NO: 7, and a light chain variable region comprising the amino acid sequence of SEQ ID NO: 17.

In some embodiments, the antibody that specifically binds to human HER2 comprises a heavy chain comprising the amino acid sequence of SEQ ID NO: 9, and a light chain comprising the amino acid sequence of SEQ ID NO: 19.

In some embodiments, the antibody that specifically binds to human HER2 comprises a heavy chain comprising the amino acid sequence of SEQ ID NO: 21, and a light chain comprising the amino acid sequence of SEQ ID NO: 19.

In some embodiments, the antibody that specifically binds to human HER2 comprises a heavy chain comprising the amino acid sequence of SEQ ID NO: 23, and a light chain comprising the amino acid sequence of SEQ ID NO: 19.

In some embodiments, the antibody that specifically binds to human HER2 comprises a heavy chain comprising the amino acid sequence of SEQ ID NO: 30, and a light chain comprising the amino acid sequence of SEQ ID NO: 19.

In some embodiments, the antibody that specifically binds to human HER2 comprises a heavy chain comprising the amino acid sequence of SEQ ID NO: 32, and a light chain comprising the amino acid sequence of SEQ ID NO: 19.

In some embodiments, the present disclosure provides antibodies or antibody fragments (e.g., antigen binding fragments) that specifically bind an epitope in human HER2. In some embodiments, the present disclosure provides antibodies or antibody fragments (e.g., antigen binding fragments) that specifically bind to an epitope in human HER2, wherein the epitope comprises one or more of the residues 557-561, 570-573, and 593-603 of SEQ ID NO: 26. In some embodiments, the present disclosure provides antibodies or antibody fragments (e.g., antigen binding fragments) that specifically bind to an epitope in human HER2, wherein the epitope comprises one or more of the residues 245-333 of SEQ ID NO: 26. In some embodiments, the present disclosure provides antibodies or antibody fragments (e.g., antigen binding fragments) that specifically bind to an epitope in human HER2, wherein the epitope comprises one or more of the following residues: His 245, Val 286, Ser 288, Leu 295, His 296, or Lys 311 of SEQ ID NO: 26.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 2003/48731. As will be appreciated by one of skill in the art, practically anything to which an antibody can specifically bind could be an epitope. An epitope can comprises those residues to which the antibody binds.

Modification of Framework or Fc Region

Antibodies and antibody conjugates disclosed herein may comprise modified antibodies or antigen binding fragments thereof that comprise modifications to framework residues within VH and/or VL, e.g. to improve the properties of the antibody/antibody conjugate.

In some embodiments, framework modifications are made to decrease immunogenicity of an antibody. For example, one approach is to "back-mutate" one or more framework residues to a corresponding germline sequence. Such residues can be identified by comparing antibody framework sequences to germline sequences from which the antibody is derived. To "match" framework region sequences to desired germline configuration, residues can be "back-mutated" to a corresponding germline sequence by, for example, site-directed mutagenesis. Such "back-mutated" antibodies are also intended to be encompassed by the invention.

Another type of framework modification involves mutating one or more residues within a framework region, or even within one or more CDR regions, to remove T-cell epitopes to thereby reduce potential immunogenicity of the antibody. This approach is also referred to as "deimmunization" and is described in further detail in U.S. Patent Publication No. 20030153043 by Carr et al.

In addition or alternative to modifications made within a framework or CDR regions, antibodies disclosed herein may be engineered to include modifications within the Fc region, typically to alter one or more functional properties of the antibody, such as serum half-life, complement fixation, Fc receptor binding, and/or antigen-dependent cellular cytotoxicity.

Furthermore, an antibody disclosed herein may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments antibodies or antibody fragments (e.g., antigen binding fragment) useful in antibody conjugates disclosed herein include modified or engineered antibodies, such as an antibody modified to introduce one or more cysteine residues as sites for conjugation to a drug moiety (Junutula J R, et al.: Nat Biotechnol 2008, 26:925-932). In one embodiment, the invention provides a modified antibody or antibody fragment thereof comprising a substitution of one or more amino acids with cysteine at the positions described herein. Sites for cysteine substitution are in the constant regions of the antibody and are thus applicable to a variety of antibodies, and the sites are selected to provide stable and homogeneous conjugates. A modified antibody or fragment can have two or more cysteine substitutions, and these substitutions can be used in combination with other antibody modification and conjugation methods as described herein. Methods for inserting cysteine at specific locations of an antibody are known in the art, see, e.g., Lyons et al, (1990) Protein Eng., 3:703-708, WO 2011/005481, WO2014/124316, WO 2015/138615. In certain embodiments a modified antibody or antibody fragment comprises a substitution of one or more amino acids with cysteine on its constant region selected from positions 117, 119, 121, 124, 139, 152, 153, 155, 157, 164, 169, 171, 174, 189, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain of the antibody or antibody fragment, and wherein the positions are numbered according to the EU system. In some embodiments a modified antibody or antibody fragment comprises a substitution of one or more amino acids with cysteine on its constant region selected from positions 107, 108, 109, 114, 129, 142, 143, 145, 152, 154, 156, 159, 161, 165, 168, 169, 170, 182, 183, 197, 199, and 203 of a light chain of the antibody or antibody fragment, wherein the positions are numbered according to the EU system, and wherein the light chain is a human kappa light chain. In certain embodiments a modified antibody or antibody fragment thereof comprises a combination of substitution of two or more amino acids with cysteine on its constant regions wherein the combinations comprise substitutions at positions 375 of an antibody heavy chain, position 152 of an antibody heavy chain, position 360 of an antibody heavy chain, or position 107 of an antibody light chain and wherein the positions are numbered according to the EU system. In certain embodiments a modified antibody or antibody fragment thereof comprises a substitution of one amino acid with cysteine on its constant regions wherein the substitution is position 375 of an antibody heavy chain, position 152 of an antibody heavy chain, position 360 of an antibody heavy chain, position 107 of an antibody light chain, position 165 of an antibody light chain or position 159 of an antibody light chain and wherein the positions are numbered according to the EU system, and wherein the light chain is a kappa chain.

In particular embodiments a modified antibody or antibody fragment thereof comprises a combination of substitution of two amino acids with cysteine on its constant regions, wherein the modified antibody or antibody fragment thereof comprises cysteines at positions 152 and 375 of an antibody heavy chain, wherein the positions are numbered according to the EU system.

In other particular embodiments a modified antibody or antibody fragment thereof comprises a substitution of one amino acid with cysteine at position 360 of an antibody heavy chain and wherein the positions are numbered according to the EU system.

In other particular embodiments a modified antibody or antibody fragment thereof comprises a substitution of one amino acid with cysteine at position 107 of an antibody light chain and wherein the positions are numbered according to the EU system, and wherein the light chain is a kappa chain.

In additional embodiments antibodies or antibody fragments (e.g., antigen binding fragment) useful in antibody conjugates disclosed herein include modified or engineered antibodies, such as an antibody modified to introduce one or more other reactive amino acid (other than cysteine), including Pcl, pyrrolysine, peptide tags (such as S6, A1 and ybbR tags), and non-natural amino acids, in place of at least one amino acid of the native sequence, thus providing a reactive site on the antibody or antigen binding fragment for conjugation to a drug moiety of Formula (I) or subformulae thereof. For example, the antibodies or antibody fragments can be modified to incorporate Pcl or pyrrolysine (W. Ou et al. (2011) PNAS 108 (26), 10437-10442; WO2014124258) or unnatural amino acids (J. Y. Axup, et al. Proc Natl Acad Sci USA, 109 (2012), pp. 16101-16106; for review, see C. C. Liu and P. G. Schultz (2010) Annu Rev Biochem 79, 413-444; C. H. Kim, et al., (2013) Curr Opin Chem Biol. 17, 412-419) as sites for conjugation to a drug. Similarly, peptide tags for enzymatic conjugation methods can be introduced into an antibody (Strop P. et al. Chem Biol. 2013, 20(2):161-7; Rabuka D., Curr Opin Chem Biol. 2010 December; 14(6):790-6; Rabuka D, et al., Nat Protoc. 2012, 7(6):1052-67). One other example is the use of 4'-phosphopantetheinyl transferases (PPTase) for the conjugation of Coenzyme A analogs (WO2013184514). Methods for conjugating such modified or engineered antibodies with payloads or linker-payload combinations are known in the art.

In another embodiment, an Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl Protein A (SpA) binding relative to native Fc-hinge domain SpA binding. This approach is described in further detail in U.S. Pat. No. 6,165,745 by Ward et al.

In yet other embodiments, an Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another embodiment, one or more amino acid residues are altered to thereby alter the ability of the antibody to fix complement. This approach is described in, e.g., the PCT Publication WO 94/29351 by Bodmer et al. Allotypic amino acid residues include, but are not limited to, constant region of a heavy chain of the IgG1, IgG2, and IgG3 subclasses as well as constant region of a light chain of the kappa isotype as described by Jefferis et al., MAbs. 1:332-338 (2009).

In yet another embodiment, the Fc region is modified to increase the ability of the antibody to mediate antibody dependent cellular cytotoxicity (ADCC) and/or antibody dependent cellular phagocytosis (ADCP), for example, by modifying one or more amino acid residues to increase the affinity of the antibody for an activating Fcγ receptor, or to decrease the affinity of the antibody for an inhibitory Fcγ receptor. Human activating Fcγ receptors include FcγRIa, FcγRIIa, FcγRIIIa, and FcγRIIIb, and human inhibitory Fcγ receptor includes FcγRIIb. This approach is described in, e.g., the PCT Publication WO 00/42072 by Presta. Moreover, binding sites on human IgG1 for FcγRI, FcγRII, FcγRIII and FcRn have been mapped and variants with improved binding have been described (see Shields et al., J. Biol. Chem. 276:6591-6604, 2001). Optimization of Fc-mediated effector functions of monoclonal antibodies such as increased ADCC/ADCP function has been described (see Strohl, W. R., Current Opinion in Biotechnology 2009; 20:685-691.) In some embodiments, an antibody conjugate comprises an immunoglobulin heavy chain comprising a mutation or combination of mutations conferring enhanced ADCC/ADCP function, e.g., one or more mutations selected from G236A, S239D, F243L, P247I, D280H, K290S, R292P, S298A, S298D, S298V, Y300L, V305I, A330L, I332E, E333A, K334A, A339D, A339Q, A339T, P396L (all positions by EU numbering).

In another embodiment, the Fc region is modified to increase the ability of the antibody to mediate ADCC and/or ADCP, for example, by modifying one or more amino acids to increase the affinity fo the antibody for an activating receptor that would typically not recognize the parent antibody, such as FcαRI. This approach is descried in, e.g., Borrok et al., mAbs. 7(4):743-751. In particular embodiments, an antibody conjugate comprises an immunoglobulin heavy chain comprising a mutation or a fusion of one or more antibody sequences conferring enhanced ADCC and/or ADCP function.

In still another embodiment, glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

Production of Anti-HER2 Antibodies

Anti-HER2 antibodies and antibody fragments (e.g., antigen binding fragments) thereof can be produced by any means known in the art, including but not limited to, recombinant expression, chemical synthesis, and enzymatic digestion of antibody tetramers, whereas full length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

Also provided herein are polynucleotides encoding antibodies described herein, e.g., polynucleotides encoding heavy or light chain variable regions or segments comprising complementarity determining regions as described herein. In some embodiments, a polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide of SEQ ID NO: 8. In some embodiments, a polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide of SEQ ID NO:18.

In some embodiments, a polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of any of SEQ ID NOs: 10, 22, or 24. In some embodiments, a polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 20 or 34.

Some polynucleotides disclosed herein encode a variable region of an anti-HER2 antibody. Some polynucleotides disclosed herein encode both a variable region and a constant region of an anti-HER2 antibody. Some polynucleotide sequences encode a polypeptide that comprises variable regions of both a heavy chain and a light chain of an anti-HER2 antibody. Some polynucleotides encode two polypeptide segments that respectively are substantially identical to the variable regions of a heavy chain and a light chain of any anti-HER2 antibodies disclosed herein.

Polynucleotide sequences can be produced by de novo solid-phase DNA synthesis or by PCR mutagenesis of an existing sequence (e.g., sequences as described in the Examples below) encoding an anti-HER2 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided are expression vectors and host cells for producing anti-HER2 antibodies described above. Various expression vectors can be employed to express polynucleotides encoding anti-HER2 antibody chains or binding fragments. Both viral-based and nonviral expression vectors can be used to produce antibodies in a mammalian host cell.

Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of anti-HER2 polynucleotides and polypeptides in mammalian (e.g., human) cells include pThioHis A, B & C, pCDNATM3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

Choice of expression vector depends on the intended host cells in which a vector is to be expressed. Typically, expression vectors contain a promoter and other regulatory sequences (e.g., enhancers) that are operably linked to polynucleotides encoding an anti-HER2 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by host cells. In addition to promoters, other regulatory elements may also be required or desired for efficient expression of an anti-HER2 antibody chain or fragment. Elements typically include an ATG initiation codon and adjacent ribosome binding site or other sequences. In addition, efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, an SV40 enhancer or CMV enhancer may be used to increase expression in mammalian host cells.

Expression vectors may also provide a secretion signal sequence position to form a fusion protein with polypeptides encoded by inserted anti-HER2 antibody sequences. More often, inserted anti-HER2 antibody sequences are linked to a signal sequence before inclusion in the vector. Vectors to be used to receive sequences encoding anti-HER2 antibody light and heavy chain variable domains sometimes also encode constant regions or parts thereof. Such vectors allow expression of variable regions as fusion proteins with constant regions, thereby leading to production of intact antibodies or fragments thereof. Typically, such constant regions are human.

Host cells for harboring and expressing anti-HER2 antibody chains can be either prokaryotic or eukaryotic. *E. coli* is one prokaryotic host useful for cloning and expressing polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as a lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-HER2 polypeptides disclosed herein. Insect cells in combination with baculovirus vectors can also be used.

In some particular embodiments, mammalian host cells are used to express and produce anti-HER2 polypeptides of the present disclosure. For example, they can be either a hybridoma cell line expressing endogenous immunoglobulin genes (e.g., myeloma hybridoma clones) or a mammalian cell line harboring an exogenous expression vector (e.g., the SP2/0 myeloma cells). These include any normal mortal or normal or abnormal immortal animal or human cell. For example, a number of suitable host cell lines capable of secreting intact immunoglobulins have been developed, including various CHO cell lines, Cos cell lines, HeLa cells, myeloma cell lines, transformed B-cells and hybridomas. Use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. Expression vectors usually contain promoters derived from mammalian genes or from mammalian viruses. Suitable promoters may be constitutive, cell type-specific, stage-specific, and/or modulatable or regulatable. Useful promoters include, but are not limited to, a metallothionein promoter, a constitutive adenovirus major late promoter, a dexamethasone inducible MMTV promoter, a SV40 promoter, a MRP polIII promoter, a constitutive MPSV promoter, a tetracycline-inducible CMV promoter (such as the human immediate-early CMV promoter), a constitutive CMV promoter, and promoter-enhancer combinations known in the art.

Methods for introducing expression vectors containing polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-HER2 antibody chains or binding fragments can be prepared using expression vectors disclosed herein which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Processes for Making Antibody Conjugate of Formula (IIa) and Formula (IIb)

A general reaction scheme for the formation of immunostimulatory conjugates of Formula (II) is shown in Scheme 13 below:

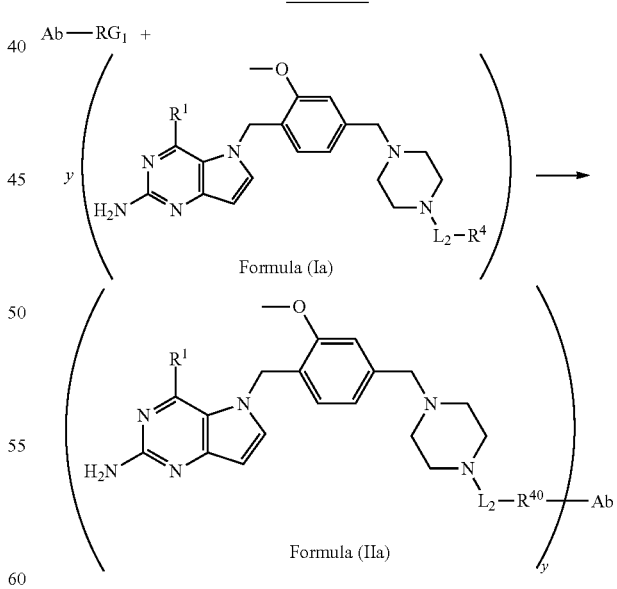

where: $RG_1$ is a reactive group which reacts with a compatible $R^4$ group of a compound of Formula (Ia) to form a corresponding $R^{40}$ group, such as maleimide reacting with a thiol to give a succinimide ring, or a hydroxylamine reacting with a ketone to give an oxime; $R^1$, $R^4$, $L_2$, Ab and $R^{40}$ are as defined herein.

A general reaction scheme for the formation of immunostimulatory conjugates of Formula (IIb) is shown in Scheme 14 below:

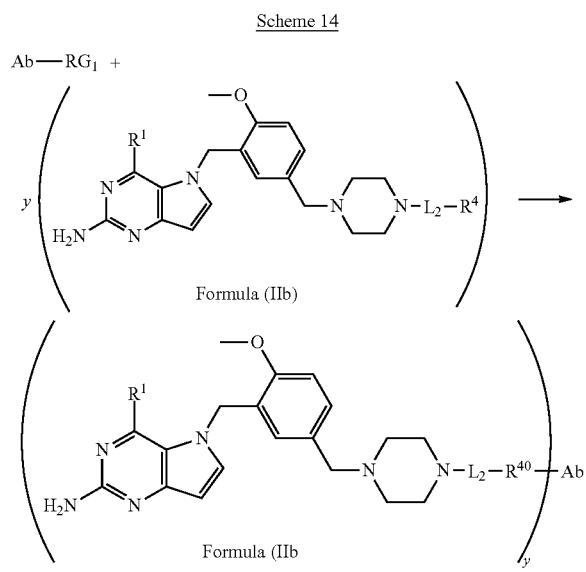

Scheme 14 where: $RG_1$ is a reactive group which reacts with a compatible $R^4$ group of a compound of Formula (Ib) to form a corresponding $R^{40}$ group, such as maleimide reacting with a thiol to give a succinimide ring, or a hydroxylamine reacting with a ketone to give an oxime; $R^1$, $R^4$, $L_2$, Ab and $R^{40}$ are as defined herein.

Therapeutic Uses and Methods of Treatment

Provided antibody conjugates are useful in a variety of applications including, but not limited to, treatment of cancer, such as HER2 positive cancer. In certain embodiments, antibody conjugates provided herein are useful for inhibiting tumor growth, reducing tumor volume, inducing differentiation, and/or reducing the tumorigenicity of a tumor, e.g., a HER2 solid tumor. The methods of use can be in vitro, ex vivo, or in vivo methods.

In some embodiments, provided herein are methods of treating, preventing, or ameliorating a disease, e.g., a HER2-positive cancer, in a subject in need thereof, e.g., a human patient, by administering to the subject any of the antibody conjugates described herein. Also provided is use of the antibody conjugates of the invention to treat or prevent disease in a subject, e.g., a human patient. Additionally provided is use of antibody conjugates in treatment or prevention of disease in a subject. In some embodiments provided are antibody conjugates for use in manufacture of a medicament for treatment or prevention of disease in a subject. In certain embodiments, the disease treated with antibody conjugates is a cancer, e.g., a HER2-positive cancer. Various cancers that can be treated with the antibody conjugates are listed in the definitions section above. The HER2-positive cancer can be any cancer comprising cells that have HER2 protein present at their cell surface. For example, a HER2-positive cancer can be either primary tumor or metastasis of any of gastric cancer, esophageal cancer, gastroesophageal junction adenocarcinoma, colon cancer, rectal cancer, breast cancer, ovarian cancer, cervical cancer, uterine cancer, endometrial cancer, bladder cancer, urinary tract cancer, pancreatic cancer, lung cancer, prostate cancer, osteosarcoma, neuroblastoma, glioblastoma, neuroendocrine tumors, and head and neck cancer. In certain embodiments, the cancer is characterized by HER2 expressing cells to which the antibodies, antibody fragments (e.g., antigen binding fragments) of the antibody conjugates bind. In certain embodiments, the cancer is characterized by concurrent expression of multiple human epidermal growth factor receptors in addition to HER2 expression. In some embodiments, the HER2-positive cancer can have high HER2 expression, e.g., having an immunohistochemistry (IHC) score of 3+, which is defined as uniform intense membrane staining of >30% of invasive tumor cells as determined by the American Society of Clinical Oncology and the College of American Pathologists (ASCO/CAP) IHC score (see English et al., Mol Diagn Ther. 2013 April; 17(2): 85-99). In some embodiments, the HER2-positive cancer can have relatively low HER2 expression, e.g., having an IHC score of 2+, which is defined as complete membrane staining that is either non-uniform or weak in intensity but with obvious circumferential distribution in at least 10% cells or very rarely tumors that show complete membranes staining of 30% or fewer tumor cells by the ASCO/CAP IHC score (see English et al., Mol Diagn Ther. 2013 April; 17(2): 85-99).

In some embodiments, provided are methods of treating a HER2-positive cancer in a subject in needed thereof, the methods comprising administering to the subject a therapeutically effective amount of any of the antibody conjugates described herein. The HER2-positive cancer can be any cancer comprising cells that have HER2 protein present at their cell surface. In some embodiments, the antibody conjugate used is capable of suppressing the HER2-positive cancer for a sustained period and/or reducing recurrence of the HER2-positive cancer, when compared to an anti-HER2 antibody alone.

It is also contemplated that the antibody conjugates described herein may be used to treat various non-malignant diseases or disorders, such as inflammatory bowel disease (IBD), gastrointestinal ulcers, Menetrier's disease, hepatitis B, hepatitis C, secreting adenomas or protein loss syndrome, renal disorders, angiogenic disorders, ocular disease such as age related macular degeneration, presumed ocular histoplasmosis syndrome, or age related macular degeneration, bone associated pathologies such as osteoarthritis, rickets and osteoporosis, hyperviscosity syndrome systemic, Osler Weber-Rendu disease, chronic occlusive pulmonary disease, or edema following burns, trauma, radiation, stroke, hypoxia or ischemia, diabetic nephropathy, Paget's disease, photoaging (e.g., caused by UV radiation of human skin), benign prostatic hypertrophy, certain microbial infections including microbial pathogens selected from adenovirus, hantaviruses, Borrelia burgdorferi, Yersinia spp., and Bordetella pertussis, thrombus caused by platelet aggregation, reproductive conditions such as endometriosis, ovarian hyperstimulation syndrome, preeclampsia, dysfunctional uterine bleeding, or menometrorrhagia, acute and chronic nephropathies (including proliferative glomerulonephritis), hypertrophic scar formation, endotoxic shock and fungal infection, familial adenomatosis polyposis, myelodysplastic syndromes, aplastic anemia, ischemic injury, fibrosis of the lung, kidney or liver, infantile hypertrophic pyloric stenosis, urinary obstructive syndrome, psoriatic arthritis.

Method of administration of such antibody conjugates include, but are not limited to, parenteral (e.g., intravenous) administration, e.g., injection as a bolus or continuous infusion over a period of time, oral administration, intramuscular administration, intratumoral administration, intramuscular administration, intraperitoneal administration, intracerobrospinal administration, subcutaneous administration, intra-articular administration, intrasynovial administration, injection to lymph nodes, or intrathecal administration.

For treatment of disease, appropriate dosage of antibody conjugates of the present invention depends on various factors, such as the type of disease to be treated, the severity and course of the disease, the responsiveness of the disease, previous therapy, patient's clinical history, and so on. Antibody conjugates can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of a particular antibody conjugate. In some embodiments, dosage is from 0.01 mg to 20 mg (e.g., 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg) per kg of body weight, and can be given once or more daily, weekly, monthly or yearly. In certain embodiments, the antibody conjugate of the present invention is given once every two weeks or once every three weeks. In certain embodiments, the antibody conjugate of the present invention is given only once. The treating physician can estimate repetition rates for dosing based on measured residence times and concentrations of the drug in bodily fluids or tissues.

Combination Therapy

In certain instances, an antibody conjugate of the present invention can be combined with other therapeutic agents, such as other anti-cancer agents, anti-allergic agents, anti-nausea agents (or anti-emetics), pain relievers, cytoprotective agents, and combinations thereof.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), epirubicin (Ellence®), oxaliplatin (Eloxatin®), exemestane (Aromasin®), letrozole (Femara®), and fulvestrant (Faslodex®).

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one embodiment, the present invention provides a method of treating cancer by administering to a subject in need thereof antibody conjugate of the present invention in combination with one or more other anti-HER2 antibodies, e.g., trastuzumab, pertuzumab, margetuximab, or HT-19 described above, or with other anti-HER2 conjugates, e.g., ado-trastuzumab emtansine (also known as Kadcyla®, or T-DM1).

In one embodiment, the present invention provides a method of treating cancer by administering to a subject in need thereof antibody conjugate of the present invention in combination with one or more tyrosine kinase inhibitors, including but not limited to, EGFR inhibitors, Her3 inhibitors, IGFR inhibitors, and Met inhibitors.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2, 4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Epidermal growth factor receptor (EGFR) inhibitors include but are not limited to, Erlotinib hydrochloride (Tarceva®), Gefitinib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Capralsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (Gilotrif®); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Other HER2 inhibitors include but are not limited to, Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

HER3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU 11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1Hpyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin 3-yl]thio]-quinoline (SGX523, CAS 1022150-57-7); and (3Z)-5-[[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGFR inhibitors include but are not limited to, BMS-754807, XL-228, OSI-906, GSK0904529A, A-928605, AXL1717, KW-2450, MK0646, AMG479, IMCA12, MEDI-573, and B1836845. See e.g., Yee, JNCI, 104; 975 (2012) for review.

In another embodiment, the present invention provides a method of treating cancer by administering to a subject in need thereof antibody conjugate of the present invention in combination with one or more proliferation signaling pathway inhibitors, including but not limited to, MEK inhibitors, BRAF inhibitors, PI3K/Akt inhibitors, SHP2 inhibitors, and also mTOR inhibitors, and CDK inhibitors.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as C1-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

BRAF inhibitors include, but are not limited to, Vemurafenib (or Zelboraf®), GDC-0879, PLX-4720 (available from Symansis), Dabrafenib (or GSK2118436), LGX 818, CEP-32496, UI-152, RAF 265, Regorafenib (BAY 73-4506), CCT239065, or Sorafenib (or Sorafenib Tosylate, or Nexavar®), or Ipilimumab (or MDX-010, MDX-101, or Yervoy).

Phosphoinositide 3-kinase (PI3K) inhibitors include, but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC0941, RG7321, GNE0941, Pictrelisib, or Pictilisib; and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethylcyclopenta[5,6]naphtho[1,2-c]pyran-2,7,10(1H)-trione (PX866, CAS 502632-66-8); 8-Phenyl-2-(morpholin-4-yl)-chromen-4-one (LY294002, CAS 154447-36-6); (S)—N1-(4-methyl-5-(2-(1,1,1-trifluoro-2-methylpropan-2-yl)pyridin-4-yl)thiazol-2-yl)pyrrolidine-1,2-dicarboxamide (also known as BYL719 or Alpelisib); 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (also known as GDC0032, RG7604, or Taselisib).

mTOR inhibitors include but are not limited to, Temsirolimus (Torisel®); Ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04,9] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N²-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1).

CDK inhibitors include but are not limited to, Palbociclib (also known as PD-0332991, Ibrance®, 6-Acetyl-8-cyclopentyl-5-methyl-2-{[5-(1-piperazinyl)-2-pyridinyl] amino}pyrido[2,3-d]pyrimidin-7(8H)-one).

In yet another embodiment, the present invention provides a method of treating cancer by administering to a subject in need thereof antibody conjugate of the present invention in combination with one or more pro-apoptotics, including but not limited to, IAP inhibitors, BCL2 inhibitors, MCl1 inhibitors, TRAIL agents, CHK inhibitors.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679, all of which are incorporated herein by reference.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl] phenyl]sulfonyl]benzamide (also known as ABT-263 and described in PCT Publication No. WO 09/155386); Tetrocarcin A; Antimycin; Gossypol ((-)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (-)-Gossypol acetic acid (AT-101); 4-[4-[(4'-Chloro[1,1'-biphenyl]-2-yl) methyl]-1-piperazinyl]-N-[[4-[[(1R)-3-(dimethylamino)-1-[(phenylthio)methyl]propyl]amino]-3-nitrophenyl] sulfonyl]-benzamide (ABT-737, CAS 852808-04-9); and Navitoclax (ABT-263, CAS 923564-51-6).

Proapoptotic receptor agonists (PARAS) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinylpyrazolo [1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL (SEQ ID NO: 33)), and CBP501 ((d-Bpa)sws(d-Phe-F5)(d-Cha)rrrqrr).

In a further embodiment, the present invention provides a method of treating cancer by administering to a subject in need thereof antibody conjugate of the present invention in combination with one or more immunomodulators (e.g., one or more of an activator of a costimulatory molecule or an inhibitor of an immune checkpoint molecule).

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFRbeta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')2, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specifity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 and PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specifities to two or more of: TIM-3, LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3 or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule.

Other combinations of immunomodulators with a PD-1 inhibitor (e.g., one or more of PD-L2, CTLA4, TIM3, LAG3, VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

In one embodiment, the PD-1 inhibitor is an anti-PD-1 antibody chosen from Nivolumab, Pembrolizumab or Pidilizumab. In some embodiments, the anti-PD-1 antibody is Nivolumab.

Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and PCT Publication No. WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) *New England Journal of Medicine* 369 (2): 134-44, PCT Publication No. WO2009/114335, and U.S. Pat. No. 8,354,509.

In some embodiments, the anti-PD-1 antibody is Pidilizumab. Pidilizumab (CT-011; Cure Tech) is a humanized IgG1 k monoclonal antibody that binds to PD1. Pidilizumab and other humanized anti-PD-1 monoclonal antibodies are disclosed in PCT Publication No. WO2009/101611. Other anti-PD1 antibodies are disclosed in U.S. Pat. No. 8,609,089, US Publication No. 2010028330, and/or US Publication No. 20120114649. Other anti-PD1 antibodies include AMP 514 (Amplimmune).

In some embodiments, the PD-1 inhibitor is an immunoadhesin (e.g., an immunoadhesin comprising an extracellular or PD-1 binding portion of PD-LI or PD-L2 fused to a constant region (e.g., an Fc region of an immunoglobulin sequence). In some embodiments, the PD-1 inhibitor is AMP-224.

In some embodiments, the PD-LI inhibitor is anti-PD-LI antibody. In some embodiments, the anti-PD-LI inhibitor is chosen from YW243.55.570, MPDL3280A, MEDI-4736, or MDX-1105MSB-0010718C (also referred to as A09-246-2) disclosed in, e.g., WO 2013/0179174, and having a sequence disclosed herein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-LI antibody described in PCT Publication No. WO 2007/005874.

In one embodiment, the PD-L1 inhibitor is YW243.55.570. The YW243.55.570 antibody is an anti-PD-LI described in PCT Publication No. WO 2010/077634.

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in PCT Publication Nos. WO2010/027827 and WO2011/066342).

In one embodiment, the LAG-3 inhibitor is an anti-LAG-3 antibody molecule. In one embodiment, the LAG-3 inhibitor is BMS-986016.

In yet another embodiment, the present invention provides a method of treating cancer by administering to a subject in need thereof antibody conjugate of the present invention in combination with one or more cytokines, including but not limited to, interferon, IL2, IL15, IL7, or IL21.

In yet another embodiment, the present invention provides a method of treating cancer by administering to a subject in need thereof antibody conjugate of the present invention in combination with one or more agonists of STING receptor (Stimulator of Interferon Genes), e.g., the compounds described in WO 2014/189805.

In another embodiment, the present invention provides a method of treating cancer by administering to a subject in need thereof antibody conjugate of the present invention in combination with one or more angiogenesis inhibitors, e.g., Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-t][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TK1258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); or Aflibercept (Eylea®).

In another embodiment, the present invention provides a method of treating cancer by administering to a subject in need thereof antibody conjugate of the present invention in combination with one or more heat shock protein inhibitors, e.g., Tanespimycin (17-allylamino-17-demethoxygeldanamycin, also known as KOS-953 and 17-AAG, available from SIGMA, and described in U.S. Pat. No. 4,261,989); Retaspimycin (IPI504), Ganetespib (STA-9090); [6-Chloro-9-(4-methoxy-3,5-dimethylpyridin-2-ylmethyl)-9H-purin-2-yl]amine (BIIB021 or CNF2024, CAS 848695-25-0); trans-4-[[2-(Aminocarbonyl)-5-[4,5,6,7-tetrahydro-6,6-dimethyl-4-oxo-3-(trifluoromethyl)-1H-indazol-1-yl]phenyl]amino]cyclohexyl glycine ester (SNX5422 or PF04929113, CAS 908115-27-5); 5-[2,4-Dihydroxy-5-(1-methylethyl)phenyl]-N-ethyl-4-[4-(4-morpholinylmethyl)phenyl]-3-Isoxazolecarboxamide (AUY922, CAS 747412-49-3); or 17-Dimethylaminoethylamino-17-demethoxygeldanamycin (17-DMAG).

In another embodiment, the present invention provides a method of treating cancer by administering to a subject in need thereof antibody conjugate of the present invention in combination with one or more HDAC inhibitors or other epigenetic modifiers. Exemplary HDAC inhibitors include, but not limited to, Voninostat (Zolinza®); Romidepsin (Istodax®); Treichostatin A (TSA); Oxamflatin; Vorinostat (Zolinza®, Suberoylanilide hydroxamic acid); Pyroxamide (syberoyl-3-aminopyridineamide hydroxamic acid); Trapoxin A (RF-1023A); Trapoxin B (RF-10238); Cyclo[(αS,2S)-α-amino-η-oxo-2-oxiraneoctanoyl-O-methyl-D-tyrosyl-L-isoleucyl-L-prolyl] (Cyl-1); Cyclo[(αS,2S)-α-amino-η-oxo-2-oxiraneoctanoyl-O-methyl-D-tyrosyl-L-isoleucyl-(2S)-2-piperidinecarbonyl] (Cyl-2); Cyclic[L-alanyl-D-alanyl-(2S)-η-oxo-L-α-aminooxiraneoctanoyl-D-prolyl] (HC-toxin); Cyclo[(αS,2S)-α-amino-η-oxo-2-oxiraneoctanoyl-D-phenylalanyl-L-leucyl-(2S)-2-piperidinecarbonyl] (WF-3161); Chlamydocin ((S)-Cyclic(2-methylalanyl-L-phenylalanyl-D-prolyl-η-oxo-L-α-aminooxiraneoctanoyl); Apicidin (Cyclo(8-oxo-L-2-aminodecanoyl-1-methoxy-L-tryptophyl-L-isoleucyl-D-2-piperidinecarbonyl); Romidepsin (Istodax®, FR-901228); 4-Phenylbutyrate; Spiruchostatin A; Mylproin (Valproic acid); Entinostat (MS-275, N-(2-Aminophenyl)-4-[N-(pyridine-3-yl-methoxycarbonyl)-amino-methyl]-benzamide); Depudecin (4,5:8,9-dianhydro-1,2,6,7,11-pentadeoxy-D-threo-D-ido-Undeca-1,6-dienitol); 4-(Acetylamino)-N-(2-aminophenyl)-benzamide (also known as CI-994); N1-(2-Aminophenyl)-N8-phenyl-octanediamide (also known as BML-210); 4-(Dimethylamino)-N-(7-(hydroxyamino)-7-oxoheptyl)benzamide (also known as M344); (E)-3-(4-(((2-(1H-indol-3-yl)ethyl)(2-hydroxyethyl)amino)-methyl)phenyl)-N-hydroxyacrylamide; Panobinostat (Farydak®); Mocetinostat, and Belinostat (also known as PXD101, Beleodaq®, or (2E)-N-Hydroxy-3-[3-(phenylsulfamoyl)phenyl]prop-2-enamide), or chidamide (also known as CS055 or HBI-8000, (E)-N-(2-amino-5-fluorophenyl)-4-((3-(pyridin-3-yl)acrylamido)methyl) benzamide). Other epigenetic modifiers include but not limited to inhibitors of EZH2 (enhancer of zeste homolog 2), EED (embryonic ectoderm development), or LSD1 (lysine-specific histone demethylase 1A or KDM1A).

In yet another embodiment, the present invention provides a method of treating cancer by administering to a subject in need thereof antibody conjugate of the present invention in combination with one or more inhibitors of indoleamine-pyrrole 2,3-dioxygenase (IDO), for example, Indoximod (also known as NLG-8189), α-Cyclohexyl-5H-imidazo[5,1-a]isoindole-5-ethanol (also known as NLG919), or (4E)-4-[(3-Chloro-4-fluoroanilino)-nitrosomethylidene]-1,2,5-oxadiazol-3-amine (also known as INCB024360).

In some embodiments, the present invention provides a method of treating cancer by administering to a subject in need thereof antibody conjugate of the present invention in combination with two or more of any of the above described inhibitors, activators, immunomodulators, agonists, or modifiers. For example, the antibody conjugate of the present invention can be used in combination with one or more checkpoint inhibitors and/or one or more immune activators.

In addition to the above therapeutic regimes, the patient may be subjected to surgical removal of cancer cells and/or radiation therapy.

Pharmaceutical Compositions

To prepare pharmaceutical or sterile compositions including one or more antibody conjugates described herein, provided antibody conjugate can be mixed with a pharmaceutically acceptable carrier or excipient.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In some embodiments, the pharmaceutical composition comprising the antibody conjugate of the present invention is a lyophilisate preparation. In certain embodiments a pharmaceutical composition comprising the antibody conjugate is a lyophilisate in a vial containing an antibody conjugate, histidine, sucrose, and polysorbate 20. In certain embodiments the pharmaceutical composition comprising the antibody conjugate is a lyophilisate in a vial containing an antibody conjugate, sodium succinate, and polysorbate 20. In certain embodiments the pharmaceutical composition comprising the antibody conjugate is a lyophilisate in a vial containing an antibody conjugate, trehalose, citrate, and polysorbate 8. The lyophilisate can be reconstituted, e.g., with water, saline, for injection. In a specific embodiment, the solution comprises the antibody conjugate, histidine, sucrose, and polysorbate 20 at a pH of about 5.0. In another specific embodiment the solution comprises the antibody conjugate, sodium succinate, and polysorbate 20. In another specific embodiment, the solution comprises the antibody conjugate, trehalose dehydrate, citrate dehydrate, citric acid, and polysorbate 8 at a pH of about 6.6. For intravenous administration, the obtained solution will usually be further diluted into a carrier solution.

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising the antibody conjugate of the invention can be provided by continuous infusion, or by doses at intervals of, e.g., one day, one week, or 1-7 times per week, once every other week, once every three weeks, once every four weeks, once every five weeks, once every six weeks, once every seven weeks, or once very eight weeks. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the antibody conjugates of the invention, the dosage administered to a patient may be 0.0001 mg/kg to 100 mg/kg of the patient's body weight. The dosage may be between 0.001 mg/kg and 50 mg/kg, 0.005 mg/kg and 20 mg/kg, 0.01 mg/kg and 20 mg/kg, 0.02 mg/kg and 10 mg/kg, 0.05 and 5 mg/kg, 0.1 mg/kg and 10 mg/kg, 0.1 mg/kg and 8 mg/kg, 0.1 mg/kg and 5 mg/kg, 0.1 mg/kg and 2 mg/kg, 0.1 mg/kg and 1 mg/kg of the patient's body weight. The dosage of the antibody conjugate may be calculated using the patient's weight in kilograms (kg) multiplied by the dose to be administered in mg/kg.

Doses of the antibody conjugates the invention may be repeated and the administrations may be separated by less than 1 day, at least 1 day, 2 days, 3 days, 5 days, 10 days, 15 days, 30 days, 45 days, 2 months, 75 days, 3 months, 4 months, 5 months, or at least 6 months. In some embodiments, an antibody conjugate of the invention is administered twice weekly, once weekly, once every two weeks, once every three weeks, once every four weeks, or less frequently. In a specific embodiment, doses of the antibody conjugates of the invention are repeated every 2 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by subcutaneous, intravenous, intraperitoneal, intracerebral, intramuscular, intraocular, intraarterial, intracerebrospinal, intralesional administration, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat.

Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

Examples of such additional ingredients are well-known in the art.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the antibody conjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibody conjugates of the invention. The two or more therapies may be administered within one same patient visit.

In certain embodiments, the antibody conjugates of the invention can be formulated to ensure proper distribution in vivo. Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant Protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising antibody conjugates of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibodies or antibody conjugates of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 5 minutes apart, less than 15 minutes apart, less than 30 minutes apart, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered within the same patient visit.

Prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The invention is further described in the following examples, which are not intended to limit the scope of the invention described in the claims.

Example 1

Synthesis of 1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-1H-pyrrole-2,5-dione (C-1)

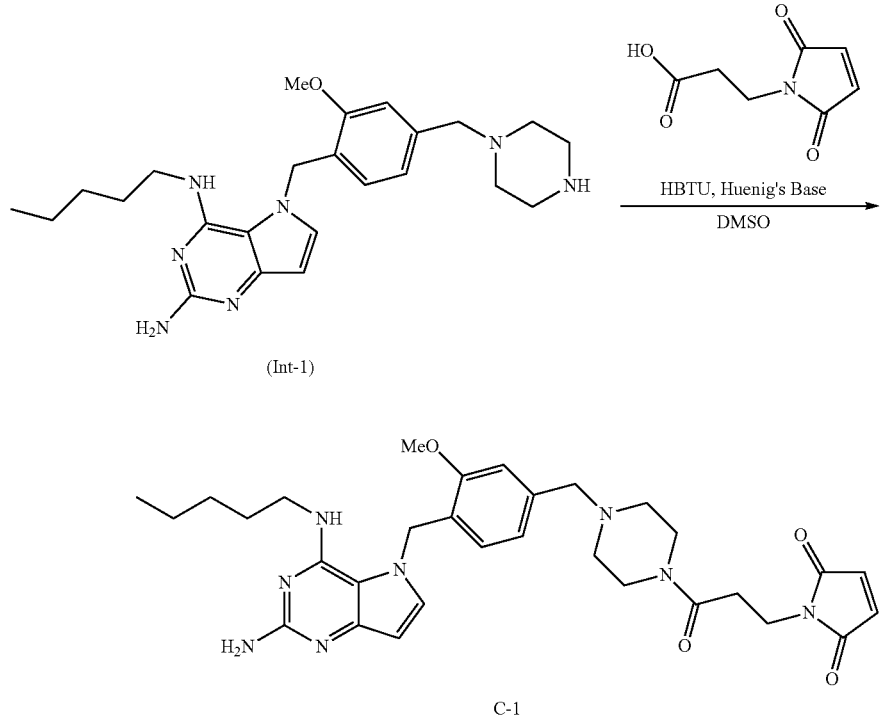

A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), HBTU (1.2 equiv.), Huenig's base (3.0 equiv.), 3-(2,5-dioxo-2,5-dihydro-1H-pyrrol-1-yl)propanoic acid (1.2 equiv.) and DMSO (0.1 M). The reaction mixture was stirred at room temperature for 3 hours and then the crude reaction mixture was purified by RP-HPLC (0.035% TFA in ACN:0.05% TFA in H₂O, C18 column) to afford 1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-1H-pyrrole-2,5-dione (C-1) as a solid as the TFA salt: $^1$H NMR (CDCl$_3$): δ 7.35 (d, 1H), 7.12 (d, 1H), 6.86 (d, 1H), 6.72 (s, 2H), 6.69 (d, 1H), 6.40 (s, 1H), 5.46 (t, 1H), 5.33 (s, 2H), 4.16 (s, 2H), 3.95 (s, 3H), 3.82 (m, 6H), 3.40 (m, 4H), 3.21 (m, 2H), 2.67 (m, 4H), 1.39 (m, 2H), 1.26 (m, 2H), 1.14 (m, 2H), 0.86 (t, 3H). LRMS [M+H]=589.3.

Example 2

Synthesis of (2R)-2-amino-3-((1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-2,5-dioxopyrrolidin-3-yl)thio)propanoic acid (C-2)

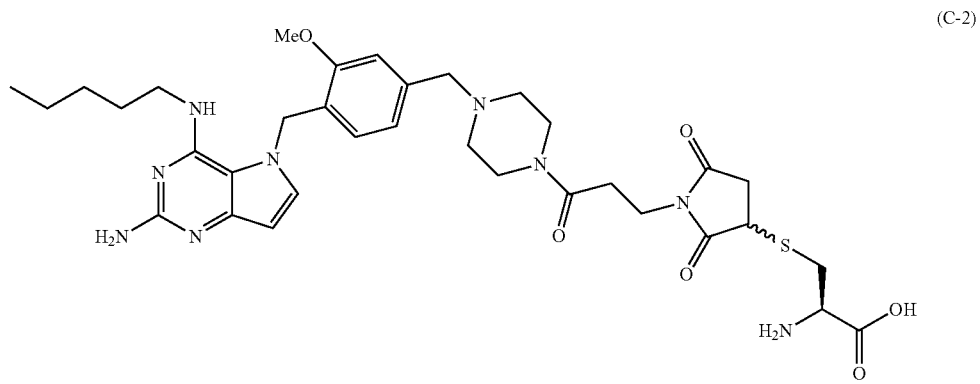 [SMILES: CCCCCNc1nc(N)nc2ccn(Cc3ccc(CN4CCN(C(=O)CCN5C(=O)CC(SC[C@H](N)C(=O)O)C5=O)CC4)cc3OC)c12]

A round bottom flask was charged with 1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-1H-pyrrole-2,5-dione (C-1, 1.0 equiv.) and dissolved in ACN-PBS buffer (1:2, 0.02 M). To this mixture was added L-cysteine (2.0 equiv.) dissolved in DPBS buffer (0.07 M). The reaction mixture was stirred at room temperature for 1 hour. The crude reaction mixture was purified by RP-HPLC (0.035% TFA in ACN:0.05% TFA in H$_2$O, C18 column) to afford (2R)-2-amino-3-((1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-2,5-dioxopyrrolidin-3-yl)thio)propanoic acid (C-2) as a solid as the TFA salt of a mixture of diastereomers: $^1$H NMR (CD$_3$OD): δ 7.36 (d, 1H), 7.28 (d, 1H), 7.05 (d, 1H), 6.81 (d, 1H), 6.24 (d, 1H), 5.57 (s, 2H), 4.26 (m, 2H), 4.02 (m, 1H), 3.95 (s, 3H), 3.78 (m, 6H), 3.55 (m, 2H), 3.44 (m, 1H), 3.23 (m, 3H), 3.12 (m, 2H), 2.76 (m, 2H), 2.53 (m, 1H), 1.53 (m, 2H), 1.30 (m, 2H), 1.19 (m, 2H), 0.88 (t, 3H). LCMS [M+H]=710.3.

Example 3

Synthesis of (6R)-6-(2-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-2-oxoethyl)-5-oxothiomorpholine-3-carboxylic acid (C-3)

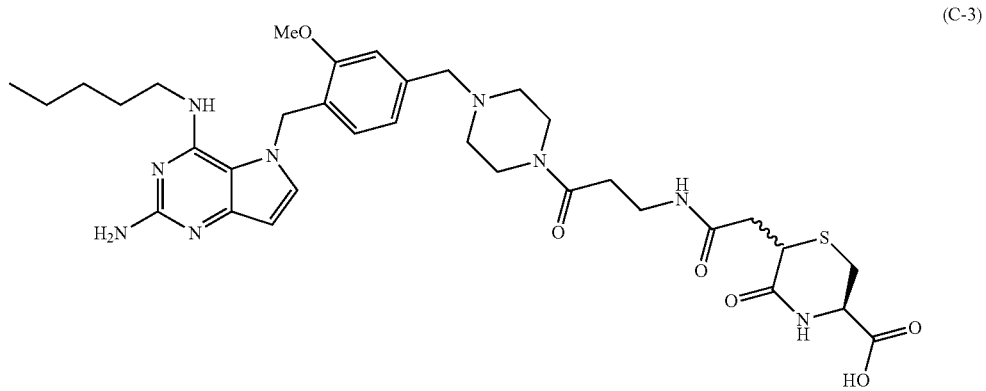

(C-3)

A round bottom flask was charged with (2R)-2-amino-3-((1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-2,5-dioxopyrrolidin-3-yl)thio)propanoic acid (C-1) and dissolved in PBS buffer (pH 7.5, 100 mM phosphate with 5 nM EDTA) and acetonitrile (1:1, 0.012 M). The reaction mixture was then stirred at 40° C. for 6 hours. At this point the crude reaction mixture was allowed to cool to room temperature and purified by RP-HPLC (0.5M NH$_4$OAc in ACN:10 mM NH$_4$OAc in H$_2$O, C18 column) to afford (6R)-6-(2-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-2-oxoethyl)-5-oxothiomorpholine-3-carboxylic acid (C-3) as a solid as a mixture of regio- and diastereomers. $^1$H NMR (CD$_3$OD): δ 7.38 (d, 1H), 7.13 (s, 1H), 6.94 (d, 1H), 6.74 (d, 1H), 6.22 (d, 1H), 5.52 (s, 2H), 4.24 (m, 1H), 3.93 (s, 3H), 3.82 (m, 1H), 3.67 (s, 2H), 3.60 (m, 4H), 3.54 (t, 2H), 3.43 (m, 2H), 3.18 (m, 1H), 3.01 (m, 1H), 2.87 (m, 1H), 2.58 (m 7H), 1.50 (m, 2H), 1.29 (m, 2H), 1.17 (m, 2H), 0.88 (t, 3H). LCMS [M+H]= 710.4.

Example 4

Synthesis of 3-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid (C-4a) and 2-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid (C-4b)

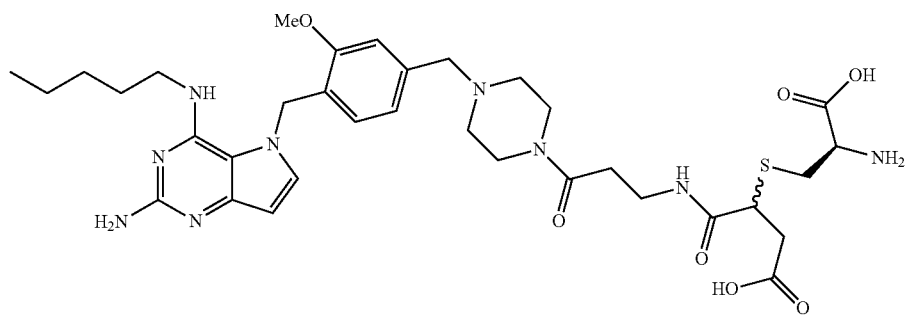

(C-4a)

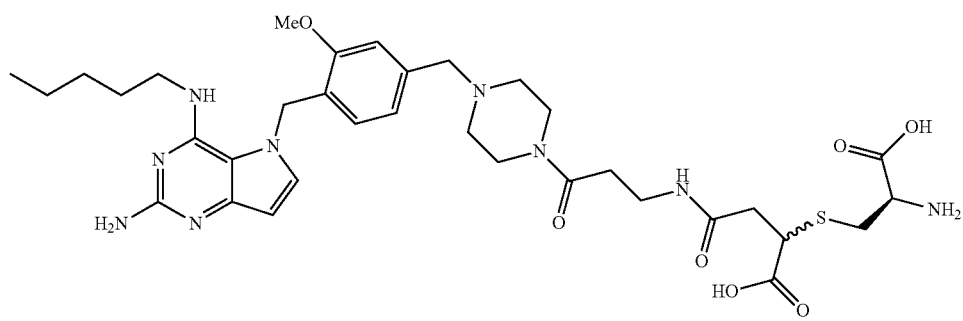

(C-4b)

A round bottom flask was charged with 1-(3-(4-(4-((2-amino-4-(pentylamino)-5H-pyrrolo[3,2-d]pyrimidin-5-yl)methyl)-3-methoxybenzyl)piperazin-1-yl)-3-oxopropyl)-1H-pyrrole-2,5-dione (C-1, 1.0 equiv.), L-cysteine (1.0 equiv.), and PBS:MeCN (2:1, 0.008 M). The reaction mixture was stirred at room temperature for 1 hour and then 1M NaOH (20.0 equiv.) was added to the reaction mixture. The reaction was then stirred an additional 3 hours, then the crude reaction mixture was purified by RP-HPLC (0.5 mM $NH_4OAc$ in MeCN:10 mM $NH_4OAc$ in $H_2O$, C18 column) to afford a mixture of 3-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid (C-4a) and 2-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid (C-4b), as their respective diasteromers (Compounds (C-4aSR), C-4aRR), (C-4bRR) and (C-4bRR) below) as a solid: $^1$H NMR (DMSO): δ 7.88 (s, 1), 7.26 (s, 1H), 6.98 (s, 1H), 6.77 (d, 1H), 6.64 (s, 1H), 6.46 (s, 1H), 6.01 (s, 1H), 5.40 (s, 2H), 3.85 (s, 3H), 3.36 (m, 17H), 2.29 (m, 8H), 1.90 (s, 2H), 1.39 (m, 2H), 1.21 (m, 2H), 1.09 (m, 2H), 0.81 (t, 3H). LRMS [M+H]=728.4.

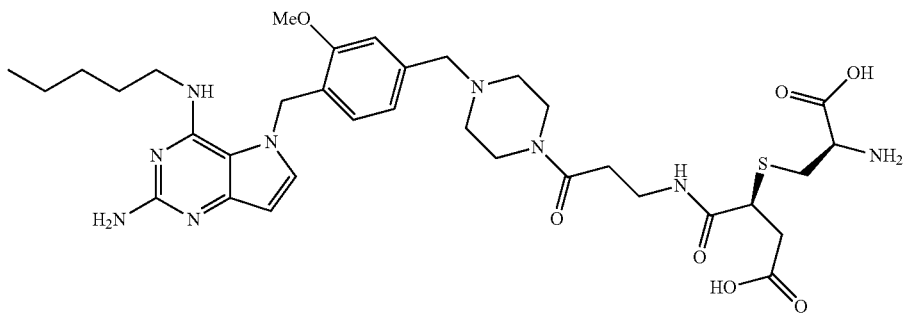
(C-4aSR)
(S)-3-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid
(C-4aSR)
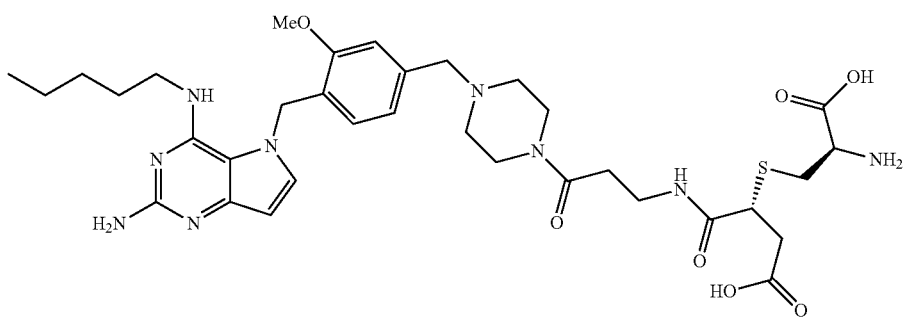
(C-4aRR)
(R)-3-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid
(C-4aRR)
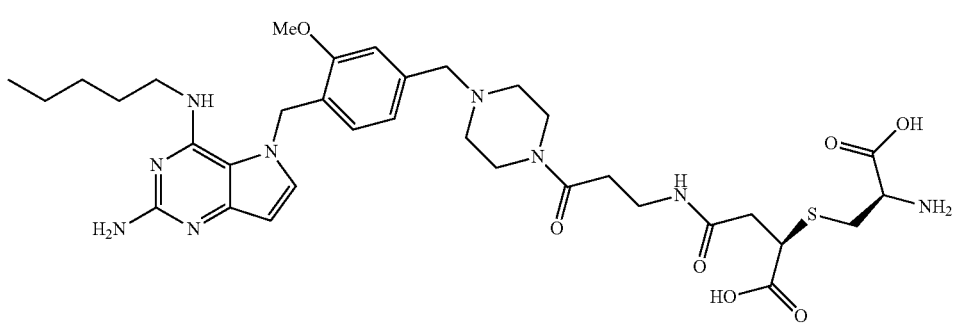
(C-4bRR)

(R)-2-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid
(C-4bRR)

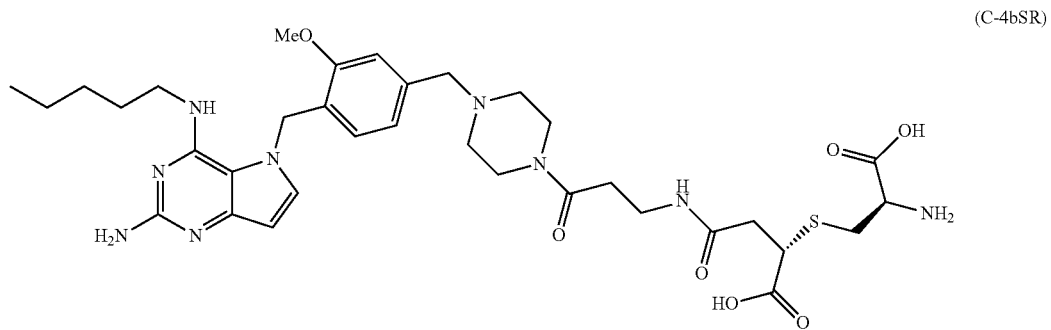 [SMILES: CCCCCNc1nc(N)nc2ccn(Cc3ccc(CN4CCN(C(=O)CCNC(=O)C[C@H](SC[C@H](N)C(=O)O)C(=O)O)CC4)cc3OC)c12]

(C-4bSR)

(S)-2-(((R)-2-amino-2-carboxyethyl)thio)-4-((3-(4-(4-((2-amino-4-(pentylamino)-5H-pyrrolo[3,2-d]pyrimidin-5-yl)methyl)-3-methoxybenzyl)piperazin-1-yl)-3-oxopropyl)amino)-4-oxobutanoic acid
(C-4bSR)

Example 5

Synthesis of 1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-pyrrole-2,5-dione (C-5)

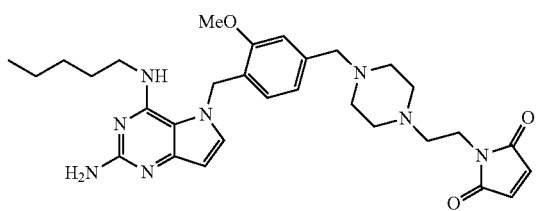

(C-5)

A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), 2-(2,5-dioxo-2,5-dihydro-1H-pyrrol-1-yl)acetaldehyde (4.0 equiv.), sodium cyanoborohydride (13.0 equiv.), and MeOH (0.04 M). The reaction mixture was stirred at room temperature for 1 hour and the crude reaction mixture was then purified by RP-HPLC (0.035% TFA in ACN:0.05% TFA in $H_2O$, C18 column) to afford 1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-pyrrole-2,5-dione (C-5) as a solid as the TFA salt: $^1$H NMR (CDCl$_3$): δ 7.32 (d, 1H), 7.12 (d, 1H), 6.87 (d, 1H), 6.72 (s, 2H), 6.70 (d, 1H), 6.41 (d, 1H), 5.45 (t, 1H), 5.31 (s, 2H), 4.07 (s, 2H), 3.95 (s, 3H), 3.73 (t, 2H), 3.40 (m, 4H), 3.17 (m, 6H), 2.89 (m, 4H), 1.39 (m, 2H), 1.26 (m, 2H), 1.14 (m, 2H), 0.86 (t, 3H). LRMS [M+H]=561.3.

Note: 2-(2,5-dioxo-2,5-dihydro-1H-pyrrol-1-yl)acetaldehyde was prepared by adding 1-(2-hydroxyethyl)-1H-pyrrole-2,5-dione (1.0 equiv.), Dess-Martin periodinane (1.5 equiv.) and DCM (0.1 M) to a round bottom flask and stirring at room temperature for 2 hours. The reaction mixture was then filtered, the volatiles removed in vacuo and the product used without further purification.

Example 6

Synthesis of (2S)-2-amino-3-((1-(2-(4-(4-((2-amino-4-(pentylamino)-5H-pyrrolo[3,2-d]pyrimidin-5-yl)methyl)-3-methoxybenzyl)piperazin-1-yl)ethyl)-2,5-dioxopyrrolidin-3-yl)thio)propanoic acid (C-6)

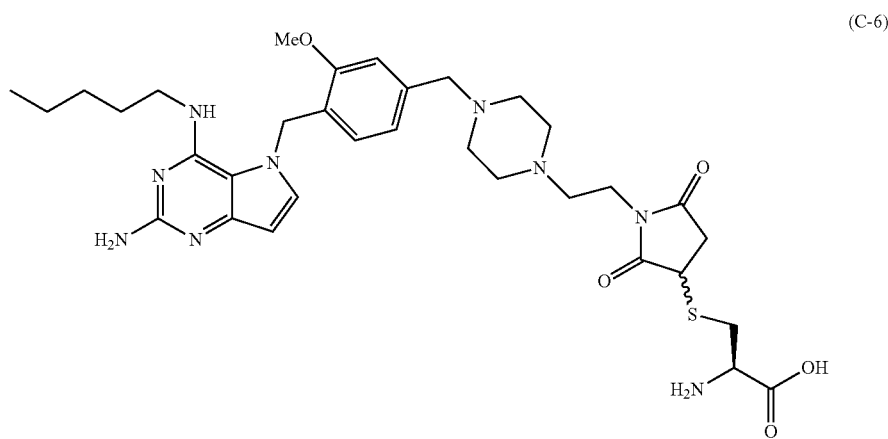 [SMILES: CCCCCNc1nc(N)nc2ccn(Cc3ccc(CN4CCN(CCN5C(=O)CC(SC[C@H](N)C(=O)O)C5=O)CC4)cc3OC)c12]

(C-6)

(2S)-2-amino-3-((1-(2-(4-(4-((2-amino-4-(pentylamino)-5H-pyrrolo[3,2-d]pyrimidin-5-yl)methyl)-3-methoxybenzyl)piperazin-1-yl)ethyl)-2,5-dioxopyrrolidin-3-yl)thio)propanoic acid (C-6) was prepared following a procedure similar to Example 2, except Compound (C-5) was used in place of Compound (C-1), to afford (2S)-2-amino-3-((1-(2-(4-(4-((2-amino-4-(pentylamino)-5H-pyrrolo[3,2-d]pyrimidin-5-yl)methyl)-3-methoxybenzyl)piperazin-1-yl)ethyl)-2,5-dioxopyrrolidin-3-yl)thio)propanoic acid (C-6) as a solid as the TFA salt of a mixture of diastereomers: $^1$H NMR (CD$_3$OD): δ 7.36 (d, 1H), 7.21 (m, 1H), 7.02 (m, 1H), 6.78 (m, 1H), 6.23 (d, 1H), 5.56 (m, 2H), 4.21 (m, 1H), 4.09 (s, 1H), 4.03 (m, 1H), 3.95 (m, 3H), 3.75 (m, 2H), 3.54 (t, 2H), 3.43 (m, 1H), 3.34 (m, 1H), 3.22 (m, 2H), 3.03 (m, 6H), 2.84 (m, 2H), 2.63 (m, 1H), 1.52 (m, 2H), 1.30 (m, 2H), 1.18 (m, 2H), 0.88 (t, 3H). LCMS [M+H]=682.4.

Example 7

Synthesis of (6R)-6-(2-((2-(4-(4-((2-amino-4-(pentylamino)-5H-pyrrolo[3,2-d]pyrimidin-5-yl)methyl)-3-methoxybenzyl)piperazin-1-yl)ethyl)amino)-2-oxoethyl)-5-oxothiomorpholine-3-carboxylic acid (C-7)

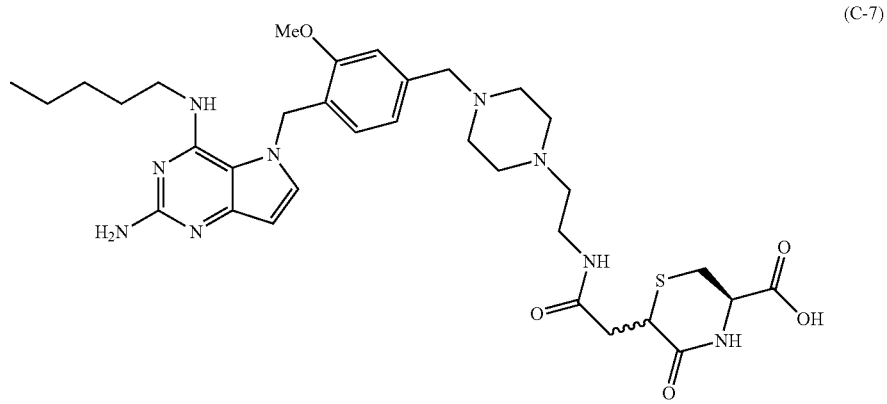

(C-7)

(6R)-6-(2-((2-(4-(4-((2-amino-4-(pentylamino)-5H-pyrrolo[3,2-d]pyrimidin-5-yl)methyl)-3-methoxybenzyl)piperazin-1-yl)ethyl)amino)-2-oxoethyl)-5-oxothiomorpholine-3-carboxylic acid (C-7) was prepared following a procedure similar to Example 3, except Compound (C-5) was used in place of Compound (C-1), to afford (6R)-6-(2-((2-(4-(4-((2-amino-4-(pentylamino)-5H-pyrrolo[3,2-d]pyrimidin-5-yl)methyl)-3-methoxybenzyl)piperazin-1-yl)ethyl)amino)-2-oxoethyl)-5-oxothiomorpholine-3-carboxylic acid (C-7) as a solid as a mixture of regio- and diastereomers: $^1$H NMR (CD$_3$OD): δ 7.37 (d, 1H), 7.10 (s, 1H), 6.91 (d, 1H), 6.72 (d, 1H), 6.22 (d, 1H), 5.51 (s, 2H), 4.13 (m, 1H), 3.92 (s, 3H), 3.88 (m, 1H), 3.58 (s, 2H), 3.52 (t, 2H), 3.40 (m, 2H), 3.16 (m, 1H), 2.99 (m, 1H), 2.86 (m, 1H), 2.67 (m 10H), 1.49 (m, 2H), 1.29 (m, 2H), 1.17 (m, 2H), 0.88 (t, 3H). LCMS [M+H]=682.3.

Example 8

Synthesis of 3-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8a) and 2-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8b)

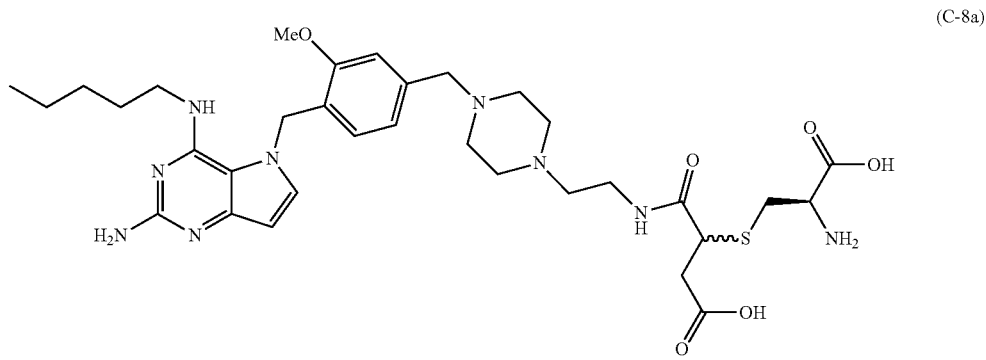 [SMILES: CCCCCNc1nc(N)nc2ccn(Cc3ccc(CN4CCN(CCNC(=O)[C@@H](CC(=O)O)SC[C@H](N)C(=O)O)CC4)cc3OC)c12]

(C-8a)

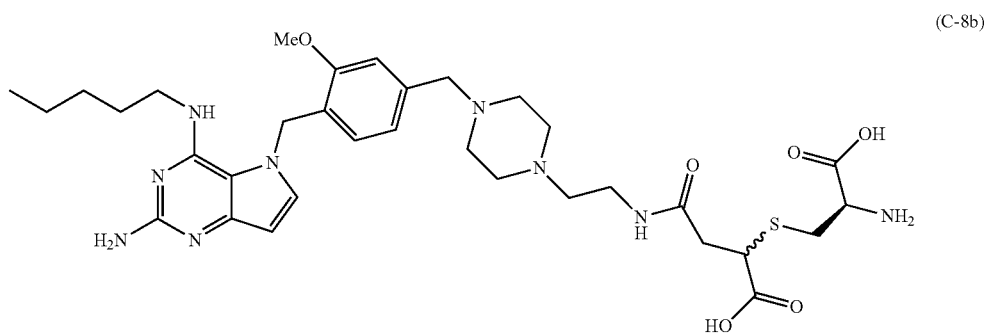

(C-8b)

3-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8a) and 2-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8b) were prepared following a procedure similar to Example 4, except Compound (C-5) was used in place of Compound (C-1), to give a mixture of Compounds (C-8a) and (C-8b), as their respective diasteromers (Compounds (C-8aSR), C-8aRR), (C-8bRR) and (C-8bRR) below), as a solid: $^1$H NMR (DMSO): δ 7.81 (s, 1), 7.33 (s, 1H), 6.96 (s, 1H), 6.76 (d, 1H), 6.69 (s, 1H), 6.48 (s, 1H), 6.10 (s, 1H), 5.45 (s, 2H), 3.82 (s, 3H), 3.37 (m, 17H), 2.35 (m, 8H), 1.90 (s, 2H), 1.41 (m, 2H), 1.20 (m, 2H), 1.08 (m, 2H), 0.80 (t, 3H). LRMS [M+H]=700.4.

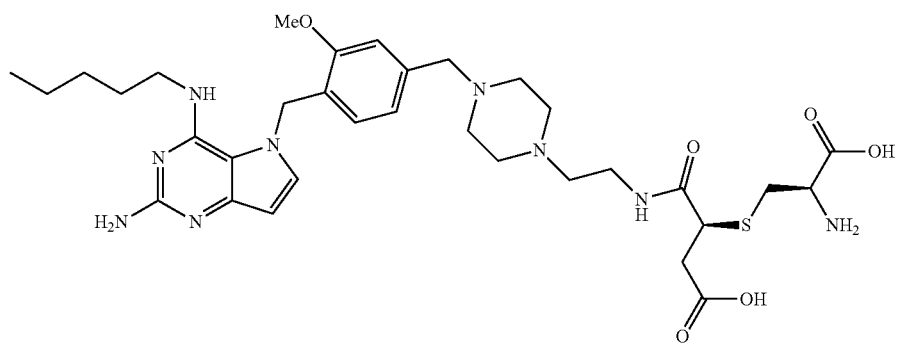
(S)-3-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8aSR)
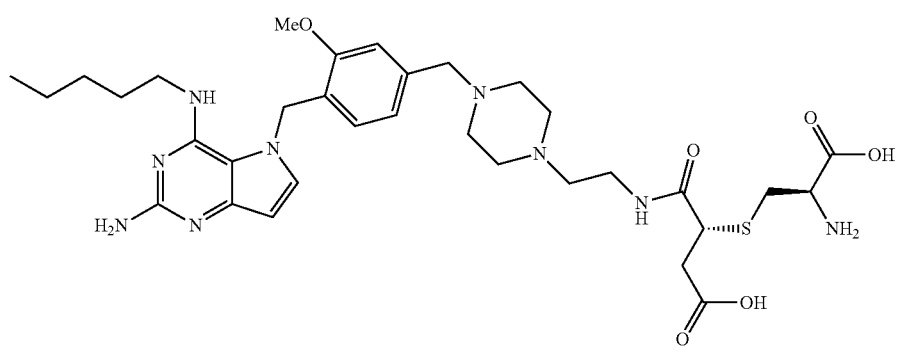
(R)-3-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8aRR)
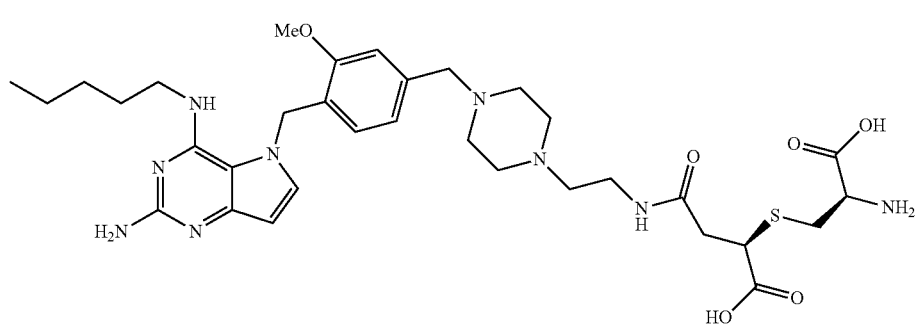

(R)-2-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8bRR)

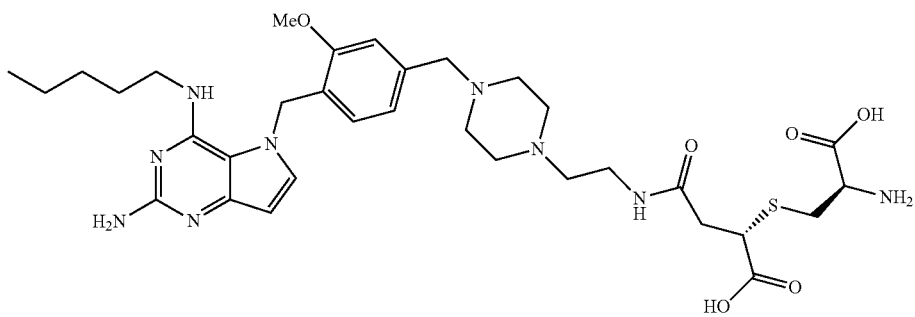

(C-8bSR)

(S)-2-(((R)-2-amino-2-carboxyethyl)thio)-4-((2-(4-(4-((2-amino-4-(pentylamino)-5H-pyrrolo[3,2-d]pyrimidin-5-yl)methyl)-3-methoxybenzyl)piperazin-1-yl)ethyl)amino)-4-oxobutanoic acid (C-8bSR)

Example 9

Synthesis of 1-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-1H-pyrrole-2,5-dione (C-9)

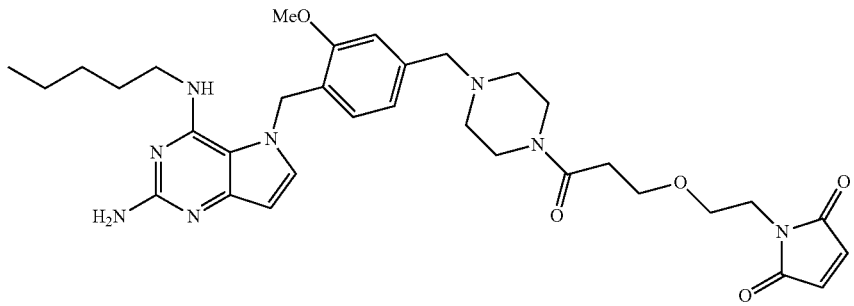

(C-9)

1-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-1H-pyrrole-2,5-dione (C-9) was prepared following a procedure similar to Example 1, except 3-(2-(2,5-dioxo-2,5-dihydro-1H-pyrrol-1-yl)ethoxy)propanoic acid was used in place of 3-(2,5-dioxo-2,5-dihydro-1H-pyrrol-1-yl)propanoic acid, to afford 1-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-1H-pyrrole-2,5-dione (C-9) as a solid as the TFA salt: $^1$H NMR (CD$_3$OD): δ 7.37 (d, 1H), 7.27 (d, 1H), 7.06 (d, 1H), 6.82 (s, 2H), 6.81 (d, 1H), 6.24 (d, 1H), 5.58 (s, 2H), 4.38 (s, 2H), 3.96 (s, 3H), 3.86 (m, 4H), 3.67 (m, 4H), 3.56 (m, 4H), 3.24 (m, 4H), 2.61 (t, 2H), 1.53 (m, 2H), 1.31 (m, 2H), 1.20 (m, 2H), 0.88 (t, 3H). LCMS [M+H]=633.3.

Example 10

Synthesis of 3-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10a) and 2-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10b)

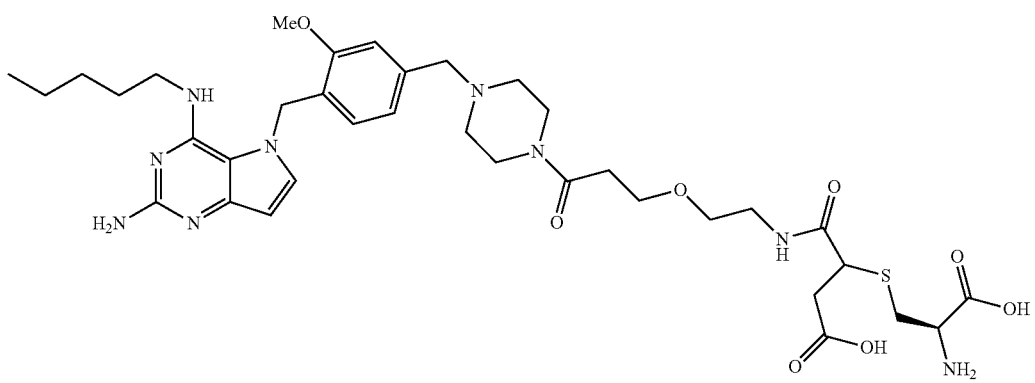

(C-10a)

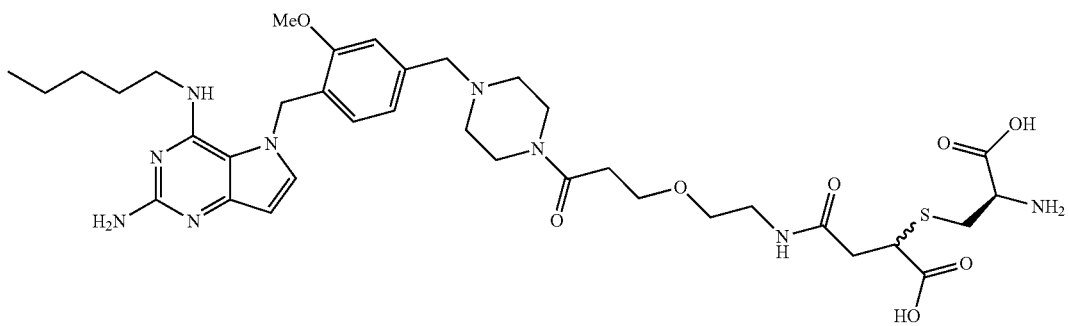

(C-10b)

3-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10a) and 2-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10b) were prepared following a procedure similar to Example 4, except Compound (C-9) was used in place of Compound (C-1), to afford a mixture of Compounds (C-10a) and (C-10b), as their respective diasteromers (Compounds (C-10aSR), C-10aRR), (C-10bRR) and (C-10bRR) below), as a solid as the TFA salt. The crude reaction mixture was purified by RP-HPLC (0.035% TFA in ACN:0.05% TFA in $H_2O$, C18 column): $^1$H NMR ($CD_3OD$): δ 7.35 (d, 1H), 7.29 (d, 1H), 7.05 (d, 1H), 6.77 (m, 1H), 6.23 (s, 1H), 5.56 (s, 2H), 4.32 (m, 2H), 3.94 (s, 3H), 3.86 (m, 3H), 3.72 (m, 3H), 3.54 (m, 10H), 3.21 (m, 4H), 2.67 (m, 4H), 1.52 (m, 2H), 1.30 (m, 2H), 1.19 (m, 2H), 0.88 (t, 3H). LCMS [M+H]=772.4.

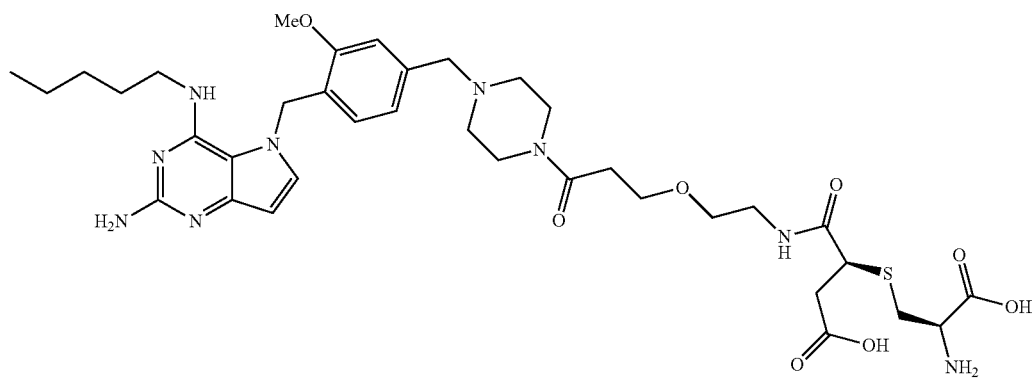
(S)-3-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10aSR)
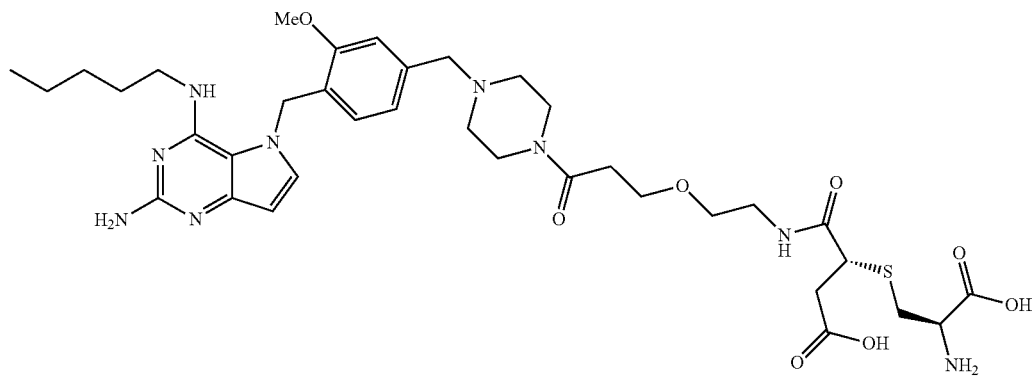
(R)-3-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10aRR)
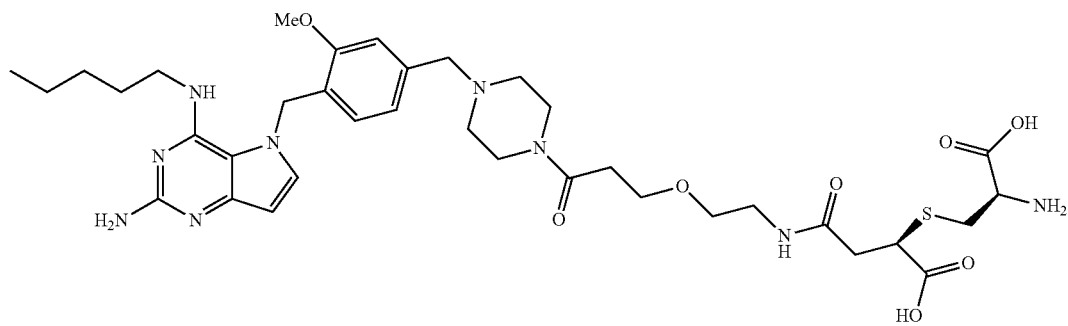

(R)-2-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10bRR)

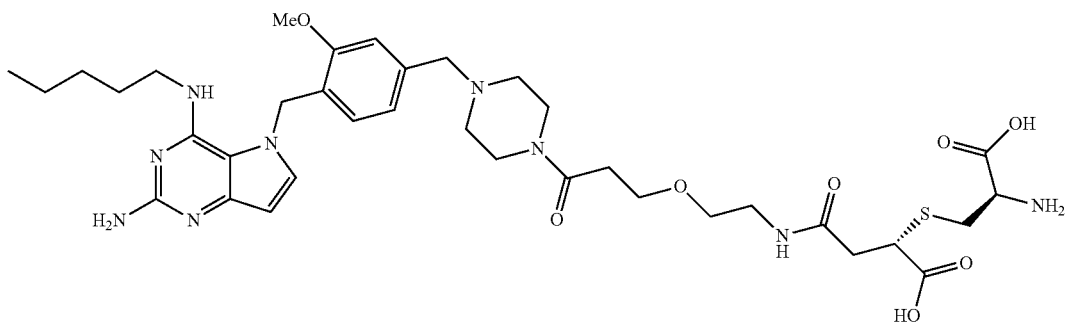

(S)-2-(((R)-2-amino-2-carboxyethyl)thio)-4-((2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)amino)-4-oxobutanoic acid (C-10bSR)

Example 11

Synthesis of 1-(2-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethoxy)ethyl)-1H-pyrrole-2,5-dione (C-11)

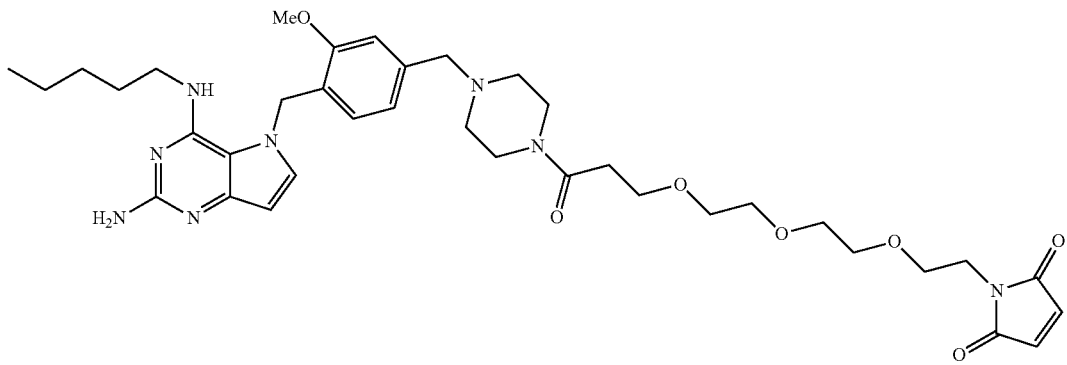

1-(2-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethoxy)ethyl)-1H-pyrrole-2,5-dione (C-11) was prepared following a procedure similar to Example 1, except 3-(2-(2-(2-(2,5-dioxo-2,5-dihydro-1H-pyrrol-1-yl)ethoxy)ethoxy)ethoxy)propanoic acid was used in place of 3-(2,5-dioxo-2,5-dihydro-1H-pyrrol-1-yl)propanoic acid, to afford 1-(2-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethoxy)ethyl)-1H-pyrrole-2,5-dione (C-11) as a solid as the TFA salt: $^1$H NMR (CD$_3$OD): δ 7.37 (d, 1H), 7.26 (d, 1H), 7.05 (d, 1H), 6.82 (d, 1H), 6.80 (s, 2H), 6.24 (d, 1H), 5.58 (s, 2H), 4.32 (s, 2H), 3.96 (s, 3H), 3.74 (t, 2H), 3.64 (m, 2H), 3.58 (m, 12H), 3.64 (m, 4H), 3.20 (m, 4H), 2.68 (m, 2H), 1.53 (m, 2H), 1.32 (m, 2H), 1.20 (m, 2H), 0.88 (t, 3H). LCMS [M+H]=721.4.

Example 12

Synthesis of (2R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,19-dioxo-10,13,16-trioxa-4-thia-7-azanonadecan-1-oic acid (C-12a) and (19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,14-dioxo-4,7,10-trioxa-17-thia-13-azaicosan-20-oic acid (C-12b)

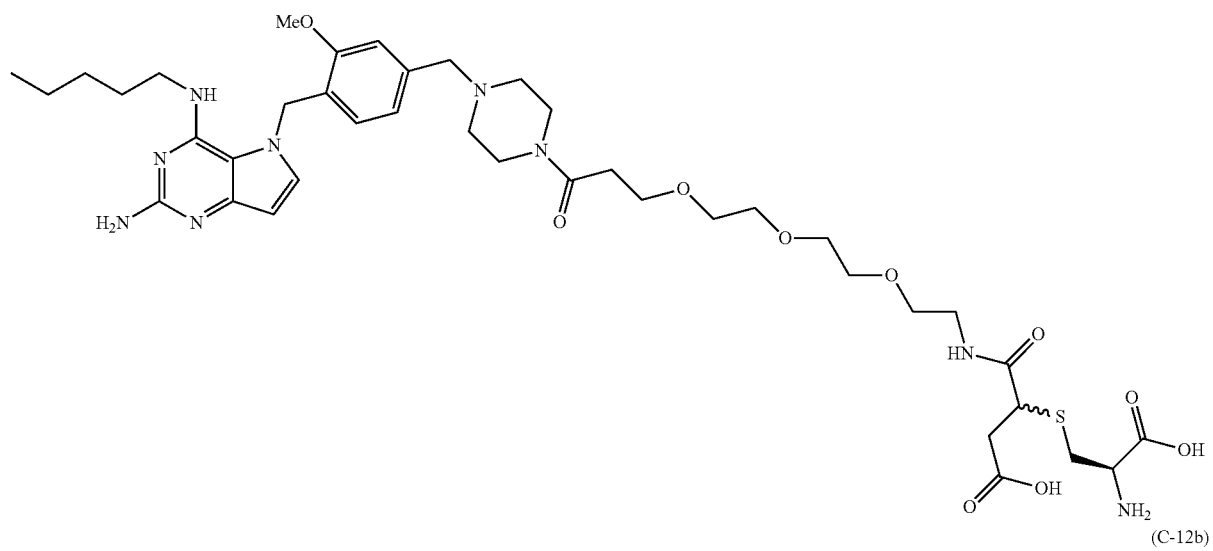

(C-12a)

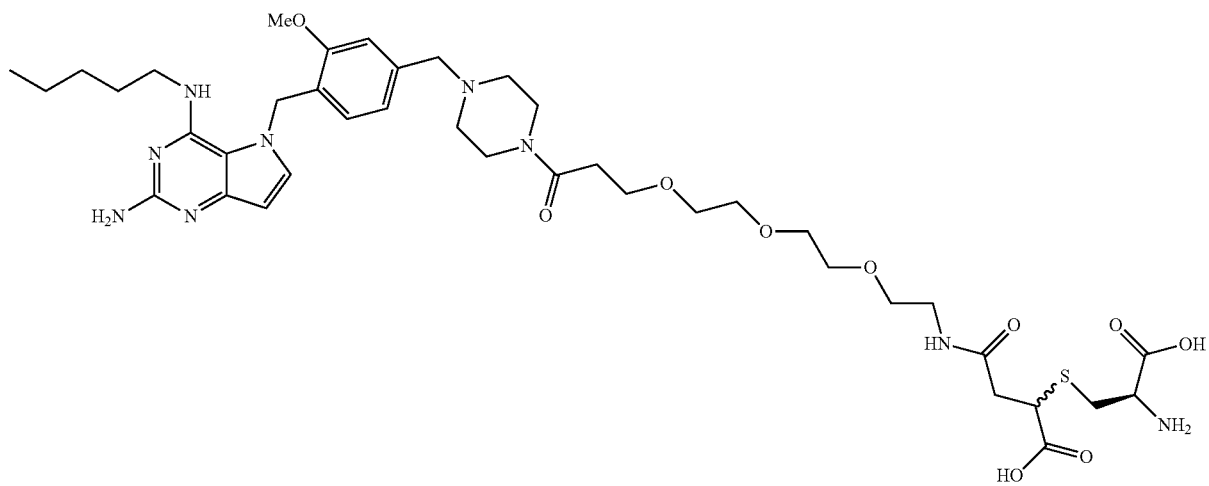

(C-12b)

(2R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,19-dioxo-10,13,16-trioxa-4-thia-7-azanonadecan-1-oic acid (C-12) and (19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,14-dioxo-4,7,10-trioxa-17-thia-13-azaicosan-20-oic acid (C-12b) were prepared following a procedure similar to Example 4, except Compound (C-11) was used in place of Compound (C-1), to afford a mixture of Compounds (C-12a) and (C-12b), as their respective diastereomers (Compounds (C-12aSR), C-12aRR), (C-12bRR) and (C-12bRR) below), as a solid as the TFA salt. The crude reaction mixture was purified by RP-HPLC (0.035% TFA in ACN:0.05% TFA in $H_2O$, C18 column): $^1H$ NMR ($CD_3OD$): δ 7.36 (d, 1H), 7.31 (s, 1H), 7.06 (d, 1H), 6.79 (d, 1H), 6.24 (d, 1H), 5.57 (s, 2H), 4.34 (s, 2H), 4.23 (m, 1H), 3.96 (s, 3H), 3.86 (m, 4H), 3.76 (m, 4H), 3.58 (m, 14H), 3.27 (m, 4H), 3.22 (m, 2H), 2.84 (m, 1H), 2.71 (m, 2H), 1.53 (m, 2H), 1.31 (m, 2H), 1.19 (m, 2H), 0.88 (t, 3H). LCMS [M+H]=860.4.

(C-12aSR)
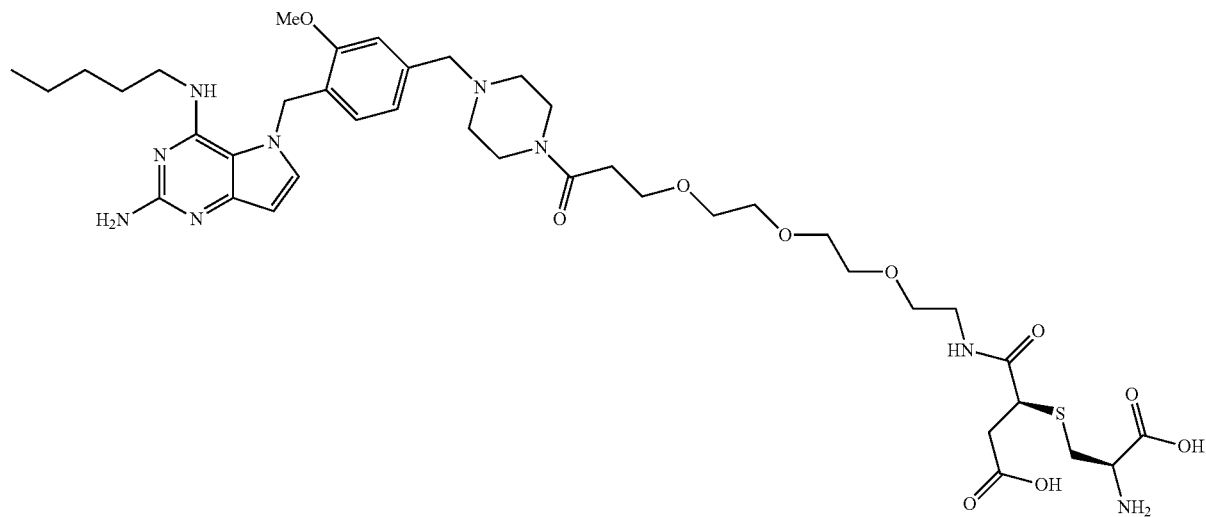
(2R,5S)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,19-dioxo-10,13,16-trioxa-4-thia-7-azanonadecan-1-oic acid (C-12aSR)
(C-12aRR)
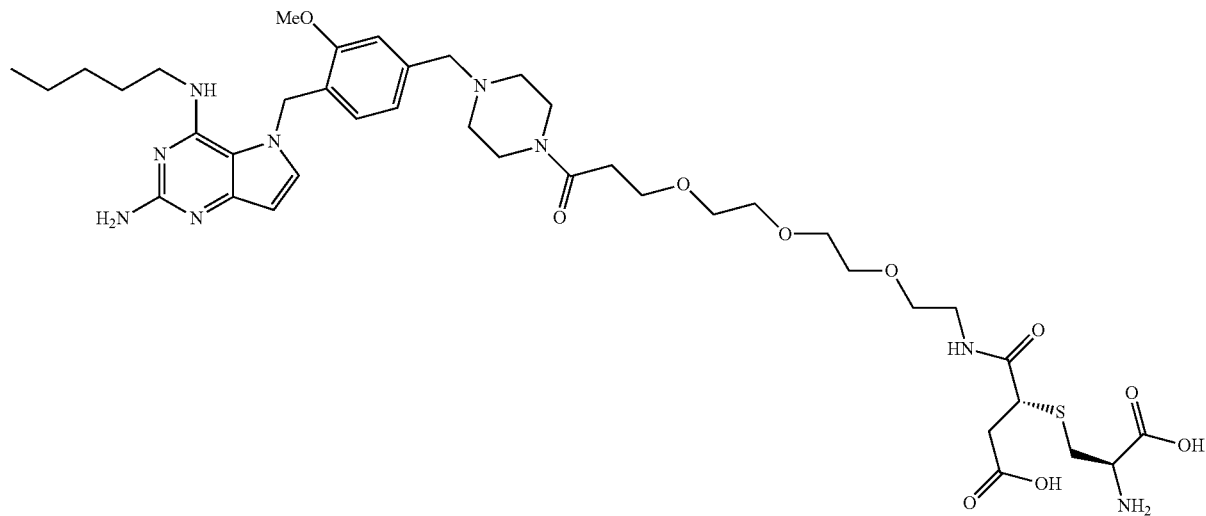

(2R,5R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,19-dioxo-10,13,16-trioxa-4-thia-7-azanonadecan-1-oic acid (C-12aRR)
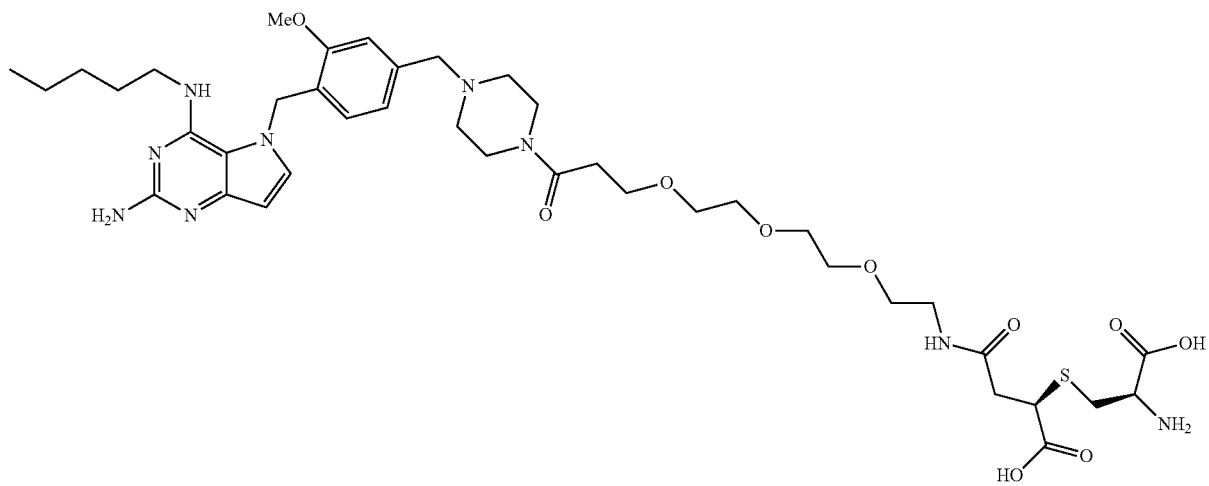
(16R,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,14-dioxo-4,7,10-trioxa-17-thia-13-azaicosan-20-oic acid (C-12bRR)
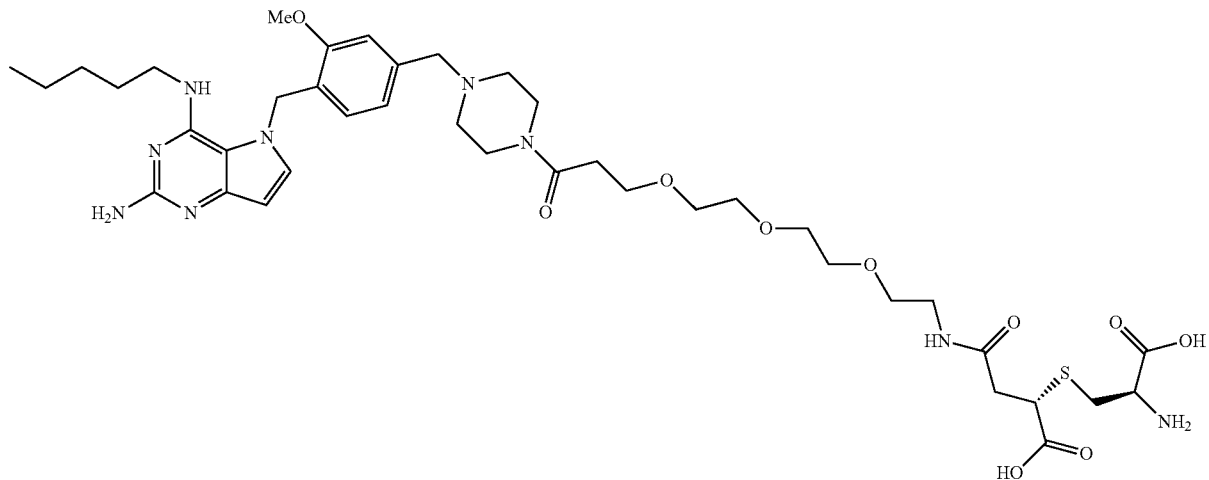

(16S,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,14-dioxo-4,7,10-trioxa-17-thia-13-azaicosan-20-oic acid (C-12bSR)

Example 13

Synthesis of 1-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-1H-pyrrole-2,5-dione (C-13)

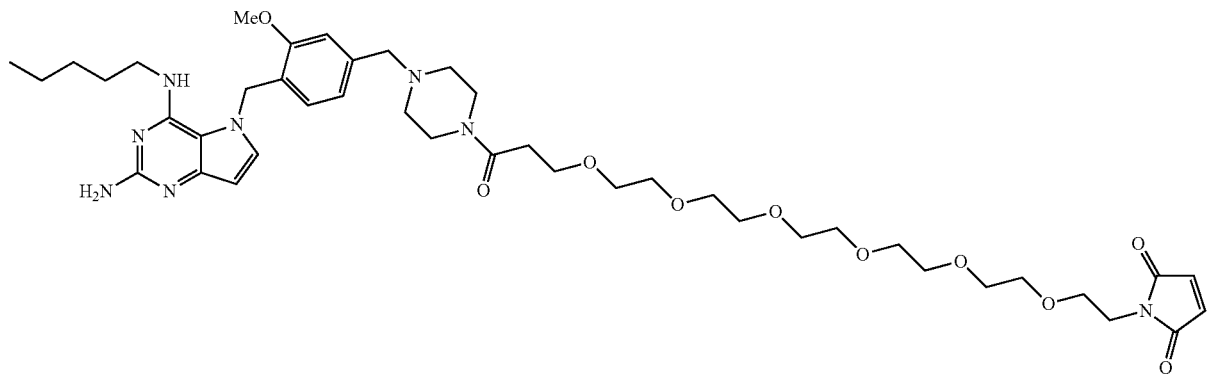

(C-13)

1-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-1H-pyrrole-2,5-dione (C-13) was prepared following a procedure similar to example 1, except 1-(2,5-dioxo-2,5-dihydro-1H-pyrrol-1-yl)-3,6,9,12,15,18-hexaoxahenicosan-21-oic acid was used in place of 3-(2,5-dioxo-2,5-dihydro-1H-pyrrol-1-yl)propanoic acid, to afford 1-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-1H-pyrrole-2,5-dione (C-13) as a solid as the TFA salt: $^1$H NMR (CD$_3$OD): δ 7.38 (d, 1H), 7.27 (d, 1H), 7.07 (d, 1H), 6.84 (d, 1H), 6.82 (s, 2H), 6.25 (d, 1H), 5.59 (s, 2H), 4.36 (s, 2H), 3.97 (s, 3H), 3.65 (m, 32H), 3.20 (m, 4H), 2.71 (m, 2H), 1.55 (m, 2H), 1.32 (m, 2H), 1.21 (m, 2H), 0.89 (t, 3H). LCMS [M+H]=853.5.

Example 14

Synthesis of (2R)-2-amino-28-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,28-dioxo-10,13,16,19,22,25-hexaoxa-4-thia-7-azaoctacosan-1-oic acid (C-14a) and (28R)-28-amino-1-(4-(4-((2-amino-4-(pentylamino)-5H-pyrrolo[3,2-d]pyrimidin-5-yl)methyl)-3-methoxybenzyl)piperazin-1-yl)-25-carboxy-1,23-dioxo-4,7,10,13,16,19-hexaoxa-26-thia-22-azanonacosan-29-oic acid (C-14b)

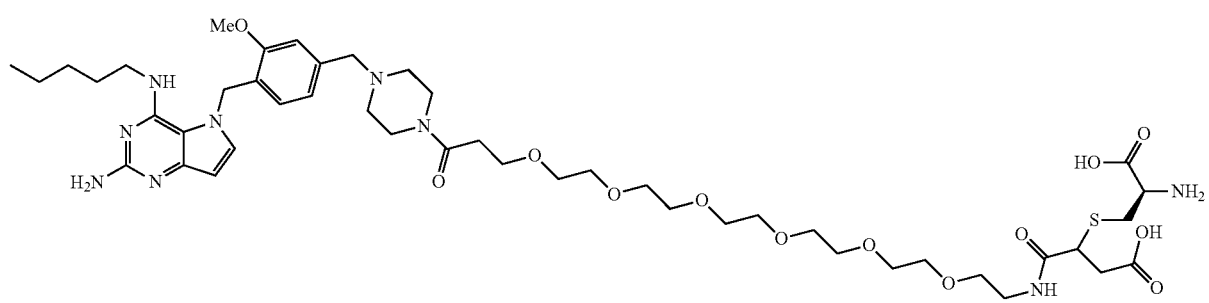

(C-14a)

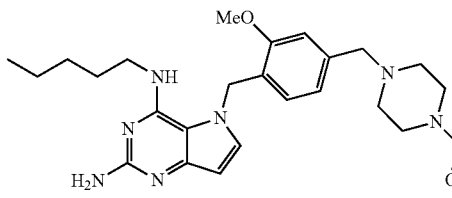
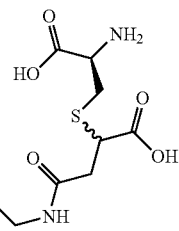

(C-14b)

(2R)-2-amino-28-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,28-dioxo-10,13,16,19,22,25-hexaoxa-4-thia-7-azaoctacosan-1-oic acid (C-14a) and (28R)-28-amino-1-(4-(4-((2-amino-4-(pentylamino)-5H-pyrrolo[3,2-d]pyrimidin-5-yl)methyl)-3-methoxybenzyl)piperazin-1-yl)-25-carboxy-1,23-dioxo-4,7,10,13,16,19-hexaoxa-26-thia-22-azanonacosan-29-oic acid (C-14b) were prepared following a procedure similar to Example 4, except Compound (C-13) was used in place of Compound (C-1), to provide a mixture of Compounds (C-14a) and (C-14b), as their respective diasteromers (Compounds (C-14aSR), C-14aRR), (C-14bRR) and (C-14bRR) below), as a solid as the HCl salt (After RP-HPLC purification the product was dissolved in acetonitrile, treated with excess 2N HCl, and then lyophilized): $^1$H NMR (CD$_3$OD): δ 7.47 (s, 1H), 7.39 (d, 1H), 7.13 (d, 1H), 6.82 (d, 1H), 6.25 (d, 1H), 5.58 (s, 2H), 4.38 (s, 2H), 4.32 (m, 1H), 4.00 (s, 3H), 3.77 (m, 4H), 3.76 (m, 4H), 3.64 (m, 28H), 3.55 (m, 5H), 3.31 (m, 4H), 3.12 (m, 1H), 2.86 (m, 1H), 2.72 (s, 2H), 2.62 (m, 1H), 1.54 (m, 2H), 1.31 (m, 2H), 1.20 (m, 2H), 0.89 (t, 3H). LCMS [M+H]=992.4.

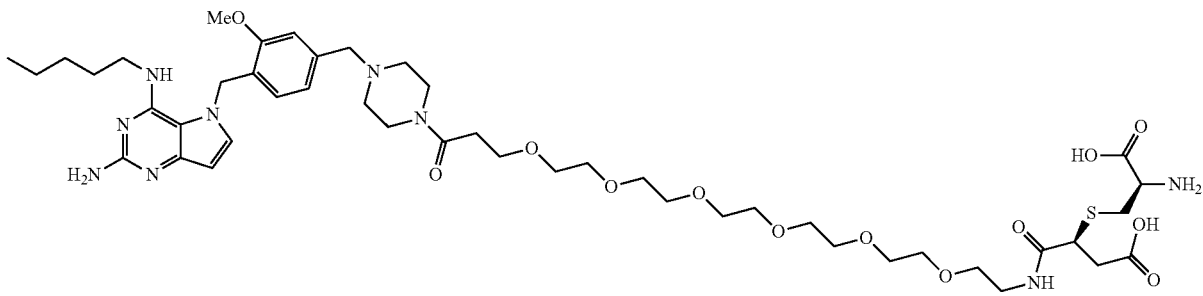

(C-14aSR)

(2R,5S)-2-amino-28-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,28-dioxo-10,13,16,19,22,25-hexaoxa-4-thia-7-azaoctacosan-1-oic acid (C-14aSR)

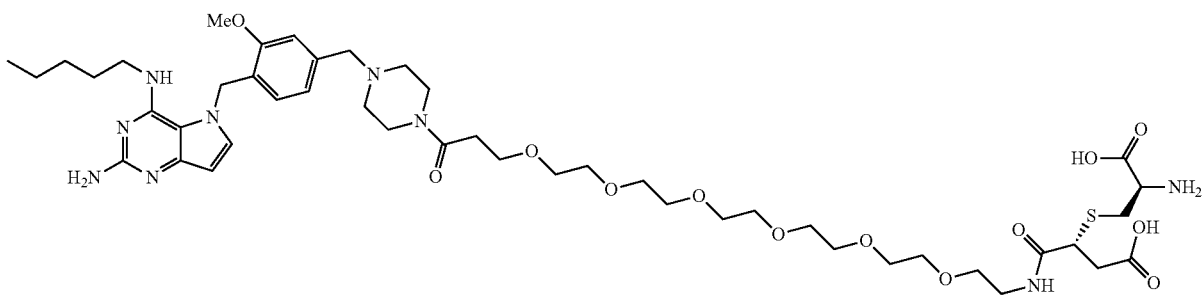

(C-14aRR)

(2R,5R)-2-amino-28-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,28-dioxo-10,13,16,19,22,25-hexaoxa-4-thia-7-azaoctacosan-1-oic acid (C-14aRR)

(C-14bRR)
(25R,28R)-28-amino-1-(4-(4-((2-amino-4-(pentylamino)-5H-pyrrolo[3,2-d]pyrimidin-5-yl)methyl)-3-methoxybenzyl)piperazin-1-yl)-25-carboxy-1,23-dioxo-4,7,10,13,16,19-hexaoxa-26-thia-22-azanonacosan-29-oic acid (C-14bRR)
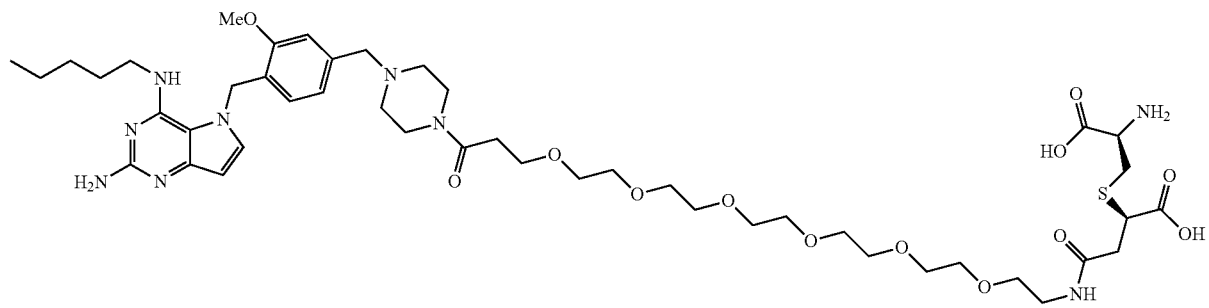
(C-14bSR)

(25S,28R)-28-amino-1-(4-(4-((2-amino-4-(pentylamino)-5H-pyrrolo[3,2-d]pyrimidin-5-yl)methyl)-3-methoxybenzyl)piperazin-1-yl)-25-carboxy-1,23-dioxo-4,7,10,13,16,19-hexaoxa-26-thia-22-azanonacosan-29-oic acid (C-14bSR)

Example 15

Synthesis of 1-((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)-1H-pyrrole-2,5-dione (C-15)

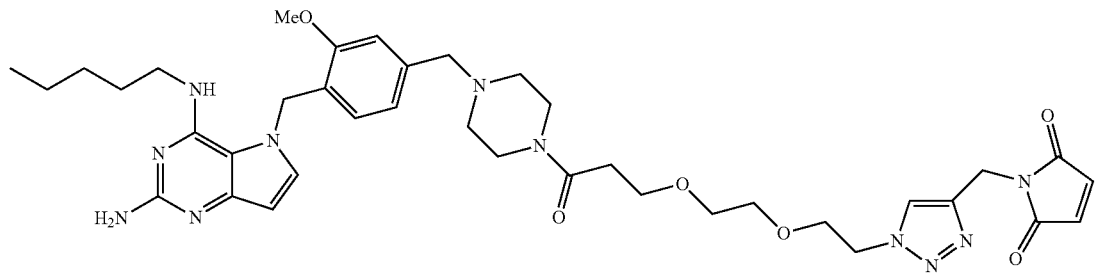

(C-15)

Step 1: 1-(4-(4-((2-amino-4-(pentylamino)-5H-pyrrolo[3,2-d]pyrimidin-5-yl)methyl)-3-methoxybenzyl)piperazin-1-yl)-3-(2-(2-azidoethoxy)ethoxy)propan-1-one was prepared following the procedure similar to Example 1, except 3-(2-(2-azidoethoxy)ethoxy)propanoic acid was used in place of 3-(2,5-dioxo-2,5-dihydro-1H-pyrrol-1-yl)propanoic acid.

Step 2: A round bottom flask was charged with 1-(4-(4-((2-amino-4-(pentylamino)-5H-pyrrolo[3,2-d]pyrimidin-5-yl)methyl)-3-methoxybenzyl)piperazin-1-yl)-3-(2-(2-azidoethoxy)ethoxy)propan-1-one (1.0 equiv.), CuSO$_4$ (0.25 equiv.), L-Ascorbic acid sodium salt (1.1 equiv.), 1-(prop-2-yn-1-yl)-1H-pyrrole-2,5-dione (2.2 equiv.), and a mixture of t-BuOH/water (1:1, v/v, 0.012 M). The reaction mixture was placed under vacuum and subsequently flushed with N$_2$ (this was repeated four more times). The reaction mixture was then stirred at room temperature for 2 hours and the crude reaction mixture was then purified by RP-HPLC (0.035% TFA in ACN:0.05% TFA in H$_2$O, C18 column) to afford 1-((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)-1H-pyrrole-2,5-dione (C-15) as a solid as the TFA salt: $^1$H NMR (CD$_3$OD): δ 7.94 (s, 1H), 7.37 (d, 1H), 7.29 (s, 1H), 7.05 (d, 1H), 6.85 (s, 2H), 6.81 (d, 1H), 6.24 (d, 1H), 5.57 (s, 2H), 4.73 (s, 2H), 4.52 (t, 2H), 4.36 (s, 2H), 3.95 (s, 3H), 3.85 (t, 2H), 3.84 (m, 4H), 3.66 (t, 2H), 3.54 (m, 6H), 3.27 (m, 4H), 2.63 (t, 2H), 1.53 (m, 2H), 1.30 (m, 2H), 1.19 (m, 2H), 0.88 (t, 3H). LCMS [M+H]=758.4.

Example 16

Synthesis of 3-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16a) and 2-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16b)

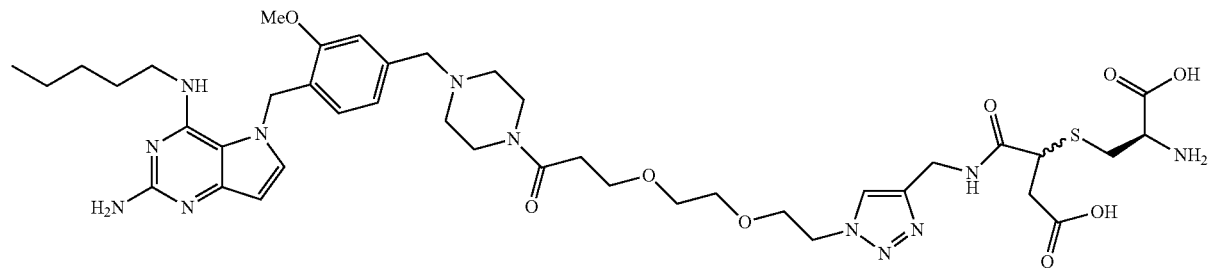

(C-16a)

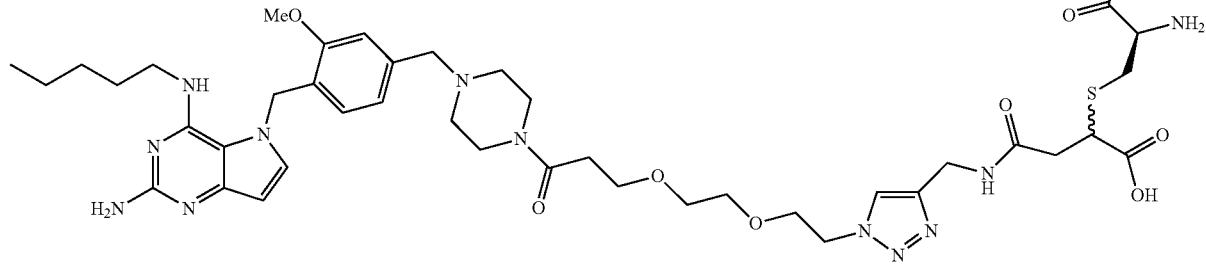

(C-16b)

3-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16a) and 2-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16b) were prepared following a procedure similar to Example 4, except Compound (C-15) was used in place of Compound (C-1), to afford a mixture of Compounds (C-16a) and (C-16b), as their respective diasteromers (Compounds (C-16aSR), C-16aRR), (C-16bRR) and (C-16bRR) below), as a solid as the TFA salt. The crude reaction mixture was purified by RP-HPLC (0.035% TFA in ACN:0.05% TFA in H$_2$O, C18 column): $^1$H NMR (CD$_3$OD): δ 7.91 (s, 1H), 7.36 (d, 1H), 7.30 (s, 1H), 7.06 (d, 1H), 6.80 (d, 1H), 6.24 (d, 1H), 5.57 (s, 2H), 4.54 (s, 2H), 4.44 (m, 2H), 4.34 (s, 2H), 4.25 (m, 1H), 3.95 (s, 3H), 4.83 (m, 6H), 3.68 (t, 2H), 3.55 (m, 6H), 3.25 (m, 2H), 2.86 (m, 1H), 2.64 (m, 2H), 1.53 (m, 2H), 1.30 (m, 2H), 1.19 (m, 2H), 0.88 (t, 3H). LCMS [M+H]= 897.4

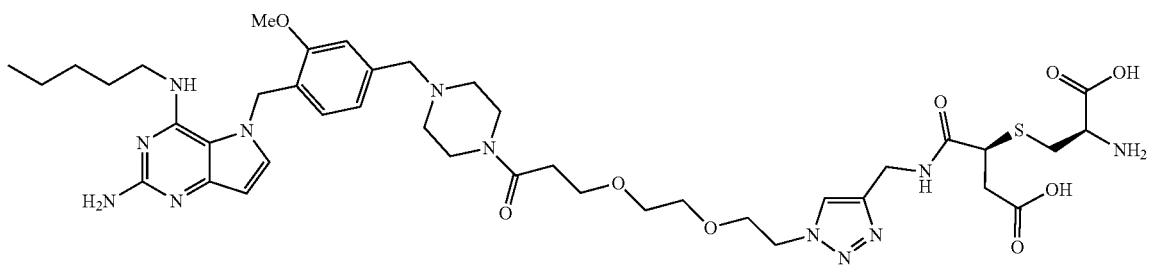

(C-16aSR)

(S)-3-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16aSR)

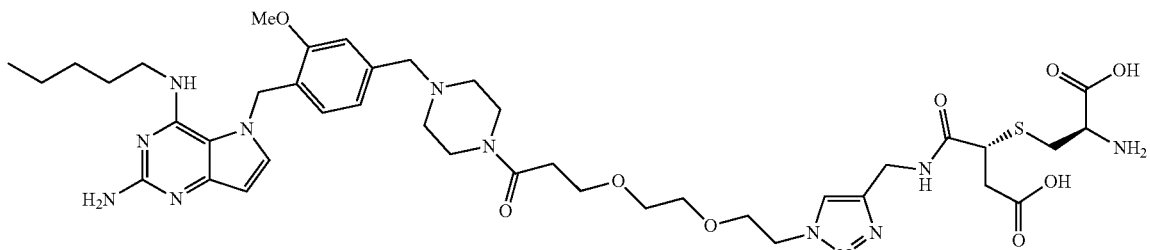

(C-16aRR)

(R)-3-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16aRR)

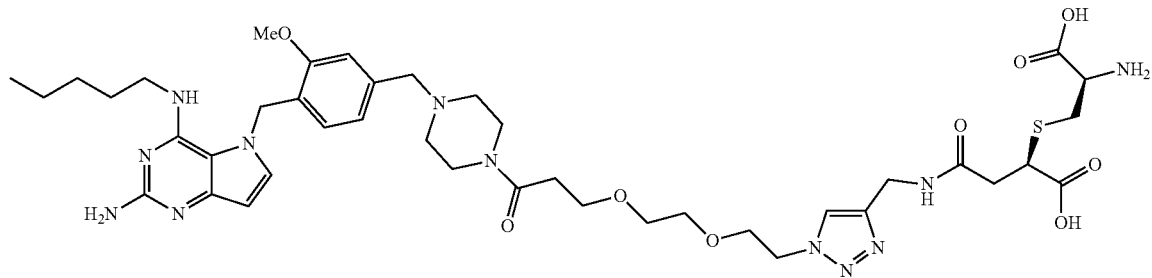

(C-16bRR)

(R)-2-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16bRR)

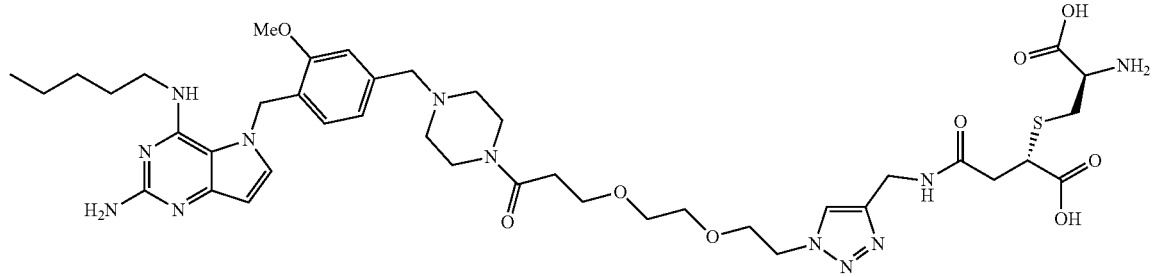

(C-16bSR)

(S)-2-(((R)-2-amino-2-carboxyethyl)thio)-4-(((1-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-1H-1,2,3-triazol-4-yl)methyl)amino)-4-oxobutanoic acid (C-16bSR)

Example 17

Synthesis of N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-3-(2,5-dioxo-2,5-dihydro-1H-pyrrol-1-yl)propanamide (C-17)

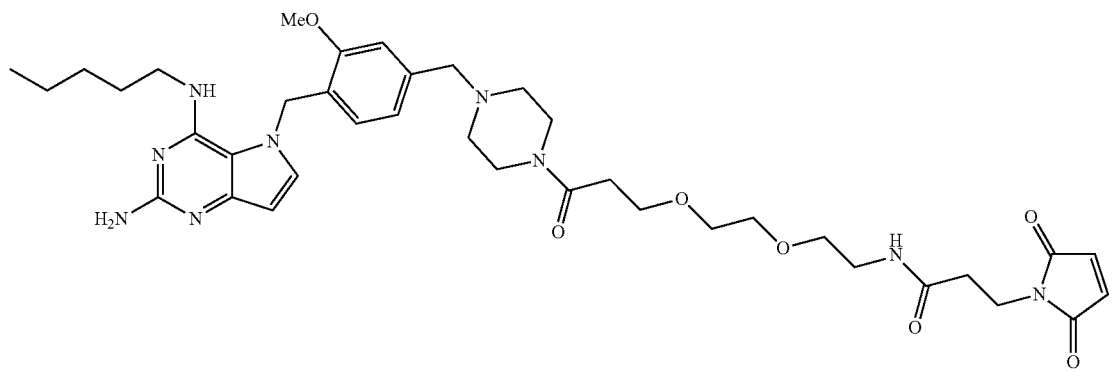

(C-17)

N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-3-(2,5-dioxo-2,5-dihydro-1H-pyrrol-1-yl)propanamide (C-17) was prepared following a procedure similar to Example 1, except 3-(2-(2-(3-(2,5-dioxo-2,5-dihydro-1H-pyrrol-1-yl)propanamido)ethoxy)ethoxy)propanoic acid was used in place of 3-(2,5-dioxo-2,5-dihydro-1H-pyrrol-1-yl)propanoic acid, to afford N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-3-(2,5-dioxo-2,5-dihydro-1H-pyrrol-1-yl)propanamide (C-17) as a solid as the TFA salt: $^1$H NMR (CD$_3$OD): δ 7.37 (d, 1H), 7.28 (d, 1H), 7.06 (d, 1H), 6.82 (d, 1H), 6.80 (s, 2H), 6.24 (d, 1H), 5.58 (s, 2H), 4.37 (s, 2H), 3.96 (s, 3H), 3.84 (m, 4H), 3.40 (m, 4H), 3.56 (m, 6H), 3.48 (t, 2H), 3.20 (m, 6H), 2.69 (t, 2H), 2.45 (t, 2H), 1.53 (m, 2H), 1.31 (m, 2H), 1.19 (m, 2H), 0.88 (t, 3H). LCMS [M+H]=748.4.

Example 18

Synthesis of (19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-(carboxymethyl)-1,11,15-trioxo-4,7-dioxa-17-thia-10,14-diazaicosan-20-oic acid (C-18a) and (20R)-20-amino-1-(4-(4-((2-amino-4-(pentylamino)-5H-pyrrolo[3,2-d]pyrimidin-5-yl)methyl)-3-methoxybenzyl)piperazin-1-yl)-17-carboxy-1,11,15-trioxo-4,7-dioxa-18-thia-10,14-diazahenicosan-21-oic acid (C-18b)

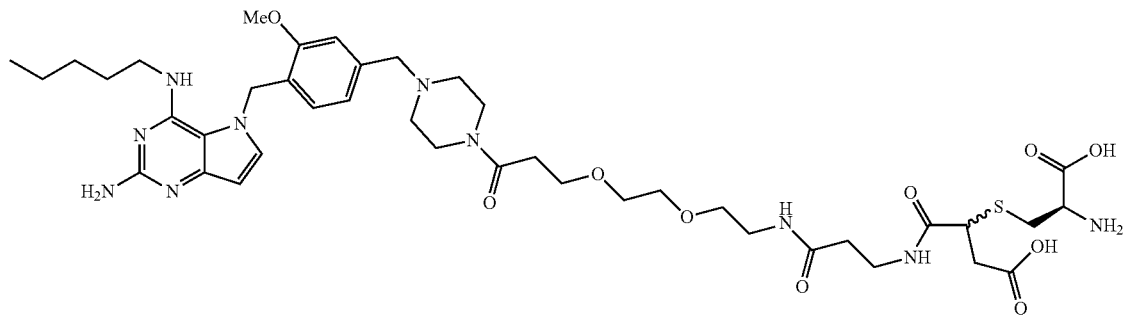

(C-18a)

(C-18b)

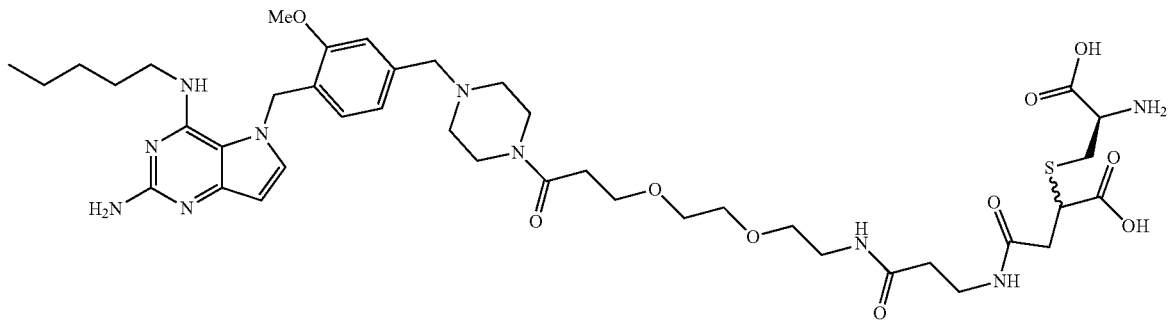

(19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-(carboxymethyl)-1,11,15-trioxo-4,7-dioxa-17-thia-10,14-diazaicosan-20-oic acid (C-18a) and (20R)-20-amino-1-(4-(4-((2-amino-4-(pentylamino)-5H-pyrrolo[3,2-d]pyrimidin-5-yl)methyl)-3-methoxybenzyl)piperazin-1-yl)-17-carboxy-1,11,15-trioxo-4,7-dioxa-18-thia-10,14-diazahenicosan-21-oic acid (C-18b) were prepared following a procedure similar to Example 4, except Compound (C-17) was used in place of Compound (C-1), to afford a mixture of Compounds (C-18a) and (C-18b), as their respective diasteromers (Compounds (C-18aSR), C-18aRR), (C-18bRR) and (C-18bRR) below), as a solid as the TFA salt. The crude reaction mixture was purified by RP-HPLC (0.035% TFA in ACN:0.05% TFA in H$_2$O, C18 column): $^1$H NMR (CD$_3$OD): δ 7.37 (d, 1H), 7.30 (s, 1H), 7.07 (d, 1H), 6.80 (d, 1H), 6.25 (d, 1H), 5.57 (s, 2H), 4.35 (s, 2H), 4.19 (m, 1H), 3.95 (s, 3H), 3.89 (s, 3H), 3.76 (m, 3H), 3.60 (s, 4H), 3.53 (m, 4H), 3.41 (m, 1H), 3.36 (m, 2H), 3.22 (s, 2H), 2.70 (t, 2H), 2.42 (2H), 1.53 (m, 2H), 1.30 (m, 2H), 1.19 (m, 2H), 0.88 (t, 3H). LCMS [M+H]=887.4.

(C-18aSR)

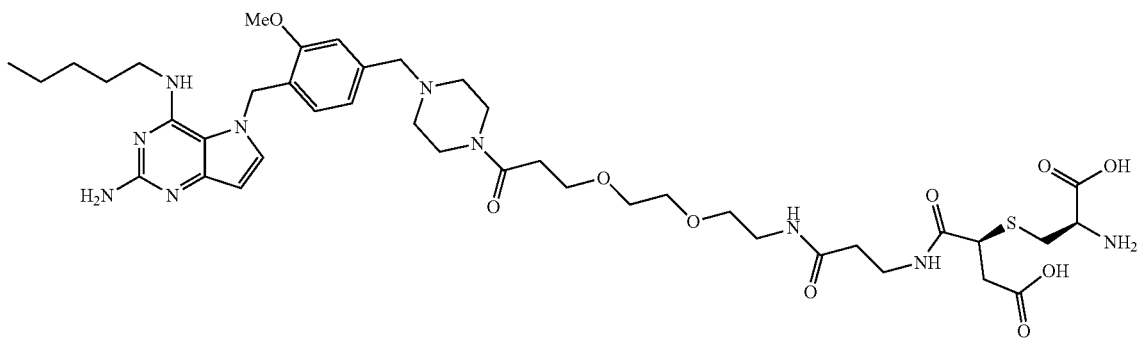

(16S,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-(carboxymethyl)-1,11,15-trioxo-4,7-dioxa-17-thia-10,14-diazaicosan-20-oic acid (C-18aSR)

(C-18bRR)

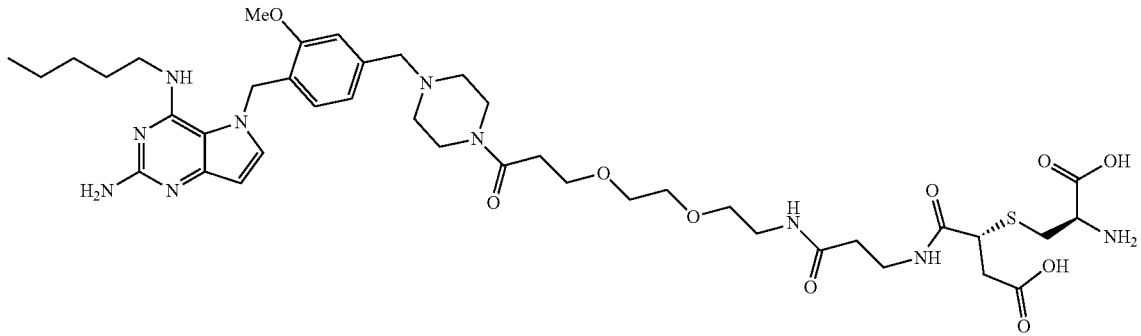

(16R,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-(carboxymethyl)-1,11,15-trioxo-4,7-dioxa-17-thia-10,14-diazaicosan-20-oic acid (C-18aRR)

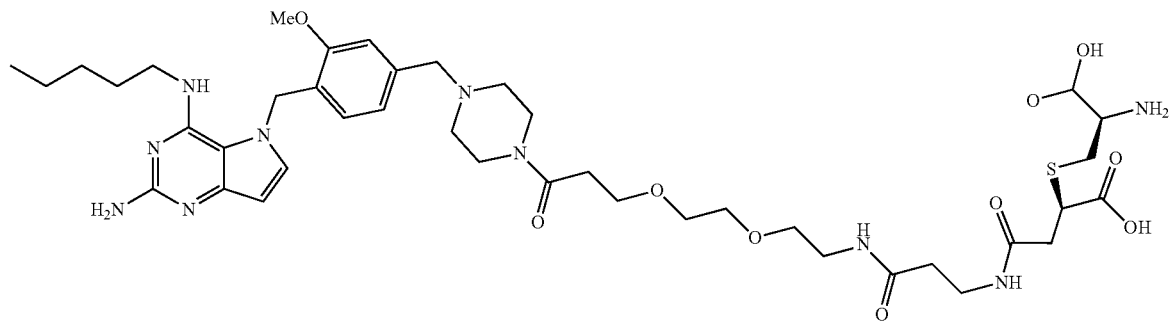

(C-18bRR)

(17R,20R)-20-amino-1-(4-(4-((2-amino-4-(pentylamino)-5H-pyrrolo[3,2-d]pyrimidin-5-yl)methyl)-3-methoxybenzyl)piperazin-1-yl)-17-carboxy-1,11,15-trioxo-4,7-dioxa-18-thia-10,14-diazahenicosan-21-oic acid (C-18bRR)

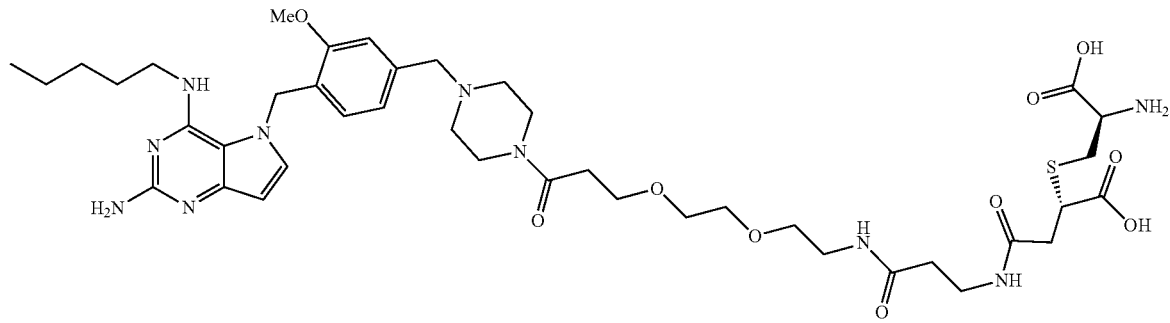

(C-18bSR)

(17S,20R)-20-amino-1-(4-(4-((2-amino-4-(pentylamino)-5H-pyrrolo[3,2-d]pyrimidin-5-yl)methyl)-3-methoxybenzyl)piperazin-1-yl)-17-carboxy-1,11,15-trioxo-4,7-dioxa-18-thia-10,14-diazahenicosan-21-oic acid (C-18bSR)

Example 19

Synthesis of 5-(4-((4-(3-aminopropyl)piperazin-1-yl)methyl)-2-methoxybenzyl)-N4-pentyl-5H-pyrrolo[3,2-d]pyrimidine-2,4-diamine (C-19)

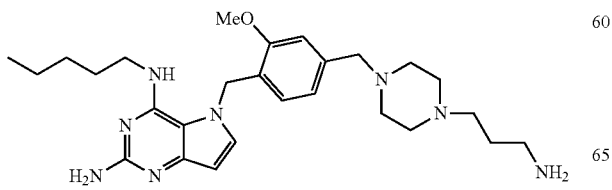

(C-19)

5-(4-((4-(3-aminopropyl)piperazin-1-yl)methyl)-2-methoxybenzyl)-N4-pentyl-5H-pyrrolo[3,2-d]pyrimidine-2,4-diamine (C-19) was prepared by a two step sequence. In the first step a round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), tert-butyl (3-bromopropyl)carbamate (1.2 equiv.), Huenig's base (2.4 equiv.), and DMF (0.2 M). The reaction mixture was heated to 60° C. and then stirred for 18 hours. The crude reaction mixture was then cooled to room temperature and purified by ISCO chromatography (0-20% MeOH:DCM) to provide the intermediate tert-butyl (3-(4-(4-((2-amino-4-(pentylamino)-5H-pyrrolo[3,2-d]pyrimidin-5-yl)methyl)-3-methoxybenzyl)piperazin-1-yl)propyl)carbamate. In the second step a procedure similar to the last step in the synthesis of (Int-1) was used to obtain 5-(4-((4-(3-aminopropyl)piperazin-1-yl)methyl)-2-methoxybenzyl)-N4-pentyl-5H-pyrrolo[3,2-d]pyrimidine-2,4-diamine (C-19) as a solid: 1H NMR (CD3OD): δ 7.24 (d, 1H), 7.10 (d, 1H), 6.85 (d, 1H), 6.57 (d, 1H), 6.11 (s, 1H), 5.42 (s, 2H), 3.95 (s, 3H), 3.52 (s, 2H), 3.35 (m, 2H), 2.80 (t, 2H), 2.51 (m, 4H), 2.45 (m, 4H), 1.72 (m, 2H), 1.40 (m, 2H), 1.28 (m, 4H), 1.15 (m, 2H), 0.88 (t, 3H). LRMS [M+H]=495.3.

Example 20

Synthesis of 1-(4-(4-((2-amino-4-(pentylamino)-5H-pyrrolo[3,2-d]pyrimidin-5-yl)methyl)-3-methoxybenzyl)piperazin-1-yl)-3-(2-(2-aminoethoxy)ethoxy)propan-1-one (C-20)

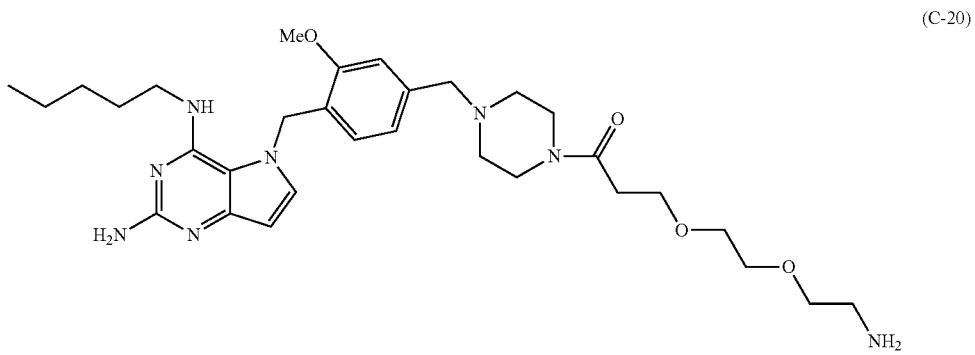 [SMILES: CCCCCNc1nc(N)nc2ccn(Cc3ccc(CN4CCN(C(=O)CCOCCOCCN)CC4)cc3OC)c12]

(C-20)

1-(4-(4-((2-amino-4-(pentylamino)-5H-pyrrolo[3,2-d]pyrimidin-5-yl)methyl)-3-methoxybenzyl)piperazin-1-yl)-3-(2-(2-aminoethoxy)ethoxy)propan-1-one (C-20) was prepared following a procedure of Example 19, except 2,2-dimethyl-4-oxo-3,8,11-trioxa-5-azatetradecan-14-oic acid was used in place of tert-butyl (3-bromopropyl)carbamate, to afford 1-(4-(4-((2-amino-4-(pentylamino)-5H-pyrrolo[3,2-d]pyrimidin-5-yl)methyl)-3-methoxybenzyl)piperazin-1-yl)-3-(2-(2-aminoethoxy)ethoxy)propan-1-one (C-20) as a solid: $^1$H NMR (CD$_3$OD): δ 7.24 (d, 1H), 7.11 (s, 1H), 6.86 (d, 1H), 6.57 (d, 1H), 6.12 (d, 1H), 5.42 (s, 2H), 3.96 (s, 3H), 3.76 (t, 2H), 3.59 (m, 12H), 3.37 (t, 2H), 2.76 (t, 2H), 2.66 (t, 2H), 2.45 (m, 4H), 1.41 (m, 2H), 1.28 (m, 2H), 1.16 (m, 2H), 0.89 (t, 3H). LRMS [M+H]=597.4.

Example 21

Synthesis of N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-2-(2,5-dioxo-2,5-dihydro-1H-pyrrol-1-yl)acetamide (C-21)

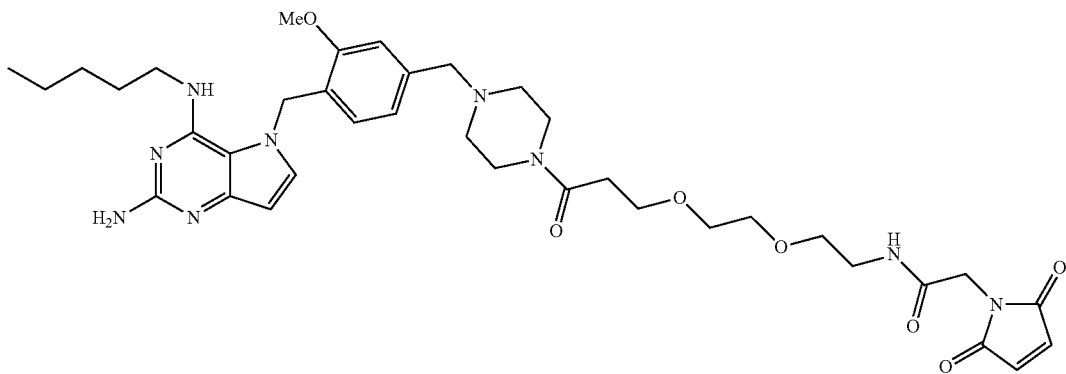

(C-21)

A round bottom flask was charged with 1-(4-(4-((2-amino-4-(pentylamino)-5H-pyrrolo[3,2-d]pyrimidin-5-yl)methyl)-3-methoxybenzyl)piperazin-1-yl)-3-(2-(2-aminoethoxy)ethoxy)propan-1-one (C-20) (1.0 equiv.), DIEA (10.0 equiv.) and DMF (0.004 M) and the mixture was stirred at room temperature for 15 minutes. A separate flask was then charged with 2,5-dioxopyrrolidin-1-yl 2-(2,5-dioxo-2,5-dihydro-1H-pyrrol-1-yl)acetate (1.5 equiv.), DIEA (10.0 equiv.) and DMF (0.006 M). This mixture was also stirred for 15 minutes at room temperature and then the two solutions were mixed and the reaction mixture stirred at room temperature for 1 hour. The crude reaction mixture was purified by RP-HPLC (0.035% TFA in ACN:0.05% TFA in H$_2$O, C18 column) to afford N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-2-(2,5-dioxo-2,5-dihydro-1H-pyrrol-1-yl)acetamide (C-21) as a solid as the TFA salt: $^1$H NMR (CD$_3$CN): δ 7.30 (d, 1H), 7.05 (s, 1H), 6.98 (s, 1H), 6.86 (d, 1H), 6.82 (s, 2H), 6.74 (s, 1H), 6.68 (d, 1H), 6.21 (d, 1H), 6.08 (t, 1H), 5.38 (s, 2H), 4.08 (s, 2H), 3.89 (s, 3H), 3.70 (t, 2H), 3.41 (m, 14H), 3.29 (m, 2H), 2.55, (t, 2H), 2.38 (m, 4H), 1.41 (m, 2H), 1.26 (m, 2H), 1.13 (m, 2H), 0.85 (t, 3H). LCMS [M+H]=734.4.

Example 22

Synthesis of (2R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,9,19-trioxo-13,16-dioxa-4-thia-7,10-diazanonadecan-1-oic acid (C-22a) and (19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,11,14-trioxo-4,7-dioxa-17-thia-10,13-diazaicosan-20-oic acid (C-22b)

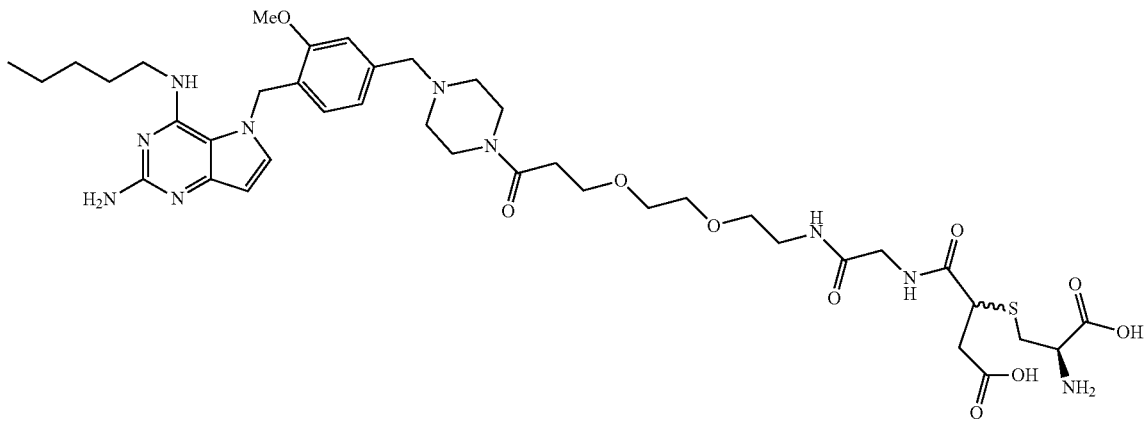

(C-22a)

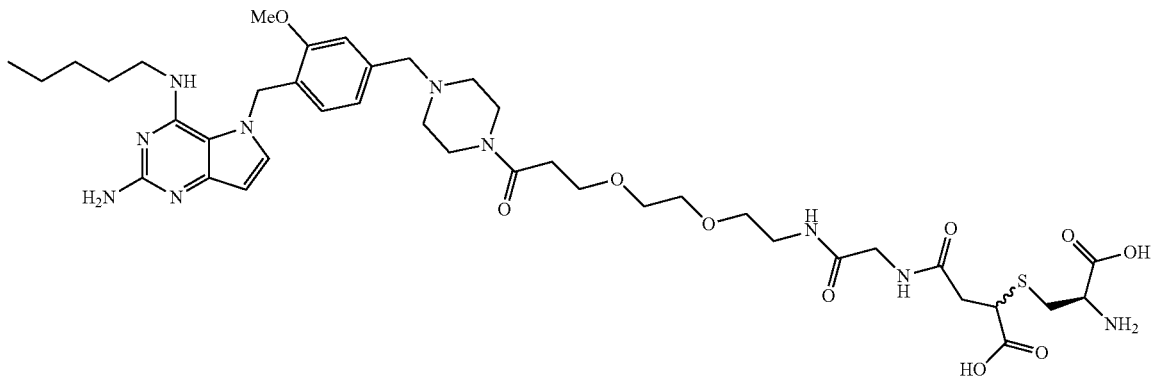

(C-22b)

(2R)-2-amino-19-(4-(4-((2-amino-4-(pentylamino)-5H-pyrrolo[3,2-d]pyrimidin-5-yl)methyl)-3-methoxybenzyl)piperazin-1-yl)-5-(carboxymethyl)-6,9,19-trioxo-13,16-dioxa-4-thia-7,10-diazanonadecan-1-oic acid (C-22a) and (19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,11,14-trioxo-4,7-dioxa-17-thia-10,13-diazaicosan-20-oic acid (C-22b) were prepared following a procedure similar to Example 4, except Compound (C-21) was used in place of Compound (C-1), to afford a mixture of Compounds (C-22a) and (C-22b), as their respective diasteromers (Compounds (C-22aSR), C-22aRR), (C-22bRR) and (C-22bRR) below), as a solid as the TFA salt. The crude reaction mixture was purified by RP-HPLC (0.035% TFA in ACN:0.05% TFA in H$_2$O, C18 column): $^1$H NMR (CD$_3$OD): δ 7.37 (d, 1H), 7.32 (s, 1H), 7.08 (d, 1H), 6.81 (d, 1H), 6.24 (d, 1H), 5.57 (s, 2H), 4.34 (s, 2H), 4.20 (m, 1H), 3.96 (s, 3H), 3.82 (m, 9H), 3.56 (m, 9H), 3.38 (m, 3H), 3.21 (m, 2H), 2.70 (t, 2H), 1.54 (m, 2H), 1.32 (m, 2H), 1.19 (m, 2H), 0.89 (t, 3H). LCMS [M+H]= 873.4.

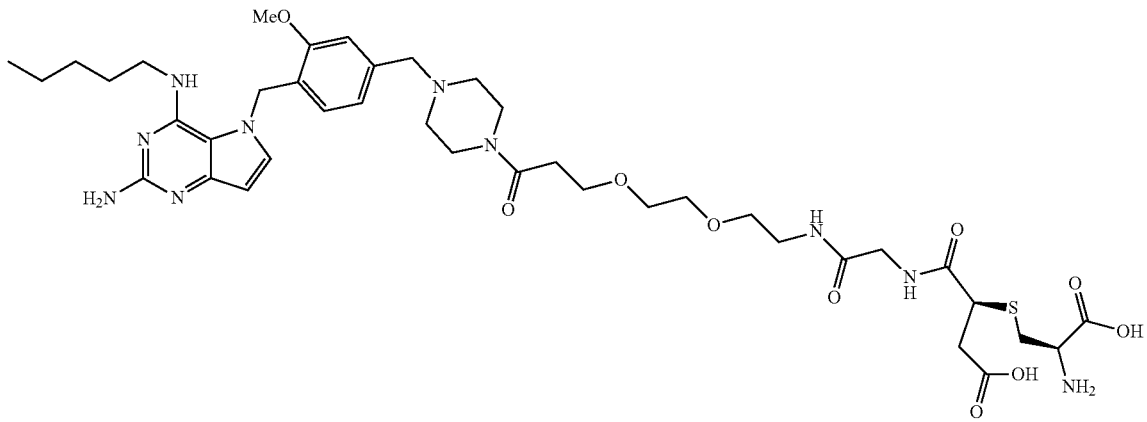

(C-22aSR)

(2R,5S)-2-amino-19-(4-(4-((2-amino-4-(penty-lamino)-5H-pyrrolo[3,2-d]pyrimidin-5-yl)methyl)-3-methoxybenzyl)piperazin-1-yl)-5-(carboxymethyl)-6,9,19-trioxo-13,16-dioxa-4-thia-7,10-diazanonadecan-1-oic acid (C-22aSR)
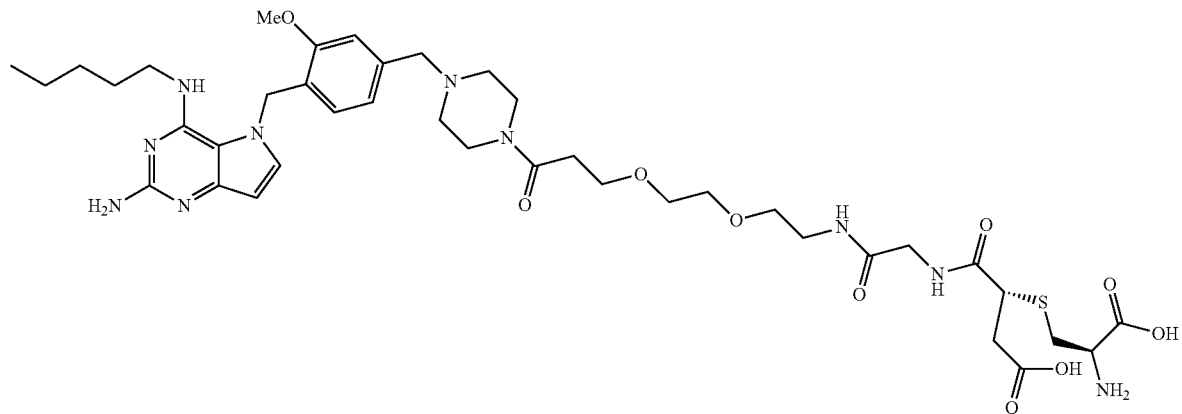
(C-22aRR)
(2R,5R)-2-amino-19-(4-(4-((2-amino-4-(penty-lamino)-5H-pyrrolo[3,2-d]pyrimidin-5-yl)methyl)-3-methoxybenzyl)piperazin-1-yl)-5-(carboxymethyl)-6,9,19-trioxo-13,16-dioxa-4-thia-7,10-diazanonadecan-1-oic acid (C-22aRR)
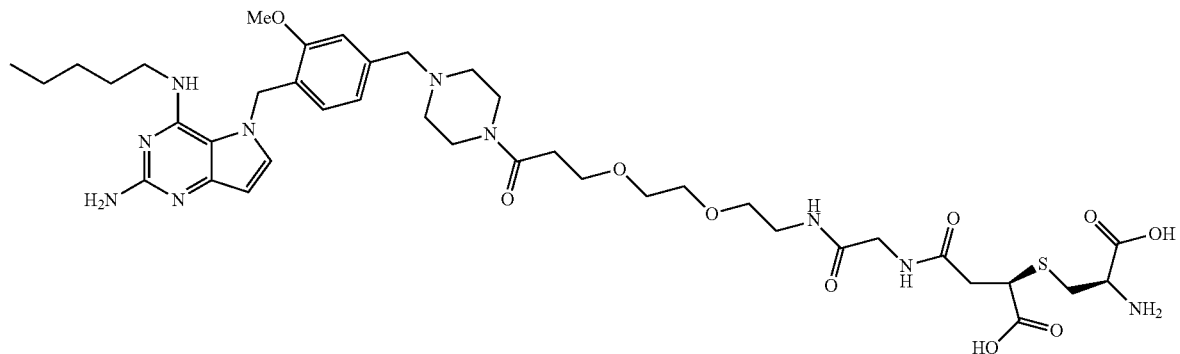
(C-22bRR)

(16R,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,11,14-trioxo-4,7-dioxa-17-thia-10,13-diazaicosan-20-oic acid (C-22bRR)

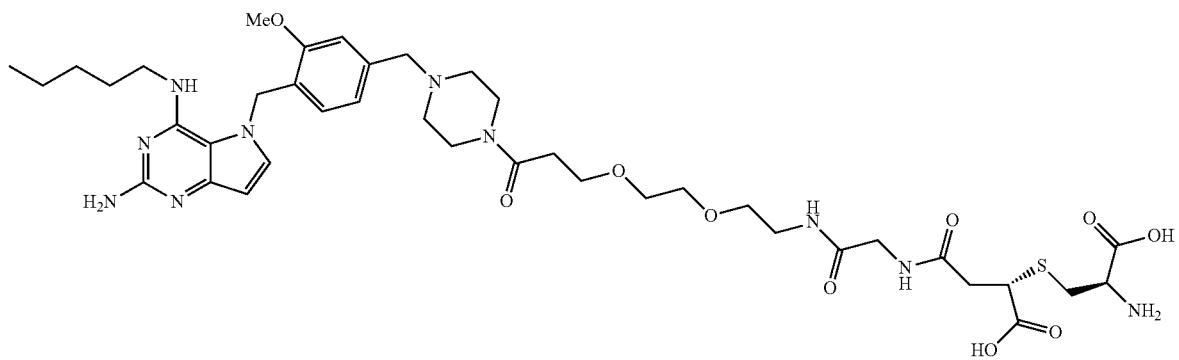

(16S,19R)-19-amino-1-(4-(4-((2-amino-4-(pentylamino)-5H-pyrrolo[3,2-d]pyrimidin-5-yl)methyl)-3-methoxybenzyl)piperazin-1-yl)-16-carboxy-1,11,14-trioxo-4,7-dioxa-17-thia-10,13-diazaicosan-20-oic acid (C-22bSR)

Example 23

Synthesis of 4-(4-((2-amino-4-(pentylamino)-5H-pyrrolo[3,2-d]pyrimidin-5-yl)methyl)-3-methoxybenzyl)-N-(2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl)piperazine-1-carboxamide (C-23)

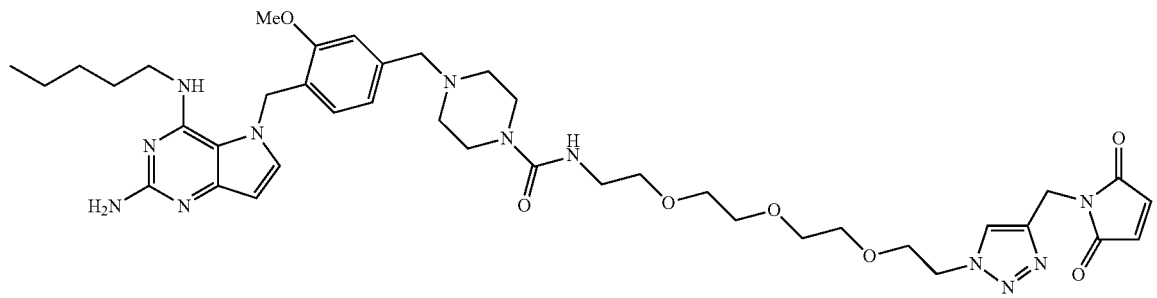

A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1 equiv.), 4-nitrophenyl (2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl) carbamate (0.9 equiv.), triethylamine (3.0 equiv.) and DMSO (0.01 M). The reaction mixture was stirred at room temperature for 2 hours and the crude reaction mixture was then purified by RP-HPLC (0.035% TFA in ACN:0.05% TFA in H$_2$O, C18 column) to afford 4-(4-(((2-amino-4-(pentylamino)-5H-pyrrolo[3,2-d]pyrimidin-5-yl)methyl)-3-methoxybenzyl)-N-(2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl)piperazine-1-carboxamide (C-23) as a solid as the TFA salt: $^1$H NMR (CD$_3$OD): δ 7.96 (s, 1H), 7.36 (d, 1H), 7.26 (d, 1H), 7.05 (d, 1H), 6.85 (s, 2H), 6.79 (d, 1H), 6.24 (d, 1H), 5.57 (s, 2H), 4.74 (s, 2H), 4.53 (t, 2H), 4.35 (s, 2H), 3.95 (s, 3H), 3.86 (t, 2H), 3.85 (m, 4H), 3.54 (m, 12H), 3.22 (m, 6H), 1.53 (m, 2H), 1.30 (m, 2H), 1.19 (m, 2H), 0.88 (t, 3H). LCMS [M+H]=817.4.

Note: 4-nitrophenyl (2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl)carbamate

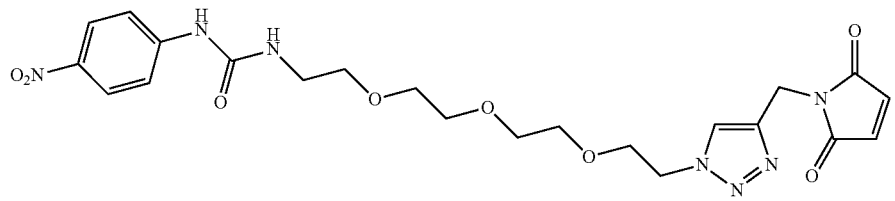 [SMILES: O=C(NCCOCCOCCOCCn1cc(CN2C(=O)C=CC2=O)nn1)Nc1ccc([N+](=O)[O-])cc1]

was prepared using the following procedure:

Step 1: Triethylamine (2.5 equiv.) and di-tert-butyl dicarbonate (1.1 equiv.) were added to a solution of 2-(2-(2-(2-azidoethoxy)ethoxy)ethoxy)ethanamine (1.0 equiv.) in $CH_2Cl_2$ (0.05 M) and the reaction mixture was stirred at room temperature for 30 minutes. The reaction mixture was then concentrated in vacuo and the residue was purified using RP-C18 ISCO and then lyophilized to give tert-butyl (2-(2-(2-(2-azidoethoxy)ethoxy)ethoxy)ethyl)carbamate.

Step 2: A solution of tert-butyl (2-(2-(2-(2-azidoethoxy)ethoxy)ethoxy)ethyl)carbamate (1 equiv.) and 1-(prop-2-yn-1-yl)-1H-pyrrole-2,5-dione (2.0 equiv.) in t-BuOH (0.08 M) was flushed with $N_2$ gas five times and then L-ascorbic acid sodium salt (1.0 equiv. 0.16 M in $H_2O$) and $CuSO_4$ (0.2 equiv. 0.03 M in $H_2O$) were added. The reaction mixture was again flushed with $N_2$ gas five times and then stirred at room temperature for 4 h. The reaction mixture was then purified by ISCO RP-C18 and lyophilized to afford tert-butyl (2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl) carbamate.

Step 3: A solution of tert-butyl (2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl) carbamate in TFA (0.02 M) was concentrated in vacuo to afford 1-((1-(23-amino-3,6,9,12,15,18,21-heptaoxatricosyl)-1H-1,2,3-triazol-4-yl)methyl)-1H-pyrrole-2,5-dione. LCMS [M+H]=354.2.

Step 4: 4-Nitrophenyl carbonochloridate (1.10 equiv.) and triethylamine (2.50 equiv.) were added to a solution of 1-((1-(2-(2-(2-(2-aminoethoxy)ethoxy)ethoxy)ethyl)-1H-1,2,3-triazol-4-yl)methyl)-1H-pyrrole-2,5-dione (1 equiv.) in $CH_2Cl_2$ (0.01 M) and the reaction mixture was stirred at room temperature for 10 minutes. The reaction mixture was then concentrated in vacuo, purified by RP-C18 ISCO and then lyophilized to afford 4-nitrophenyl (2-(2-(2-(2-(4-((2,5-dioxo-2,5-dihydro-1H-pyrrol-1-yl)methyl)-1H-1,2,3-triazol-1-yl)ethoxy)ethoxy)ethoxy)ethyl)carbamate LCMS [M+H]=519.2.

Example 24

Synthesis of 3-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24a) and 2-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24b)

(C-24a)

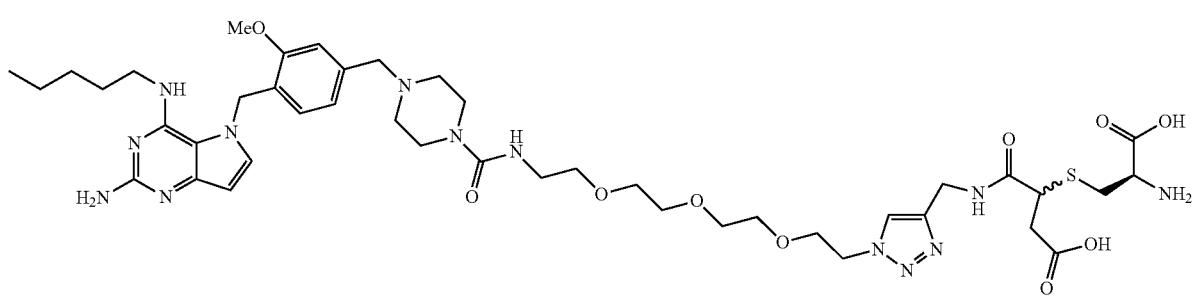

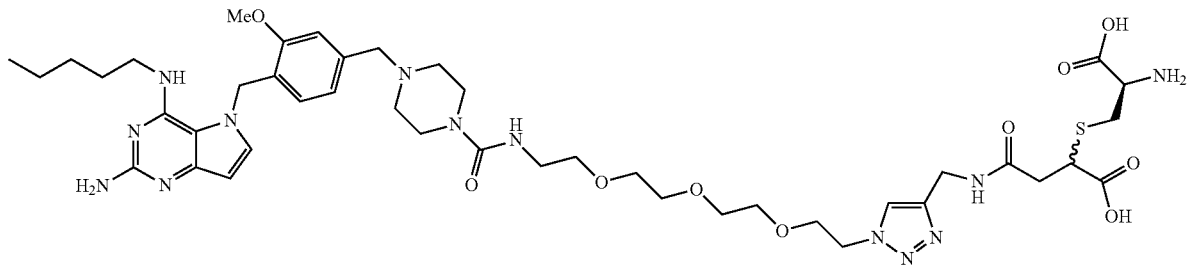
(C-24b)

3-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24a) and 2-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24b) were prepared following a procedure similar to Example 4, except Compound (C-23) was used in place of Compound (C-1), to provide a mixture of Compounds (C-24a) and (C-24b), as their respective diastereomers (Compounds (C-24aSR), C-24aRR), (C-24bRR) and (C-24bRR) below), as a solid as the TFA salt. The crude reaction mixture was purified by RP-HPLC (0.035% TFA in ACN:0.05% TFA in H$_2$O, C18 column): LCMS [M+H]= 956.4.

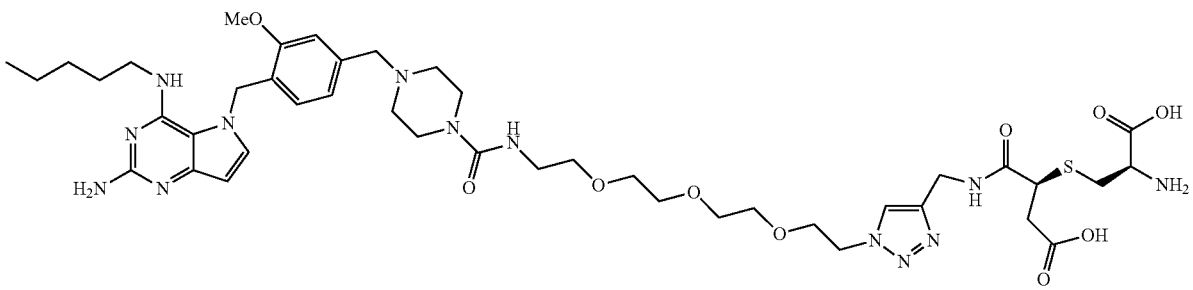
(C-24aSR)

(S)-3-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24aSR)

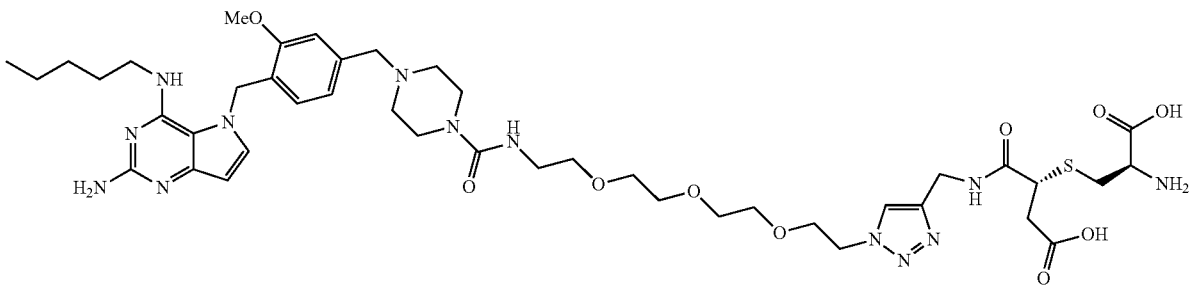
(C-24aRR)

(R)-3-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24aRR)

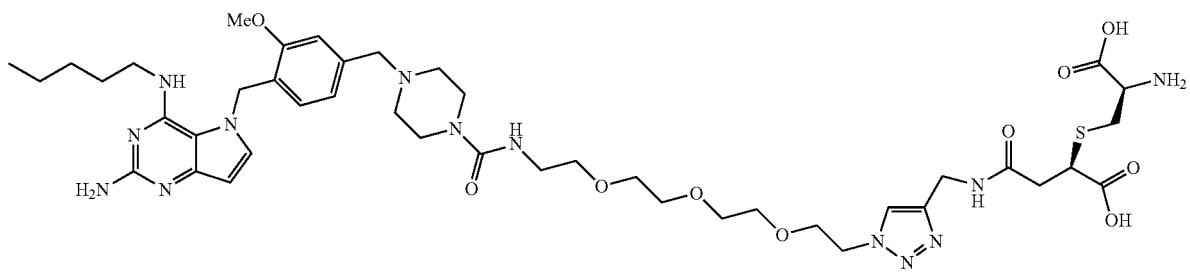
(C-24bRR)

(R)-2-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24bRR)

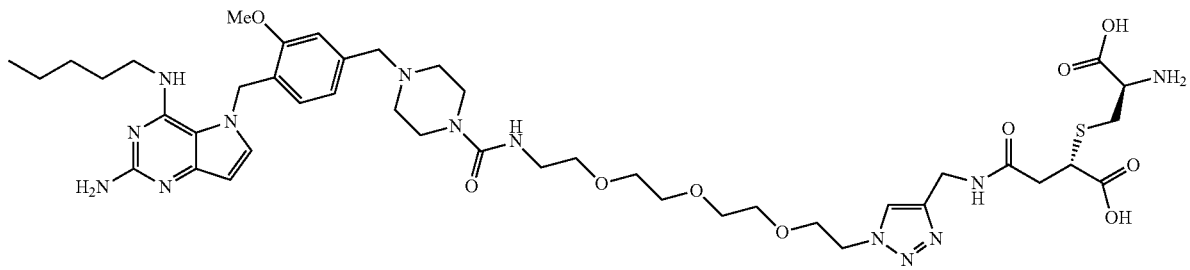
(C-24bSR)

(S)-2-(((R)-2-amino-2-carboxyethyl)thio)-4-(((1-(1-(4-(4-((2-amino-4-(pentylamino)-5H-pyrrolo[3,2-d]pyrimidin-5-yl)methyl)-3-methoxybenzyl)piperazin-1-yl)-1-oxo-5,8,11-trioxa-2-azatridecan-13-yl)-1H-1,2,3-triazol-4-yl)methyl)amino)-4-oxobutanoic acid (C-24bSR)

Example 25

Synthesis of 1-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)-1H-pyrrole-2,5-dione (C-25)

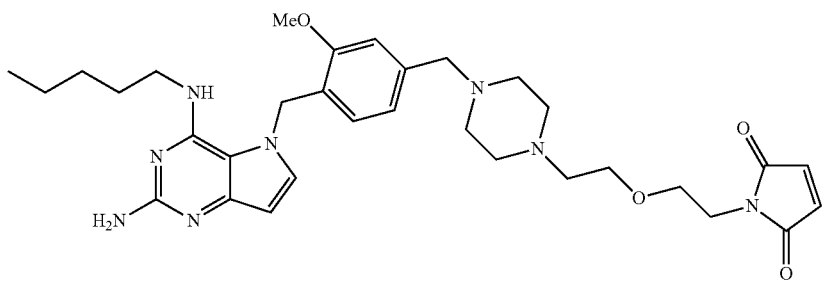

(C-25)

A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), 2-(2-(2,5-dioxo-2,5-dihydro-1H-pyrrol-1-yl)ethoxy)acetaldehyde (4.0 equiv.), sodium cyanoborohydride (13.0 equiv.), and MeOH (0.04 M). The reaction mixture was stirred at room temperature for 1 hour. The crude reaction mixture was then purified by RP-HPLC (0.035% TFA in ACN:0.05% TFA in H$_2$O, C18 column) to afford 1-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)-1H-pyrrole-2,5-dione (C-25) as a solid as the TFA salt: $^1$H NMR (CD$_3$OD): δ 7.36 (d, 1H), 7.16 (d, 1H), 6.96 (d, 1H), 6.83 (s, 2H), 6.76 (d, 1H), 6.23 (d, 1H), 5.53 (s, 2H), 3.93 (s, 3H), 3.84 (s, 2H), 3.78 (m, 2H), 3.71 (m, 2H), 3.64 (m, 2H), 3.54 (m, 2H), 3.35 (m, 4H), 3.27 (t, 2H), 2.95 (m, 4H), 1.52 (m, 2H), 1.30 (m, 2H), 1.19 (m, 2H), 0.88 (t, 3H). LCMS [M+H]=605.4.

Note: 2-(2-(2,5-dioxo-2,5-dihydro-1H-pyrrol-1-yl)ethoxy)acetaldehyde was prepared by adding 1-(2-(2-hydroxyethoxy)ethyl)-1H-pyrrole-2,5-dione (1.0 equiv.), Dess-Martin periodinane (1.5 equiv.) and DCM (0.1 M) to a round bottom flask and stirring the reaction mixture at room temperature for 2 hours. The reaction mixture was then filtered, the volatiles removed in vacuo and the product used without further purification.

Example 26

Synthesis of 3-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid (C-26a) and 2-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid (C-26b)

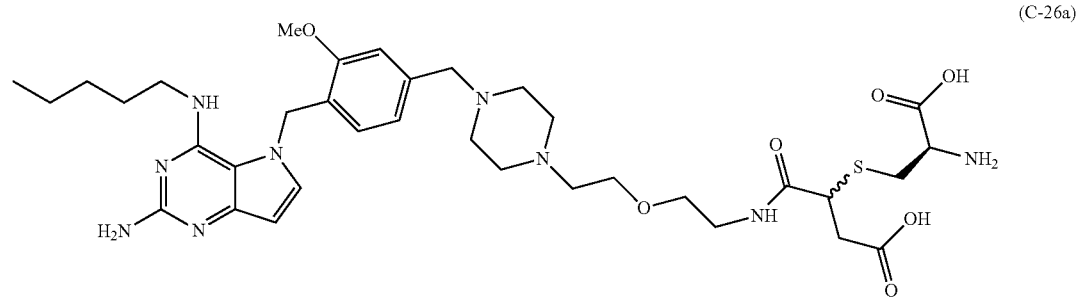

(C-26a)

-continued

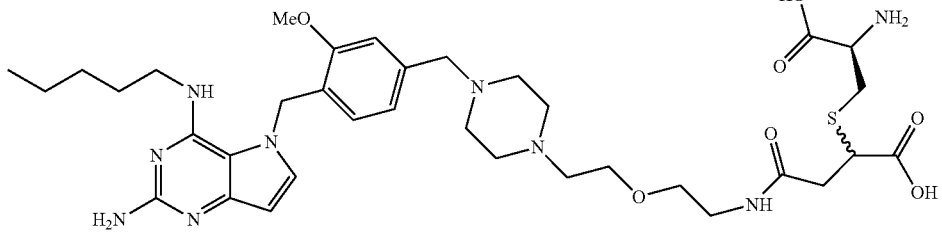

(C-26b)

3-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid (C-26) and 2-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid (C-26b) were prepared following a procedure similar to Example 4, except Compound (C-25) was used in place of Compound (C-1), to afford a mixture of Compounds (C-26a) and (C-26b), as their respective diasteromers (Compounds (C-26aSR), C-26aRR), (C-26bRR) and (C-26bRR) below), as a solid as the TFA salt. The crude reaction mixture was purified by RP-HPLC (0.035% TFA in ACN:0.05% TFA in H$_2$O, C18 column): LCMS [M+H]=744.4

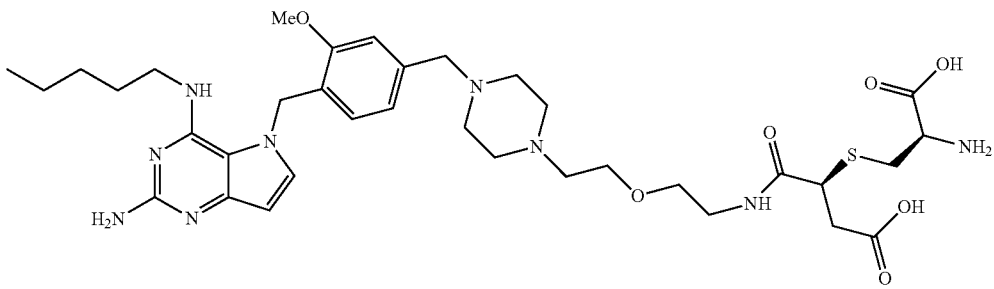

(C-26aSR)

(S)-3-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid (C-26aSR)

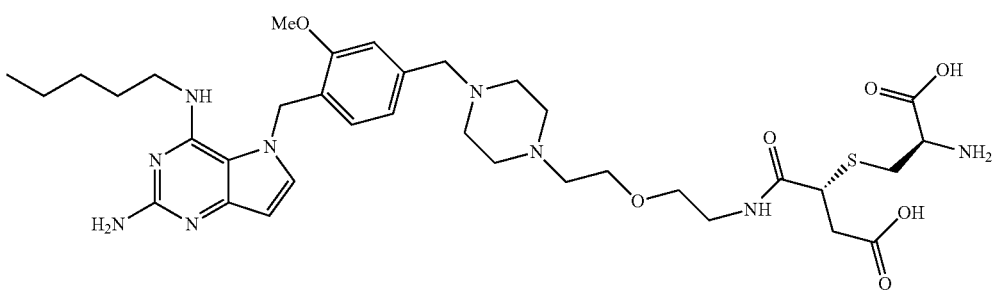

(C-26aRR)

(R)-3-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid
(C-26aRR)

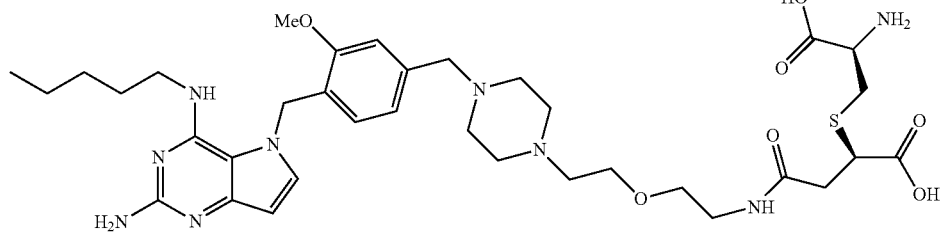

(C-26bRR)

(R)-2-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid
(C-26bRR)

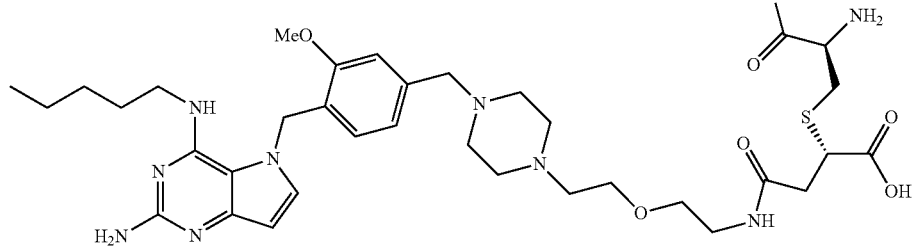

(C-26bSR)

(S)-2-(((R)-2-amino-2-carboxyethyl)thio)-4-((2-(2-(4-(4-((2-amino-4-(pentylamino)-5H-pyrrolo[3,2-d]pyrimidin-5-yl)methyl)-3-methoxybenzyl)piperazin-1-yl)ethoxy)ethyl)amino)-4-oxobutanoic acid
(C-26bSR)

Example 27

Synthesis of 1-((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)-1H-pyrrole-2,5-dione (C-27)

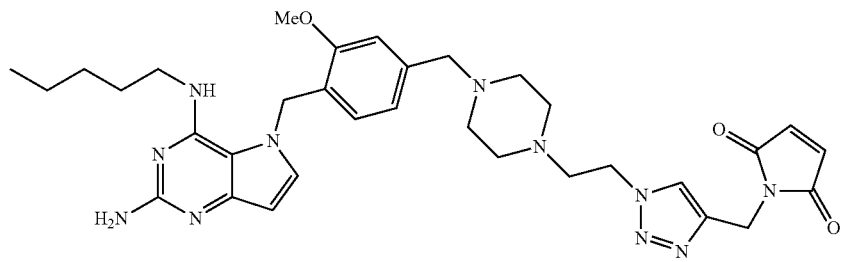

(C-27)

Step 1: A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), 2-azidoacetaldehyde (4.0 equiv.), sodium cyanoborohydride (32.0 equiv.), and MeOH (0.02 M). The reaction mixture was stirred at room temperature for 2 hours. The crude reaction mixture was then purified by RP-HPLC (0.035% TFA in ACN:0.05% TFA in H$_2$O, C18 column) to afford 5-(4-((4-(2-azidoethyl)piperazin-1-yl)methyl)-2-methoxybenzyl)-N4-pentyl-5H-pyrrolo[3,2-d]pyrimidine-2,4-diamine as a solid: LCMS [M+H]=507.3.

Step 2: A round bottom flask was charged with 5-(4-((4-(2-azidoethyl)piperazin-1-yl)methyl)-2-methoxybenzyl)-N4-pentyl-5H-pyrrolo[3,2-d]pyrimidine-2,4-diamine (1.0 equiv), 1-(prop-2-yn-1-yl)-1H-pyrrole-2,5-dione (2.3 equiv.) and a mixture of t-BuOH and water (2:1, v/v, 0.008 M). The reaction mixture was degassed under vacuum and flushed with N$_2$ five times to remove O$_2$. L-ascorbic acid sodium salt (1.1 equiv in 0.5 ml H$_2$O, degassed under and flushed with N$_2$ five times to remove O$_2$) wad added using a syringe to the reaction mixture, then and CuSO$_4$ (0.2 equiv. in 0.5 ml water, degassed under vacuum and flushed with N$_2$ five times to remove O$_2$) was added using a syringe. The reaction mixture was then stirred at room temperature for 2 hours. The crude reaction mixture was then purified by RP-HPLC (0.035% TFA in ACN:0.05% TFA in H$_2$O, C18 column) to afford 1-((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)-1H-pyrrole-2,5-dione (C-27) as a solid as the TFA salt: $^1$H NMR (CD$_3$OD): δ 7.95 (s, 1H), 7.36 (d, 1H), 7.22 (d, 1H), 7.02 (d, 1H), 6.86 (s, 2H), 6.79 (d, 1H), 6.23 (d, 1H), 5.57 (s, 2H), 4.76 (s, 2H), 4.52 (t, 2H), 4.26 (s, 2H), 3.95 (s, 3H), 3.54 (t, 2H), 2.85 (m, 8H), 2.94 (t, 2H), 1.53 (m, 2H), 1.31 (m, 2H), 1.18 (m, 2H), 0.88 (t, 3H). LCMS [M+H]= 642.4.

Note: 2-azidoacetaldehyde was prepared by adding 2-azidoethanol (1.0 equiv.), Dess-Martin periodinane (1.5 equiv.) and DCM (0.20 M) to a round bottom flask and then stirring the reaction mixture at room temperature for 2 hours. The reaction mixture was then filtered, the volatiles removed in vacuo and the product used without further purification.

Example 28

Synthesis of 3-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28a) and 2-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28b)

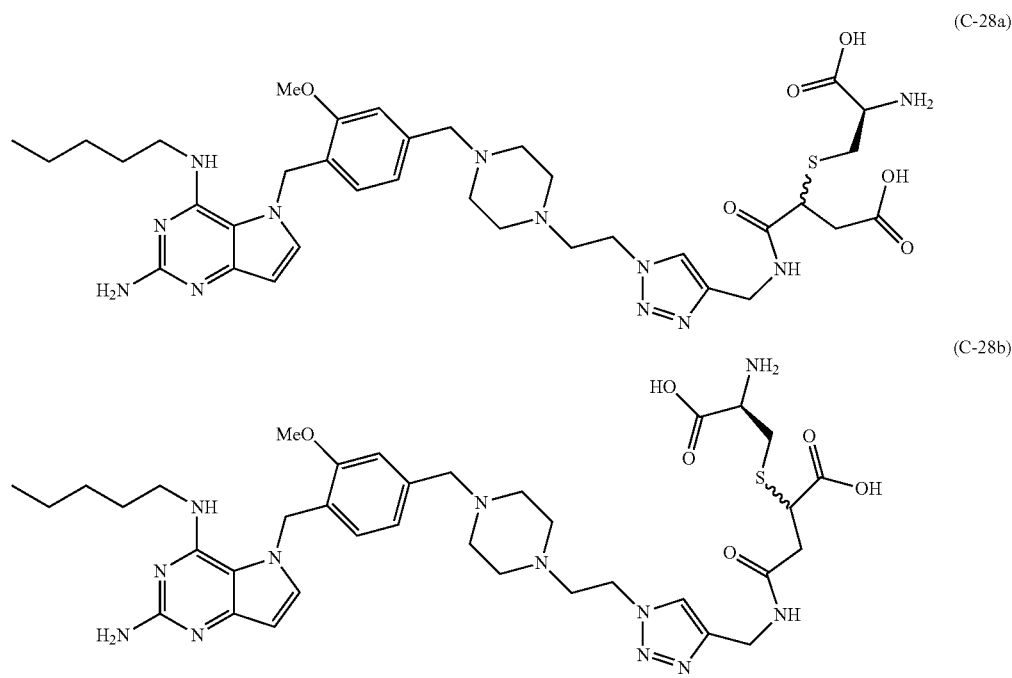

3-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28a) and 2-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28b) were prepared following a procedure similar to Example 4, except Compound (C-27) was used in place of Compound (C-1), to afford a mixture of Compounds (C-28a) and (C-28b), as their respective diasteromers (Compounds (C-28aSR), C-28aRR), (C-28bRR) and (C-28bRR) below), as a solid as the TFA salt. The crude reaction mixture was purified by RP-HPLC (0.035% TFA in ACN:0.05% TFA in H$_2$O, C18 column): LCMS [M+H]=781.4

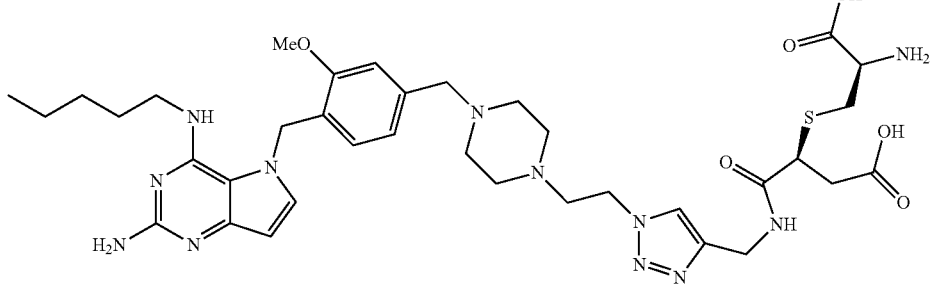
(S)-3-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28aSR)
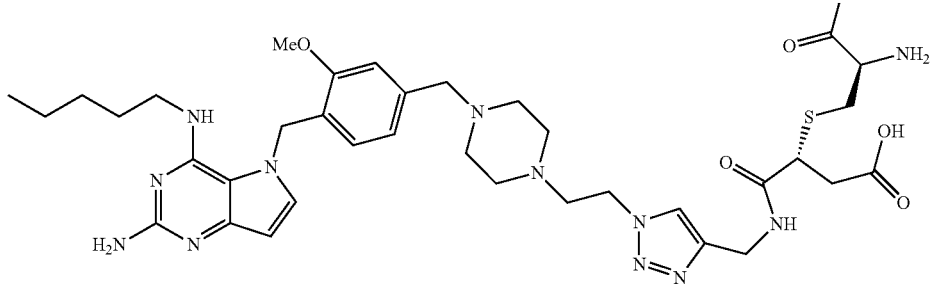
(R)-3-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28aRR)
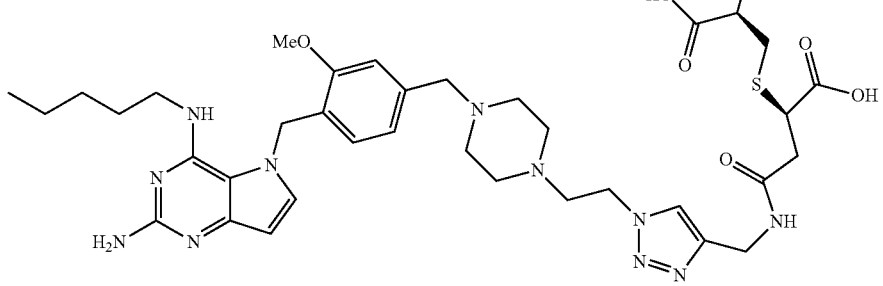

(R)-2-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28bRR)

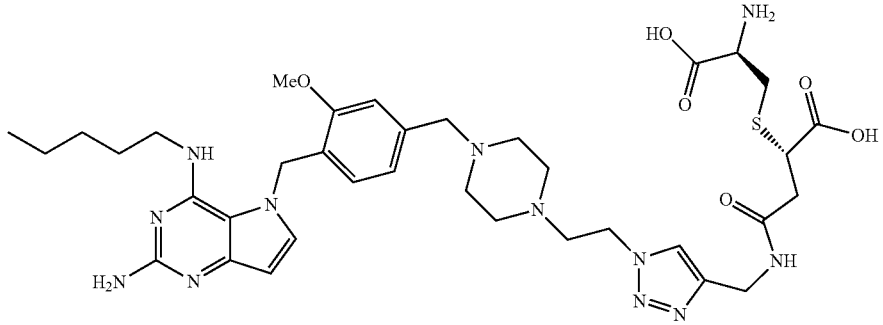
(C-28bSR)

(S)-2-(((R)-2-amino-2-carboxyethyl)thio)-4-(((1-(2-(4-(4-((2-amino-4-(pentylamino)-5H-pyrrolo[3,2-d]pyrimidin-5-yl)methyl)-3-methoxybenzyl)piperazin-1-yl)ethyl)-1H-1,2,3-triazol-4-yl)methyl)amino)-4-oxobutanoic acid (C-28bSR)

Example 29

Synthesis of N-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-3-(2,5-dioxo-2,5-dihydro-1H-pyrrol-1-yl)propanamide (C-29)

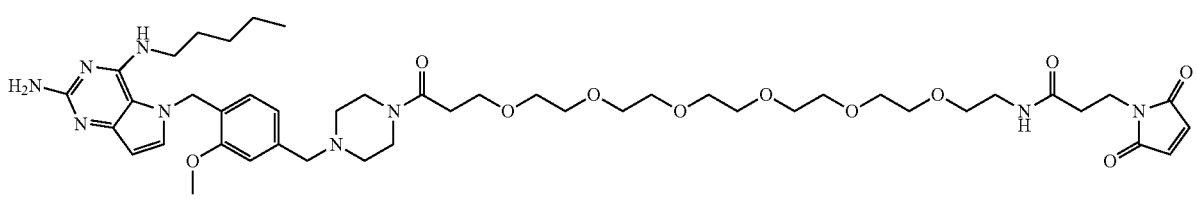
(C-29)

N-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-3-(2,5-dioxo-2,5-dihydro-1H-pyrrol-1-yl)propanamide (C-29) was prepared following a procedure similar to Example 1, except 1-(2,5-dioxo-2,5-dihydro-1H-pyrrol-1-yl)-3-oxo-7,10,13,16,19,22-hexaoxa-4-azapentacosan-25-oic acid was used in place of 3-(2,5-dioxo-2,5-dihydro-1H-pyrrol-1-yl)propanoic acid, to afford N-(21-(4-(4-((2-amino-4-(pentylamino)-5H-pyrrolo[3,2-d]pyrimidin-5-yl)methyl)-3-methoxybenzyl)piperazin-1-yl)-21-oxo-3,6,9,12,15,18-hexaoxahenicosyl)-3-(2,5-dioxo-2,5-dihydro-1H-pyrrol-1-yl)propanamide (C-29) as a solid as the TFA salt: $^1$H NMR (DMSO): δ 8.00 (t, 1H), 7.42 (d, 1H), 7.38 (s, 3H), 7.20 (s, 1H), 7.00 (s, 2H), 6.95 (s, 1H), 6.57 (s, 1H), 6.23 (d, 1H), 5.57 (s, 2H), 4.30 (s, 2H), 3.87 (s, 3H), 3.59 (m, 4H), 3.49 (m, 28H), 3.35 (t, 2H), 3.14 (m, 2H), 2.32 (m, 2H), 1.45 (m, 2H), 1.21 (m, 2H), 1.09 (m, 2H), 0.81 (t, 3H). LRMS [M+H]=924.4.

Example 30
Synthesis of 4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl 4-(4-((2-amino-4-(pentylamino)-5H-pyrrolo[3,2-d]pyrimidin-5-yl)methyl)-3-methoxybenzyl)piperazine-1-carboxylate (C-30)
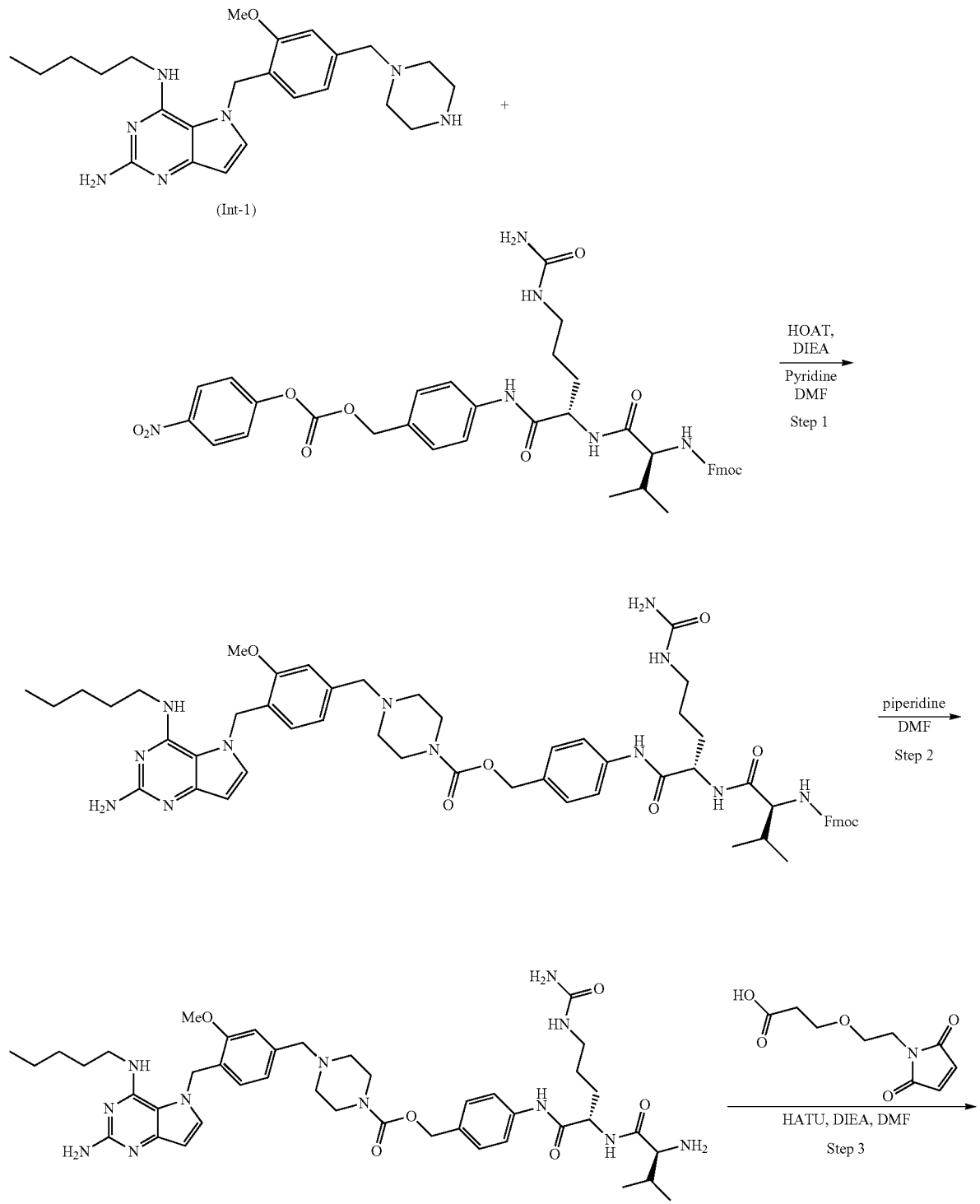

-continued

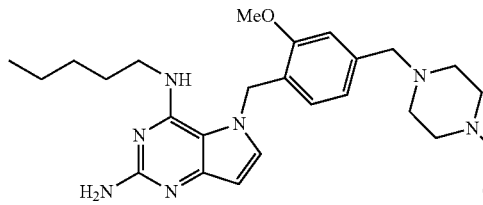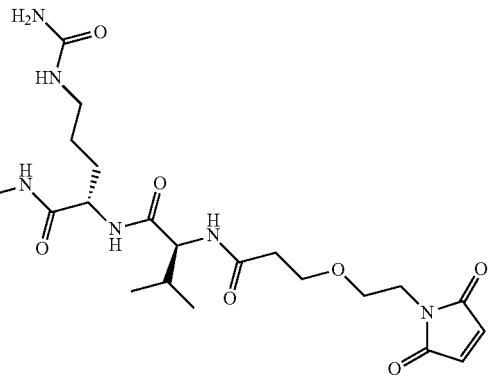

(C-30)

Step 1: A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), HOAT (2.0 equiv.), Huenig's base (14.0 equiv.), (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate (1.2 equiv.), and pyridine:DMF (1:4, 0.02 M). The reaction mixture was stirred at room temperature for 4 hours, and the crude reaction mixture was then purified by RP-HPLC (0.035% TFA in ACN:0.05% TFA in $H_2O$, C18 column) to afford 4-((S)-2-((S)-2-(M9H-fluoren-9-yl)methoxy)carbonyl)amino)-3-methylbutanamido)-5-ureidopentanamido)benzyl 4-(4-((2-amino-4-(pentylamino)-5H-pyrrolo[3,2-d]pyrimidin-5-yl)methyl)-3-methoxybenzyl)piperazine-1-carboxylate as a solid: LCMS [M+H]=1065.5.

Step 2: 4-((S)-2-((S)-2-((((9H-fluoren-9-yl)methoxy)carbonyl)amino)-3-methylbutanamido)-5-ureidopentanamido)benzyl 4-(4-((2-amino-4-(pentylamino)-5H-pyrrolo[3,2-d]pyrimidin-5-yl)methyl)-3-methoxybenzyl)piperazine-1-carboxylate was dissolved in DMF (0.007 M) and piperidine (100.0 equiv.) was added. The reaction was stirred at room temperature for 30 minutes. The crude reaction mixture was then purified by RP-HPLC (0.035% TFA in ACN:0.05% TFA in $H_2O$, C18 column) to afford 4-((S)-2-((S)-2-amino-3-methylbutanamido)-5-ureidopentanamido)benzyl 4-(4-((2-amino-4-(pentylamino)-5H-pyrrolo[3,2-d]pyrimidin-5-yl)methyl)-3-methoxybenzyl)piperazine-1-carboxylate as a solid: LCMS [M+H]=843.5.

Step 3: A round bottom flask was charged with 4-((S)-2-((S)-2-amino-3-methylbutanamido)-5-ureidopentanamido)benzyl 4-(4-((2-amino-4-(pentylamino)-5H-pyrrolo[3,2-d]pyrimidin-5-yl)methyl)-3-methoxybenzyl)piperazine-1-carboxylate (1.0 equiv.), 3-(2-(2,5-dioxo-2,5-dihydro-1H-pyrrol-1-yl)ethoxy)propanoic acid (1.1 equiv.), Huenig's base (5.0 equiv.), HATU (1.05 equiv.) and DMF (0.004 M). The reaction mixture was stirred at room temperature for 2 hours. The crude reaction mixture was then purified by RP-HPLC (0.035% TFA in ACN:0.05% TFA in $H_2O$, C18 column) to afford 4-((S)-2-((S)-2-(3-(2-(2,5-dioxo-2,5-dihydro-1H-pyrrol-1-yl)ethoxy)propanamido)-3-methylbutanamido)-5-ureidopentanamido)benzyl 4-(4-((2-amino-4-(pentylamino)-5H-pyrrolo[3,2-d]pyrimidin-5-yl)methyl)-3-methoxybenzyl)piperazine-1-carboxylate (C-30) as a solid as the TFA salt: LCMS [M+H]=1038.5.

Example 31

Synthesis of (2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2-(2,5-dioxo-2,5-dihydro-1H-pyrrol-1-yl)propanamido)propanamido)phenoxy)-3,4,5-trihydroxytetrahydro-2H-pyran-2-carboxylic acid (C-31)

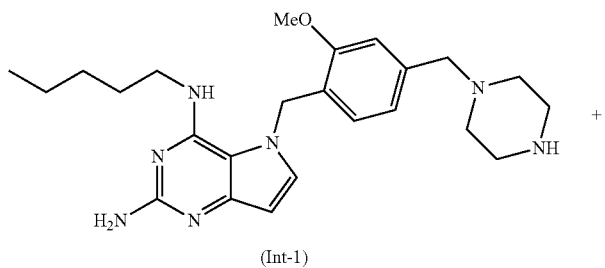

(Int-1)

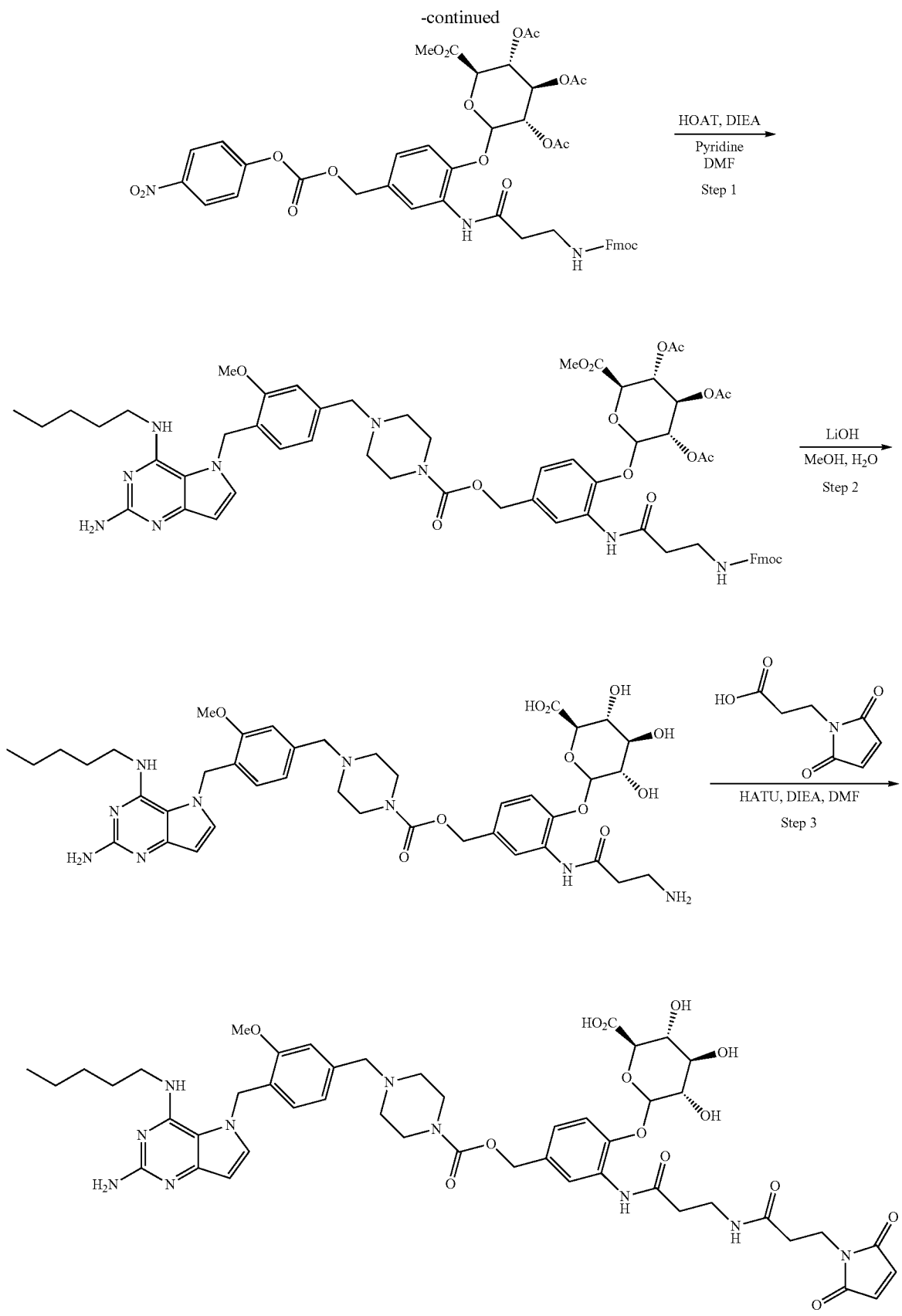

Step 1: A round bottom flask was charged with 5-(2-methoxy-4-(piperazin-1-ylmethyl)benzyl)-N4-pentyl-5H-pyrrolo[3,2-d]pyrimidine-2,4-diamine (Int-1, 1.0 equiv.), HOAT (2.0 equiv.), Huenig's base (14.0 equiv.), (3S,4R,5R,6R)-2-(2-(3-((((9H-fluoren-9-yl)methoxy)carbonyl)amino)propanamido)-4-((((4-nitrophenoxy)carbonyl)oxy)methyl)phenoxy)-6-(methoxycarbonyl)tetrahydro-2H-pyran-3,4,5-triyltriacetate (1.2 equiv.), and pyridine:DMF (1:4, 0.015 M). The reaction mixture was stirred at room temperature for 4 hours. The crude reaction mixture was then purified by RP-HPLC (0.035% TFA in ACN:0.05% TFA in H₂O, C18 column) to afford (3S,4R,5R,6R)-2-(2-(3-((((9H-fluoren-9-yl)methoxy)carbonyl)amino)propanamido)-4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)phenoxy)-6-(methoxycarbonyl)tetrahydro-2H-pyran-3,4,5-triyl triacetate as a solid: LCMS [M+H]= 1212.4.

Step 2: (3S,4R,5R,6R)-2-(2-(3-((((9H-fluoren-9-yl)methoxy)carbonyl)amino)propanamido)-4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)phenoxy)-6-(methoxycarbonyl)tetrahydro-2H-pyran-3,4,5-triyl triacetate (1.0 equiv.) was dissolved in MeOH, THF and water (2:1:0.4) (0.005 M). LiOH (8.0 equiv.) was then added and the reaction was stirred at room temperature for 2 hours. The crude reaction mixture was then purified by RP-HPLC (0.035% TFA in ACN:0.05% TFA in H₂O, C18 column) to afford (2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-aminopropanamido)phenoxy)-3,4,5-trihydroxytetrahydro-2H-pyran-2-carboxylic acid as a solid: LCMS [M+H]=850.4.

Step 3: A round bottom flask was charged with (2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-aminopropanamido)phenoxy)-3,4,5-trihydroxytetrahydro-2H-pyran-2-carboxylic acid (1.0 equiv.), 3-(2,5-dioxo-2,5-dihydro-1H-pyrrol-1-yl)propanoic acid (2.0 equiv.), Huenig's base (6.0 equiv.), HBTU (1.8 equiv.) and DMF (0.003 M). The reaction was kept stirring at room temperature for 15 minutes. The reaction mixture was stirred at room temperature for 2 hours. The crude reaction mixture was then purified by RP-HPLC (0.035% TFA in ACN:0.05% TFA in H₂O, C18 column) to afford (2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2,5-dioxo-2,5-dihydro-1H-pyrrol-1-yl)propanamido)propanamido)phenoxy)-3,4,5-trihydroxytetrahydro-2H-pyran-2-carboxylic acid (C-31) as a solid as the TFA salt: LCMS [M+H]=1001.3.

Example 32

Synthesis of (S)-1-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropyl)-1H-pyrrole-2,5-dione (C-32)

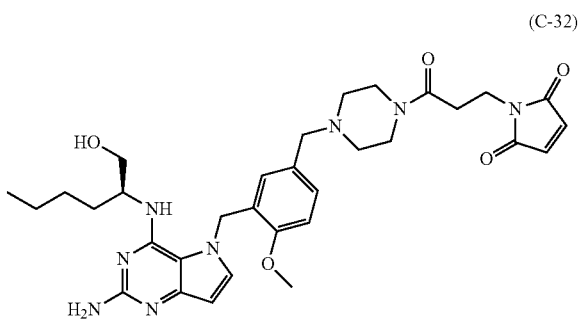 [SMILES: CCCC[C@@H](CO)Nc1nc(N)nc2ccn(Cc3cc(CN4CCN(C(=O)CCN5C(=O)C=CC5=O)CC4)ccc3OC)c12]

(C-32)

(S)-1-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropyl)-1H-pyrrole-2,5-dione (C-32) was prepared following a procedure similar to Example 1, except Compound (Int-2) was used in place of Compound (Int-1), to afford (S)-1-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropyl)-1H-pyrrole-2,5-dione (C-32) as a solid as the TFA salt: $^1$H NMR (CD₃OD): δ 7.49 (d, 2H), 7.21 (d, 1H), 6.82 (s, 2H), 6.77 (d, 1), 6.28 (d, 1H), 5.67 (d, 1H), 5.51 (d, 1H), 4.36 (m, 1H), 4.18 (s, 2H), 3.98 (s, 3H), 3.76 (t, 2H), 3.54 (dd, 1H), 3.46 (dd, 1H), 3.16 (m, 4H), 3.05 (m, 4H), 2.71 (t, 2H), 1.48 (m, 1H), 1.26 (m, 3H), 1.05 (m, 1H), 0.84 (t, 3H). LRMS [M+H]=619.4.

Example 33

Synthesis of 1-(3-(4-(3-((2-amino-4-(pentylamino)-5H-pyrrolo[3,2-d]pyrimidin-5-yl)methyl)-4-methoxybenzyl)piperazin-1-yl)-3-oxopropyl)-1H-pyrrole-2,5-dione (C-33)

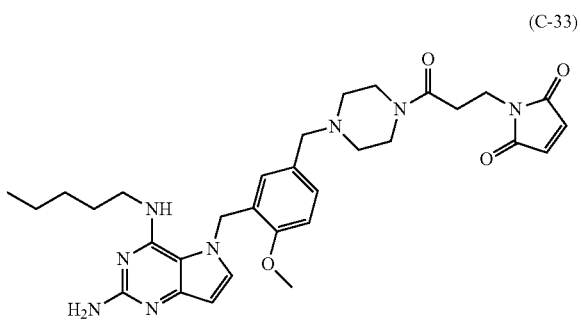 [SMILES: CCCCCNc1nc(N)nc2ccn(Cc3cc(CN4CCN(C(=O)CCN5C(=O)C=CC5=O)CC4)ccc3OC)c12]

(C-33)

1-(3-(4-(3-((2-amino-4-(pentylamino)-5H-pyrrolo[3,2-d]pyrimidin-5-yl)methyl)-4-methoxybenzyl)piperazin-1-yl)-3-oxopropyl)-1H-pyrrole-2,5-dione (C-33) was prepared following a procedure similar to Example 1, except Compound (Int-3) was used in place of Compound (Int-1), to afford 1-(3-(4-(3-((2-amino-4-(pentylamino)-5H-pyrrolo[3,2-d]pyrimidin-5-yl)methyl)-4-methoxybenzyl)piperazin-1-yl)-3-oxopropyl)-1H-pyrrole-2,5-dione (C-33) as a solid as the TFA salt. LRMS [M+H]=589.3.

Example 34

Synthesis of 3-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid (C-34a) and 2-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid (C-34b)

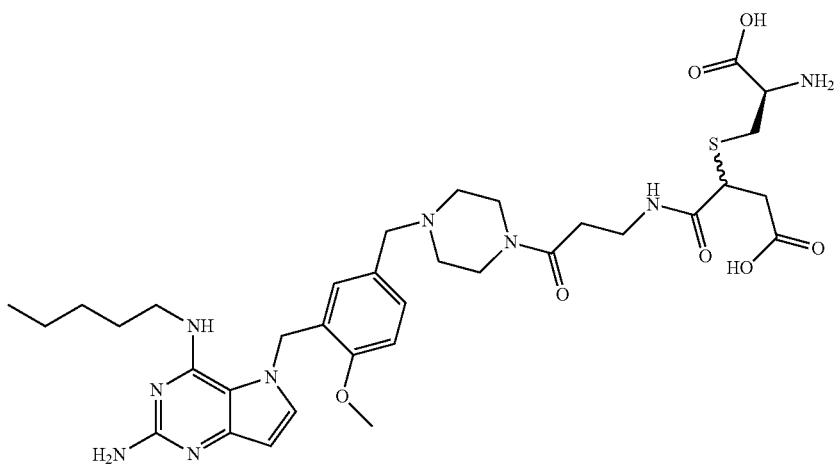

(C-34a)

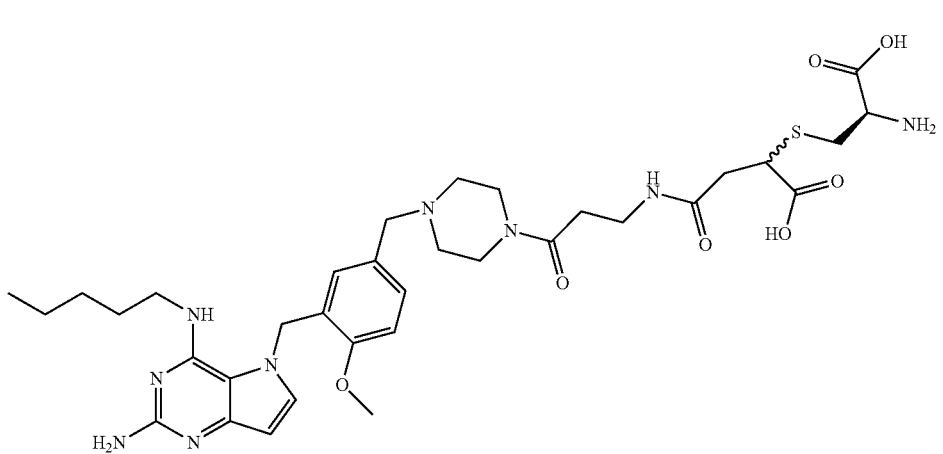

(C-34b)

3-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid (C-34) and 2-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid (C-34b) were prepared following a procedure similar to Example 4, except Compound (C-33) was used in place of Compound (C-1), to afford a mixture of Compounds (C-34a) and (C-34b), as their respective diasteromers (Compounds (C-34aSR), C-34aRR), (C-34bRR) and (C-34bRR) below), as a solid as the TFA salt. The crude reaction mixture was purified by RP-HPLC (0.035% TFA in ACN:0.05% TFA in $H_2O$, C18 column): $^1$H NMR (DMSO): δ 7.51 (s, 2H), 7.39 (m, 2H), 7.27 (d, 1H), 7.15 (d, 1H), 6.59 (s, 1H), 6.22 (t, 1H), 5.56 (s, 2H), 3.86 (s, 4H), 3.66 (m, 3H), 3.42 (m, 8H), 3.25 (m, 4H), 3.08 (m, 2H), 2.81 (m, 3H), 2.65 (m, 1H), 1.43 (m, 2H), 1.22 (m, 3H), 1.07 (m, 2H), 0.83 (t, 3H). LCMS [M+H]=728.3

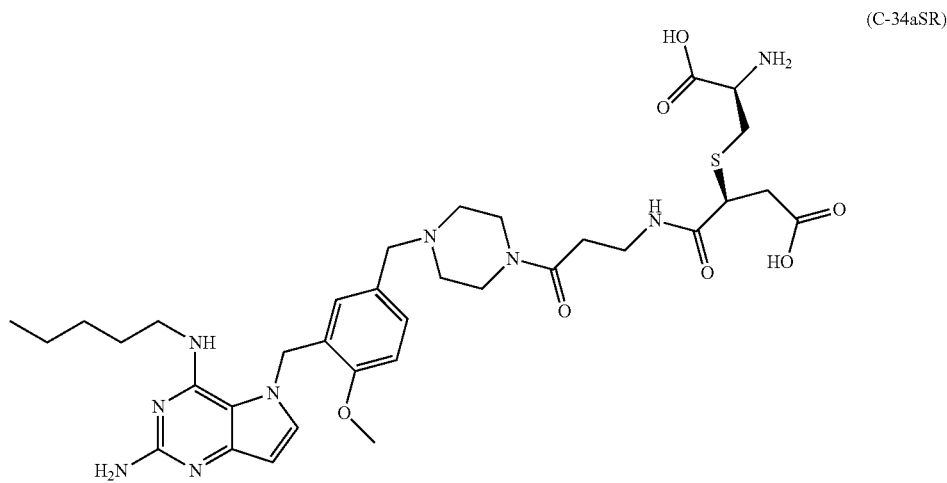 [SMILES: CCCCCNc1nc(N)nc2ccn(Cc3cc(CN4CCN(C(=O)CCNC(=O)[C@H](CC(=O)O)SC[C@H](N)C(=O)O)CC4)ccc3OC)c12]
(S)-3-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid (C-34aSR)
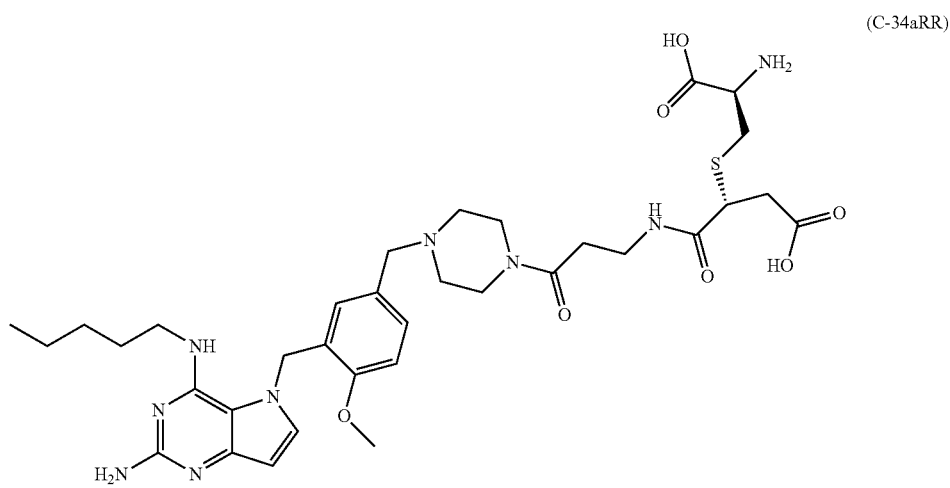 [SMILES: CCCCCNc1nc(N)nc2ccn(Cc3cc(CN4CCN(C(=O)CCNC(=O)[C@@H](CC(=O)O)SC[C@H](N)C(=O)O)CC4)ccc3OC)c12]

(R)-3-(((R)-2-amino-2-carboxyethyl)thio)-4-((3-(4-
(3-((2-amino-4-(pentylamino)-5H-pyrrolo[3,2-d]
pyrimidin-5-yl)methyl)-4-methoxybenzyl)piperazin-
1-yl)-3-oxopropyl)amino)-4-oxobutanoic acid
(C-34aRR)
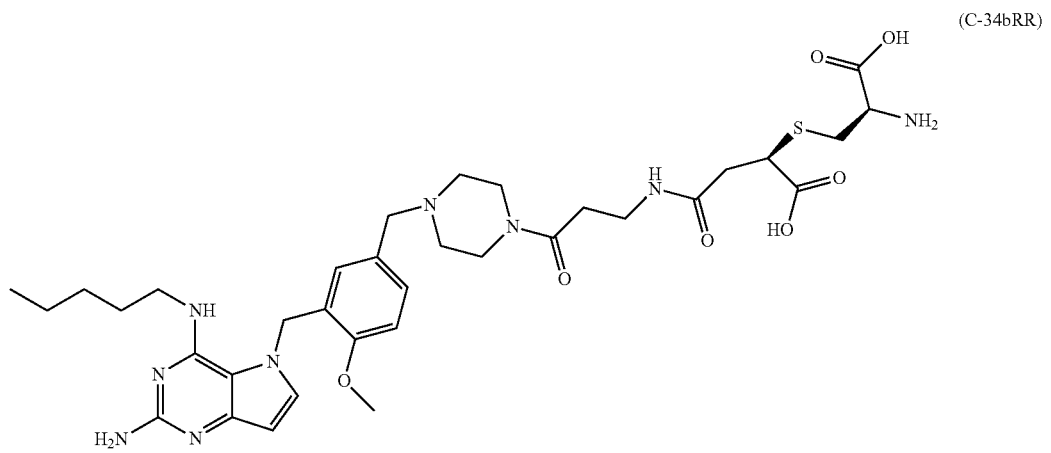 [SMILES: CCCCCNc1nc(N)nc2ccn(Cc3cc(CN4CCN(C(=O)CCNC(=O)C[C@@H](SC[C@H](N)C(=O)O)C(=O)O)CC4)ccc3OC)c12]
(R)-2-(((R)-2-amino-2-carboxyethyl)thio)-4-((3-(4-
(3-((2-amino-4-(pentylamino)-5H-pyrrolo[3,2-d]
pyrimidin-5-yl)methyl)-4-methoxybenzyl)piperazin-
1-yl)-3-oxopropyl)amino)-4-oxobutanoic acid
(C-34bRR)
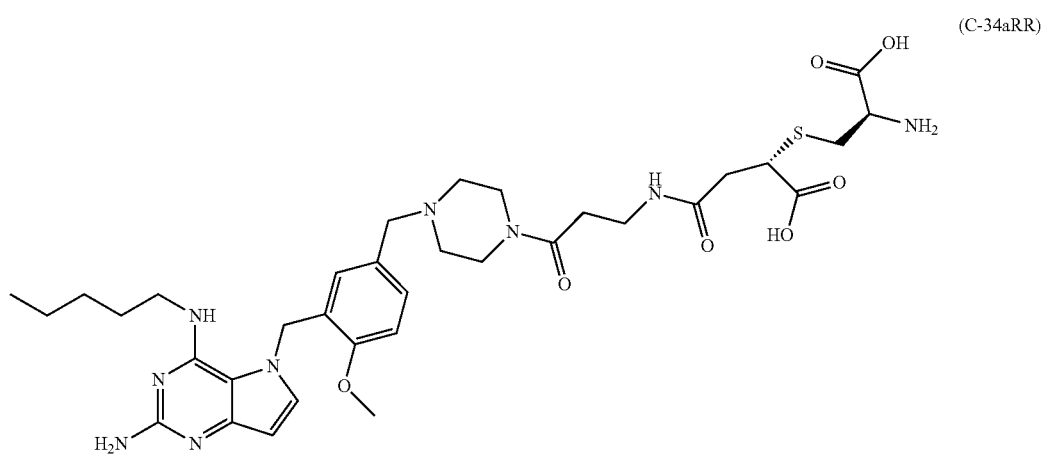 [SMILES: CCCCCNc1nc(N)nc2ccn(Cc3cc(CN4CCN(C(=O)CCNC(=O)C[C@H](SC[C@H](N)C(=O)O)C(=O)O)CC4)ccc3OC)c12]

(S)-2-(((R)-2-amino-2-carboxyethyl)thio)-4-((3-(4-(3-((2-amino-4-(pentylamino)-5H-pyrrolo[3,2-d]pyrimidin-5-yl)methyl)-4-methoxybenzyl)piperazin-1-yl)-3-oxopropyl)amino)-4-oxobutanoic acid (C-34bSR)

Example 35

Synthesis of 1-(4-(4-((2-amino-4-(pentylamino)-5H-pyrrolo[3,2-d]pyrimidin-5-yl)methyl)-3-methoxy-benzyl)piperazin-1-yl)-2-(aminooxy)ethanone (C-35)

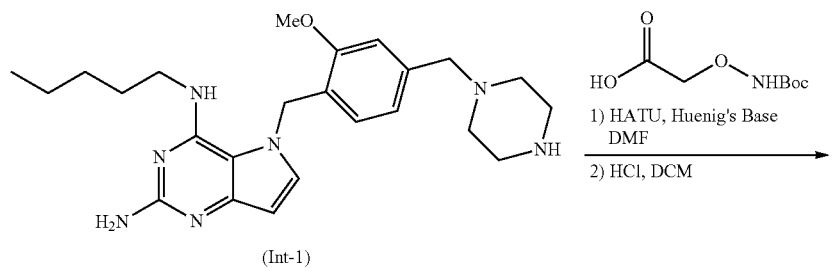

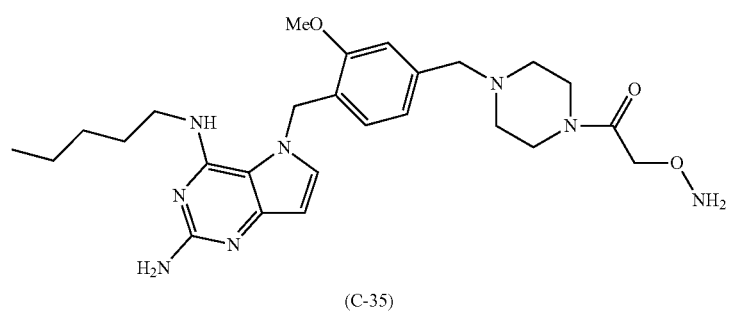

Step 1: A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), 2-(((tert-butoxycarbonyl)amino)oxy)acetic acid (1.1 equiv.), HATU (1.05 equiv.), Huenig's base (5.0 equiv.), and DMF (0.2 M). The reaction mixture was stirred at room temperature for 18 hours and the crude reaction mixture was then purified by ISCO chromatography (0-20% MeOH:DCM) to provide tert-butyl 2-(4-(4-((2-amino-4-(pentylamino)-5H-pyrrolo[3,2-d]pyrimidin-5-yl)methyl)-3-methoxybenzyl)piperazin-1-yl)-2-oxoethoxycarbamate.

Step 2: HCl (20.0 equiv., 4M in dioxane) was added to a round bottom flask charged with tert-butyl 2-(4-(4-((2-amino-4-(pentylamino)-5H-pyrrolo[3,2-d]pyrimidin-5-yl)methyl)-3-methoxybenzyl)piperazin-1-yl)-2-oxoethoxycarbamate (1.0 equiv.) and DCM (0.1 M) at 0° C. The ice bath was removed and reaction mixture stirred at room temperature for 3 hours. The volatiles were removed in vacuo. MeOH (with 8% $NH_4OH$) was added to the resulting residue and the volatiles removed in vacuo. This was repeated 2 more times. The crude reaction mixture was then purified by ISCO chromatography (0-10% MeOH (8% $NH_4OH$):DCM) to deliver 1-(4-(4-((2-amino-4-(pentylamino)-5H-pyrrolo[3,2-d]pyrimidin-5-yl)methyl)-3-methoxybenzyl)piperazin-1-yl)-2-(aminooxy)ethanone (C-35) as a solid: $^1$H NMR ($CDCl_3$): δ 7.12 (d, 1H), 7.00 (s, 1H), 6.90 (s, 1H), 6.69 (d, 1H), 6.38 (d, 1H), 5.52 (t, 1H), 5.30 (s, 2H), 4.35 (s, 2H), 3.94 (s, 3H), 3.64 (s, 2H), 3.52 (m, 2H), 3.38 (m, 4H), 2.44 (m, 4H), 1.62 (s, 2H), 1.45 (m, 2H), 1.38 (m, 2H), 1.25 (m, 2H), 1.12 (m, 2H), 0.87 (t, 3H). LRMS [M+H]=511.4.

Example 36

Synthesis of 1-(4-(4-((2-amino-4-(pentylamino)-5H-pyrrolo[3,2-d]pyrimidin-5-yl)methyl)-3-methoxybenzyl)piperazin-1-yl)-3-(2-aminoethoxy)propan-1-one (C-36)

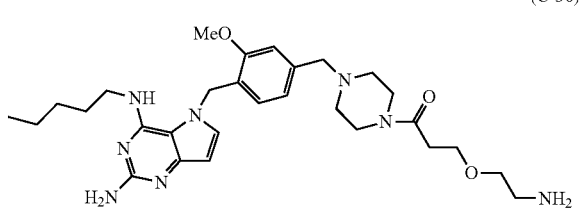

(C-36)

1-(4-(4-((2-amino-4-(pentylamino)-5H-pyrrolo[3,2-d]pyrimidin-5-yl)methyl)-3-methoxybenzyl)piperazin-1-yl)-3-(2-aminoethoxy)propan-1-one (C-36) was prepared following a procedure similar to Example 35, except 3-(2-((tert-butoxycarbonyl)amino)ethoxy)propanoic acid was used in place of 2-(((tert-butoxycarbonyl)amino)oxy)acetic acid, to afford 1-(4-(4-((2-amino-4-(pentylamino)-5H-pyrrolo[3,2-d]pyrimidin-5-yl)methyl)-3-methoxybenzyl)piperazin-1-yl)-3-(2-aminoethoxy)propan-1-one (C-36) as a solid: $^1$H NMR (CD$_3$OD): δ 7.26 (d, 1H), 7.09 (d, 1H), 6.86 (d, 1H), 6.59 (d, 1H), 6.13 (d, 1H), 5.43 (s, 2H), 4.57 (s, 2H), 3.94 (s, 3H), 3.73 (t, 2H), 3.58 (m, 4H), 3.54 (m, 2H), 3.37 (m, 2H), 2.93 (t, 2H), 2.66 (m, 2H), 2.44 (m, 4H), 1.41 (m, 2H), 1.27 (m, 2H), 1.15 (m, 2H), 0.87 (t, 3H). LRMS [M+H]=553.4.

Example 37

Synthesis of N-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-2-(aminooxy)acetamide (C-37)

N-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-2-(aminooxy)acetamide (C-37) was prepared following a procedure similar to Example 35, except 1-(4-(4-((2-amino-4-(pentylamino)-5H-pyrrolo[3,2-d]pyrimidin-5-yl)methyl)-3-methoxybenzyl)piperazin-1-yl)-3-(2-aminoethoxy)propan-1-one (C-36) was used in place of Int-1, to afford N-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-2-(aminooxy)acetamide (C-37) as a solid: $^1$H NMR (CD$_3$OD): δ 7.27 (d, 1H), 7.09 (d, 1H), 6.86 (d, 1H), 6.59 (d, 1H), 6.13 (d, 1H), 5.44 (s, 2H), 4.08 (s, 2H), 3.93 (s, 3H), 3.72 (t, 2H), 3.56 (m, 8H), 3.40 (m, 4H), 2.64 (t, 2H), 2.44 (m, 4H), 1.43 (m, 2H), 1.27 (m, 2H), 1.14 (m, 2H), 0.87 (t, 3H). LRMS [M+H]=626.4.

Example 38

Synthesis of (S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-2-(aminooxy)ethanone (C-38)

(C-38)

(S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-2-(aminooxy)ethanone (C-38) was prepared following a procedure similar to Example 35, except Compound (Int-2) was used in place of Compound (Int-1), to afford (S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-2-(aminooxy)ethanone (C-38) as a solid: $^1$H NMR (CD$_3$OD): δ 7.54 (d, 1), 7.40 (d, 1H), 7.13 (d, 1H), 6.68 (s, 1H), 6.29 (d, 1H), 5.69 (d, 1H), 5.48 (d, 1H), 4.36 (m, 3H), 3.96 (s, 3H), 3.74 (m, 2H), 3.51 (m, 4H), 2.66 (m, 4H), 1.49 (m, 1H), 1.38 (m, 3H), 1.24 (m, 2H), 0.96 (m, 2H), 0.84 (t, 3H). LRMS [M+H]=541.3.

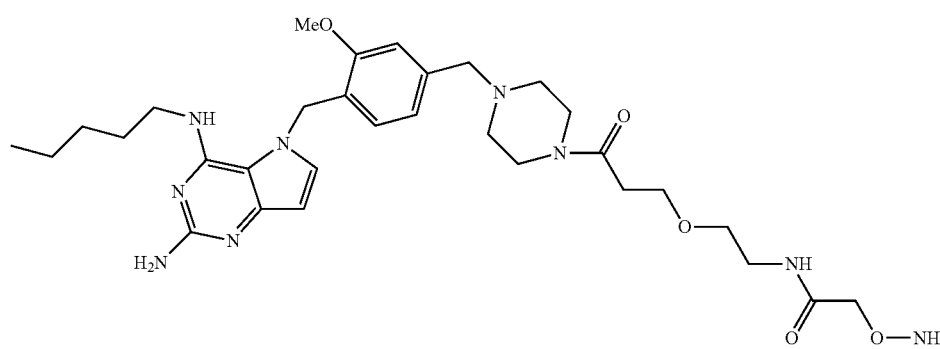

(C-37)

Example 39

(S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-(2-(2-aminoethoxy)ethoxy)propan-1-one (C-39)

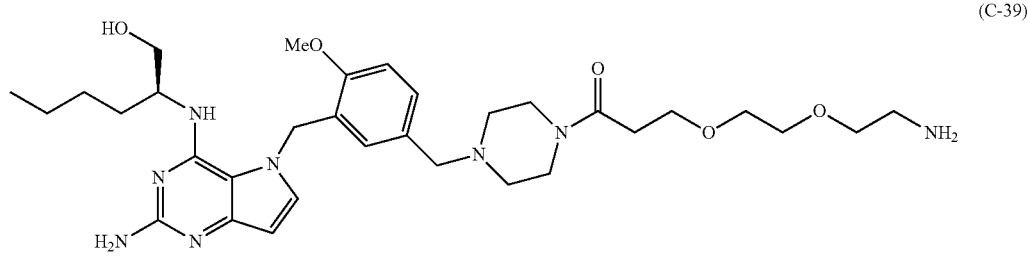 [SMILES: CCCC[C@@H](CO)Nc1nc(N)nc2ccn(Cc3cc(CN4CCN(C(=O)CCOCCOCCN)CC4)ccc3OC)c12]

(C-39)

(S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-(2-(2-aminoethoxy)ethoxy)propan-1-one (C-39) was prepared following a procedure similar to Example 35, except Compound (Int-2) was used in place of Compound (Int-1) and 2,2-dimethyl-4-oxo-3,8,11-trioxa-5-azatetradecan-14-oic acid was used in place of 2-(((tert-butoxycarbonyl)amino)oxy)acetic acid, to afford (S)-1-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-(2-(2-aminoethoxy)ethoxy)propan-1-one (C-39) as a solid: $^1$H NMR (CD$_3$OD): δ 7.56 (d, 1H), 7.44 (d, 1H), 7.16 (d, 1H), 6.77 (s, 1H), 6.31 (d, 1H), 5.71 (d, 1H), 5.50 (d, 1H), 4.38 (m, 1H), 3.98 (s, 3H), 3.78 (m, 4H), 3.72 (m, 2H), 3.67 (m, 6H), 3.53 (m, 4H), 3.14 (m, 2H), 2.77 (m, 2H), 2.69 (m, 4H), 1.51 (m, 1H), 1.26 (m, 3H), 1.02 (m, 2H), 0.86 (t, 3H). LRMS [M+H]=627.5.

Example 40

Synthesis of (S)—N-(2-(2-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropoxy)ethoxy)ethyl)-2-(aminooxy)acetamide (C-40)

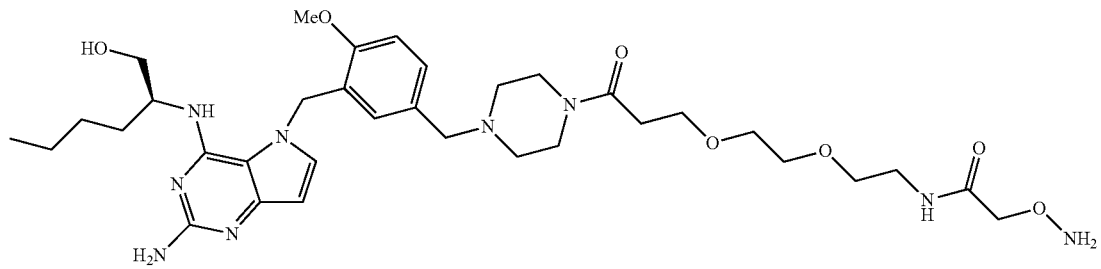

(C-40)

(S)—N-(2-(2-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropoxy)ethoxy)ethyl)-2-(aminooxy)acetamide (C-40) was prepared following a procedure similar to Example 35, except Compound (C-39) was used in place of Compound (Int-1), to afford (S)—N-(2-(2-(3-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-3-oxopropoxy)ethoxy)ethyl)-2-(aminooxy)acetamide (C-40) as a solid: $^1$H NMR (CD$_3$OD): δ 7.54 (d, 1H), 7.47 (d, 1H), 7.17 (d, 1H), 6.78 (s, 1H), 6.30 (d, 1H), 5.68 (d, 1H), 5.50 (d, 1H), 4.36 (m, 1H), 4.09 (s, 2H), 3.97 (s, 3H), 3.73 (m, 8H), 3.56 (m, 4H), 3.43 (t, 2H), 3.23 (m, 2H), 2.88 (m, 4H), 2.66 (t, 2H), 1.49 (m, 1H), 1.26 (m, 3H), 1.04 (m, 2H), 0.84 (t, 3H). LRMS [M+H]=700.4.

Example 41

Synthesis of N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-2-(aminooxy)acetamide (C-41)

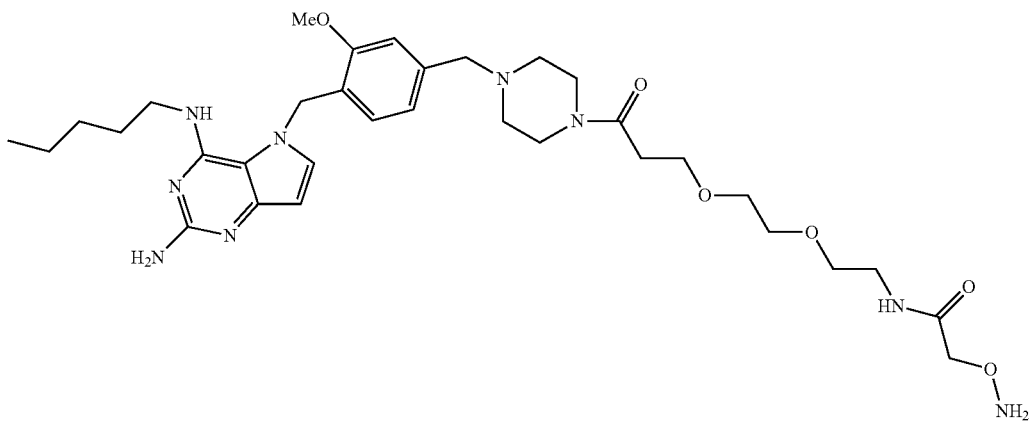

(C-41)

N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-2-(aminooxy)acetamide (C-41) was prepared following a procedure similar to Example 35, except Compound (C-20) was used in place of Compound (Int-1), to afford N-(2-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)ethyl)-2-(aminooxy)acetamide (C-41) as a solid: $^1$H NMR (CD$_3$OD): δ 7.25 (d, 1H), 7.11 (s, 1H), 6.86 (d, 1H), 6.58 (d, 1H), 6.12 (d, 1H), 5.43 (s, 2H), 4.10 (s, 2H), 3.96 (s, 3H), 3.76 (t, 2H), 3.60 (m, 12H), 3.44 (t, 2H), 3.36 (t, 2H), 2.66 (t, 2H), 2.46 (m, 4H), 1.40 (m, 2H), 1.30 (m, 2H), 1.15 (m, 2H), 0.89 (t, 3H). LRMS [M+H]=670.4.

Example 42

Synthesis of 5-(4-((4-(2-(2-(aminooxy)ethoxy)ethyl)piperazin-1-yl)methyl)-2-methoxybenzyl)-N4-pentyl-5H-pyrrolo[3,2-d]pyrimidine-2,4-diamine (C-42)

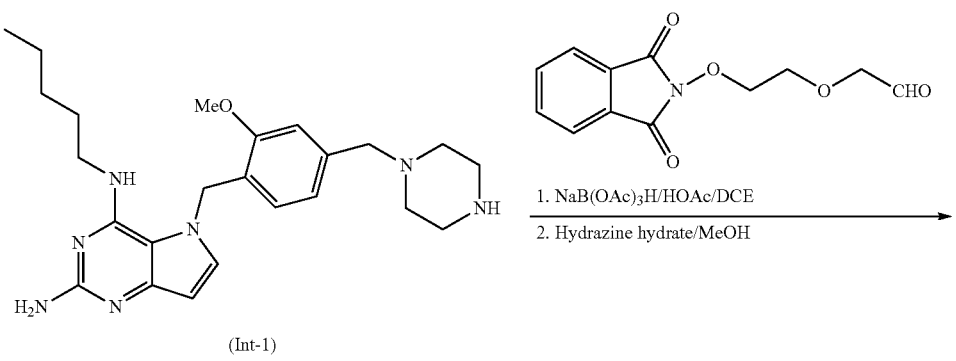

(Int-1)

1. NaB(OAc)$_3$H/HOAc/DCE
2. Hydrazine hydrate/MeOH

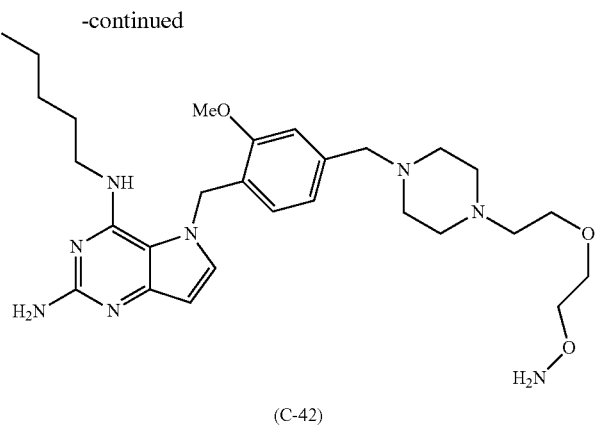

(C-42)

Step 1. In the first step a round bottom flask was charged with 5-(2-methoxy-4-(piperazin-1-ylmethyl)benzyl)-N4-pentyl-5H-pyrrolo[3,2-d]pyrimidine-2,4-diamine (Int-1, 1.0 equiv.) and 2-(2-((1,3-dioxoisoindolin-2-yl)oxy)ethoxy)acetaldehyde (1.2 equiv.) in DCE (0.02 M) and to this mixture was added acetic acid (6.0 equiv.), the mixture was stirred for 15 minutes at room temperature, then sodium triacetoxyborohydride (3.0 equiv.) was added. Stirring was continued for another 3 hours at room temperature. The volatiles were then removed in vacuo. The residue was dissolved in MeOH and purified by reverse phase HPLC, using C18 column (eluted with 10-50% acetonitrile-H₂O containing 0.05% TFA) to deliver 2-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethoxy)isoindoline-1,3-dione. LCMS [M+H]=671.40.

Step 2. A round bottom flask was charged with 2-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethoxy)isoindoline-1,3-dione (1.0 equiv.), hydrazine hydrate (10.0 equiv.), MeOH (0.02 M) and water (0.2 M). The mixture was stirred for 4 hours at room temperature. The reaction mixture was purified by reverse phase HPLC, using C18 column (eluted with 10-50% acetonitrile-H₂O containing 0.05% TFA). The fractions containing desired product were pooled and concentrated under reduced pressure, the residue was then dissolved in MeOH and loaded to a preconditioned Sphere PL-HCO3 MP-resin column and eluted with MeOH, the eluent was concentrated to afford 5-(4-((4-(2-(2-(aminooxy)ethoxy)ethyl)piperazin-1-yl)methyl)-2-methoxybenzyl)-N4-pentyl-5H-pyrrolo[3,2-d]pyrimidine-2,4-diamine (C-42) as a solid: ¹H NMR (CD₃OD): δ 7.22 (d, 1H), 7.08 (d, 1H), 6.83 (d, 1H), 6.56 (d, 1H), 6.10 (d, 1H), 5.40 (s, 2H), 3.94 (s, 3H), 3.76 (m, 2H), 3.60 (m, 4H), 3.50 (s, 2H), 3.34 (d, 3H), 2.59 (m, 4H), 2.49 (s, 4H), 1.38 (m, 2H), 1.26 (m, 2H), 1.12 (m, 2H), 0.87 (t, 3H). LCMS [M+H]=541.40.

Note: 2-(2-((1,3-dioxoisoindolin-2-yl)oxy)ethoxy)acetaldehyde was prepared in a two step process:

Step 1: To a solution of N-hydroxyphthalimide (1.0 equiv.), diethylene glycol (1.0 equiv.) and triphenylphosphine (1.3 equiv.) in THF (0.2 M) was added DEAD (2.2 M solution in toluene, 1.3 equiv.) at 0° C. The resulting solution was stirred overnight at room temperature. The reaction mixture was concentrated in vacuo. The residue was purified by silica gel chromatography (eluted with 20-70% EtOA/Hexanes). The product still contained some Ph₃PO after this chromatography, it was then repurified by reverse phase chromatography (C18 column, eluted with 20-40-100% CH₃CN/water) to afford 2-(2-(2-hydroxyethoxy)ethoxy)isoindoline-1,3-dione LCMS [M+H]=252.10.

Step 2: To a stirred mixture of 2-(2-(2-hydroxyethoxy)ethoxy)isoindoline-1,3-dione (1.0 equiv.) and sodium bicarbonate (2.0 equiv.) in dry DCM (0.08 M) was added Dess-Martin periodinane (2.0 equiv.), the resulting mixture was stirred for 3 hours at room temperature. The reaction mixture was diluted with DCM, then washed with 1N NaOH solution and brine, the organic layer was separated and dried over MgSO4 and evaporated in vacuo. The crude mixture was purified by silica gel chromatography (eluted with 30-70% EtAOc/Hexanes), to deliver 2-(2-((1,3-dioxoisoindolin-2-yl)oxy)ethoxy)acetaldehyde. LCMS [M+H]=250.10.

Example 43

Synthesis of N-(3-(4-(4-((2-amino-4-(pentylamino)-5H-pyrrolo[3,2-d]pyrimidin-5-yl)methyl)-3-methoxybenzyl)piperazin-1-yl)propyl)-2-(aminooxy)acetamide (C-43)

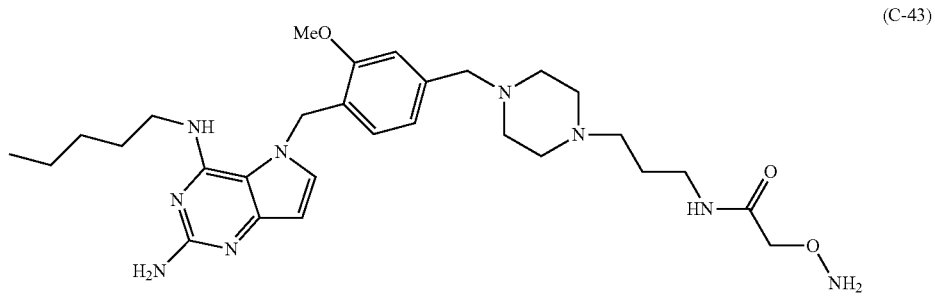 [SMILES: CCCCCNc1nc(N)nc2ccn(Cc3ccc(CN4CCN(CCCNC(=O)CON)CC4)cc3OC)c12]

(C-43)

N-(3-(4-(4-((2-amino-4-(pentylamino)-5H-pyrrolo[3,2-d]pyrimidin-5-yl)methyl)-3-methoxybenzyl)piperazin-1-yl)propyl)-2-(aminooxy)acetamide (C-43) was prepared following a procedure similar to Example 35, except Compound (C-19) was used in place of Compound (Int-1), to afford N-(3-(4-(4-((2-amino-4-(pentylamino)-5H-pyrrolo[3,2-d]pyrimidin-5-yl)methyl)-3-methoxybenzyl)piperazin-1-yl)propyl)-2-(aminooxy)acetamide (C-43) as a solid: $^1$H NMR (CD$_3$OD): δ 7.12 (d, 1H), 6.98 (d, 1H), 6.73 (d, 1H), 6.45 (d, 1H), 6.00 (d, 1H), 5.30 (s, 2H), 3.97 (s, 2H), 3.84 (s, 3H), 3.41 (s, 2H), 3.25 (s, 2H), 2.40 (s, 6H), 2.27 (m, 3H), 1.63 (m, 2H), 1.28 (m, 2H), 1.17 (m, 3H), 1.02 (m, 2H), 0.77 (t, 3H). LCMS [M+H]=568.40.

Example 44

Synthesis of 5-(4-((4-(2-(2-(2-aminoethoxy)ethoxy)ethyl)piperazin-1-yl)methyl)-2-methoxybenzyl)-N4-pentyl-5H-pyrrolo[3,2-d]pyrimidine-2,4-diamine (C-44)

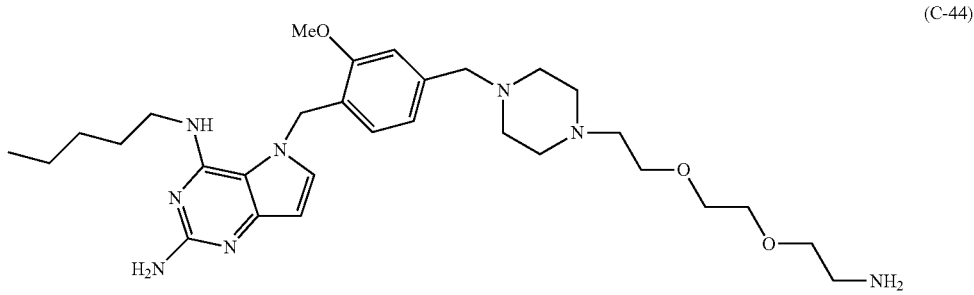 [SMILES: CCCCCNc1nc(N)nc2ccn(Cc3ccc(CN4CCN(CCOCCOCCN)CC4)cc3OC)c12]

5-(4-((4-(2-(2-(2-aminoethoxy)ethoxy)ethyl)piperazin-1-yl)methyl)-2-methoxybenzyl)-N4-pentyl-5H-pyrrolo[3,2-d]pyrimidine-2,4-diamine (C-44) was prepared following a procedure similar to Example 19, except tert-butyl (2-(2-(2-bromoethoxy)ethoxy)ethyl)carbamate was used in place tert-butyl (3-bromopropyl)carbamate, to afford 5-(4-((4-(2-(2-(2-aminoethoxy)ethoxy)ethyl)piperazin-1-yl)methyl)-2-methoxybenzyl)-N4-pentyl-5H-pyrrolo[3,2-d]pyrimidine-2,4-diamine (C-44) as a solid: $^1$H NMR (CD$_3$OD): δ 7.36 (d, 1H), 7.13 (d, 1H), 6.92 (d, 1H), 6.73 (d, 1H), 6.21 (s, 1H), 5.51 (s, 2H), 3.92 (s, 3H), 3.69 (m, 12H), 3.53 (t, 2H), 3.12 (m, 2H), 2.84 (m, 8H), 1.50 (m, 2H), 1.28 (m, 2H), 1.17 (m, 2H), 0.87 (t, 3H). LRMS [M+H]=569.3.

Example 45

Synthesis of N-(2-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethoxy)ethyl)-2-(aminooxy)acetamide (C-45)

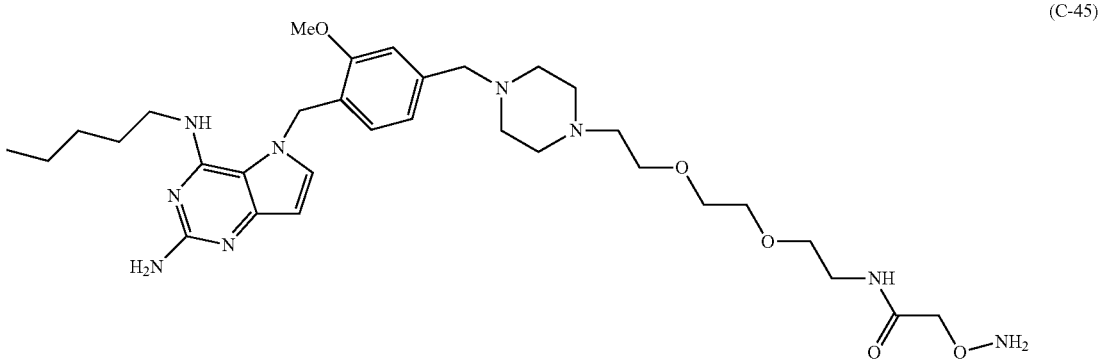 [SMILES: CCCCCNc1nc(N)nc2ccn(Cc3ccc(CN4CCN(CCOCCOCCNC(=O)CON)CC4)cc3OC)c12]

N-(2-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethoxy)ethyl)-2-(aminooxy)acetamide (C-43) was prepared following a procedure similar to Example 35, except Compound (C-44) was used in place of Compound (Int-1), to afford N-(2-(2-(2-(4-(4-((2-amino-4-(pentylamino)-5H-pyrrolo[3,2-d]pyrimidin-5-yl)methyl)-3-methoxybenzyl)piperazin-1-yl)ethoxy)ethoxy)ethyl)-2-(aminooxy)acetamide (C-45) as a solid: $^1$H NMR (CDCl$_3$): δ 7.20 (s, 1H), 6.97 (d, 1H), 6.90 (s, 1H), 6.87 (s, 1H), 6.76 (d, 1H), 6.56 (d, 1H), 6.17 (d, 1H), 5.84 (s, 2H), 5.21 (s, 2H), 4.69 (m, 2H), 4.07 (s, 2H), 3.85 (s, 3H), 3.53 (m, 8H), 3.45 (m, 2H), 3.39 (s, 2H), 3.24 (m, 2H), 2.52 (t, 2H), 2.40 (m, 8H), 1.22 (m, 2H), 1.16 (m, 2H), 1.02 (m, 2H), 0.78 (t, 3H). LRMS [M+H]=642.4.

Example 46

Synthesis of 2,5-dioxopyrrolidin-1-yl 5-(4-(4-((2-amino-4-(pentylamino)-5H-pyrrolo[3,2-d]pyrimidin-5-yl)methyl)-3-methoxybenzyl)piperazin-1-yl)-5-oxopentanoate (C-46)

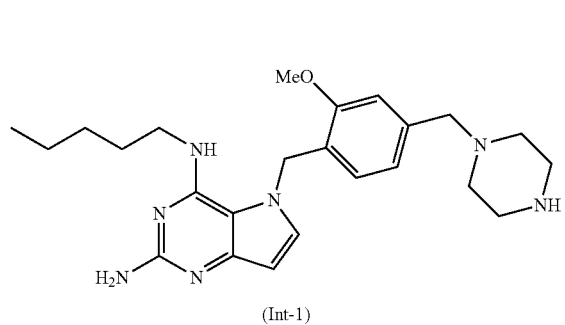

(Int-1)

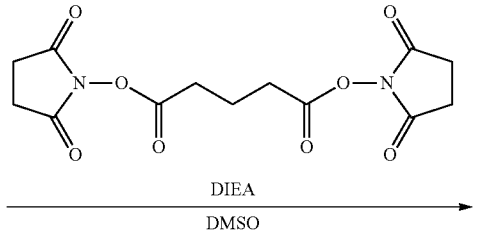

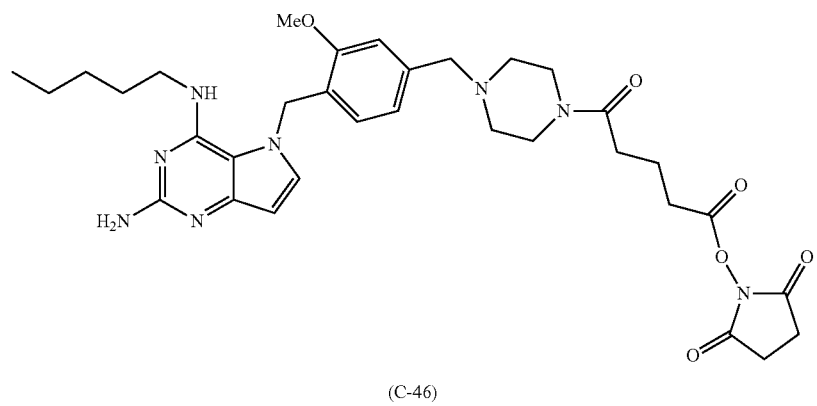

(C-46)

A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), diisopropyl amine (1.3 equiv.), disuccinimidal glutarate (1.3 equiv.), and DMSO (0.1 M). The reaction mixture was stirred room temperature for 3 hours. The crude reaction mixture was then purified by RP-HPLC (0.035% TFA in ACN:0.05% TFA in H$_2$O, C18 column) to afford 2,5-dioxopyrrolidin-1-yl 5-(4-(4-((2-amino-4-(pentylamino)-5H-pyrrolo[3,2-d]pyrimidin-5-yl)methyl)-3-methoxybenzyl)piperazin-1-yl)-5-oxopentanoate (C-46) as a solid as the TFA salt: $^1$H NMR (DMSO): δ 7.41 (s, 1H), 7.37 (s, 3H), 7.19 (s, 1H), 6.94 (s, 1H), 6.57 (s, 1H), 6.22 (d, 1H), 5.56 (s, 2H), 4.30 (s, 2H), 3.86 (s, 3H), 3.44 (m, 4H), 3.35 (m, 2H), 2.92 (m, 2H), 2.80 (m, 8H), 2.71 (m, 2H), 1.83 (m, 2H), 1.44 (m, 2H), 1.20 (m, 2H), 1.09 (m, 2H), 0.80 (t, 3H). LRMS [M+H]=649.3.

Example 47

Synthesis of (S)-2,5-dioxopyrrolidin-1-yl 5-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-5-oxopentanoate (C-47)

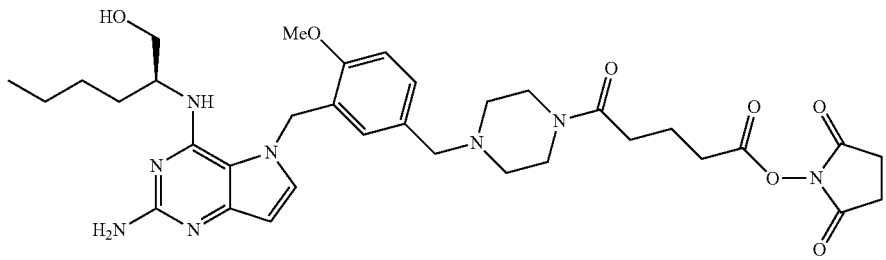

(C-47)

(S)-2,5-dioxopyrrolidin-1-yl 5-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-5-oxopentanoate (C-47) was prepared following a procedure similar to Example 46, except Compound (Int-2) was used in place of Compound (Int-1), to afford (S)-2,5-dioxopyrrolidin-1-yl 5-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-5-oxopentanoate (C-47) as a solid as the TFA salt: $^1$H NMR (DMSO): δ 7.54 (s, 1H), 7.43 (s, 3H), 7.22 (s, 1H), 6.61 (s, 1H), 6.28 (d, 1H), 6.24 (d, 1H), 5.67 (d, 1H), 5.50 (d, 1H), 4.82 (s, 1H), 4.39 (s, 1H), 4.22 (m, 2H), 3.89 (s, 3H), 3.36 (m, 4H), 3.28 (m, 2H), 2.92 (m, 2H), 2.82 (m, 8H), 2.72 (m, 2H), 1.84 (m, 2H), 1.34 (m, 2H), 1.15 (m, 2H), 0.86 (m, 2H), 0.77 (t, 3H). LRMS [M+H]=679.3.

Example 48

Synthesis of (S)-2-amino-6-(5-(4-(3-((2-amino-4-(((S)-1-hydroxyhexan-2-yl)amino)-5H-pyrrolo[3,2-d]pyrimidin-5-yl)methyl)-4-methoxybenzyl)piperazin-1-yl)-5-oxopentanamido)hexanoic acid (C-48)

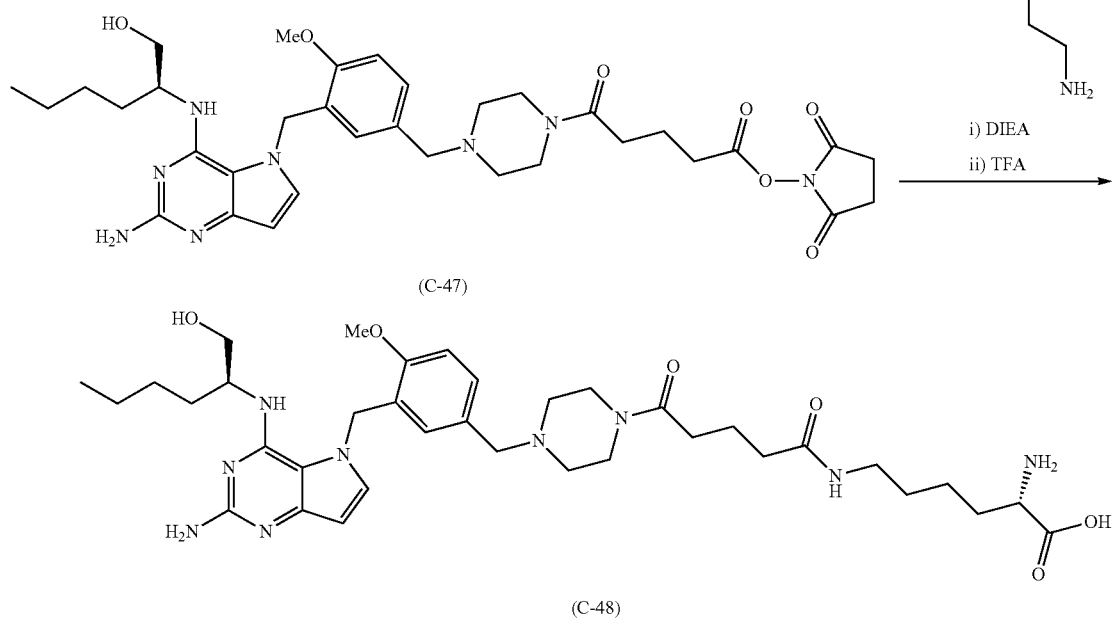

A round bottom flask was charged with (S)-2,5-dioxopyrrolidin-1-yl 5-(4-(3-((2-amino-4-((1-hydroxyhexan-2-yl)amino)-5H-pyrrolo[3,2-d]pyrimidin-5-yl)methyl)-4-methoxybenzyl)piperazin-1-yl)-5-oxopentanoate (C-47 (1.0 eq), Boc-Lys-OH (2.0 eq), DIEA (5.0 eq) and DMF (30 mM). The reaction was stirred at room temperature for 16 hours and the volatiles were removed in vacuo. The crude reaction mixture was purified using RP-HPLC (0.035% TFA in ACN:0.05% TFA in H$_2$O, C18 column) to obtain (S)-6-(5-(4-(3-((2-amino-4-(((S)-1-hydroxyhexan-2-yl)amino)-5H-pyrrolo[3,2-d]pyrimidin-5-yl)methyl)-4-methoxybenzyl)piperazin-1-yl)-5-oxopentanamido)-2-((tert-butoxycarbonyl)amino)hexanoic acid LCMS [M+1]=810.5. (S)-6-(5-(4-(3-((2-amino-4-(((S)-1-hydroxyhexan-2-yl)amino)-5H-pyrrolo[3,2-d]pyrimidin-5-yl)methyl)-4-methoxybenzyl)piperazin-1-yl)-5-oxopentanamido)-2-((tert-butoxycarbonyl)amino)hexanoic acid was treated with 30% TFA by volume in 0.1 M DCM and the volatiles removed in vacuo to obtain (S)-2-amino-6-(5-(4-(3-((2-amino-4-(((S)-1-hydroxyhexan-2-yl)amino)-5H-pyrrolo[3,2-d]pyrimidin-5-yl)methyl)-4-methoxybenzyl)piperazin-1-yl)-5-oxopentanamido)hexanoic acid (C-48) as a solid as the TFA salt: $^1$H NMR (CD$_3$OD): δ 7.49 (m, 2H), 7.21 (d, 1H), 6.77 (s, 1H), 6.29 (d, 1H), 5.68 (d, 1H), 5.50 (d, 1H), 4.36 (m, 1H), 4.20 (m, 2H), 3.99 (S, 3H), 3.93 (m, 1H), 3.76 (m, 2H), 3.50 (m, 2H), 3.19 (m, 4H), 2.44 (t, 2H), 2.24 (t, 2H), 2.16 (m, 4H), 1.88 (m, 4H), 1.51 (m, 2H), 1.25 (m, 6H), 1.03 (m, 2H), 0.84 (t, 3H). LRMS [M+H]=710.3.

Example 49

Synthesis of (S)-2-amino-6-(5-(4-(4-((2-amino-4-(pentylamino)-5H-pyrrolo[3,2-d]pyrimidin-5-yl)methyl)-3-methoxybenzyl)piperazin-1-yl)-5-oxopentanamido)hexanoic acid (C-49)

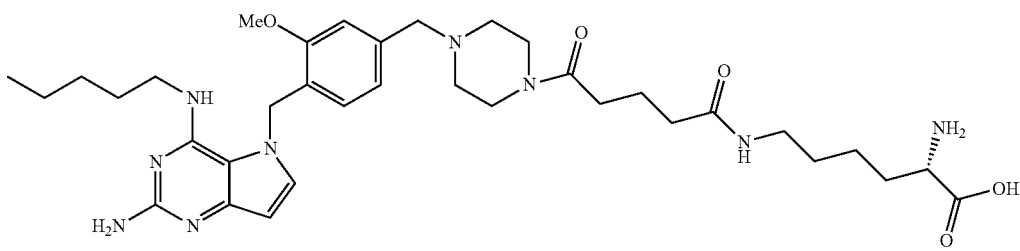

(C-49)

(S)-2-amino-6-(5-(4-(4-((2-amino-4-(pentylamino)-5H-pyrrolo[3,2-d]pyrimidin-5-yl)methyl)-3-methoxybenzyl)piperazin-1-yl)-5-oxopentanamido)hexanoic acid (C-49) was prepared following a procedure similar to Example 48, except Compound (C-46) was used in place of Compound (C-47), to afford (S)-2-amino-6-(5-(4-(4-((2-amino-4-(pentylamino)-5H-pyrrolo[3,2-d]pyrimidin-5-yl)methyl)-3-methoxybenzyl)piperazin-1-yl)-5-oxopentanamido) hexanoic acid (C-49) as a solid as the TFA salt: $^1$H NMR (CD$_3$OD): δ 7.37 (d, 1H), 7.22 (d, 1H), 7.01 (d, 1H), 6.78 (d, 1H), 6.23 (s, 1H), 5.56 (s, 2H), 4.07 (m, 2H), 3.95 (s, 3H), 3.79 (m, 1H), 3.73 (m, 2H), 3.55 (m, 2H), 2.98 (m, 4H), 2.43 (t, 2H), 2.23 (t, 2H), 2.04 (m, 4H), 1.89 (m, 4H), 1.54 (m, 6H), 1.30 (m, 2H), 1.19 (m, 2H), 0.88 (t, 3H). LRMS [M+H]=680.4.

Example 50

Synthesis of 2,5-dioxopyrrolidin-1-yl 5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanoate (C-50)

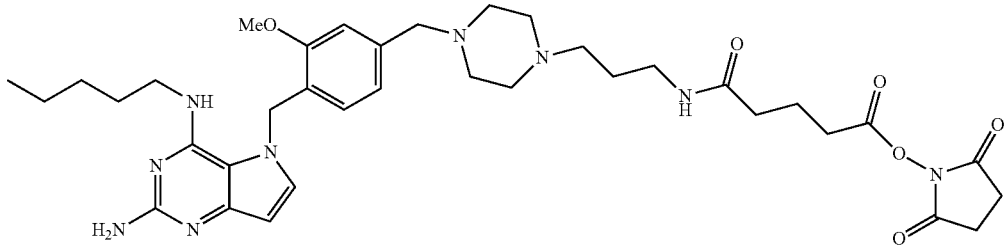

(C-50)

2,5-dioxopyrrolidin-1-yl 5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanoate (C-50) was prepared following a procedure similar to Example 46, except Compound (C-19) was used in place of Compound (Int-1), to afford 2,5-dioxopyrrolidin-1-yl 5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanoate (C-50) as a solid as the TFA salt: $^1$H NMR (DMSO): δ 8.00 (s, 1H), 7.40 (m, 4H), 7.02 (s, 1H), 6.82 (s, 1H), 6.55 (d, 1H), 6.21 (d, 1H), 5.53 (s, 2H), 3.83 (m, 5H), 3.00 (m, 8H), 2.81 (m, 4H), 2.69 (m, 2H), 2.19 (m, 2H), 1.84 (m, 2H), 1.75 (m, 4H), 1.45 (m, 2H), 1.22 (m, 4H), 1.09 (m, 4H), 0.80 (t, 3H). LRMS [M+H]=706.4.

Example 51

Synthesis of (S)-2-amino-6-(5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanamido)hexanoic acid (C-51)

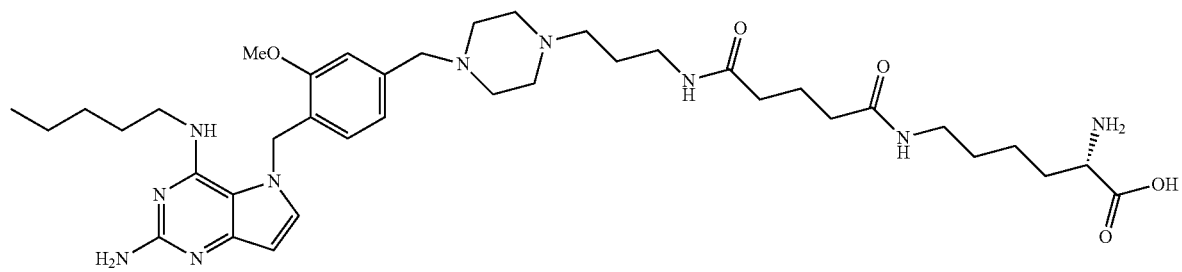

(C-51)

(S)-2-amino-6-(5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanamido) hexanoic acid (C-51) was prepared following a procedure similar to Example 48, except Compound (C-50) was used in place of Compound (C-47), to afford (S)-2-amino-6-(5-((3-(4-(4-((2-amino-4-(pentylamino)-5H-pyrrolo[3,2-d]pyrimidin-5-yl)methyl)-3-methoxybenzyl)piperazin-1-yl)propyl)amino)-5-oxopentanamido)hexanoic acid (C-51) as a solid as the TFA salt: $^1$H NMR (CD$_3$OD): δ 7.35 (d, 1H), 7.12 (s, 1H), 6.94 (d, 1H), 6.75 (d, 1H), 6.22 (s, 1H), 5.52 (s, 2H), 3.92 (s, 3H), 3.86 (t, 1H), 3.71 (s, 2H), 3.54 (m, 2H), 3.22 (m, 8H), 3.05 (m, 2H), 2.82 (m, 2H), 2.21 (m, 4H), 1.89 (m, 4H), 1.53 (m, 6H), 1.30 (m, 4H), 1.18 (m, 2H), 0.88 (t, 3H). LRMS [M+H]=737.4.

Example 52

Synthesis of 2,5-dioxopyrrolidin-1-yl 5-(4-(3-((2-amino-4-(pentylamino)-5H-pyrrolo[3,2-d]pyrimidin-5-yl)methyl)-4-methoxybenzyl)piperazin-1-yl)-5-oxopentanoate (C-52)

(C-52)

2,5-dioxopyrrolidin-1-yl 5-(4-(3-((2-amino-4-(pentylamino)-5H-pyrrolo[3,2-d]pyrimidin-5-yl)methyl)-4-methoxybenzyl)piperazin-1-yl)-5-oxopentanoate (C-52) was prepared following a procedure similar to Example 46, except Compound (Int-3) was used in place of Compound (Int-1), to afford 2,5-dioxopyrrolidin-1-yl 5-(4-(3-((2-amino-4-(pentylamino)-5H-pyrrolo[3,2-d]pyrimidin-5-yl)methyl)-4-methoxybenzyl)piperazin-1-yl)-5-oxopentanoate (C-52) as a solid as the TFA salt: LRMS [M+H]=649.4.

Example 53

Synthesis of (S)-2-amino-6-(5-(4-(3-((2-amino-4-(pentylamino)-5H-pyrrolo[3,2-d]pyrimidin-5-yl)methyl)-4-methoxybenzyl)piperazin-1-yl)-5-oxopentanamido)hexanoic acid (C-53)

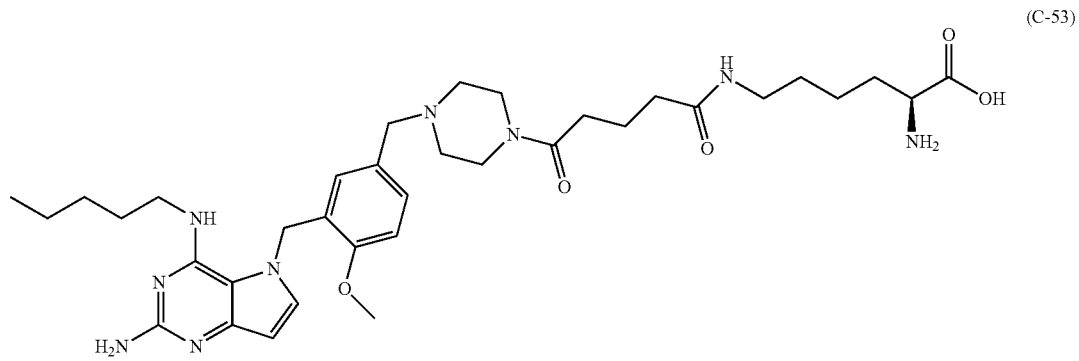 [SMILES: CCCCCNc1nc(N)nc2ccn(Cc3cc(CN4CCN(C(=O)CCCC(=O)NCCCC[C@H](N)C(=O)O)CC4)ccc3OC)c12]

(C-53)

(S)-2-amino-6-(5-(4-(3-((2-amino-4-(pentylamino)-5H-pyrrolo[3,2-d]pyrimidin-5-yl)methyl)-4-methoxybenzyl)piperazin-1-yl)-5-oxopentanamido)hexanoic acid (C-53) was prepared following a procedure similar to Example 48, except Compound (C-52) was used in place of Compound (C-47), to afford S)-2-amino-6-(5-(4-(3-((2-amino-4-(pentylamino)-5H-pyrrolo[3,2-d]pyrimidin-5-yl)methyl)-4-methoxybenzyl)piperazin-1-yl)-5-oxopentanamido)hexanoic acid (C-53) as a solid as the TFA salt: $^1$H NMR (DMSO): δ 8.22 (s, 3H), 7.79 (t, 1H), 7.51 (s, 2H), 7.42 (m, 2H), 7.27 (t, 1H), 7.17 (d, 1H), 6.61 (s, 1H), 6.23 (d, 1H), 5.57 (s, 2H), 4.05 (m, 2H), 3.87 (s, 5H), 3.42 (m, 3H), 3.02 (m, 3H), 2.89 (m, 2H), 2.31 (t, 2H), 2.09 (t, 2H), 1.72 (m, 4H), 1.41 (m, 5H), 1.22 (m, 2H), 1.07 (m, 2H), 0.83 (t, 3H). LRMS [M+H]=680.4.

Example 54

Synthesis of perfluorophenyl 5-(4-(4-((2-amino-4-(pentylamino)-5H-pyrrolo[3,2-d]pyrimidin-5-yl)methyl)-3-methoxybenzyl)piperazin-1-yl)-5-oxopentanoate (C-54)

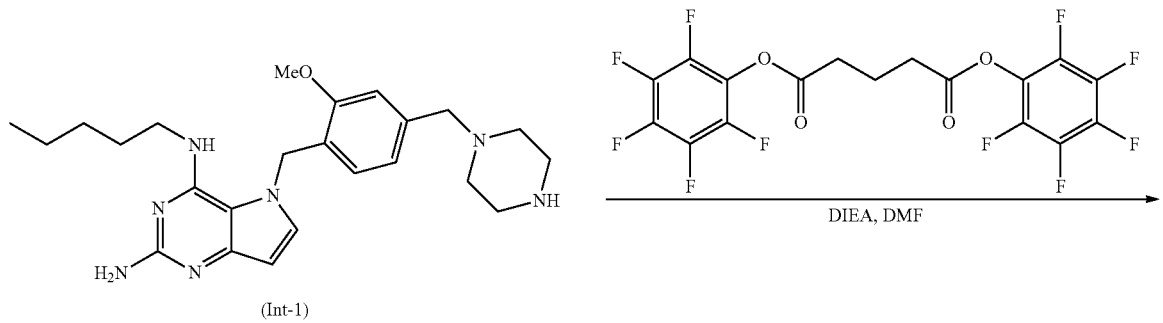

(Int-1)

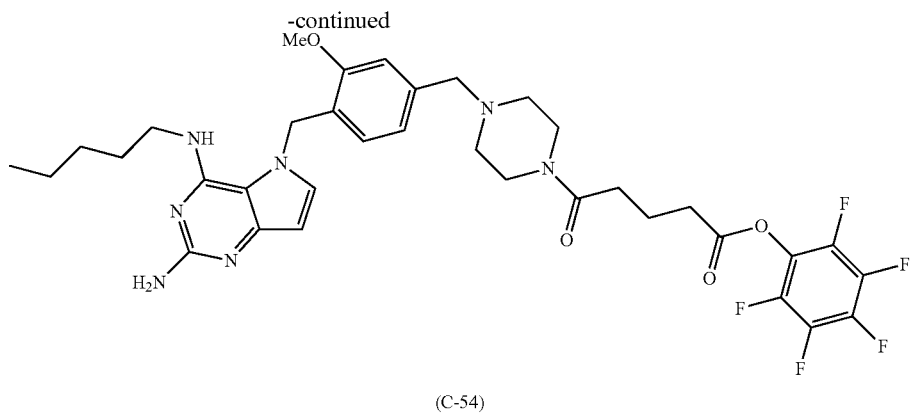

(C-54)

A round-bottom flask was charged with 5-(2-methoxy-4-(piperazin-1-ylmethyl)benzyl)-N4-pentyl-5H-pyrrolo[3,2-d]pyrimidine-2,4-diamine (Int-1, 1.0 equiv.), DIEA (3.0 equiv.), bis(perfluorophenyl) glutarate (2.0 equiv.), and DMF (0.01 M). The reaction was stirred at room temperature for 2 hours and then the crude reaction mixture was purified by RP-HPLC (0.035% TFA in ACN:0.05% TFA in H₂O, C18 column) yielding perfluorophenyl 5-(4-(4-((2-amino-4-(pentylamino)-5H-pyrrolo[3,2-d]pyrimidin-5-yl)methyl)-3-methoxybenzyl)piperazin-1-yl)-5-oxopentanoate (C-54) as a solid as the TFA salt. LCMS [M+1]=718.4.

Note: Bis(perfluorophenyl) glutarate was prepared by glutaroyl dichloride (1.0 equiv.), THF (0.15 M) and triethylamine (2.2 equiv.) to a round bottom flask and cooling the reaction mixture to 0° C. A solution of 2,3,4,5,6-pentafluorophenol (2.1 equiv.) in THF (1.2 M) was then added slowly. The reaction mixture was stirred for 2 hours at room temperature. The mixture was filtered through silica gel and then concentrated in vacuo. The residue was purified by silica gel column eluted with hexane-ethyl acetate (9:1) and concentrated to give bis(perfluorophenyl) glutarate as solid. LCMS [M+23]=487.2.

Example 55

Synthesis of perfluorophenyl 3-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanoate (C-55)

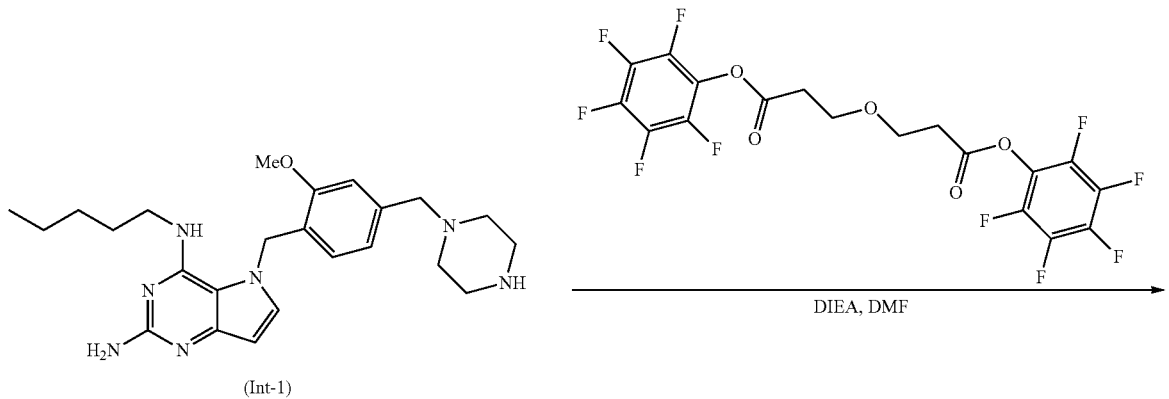

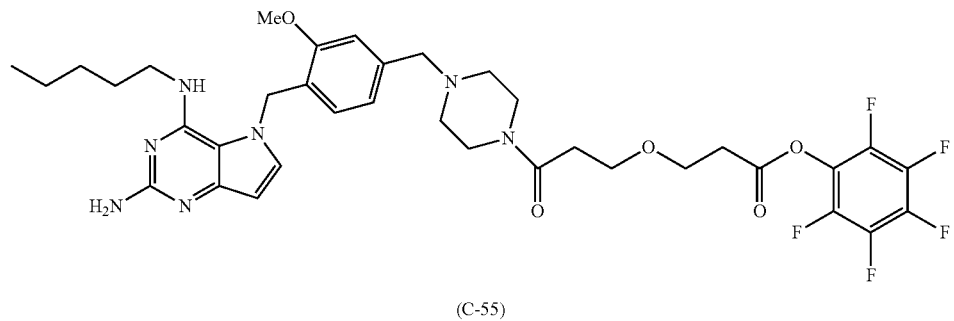

(C-55)

Perfluorophenyl 3-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanoate (C-55) was prepared as a solid as the TFA salt following a procedure similar to Example 54, except bis(perfluorophenyl) 3,3'-oxydipropanoate was used in place of bis(perfluorophenyl) glutarate. $^1$H NMR (Acetonitrile-$d_3$) δ 7.33 (d, 1H), 7.30 (d, 1H), 6.95 (d, 1H), 6.73 (d, 1H), 6.22 (d, 1H), 6.06 (m, 1H), 5.43 (s, 2H), 4.18 (s, 2H), 3.92 (s, 3H), 3.81 (t, 2H), 3.74 (t, 2H), 3.47 (m, 2H), 2.95 (t, 2H), 2.60 (t, 2H), 2.14 (d, 2H), 1.45 (m, 2H), 1.28 (m, 2H), 1.15 (m, 2H), 0.87 (t, 3H).

LRMS [M+H]=748.4. $^{19}$F NMR (471 MHz, Acetonitrile-$d_3$) δ-154.71 (d, 2F), −160.40 (d, 1F), −164.57 (dd, 2F).

Example 56

Synthesis of perfluorophenyl 3-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)propanoate (C-56)

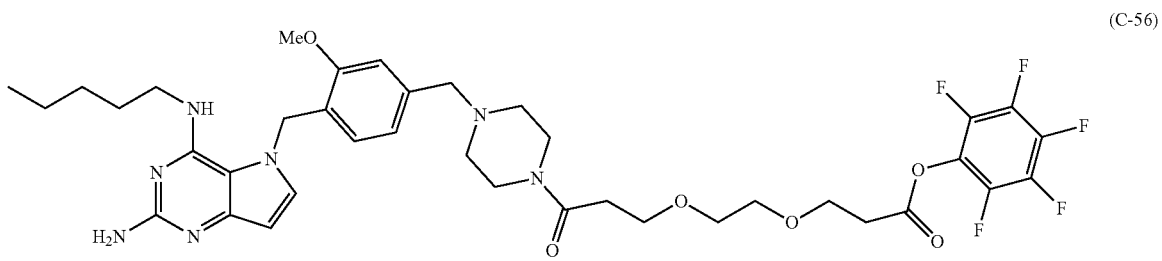 [SMILES: CCCCCNc1nc(N)nc2ccn(Cc3ccc(CN4CCN(C(=O)CCOCCOCCC(=O)Oc5c(F)c(F)c(F)c(F)c5F)CC4)cc3OC)c12]

(C-56)

3-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)propanoate (C-56) was prepared following a procedure similar to Example 54, except bis(perfluorophenyl) 3,3'-(ethane-1,2-diylbis(oxy))dipropanoate was used in place of bis(perfluorophenyl) glutarate to obtain 3-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethoxy)propanoate (C-54). LRMS [M+H]=792.4.

Example 57

Synthesis of (S)-2-amino-6-(3-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanamido)hexanoic acid (C-57)

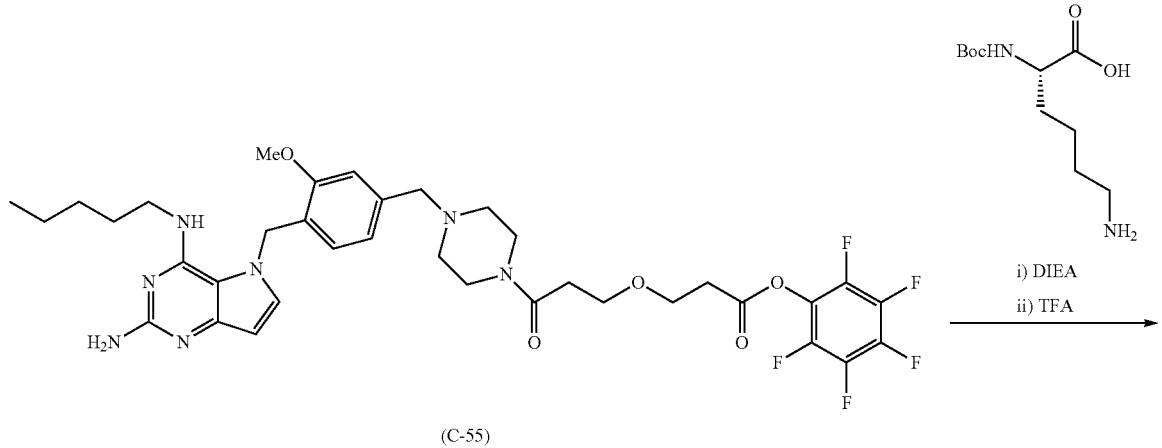

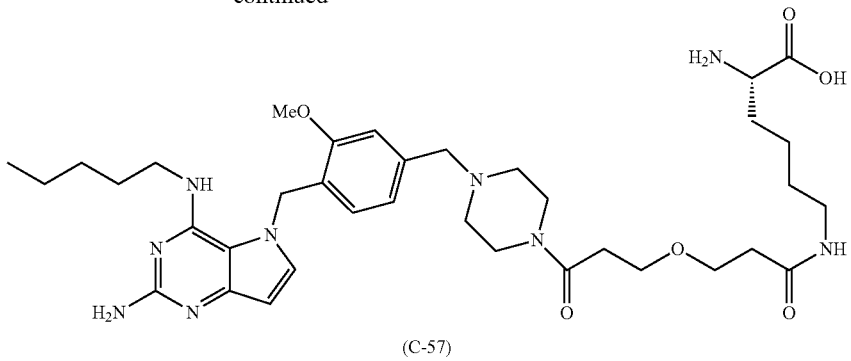

(C-57)

A round bottom flask was charged with perfluorophenyl 3-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanoate (C-55, 1.0 equiv.), Boc-Lys-OH (2.0 equiv.), DIEA (5.0 equiv.) and DMF (30 mM). The reaction was stirred at room temperature for 16 hours and the volatiles were removed in vacuo. The crude reaction mixture was purified using RP-HPLC (0.035% TFA in ACN:0.05% TFA in H$_2$O, C18 column) to obtain (S)-6-(3-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanamido)-2-((tert-butoxycarbonyl)amino)hexanoic acid. LCMS [M+1]=810.5. The boc protected compound was treated with 30% TFA by volume in 0.1M DCM and then the volatiles removed in vacuo to obtain (S)-2-amino-6-(3-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)propanamido)hexanoic acid (C-57) as a solid as the TFA salt: $^1$H NMR (DMSO): δ 8.18 (m, 3H), 7.80 (s, 1H), 7.41 (m, 4H), 7.18 (s, 1H), 6.94 (d, 1H), 6.59 (d, 1H), 6.22 (d, 1H), 5.56 (s, 2H), 4.24 (m, 1H), 3.86 (m, 7H), 3.56 (m, 4H), 3.44 (m, 4H), 3.01 (m, 4H), 2.60 (m, 2H), 2.28 (m, 2H), 1.74 (m, 2H), 1.45 (m, 2H), 1.38 (m, 3H), 1.21 (m, 3H), 1.09 (m, 2H), 0.80 (t, 3H). LCMS [M+1]=710.5.

Example 58

Synthesis of N-(15-(4-(4-((2-amino-4-(pentylamino)-5H-pyrrolo[3,2-d]pyrimidin-5-yl)methyl)-3-methoxybenzyl)piperazin-1-yl)-15-oxo-3,6,9,12-tetraoxapentadecyl)-5-((3aS,4S,6aR)-2-oxohexahydro-1H-thieno[3,4-d]imidazol-4-yl)pentanamide (C-58)

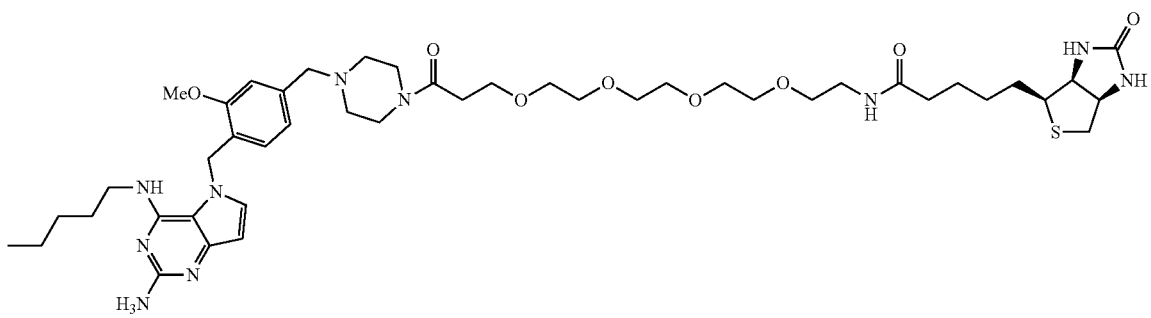

(C-58)

N-(15-(4-(4-((2-amino-4-(pentylamino)-5H-pyrrolo[3,2-d]pyrimidin-5-yl)methyl)-3-methoxybenzyl)piperazin-1-yl)-15-oxo-3,6,9,12-tetraoxapentadecyl)-5-((3aS,4S,6aR)-2-oxohexahydro-1H-thieno[3,4-d]imidazol-4-yl)pentanamide (C-58) was prepared following a procedure similar to Example 46, except 2,5-dioxopyrrolidin-1-yl 17-oxo-21-((3aS,4S,6aR)-2-oxohexahydro-1H-thieno[3,4-d]imidazol-4-yl)-4,7,10,13-tetraoxa-16-azahenicosan-1-oate was used in place of disuccinimidal glutarate, to afford N-(15-(4-(4-((2-amino-4-(pentylamino)-5H-pyrrolo[3,2-d]pyrimidin-5-yl)methyl)-3-methoxybenzyl)piperazin-1-yl)-15-oxo-3,6,9,12-tetraoxapentadecyl)-5-((3aS,4S,6aR)-2-oxohexahydro-1H-thieno[3,4-d]imidazol-4-yl)pentanamide (C-58) as a solid as the TFA salt: $^1$H NMR (DMSO): δ 7.84 (m, 2H), 7.42 (m, 4H), 7.22 (m, 1H), 6.94 (d, 1H), 6.56 (d, 1H), 6.42 (s, 1H), 6.37 (s, 1H), 6.22 (s, 1H), 5.57 (s, 2H), 4.29 (m, 2H), 4.11 (m, 2H), 3.86 (s, 3H), 3.60 (m, 4H), 3.48 (m, 16H), 3.37 (m, 4H), 3.16 (m, 4H), 3.08 (m, 2H), 2.80 (m, 1H), 2.56 (m, 2H), 2.05 (m, 2H), 1.58 (m, 1H), 1.45 (m, 5H), 1.23 (m, 4H), 1.07 (m, 2H), 0.80 (t, 3H). LRMS [M+H]=911.6.

Example 59

Synthesis of 4-((R)-6-amino-2-((S)-2-(3-(2,5-dioxo-2,5-dihydro-1H-pyrrol-1-yl)propanamido)-3-phenylpropanamido)hexanamido)benzyl 4-(4-((2-amino-4-(pentylamino)-5H-pyrrolo[3,2-d]pyrimidin-5-yl)methyl)-3-methoxybenzyl)piperazine-1-carboxylate (C-59)

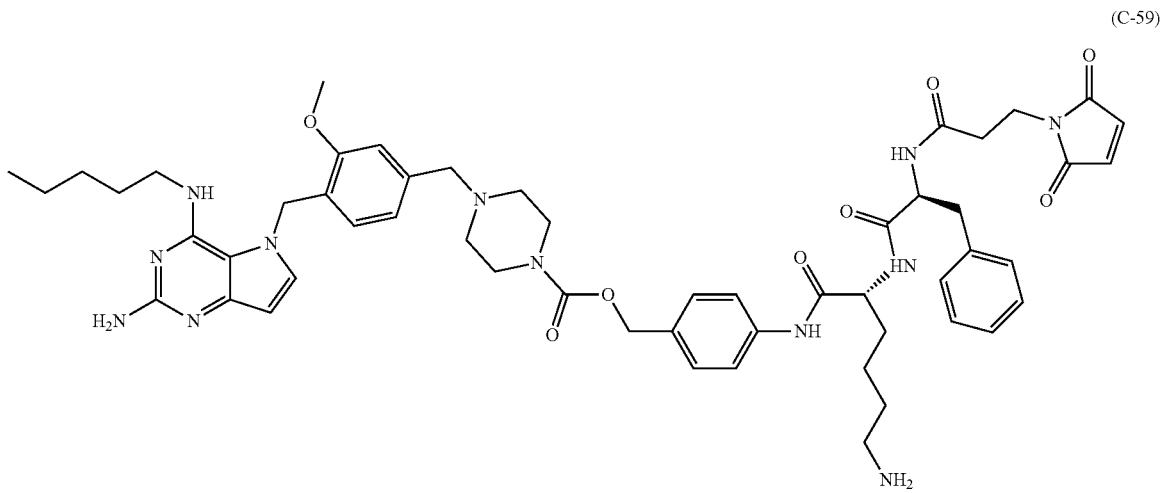 [SMILES: CCCCCNc1nc(N)nc2ccn(Cc3ccc(CN4CCN(C(=O)OCc5ccc(NC(=O)[C@@H](CCCCN)NC(=O)[C@H](Cc6ccccc6)NC(=O)CCN6C(=O)C=CC6=O)cc5)CC4)cc3OC)c12]

(C-59)

4-((R)-6-amino-2-((S)-2-(3-(2,5-dioxo-2,5-dihydro-1H-pyrrol-1-yl)propanamido)-3-phenylpropanamido)hexanamido)benzyl 4-(4-((2-amino-4-(pentylamino)-5H-pyrrolo[3,2-d]pyrimidin-5-yl)methyl)-3-methoxybenzyl)piperazine-1-carboxylate (C-59) was prepared as a solid as the TFA salt according to the scheme shown for Example (C-30), except (9H-fluoren-9-yl)methyl ((S)-1-(((R)-6-amino-1-((4-((((4-nitrophenoxy)carbonyl)oxy)methyl)phenyl)amino)-1-oxohexan-2-yl)amino)-1-oxo-3-phenylpropan-2-yl)carbamate was used in place of (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate in the first step: $^1$H NMR (CD$_3$OD): δ 8.26 (d, 1H), 7.91 (t, 1H), 7.61 (d, 2H), 7.35 (m, 3H), 7.25 (m, 3H), 7.19 (m, 3H), 7.03 (d, 1H), 6.79 (d, 1H), 6.76 (s, 2H), 6.24 (d, 1H), 5.57 (s, 2H), 5.11 (s, 2H), 4.41 (m, 1H), 4.33 (s, 2H), 3.98 (t, 1H), 3.95 (s, 3H), 3.70 (m, 3H), 3.54 (t, 2H), 3.24 (m, 4H), 3.10 (m, 1H), 3.02 (m, 1H), 2.83 (m, 1H), 2.47 (t, 2H), 1.92 (m, 2H), 1.52 (m, 4H), 1.42 (m, 2H), 1.30 (m, 3H), 1.18 (m, 2H), 0.88 (t, 3H). LRMS [M+H]=1013.5.

Example 60

Synthesis of 4-((S)-2-((S)-2-(3-(2-(2,5-dioxo-2,5-dihydro-1H-pyrrol-1-yl)ethoxy)propanamido)-3-methylbutanamido)propanamido)benzyl 4-(4-((2-amino-4-(pentylamino)-5H-pyrrolo[3,2-d]pyrimidin-5-yl)methyl)-3-methoxybenzyl)piperazine-1-carboxylate (C-60)

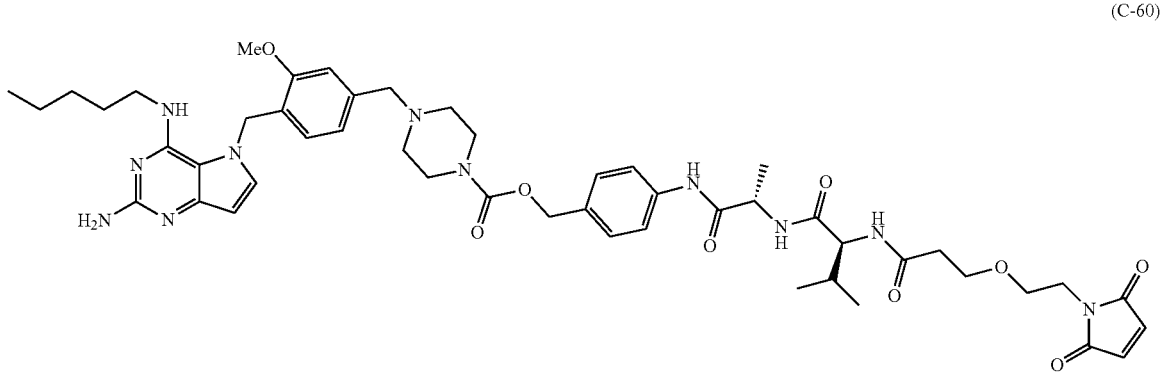 [SMILES: CCCCCNc1nc(N)nc2ccn(Cc3ccc(CN4CCN(C(=O)OCc5ccc(NC(=O)[C@H](C)NC(=O)[C@@H](NC(=O)CCOCCN6C(=O)C=CC6=O)C(C)C)cc5)CC4)cc3OC)c12]

(C-60)

4-((S)-2-((S)-2-(3-(2-(2,5-dioxo-2,5-dihydro-1H-pyrrol-1-yl)ethoxy)propanamido)-3-methylbutanamido)propanamido)benzyl 4-(4-((2-amino-4-(pentylamino)-5H-pyrrolo[3,2-d]pyrimidin-5-yl)methyl)-3-methoxybenzyl)piperazine-1-carboxylate (C-60) was prepared as a solid as the TFA salt according to the scheme shown for Example (C-30), except (9H-fluoren-9-yl)methyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate was used in place of (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate in the first step: $^1$H NMR (CD$_3$OD): δ 9.65 (s, 1H), 8.20 (d, 1H), 7.97 (d, 1H), 7.60 (m, 2H), 7.34 (m, 2H), 7.31 (s, 1H), 7.22 (d, 1H), 7.03 (d, 1H), 6.80 (m, 2H), 6.77 (s, 2H), 6.23 (d, 1H), 5.57 (s, 2H), 5.11 (s, 2H), 4.48 (t, 1H), 4.31 (s, 3H), 4.15 (t, 1H), 3.95 (m, 4H), 3.68 (m, 4H), 3.62 (m, 2H), 3.53 (m, 8H), 2.49 (t, 2H), 2.11 (m, 1H), 1.52 (m, 2H), 1.44 (d, 3H), 1.28 (m, 2H), 1.18 (m, 2H), 0.98 (m, 6H), 0.87 (t, 3H). LRMS [M+H]=952.6.

Example 61

Synthesis of (2S,3S,4S,5R,6S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2,5-dioxo-2,5-dihydro-1H-pyrrol-1-yl)propanamido)propanamido)phenoxy)-3,4,5-trihydroxytetrahydro-2H-pyran-2-carboxylic acid (C-61)

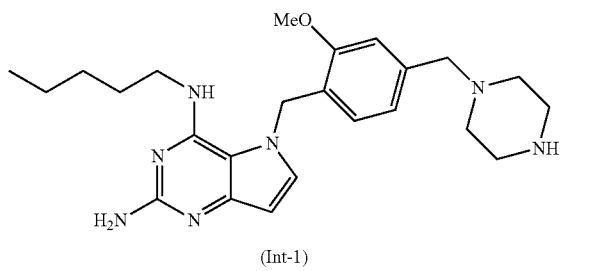

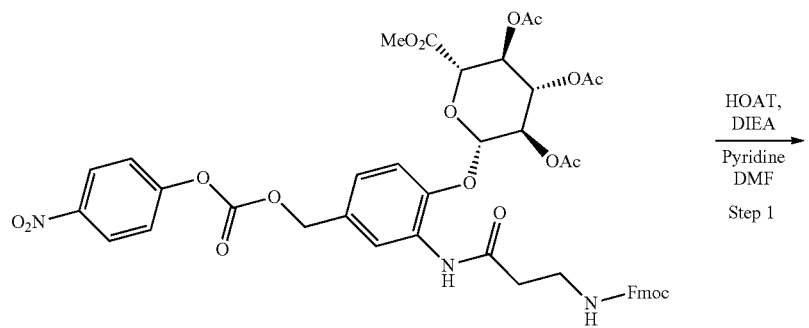

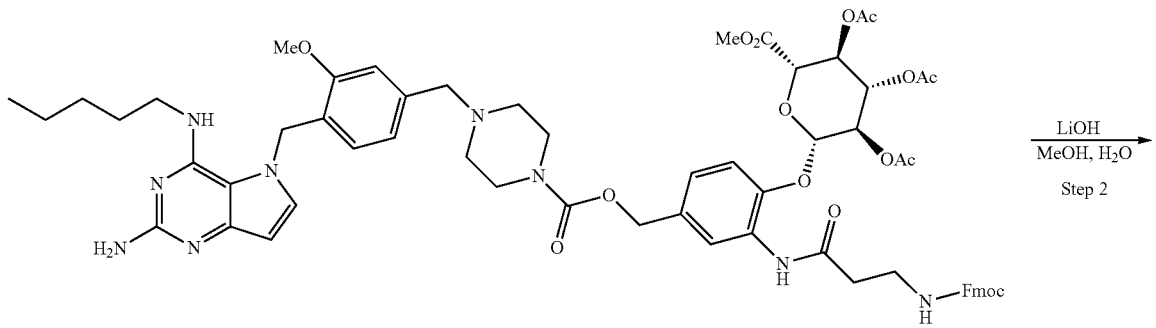

-continued

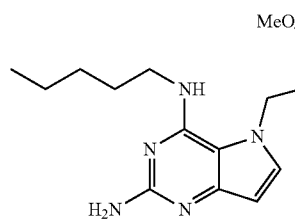 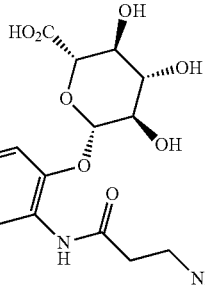 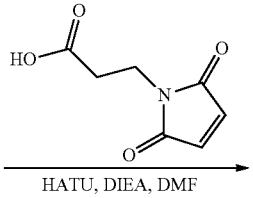

HATU, DIEA, DMF
Step 3

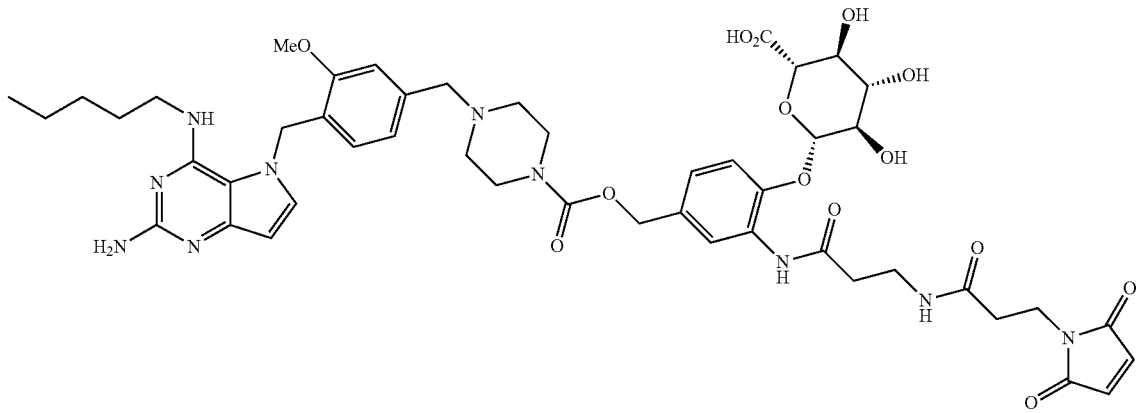

(C-61)

Step 1: A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), HOAT (2.0 equiv.), Huenig's base (14.0 equiv.), (3S,4R,5R,6R)-2-(2-(3-(((((9H-fluoren-9-yl)methoxy)carbonyl)amino)propanamido)-4-((((4-nitrophenoxy)carbonyl)oxy)methyl)phenoxy)-6-(methoxycarbonyl)tetrahydro-2H-pyran-3,4,5-triyltriacetate (1.2 equiv.), and pyridine:DMF (1:4, 0.015 M). The reaction mixture was stirred at room temperature for 4 hours. The crude reaction mixture was then purified by RP-HPLC (0.035% TFA in ACN:0.05% TFA in H$_2$O, C18 column) to afford (3S,4R,5R,6R)-2-(2-(3-(((((9H-fluoren-9-yl)methoxy)carbonyl)amino)propanamido)-4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)phenoxy)-6-(methoxycarbonyl)tetrahydro-2H-pyran-3,4,5-triyl triacetate as a solid: LCMS [M+H]= 1212.4.

Step 2: (3S,4R,5R,6R)-2-(2-(3-(((((9H-fluoren-9-yl)methoxy)carbonyl)amino)propanamido)-4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)phenoxy)-6-(methoxycarbonyl)tetrahydro-2H-pyran-3,4,5-triyltriacetate (1.0 equiv.) was dissolved in MeOH, THF and water (2:1:0.4) (0.005 M). LiOH (8.0 equiv.) was then added and the reaction was stirred at room temperature for 2 hours. The crude reaction mixture was then purified by RP-HPLC (0.035% TFA in ACN:0.05% TFA in H$_2$O, C18 column) to afford (2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-aminopropanamido)phenoxy)-3,4,5-trihydroxytetrahydro-2H-pyran-2-carboxylic acid as a solid: LCMS [M+H]=850.4.

Step 3: A round bottom flask was charged with (2R,3R,4R,5S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-aminopropanamido)phenoxy)-3,4,5-trihydroxytetrahydro-2H-pyran-2-carboxylic acid (1.0 equiv.), 3-(2,5-dioxo-2,5-dihydro-1H-pyrrol-1-yl)propanoic acid (2.0 equiv.), Huenig's base (6.0 equiv.), HBTU (1.8 equiv.) and DMF (0.003 M). The reaction was kept stirring at room temperature for 15 minutes. The reaction mixture was stirred at room temperature for 2 hours. The crude reaction mixture was then purified by RP-HPLC (0.035% TFA in ACN:0.05% TFA in H$_2$O, C18 column) to afford (2S,3S,4S,5R,6S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2,5-dioxo-2,5-dihydro-1H-pyrrol-1-yl)propanamido)propanamido)phenoxy)-3,4,5-trihydroxytetrahydro-2H-pyran-2-carboxylic acid (C-61) as a solid as the TFA salt: LCMS [M+H]=1001.3.

Example 62

Synthesis of (2S,3S,4S,5R,6S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2-(2,5-dioxo-2,5-dihydro-1H-pyrrol-1-yl)ethoxy)propanamido)propanamido)phenoxy)-3,4,5-trihydroxytetrahydro-2H-pyran-2-carboxylic acid (C-62)

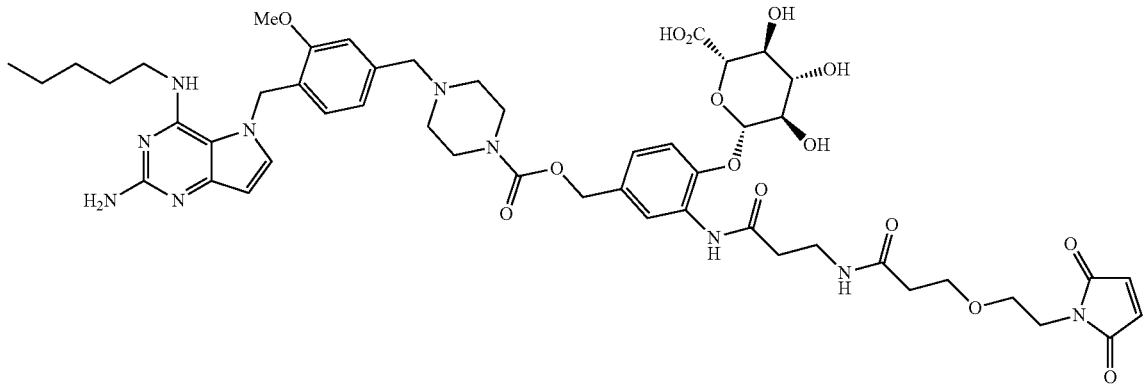

(C-62)

(2S,3S,4S,5R,6S)-6-(4-(((4-(4-((2-amino-4-(pentylamino)-5H-pyrrolo[3,2-d]pyrimidin-5-yl)methyl)-3-methoxybenzyl)piperazine-1-carbonyl)oxy)methyl)-2-(3-(3-(2-(2,5-dioxo-2,5-dihydro-1H-pyrrol-1-yl)ethoxy)propanamido)propanamido)phenoxy)-3,4,5-trihydroxytetrahydro-2H-pyran-2-carboxylic acid (C-62) was prepared as a solid as the TFA salt according to the scheme shown for Example (C-61), except 3-(2-(2,5-dioxo-2,5-dihydro-1H-pyrrol-1-yl)ethoxy)propanoic acid was used in place of 3-(2,5-dioxo-2,5-dihydro-1H-pyrrol-1-yl)propanoic acid in the last step: $^1$H NMR (CD$_3$OD): δ 8.20 (d, 1H), 7.37 (d, 1H), 7.21 (m, 2H), 7.05 (m, 1H), 6.99 (d, 1H), 6.78 (m, 3H), 6.23 (d, 1H), 5.55 (s, 2H), 5.09 (s, 2H), 3.92 (m, 4H), 4.81 (d, 1H), 4.00 (s, 2H), 3.94 (s, 3H), 3.89 (d, 1H), 3.62 (m, 9H), 3.53 (m, 8H), 2.90 (m, 3H), 2.66 (t, 2H), 2.37 (t, 2H), 1.51 (m, 2H), 1.29 (m, 2H), 1.17 (m, 2H), 0.87 (t, 3H). LRMS [M+H]=1045.4.

Example 63

Synthesis of N-(2-((5-(4-(4-((2-amino-4-(pentylamino)-5H-pyrrolo[3,2-d]pyrimidin-5-yl)methyl)-3-methoxybenzyl)piperazin-1-yl)-2-methyl-5-oxopentan-2-yl)disulfanyl)ethyl)-3-(2,5-dioxo-2,5-dihydro-1H-pyrrol-1-yl)propanamide (C-63)

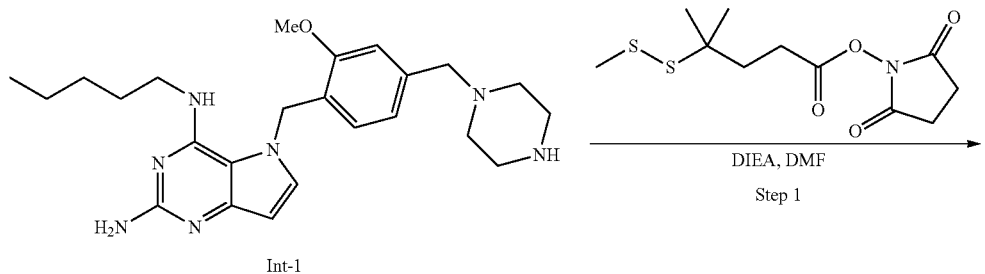

Int-1

DIEA, DMF

Step 1

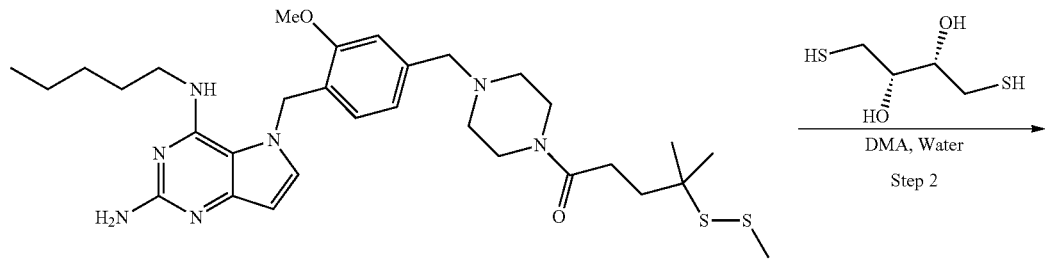

DMA, Water

Step 2

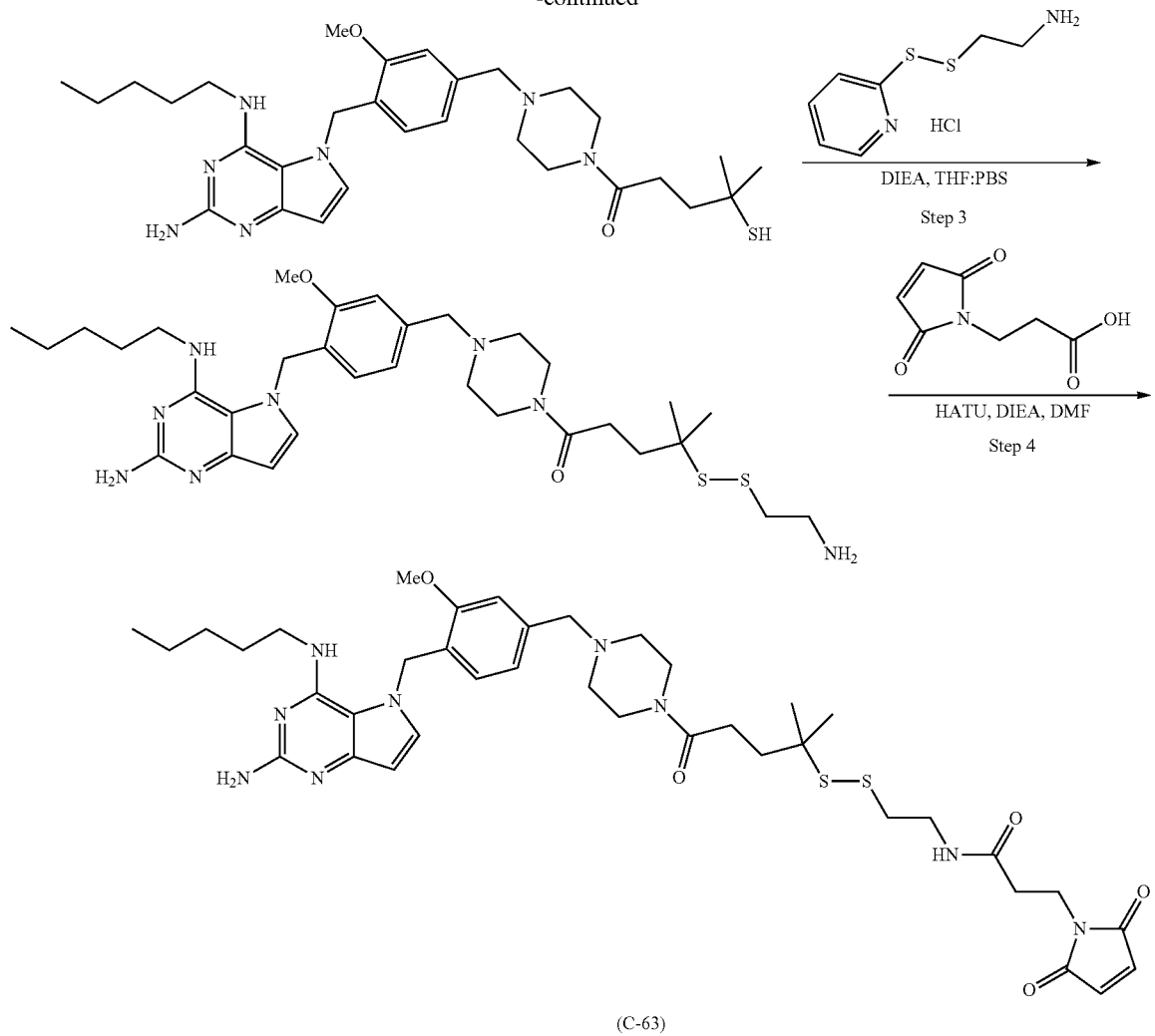

(C-63)

Step 1: A round bottom flask was charged with 5-(2-methoxy-5-(piperazin-1-ylmethyl)benzyl)-N4-pentyl-5H-pyrrolo[3,2-d]pyrimidine-2,4-diamine (Int-1, 1.0 equiv.), 2,5-dioxopyrrolidin-1-yl 4-methyl-4-(methyldisulfanyl)pentanoate (1.3 equiv.), Huenig's base (20.0 equiv.), and DMF (0.03 M). The reaction mixture was stirred at room temperature for 2 hours. The crude reaction mixture was then purified using RP-C18 ISCO (ACN:H$_2$O, with TFA as modifier) and then lyophilized to give 1-(4-(4-((2-amino-4-(pentylamino)-5H-pyrrolo[3,2-d]pyrimidin-5-yl)methyl)-3-methoxybenzyl)piperazin-1-yl)-4-methyl-4-(methyldisulfanyl)pentan-1-one as a solid as the TFA salt: LCMS [M+H]= 614.3.

Step 2: A round bottom flask was charged with 1-(4-(4-((2-amino-4-(pentylamino)-5H-pyrrolo[3,2-d]pyrimidin-5-yl)methyl)-3-methoxybenzyl)piperazin-1-yl)-4-methyl-4-(methyldisulfanyl)pentan-1-one 1.0 equiv.), (2S,3S)-1,4-dimercaptobutane-2,3-diol (1.0 equiv.), and dimethyl acetamide:H$_2$O (1:1, 0.03 M). The reaction mixture was stirred at room temperature for 2 hours. The crude reaction mixture was then purified using RP-C18 ISCO (ACN:H$_2$O, with TFA as modifier) and then lyophilized to give 1-(4-(4-((2-amino-4-(pentylamino)-5H-pyrrolo[3,2-d]pyrimidin-5-yl)methyl)-3-methoxybenzyl)piperazin-1-yl)-4-mercapto-4-methylpentan-1-one as a solid as the TFA salt: LCMS [M+H]=568.3.

Step 3: A round bottom flask was charged with 1-(4-(4-((2-amino-4-(pentylamino)-5H-pyrrolo[3,2-d]pyrimidin-5-yl)methyl)-3-methoxybenzyl)piperazin-1-yl)-4-mercapto-4-methylpentan-1-one (1.0 equiv.), 2-(pyridin-2-yldisulfanyl)ethan-1-amine HCl salt (2.0 equiv.), Huenig's base (10.0 equiv.), and THF:PBS (1:1, 0.03 M). The reaction mixture was stirred at room temperature for 15 minutes. The crude reaction mixture was then purified using RP-C18 ISCO (ACN:H$_2$O, with TFA as modifier) and then lyophilized to give 1-(4-(4-((2-amino-4-(pentylamino)-5H-pyrrolo[3,2-d]pyrimidin-5-yl)methyl)-3-methoxybenzyl)piperazin-1-yl)-4-((2-aminoethyl)disulfanyl)-4-methylpentan-1-one as a solid as the TFA salt: LCMS [M+H]=643.4.

Step 4: A round bottom flask was charged with 1-(4-(4-((2-amino-4-(pentylamino)-5H-pyrrolo[3,2-d]pyrimidin-5-yl)methyl)-3-methoxybenzyl)piperazin-1-yl)-4-((2-aminoethyl)disulfanyl)-4-methylpentan-1-one (1.0 equiv.), 3-(2,5-dioxo-2,5-dihydro-1H-pyrrol-1-yl)propanoic acid (1.0 equiv.), Huenig's base (5.0 equiv.), HATU (1.0 equiv.) and DMF (0.02 M). The reaction mixture was stirred at room temperature for 2 hours. The crude reaction mixture was then purified using RP-C18 ISCO (ACN:H$_2$O, with TFA as modifier) and then lyophilized to give N-(2-((5-(4-(4-((2-amino-4-(pentylamino)-5H-pyrrolo[3,2-d]pyrimidin-5-yl)methyl)-3-methoxybenzyl)piperazin-1-yl)-2-methyl-5-oxopentan-2-yl)disulfanyl)ethyl)-3-(2,5-dioxo-2,5-dihydro-1H-pyrrol-1-yl)propanamide (C-63) as a solid as the TFA salt: $^1$H NMR (CD$_3$OD): δ 7.37 (d, 1H), 7.26 (d, 1H), 7.08 (m, 1H), 6.83 (d, 1H), 6.81 (s, 2H), 6.24 (d, 1H), 5.58 (s, 2H), 4.37 (s, 2H), 4.20 (br, 4H), 3.97 (s, 3H), 3.75 (t, 2H), 3.55 (t, 2H), 3.38 (m, 2H), 3.38 (br, 4H), 2.72 (t, 2H), 2.55 (m, 2H), 2.45 (t, 2H), 1.89 (m, 2H), 1.54 (m, 2H), 1.31 (m, 8H), 1.19 (m, 2H), 0.88 (t, 3H). LRMS [M+H]=794.4.

Example 64

Synthesis of 1-(4-(4-((2-amino-4-(pentylamino)-5H-pyrrolo[3,2-d]pyrimidin-5-yl)methyl)-3-methoxybenzyl)piperazin-1-yl)-4-methyl-4-(methylthio)pentan-1-one (C-64)

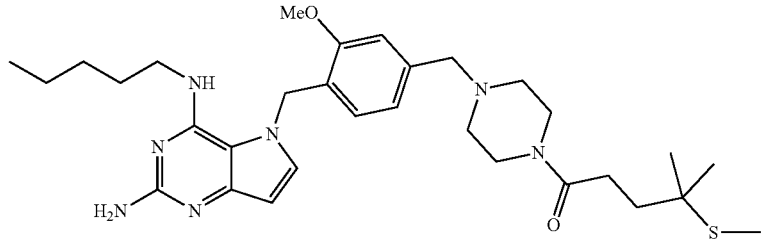

(C-24)

1-(4-(4-((2-amino-4-(pentylamino)-5H-pyrrolo[3,2-d]pyrimidin-5-yl)methyl)-3-methoxybenzyl)piperazin-1-yl)-4-methyl-4-(methylthio)pentan-1-one (C-63) was prepared following the procedure described for intermediate Int-1, except using 4-methyl-4-(methylthio)-1-(piperazin-1-yl)pentan-1-one in place of tert-butyl piperazine-1-carboxylate in step 3. The crude reaction mixture was purified using RP-C18 ISCO (ACN:H$_2$O, with TFA as modifier) and then lyophilized to give 1-(4-(4-((2-amino-4-(pentylamino)-5H-pyrrolo[3,2-d]pyrimidin-5-yl)methyl)-3-methoxybenzyl)piperazin-1-yl)-4-methyl-4-(methylthio)pentan-1-one (C-64) as a solid as the TFA salt: $^1$H NMR (CD$_3$OD): δ 7.36 (d, 1H), 7.25 (d, 1H), 7.05 (m, 1H), 6.81 (d, 1H), 6.24 (d, 1H), 5.58 (s, 2H), 4.34 (s, 2H), 3.90 (br, 4H), 3.96 (s, 3H), 3.55 (t, 2H), 3.28 (br, 4H), 2.55 (m, 2H), 1.95 (s, 3H), 1.80 (m, 2H), 1.54 (m, 2H), 1.31 (m, 2H), 1.27 (s, 6H), 1.19 (m, 2H), 0.88 (t, 3H). LRMS [M+H]=582.4.

Example 65

Synthesis of (2S,3S,4S,5R,6S)-6-(4-((((2-(4-(4-((2-amino-4-(pentylamino)-5H-pyrrolo[3,2-d]pyrimidin-5-yl)methyl)-3-methoxybenzyl)piperazin-1-yl)ethoxy)(hydroxy)phosphoryl)oxy)methyl)-2-(3-(3-(2-(2,5-dioxo-2,5-dihydro-1H-pyrrol-1-yl)ethoxy)propanamido)propanamido)phenoxy)-3,4,5-trihydroxytetrahydro-2H-pyran-2-carboxylic acid (C-65)

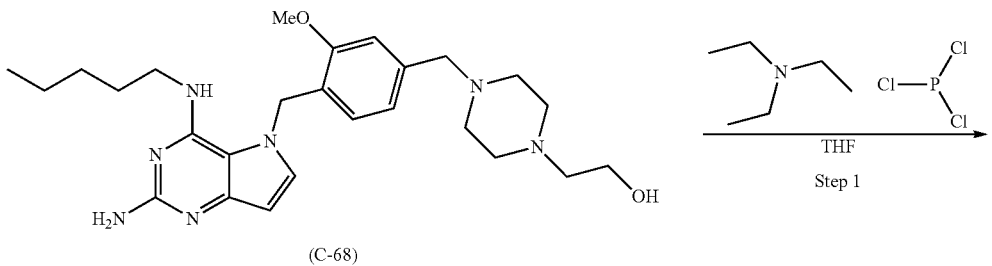

(C-68)

Step 1

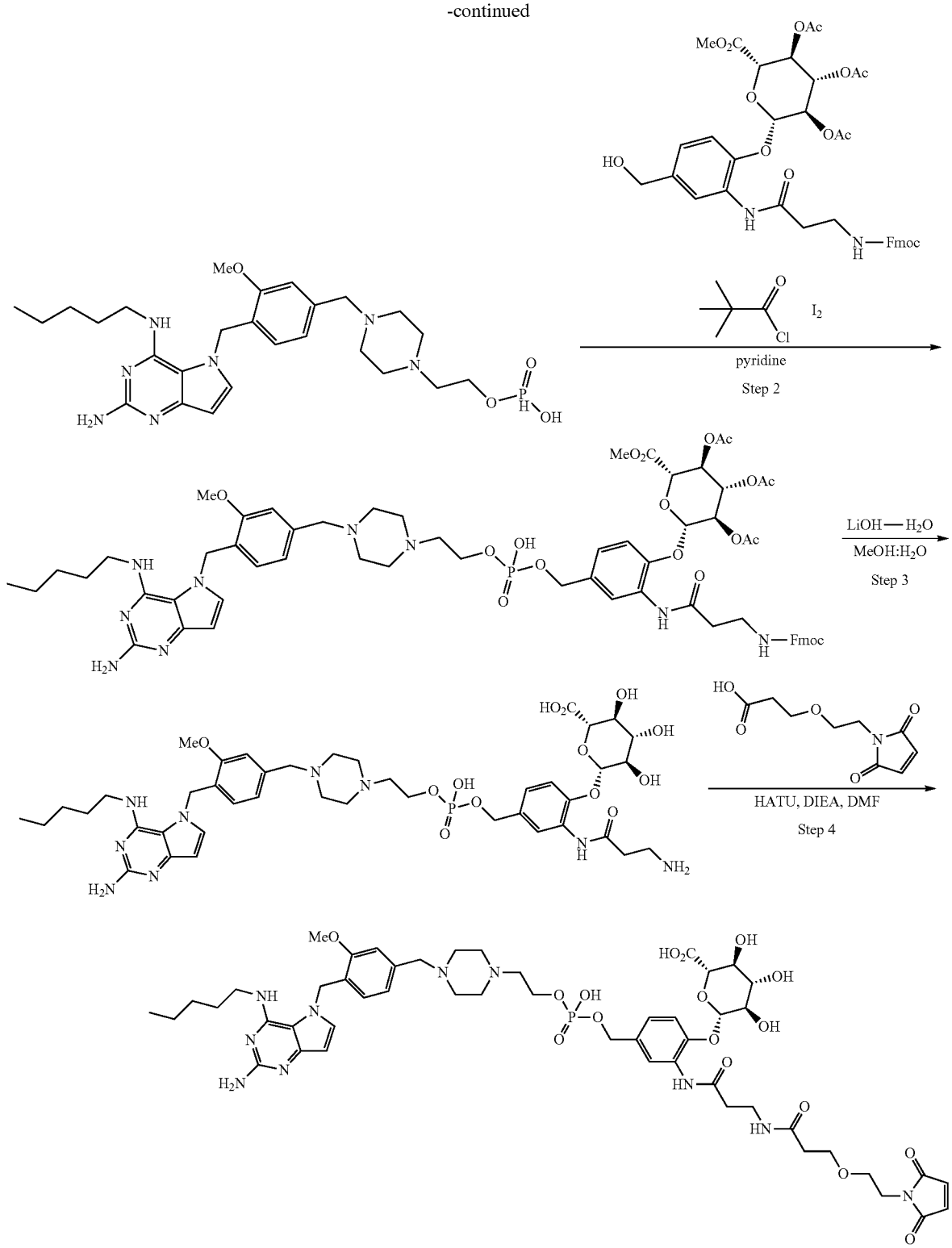

Step 1: A round bottom flask was charged with 2-(4-(4-((2-amino-4-(pentylamino)-5H-pyrrolo[3,2-d]pyrimidin-5-yl)methyl)-3-methoxybenzyl)piperazin-1-yl)ethan-1-ol (C-68) (1.0 equiv.), trichlorophosphane (3.0 equiv.), triethylamine (9.0 equiv.), and THF (0.2 M) at 0° C. and allowed to stir for 1 h. The reaction was then quenched by the slow addition of ice-water and washed with EtOAc 3×. The aqueous layer containing the desired product was then lyophilized. 2-(4-(4-((2-amino-4-(pentylamino)-5H-pyrrolo[3,2-d]pyrimidin-5-yl)methyl)-3-methoxybenzyl)piperazin- 1-yl)ethyl hydrogen phosphonate was isolated and used in the next step without further purification: LCMS [M+H]= 546.3.

Step 2: A round bottom flask was charged with (2S,3R,4S,5S,6S)-2-(2-(3-(((((9H-fluoren-9-yl)methoxy)carbonyl)amino)propanamido)-4-(hydroxymethyl)phenoxy)-6-(methoxycarbonyl)tetrahydro-2H-pyran-3,4,5-triyltriacetate (1.0 equiv.), 2-(4-(4-((2-amino-4-(pentylamino)-5H-pyrrolo[3,2-d]pyrimidin-5-yl)methyl)-3-methoxybenzyl)piperazin-1-yl)ethyl hydrogen phosphonate (2.0 equiv.), pivaloyl chloride (42.0 equiv.), and pyridine (0.03 M). The reaction mixture was stirred at room temperature for 2 hours. At this point diiodide (1.06 equiv.) in pyridine:H$_2$O (1:0.1, 0.14 M) was added and the mixture stirred for 10 min. The crude reaction mixture was then purified using RP-HPLC (0.035% TFA in ACN:0.05% TFA in H$_2$O, C18 column) to obtain (2S,3R,4S,5S,6S)-2-(2-(3-(((((9H-fluoren-9-yl)methoxy)carbonyl)amino)propanamido)-4-(((((2-(4-(4-((2-amino-4-(pentylamino)-5H-pyrrolo[3,2-d]pyrimidin-5-yl)methyl)-3-methoxybenzyl)piperazin-1-yl)ethoxy)(hydroxy)phosphoryl)oxy)methyl)phenoxy)-6-(methoxycarbonyl)tetrahydro-2H-pyran-3,4,5-triyl triacetate as a solid as the TFA salt: LCMS [M+H]=1292.5.

Step 3: A round bottom flask was charged with (2S,3R,4S,5S,6S)-2-(2-(3-(((((9H-fluoren-9-yl)methoxy)carbonyl)amino)propanamido)-4-(((((2-(4-(4-((2-amino-4-(pentylamino)-5H-pyrrolo[3,2-d]pyrimidin-5-yl)methyl)-3-methoxybenzyl)piperazin-1-yl)ethoxy)(hydroxy)phosphoryl)oxy)methyl)phenoxy)-6-(methoxycarbonyl)tetrahydro-2H-pyran-3,4,5-triyltriacetate (1.0 equiv.), lithium hydroxide-H$_2$O (10.0 equiv.) and MeOH:H$_2$O (3:1.5, 0.007 M). The reaction mixture was stirred at room temperature for 2 hours. The crude reaction mixture was then purified using RP-C18 ISCO (ACN:H$_2$O, with TFA as modifier) and then lyophilized to give (2S,3S,4S,5R,6S)-6-(4-(((((2-(4-(4-((2-amino-4-(pentylamino)-5H-pyrrolo[3,2-d]pyrimidin-5-yl)methyl)-3-methoxybenzyl)piperazin-1-yl)ethoxy)(hydroxy)phosphoryl)oxy)methyl)-2-(3-aminopropanamido)phenoxy)-3,4,5-trihydroxytetrahydro-2H-pyran-2-carboxylic acid as a solid as the TFA salt: LCMS [M+H]=930.4.

Step 4: A round bottom flask was charged with (2S,3S,4S,5R,6S)-6-(4-(((((2-(4-(4-((2-amino-4-(pentylamino)-5H-pyrrolo[3,2-d]pyrimidin-5-yl)methyl)-3-methoxybenzyl)piperazin-1-yl)ethoxy)(hydroxy)phosphoryl)oxy)methyl)-2-(3-aminopropanamido)phenoxy)-3,4,5-trihydroxytetrahydro-2H-pyran-2-carboxylic acid (1.0 equiv.), 3-(2-(2,5-dioxo-2,5-dihydro-1H-pyrrol-1-yl)ethoxy)propanoic acid (1.0 equiv.), Huenig's base (6.0 equiv.), HATU (1.0 equiv.) and DMF (0.005 M). The reaction was kept stirring at room temperature for 15 minutes. The crude reaction mixture was then purified by RP-HPLC (0.035% TFA in ACN:0.05% TFA in H$_2$O, C18 column) to afford (2S,3S,4S,5R,6S)-6-(4-(((((2-(4-(4-((2-amino-4-(pentylamino)-5H-pyrrolo[3,2-d]pyrimidin-5-yl)methyl)-3-methoxybenzyl)piperazin-1-yl)ethoxy)(hydroxy)phosphoryl)oxy)methyl)-2-(3-(3-(2-(2,5-dioxo-2,5-dihydro-1H-pyrrol-1-yl)ethoxy)propanamido)propanamido)phenoxy)-3,4,5-trihydroxytetrahydro-2H-pyran-2-carboxylic acid (C-65) as a solid as the TFA salt: $^1$H NMR (CD$_3$OD): δ 8.19 (s, 1H), 7.37 (d, 1H), 7.14 (m, 3H), 6.79 (s, 2H), 6.77 (d, 1H), 6.22 (d, 1H), 5.53 (s, 2H), 4.86 (s, 2H), 4.84 (d, 1H), 4.08 (s, 2H), 3.95 (d, 1H), 3.92 (s, 3H), 4.00 (br, 4H), 3.76 (s, 2H), 3.62 (m, 5H), 3.53 (m, 10H), 3.27 (m, 2H), 2.85 (m, 4H), 2.63 (m, 2H), 2.37 (t, 2H), 1.52 (m, 2H), 1.31 (m, 2H), 1.17 (m, 2H), 0.88 (t, 3H). LRMS [M+H/2Z]=563.4.

Example 66

Synthesis of (2R,2'R)-3,3'-(2-((2-(4-(4-((2-amino-4-(pentylamino)-5H-pyrrolo[3,2-d]pyrimidin-5-yl)methyl)-3-methoxybenzyl)piperazin-1-yl)-2-oxoethoxy)imino)propane-1,3-diyl)bis(sulfanediyl)bis(2-aminopropanoic acid) (C-66)

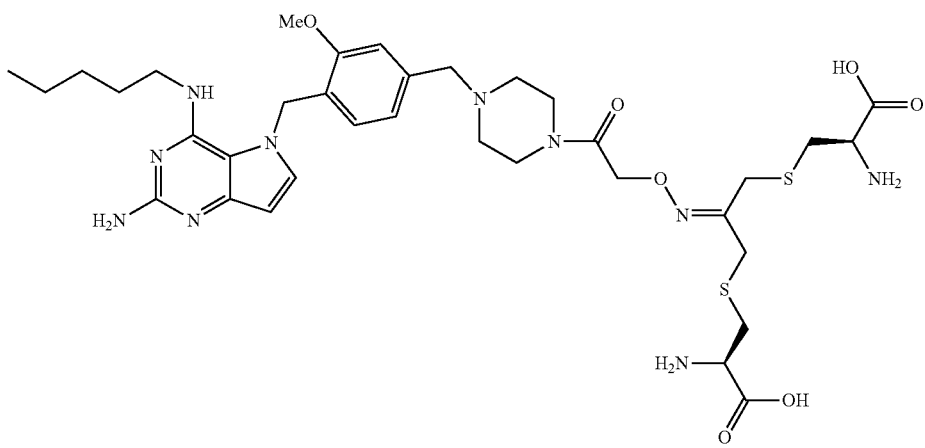

(C-66)

A round bottom flask was charged with 1-(4-(4-((2-amino-4-(pentylamino)-5H-pyrrolo[3,2-d]pyrimidin-5-yl)methyl)-3-methoxybenzyl)piperazin-1-yl)-2-(aminooxy)ethan-1-one (C-35) (2.4 equiv.), (2R,2'R)-3,3'-((2-oxopropane-1,3-diyl)bis(sulfanediyl))bis(2-aminopropanoic acid) (1.0 equiv.), and ethanol (0.02 M). The reaction mixture was stirred at room temperature for 30 min. The crude reaction mixture was purified using RP-C18 ISCO (ACN:H$_2$O, with TFA as modifier) and then lyophilized to give (2R,2'R)-3,3'-(2-((2-(4-(4-((2-amino-4-(pentylamino)-5H-pyrrolo[3,2-d]pyrimidin-5-yl)methyl)-3-methoxybenzyl)piperazin-1-yl)-2-oxoethoxy)imino)propane-1,3-diyl)bis(sulfanediyl))bis(2-aminopropanoic acid) (C-66) as a solid: $^1$H NMR (CD$_3$OD): δ 7.35 (d, 1H), 7.28 (d, 1H), 7.05 (m, 1H), 6.80 (d, 1H), 6.23 (d, 1H), 5.57 (s, 2H), 4.32 (s, 2H), 4.20 (m, 1H), 4.05 (m, 1H), 3.94 (s, 3H), 3.81 (m, 4H), 3.55 (m, 2H), 3.44 (m, 2H), 3.20 (m, 4H), 2.96 (m, 1H), 2.88 (m, 1H), 1.53 (m, 2H), 1.31 (m, 2H), 1.18 (m, 2H), 0.88 (t, 3H). LRMS [M+H]=789.3.

Example 67

Synthesis of (R)-2-amino-6-((((R)-2-amino-2-carboxyethyl)thio)methyl)-17-(4-(4-((2-amino-4-(pentylamino)-5H-pyrrolo[3,2-d]pyrimidin-5-yl)methyl)-3-methoxybenzyl)piperazin-1-yl)-10,17-dioxo-8,14-dioxa-4-thia-7,11-diazaheptadec-6-enoic acid (C-67)

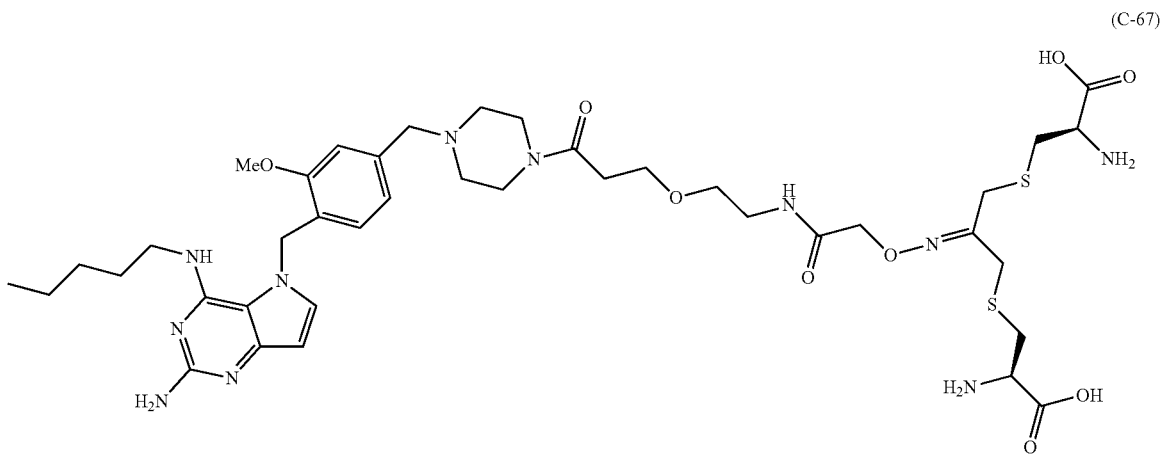 [SMILES: CCCCCNc1nc(N)nc2ccn(Cc3ccc(CN4CCN(C(=O)CCOCCNC(=O)CON=C(CSC[C@H](N)C(=O)O)CSC[C@H](N)C(=O)O)CC4)cc3OC)c12]

(C-67)

A round bottom flask was charged with N-(2-(3-(4-(4-((2-amino-4-(pentylamino)-5H-pyrrolo[3,2-d]pyrimidin-5-yl)methyl)-3-methoxybenzyl)piperazin-1-yl)-3-oxopropoxy)ethyl)-2-(aminooxy)acetamide (C-37) (2.4 equiv.), (2R,2'R)-3,3'-(2-oxopropane-1,3-diyl)bis(sulfanediyl))bis(2-aminopropanoic acid) (1.0 equiv.), and ethanol (0.02 M). The reaction mixture was stirred at room temperature for 30 min. The crude reaction mixture was purified using RP-C18 ISCO (ACN:H$_2$O, with TFA as modifier) and then lyophilized to give (R)-2-amino-6-((((R)-2-amino-2-carboxyethyl)thio)methyl)-17-(4-(4-((2-amino-4-(pentylamino)-5H-pyrrolo[3,2-d]pyrimidin-5-yl)methyl)-3-methoxybenzyl)piperazin-1-yl)-10,17-dioxo-8,14-dioxa-4-thia-7,11-diazaheptadec-6-enoic acid (C-67) as a solid: $^1$H NMR (CD$_3$OD): δ 7.36 (d, 1H), 7.29 (d, 1H), 7.07 (m, 1H), 6.80 (d, 1H), 6.24 (d, 1H), 5.57 (s, 2H), 4.57 (s, 2H), 4.31 (m, 2H), 4.11 (m, 1H), 4.03 (m, 1H), 3.95 (s, 3H), 3.86 (br, 4H), 3.73 (t, 2H), 3.54 (m, 6H), 3.40 (m, 2H), 3.20 (m, 8H), 2.96 (m, 2H), 2.67 (t, 2H), 1.52 (m, 2H), 1.30 (m, 2H), 1.19 (m, 2H), 0.88 (t, 3H). LRMS [M+H]=904.4.

Example 68

Synthesis of 2-(4-(4-((2-amino-4-(pentylamino)-5H-pyrrolo[3,2-d]pyrimidin-5-yl)methyl)-3-methoxybenzyl)piperazin-1-yl)ethan-1-ol (C-68)

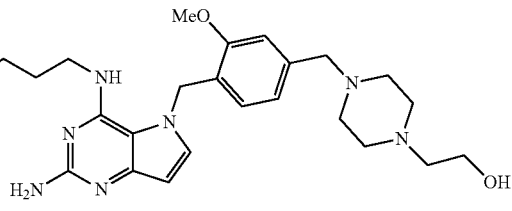

(C-68)

A round bottom flask was charged with 5-(2-methoxy-4-(piperazin-1-ylmethyl)benzyl)-N4-pentyl-5H-pyrrolo[3,2-d]pyrimidine-2,4-diamine (Int-1, 1.0 equiv.), 2-bromoethan-1-ol (1.3 equiv.), triethylamine (20.0 equiv.), and acetonitrile (0.03 M). The reaction mixture was stirred at room temperature for 2 hours. The crude reaction mixture was then purified by ISCO chromatography (0-10% MeOH:DCM, gradient) to afford 2-(4-(4-((2-amino-4-(pentylamino)-5H-pyrrolo[3,2-d]pyrimidin-5-yl)methyl)-3-methoxybenzyl) piperazin-1-yl)ethan-1-ol (C-68) as a solid: $^1$H NMR (CD$_3$OD): δ 7.22 (d, 1H), 7.08 (d, 1H), 6.83 (d, 1H), 6.55 (d, 1H), 6.10 (d, 1H), 5.39 (s, 2H), 3.93 (s, 3H), 3.66 (t, 2H), 3.50 (s, 2H), 3.32 (m, 2H), 3.20 (s, 1H), 2.51 (m, 10H), 1.37 (m, 2H), 1.27 (m, 2H), 1.25 (s, 1H), 1.12 (m, 2H), 0.86 (t, 3H). LRMS [M+H]=482.4.

Example 69

Compounds of Formula (I) were assayed to measure their activity as toll-like receptor 7 agonists.

Reporter Gene Assay

Human embryonic kidney 293 (HEK293) cells were stably transfected with human TLR7 and an NF-kB-driven luciferase reporter vector (pNifty-Luciferase). As a control assay, normal HEK293 transfected with pNifty-Luc were used. Cells were cultured in DMEM supplemented with 2 mM L-glutamine, 10% heart inactivated FBS, 1% penicillin and streptomycin, 2 μg/ml puromycin (InvivoGen #ant-pr-5) and 5 μg/ml of blasticidin (Invitrogen #46-1120). Bright-Glo™ Luciferase assay buffer and substrate were supplied by Promega #E263B and #E264B (assay substrate and buffer respectively). 384 well clear-bottom plates were supplied by Greiner bio-one (#789163-G) and were custom bar-coded plates.

Cells were plated at 25,000 cells/well in 384-well plates in a final volume of 50 μl of media. Cells were allowed to adhere to the plates after overnight (18 hours) culture at 37° C. and 5% CO$_2$. Serially diluted experimental and positive control compounds were then dispensed to each well and incubated for 7 hours at 37° C. and 5% CO$_2$. Cells stimulated with DMSO alone also serve as negative controls. After the incubation, 30 μl of the pre-mix assay buffer and substrate buffer were added to each well according to manufacturer's instructions. The luminescence signal was read on a CLIPR machine with an integration time of 20 seconds per plate.

Dose response curves are generated for each compound and EC$_{50}$ values were determined as the concentration that gives 50% of the maximal signal.

Selected Assay Results

Various compounds of Formula (I), in free form or in pharmaceutically acceptable salt form, exhibit pharmacological properties, for example, as indicated by the in vitro tests described in this application. The EC$_{50}$ value in those experiments is given as that concentration of the test compound in question that provokes a response halfway between the baseline and maximum responses. In other examples, compounds of Formula (I) have EC$_{50}$ values in the range from 1 nM to 2 μM. In other examples, compounds of Formula (I) have EC$_{50}$ values in the range from 1 nM to 1 μM. In other examples, compounds of Formula (I) have EC$_{50}$ values in the range from 1 nM to 500 nM. In other examples, compounds of Formula (I) have EC$_{50}$ values in the range from 1 nM to 250 nM. In other examples, compounds of Formula (I) have EC$_{50}$ values in the range from 1 nM to 100 nM. In other examples, compounds of Formula (I) have EC$_{50}$ values in the range from 1 nM to 50 nM. In other examples, compounds of Formula (I) have EC$_{50}$ values in the range from 1 nM to 25 nM. In other examples, compounds of Formula (I) have EC$_{50}$ values in the range from 1 nM to 10 nM.

To illustrate the in-vitro activity of the compounds of the invention, the EC$_{50}$ values for TLR7 stimulation by certain compounds of Formula (I) are listed in Table 2. Cysteine adduct are thought to be putative catabolytes that arise from degradation within the lysosome (Bioconjugate Chem. 2006, 17, 114-124). Certain compounds of Table 2 are the result of derivatization of the corresponding parent compound with cysteine.

TABLE 2

| Compound Number | Human TLR7 EC$_{50}$ (nM) HEK293 |
|---|---|
| C-2 | 10 |
| C-3 | 96 |
| C-4 | 35 |
| C-6 | 16 |
| C-7 | 77 |
| C-8 | 32 |
| C-10 | 157 |
| C-12 | 144 |
| C-14 | 8 |
| C-16 | 289 |
| C-18 | 518 |
| C-19 | 2 |
| C-20 | 11 |
| C-22 | 598 |
| C-24 | 277 |
| C-26 | 134 |
| C-28 | 230 |
| C-34 | 585 |
| C-35 | 5 |
| C-36 | 4 |
| C-37 | 57 |
| C-38 | 278 |
| C-39 | 192 |
| C-40 | 2101 |
| C-41 | 52 |
| C-42 | 1 |
| C-43 | 6 |
| C-44 | 2 |
| C-45 | 11 |
| C-48 | 1900 |
| C-49 | 264 |
| C-51 | 80 |
| C-53 | 753 |
| C-57 | 16 |
| C-64 | 3 |
| C-66 | 2 |
| C-67 | 30 |
| C-68 | <1 |

Example 70

Generation of Anti-HER2-TLR7 Agonist Conjugates by Conjugation of TLR7 Agonists to Specific Cysteine Residues of Anti-HER2 Antibody Mutants Preparation of Anti-HER2 Antibody with Specific Cysteine (Cys) Mutations Preparation of anti-HER2 antibodies, e.g., trastuzumab, with site-specific cysteine mutations has been described previously in WO 2014/124316 and WO 2015/138615, each of which was incorporated by reference herein. Briefly, DNA encoding variable regions of the heavy and light chains of an anti-HER2 antibody, e.g., trastuzumab, were chemically synthesized and cloned into two mammalian expression vectors, pOG-HC and pOG-LC, that contain constant regions of human IgG1 and human kappa light chain. Vectors contain a CMV promoter and a signal sequence: MKTFILLLWVLLLWVIFLLPGATA (SEQ ID NO: 27). Oligonucleotide directed mutagenesis was employed to prepare Cys mutant constructs of the anti- HER2 antibody, and the sequences of Cys mutant constructs were confirmed by DNA sequencing.

For example, cysteine can be introduced at one or more of the following positions (all positions by EU numbering) in an anti-HER2 antibody: (a) positions 152, 360 and/or 375 of the antibody heavy chain, and (b) positions 107, 159, and/or 165 of the antibody light chain. For example, cysteine can be introduced at position 152 of the heavy chain resulting in anti-HER2 mAb4, which has a light chain sequence of SEQ ID NO: 19 and a heavy chain sequence of SEQ ID NO: 30.

Cys mutants of the anti-HER2 antibody were expressed in 293 Freestyle™ cells by co-transfecting heavy chain and light chain plasmids using transient transfection methods as described previously (Meissner, et al., *Biotechnol Bioeng.* 75:197-203 (2001)). The expressed antibodies were purified from the cell supernatants by standard Protein A affinity chromatography.

Similar methods were used to clone the variable regions of the heavy chain and light chain of trastuzumab into two vectors for expression in CHO cells. The heavy chain vector encodes the constant region of the human IgG1 antibody, includes a signal peptide (MPLLLLLPLLWAGALA) (SEQ ID NO: 28), a CMV promoter to drive expression of the heavy chain, and appropriate signal and selection sequences for stable transfection into CHO cells. The light chain vector encodes the constant region of the human kappa light chain, includes a signal peptide (MSVLTQVLALLLLWLTGTRC) (SEQ ID NO: 29), a CMV promoter to drive expression of the light chain, and appropriate signal and selection sequences for stable transfection into CHO cells. To produce antibodies, a heavy chain vector and a light chain vector were co-transfected into a CHO cell line. Cells underwent selection, and stably transfected cells were then cultured under conditions optimized for antibody production. Antibodies were purified from the cell supernatants by standard Protein A affinity chromatography.

Additional mutations to the constant region of the antibody vectors were made using standard mutagenesis methods.

Reduction, Re-Oxidation and Conjugation of Cys Mutant Anti-HER2 Antibodies to TLR7 Agonists Compounds of Formula (I) of the invention comprising a linker were conjugated to Cys residues engineered into an antibody using methods described in Junutula J R, et al., Nature Biotechnology 26:925-932 (2008).

Because engineered Cys residues in antibodies expressed in mammalian cells are modified by adducts (disulfides) such as glutathione (GSH) and/or cysteine during biosynthesis (Chen et al. 2009), the modified Cys as initially expressed is unreactive to thiol reactive reagents such as maleimido or bromo-acetamide or iodo-acetamide groups. To conjugate engineered Cys residues, glutathione or cysteine adducts need to be removed by reducing disulfides, which generally entails reducing all disulfides in the expressed antibody. This can be accomplished by first exposing antibody to a reducing agent such as dithiothreitol (DTT) followed by re-oxidation of all native disulfide bonds of the antibody to restore and/or stabilize the functional antibody structure. Accordingly, in order to reduce native disulfide bonds and disulfide bond between the cysteine or GSH adducts of engineered Cys residue(s), freshly prepared DTT was added to previously purified Cys mutants of trastuzumab, to a final concentration of 10 mM or 20 mM. After antibody incubation with DTT at 37° C. for 1 hour, mixtures were dialyzed against PBS for three days with daily buffer exchange to remove DTT and re-oxidize native disulfide bonds. The re-oxidation process was monitored by reverse-phase HPLC, which is able to separate antibody tetramer from individual heavy and light chain molecules. Reactions were analyzed on a PRLP-S 4000A column (50 mm×2.1 mm, Agilent) heated to 80° C. and column elution was carried out by a linear gradient of 30-60% acetonitrile in water containing 0.1% TFA at a flow rate of 1.5 ml/min. The elution of proteins from the column was monitored at 280 nm. Dialysis was allowed to continue until reoxidation was complete. Reoxidation restores intra-chain and inter-chain disulfides, while dialysis allows cysteines and glutathiones connected to the newly-introduced Cys residue(s) to dialyze away.

After re-oxidation, maleimide-containing compounds were added to re-oxidized antibodies in PBS buffer (pH 7.2) at ratios of typically 1.5:1, 2:1, or 5:1 to engineered Cys, and incubations were carried out for 1 hour. Typically, excess free compound was removed by purification over Protein A resin by standard methods followed by buffer exchange into PBS.

Cys mutants of anti-HER2 antibody, e.g., trastuzumab, were alternatively reduced and re-oxidized using an on-resin method. Protein A Sepharose beads (1 ml per 10 mg antibody) were equilibrated in PBS (no calcium or magnesium salts) and then added to an antibody sample in batch mode. A stock of 0.5 M cysteine was prepared by dissolving 850 mg of cysteine HCl in 10 ml of a solution prepared by adding 3.4 g of NaOH to 250 ml of 0.5 M sodium phosphate pH 8.0 and then 20 mM cysteine was added to the antibody/bead slurry, and mixed gently at room temperature for 30-60 minutes. Beads were loaded to a gravity column and washed with 50 bed volumes of PBS in less than 30 minutes, then the column was capped with beads resuspended in one bed volume of PBS. To modulate the rate of re-oxidation, 50 nM to 1 µM copper chloride was optionally added. The re-oxidation progress was monitored by removing a small test sample of the resin, eluting in IgG Elution buffer (Thermo), and analyzing by RP-HPLC as described above. Once re-oxidation progressed to desired completeness, conjugation could be initiated immediately by addition of 2-3 molar excess of compound over engineered cysteines, and allowing the mixture to react for 5-10 minutes at room temperature before the column was washed with at least 20 column volumes of PBS. Antibody conjugates were eluted with IgG elution buffer and neutralized with 0.1 volumes 0.5 M sodium phosphate pH 8.0 and buffer exchanged to PBS. Alternatively, instead of initiating conjugation with antibody on the resin, the column was washed with at least 20 column volumes of PBS, and antibody was eluted with IgG elution buffer and neutralized with buffer pH 8.0. Antibodies were then either used for conjugation reactions or flash frozen for future use.

Properties of the Anti-HER2-TLR7 Agonist Conjugates

Antibody-TLR7 agonist conjugates were analyzed to determine extent of conjugation. A compound-to-antibody ratio was extrapolated from LC-MS data for reduced and deglycosylated samples. LC/MS allows quantitation of the average number of molecules of linker-payload (compound) attached to an antibody in a conjugate sample. HPLC separates antibody into light and heavy chains, and separates heavy chain (HC) and light chain (LC) according to the number of linker-payload groups per chain. Mass spectral data enables identification of the component species in the mixture, e.g., LC, LC+1, LC+2, HC, HC+1, HC+2, etc. From the average loading on the LC and HC chains, the average compound to antibody ratio can be calculated for an antibody conjugate. A compound-to-antibody ratio for a given conjugate sample represents the average number of compound (linker-payload) molecules attached to a tetrameric antibody containing two light chains and two heavy chains.

Conjugates were profiled using analytical size-exclusion chromatography (AnSEC) on Superdex 200 10/300 GL (GE Healthcare) and/or Protein KW-803 5 μm 300×8 mm (Shodex) columns; aggregation was analyzed based on analytical size exclusion chromatography. Conjugates were also profiled by analytical hydrophobic interaction chromatography (AnHIC) on a Tosoh Bioscience (King of Prussia, Pa., USA) TSKgel Butyl-NPR column (100 mm×4.6 mm, 2.5 μm) installed on an Agilent 1260 LC system (Santa Clara, Calif., USA) using a binary gradient of buffer A (20 mM His-HCl, 1.5 M ammonium sulfate, pH 6.0) and buffer B (20 mM His-HCl, 15% isopropanol, pH 6.0) with samples prepared by diluting approximately 20 μg of antibody (initially in PBS) with 0.5 volume of 3 M ammonium sulfate. The hydrophobicity index is calculated against a linear regression of four standard samples of known hydrophobicity. The hydrophobicity of the largest peak by area is reported.

Most conjugates achieved high compound-to-antibody ratio, were mainly monomeric and showed low hydrophobicity (high hydrophobicity index corresponding to early elution from the HIC column). Conjugation through this method results in conjugation efficiencies of greater than 95% for most compounds (Table 3). The majority of the conjugates contain less than 4% dimeric and oligomeric material (Table 3). A hydrophobicity index (HI) of 0.80 or greater is considered a favorable characteristic. A majority of the conjugates showed HI values of greater than 0.8 (Table 3). This suggests that conjugates can be made efficiently and have favorable characteristics.

TABLE 3

Properties of anti-HER2-TLR7 agonist conjugates

| Conjugate[a] | Conjugation efficiency (by LCMS) | Compound-to-antibody ratio[b] | Aggregation (%)[c] | Hydrophobicity Index (HI)[d] |
|---|---|---|---|---|
| anti-HER2 mAb2-(C-9) | 98 | 3.9 | 3.2 | 0.90 |
| anti-HER2 mAb2-(C-11) | 98 | 3.9 | 3.4 | 0.88 |
| anti-HER2 mAb2-(C-13) | 98 | 3.9 | 3.1 | 0.84 |
| anti-HER2 mAb2-(C-23) | 98 | 3.9 | 2.9 | 0.87 |
| anti-HER2 mAb2-(C-15) | 98 | 3.9 | 3.2 | 0.89 |
| anti-HER2 mAb2-(C-17) | 98 | 3.9 | 3.6 | 0.87 |
| anti-HER2 mAb2-(C-5) | 95 | 3.8 | 3.8 | 0.91 |
| anti-HER2 mAb2-(C-25) | 98 | 3.9 | 3.0 | 0.90 |
| anti-HER2 mAb2-(C-21) | 95 | 3.8 | 3.1 | 0.87 |
| anti-HER2 mAb2-(C-1) | 98 | 3.9 | 3.2 | 0.88 |
| anti-HER2 mAb2-(C-27) | 95 | 3.8 | 0.5 | 0.89 |
| anti-HER2 mAb2-(C-31) | 88 | 3.5 | 1.1 | 0.87 |
| anti-HER2 mAb2-(C-30) | 88 | 3.5 | 0.6 | 0.75 |
| anti-HER2 mAb3-(C-46) | n/a | 1.9 | 0.7[e] | 0.81 |
| anti-HER2 mAb1-(C-5) | 95 | 3.8 | 3.1 | 0.90 |
| anti-HER2 mAb1-(C-1) | 95 | 3.8 | 2.3 | 0.87 |
| anti-HER2 mAb4-(C-29) | >95 | 2.0 | 0.6 | Not determined |
| anti-HER2 mAb3-(C-35) | 90 | 3.6 | 1.1 | 0.90 |
| anti-HER2 mAb3-(C-37) | 88 | 3.5 | 1.9 | 0.87 |
| anti-HER2 mAb3-(C-1) | n/a | 7.0 | 0.3 | 0.65 |
| anti-HER2 mAb5-(C-69)-(C-35) | >95 | 2.0 | 0.7 | 0.70 |
| anti-HER2 mAb5-(C-69)-(C-37) | >95 | 2.0 | 1 | 0.70 |
| anti-ratHER2-(C-47) | n/a | 2.6 | BLQ[e] | Not determined |
| anti-ratHER2-(C-50) | n/a | 1.3 | BLQ[e] | Not determined |
| anti-ratHER2-(C-46) | n/a | 2.8 | BLQ[e] | Not determined |
| anti-Her2-HC-E152C-S3750-(C-61) | >95 | 4 | 4 | Not determined |
| anti-Her2-HC-E152C-S375C-(C-59) | 95 | 3.8 | 0 | Not determined |
| anti-Her2-HC-E152C-S375C-(C-60) | >95 | 4 | 4 | Not determined |
| anti-Her2-HC-E152Q-S3750-(C-64) | 90 | 3.6 | 3 | Not determined |
| anti-Her2-HC-E152Q-S3750-(C-62) | >95 | 4 | 0 | Not determined |

[a]The anti-HER2 antibodies in the conjugates are: the anti-HER2 mAb1 has a LC of SEQ ID NO: 19; a HC of SEQ ID NO: 9. The anti-HER2 mAb2 has a LC of SEQ ID NO: 19; a HC of SEQ ID NO: 21. The anti-hHER2 mAb3 has a LC of SEQ ID NO: 19; a HC of SEQ ID NO: 23. The anti-HER2 mAb4 has a LC of SEQ ID NO: 19; a HC of SEQ ID NO: 30. The anti-HER2 mAb5 has a LC of SEQ ID NO: 19; a HC of SEQ ID NO: 32.
[b]Compound-to-antibody ratio according to LCMS.
[c]Aggregation measured by analytical size exclusion chromatography; includes dimeric and oligomeric species.
BLQ = below limit of quantitation.
[d]Hydrophobic Interaction Chromatography (HIC) measurements: Retention time of the peak maximum was used to calculate the hydrophobicity index.
[e]Although aggregation was not observed or observed at a low level by AnSEC, late elution from the column suggests an invalid result.

Example 71

Generation of Anti-HER2-TLR7 Agonist Conjugates Through Partial Reduction of Native Disulfide Bonds of Non-Engineered Anti-HER2 Antibodies Some compounds of the invention can also be conjugated to native cysteine residues of non-engineered antibodies using a procedure that involves partial reduction of the antibodies (Doronina, S. O. et al., Nat. Biotechnol. 21, 778-784, 2003). Inter- and intra-chain disulfides bonds of anti-HER2 antibody (at a concentration of 5 to 10 mg/ml) were first partially reduced in PBS containing 2 mM EDTA by adding TCEP to a final concentration of 10 mM and incubating the mixture at 37° C. for 1 hour. After desalting and addition of 1% w/v PS-20 detergent, the partially reduced antibodies (1-2 mg/ml) were reacted overnight at 4° C. with 0.5 to 1 mg TLR7 agonist compound per 10 mg antibody. Resulting conjugates were purified by Protein A chromatography by standard methods and buffer exchanged to PBS, and profiled by MS, AnSEC, and AnHIC as described above. Measured compound-to-antibody ratio, aggregation behavior, and hydrophobicity data are summarized in Table 3 for one conjugate example made by reduction of anti-HER2 mAb3 followed by conjugation with Compound C-1.

Example 72

Generation of Anti-HER2-TLR7 Agonist Conjugates Using 1,3-Dichloropropan-2-One to Reconnect Native Interchain Disulfide Bonds of Non-Engineered Anti-HER2 Antibodies In an alternative method (United States Patent Application 20150150998), interchain disulfides bonds of a non-engineered, recombinant anti-HER2 antibody can be modified and conjugated to an agonist compound of the invention using the following two steps.

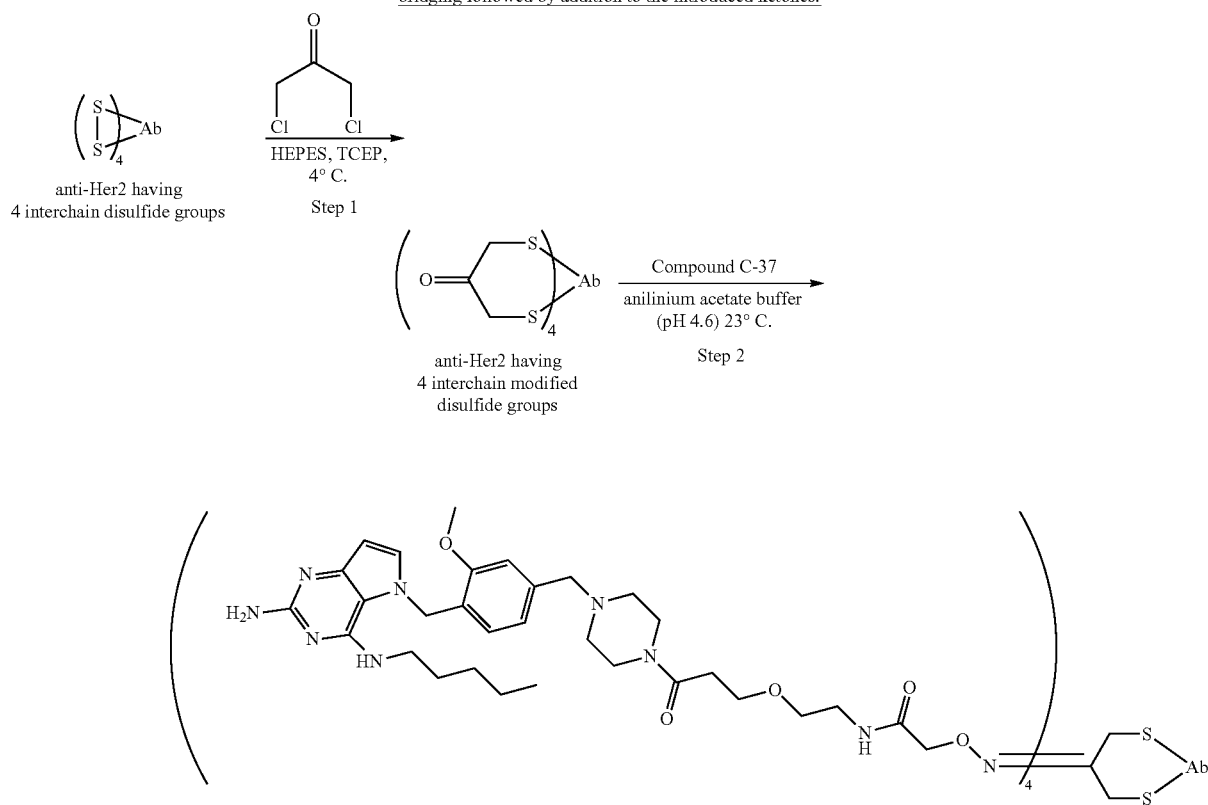

Step 1: Reduction of interchain disulfide bridges and re-bridging using 1,3-dichloropropan-2-one: TCEP.HCl (1.63 mM) was added to a solution of anti-HER2 antibody mAb3 (136 μM) and 1,3-dichloropropan-2-one (33 mM) in 0.1 M HEPES buffer (pH 8.0) at 4° C. The resulting mixture was gently agitated at 4° C. for 16 h. The reaction mixture was then buffer-exchanged into PBS using a PD-10 desalting column (GE Healthcare). The resulting solution was concentrated using a 50K Amicon filter to give the modified anti-HER2 antibody. The modification was confirmed by ESI-MS (Eluent A: water+0.1% Formic acid; Eluent B: Acetonitrile+0.04% Formic acid; Gradient: from 3 to 80% B in 2 minutes—Flow 1.0 ml/min. Column: Proswift Monolith 4.6*50 mm 40° C.); 145398 Da (after deglycosylation by PNGase F.

Step 2: Conjugation of the agonists Compound (C-37): The modified anti-HER2 antibody (30 mg/ml) was reacted with 3.0 mM Compound (C-37) comprising a linked aminowry moiety in 0.1 M anilinium acetate buffer (pH 4.6) at a final concentration of 15% (v/v) DMSO. The reaction mixture was incubated for approximately 16 hours at 23° C. The reaction mixture was then buffer-exchanged into PBS (pH 7.4) using a 50K Amicon filters, giving rise to the modified anti-HER2-compound conjugate.

Similar conjugates were obtained using Compound (C-35) to conjugate to the modified anti-HER2 antibody.

Conjugates were profiled by MS, AnSEC, and AnHIC as described above. The measured compound-to-antibody ratio, aggregation behavior, and hydrophobicity data are summarized in Table 3. The two example conjugates achieved high compound-to-antibody ratio, were mainly monomeric and showed low hydrophobicity (high hydrophobicity index corresponding to early elution from the HIC column). Conjugation through this method results in conjugation efficiencies of greater than 85% (Table 3). The conjugates contain less than 2% dimeric and oligomeric material (Table 3). The conjugates showed HI values of greater than 0.85 (Table 3). This suggests that conjugates can be made efficiently and have favorable characteristics.

Example 73

Generation of Anti-HER2-TLR7 Agonist Conjugates by Conjugation to Native Lysine Residues of Anti-HER2 Antibody Native antibodies can be functionalized with certain compounds of the invention through established methods. For example, anti-ratHER2 antibody (7.16.4; purchased from Bio X Cell; West Lebanon, N.H.) in PBS pH 7.2 at 4 mg/ml was mixed with 760 μM of Compound C-47) with a final DMSO concentration of 20% (v/v). The reaction was incubated at room temperature overnight, and then quenched with 50 mM Tris pH 8. Similar methods were used to make conjugates with anti-HER2 mAb3 or with agonist Compounds C-46 and C-50. The resulting antibody conjugates were purified by Protein A chromatography by standard methods and buffer exchanged to PBS.

Antibody conjugates were profiled by MS, AnSEC, and AnHIC as described above. Measured compound-to-antibody ratio, aggregation behavior, and hydrophobicity data are summarized in Table 3. Several lysine-reacted antibody conjugates show late elution and/or tailing of peaks on the AnSEC columns used, suggesting column interaction, which made detection of aggregate difficult.

Example 74

Generation of Anti-HER2-TLR7 Agonist Conjugates Using Two-Step Conjugation of an A1-Tagged Anti-HER2 Mutant Antibody with Agonist Compounds Containing an AminoOxy Reactive Group Post-translational 4'-phosphopantetheinylation is a versatile method for the site-specific labeling of recombinant proteins with structurally diverse small molecules (Yin J, et al., Proc. Natl. Acad. Sci. U.S.A. 102:15815-15820, 2005; Zhou Z, et al., ACS Chem. Biol. 2:337-346, 2007). This enzymatic approach, which is based on the catalytic action of promiscuous 4'-phosphopantetheinyl transferases (PPTases), was adopted for the preparation of highly homogeneous antibody conjugates (see WO2013184514). Enzymatic labeling is accomplished by incorporating 11 or 12-mer S6, ybbR, and A1 peptide sequences at various sites of the constant region of an antibody. For example, an A1 tag of sequence GDSLDMLEWSLM (SEQ ID NO: 31) can be incorporated after residue E388 (EU numbering) in the heavy chain of anti-HER2 mAb2 to produce anti-HER2 mAb5, which has a light chain sequence of SEQ ID NO: 19 and a heavy chain sequence of SEQ ID NO: 32. One strategy is a two-step method to prepare site-specific antibody-compound conjugates by post-translational 4'-phosphopantetheinylation (see WO2013184514). The first step of this approach is based on the PPTase-catalyzed labeling of a peptide-tagged antibody with a CoA analogue containing a bioorthogonal group, such as an azido, alkene, alkyne, ketone, or aldehyde moiety. Following affinity purification of the bioorthogonally labeled antibody, the second step of the two-step method involves the conjugation of a compound comprising a moiety reactive with the bioorthogonal group. As way of example, the following section describes the two-step method for anti-HER2 mutant antibodies containing an A1 tag insertion at a specific site within the constant region of the heavy chain. In addition, although the two-step method is exemplified for oxime ligation chemistry, this strategy can be extended to other bioorthogonal chemistries, such as click chemistry, including copper-free click chemistry, Staudinger ligation, isonitrile-based click chemistry, and tetrazine ligation.

Oxime ligation chemistry have been used by several research groups as an efficient, bioorthogonal method for the preparation of site-specific protein conjugates (Axup J Y, et al., Proc Natl Acad Sci USA. 109:16101-16106, 2012; Rabuka D, et al., Nat Protoc. 7:1052-1067, 2012). In order to combine post-translational 4'-phosphopantetheinylation with oxime ligation, a ketone-modified CoA analog was prepared chemoenzymatically from the corresponding pantothenate precursor molecule (Compound int-4) using the CoA biosynthetic enzymes CoAA, CoAD, and CoAE (Worthington A S, Burkart M D (2006) Org Biomol Chem. 4:44-46) (Kosa N M, Haushalter R W, Smith A R, Burkart M D (2012) Nat Methods 9:981-984). Next, PPTase catalysis was used to enzymatically conjugate the bioorthogonal ketone group site-specifically onto the embedded A1 tag of an anti-HER2 antibody. Specifically, 2.5 μM of anti-HER2 mAb5 was conjugated with 30 μM of ketone-CoA analogue (Compound C-69) (12 molar equivalents relative to the antibody) in the presence of about 0.5 μM of AcpS PPTase from *Escherichia coli* for 2 days at 37° C. in 75 mM Tris-HCl buffer (pH 8.0) supplemented with 12.5 mM $MgCl_2$ and 20 mM NaCl. To drive the conjugation reaction to completion, the reaction mixture was supplemented with approximately 1 μM *B. subtilius* Sfp PPTase, while the concentration of Compound C-69 was increased to about 60 μM. The reaction was incubated for another 4 days at room temperature. Labeling of the anti-HER2 mAb5 antibody with the ketone-CoA analogue (Compound C-69) was verified by obtaining deconvoluted ESI-MS spectra of the reduced and deglycosylated sample. The observed masses were in agreement with the calculated molecular weights of the corresponding ketone-functionalized heavy chains. After removing PPTase enzymes and excess ketone-CoA analogue by Protein A affinity chromatography (MabSelect SuRe, GE Healthcare Life Sciences), the ketone-activated antibody, anti-HER2-mAb5-(C-69) was eluted with Pierce™ IgG Elution Buffer (Thermo Fisher Scientific) followed by immediate neutralization with 1 M Tris-HCl buffer (pH 8.0). The neutralized antibody solution was buffer-exchanged into PBS and concentrated using a 50K Amicon filter.

Site-specific attachment of a ketone group enabled subsequent oxime ligation of an agonist compound to ketone-activated anti-HER2 mAb5-(C-69) as the second step of the two-step method. 48 μM of ketone-functionalized antibody was reacted with 30-fold molar excess (1.4 mM) of the aminooxy-agonists C-35 and C-37 in 100 mM anilinium acetate buffer (pH 4.6) containing 7% (v/v) DMSO. After 17 hours of incubation at room temperature, excess aminooxy reagent was removed by ultrafiltration with a 50K Amicon filter and repeated washing with PBS. Antibody conjugates were profiled by MS, AnSEC, and AnHIC as described above. Measured compound-to-antibody ratio, aggregation behavior, and hydrophobicity data are summarized in Table 3. As shown in Table 3, the two-step method afforded near quantitative labeling of ketone-activated anti-HER2 mAb5-(C-69) with the aminooxy-agonists C-35 and C-37.

Ketone-Coenzyme A Analogue (Compound C-69)

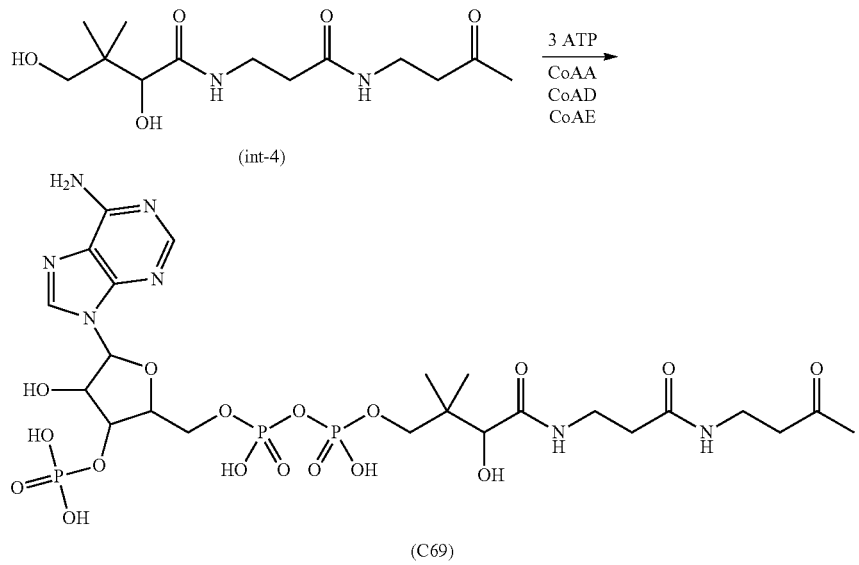

Compound (int-4) was converted into the ketone-functionalized CoA analog (C69) by reacting 5 mM of compound (int-4) with 25 mM of ATP in the presence of 10 μM *Staphylococcus aureus* CoAA, 25 μM *Escherichia coli* CoAD, and 20 μM *Escherichia coli* CoAE for about 16 h at 37° C. in 50 mM HEPES buffer (pH 8.0) containing 20 mM $MgCl_2$. After centrifugation of the reaction mixture at 20,817×g for 2 min, soluble enzyme was separated by ultrafiltration through an Amicon Ultra centrifugal filter with 10 kDa cutoff. Enzymatic conversion of compound (i-4) into the ketone-functionalized CoA analog (C59) was verified by formation of anti-HER2 mAb5-(C-69)-(C-35) and anti-HER2 mAb5-(C-69)-(C-37) (see Table 3).

Example 75

In Vitro Stability Testing of Anti-HER2-TLR7 Agonist Conjugates

The stability of the bond formed between maleimide containing payloads and Cys residues of the antibody is enhanced by the hydrolysis of the succinimide ring formed in this reaction. The effects of succinimide ring hydrolysis on the stability of antibody conjugates prepared with agonist compounds of the invention were studied after in vitro incubation in mouse serum. Mass changes resulting from payload deconjugation and the hydrolysis of the succinimide ring of maleimide payloads conjugated to antibodies were monitored by LC-MS. The hydrolysis of the succinimide ring has been reported to be stimulated by certain conditions such as high pH, high temperature, or high salts (J. Am. Chem. Soc. 1955, 77: 3922; Biochemistry 1976, 15: 2836; Biochem. J. 1979, 179: 191-197; J Pharm Sci. 1984, 73:1767-1771; Bioorg. Med. Chem. Lett. 17: 6286-6289, 2007). To probe the in vitro stability of conjugates, anti-HER2 antibody mAb2 conjugates were incubated at 37° C. in 50-70% mouse serum. Fifty microgram samples of conjugate were taken at each timepoint (typically 0, 8, 24, 48, and 72 hours) and flash frozen immediately. The samples were later thawed for processing and analysis. Briefly, antibodies were treated with PNGaseF to remove N-linked glycans and a proteolytic enzyme that cuts near the hinge region of the heavy chain in order to separate the Fab from the Fc before reduction with DTT to break the disulfide bonds. The light chain, heavy chain Fab, and heavy chain Fc fragments were then analyzed by ESI-MS. The relative populations of deconjugated antibody, conjugates with attached payload with hydrolyzed succinimide ring, and conjugates with attached payload with intact succinimide ring, were calculated from the relative MS intensities of the corresponding conjugate species. The extent of deconjugation and the extent of succinimide hydrolysis are shown in Tables 4 and 5 for a subset of conjugates. In general, the conjugates lose less than 13% of compound loaded during a 72 hour in vitro incubation and generally the succinimide ring hydrolysis is above 85% complete by 48 hours. Certain compounds of the invention, exemplified by Compound (C-5) and Compound (C-21) exhibit improved conjugate stability due to lower susceptiblity to deconjugation through the reverse maleimide reaction and further stabilization through succinimide ring hydrolysis.

TABLE 4

Succinimide ring hydrolysis of anti-HER2-TLR7 agonist conjugates as a function of in vitro incubation time in mouse serum.

| | % Ring opening (MS) | | | | | | | | |
|---|---|---|---|---|---|---|---|---|---|
| | S375C Adduct | | | | | E152C Adduct | | | |
| Conjugate[a] | 0 | 8 hr | 24 hr | 48 hr | 72 hr | 0 | 8 hr | 24 hr | 48 hr | 72 hr |
| anti-HER2 mAb2-(C-9) | 0 | 45 | 64 | 86 | 94 | 19 | 58 | 73 | 86 | 88 |
| anti-HER2 mAb2-(C-11) | 0 | 52 | 71 | 91 | 95 | 0 | 51 | 66 | 84 | 87 |
| anti-HER2 mAb2-(C-13) | 0 | 50 | 69 | 90 | 96 | 0 | 58 | 75 | 87 | 89 |
| anti-HER2 mAb2-(C-23) | 20 | 82 | 93 | 96 | 96 | 0 | 60 | 74 | 86 | 88 |
| anti-HER2 mAb2-(C-15) | 0 | 81 | 91 | 95 | 96 | 0 | 58 | 71 | 85 | 87 |

TABLE 4-continued

Succinimide ring hydrolysis of anti-HER2-TLR7 agonist conjugates as a function of in vitro incubation time in mouse serum.

| | % Ring opening (MS) | | | | | | | | | |
|---|---|---|---|---|---|---|---|---|---|---|
| | S375C Adduct | | | | | E152C Adduct | | | | |
| Conjugate[a] | 0 | 8 hr | 24 hr | 48 hr | 72 hr | 0 | 8 hr | 24 hr | 48 hr | 72 hr |
| anti-HER2 mAb2-(C-17) | 17 | 64 | 81 | 94 | 96 | 0 | 59 | 75 | 88 | 90 |
| anti-HER2 mAb2-(C-5) | 79 | 93 | 93 | 93 | 94 | 51 | 88 | 87 | 90 | 88 |
| anti-HER2 mAb2-(C-25) | 18 | 55 | 73 | 91 | 95 | 0 | 61 | 76 | 87 | 87 |
| anti-HER2 mAb2-(C-21) | 49 | 97 | 96 | 96 | 96 | 26 | 87 | 91 | 92 | 92 |
| anti-HER2 mAb2-(C-1) | 0 | 58 | 76 | 92 | 96 | 0 | 82 | 86 | 86 | 89 |
| anti-HER2 mAb2-(C-27) | 35 | 90 | 97 | 98 | 100 | 27 | 82 | 90 | 90 | 90 |
| anti-HER2 mAb2-(C-31) | 23 | 64 | 90 | 95 | 97 | 23 | 48 | 74 | 85 | 88 |
| anti-HER2 mAb2-(C-30) | 24 | 59 | 86 | 97 | 100 | 25 | 49 | 76 | 89 | 90 |

[a]The anti-HER2 mAb2 has a LC of SEQ ID NO: 19; a HC of SEQ ID NO: 21.

TABLE 5

Compound-to-antibody ratio of anti-HER2-TLR7 agonist conjugates as a function of in vitro incubation time in mouse serum

| | Compound-to-antibody ratio | | | | | | | | | |
|---|---|---|---|---|---|---|---|---|---|---|
| | S375C Adduct | | | | | E152C Adduct | | | | |
| Conjugate[a] | 0 | 8 hr | 24 hr | 48 hr | 72 hr | 0 | 8 hr | 24 hr | 48 hr | 72 hr |
| anti-HER2 mAb2-(C-9) | 0.93 | 0.88 | 0.84 | 0.82 | 0.80 | 1.00 | 0.92 | 0.91 | 0.87 | 0.87 |
| anti-HER2 mAb2-(C-11) | 0.94 | 0.90 | 0.86 | 0.84 | 0.84 | 1.00 | 0.93 | 0.90 | 0.89 | 0.87 |
| anti-HER2 mAb2-(C-13) | 0.93 | 0.88 | 0.85 | 0.82 | 0.80 | 1.00 | 0.94 | 0.91 | 0.88 | 0.86 |
| anti-HER2 mAb2-(C-23) | 0.93 | 0.93 | 0.86 | 0.86 | 0.86 | 1.00 | 0.95 | 0.93 | 0.92 | 0.92 |
| anti-HER2 mAb2-(C-15) | 0.93 | 0.88 | 0.87 | 0.86 | 0.85 | 1.00 | 0.95 | 0.93 | 0.90 | 0.90 |
| anti-HER2 mAb2-(C-17) | 0.94 | 0.85 | 0.86 | 0.84 | 0.84 | 1.00 | 0.92 | 0.91 | 0.87 | 0.88 |
| anti-HER2 mAb2-(C-5) | 0.95 | 0.95 | 0.94 | 0.94 | 0.94 | 1.00 | 0.98 | 0.98 | 0.90 | 0.96 |
| anti-HER2 mAb2-(C-25) | 0.92 | 0.89 | 0.87 | 0.85 | 0.85 | 1.00 | 0.96 | 0.95 | 0.93 | 0.92 |
| anti-HER2 mAb2-(C-21) | 0.94 | 0.91 | 0.91 | 0.91 | 0.90 | 1.00 | 0.96 | 0.95 | 0.95 | 0.94 |
| anti-HER2 mAb2-(C-1) | 0.93 | 0.86 | 0.83 | 0.81 | 0.79 | 1.00 | 0.97 | 0.96 | 0.96 | 0.96 |
| anti-HER2 mAb2-(C-27) | 0.95 | 0.87 | 0.85 | 0.85 | 0.85 | 0.95 | 0.91 | 0.90 | 0.90 | 0.90 |
| anti-HER2 mAb2-(C-31) | 0.94 | 0.88 | 0.84 | 0.81 | 0.80 | 0.85 | 0.93 | 0.88 | 0.87 | 0.85 |
| anti-HER2 mAb2-(C-30) | 0.94 | 0.86 | 0.80 | 0.80 | 0.79 | 0.95 | 0.88 | 0.81 | 0.80 | 0.78 |

[a]The anti-HER2 mAb2 has a LC of SEQ ID NO: 19; a HC of SEQ ID NO: 21.

Example 76

In Vivo Testing of Anti-HER2-TLR7 Agonist Conjugates in a N87 Gastric Tumor Xenograft Model Materials and Methods For N87 gastric carcinoma xenograft mouse model, female SCID-beige mice at 6-8 weeks of age (purchased from Harlan Laboratories) were used for implantation. N87 cells (obtained from ATCC, Catalog #CRL-5822, Vendor lot #7686255) were grown in sterile conditions in a 37° C. incubator with 5% $CO_2$ for two weeks. Cells were grown in RPMI medium with 10% fetal bovine serum. Cells were passaged every 3-4 days with 0.05% Trypsin/EDTA. On the day of implantation, N87 cells were lifted (passage×4) and re-suspended in RPMI1640 serum-free media at a concentration of $1\times10^6$ cells and 50% matrigel/100 μl. Cells were Radii tested to assure that they are free of *mycoplasma* and murine viruses.

N87 cells were implanted with a subcutaneous injection into the lower flank using a 28 g needle (100 μl injection volume). After implant, tumors were measured by caliper and mice weighed two times per week once tumors were palpable. Tumors then were measured twice a week in two dimensions. Caliper measurements were calculated using (L×W²)/2. Mice were fed with normal diet and housed in SPF animal facility in accordance with the Guide for Care and Use of Laboratory Animals and regulations of the Institutional Animal Care and Use Committee.

When xenograft tumors reached about 200 mm³, mice were administered by intravenous route 0.3-10 mg/kg of anti-HER2 antibody or anti-HER2-TLR7 agonist conjugate. Isotype control antibody was generated by expressing an antibody against a target not found in rodents and conjugating through similar methods described for anti-HER2 antibodies. Tumors were measured twice a week. Average tumor volumes were plotted using Prism 5 (GraphPad) software. An endpoint for efficacy studies was achieved when tumor size reached a volume of 2000 mm³. Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

Results

N87 gastric tumor xenograft mice were treated intravenously with a single dose of anti-HER2-mAb2-(C-1) conjugate, where Compound (C-1) is conjugated to Cys 152 and Cys 375 of the anti-HER2-mAb2 heavy chain, at 1 mg/kg, 2.5 mg/kg, 5 mg/kg, or 10 mg/kg. Complete regression of N87 xenograft tumors was observed in mice treated with anti-HER2-mAb2-(C-1) conjugate at all doses tested, including the lowest dose tested-1 mg/kg (FIG. 1). Tumor regression was not observed in the N87 xenograft mice treated with 10 mg/kg of unconjugated anti-HER2-mAb2 alone, or an isotype control antibody-(C-1) conjugate, when compared to untreated animals (FIG. 1).

Figure 2:
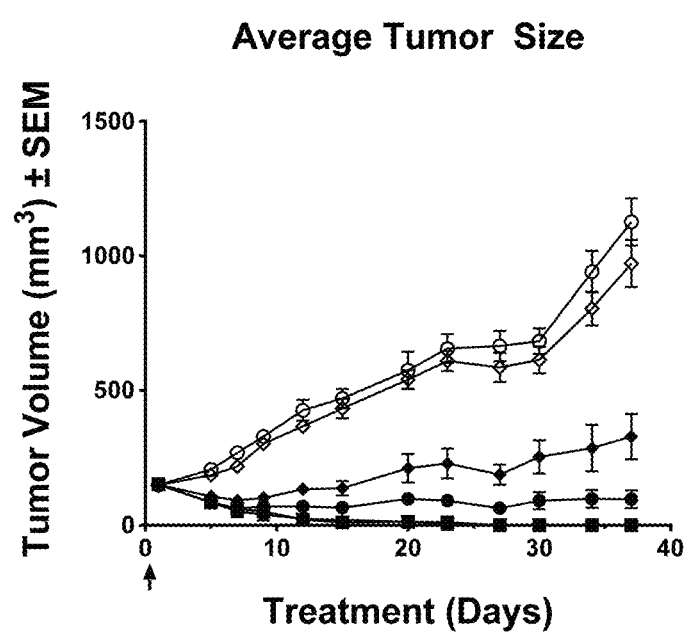
FIG. 2 depicts results following treatment of human N87 xenograft tumors with a single dose of anti-HER2-mAb1-(C-1) or anti-HER2-mAb1-(C-5). Regression of human N87 xenograft tumors was observed after treatment with 1 mg/kg of anti-HER2-mAb1-(C-1) (filled square) or 1 mg/kg of anti-HER2-mAb1-(C-5) (filled triangle), while treatment with 0.3 mg/kg of anti-HER2-mAb1-(C-1) (filled circle) or 0.3 mg/kg of anti-HER2-mAb1-(C-5) (filled diamond) resulted in tumor stasis, when compared to untreated animals (open circle). Regression of N87 gastric tumors was not observed in the N87 xenograft mice treated with an isotype control antibody-(C-5) conjugate (open diamond) when compared to untreated animals (open circle). Data represent mean tumor volumes (mean+/−SEM) over time (post-dose).

N87 gastric tumor xenograft mice were treated with a single dose of anti-HER2-mAb1-(C-1) or anti-HER2-mAb1-(C-5), at either 0.3 mg/kg or 1 mg/kg (10 mice per group). While treatment with a single dose of 1 mg/kg anti-HER2-mAb1-(C-1) led to complete regression of human N87 xenograft tumors, 0.3 mg/kg anti-HER2-mAb1-(C-1) resulted in tumor stasis (FIG. 2). Similarly, while treatment with a single dose of 1 mg/kg anti-HER2-mAb1-(C-5) led to complete regression of human N87 xenograft tumors, 0.3 mg/kg anti-HER2-mAb1-(C-5) resulted in tumor stasis (FIG. 2). Regression of N87 gastric tumors was not observed in the N87 xenograft mice treated with an isotype control antibody-(C-5) conjugate when compared to untreated animals. These data showed that tumor regression can be achieved by a single treatment of an anti-HER2-TLR7 agonist conjugate (e.g., anti-HER2-mAb1-(C-1) or anti-HER2-mAb1-(C-5), anti-HER2-mAb2-(C-1)) at a low dose, e.g., 1 mg/kg.

Figure 3:
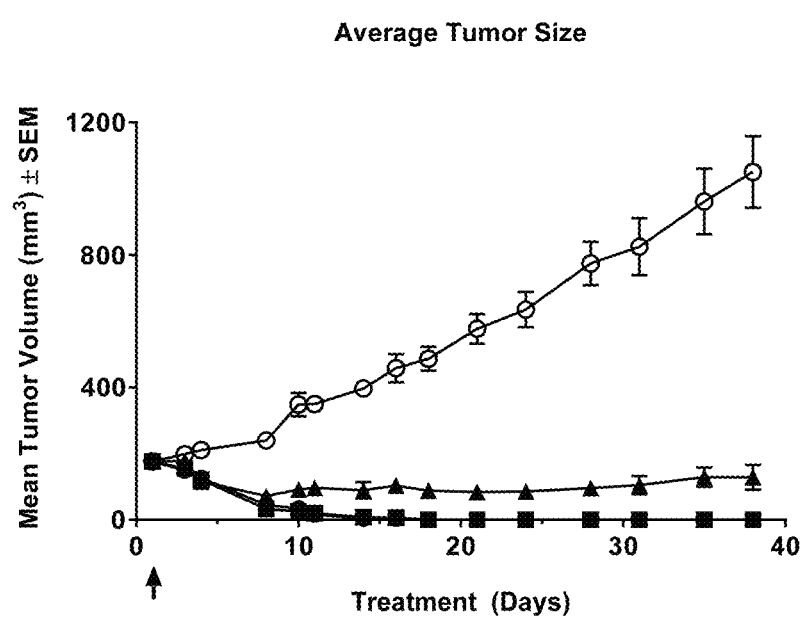
FIG. 3 depicts results following treatment of human N87 xenograft tumors with a single dose of anti-HER2-mAb1-(C-5). Regression of human N87 xenograft tumors was observed after treatment with 5 mg/kg of anti-HER2-mAb1-(C-5) (filled square) or 3 mg/kg of anti-HER2-mAb1-(C-5) (filled circle), while treatment with 1 mg/kg of anti-HER2-mAb1-(C-5) (filled triangle) resulted in tumor stasis, when compared to untreated animals (open circle). Data represent mean tumor volumes (mean+/−SEM) over time (post-dose).

In a separate study, N87 gastric tumor xenograft mice were treated with a single dose of anti-HER2-mAb1-(C-5), at 1 mg/kg, 3 mg/kg or 5 mg/kg (8 mice per group). While treatment with a single dose of either 3 mg/kg or 5 mg/kg anti-HER2-mAb1-(C-5) led to complete regression of human N87 xenograft tumors, 1 mg/kg anti-HER2-mAb1-(C-5) resulted in tumor stasis (FIG. 3) in this study.

Figure 4:
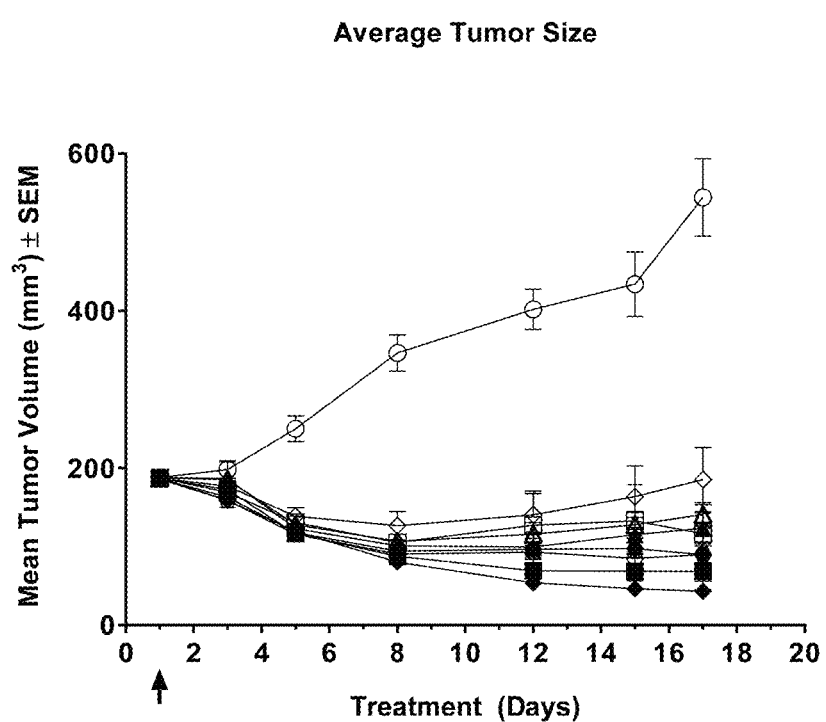
FIG. 4 depicts results following treatment of human N87 xenograft tumors with a single dose of anti-HER2-mAb1 conjugated with different compounds. Initial regression, followed by stasis of human N87 xenograft tumors was observed after treatment with 1 mg/kg of anti-HER2-mAb1-(C-5) (filled triangles), anti-HER2-mAb1-(C-60) (open triangles), anti-HER2-mAb1-(C-59) (filled square), anti-HER2-mAb1-(C-61) (open square), anti-HER2-mAb1-(C-35) (filed hexagon), anti-HER2-mAb1-(C-37) (open hexagon), anti-HER2-mAb1-(C-64) (filled diamond) or anti-HER2-mAb1-(C-62) (open diamond), when compared to untreated animals (open circle). Data represent mean tumor volumes (mean+/−SEM) over time (post-dose).

In addition, N87 gastric tumor xenograft mice were treated with a single dose of either anti-HER2-mAb1-(C-5), anti-HER2-mAb1-(C-35), anti-HER2-mAb1-(C-37), anti-HER2-mAb1-(C-59), anti-HER2-mAb1-(C-60), anti-HER2-mAb1-(C-61), anti-HER2-mAb1-(C-62) or anti-HER2-mAb1-(C-64) at 1 mg/kg (6 mice per group). Treatment with a single dose of 1 mg/kg anti-HER2-mAb1 conjugated with different compounds resulted in tumor stasis (FIG. 4), similar to what was observed after a single dose treatment of 1 mg/kg anti-HER2-mAb1-(C-5).

Example 77

In Vivo Testing of an Anti-ratHER2-TLR7 Agonist Conjugate in MMC (ratHER2⁺) Breast Cancer Syngeneic Model Materials and Methods For the MMC (ratHER2⁺) breast cancer syngeneic model, 6-10 week old female FVB/N transgenic mice expressing the activated rat Erbb2 (c-neu) oncogene containing the $Val^{664}$ to $Glu^{664}$ mutation (FVB-Tg(MMTV-Erbb2)NK1Mul/J; originally purchased from Jackson Laboratories, breed in house) were used for implantation. MMC cells (derived from tumors obtained from FVB/N transgenic mice, obtained from Professor Nora Disis, University of Washington) were grown in sterile conditions in a 37° C. incubator with 5% $CO_2$ for two weeks. Cells were grown in DMEM medium with 20% fetal bovine serum and Penicillin/Strep. Cells were passaged every 3-4 days with 0.05% Trypsin/EDTA. On the day of implantation, cells were lifted (passage×4) and re-suspended in RPMI1640 serum-free media at a concentration of 2.5×10⁵ cells and 10% matrigel/100 μl. Cells were Radii tested to assure that they are free of *mycoplasma* and murine viruses.

MMC cells were implanted with a subcutaneous injection into the lower flank using a 28 gauge needle (100 μl injection volume). After implant, tumors were measured by caliper and mice weighed 2 times per week once tumors were palpable. Tumors then were measured twice a week in two dimensions. Caliper measurements were calculated using (L×W²)/2. Mice were fed with normal diet and housed in SPF animal facility in accordance with the Guide for Care and Use of Laboratory Animals and regulations of the Institutional Animal Care and Use Committee.

When tumors reached about 200 mm³, groups of eight mice were administered by intravenous route with 1 mg/kg of anti-ratHER2 antibody (7.16.4, purchased from Bio X Cell; West Lebanon, N.H.) or 1 mg/kg of anti-ratHER2-TLR7 agonist conjugate (anti-ratHER2-(C-46)). Tumors were measured twice a week. Average tumor volumes were plotted using Prism 5 (GraphPad) software. An endpoint for efficacy studies was achieved when tumor size reached a volume of 2000 mm³. Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

Results

Figure 5A:
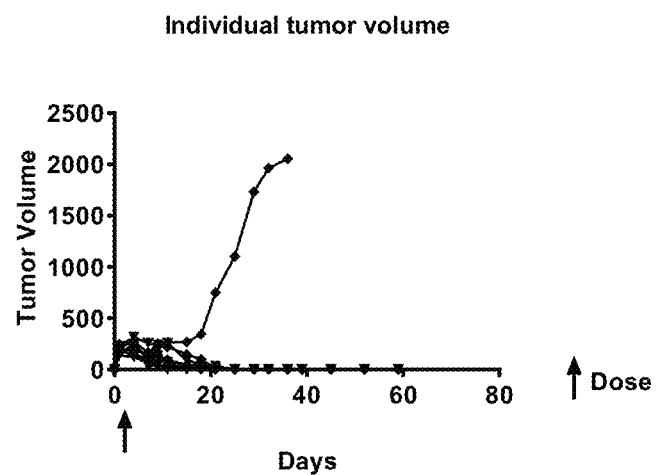
FIGS. 5A and 5B depict the results of treatment of MMC mouse breast tumors (ratHER2-positive) with a single dose of anti-ratHER2-(C-46) conjugate. Results demonstrate complete tumor regression was observed in seven out of eight mice treated with anti-ratHER2-(C-46) conjugate (FIG. 5A), but only in three out of eight mice treated with the naked anti-ratHER2 antibody (FIG. 5B). Treatment was initiated when tumors reached an average size of 200 mm$^3$ in MMC breast cancer syngeneic model. Data represent mean tumor volumes (mean+/−SEM) over time (post-dose).
Figure 5B:
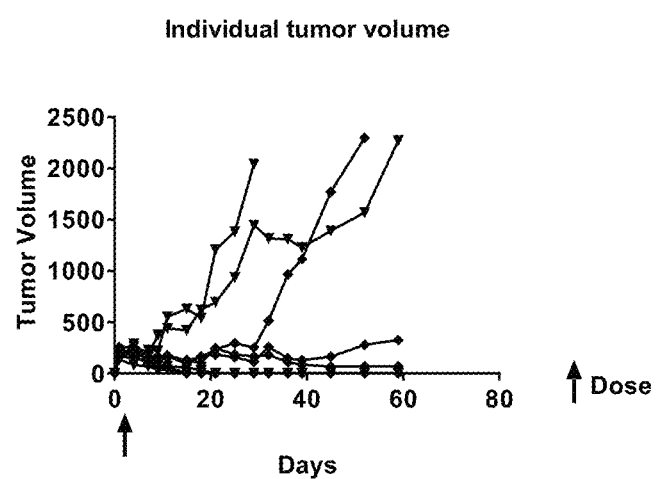

To test the efficacy of anti-ratHER2-(C-46) conjugates in MMC ratHER2+ breast cancer syngeneic model, mice bearing subcutaneous MMC breast tumors were treated intravenously with 1 mg/kg of anti-ratHER2-(C-46) conjugate, or unconjugated anti-ratHER2 (8 mice per group). As shown in FIGS. 5A and 5B, complete regression of MMC mouse breast tumors (ratHER2+) was observed in seven out of eight mice treated with a single dose of anti-ratHER2-(C-46) conjugates (FIG. 5A), but only in three out of eight mice treated with the naked anti-ratHER2 antibody (FIG. 5B).

These data suggest that the anti-ratHER2-(C-46) conjugate is therapeutically more effective against ratHER2-positive syngeneic breast cancer than the unconjugated anti-ratHER2 antibody alone.

Example 78

In Vivo Testing of Anti-HER2-TLR7 Agonist Conjugates in a HCC1954 Breast Tumor Xenograft Model Materials and Methods For HCC1954 breast xenograft mouse model, female SCID-beige mice at 6-8 weeks of age (purchased from Harlan Laboratories) were used for implantation. HCC1954 cells (obtained from ATCC, Catalog #CRL-2338, Vendor lot #5107643) were grown in sterile conditions in a 37° C. incubator with 5% $CO_2$ for two weeks. Cells were grown in RPMI medium with 10% fetal bovine serum. Cells were passaged every 3-4 days with 0.05% Trypsin/EDTA. On the day of implantation, HCC1954 cells were (harvested) lifted (passage×17) and re-suspended in RPMI1640 serum-free media at a concentration of $1\times10^6$ cells and 50% matrigel/100 µl. Cells were Radii tested to assure that they are free of *mycoplasma* and murine viruses.

HCC1954 cells were implanted with a subcutaneous injection into the right mammary fat pad using a 27G needle (100 µl injection volume). After implant, tumors were measured by caliper and mice weighed two times per week once tumors were palpable. Tumors then were measured twice a week in two dimensions. Caliper measurements were calculated using $(L\times W^2)/2$. Mice were fed with normal diet and housed in SPF animal facility in accordance with the Guide for Care and Use of Laboratory Animals and regulations of the Institutional Animal Care and Use Committee.

When xenograft tumors reached about 200 mm³, mice were administered by intravenous route 1-10 mg/kg of anti-HER2 antibody or anti-HER2-TLR7 agonist conjugate. Isotype control antibody was generated by expressing an antibody against a target not found in rodents and conjugating through similar methods described for anti-HER2 antibodies. Tumors were measured twice a week. Average tumor volumes were plotted using Prism 5 (GraphPad) software. An endpoint for efficacy studies was achieved when tumor size reached a volume of 2000 mm³. Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

Results

HCC1954 breast tumor xenograft mice were treated intravenously with a single dose of anti-HER2-mAb1-(C-5) conjugate, where Compound (C-5) is conjugated to Cys 152 and Cys 375 of the anti-HER2-mAb1 heavy chain, at 1 mg/kg, 3 mg/kg or 10 mg/kg (8 mice per group). While treatment with a single dose of 10 mg/kg or 3 mg/kg anti-HER2-mAb1-(C-5) led to complete regression of human HCC1954 xenograft tumors, 1 mg/kg anti-HER2-mAb1-(C-5) resulted in initial tumor regression followed by tumor stasis (FIG. 6). Tumor regression was not observed in the HCC1954 xenograft mice treated with 10 mg/kg of unconjugated anti-HER2-mAb2 alone (FIG. 6).

These data show that tumor regression can be achieved in the high HER2 expressing HCC1954 breast tumor xenograft by a single treatment of an anti-HER2-TLR7 agonist conjugate (anti-HER2-mAb1-(C-5)) at 3 mg/kg.

Example 79

In Vivo Testing of Anti-HER2-TLR7 Agonist Conjugates in a SKOV3 Ovarian Tumor Xenograft Model Materials and Methods For SKOV3 ovarian xenograft mouse model, female SCID-beige mice at 6-8 weeks of age (purchased from Harlan Laboratories) were used for implantation. SKOV3 cells (obtained from ATCC, Catalog #HTB-77, Vendor lot #7349765) were grown in sterile conditions in a 37° C. incubator with 5% $CO_2$ for two weeks. Cells were grown in McCoy's5A medium with 10% fetal bovine serum. Cells were passaged every 3-4 days with 0.05% Trypsin/EDTA. On the day of implantation, SKOV3 cells were (harvested) lifted (passage×11) and re-suspended in McCoy's5A serum-free media at a concentration of $5\times10^6$ cells and 50% matrigel/100 µl. Cells were Radii tested to assure that they are free of *mycoplasma* and murine viruses.

SKOV3 cells were implanted with a subcutaneous injection into the lower flank using a 28½ G (100 µl injection volume). After implant, tumors were measured by caliper and mice weighed two times per week once tumors were palpable. Tumors then were measured twice a week in two dimensions. Caliper measurements were calculated using $(L\times W^2)/2$. Mice were fed with normal diet and housed in SPF animal facility in accordance with the Guide for Care and Use of Laboratory Animals and regulations of the Institutional Animal Care and Use Committee.

When xenograft tumors reached about 200 mm³, mice were administered by intravenous route 3-10 mg/kg of anti-HER2 antibody or anti-HER2-TLR7 agonist conjugate. Isotype control antibody was generated by expressing an antibody against a target not found in rodents and conjugating through similar methods described for anti-HER2 antibodies. Tumors were measured twice a week. Average tumor volumes were plotted using Prism 5 (GraphPad) software. An endpoint for efficacy studies was achieved when tumor size reached a volume of 2000 mm³. Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

For HER2 ImmunoHistoChemistry (IHC), standardized guidelines and protocols for HER2 staining and xenograft HER2 scoring were used (see e.g., English et al., Mol Diagn Ther. 2013 April; 17(2): 85-99).

Results

Figure 7:
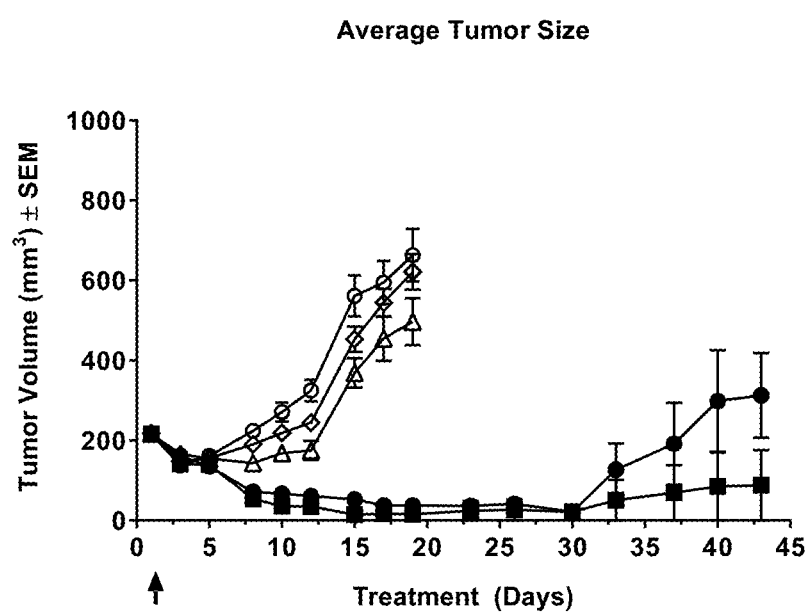
FIG. 7 depicts results following treatment of human SKOV3 ovarian xenograft tumors with a single dose of anti-HER2-mAb1-(C-5). Regression of human SKOV3 xenograft tumors was observed after treatment with 10 mg/kg of anti-HER2-mAb1-(C-5) (filled square), while treatment with 3 mg/kg of anti-HER2-mAb1-(C-5) (filled circle) resulted in initial tumor regression followed by tumor regrowth, when compared to untreated animals (open circle). Regression of tumors was not observed in the SKOV3 xenograft mice treated with 10 mg/kg of an isotype control antibody-(C-5) conjugate (open diamond) or unconjugated anti-HER2-mAb1 alone (open triangle) when compared to untreated animals (open circle). Data represent mean tumor volumes (mean+/−SEM) over time (post-dose).

SKOV3 ovarian tumor xenograft mice were treated intravenously with a single dose of anti-HER2-mAb1-(C-5) conjugate, where Compound (C-5) is conjugated to Cys 152 and Cys 375 of the anti-HER2-mAb1 heavy chain, at 3 mg/kg or 10 mg/kg. While treatment with a single dose of 10 mg/kg anti-HER2-mAb1-(C-5) led to complete regression of human SKOV3 xenograft tumors in 7 out of 8 mice, 3 mg/kg anti-HER2-mAb1-(C-5) resulted in initial tumor regression followed by tumor regrowth (FIG. 7). Tumor regression was not observed in the SKOV3 xenograft mice treated with 10 mg/kg of unconjugated anti-HER2-mAb1 alone, or an isotype control antibody-(C-5) conjugate, when compared to untreated animals (FIG. 7).

Figure 8A:
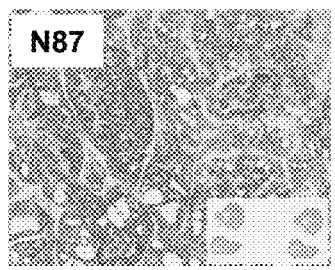
FIGS. 8A-8C depict representative ImmunoHistoChemistry (IHC) images showing HER2 expression on N87 (FIG. 8A), HCC1954 (FIG. 8B) and SKOV3 (FIG. 8C) xenografts tumors. Tumors were scored based on their HER2 expression level as 3+ (N87 and HCC1954) and 2+ (SKOV3).
Figure 8B:
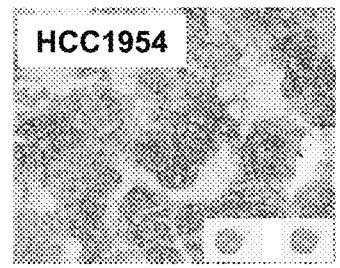
Figure 8C:
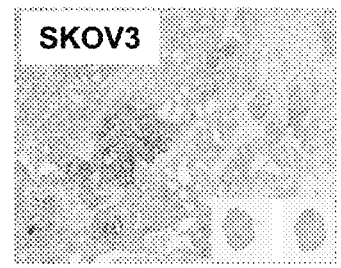

These data show that tumor regression can be achieved by a single treatment of an anti-HER2-TLR7 agonist conjugate (e.g., anti-HER2-mAb1-(C-1) or anti-HER2-mAb1-(C-5)) at 10 mg/kg in a xenograft model in which Her2 is expressed at lower levels compared to N87 and HCC xenograft models (FIG. 8C as compared to FIGS. 8A and 8B). Based on HER2 expression level, N87 and HCC1954 have 3+ IHC score, and SKOV3 has 2+ IHC score. Therefore, the anti-HER2-TLR7 agonist conjugates described herein can suppress tumor growth not only in high HER2-expressing tumors (e.g., having 3+ IHC scores), but also in low HER2-expressing tumors (e.g., having 2+ IHC scores).

We claim:
1. A conjugate of Formula (II), or pharmaceutically acceptable salt thereof:

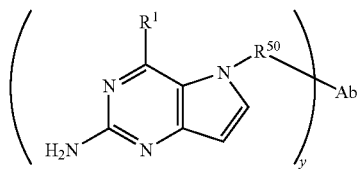

Formula (II)

wherein:
R$^{50}$ is

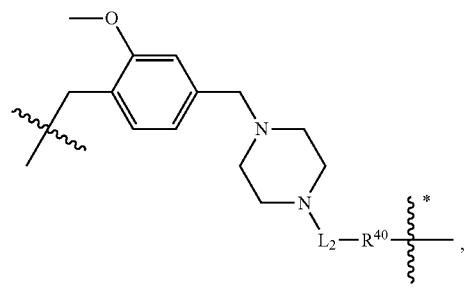

where the * indicates the point of attachment to Ab;
Ab is an antibody or antigen binding fragment thereof that specifically binds to human HER2, wherein Ab is selected from any of the following:
(a) an antibody that comprises:
a heavy chain complementary determining region 1 (HCDR1) comprising the amino acid sequence of SEQ ID NO: 1;
a heavy chain complementary determining region 2 (HCDR2) comprising the amino acid sequence of SEQ ID NO: 2;
a heavy chain complementary determining region 3 (HCDR3) comprising the amino acid sequence of SEQ ID NO: 3;
a light chain complementary determining region 1 (LCDR1) comprising the amino acid sequence of SEQ ID NO: 11;
a light chain complementary determining region 2 (LCDR2) comprising the amino acid sequence of SEQ ID NO: 12; and
a light chain complementary determining region 3 (LCDR3) comprising the amino acid sequence of SEQ ID NO: 13;
(b) an antibody that comprises:
a HCDR1 comprising the amino acid sequence of SEQ ID NO: 4;
a HCDR2 comprising the amino acid sequence of SEQ ID NO: 5;
a HCDR3 comprising the amino acid sequence of SEQ ID NO: 3;
a LCDR1 comprising the amino acid sequence of SEQ ID NO: 14;
a LCDR2 comprising the amino acid sequence of SEQ ID NO: 15; and
a LCDR3 comprising the amino acid sequence of SEQ ID NO: 16;
(c) an antibody that comprises a heavy chain variable region comprising the amino acid sequence of SEQ ID NO: 7, and a light chain variable region comprising the amino acid sequence of SEQ ID NO: 17;
(d) an antibody that comprises a heavy chain comprising the amino acid sequence of SEQ ID NO: 9, and a light chain comprising the amino acid sequence of SEQ ID NO: 19;
(e) an antibody that comprises a heavy chain comprising the amino acid sequence of SEQ ID NO: 21, and a light chain comprising the amino acid sequence of SEQ ID NO: 19;
(f) an antibody that comprises a heavy chain comprising the amino acid sequence of SEQ ID NO: 23, and a light chain comprising the amino acid sequence of SEQ ID NO: 19;
(g) an antibody that comprises a heavy chain comprising the amino acid sequence of SEQ ID NO: 32, and a light chain comprising the amino acid sequence of SEQ ID NO: 19; or
(h) pertuzumab;
and wherein
R$^1$ is —NHR$^2$ or —NHCHR$^2$R$^3$;
R$^2$ is —C$_3$-C$_6$alkyl or —C$_4$-C$_6$alkyl;
R$^3$ is L$_1$OH;
L$_1$ is —(CH$_2$)$_m$—;
L$_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$—, —((CH$_2$)$_n$O)$_t$(CH$_2$)$_n$NHC(=O)(CH$_2$)$_n$, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$X$_3$C(=O)(CH$_2$)$_n$—, —C(=O)X$_2$C(=O)(CH$_2$)$_n$NHC(=O)(CH$_2$)$_n$—, —C(=O)X$_2$C(=O)(CH$_2$)$_n$NHC(=O)((CH$_2$)$_n$O)$_t$(CH$_2$)$_n$—, —C(=O)(CH$_2$)$_n$C(R$_7$)$_2$—, —C(=O)(CH$_2$)$_n$C(R$_7$)$_2$SS(CH$_2$)$_n$NHC(=O)(CH$_2$)$_n$—, —(CH$_2$)$_n$X$_2$C(=O)(CH$_2$)$_n$NHC(=O)((CH$_2$)$_n$O)$_t$(CH$_2$)$_n$— or —C(=O)(CH$_2$)$_n$C(=O)NH(CH$_2$)$_n$;
R$_{40}$ is

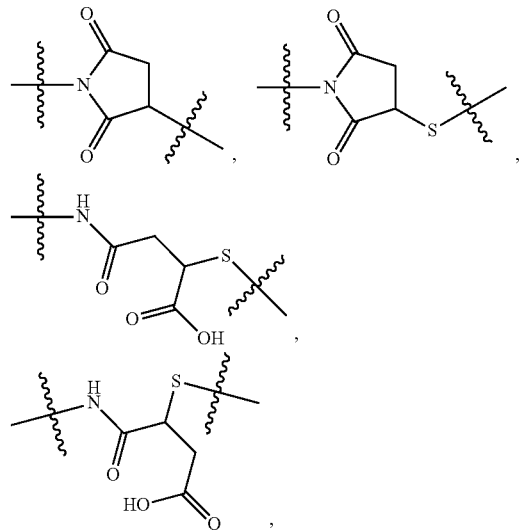

481
-continued
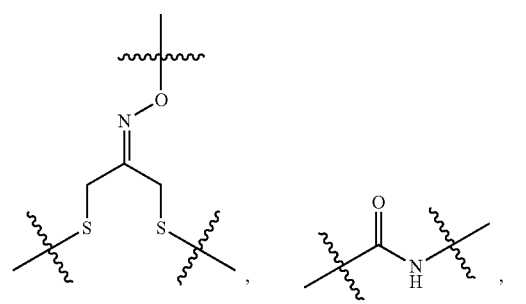
—S—, —NHC(=O)CH₂—, —S(=O)₂CH₂CH₂—,
—(CH₂)₂S(=O)₂CH₂CH₂—, —NHS(=O)₂CH₂CH₂,
—NHC(=O)CH₂CH₂—, —CH₂NHCH₂CH₂—,
—NHCH₂CH₂—,
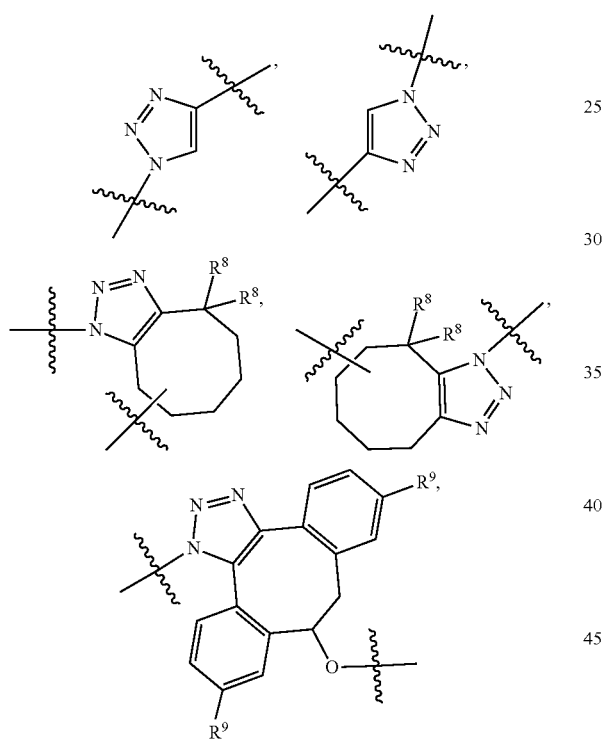
482
-continued
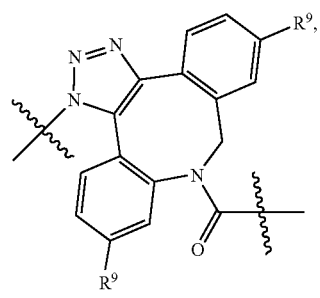
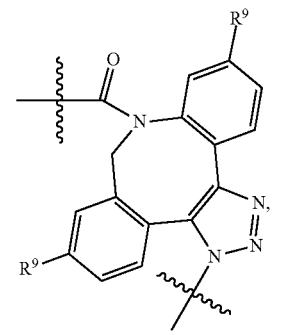
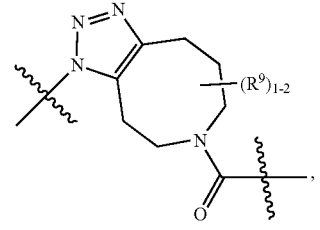
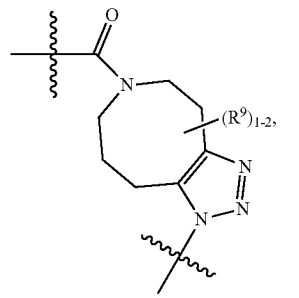
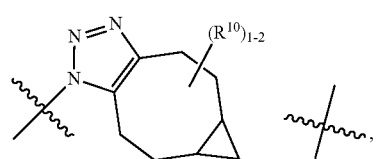
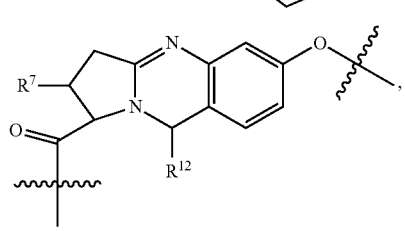

483
-continued
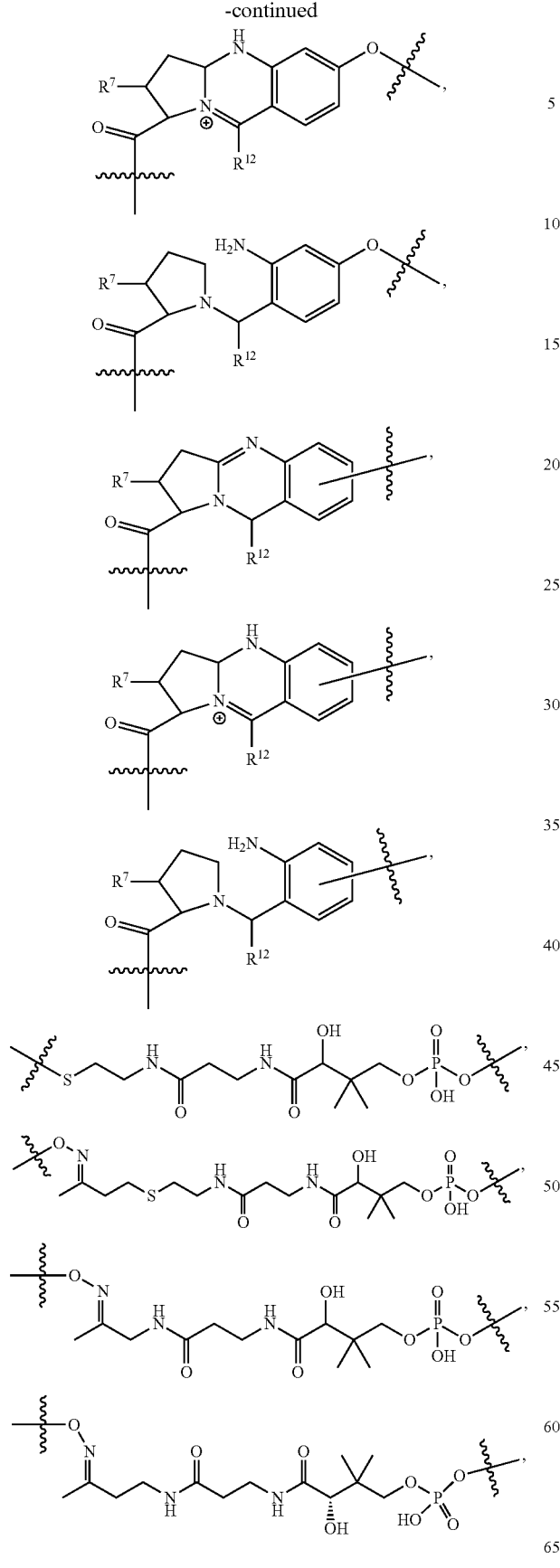
484
-continued
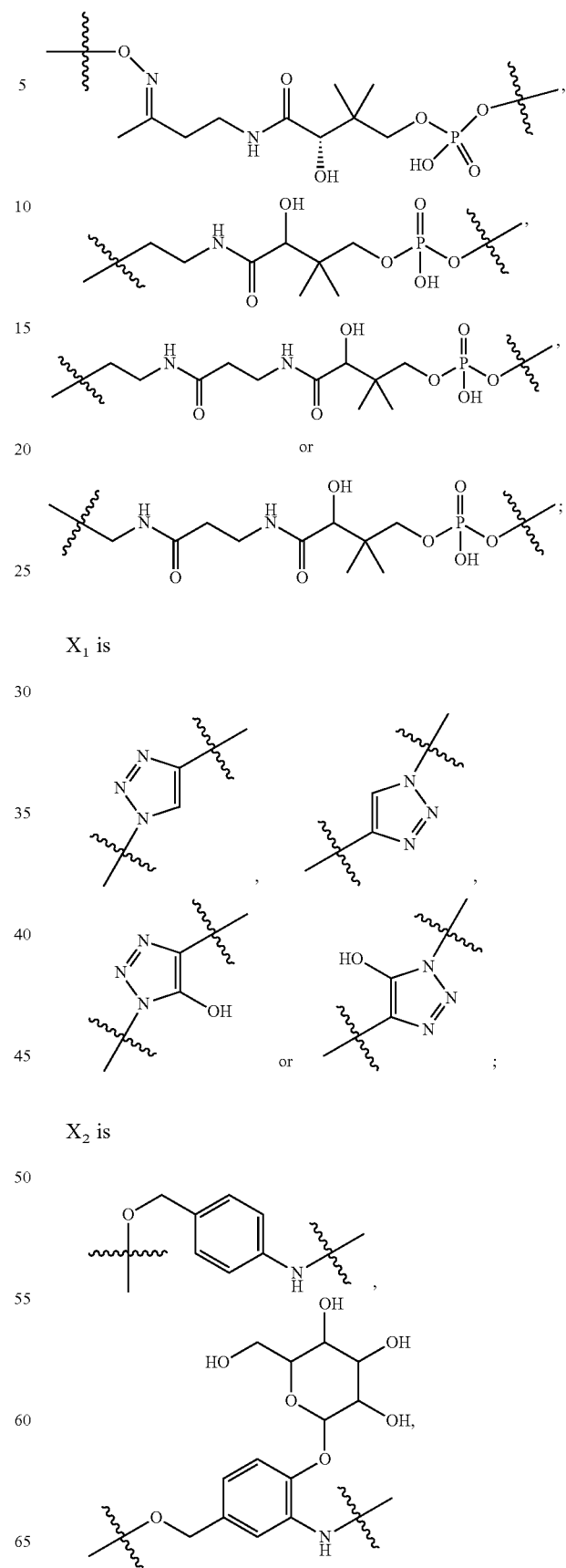
$X_1$ is
$X_2$ is

485

-continued

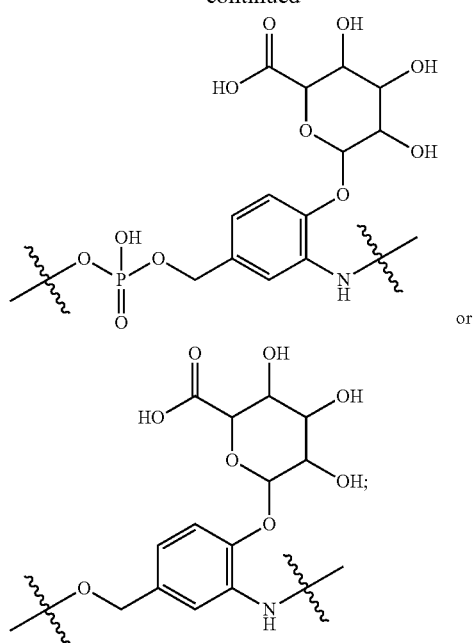

or $X_3$ is

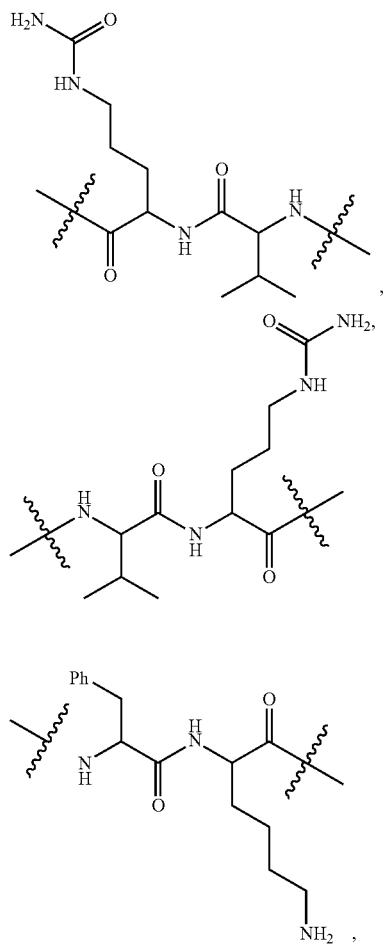

486

-continued

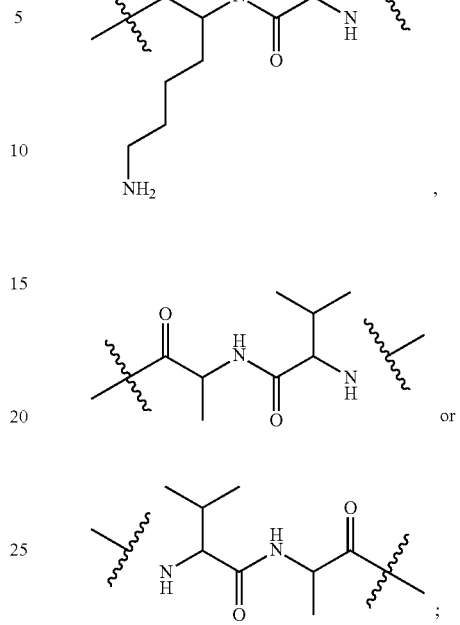

;

each $R^7$ is independently selected from H and $C_1$-$C_6$alkyl;

each $R^8$ is independently selected from H, $C_1$-$C_6$alkyl, F, Cl, and —OH;

each $R^9$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^{12}$ is H, methyl or phenyl;

each m is independently selected from 1, 2, 3, and 4;

each n is independently selected from 1, 2, 3, and 4;

each t is independently selected from 1, 2, 3, 4, 5, 6, 7, 8, 9, 10, 11, 12, 13, 14, 15, 16, 17 and 18, and y is an integer from 1 to 16.

2. The conjugate of claim 1, wherein Ab comprises a modified Fc region compared to a wild-type constant region.

3. The conjugate of claim 1, wherein Ab comprises cysteine at one or more of the following positions (all positions by EU numbering):

(a) positions 152, 360 and 375 of the antibody heavy chain, and (b) positions 107, 159, and 165 of the antibody light chain.

4. The conjugate of claim 1, wherein Ab comprises cysteines at positions 152 and 375 of the antibody heavy chains (all positions by EU numbering).

5. The conjugate of claim 1, wherein the antibody conjugate of Formula (II) comprises the structure of Formula (IIa):

Formula (IIa)

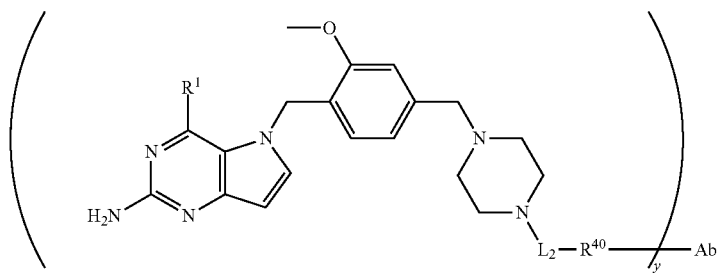

wherein:

R¹ is —NHR²;
R² is —C₄-C₆alkyl;
L₂ is —(CH₂)$_n$—, —((CH₂)$_n$O)$_t$(CH₂)$_n$—, —(CH₂)$_n$X₁(CH₂)$_n$—, —C(=O)(CH₂)$_n$—, —C(=O)((CH₂)$_n$O)$_t$(CH₂)$_n$—, —C(=O)((CH₂)$_n$O)$_t$(CH₂)$_n$X₁(CH₂)$_n$—, —C(=O)NH((CH₂)$_n$O)$_t$(CH₂)$_n$X₁(CH₂)$_n$—, —C(=O)X₂X₃C(=O)((CH₂)$_n$O)$_t$(CH₂)$_n$— or —C(=O)X₂C(=O)(CH₂)$_n$NHC(=O)(CH₂)$_n$—;

R₄₀ is

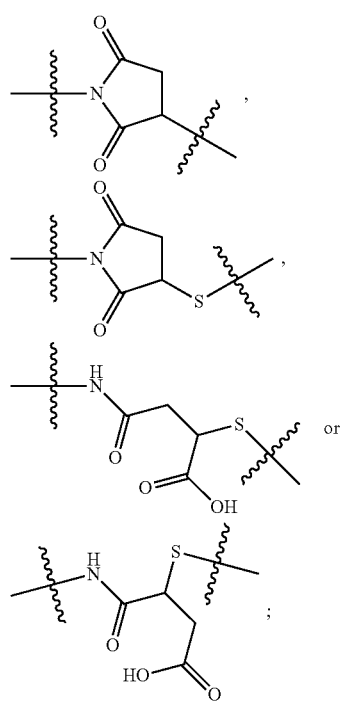

X₁ is

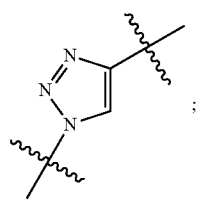

X₂ is 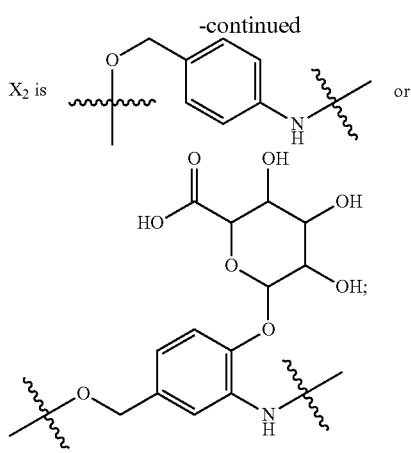

X₃ is

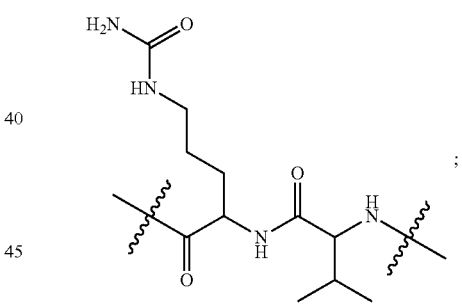

each n is independently selected from 1, 2, 3, and 4;
each t is independently selected from 1, 2, 3, 4, 5, 6, 7, 8, 9, 10, 11, 12, 13, 14, 15, 16, 17 and 18, and
y is an integer from 1 to 16.

6. The conjugate of claim 1, wherein
R¹ is —NHR²;
R² is —C₄-C₆alkyl;
L₂ is —(CH₂)$_n$— or —C(=O)(CH₂)$_n$;
R₄₀ is

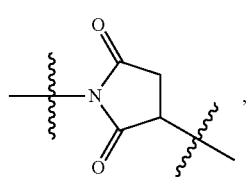

489
-continued

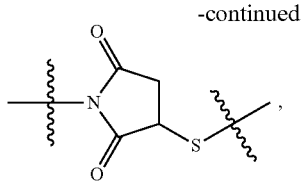

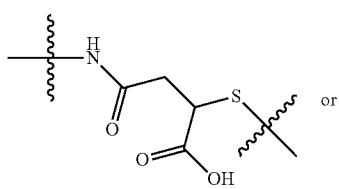
, or

490
-continued

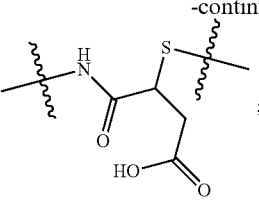
;

and
each n is independently selected from 1, 2, 3, and 4, and y is an integer from 1 to 16.

7. The conjugate of claim 1, wherein the conjugate has a hydrophobicity index of 0.8 or greater, as determined by hydrophobic interaction chromatography.

8. The conjugate of claim 1, wherein the Ab is trastuzumab, or margetuximab.

9. A pharmaceutical composition comprising one or more conjugates of claim 1 and a pharmaceutically acceptable carrier.

10. A conjugate comprising any of the following formulas:

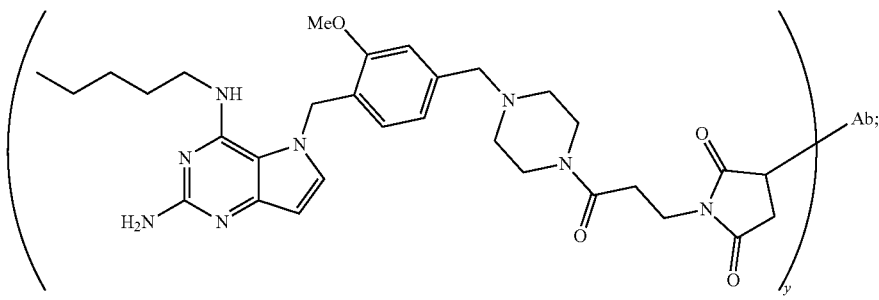

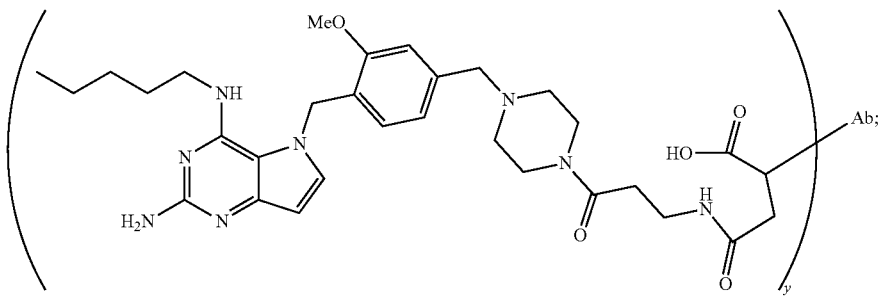

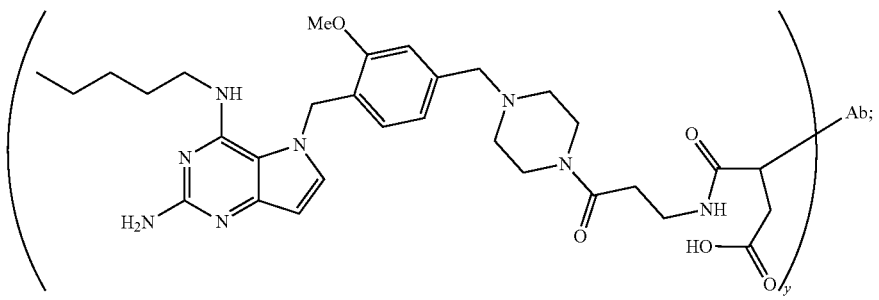

-continued
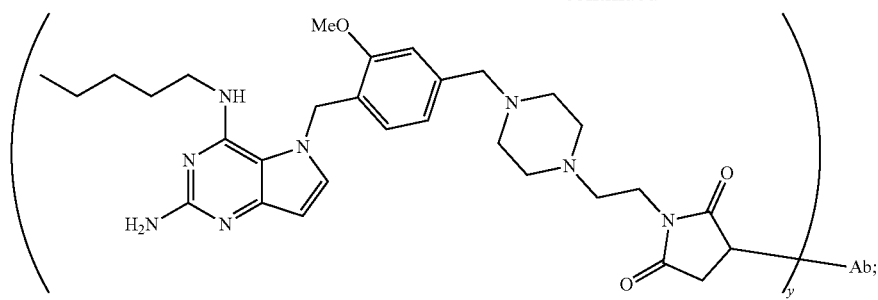
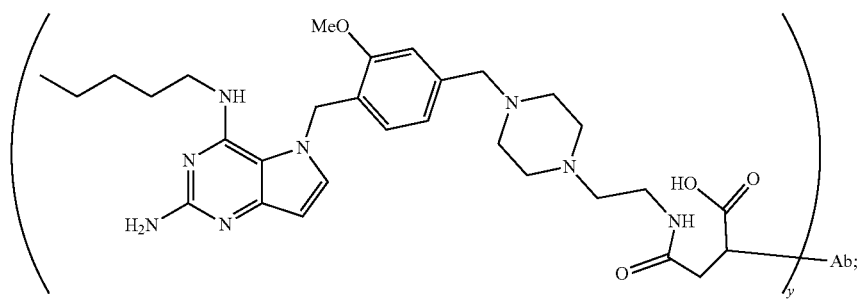
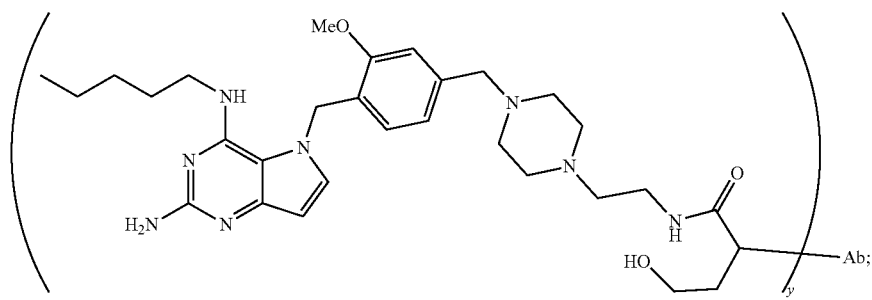
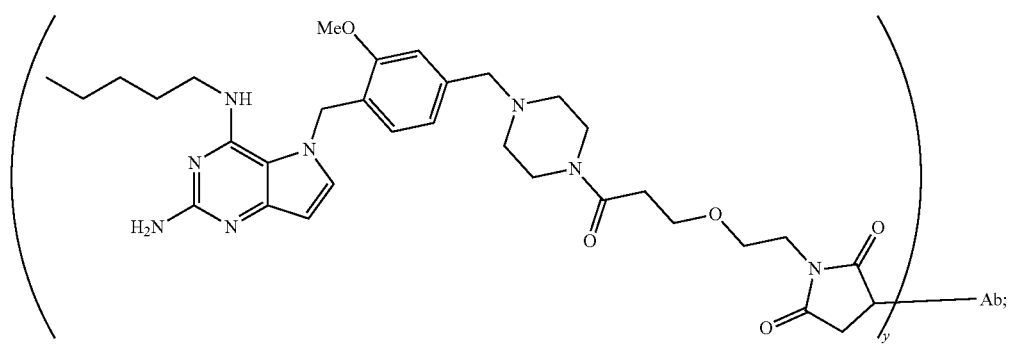
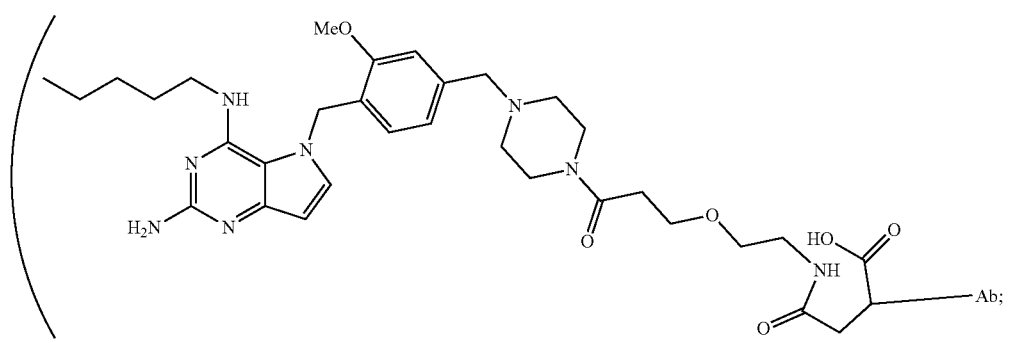

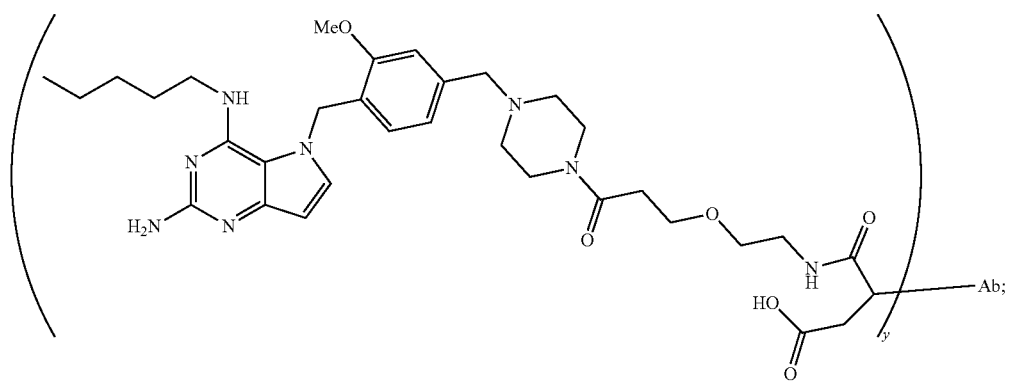
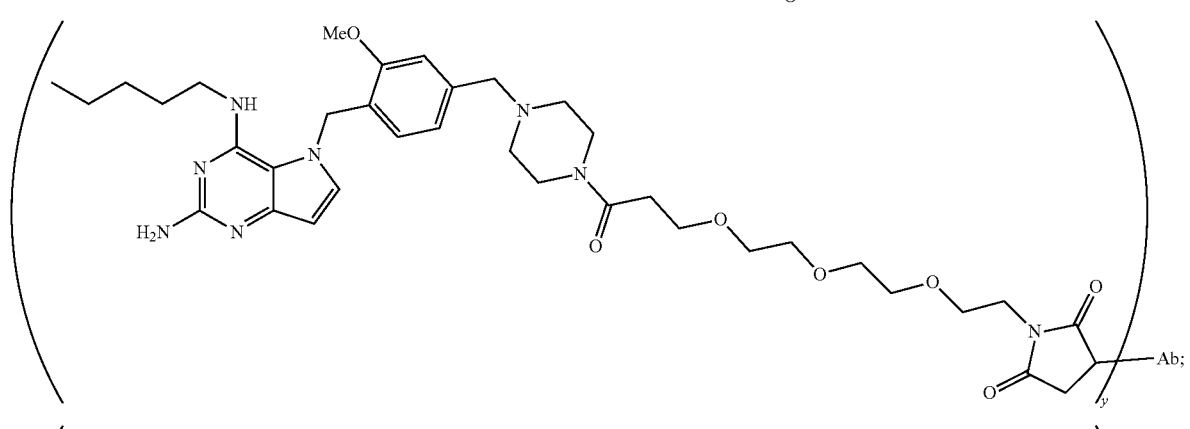
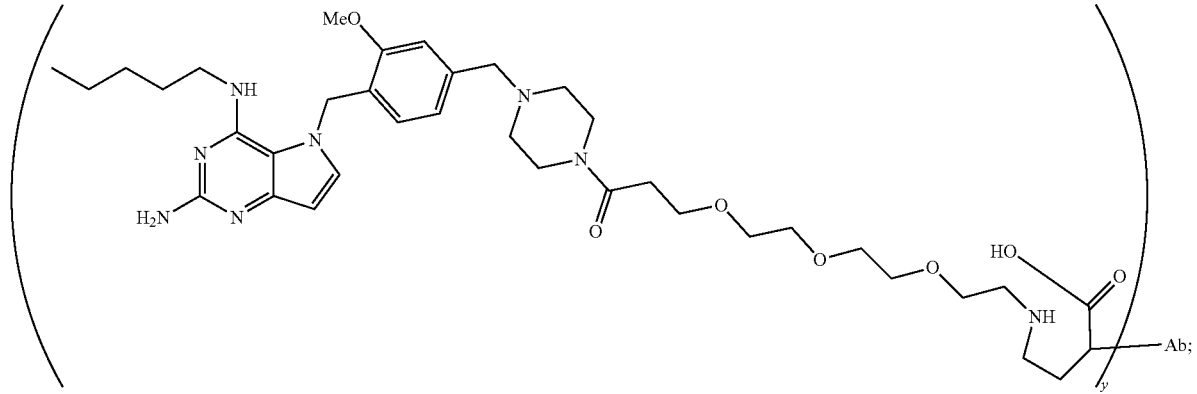
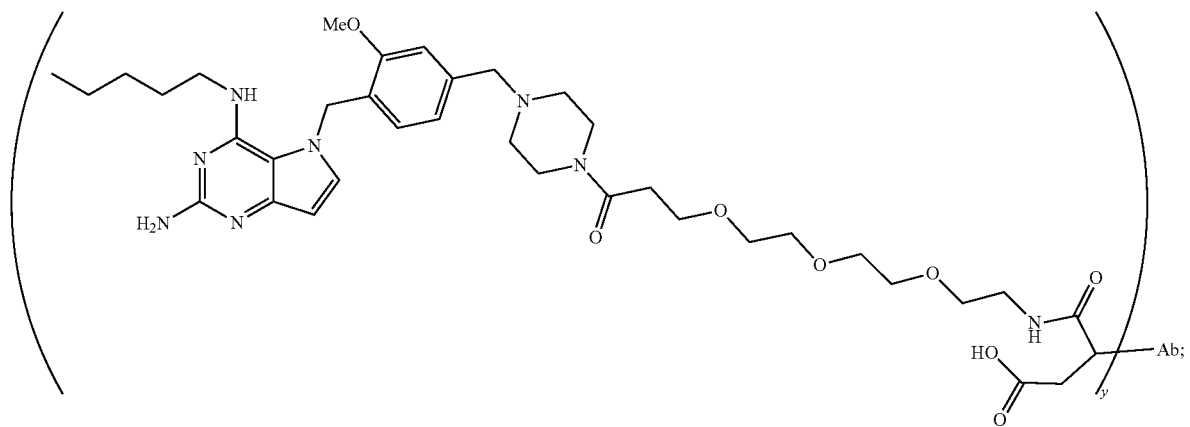

495
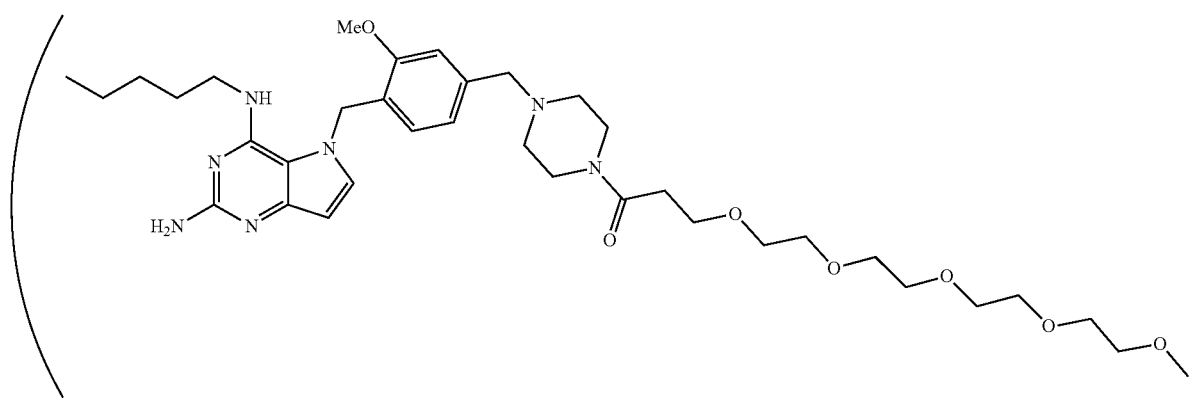
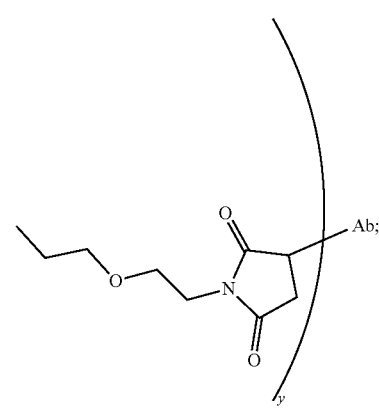
496
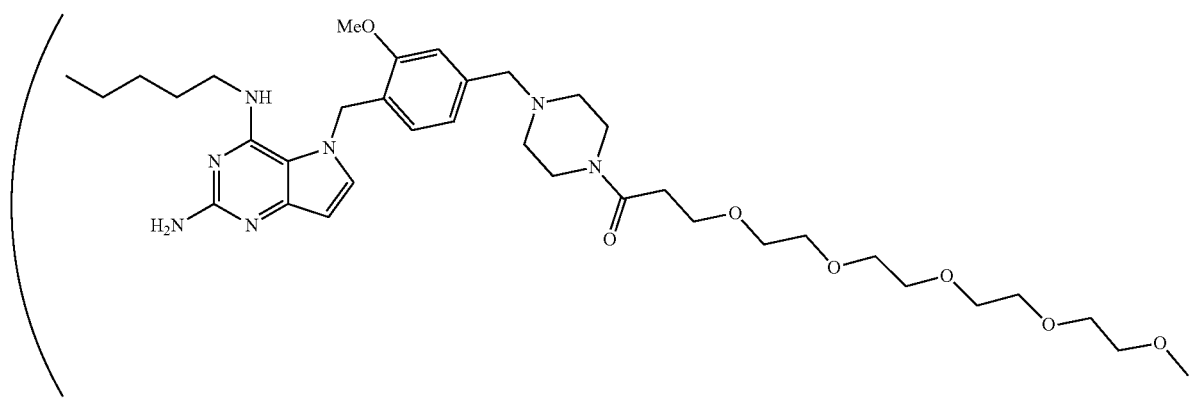
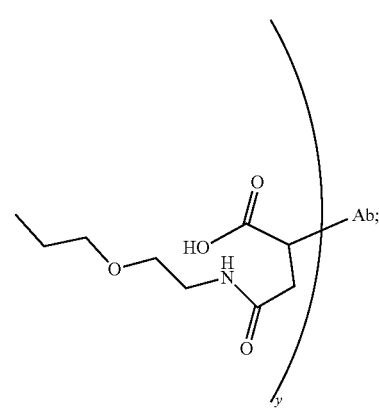

497
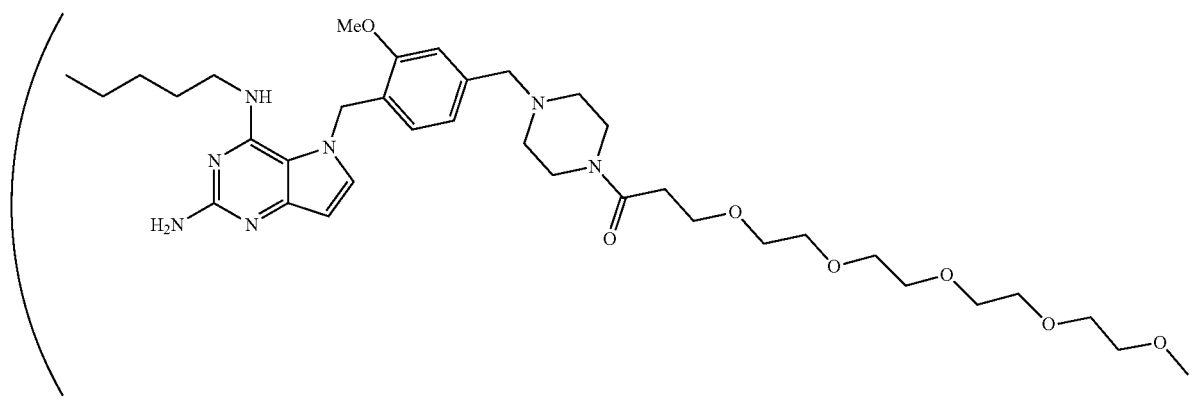
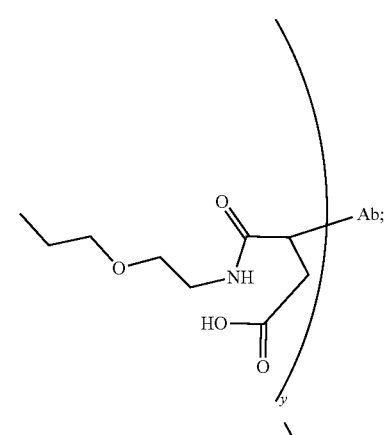
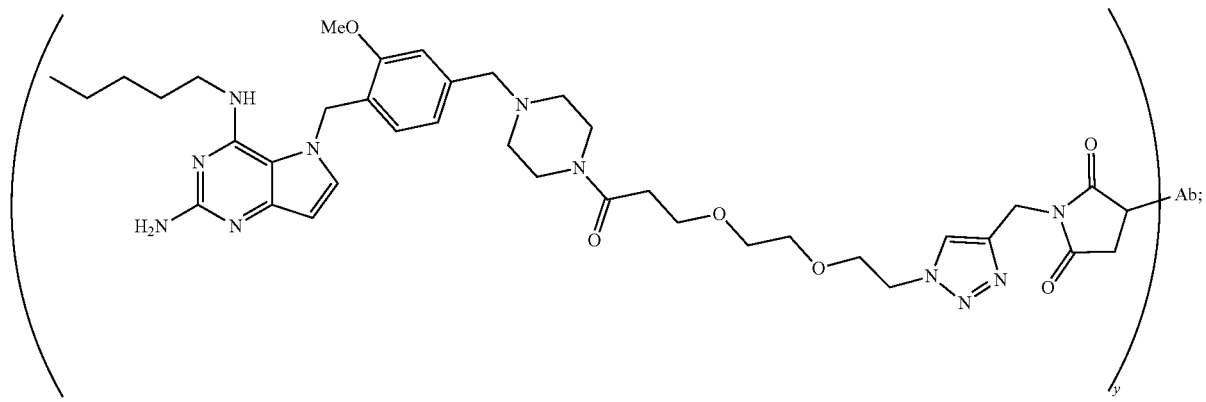
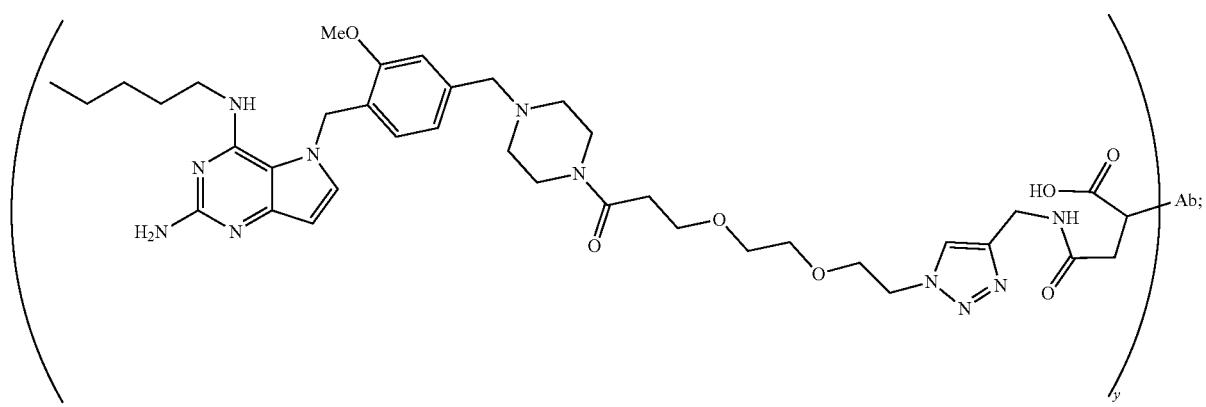

-continued
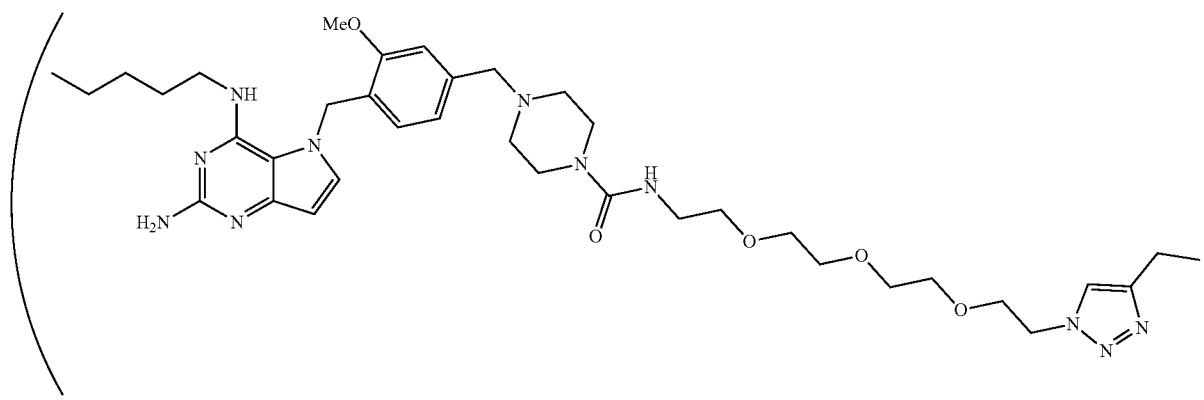
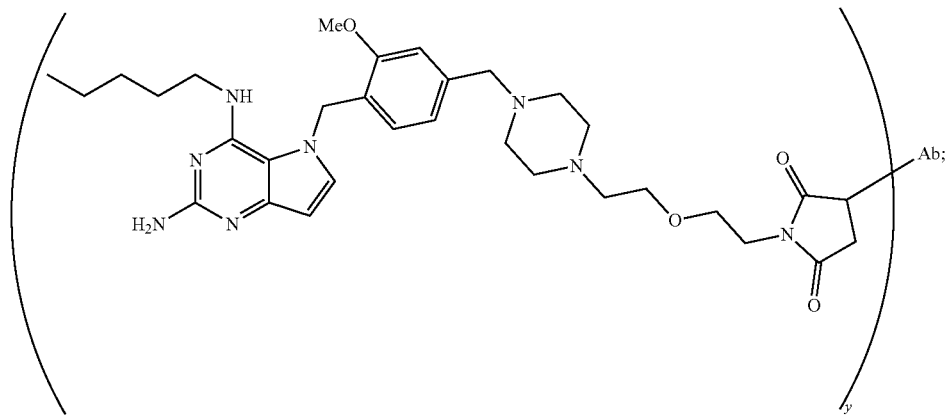
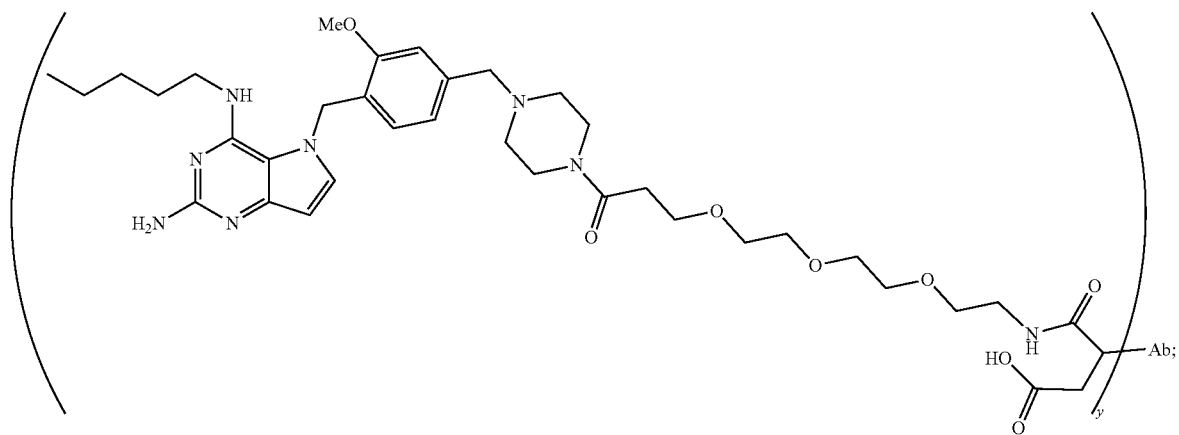

501                                    502
-continued
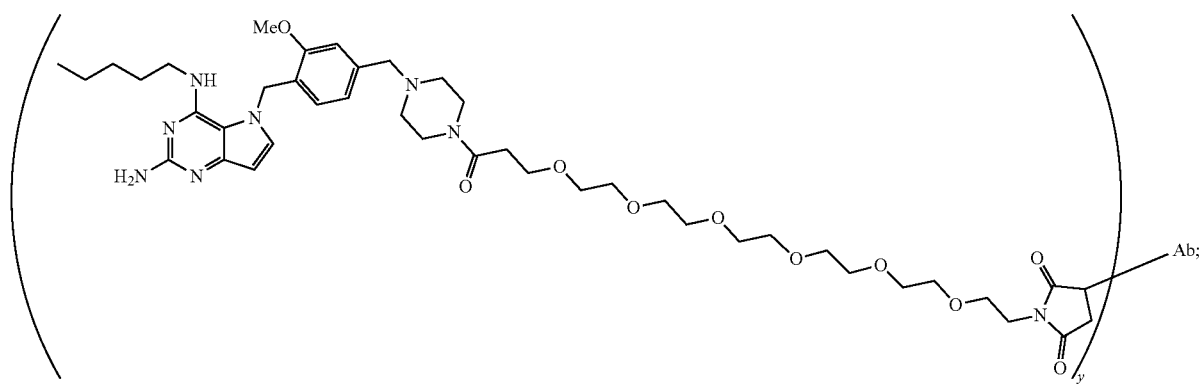
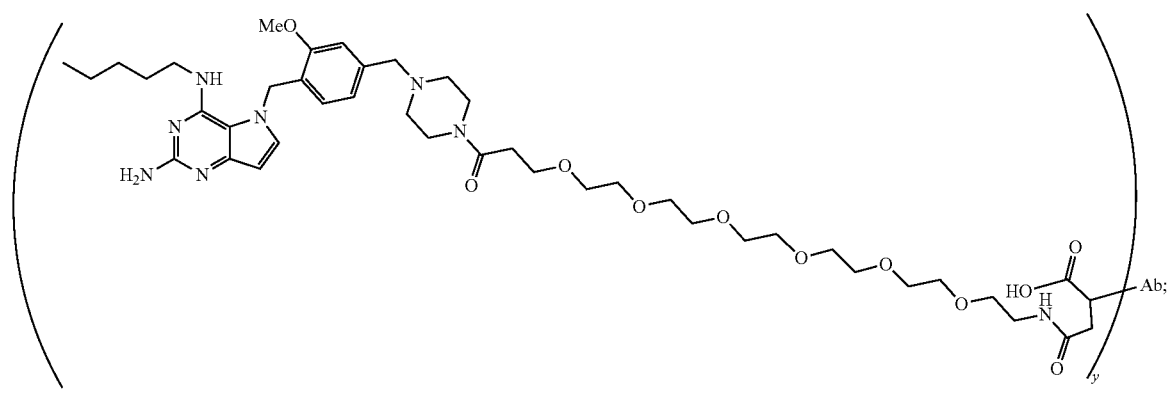
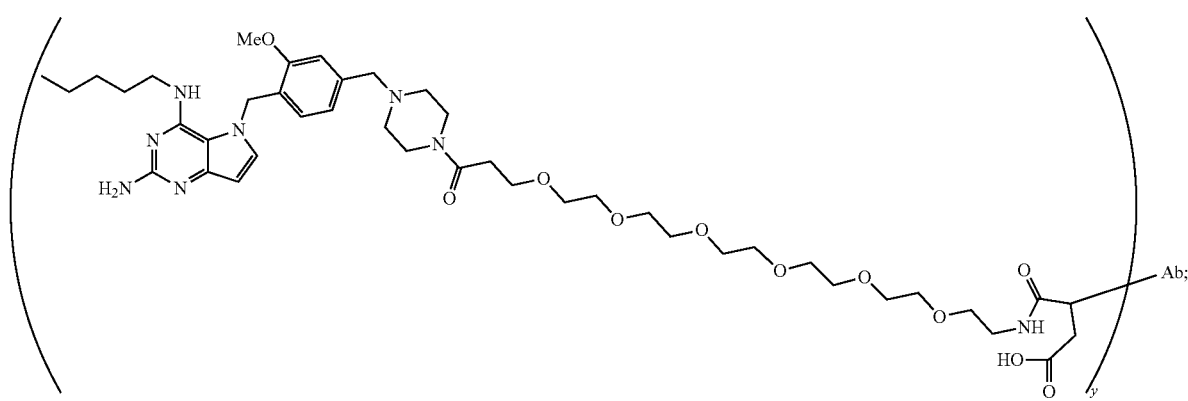
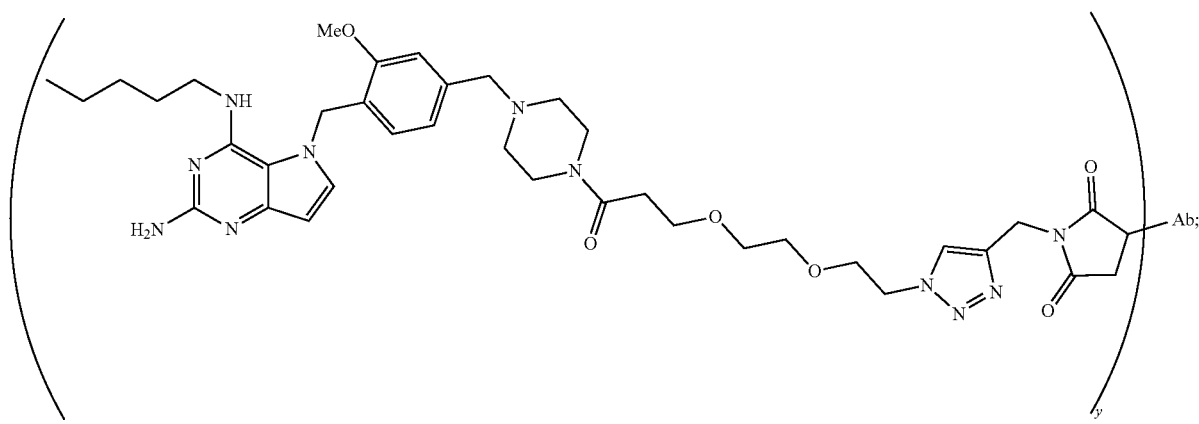

-continued
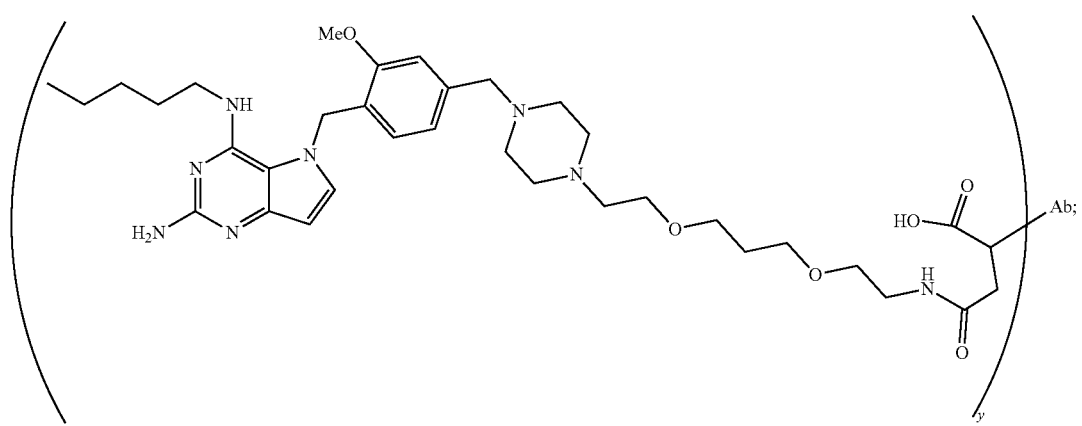
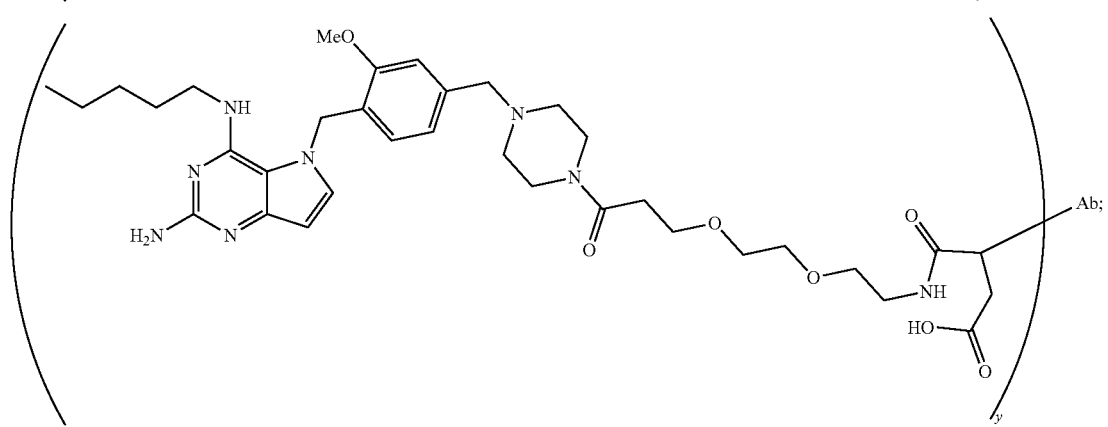
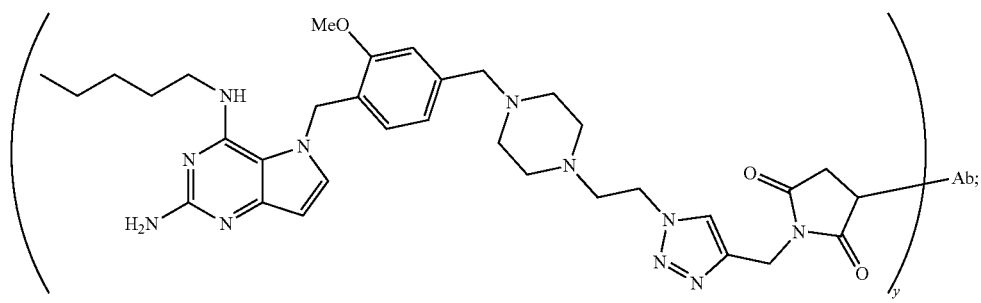
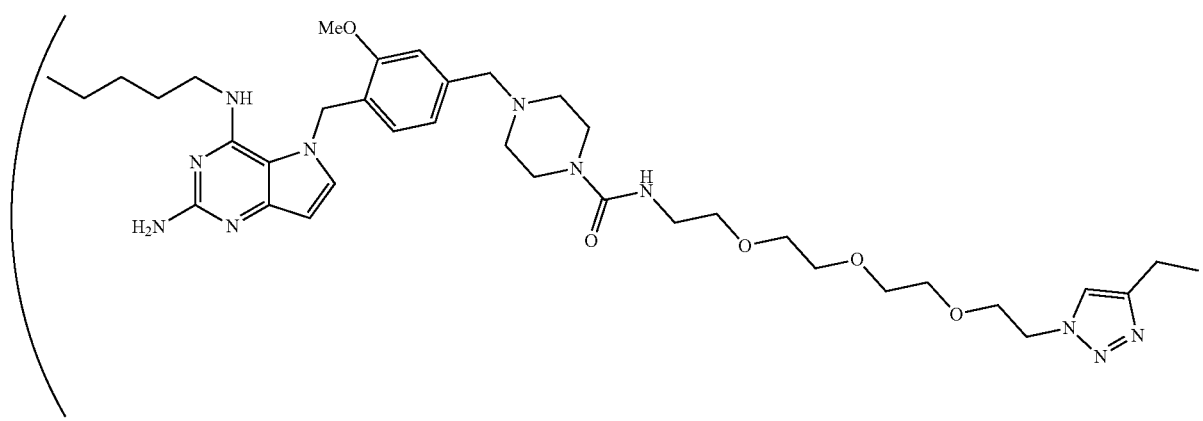

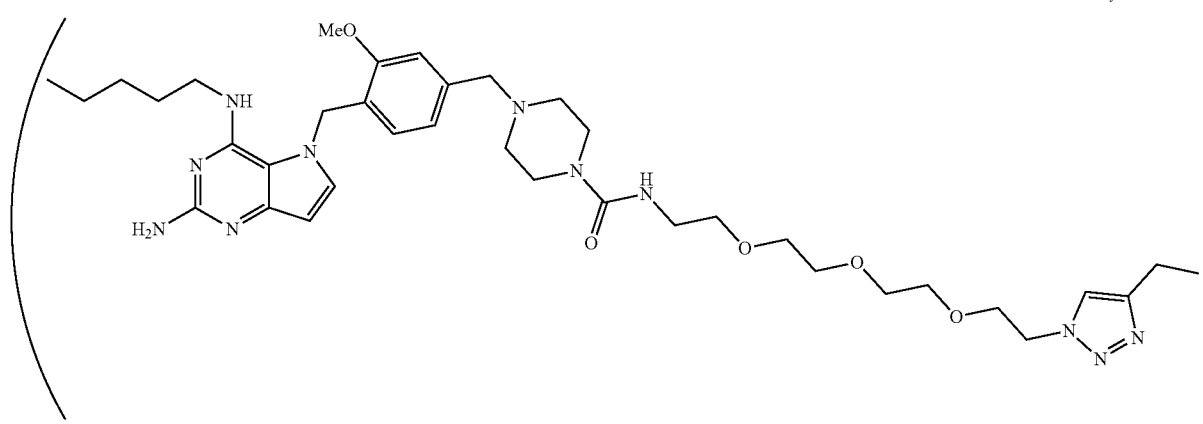
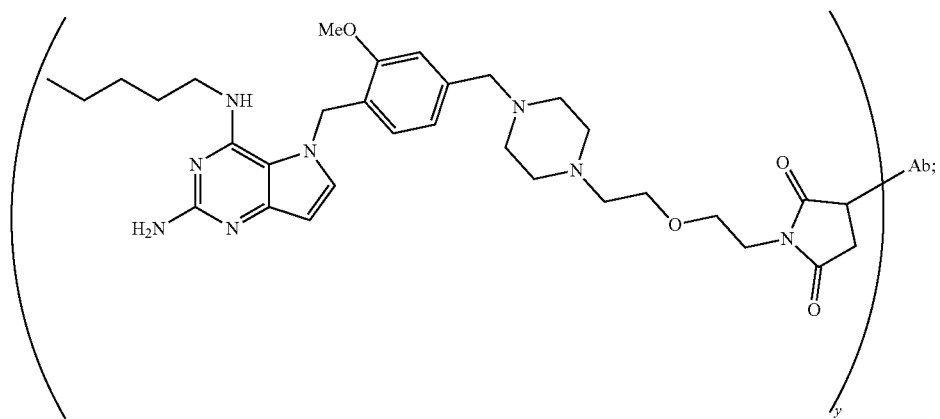

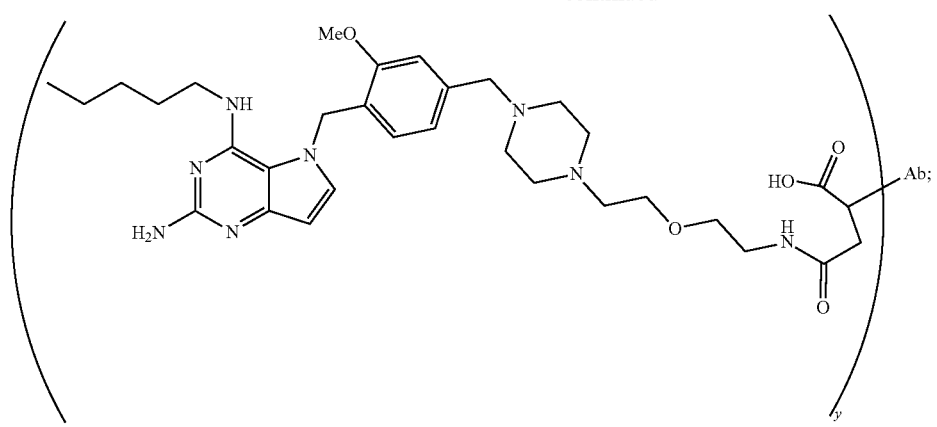
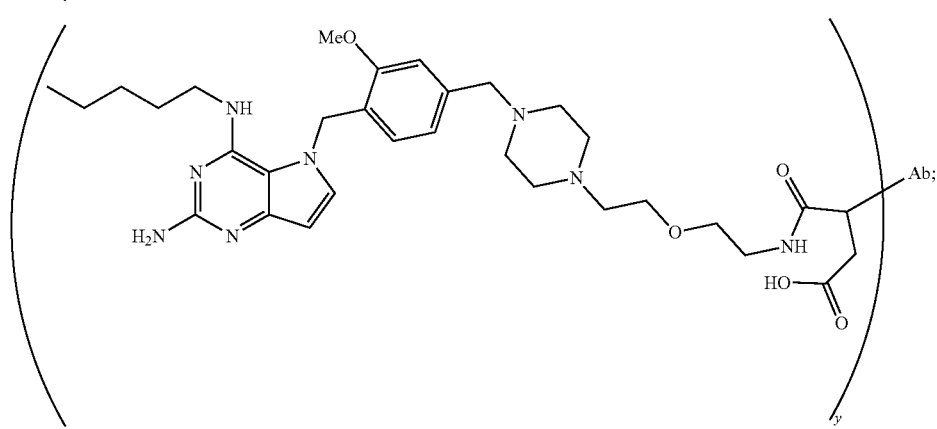
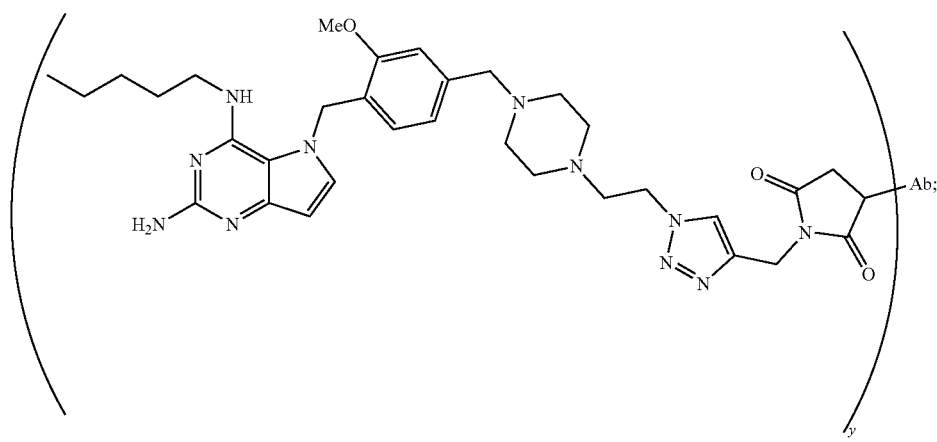
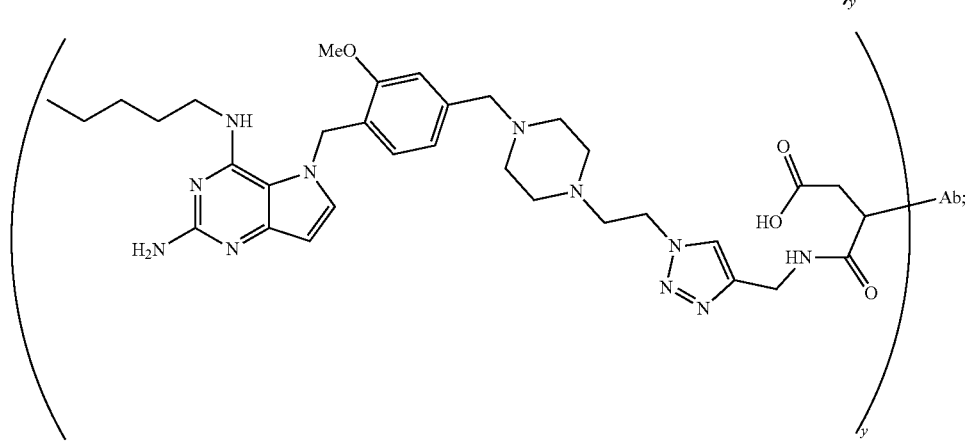

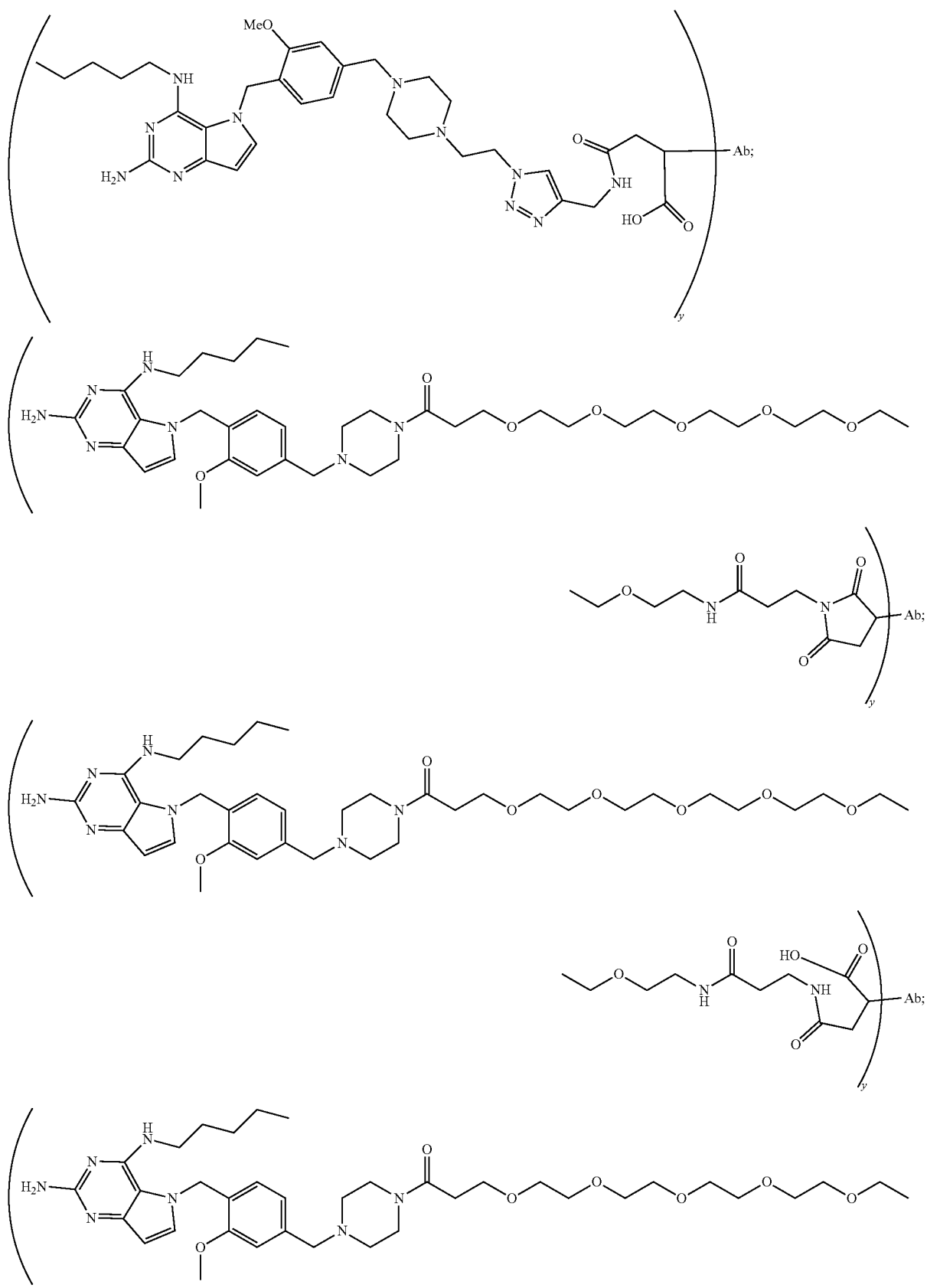

511
512
-continued
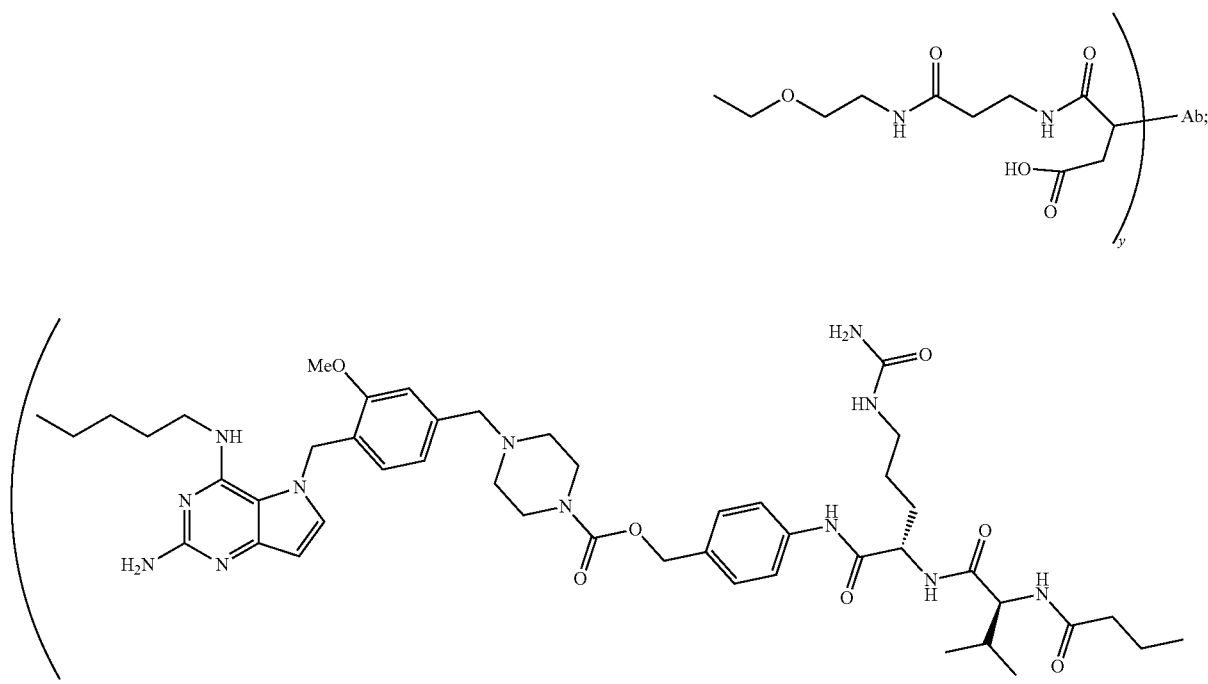
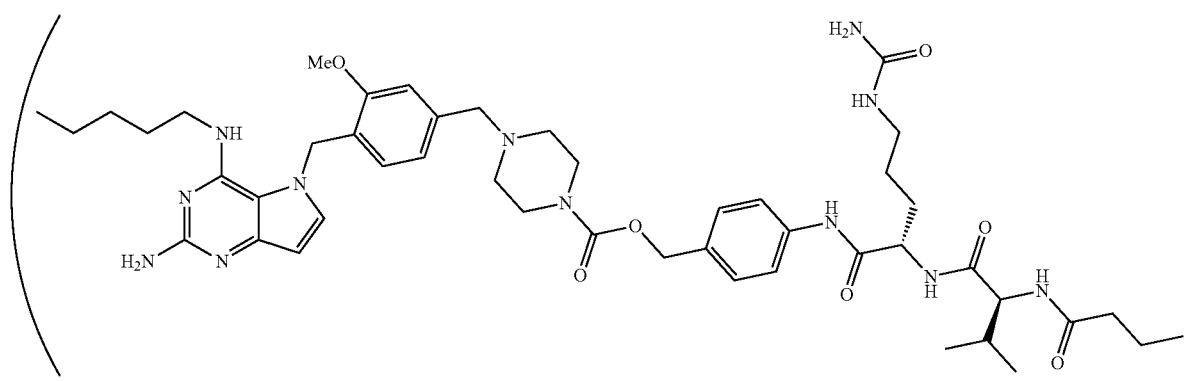

513 514
-continued
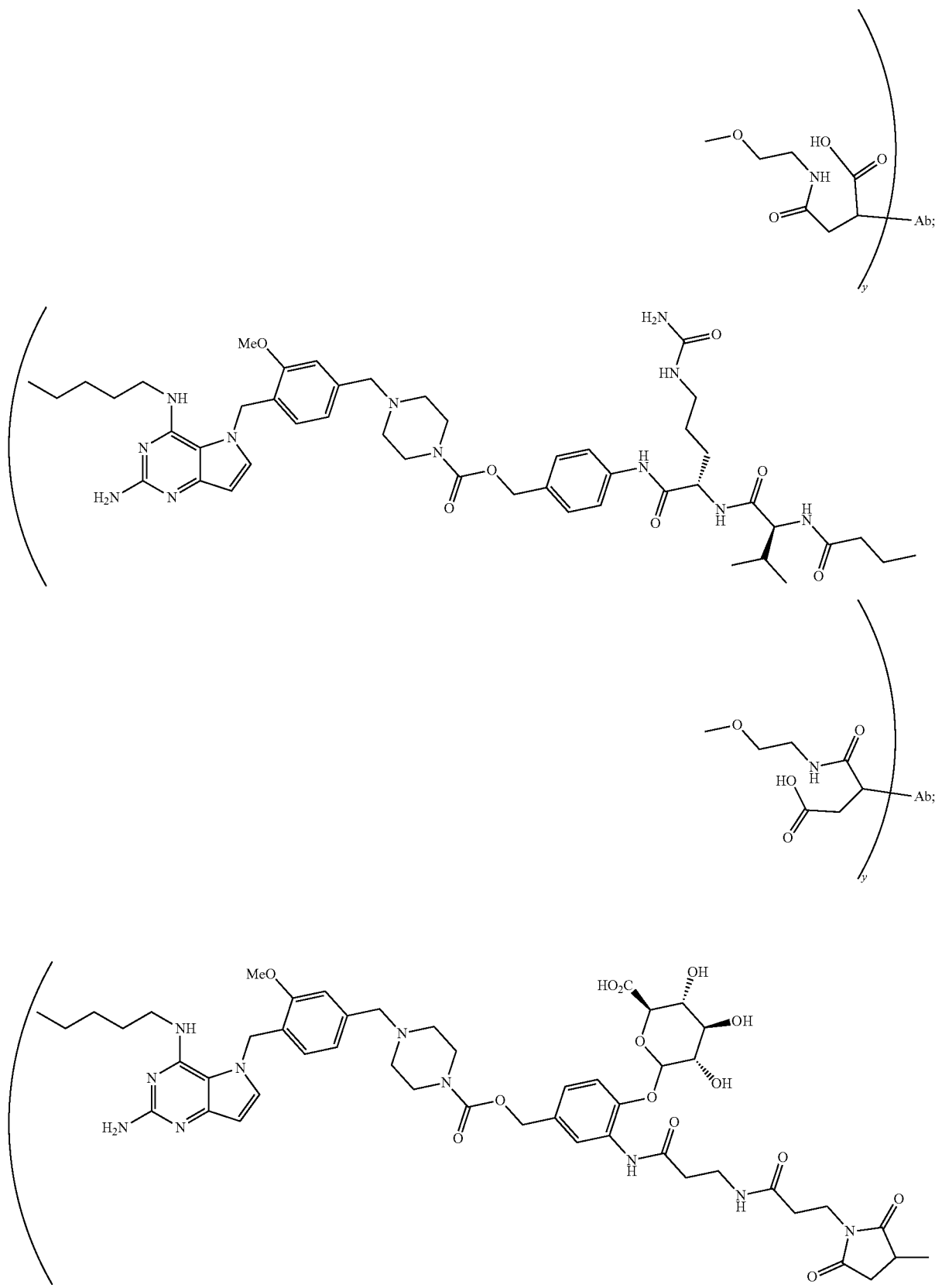

-continued
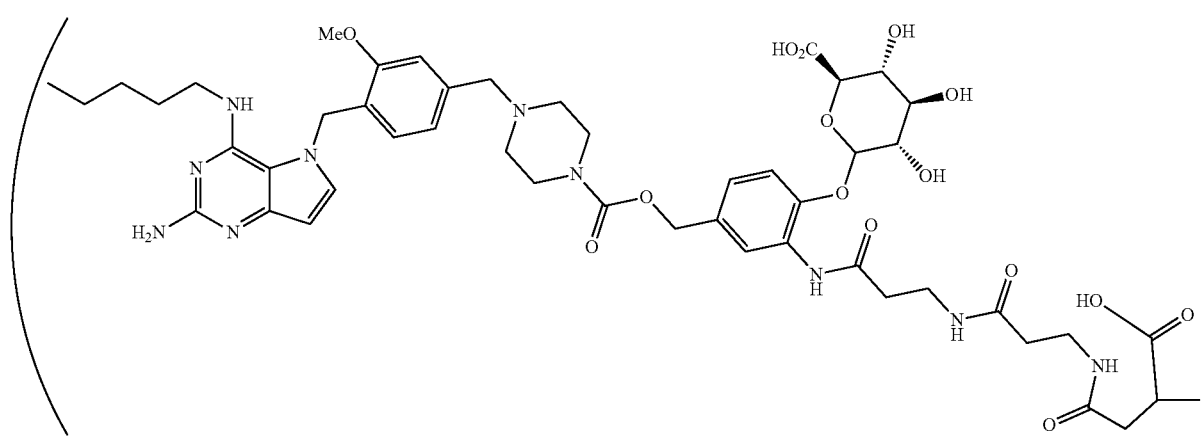

-continued
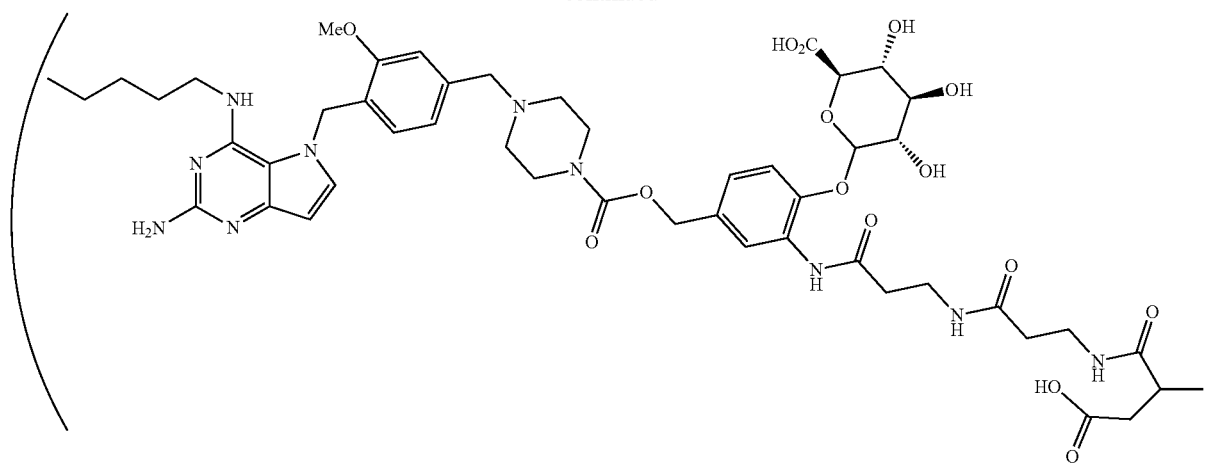

-continued
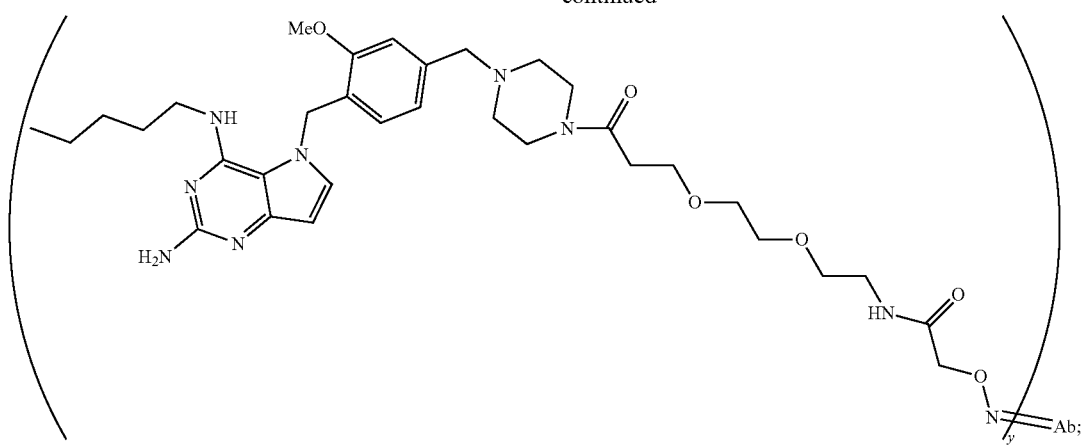
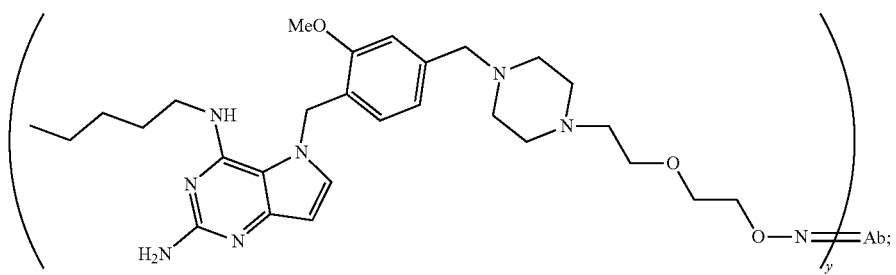
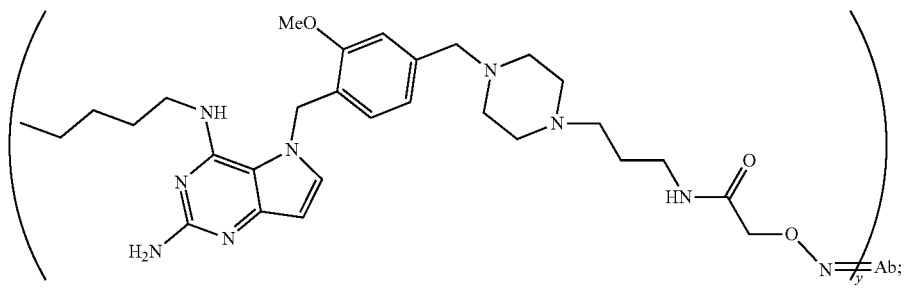
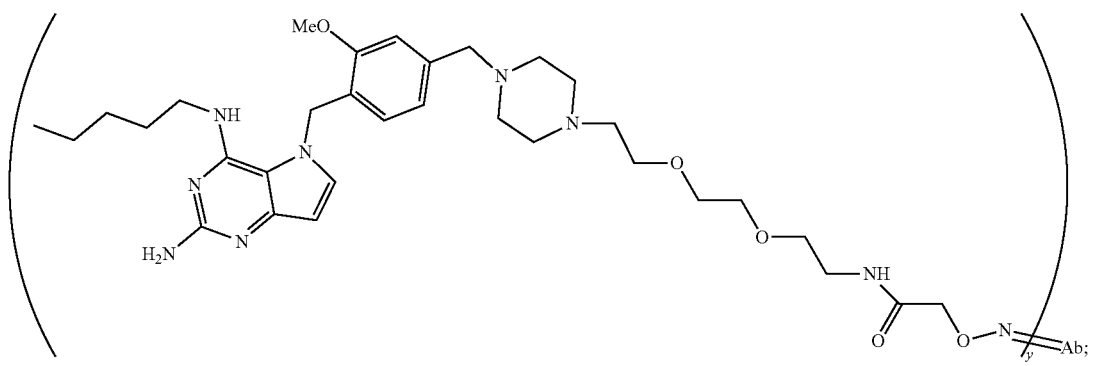
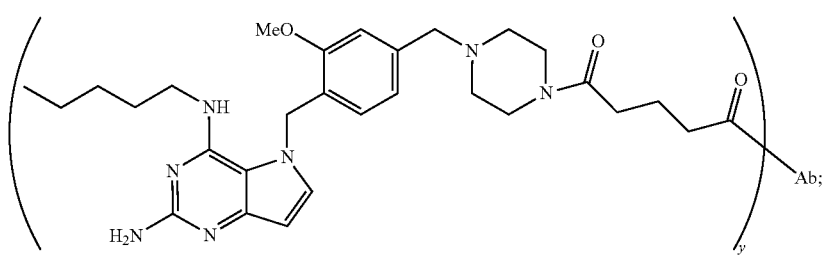

-continued
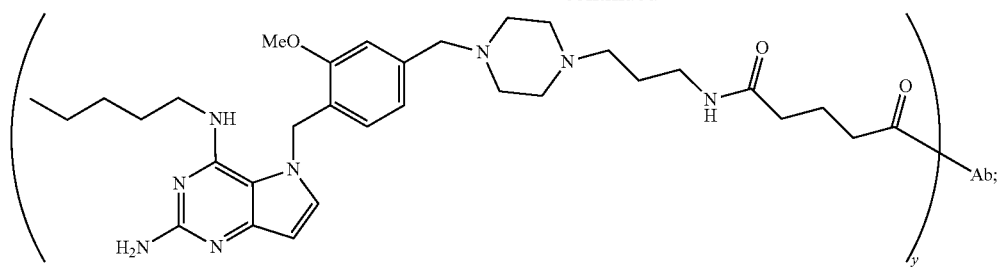
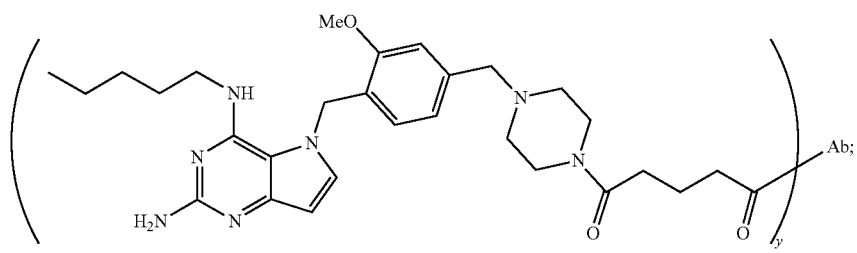
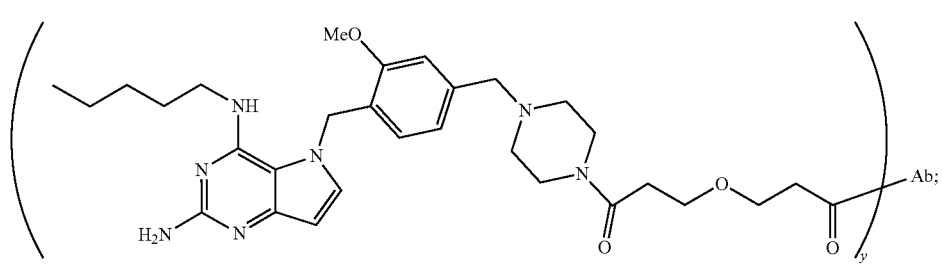
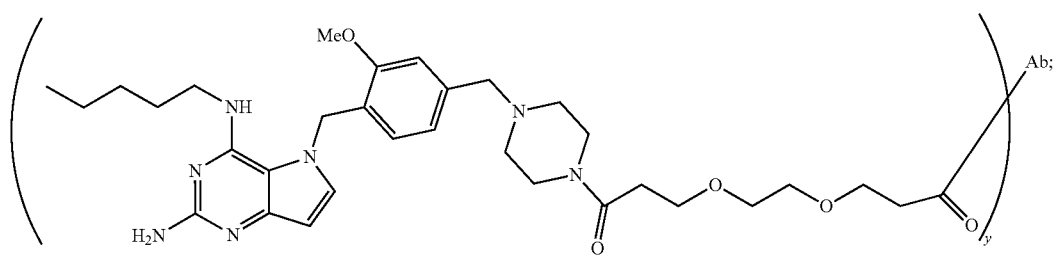
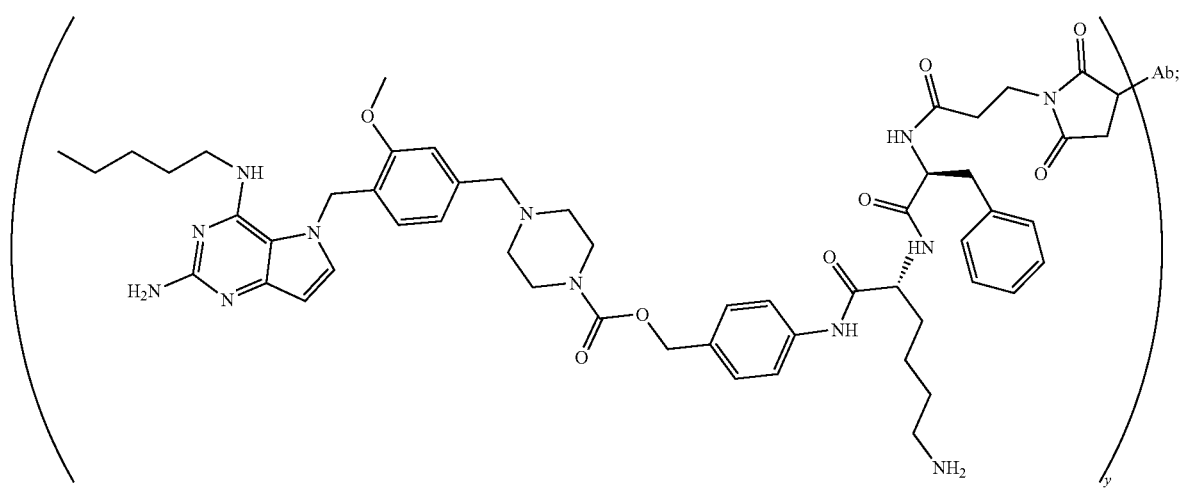

523
524
-continued
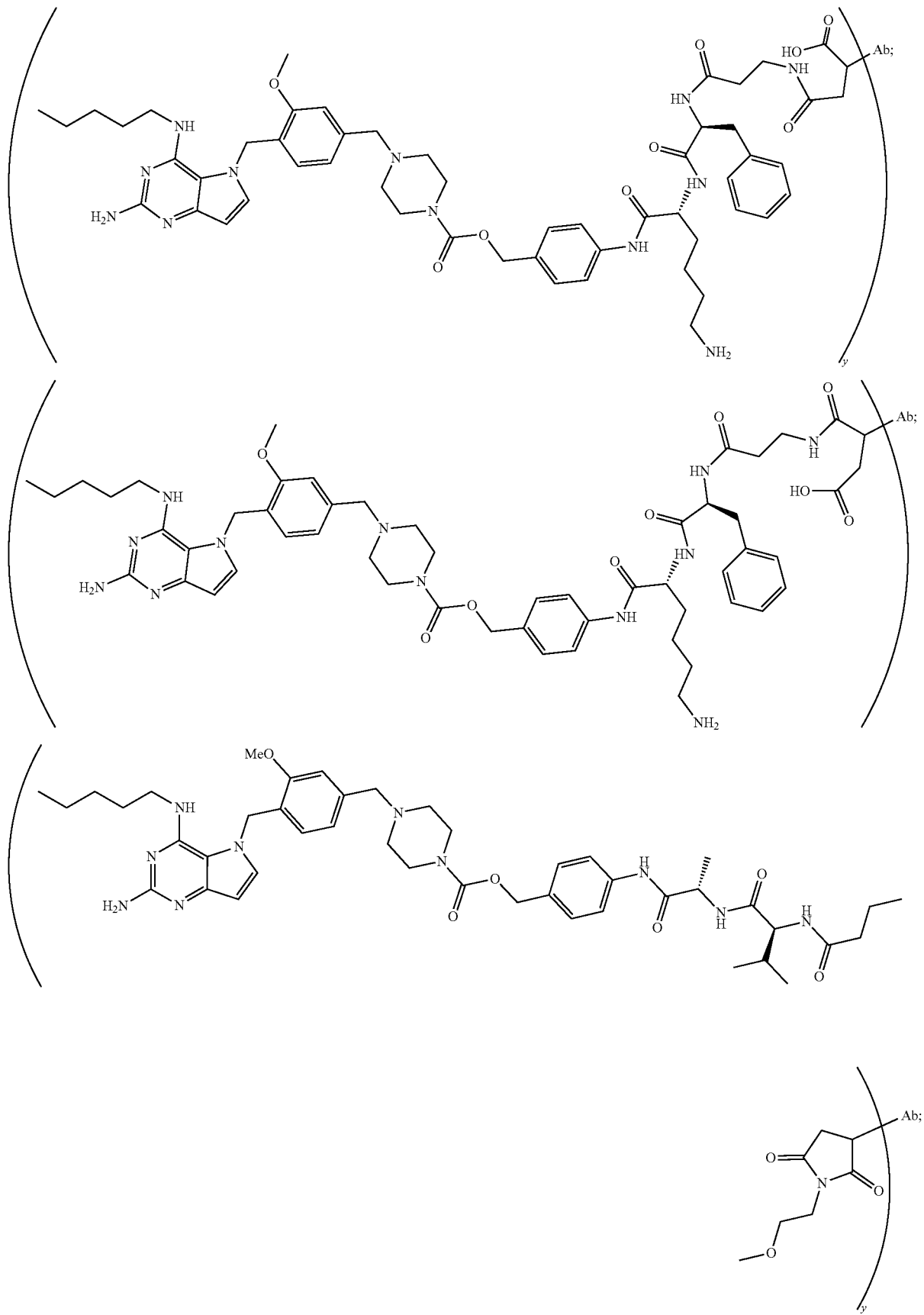

525
-continued
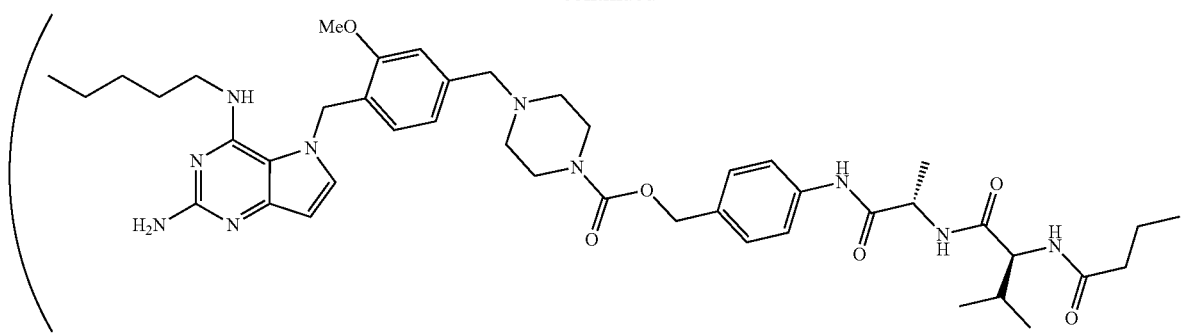
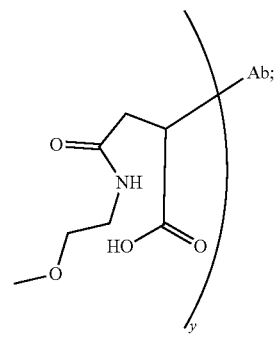
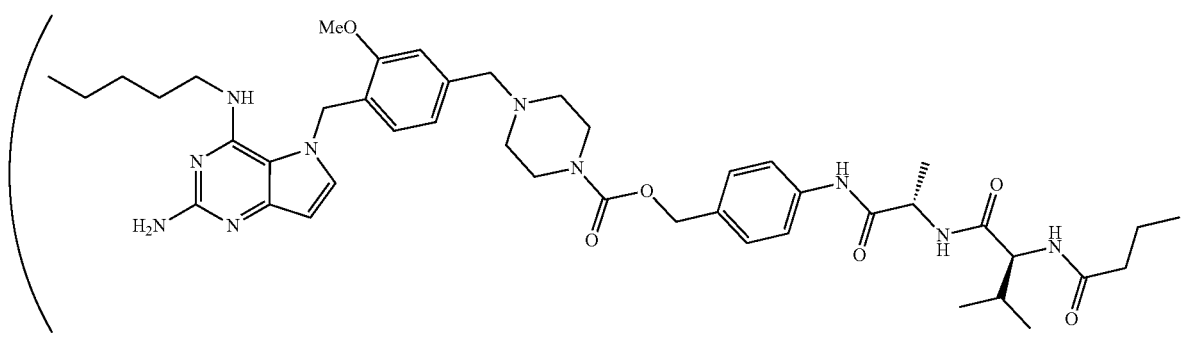
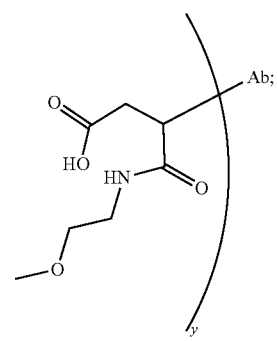

527
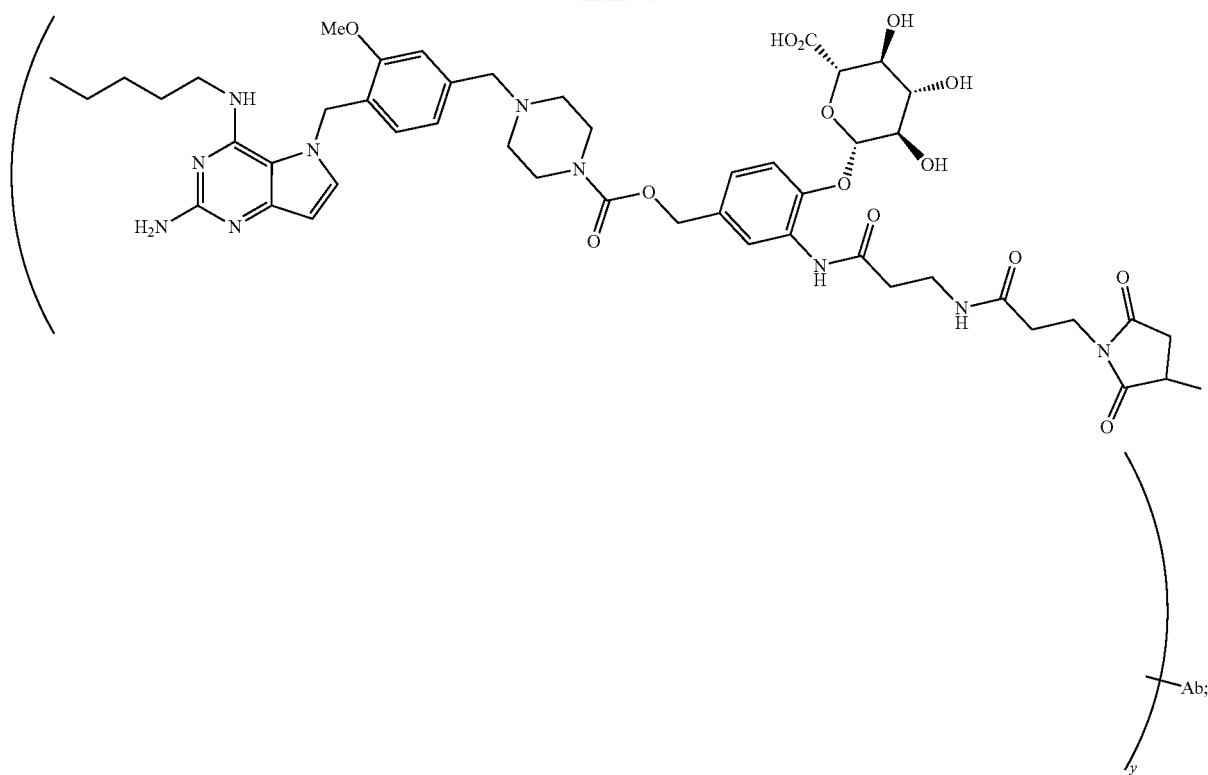
528
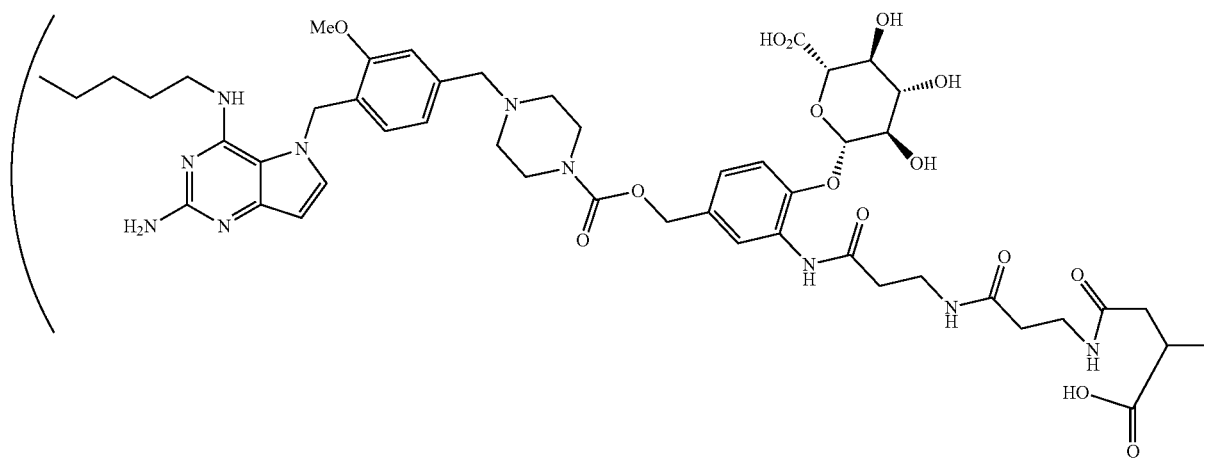

529 530
-continued
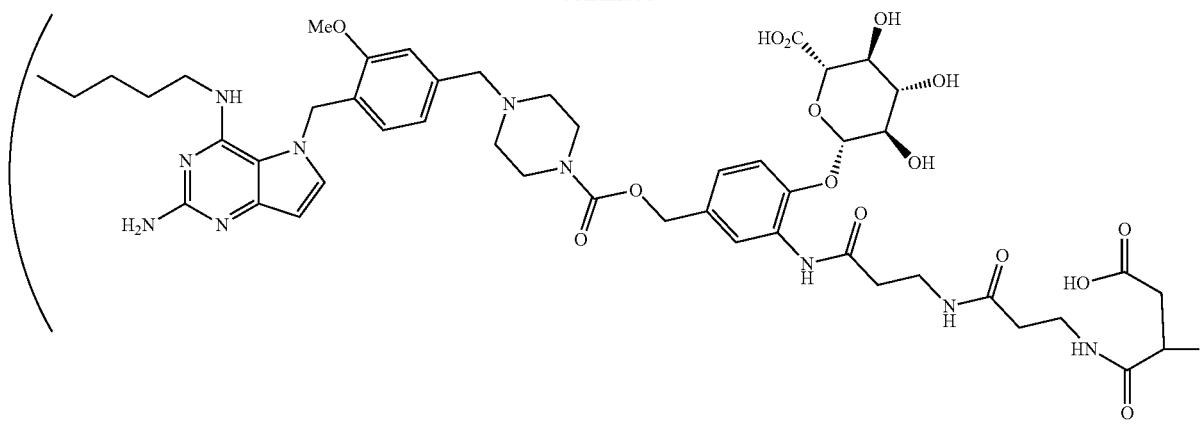
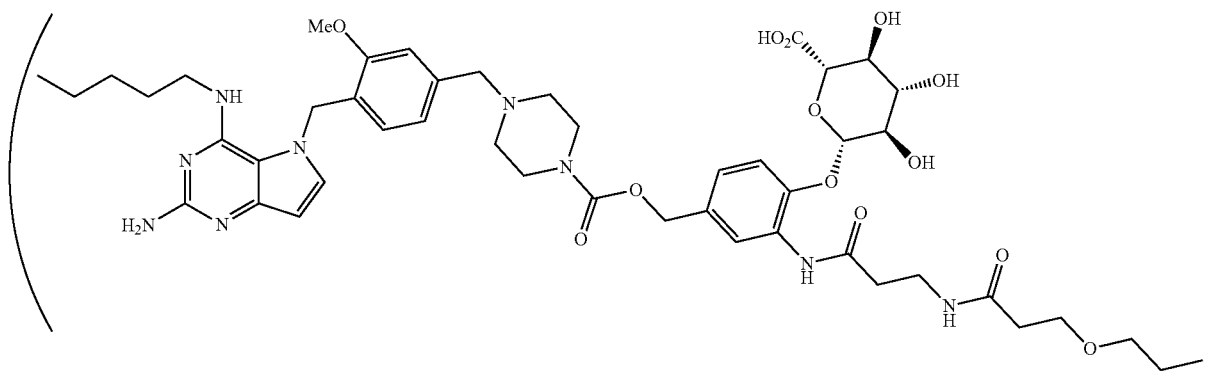

531 532
-continued
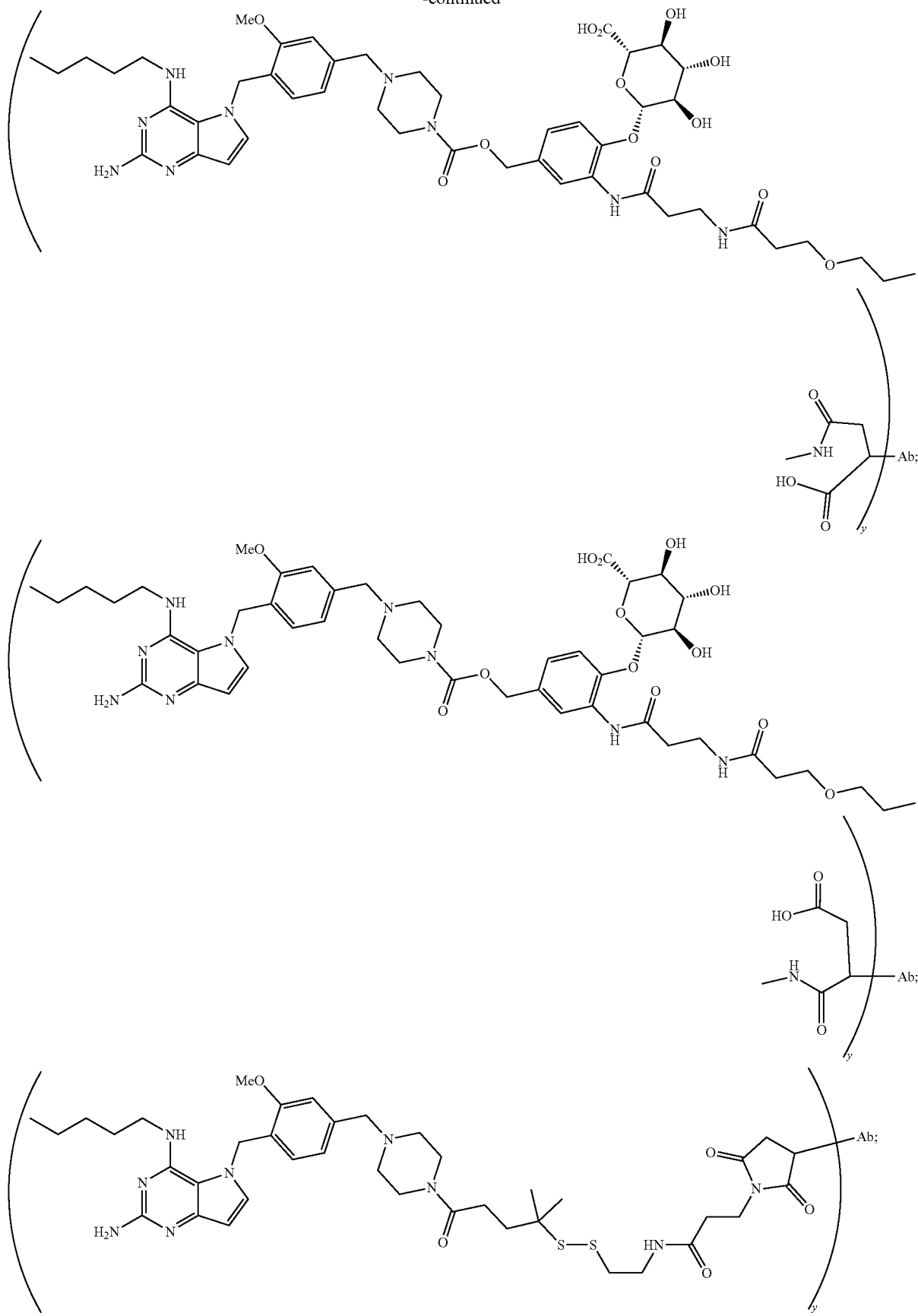

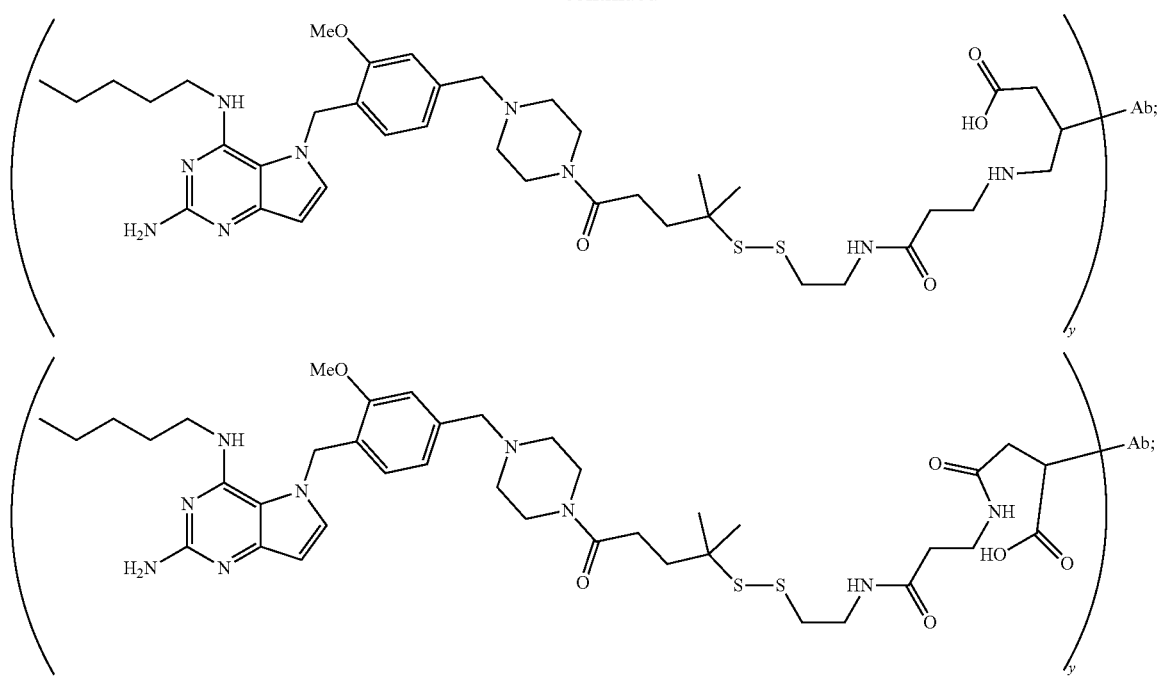
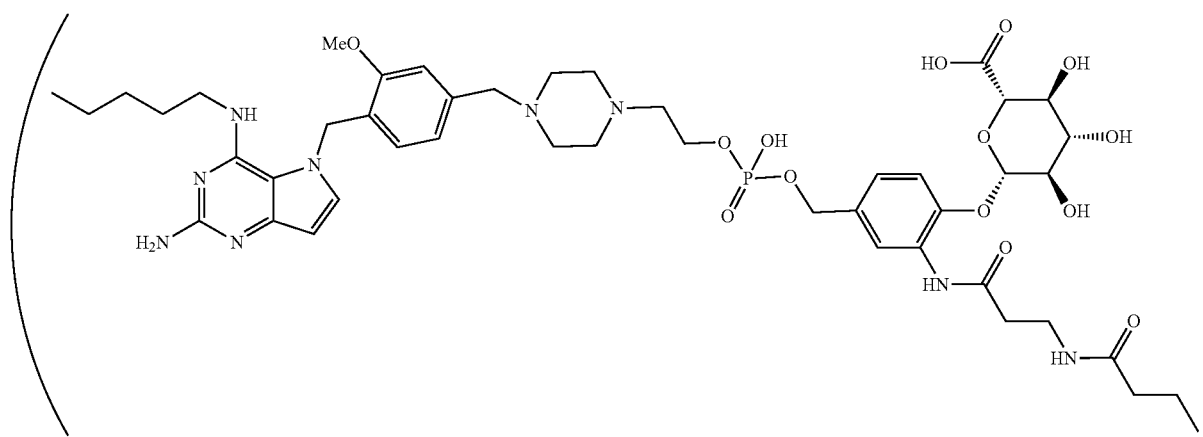
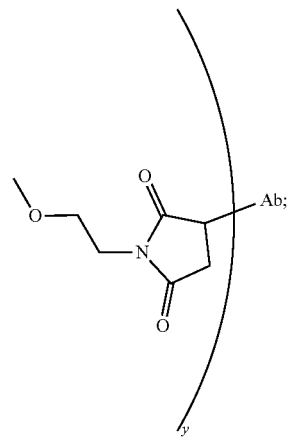

-continued
535
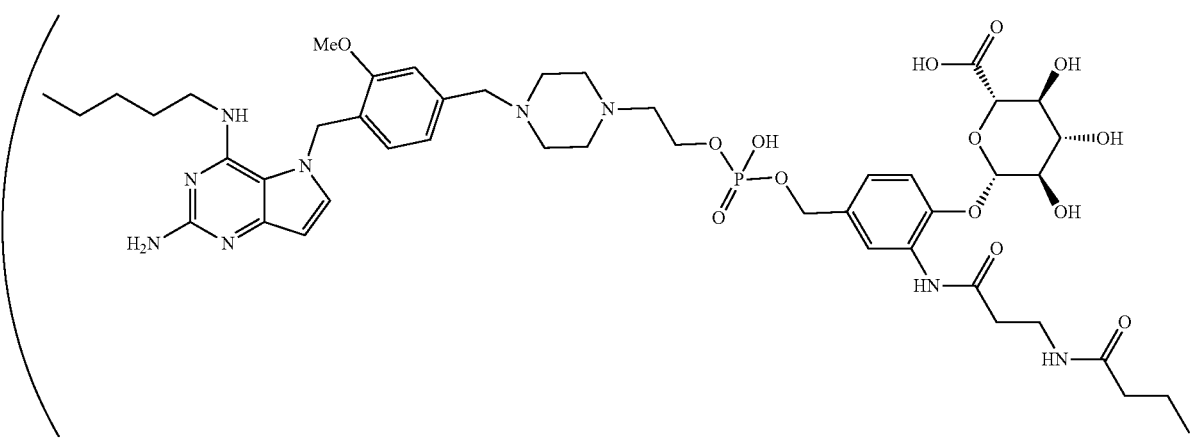
536
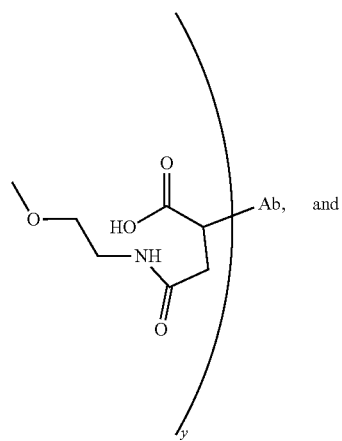
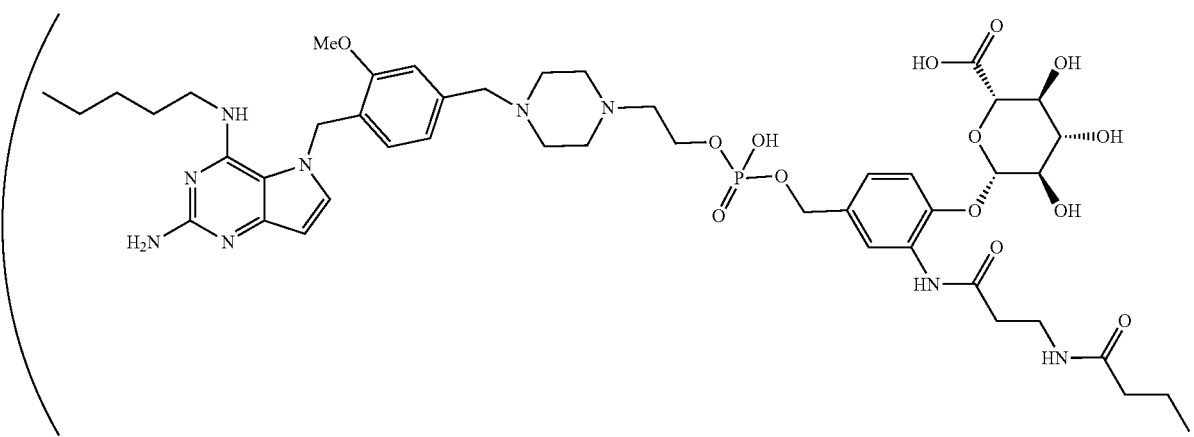

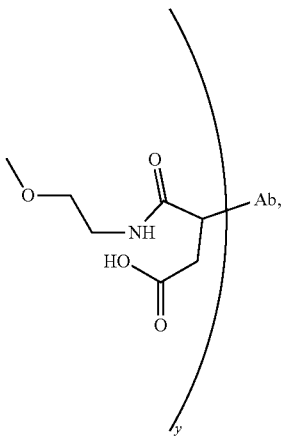

wherein Ab is an antibody or antigen binding fragment thereof that specifically binds to human HER2, and y is an integer from 1 to 4, wherein Ab is selected from any of the following:

(a) an antibody that comprises:
a heavy chain complementary determining region 1 (HCDR1) comprising the amino acid sequence of SEQ ID NO: 1;
a heavy chain complementary determining region 2 (HCDR2) comprising the amino acid sequence of SEQ ID NO: 2;
a heavy chain complementary determining region 3 (HCDR3) comprising the amino acid sequence of SEQ ID NO: 3;
a light chain complementary determining region 1 (LCDR1) comprising the amino acid sequence of SEQ ID NO: 11;
a light chain complementary determining region 2 (LCDR2) comprising the amino acid sequence of SEQ ID NO: 12; and
a light chain complementary determining region 3 (LCDR3) comprising the amino acid sequence of SEQ ID NO: 13;

(b) an antibody that comprises:
a HCDR1 comprising the amino acid sequence of SEQ ID NO: 4;
a HCDR2 comprising the amino acid sequence of SEQ ID NO: 5;
a HCDR3 comprising the amino acid sequence of SEQ ID NO: 3;
a LCDR1 comprising the amino acid sequence of SEQ ID NO: 14;
a LCDR2 comprising the amino acid sequence of SEQ ID NO: 15; and
a LCDR3 comprising the amino acid sequence of SEQ ID NO: 16;

(c) an antibody that comprises a heavy chain variable region comprising the amino acid sequence of SEQ ID NO: 7, and a light chain variable region comprising the amino acid sequence of SEQ ID NO: 17;

(d) an antibody that comprises a heavy chain comprising the amino acid sequence of SEQ ID NO: 9, and a light chain comprising the amino acid sequence of SEQ ID NO: 19;

(e) an antibody that comprises a heavy chain comprising the amino acid sequence of SEQ ID NO: 21, and a light chain comprising the amino acid sequence of SEQ ID NO: 19;

(f) an antibody that comprises a heavy chain comprising the amino acid sequence of SEQ ID NO: 23, and a light chain comprising the amino acid sequence of SEQ ID NO: 19;

(g) an antibody that comprises a heavy chain comprising the amino acid sequence of SEQ ID NO: 32, and a light chain comprising the amino acid sequence of SEQ ID NO: 19; or (h) pertuzumab.

11. The conjugate of claim 10, wherein Ab comprises cysteine at one or more of the following positions (all positions by EU numbering):
(a) positions 152, 360 and 375 of the antibody heavy chain, and
(b) positions 107, 159, and 165 of the antibody light chain.

12. The conjugate of claim 10, wherein Ab comprises a heavy chain comprising the amino acid sequence of SEQ ID NO: 9, and a light chain comprising the amino acid sequence of SEQ ID NO: 19.

13. The conjugate of claim 11, wherein the compound is attached to cysteines at positions 152 and 375 of the antibody heavy chain (all positions by EU numbering).

14. The conjugate of claim 10, wherein y is about 3 to 4.

15. The conjugate of claim 10, wherein the conjugate has a hydrophobicity index of 0.8 or greater, as determined by hydrophobic interaction chromatography.

16. The conjugate of claim 10, wherein the Ab is trastuzumab, or margetuximab.

17. A pharmaceutical composition comprising one or more conjugates of claim 10 and a pharmaceutically acceptable carrier.

18. A method of treating a HER2-positive cancer in a subject in need thereof, the method comprising administering to the subject a therapeutically effective amount of the conjugate of claim 1, wherein the HER2-positive cancer is selected from gastric cancer, breast cancer, and ovarian cancer, and wherein the HER2-positive cancer has an IHC score of 2+ or 3+.

19. The method of claim 18, wherein the conjugate is capable of suppressing the HER2-positive cancer for a sustained period and/or reducing recurrence of the HER2-positive cancer, when compared to an anti-HER2 antibody alone.

20. The method of claim 18, wherein the conjugate is administered to the subject intravenously, intratumorally, or subcutaneously.

21. The method of claim 18, wherein the conjugate is administered at a dose of about 0.01-20 mg per kg of body weight.

22. The method of claim 18 further comprising administering a second agent to the subject.

23. A method of treating a HER2-positive cancer in a subject in need thereof, the method comprising administering to the subject a therapeutically effective amount of the conjugate of claim 10, wherein the HER2-positive cancer is selected from gastric cancer, breast cancer, and ovarian cancer, and wherein the HER2-positive cancer has an IHC score of 2+ or 3+.

24. The method of claim 23, wherein the conjugate is capable of suppressing the HER2-positive cancer for a sustained period and/or reducing recurrence of the HER2-positive cancer, when compared to an anti-HER2 antibody alone.

25. The method of claim 23, wherein the conjugate is administered to the subject intravenously, intratumorally, or subcutaneously.

26. The method of claim 23, wherein the conjugate is administered at a dose of about 0.01-20 mg per kg of body weight.

27. The method of claim 23 further comprising administering a second agent to the subject.

28. A compound having the structure of Formula (I), or the pharmaceutically acceptable salts thereof:

Formula (I)

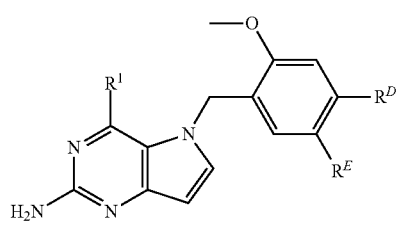

wherein:
$R^D$ is

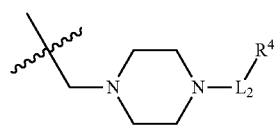

and $R^E$ is H;
$R^1$ is —NHR$^2$ or —NHCHR$^2$R$^3$;
$R^2$ is —C$_3$-C$_6$alkyl or —C$_4$-C$_6$alkyl;
$R^3$ is L$_1$OH;
L$_1$ is —(CH$_2$)$_m$—;
L$_2$ is —(CH$_2$)$_n$—, —((CH$_2$)$_n$O)$_t$(CH$_2$)$_n$—, —(CH$_2$)$_n$X$_1$(CH$_2$)$_n$—, —(CH$_2$)$_n$NHC(=O)(CH$_2$)$_n$—, —(CH$_2$)$_n$NHC(=O)(CH$_2$)$_n$C(=O)NH(CH$_2$)$_n$—, —((CH$_2$)$_n$O)$_t$(CH$_2$)$_n$NHC(=O)(CH$_2$)$_n$, —C(=O)(CH$_2$)$_n$—, —C(=O)((CH$_2$)$_n$O)$_t$(CH$_2$)$_n$—, —C(=O)((CH$_2$)$_n$O)$_t$(CH$_2$)$_n$X$_1$(CH$_2$)$_n$—, —C(=O)((CH$_2$)$_n$O)$_t$(CH$_2$)$_n$C(=O)NH(CH$_2$)$_n$—, —C(=O)NH((CH$_2$)$_n$O)$_t$(CH$_2$)$_n$X$_1$(CH$_2$)$_n$—, —C(=O)X$_2$X$_3$C(=O)((CH$_2$)$_n$O)$_t$(CH$_2$)$_n$—, —C(=O)X$_2$X$_3$C(=O)(CH$_2$)$_n$—, —C(=O)X$_2$C(=O)(CH$_2$)$_n$NHC(=O)(CH$_2$)$_n$—, —C(=O)X$_2$C(=O)(CH$_2$)$_n$NHC(=O)((CH$_2$)$_n$O)$_t$(CH$_2$)$_n$—, —C(=O)(CH$_2$)$_n$C(R$_7$)$_2$—, —C(=O)(CH$_2$)$_n$C(R$_7$)$_2$SS (CH$_2$)$_n$NHC(=O)(CH$_2$)$_n$—, —(CH$_2$)$_n$X$_2$C(=O) (CH$_2$)$_n$NHC(=O)((CH$_2$)$_n$O)$_t$(CH$_2$)$_n$— or —C(=O) (CH$_2$)$_n$C(=O)NH(CH$_2$)$_n$;

$R^4$ is

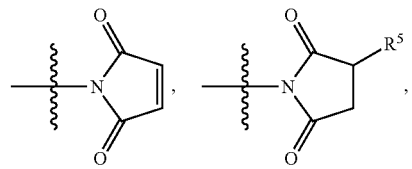

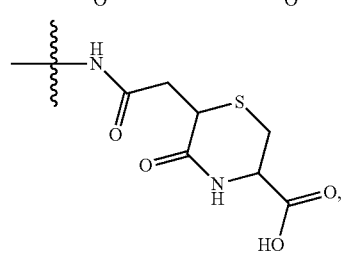

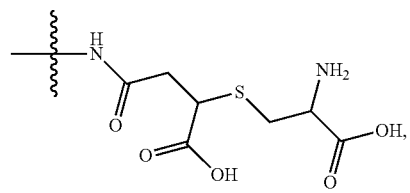

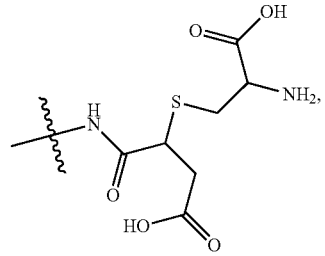

—ONH$_2$, —NH$_2$,

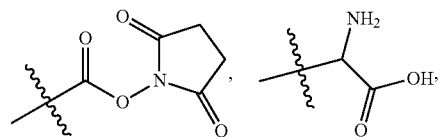

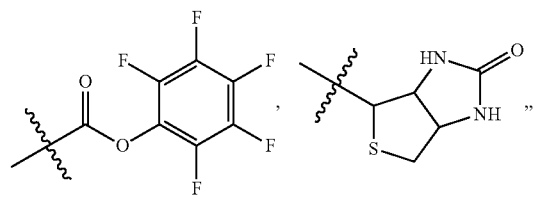

—N$_3$, -ξ-C≡CH, —NHC(=O)CH=CH$_2$, —SH, —SR$^7$, —OH —SSR$^6$, —S(=O)$_2$(CH=CH$_2$), —(CH$_2$)$_2$S(=O)$_2$(CH=CH$_2$), —NHS(=O)$_2$(CH=CH$_2$), —NHC(=O)CH$_2$Br, —NHC(=O)CH$_2$I, —C(O)NHNH$_2$,

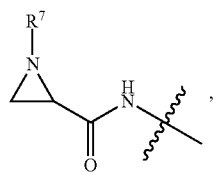
—CO₂H, —C(O)NHNH₂,
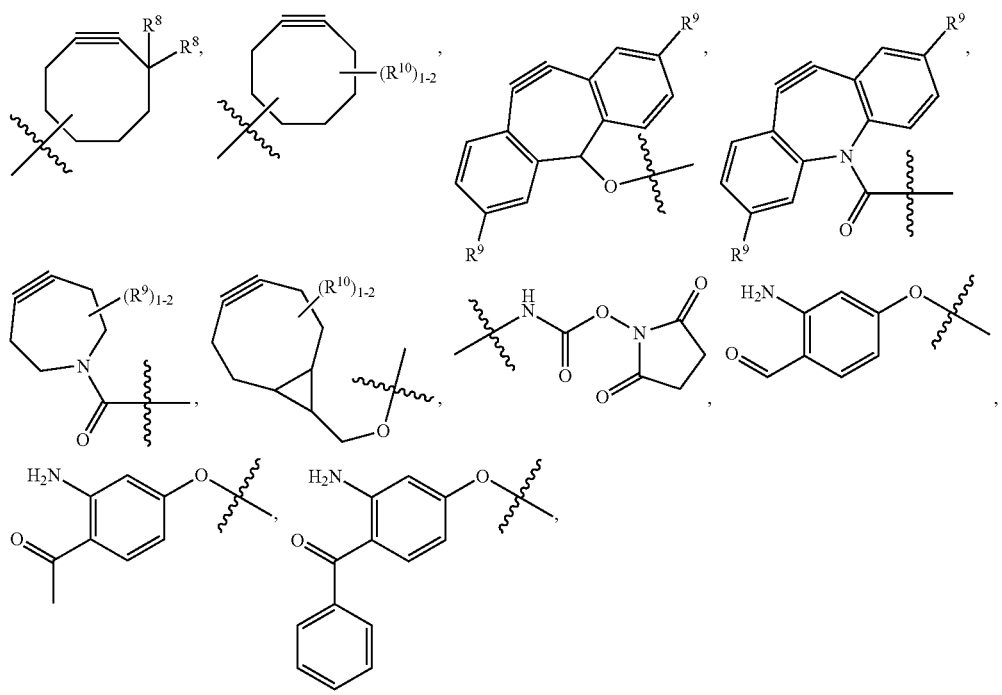
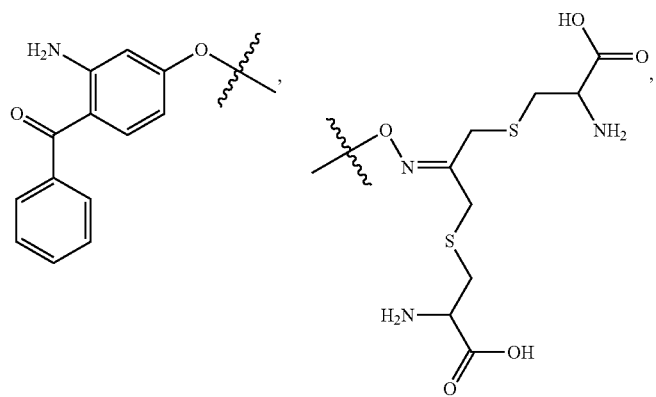
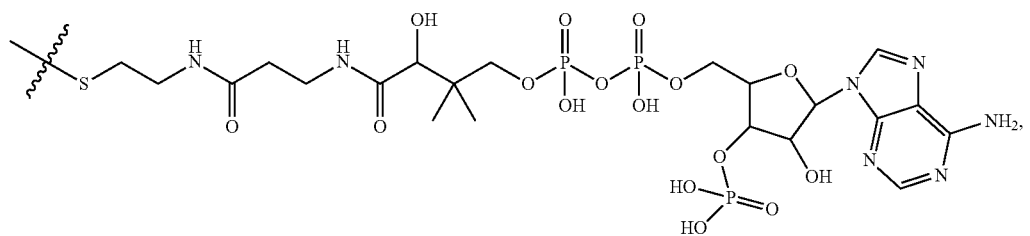

-continued
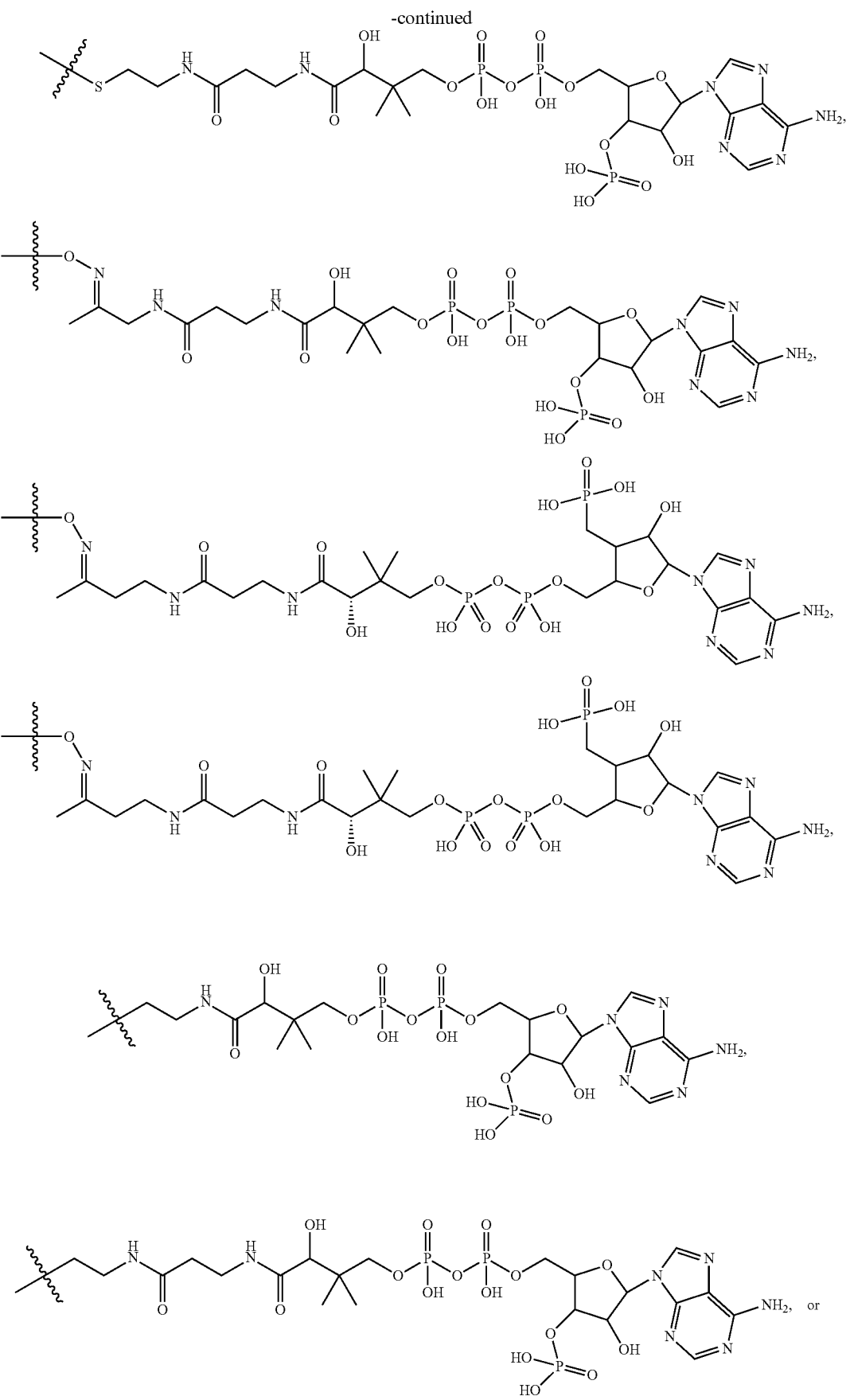

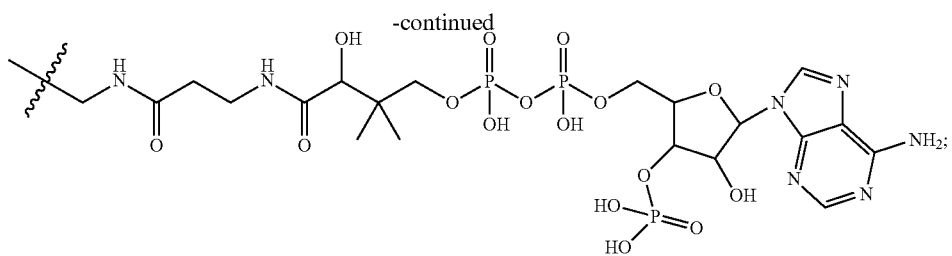
$R^5$ is
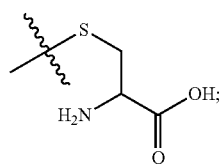 [SMILES: *SCC(N)C(=O)O]
$X_1$ is
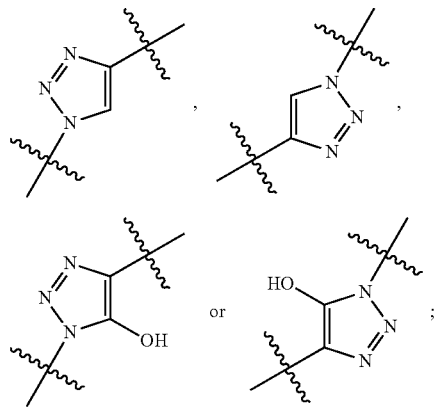
$X_2$ is
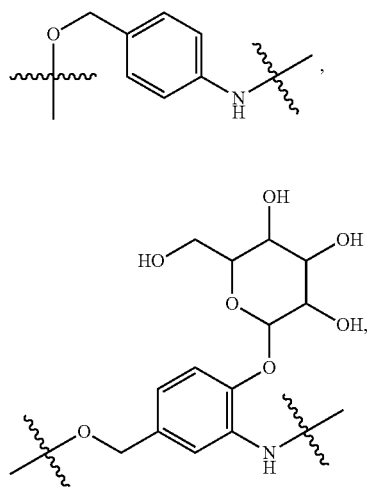
-continued
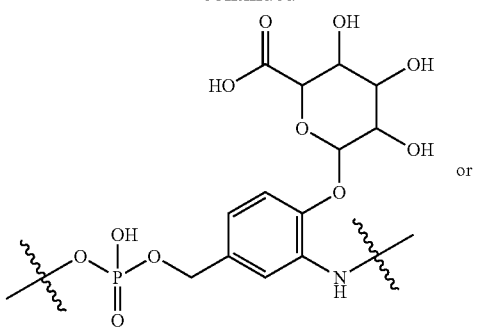
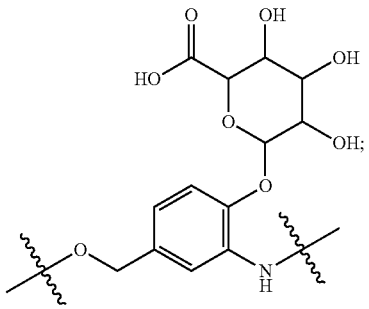
$X_3$ is
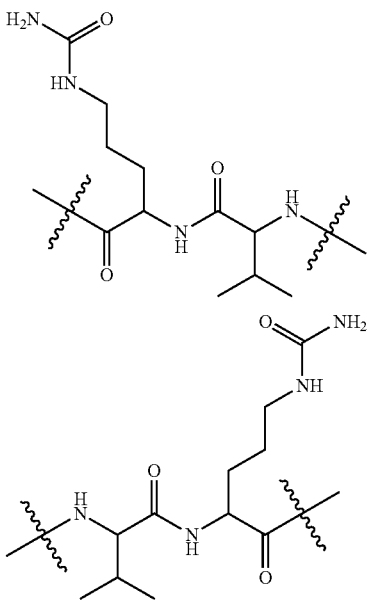

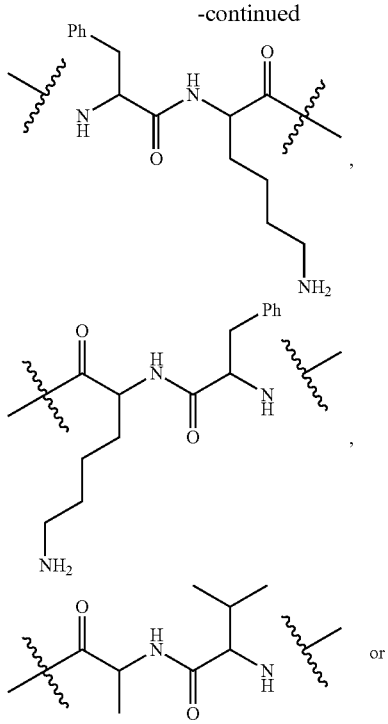

$R^6$ is 2-pyridyl or 4-pyridyl;

each $R^7$ is independently selected from H and $C_1$-$C_6$alkyl;

each $R^8$ is independently selected from H, $C_1$-$C_6$alkyl, F, Cl, and —OH;

each $R^9$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{10}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, and 4;

each n is independently selected from 1, 2, 3, and 4; and each t is independently selected from 1, 2, 3, 4, 5, 6, 7, 8, 9, 10, 11, 12, 13, 14, 15, 16, 17 and 18.

* * * * *